US011160807B1

(12) United States Patent
Kelner

(10) Patent No.: US 11,160,807 B1
(45) Date of Patent: Nov. 2, 2021

(54) METHODS, COMPOSITIONS AND DEVICES FOR TREATING CANCER WITH ILLUDOFULVENES

(71) Applicant: AF Chemicals, LLC

(72) Inventor: Michael Kelner, San Diego, CA (US)

(73) Assignee: AF Chemicals, LLC, San Diego, CA (US)

( * ) Notice: Subject to any disclaimer, the term of this patent is extended or adjusted under 35 U.S.C. 154(b) by 69 days.

(21) Appl. No.: 16/708,005

(22) Filed: Dec. 9, 2019

Related U.S. Application Data

(60) Provisional application No. 62/940,081, filed on Nov. 25, 2019, provisional application No. 62/796,409, filed on Jan. 24, 2019, provisional application No. 62/777,774, filed on Dec. 11, 2018.

(30) Foreign Application Priority Data

Dec. 9, 2019 (EP) ..................................... 19214360

(51) Int. Cl.
| | | |
|---|---|---|
| A61K 31/5375 | (2006.01) | |
| A61K 31/122 | (2006.01) | |
| A61K 31/121 | (2006.01) | |
| A61K 31/357 | (2006.01) | |
| A61K 31/351 | (2006.01) | |
| A61K 31/192 | (2006.01) | |
| A61K 31/047 | (2006.01) | |
| A61K 31/135 | (2006.01) | |
| A61K 31/16 | (2006.01) | |
| A61K 31/198 | (2006.01) | |
| A61K 31/15 | (2006.01) | |
| A61K 31/401 | (2006.01) | |
| A61K 31/18 | (2006.01) | |
| C12Q 1/6886 | (2018.01) | |

(52) U.S. Cl.
CPC ........ *A61K 31/5375* (2013.01); *A61K 31/047* (2013.01); *A61K 31/121* (2013.01); *A61K 31/122* (2013.01); *A61K 31/135* (2013.01); *A61K 31/15* (2013.01); *A61K 31/16* (2013.01); *A61K 31/18* (2013.01); *A61K 31/192* (2013.01); *A61K 31/198* (2013.01); *A61K 31/351* (2013.01); *A61K 31/357* (2013.01); *A61K 31/401* (2013.01); *C12Q 1/6886* (2013.01); *C12Q 2600/158* (2013.01); *C12Q 2600/16* (2013.01)

(58) Field of Classification Search
CPC ............................ C12Q 1/6886; A61K 31/122
See application file for complete search history.

(56) References Cited

U.S. PATENT DOCUMENTS

| | | |
|---|---|---|
| 3,230,201 A | 1/1966 | Hart |
| 5,439,936 A | 8/1995 | Kelner |
| 5,439,942 A | 8/1995 | Kelner |
| 5,523,490 A | 6/1996 | Kelner |
| 5,563,176 A | 10/1996 | Kelner |
| 5,723,632 A | 3/1998 | McMorris |
| 5,932,553 A | 8/1999 | McMorris |
| 6,025,328 A | 2/2000 | McMorris |
| 6,069,283 A | 5/2000 | McMorris |
| 6,160,184 A | 12/2000 | McMorris |
| 6,252,093 B1 | 6/2001 | McMorris |
| 6,323,181 B1 | 11/2001 | McMorris |
| 6,380,403 B1 | 4/2002 | McMorris |
| 6,469,184 B1 | 10/2002 | McMorris |
| 6,548,679 B1 | 4/2003 | McMorris |
| 6,639,105 B2 | 10/2003 | McMorris |
| 6,717,017 B2 | 4/2004 | McMorris |
| 6,855,696 B2 | 2/2005 | McMorris |
| 6,908,918 B2 | 6/2005 | McMorris |
| 6,987,193 B2 | 1/2006 | McMorris |
| 7,141,603 B2 | 11/2006 | McMorris |
| 7,329,759 B2 | 2/2008 | McMorris |
| 7,629,380 B2 | 12/2009 | McMorris |
| 7,655,695 B2 | 2/2010 | McMorris |
| 7,713,939 B2 | 5/2010 | McMorris |
| 7,855,275 B2 | 12/2010 | Eigenbrot |
| 8,937,161 B2 | 1/2015 | Mao |
| 9,381,178 B2 | 7/2016 | Kelner |
| 9,725,769 B1 * | 8/2017 | Knudsen .............. C12Q 1/6886 |
| 9,980,926 B1 | 5/2018 | Kelner |
| 10,285,955 B2 | 5/2019 | Kelner |
| 10,806,708 B2 | 10/2020 | Kelner |
| 2005/0250675 A1 | 11/2005 | McMorris |

(Continued)

FOREIGN PATENT DOCUMENTS

WO PCT/US2005/017804    12/2005
WO PCT/US2015/025208    10/2015

OTHER PUBLICATIONS

Hounkpe et al. Nucleic Acids Research, 2021, vol. 49, Database issue, page D947-D955 (Year: 2021).*

(Continued)

*Primary Examiner* — James D. Anderson
(74) *Attorney, Agent, or Firm* — Sci-Law Strategies, PC

(57) ABSTRACT

In an embodiment of the invention, a method of treating cancer includes screening to select a patient population that will respond to an Illudofulvene Analog composition based on the presence of one or more Transcription Coupled Repair (TCR) mutations, deletions or other events interfering with TCR biomarker expression in combination with upregulation of Myc and/or PTGR biomarker expression and treating the patient population with the Illudofulvene Analog composition.

19 Claims, 4 Drawing Sheets

Specification includes a Sequence Listing.

(56) References Cited

U.S. PATENT DOCUMENTS

| | | |
|---|---|---|
| 2007/0072790 A1 | 3/2007 | McMorris |
| 2007/0092940 A1 | 4/2007 | Eigenbrot |
| 2008/0306147 A1 | 12/2008 | McMorris |
| 2011/0033378 A1 | 2/2011 | Dimasi |
| 2018/0100197 A1 | 4/2018 | Knudsen |
| 2019/0231795 A1 | 8/2019 | Knudsen |
| 2020/0340067 A1 | 10/2020 | Knudsen |

OTHER PUBLICATIONS

SPIVAK (Arch. Toxicol., 2016, vol. 90, pp. 2583-2594) (Year: 2016).*
A. Annamalai et al., Reaction of the Adenine Nucleotide Analogue W-p-Fluorosulfonylbenzoyl Adenosine at Distinct Tyrosine and Cysteine Residues of Rabbit Muscle Pyruvate Kinase, J. Biol. Chem., 256, 10276-10283, 1981.
E. Brandsteterova, M.J. Kelner, T.C. McMorris, W. Wang, and R. Bagnell. HPLC analysis of novel anticancer agents Illudins and analogs. *J. Liquid Chromatography*. 16:115-126, 1993.
E. Brandsteterova, M.J. Kelner, T.C. McMorris, L. Estes, R. Bagnell, and M. Montoya.HPLC determination of a new anticancer agent (acylfulvene).in serum. *Neoplasma* 39:369-373, 1992.
R.F. Colman, Affinity Labelling of Purine Nucleotide Sites in proteins, 52, 67-91, 1983.
SR Demeade et al., Prostate-Specific Antigen-Activated Thapsigargin Prodrug as Targeted Therapy for Prostate Cancer, JNCI 95, 990, 2003.
R.P.M. Dings, et al., Chapter 18: Non-peptidic mimietics as cancer-sensitizing agents. In: Sensitization of cancer cells for Chemo/Immuno/Radiotherapy, 305-325. Human Press, 2008.
R.P. M. Dings, et al., Inhibiting Tumor Growth by Targeting Tumor Vasculature with Galectin-1 Antagonist Anginex Conjugated to the Cytotoxic Acylfulvene, 6-Hydroxylpropylacylfulvene. Bioconjugate Chemistry 21:20-27, 2010.
R.P. M. Dings, et al., Ovarian tumor growth regression using a combination of vascular targeting agents anginex or topomimetic 0118 and the chemotherapeutic irofulven. Cancer Letters 265: 270-280, 2008.
K.E. Dombrowski, et al., 5'-p-(Fluorosulfonyl)benzoyl-8-azidoadenosine: A New Bifunctional Affinity Label for Nucleotide Binding Sites in Proteins, Arch. Biochem. Biophys. 275, 302-308, 1989.
F.S. Esch et al., A procedure for the synthesis of p-Fluorosulfonyl[14C]benzoyl-5'-Adenosine with [14C] in the benzoyl moiety, Anal Biochem, 84, 642-645, 1978.
F.S. Esch et al., Identification of a tyrosine residue at a nucleotide binding site in the B subunit of the mitochondrial ATPase with p-Fluorosulfonyl[14C]benzoyl-5'-Adenosine, J. Biol. Chem., 253, 6100-6106, 1978.
VM Garsky, The Synthesis of a Prodrug of Doxorubicin Designed to Provide Reduced Systemic Toxicity and Greater Target Efficacy, J. Med. Chem. 44, 4216-4224, 2001.
M. J affe et al., Use of 5'-[p-Fluorosulfonylbenzoyl] guanosine as an affinity probe for the Guanine Nucleotide Binding Site of Transducin, The Prot. Journal, 26, 125-133, 2007.
N.G.J. Jaspers, et al., Anti-tumor compounds illudin S and Irofulven induce DNA lesions ignored by global repair and exclusively processed by transcription- and replication-coupled repair pathways. *DNA Repair* 1:1027-1038, 2002.
M.J. Kelner, et al., Preclinical evaluations of Illudins as anticancer agents. *Cancer Res*. 47:3186-9, 1987.
M.J. Kelner, et al., Preclinical evaluation of Illudins as anti-cancer agents. Basis for selective cytotoxicity. *J. Natl. Cancer Inst*. 82:1562-1565, 1990.
M.J. Kelner, et al., Characterization of Illudin S sensitivity of DNA repair-deficient Chinese Hamster cells: unusually high sensitivity of ERCC2 and ERCC3 DNA-helicase deficient mutants in comparison to other chemotherapeutic agents. *Biochem. Pharmacol*. 48:403-409, 1994.

M.J. Kelner, et al., Nonresponsiveness of the metastatic human lung carcinoma MV522 xenograft to conventional anticancer agents. *Anticancer Res*. 15:867-872, 1995.
M.J. Kelner, et al., In vitro and In vivo studies on the anticancer activity of dehydroilludin M. *Anticancer Res*. 15:873-878, 1995.
M.J. Kelner, et al., Efficacy of Acylfulvene Illudin analogs against a metastatic lung carcinoma MV522 xenograft nonresponsive to traditional anticancer agents retention of activity against various mdr phenotypes and unusual cytotoxicity against ERCC2 and ERCC3 DNA helicase-deficient cells. *Cancer Res*. 55:4936-4940, 1995.
M.J. Kelner, et al., Efficacy of HMAF (MGI-114) in the MV522 metastatic lung carcinoma xenograft model nonresponsive to traditional anticancer agents. *Invest. New Drugs* 14:161-167, 1996.
M.J. Kelner, et al., Characterization of cellular accumulation and toxicity of Illudin S in sensitive and non-sensitive tumor cells. *Cancer Chemother. Pharmacol*. 40:65-71, 1997.
M.J. Kelner, et al., Characterization of Acylfulvene histiospecific toxicity in human tumor cell lines. *Cancer Chemother. Pharmacol*. 41:237-242, 1998.
M.J. Kelner, et al., Efficacy of MGI 114 (6-hydroxymethylacylfulvene, HMAF) against the mdr1/gp170 Metastatic MV522 lung carcinoma xenograft. *Eur. J. Cancer*. 34:908-913, 1998.
M.J. Kelner, et al., Characterization of MGI 114 (HMAF): Histiospecific toxicity in human tumor cell lines. *Cancer Chemother. Pharmacol*. 44:235-240, 1999.
M.J. Kelner, et al., Anti-leukemic action of the novel agent MGI 114 (HMAF) and synergistic action with Topotecan. *Leukemia* 14:136-141, 2000.
M.J. Kelner, et al., Efficacy of MGI 114 against the MRP-positive metastatic MV522 lung carcinoma Xenograft. *Anti-Cancer Drugs* 11: 217-224, 2000.
M.J. Kelner, et al., Enhanced antitumor activity of irofulven in combination with thiotepa or mitomycin C. *Cancer Chemother. Pharmacol*. 49:412-8, 2002.
M.J. Kelner, et al., Enhanced antitumor activity of Irofulven in combination with antimitotic agents. *Invest New Drugs* 20:271-279, 2002.
M.J. Kelner, et al., Synergy of Irofulven in combination with other DNA damaging Agents: synergistic interaction with altretamine, alkylating, and platinum-derived agents in the MV522 lung tumor model. *Cancer Chemotherap Pharmacol*. 63:19-26, 2008.
M.J. Kelner, et al., Synergy of Irofulven in combination with various anti-metabolites, enzyme inhibitors, and miscellaneous agents in MV522 lung carcinoma cells: marked interaction with gemcitabine and 5-fluorouracil. *Invest. New Drugs*. 26:407-415, 2008.
J.J. Likos et al., Affinity labelling of the active site of yeast Pyruvate Kinase by 5'-p-Fluorosulfonyl benzoyl Adenosine, J. Biol. Chem., 255, 9388-9398, 1980.
J.R. MacDonald, et al., Preclinical antitumor activity of 6-Hydroxymethylacylfulvene, a semisynthetic derivative of the mushroom toxin Illudin S. *Cancer Res*. 57:279-283, 1997.
T.C. McMorris, et al., Structure and reactivity of Illudins. *Tetrahedron* 45:5433-5440, 1989.
T.C. McMorris, et al., On the mechanism of toxicity of Illudins. The role of glutathione. *Chem. Res. Toxicol*. 3:574-579, 1990.
T.C. McMorris, et al., Structure activity-relationships of Illudins Analogs with improved therapeutic index. *J. Org. Chem*. 57:6876-6883, 1992.
T.C. McMorris, at 211., Acylfulvenes, a new class of potent anti-tumor agents. *Experientia* 52:75-80, 1996.
T.C. McMorris, et al., (Hydroxymethyl)acylfulvene: an Illudin derivative with superior antiturnor properties. *J. Natural Products* 59:896-899, 1996.
T.C. McMorris, et al., Total synthesis of Hydroxymethylacylfulvene; an antitumor derivative of Illudin S. *Chem. Commun*. 3:315-316, 1997.
T.C. McMorris, at al., An Acetal derivative of Illudin S with improved tumor activity. *Tetrahedron Lett*. 38:1697-1698, 1997.
T.C. McMorris, et al., The design and total synthesis of antitumor acylfulvenes. *J. Organic Chem*. 62:3015-3018, 1997.
T.C. McMorris, at al., Reaction of antitumor hydroxymethylacylfulvene (HMAF) with thiols. *Tetrahedron*.53: 14579-90, 1997.

(56) References Cited

OTHER PUBLICATIONS

T.C. McMorris, at al., Synthesis of [$^3$H]-Illudin S, [$^3$H]-Acylfulvene, [$^3$H] & [$^{14}$C]-Hydroxymethylacylfulvene (MGI 114). *J. Labelled Cpd. Radiopharm*. XLI: 279-285, 1998.
T.C. McMorris, at al., Metabolism of antitumor Acylfulvene by rat liver cytosol. *Biochem. Pharmacol*. 57:83-88, 1999.
T.C. McMorris, at al., Metabolism of antitumor hydroxymethylacylfulvene by rat liver cytosol. *Drug Metab. Dispos*. 27:983-985, 1999.
T.C. McMorris, et al., Preparation and biological activity of amino acid and peptide conjugates of antitumor hydroxymethylacylfulvene. *J. Med. Chem*. 43: 3577-3580, 2000.
T.C. McMorris, at al., Sequiterpenes from the Basidiomycete *Omphalotus illudens*. *J. Nat. Prod*. 63:1557-1559, 2000.
T.C. McMorris, et al., Structure-activity studies of antitumor agent irofulven (hydroxymethylacylfulvene) and related analogues. *J. Org. Chem*. 66:6158-6163, 2001.
T.C. McMorris, et al., Sesquiterpenes from Omphalotus illudens. *Phytochemistry* 61:395-398, 2002.
T.C. McMorris, at al., Reaction of Irofulven with Zinc and Acid. *J Nat Products*. 66:310-312, 2003.
T.C. McMorris, et al., Structure-activity relationship studies of Illudins: Analogues possessing a spiro-cuclobutane ring. J. Org. Chem. 68:9648-53, 2003.
T.C. McMorris, at al., Synthesis and biological activity of enantiomers of antitumor Irofulven. *J. Org. Chem* 69:619-623, 2004.
T.C. McMorris, at al., Synthesis and Antitumor Activity of Amine Analogs of Irofulven *Bioorganic & Medicinal Chemistry Letters*. 17: 6770-72, 2007.
T.C. McMorris, et al., Structure-Activity Studies of Urea, Carbamate and Sulfonamide Derivatives of Acylfulvene. *J. Med. Chem*. 53: 1109-16, 2010.
Narayanan, A. and Jones, L.H. Sulfonyl fluorides as privileged warheads in chemical biology, Chem Sci., 6, 2650, 2015.
P.K. Pal et al, Affinity Labeling of a Regulatory Site of Bovine Liver Glutamate Dehydrogenase, Biochem., 14, 707-714, 1975.
P.K. Pal et al, Affinity Labeling of a inhibitory DPNH Site of Bovine Liver Glutamate Dehydrogenase by 5'-Fluorosulfonylbenzoyl Adenosine, J.Biol. Chem. 250, 8140-8147, 1975.
T.L. Poulos, The involvement of serine and carboxyl groups in the activity of Bovine Pancreatic Deoxyribonuclease A, J. Biol. Chem. 249, 1453-1457, 1974.
S. Roy et al., Affinity Labeling of a Lysine Residue in the Coenzyme Binding Site of Pig Heart Mitochondrial Malate Dehydrogenase, Biochemistry, 18, 4683-4690, 1979.
K.V. Saradambal ey al., Lysine and Tyrosine in the NADH Inhibitory Site of Bovine Liver Glutamate Dehydrogenase, J. Biol. Chem. 256, 11866-11872, 1981.
R. Schobert, et al., Conjugates of the fungal cytotoxin illudin M with improved tumour specificity. Biorg Med Chem 16:8592-97, 2008.
R. Schobert, et al., Cancer selective metallocenedicarboxylates of the fungal cytotoxin Illudin M. J Med Chem. 54: 6177-82, 2011.
R. Schobert, et al., Anticancer Active Illudins: Recent developments of a potent alkylating compound class. Current Medicinal Chemistry 18:790-807, 2011.

M.D. Staake , at al., Hydroxyurea derivatives of irofulven with improved antitumor efficacy. *Bioorg. Med. Chem. Lett*. 26: 2836-38, 2016.2010.
M. Tanasova, S.J. Sturla. "Chemistry and Biology of Acylfulvenes: Sesquiterpene-derived antitumor agents" (2012) Chemical Reviews. 112, 3578-3610.
C.T. Togashi et al., 5'-p-Fluorosulfonylbenzoyladenosine: Inactivatio of myosine subfragment I and a model reaction with Cysteine (1981) J Biol. Chem. 257, 10112-10118.
J .M. Tomich et al., Modification of two essential cysteines in rabbit muscle pyruvate kinase by the guanosine nucleotide analogue 5'-[p-(Fluorosulfonyl)benzoyl] guanosine, 1981 Biochem, 20, 6711-6720.
PCT/US2015/025208, ISR dated Oct. 23, 2015, 26 pages.
A. Narayanan et al., Sulfonyl fluorides as privileged warheads in chemical biology, Chem Sci, 2650, 6 (2015).
A Paci et al., "Pharmacokinetics, Metabolism, and Routes of Excretion of Intravenous Irofulven in Patients with Advanced Solid Tumors", Drug Metabolism and Disposition, vol. 34, No. 11, Aug. 16, 2006.
J. Gong et al., "Depurinating Acylfulvene-DNA Adducts: Characterizing Cellular Chemical Reactions of a Selective Antitumor Agent", Journal of the American Chemical Society, vol. 129, No. 7, Feb. 1, 2007, pp. 2101-2111.
Partial Supplementary eSR 15776253.5 PCT/US2015/025208, dated February 5, 2018 (stamped by foreign associate as incoming on January 31, 2018), 18 pages.
A. Stornetta, "DNA Adducts from Anticancer Drugs as Candidate Predictive Markers for Precision Medicine", (2017) Chemical Research in Toxicology, 30, 388-409.
A. Intra, "Regioselective Enzymatic Acylation of Polyhydroxylated Sesquiterpenoids" (2004) J. Molecular Catalysis B: Enzymatic 29, 95-98.
C. Nord, "Cytotoxic Illudane Sesquiterpenes from the Fungus *Granulobasidium vellereum* (Ellis and Cragin) Jülich", J. of Natural Products (2015) 78, 2559-2564.
T. Horn et al., "High-Order Drug Combinations Are Required to Effectively Kill Colorectal Cancer Cells", (2016) Cancer Res. 76, 6950-6963.
K. Mouw, "Improving Methods to Dectect and Target nucleotide Excision Repair (NER) Deficiency in Bladder Cancer" (2020) IBCN, https://www.urotoday.com/conference-highlights/ibcn-2020/125289-ibcn-2020-improving-methods-to-detect-and-target-nucleotide-excision-repair-deficiency-in-bladder-cancer.html, last visited Feb. 25, 2021.
European Search Report, Application 3667323, Feb. 11, 2020, 4 pages.
C. McCann et al., "Molecular Targets and Cancer Therapeutics" (2015) Poster Abstract, htpps://www.aacr.org/Documents/Targets15_AbstractsPosterC.pdf.
K. E. Pietsch et al., "Quantification of Acylfulvene- and Illudin S-DNA Adducts in Cells with Variable Bioactivation Capacities" (2013) Chemical Res. In Toxicology, 26 146-155.
W. Yang et al., "Genomics of Drug Sensitivity in Cancer (GDSC): a resource for therapeutic biomarker discovery in cancer cells" (2013) Nucleic Acids Res. 41 D955-D961.

\* cited by examiner

Fig. 4A
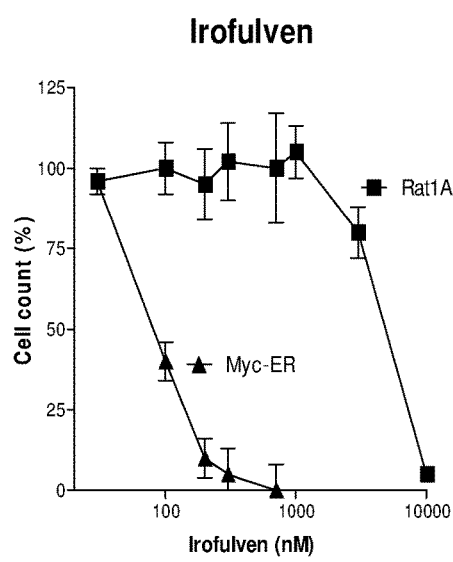
Fig. 4B
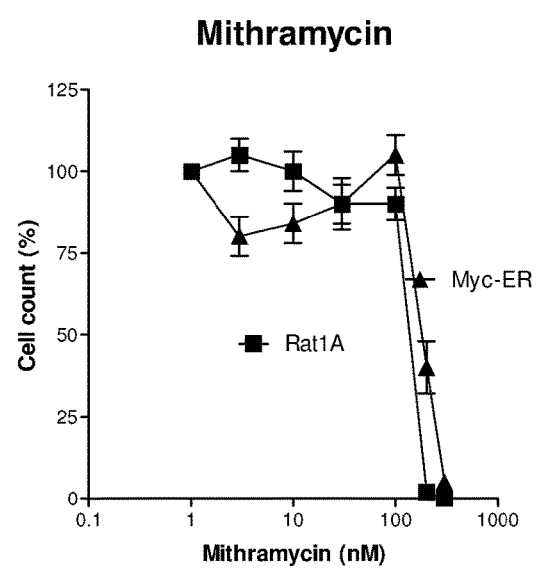
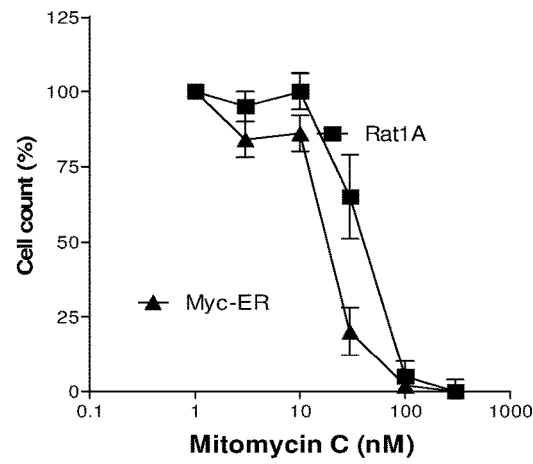
Fig. 4C
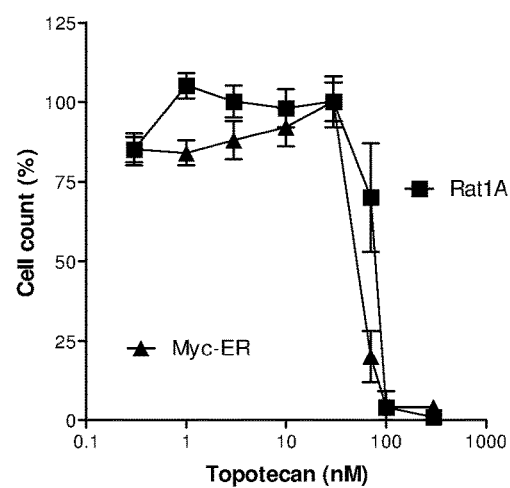
Fig. 4D

SEQUENCE LISTING

<160> NUMBER OF SEQ ID NOS: 926

<210> SEQ ID NO 1
<211> LENGTH: 1962
<212> TYPE: DNA
<213> ORGANISM: Homo sapiens

<400> SEQUENCE: 1

```
gctgttccag tcccgcccct gagctctgtc atggcgacgt ccagtgctcc agccggtgtg      60
aggacacgat atgctggggt ttttgtccgc acgccaaacg ggtttggagg accctcttcg     120
ccttcggaga gcagagtcaa cacggagagt tttgggactg gaattaaata aagacagaga     180
```

| | | |
|---|---|---|
| tgttgaaaga atccacggcg gtggaattaa cacccttgac attgaacctg ttgaagggag | 240 | |
| atacatgtta tcaggtggtt cagatggtgt gattgtactt tatgaccttg agaactccag | 300 | |
| cagacaatct tattacacat gtaaagcagt gtgttccatt ggcagagatc atcctgatgt | 360 | |
| tcacagatac agtgtggaga ctgtacagtg gtatcctcat gacactggca tgttcacatc | 420 | |
| aagctcattt gataaaactc tgaaagtatg ggatacaaat acattacaat tggtactaga | 480 | |
| ggacccaaag tacaactttg tgacttgaag tctggatcct gttctcacat tctacagggt | 540 | |
| cacagacaag aaatattagc agtttcctgg tctccacgtt atgactatat cttggcaaca | 600 | |
| gcaagtgctg acagtagagt aaaattatgg gatgtgagaa gagcatcagg atgtttgatt | 660 | |
| actcttgatc aacataatgg gaaaagtca caagctgttg aatcagcaaa cactgctcat | 720 | |
| aatgggaaag ttaatggctt atgttttaca agtgatggac ttcacctcct cactgttggt | 780 | |
| acagataatc gaatgaggct ctggaatagt tccaatggag aaaacacact tgtgaactat | 840 | |
| ggaaaagttt gtaataacag taaaaaagga ttgaaattca ctgtctcctg tggctgcagt | 900 | |
| tcagaatttg ttttttgtacc atatggtagc accattgctg tttatacagt ttactcagga | 960 | |
| gaacagataa ctatgcttaa gggacattat aaaactgttg actgctgtgt atttcagtca | 1020 | |
| aatttccagg aactttatag tggtagcaga gactgcaaca ttctggcttg ggttccatcc | 1080 | |
| ttatatgaac cagttcctga tgatgatgag actacaacaa aatcacaatt aaatccggcc | 1140 | |
| tttgaagatg cctggagcag cagtgatgaa gaaggatgaa tatcatcttt agtacctttt | 1200 | |
| tgtctctgct gaaacttttt aaatgagact gtgttttttt caactgtatg gtctattcct | 1260 | |
| gacagctaaa ttagccctaa atgtgggtaa tattttttcct catgttttaa aatgaggtta | 1320 | |
| atatttgcat aaaatcctaa aacagacttc tgtatagttt atttagtcaa aatgtgttcc | 1380 | |
| ttgatcccag atgttgtggc ctgggaaagc cctcattgct acagtacaag taacacaagt | 1440 | |
| cgttgtacct cagttgtgac cttcagcaga ttttatgaac tataagatgc agtctcagag | 1500 | |
| gatcagcaag tggaggccat cagtattgac tttctcttac ttgctgtact atcagcctgc | 1560 | |
| tcgtttccac ctttaagaat gattttgcca agaatgatta tatcaaaaat agtagttgaa | 1620 | |
| atggtaacat caaaattatt ttattctttc ttcttcatgt attcacattt ttcagtggtt | 1680 | |
| tcatttaatt aaccatgctt tatgttaaac attttggggc tcaatgtctc ctactatcca | 1740 | |
| aaatgtgcat cacaggaggc ttttaacttt gtgaaaatcc catgtttgct ttatttatt | 1800 | |
| ttaatgtcag aaggcagttt gcgctaatgc ttgaactctt tttctgtgaa actcattaag | 1860 | |
| gtatgaccaa atcctgcctc attaattcaa gcagaaaata tcctggcagg gaatctggct | 1920 | |
| taaacatgaa atgctgtaat aaaatttcta tgttattgtc tc | 1962 | |

<210> SEQ ID NO 2
<211> LENGTH: 396
<212> TYPE: PRT
<213> ORGANISM: Homo sapiens

<400> SEQUENCE: 2

Met Leu Gly Phe Leu Ser Ala Arg Gln Thr Gly Leu Glu Asp Pro Leu
1               5                   10                  15

Arg Leu Arg Arg Ala Glu Ser Thr Arg Arg Val Leu Gly Leu Glu Leu
            20                  25                  30

Asn Lys Asp Arg Asp Val Glu Arg Ile His Gly Gly Ile Asn Thr
        35                  40                  45

Leu Asp Ile Glu Pro Val Glu Gly Arg Tyr Met Leu Ser Gly Gly Ser
    50                  55                  60

```
Asp Gly Val Ile Val Leu Tyr Asp Leu Glu Asn Ser Ser Arg Gln Ser
65                  70                  75                  80

Tyr Tyr Thr Cys Lys Ala Val Cys Ser Ile Gly Arg Asp His Pro Asp
                85                  90                  95

Val His Arg Tyr Ser Val Glu Thr Val Gln Trp Tyr Pro His Asp Thr
                100                 105                 110

Gly Met Phe Thr Ser Ser Ser Phe Asp Lys Thr Leu Lys Val Trp Asp
                115                 120                 125

Thr Asn Thr Leu Gln Thr Ala Asp Val Phe Asn Phe Glu Glu Thr Val
130                 135                 140

Tyr Ser His His Met Ser Pro Val Ser Thr Lys His Cys Leu Val Ala
145                 150                 155                 160

Val Gly Thr Arg Gly Pro Lys Val Gln Leu Cys Asp Leu Lys Ser Gly
                165                 170                 175

Ser Cys Ser His Ile Leu Gln Gly His Arg Gln Glu Ile Leu Ala Val
                180                 185                 190

Ser Trp Ser Pro Arg Tyr Asp Tyr Ile Leu Ala Thr Ala Ser Ala Asp
                195                 200                 205

Ser Arg Val Lys Leu Trp Asp Val Arg Arg Ala Ser Gly Cys Leu Ile
210                 215                 220

Thr Leu Asp Gln His Asn Gly Lys Lys Ser Gln Ala Val Glu Ser Ala
225                 230                 235                 240

Asn Thr Ala His Asn Gly Lys Val Asn Gly Leu Cys Phe Thr Ser Asp
                245                 250                 255

Gly Leu His Leu Leu Thr Val Gly Thr Asp Asn Arg Met Arg Leu Trp
                260                 265                 270

Asn Ser Ser Asn Gly Glu Asn Thr Leu Val Asn Tyr Gly Lys Val Cys
                275                 280                 285

Asn Asn Ser Lys Lys Gly Leu Lys Phe Thr Val Ser Cys Gly Cys Ser
290                 295                 300

Ser Glu Phe Val Phe Val Pro Tyr Gly Ser Thr Ile Ala Val Tyr Thr
305                 310                 315                 320

Val Tyr Ser Gly Glu Gln Ile Thr Met Leu Lys Gly His Tyr Lys Thr
                325                 330                 335

Val Asp Cys Cys Val Phe Gln Ser Asn Phe Gln Glu Leu Tyr Ser Gly
                340                 345                 350

Ser Arg Asp Cys Asn Ile Leu Ala Trp Val Pro Ser Leu Tyr Glu Pro
                355                 360                 365

Val Pro Asp Asp Asp Glu Thr Thr Thr Lys Ser Gln Leu Asn Pro Ala
                370                 375                 380

Phe Glu Asp Ala Trp Ser Ser Ser Asp Glu Glu Gly
385                 390                 395

<210> SEQ ID NO 3
<211> LENGTH: 3590
<212> TYPE: DNA
<213> ORGANISM: Homo sapiens

<400> SEQUENCE: 3
gcgccacggg cctccccgca ccagcagaag tcggagtcgc tgttgggggc ggtgtctatg      60
gttgagctga gggcgcaggc gccacggccc gtcgagctgg gttccaaggc ggctggcggc     120
ggtagcgtct ctgtttcctt gtgggcgctc gcgcggccct gggtagtctg tagagaatgc     180
caaatgaggg aatcccccac tcaagtcaaa ctcaggagca agactgttta cagagtcaac     240
```

```
ctgtcagtaa taatgaagaa atggcaatca agcaagaaag tggtggtgat ggggaggtgg      300
aggagtacct ctcctttcgt tctgtgggtg acgggctgtc cacctctgct gtggggtgcg      360
catcagcagc tccgaggaga gggccagccc tgctgcacat cgaccgacat cagatccagg      420
cagtagagcc tagcgcccag gcccttgagc tgcagggttt gggtgtggac gtctatgacc      480
aggacgtgct ggaacaggga gtgcttcagc aggtggacaa tgccatccat gaggccagcc      540
gtgcctccca gctcgttgac gtggagaagg agtatcggtc ggtcctggat gacctcacgt      600
catgtacgac atccctaagg caaatcaata aaattattga acagcttagc cctcaagctg      660
ccaccagcag agacatcaac aggaaactag attctgtaaa acgacagaag tataataagg      720
aacaacagct aaaaaagatc actgcaaaac aaaagcatct ccaggccatc cttggaggag      780
cagaggtgaa aattgaacta gatcacgcca gtctggagga ggatgcagag ccggggccat      840
ccagtcttgg cagcatgctc atgcctgtcc aggagactgc ctgggaagag ctcatccgca      900
ctggccagat gacacctttt ggtacccaga tccctcagaa acaggagaaa agcccagaa       960 aaatcatgct taatgaagca tcaggcttcg aaaagtattt ggcagatcaa gcaaaactgt     1020
cttttgaaag gaagaagcaa ggttgtaata aagagcagc tagaaaagct ccagccccag      1080
tcacgcctcc agccccagtg caaaataaaa acaaaccaaa caagaaagcc agagttctgt     1140
ccaaaaaaga ggagcgtttg aaaaagcaca tcaagaaact ccagaagagg gctttgcagt     1200 tccagggaa agtgggattg ccaaaggcaa ggagaccttg ggagtcagac atgaggccag       1260
aggcagaggg agactctgag ggtgaagagt ctgagtattt ccccacagag gaggaggaag     1320
aggaggaaga tgacgaggtg gagggggcag aggcggacct gtctggagat ggtactgact     1380
atgagctgaa gcctctgccc aagggcggga acggcagaa gaaagtgcca gtgcaggaga      1440
ttgatgatga cttttttccca gttctgggg aagaagctga agctgcttct gtaggagaag     1500
gaggaggagg aggtcggaaa gtgggaagat accgagatga tggagatgaa gattattata     1560
agcagcggtt aagtcccaag atgcctcgaa cactaagttt acatgaaata actgaccttt     1620
tagagacaga tgacagcata gaagcaagtg ctatagtgat acaaccacct gaaaatgcta     1680
cagcacctgt ttctgatgag gaatcaggag atgaagaagg tggaacaata aataatctgc     1740
caggttcttt gttgcacaca gctgcgtatc ttattcaaga tggctctgat gctgagtctg     1800
actcagatga tccctcatac gcacctaaag atgactctcc tgatgaagtt ccatctacgt     1860
ttactgtgca gcaacctcca ccatcaagga ggaggaaaat gacaaaaatt ctttgcaaat     1920
ggaaaaaagc cgacctaact gtacaacccg tagcaggtag agttacagca ccaccaaacg     1980
atttcttcac cgtaatgaga actcccacag aaattcttga acttttcttt gatgacgagg     2040
tcattgaact cattgtcaag tactccaact tatatgcttg cagtaaaggt gtacatcttg     2100
gcttgactag ctctgaattc aaatgttttc tgggaattat ttttctgagt ggttatgtct     2160
cagttcctag aaggcgtatg ttttgggaac aaagaacaga tgtgcataat gtactggtta     2220
gtgctgccat gagacgtgac cggtttgaaa ctatattttc taatttgcat gttgctgaca     2280
atgcaaattt ggatccagtg gacaaatttt ccaaattgcg acctctcata agcaaactta     2340
atgagagatg catgaaattt gttccaaatg aaacatattt cagctttgat gaattcatgg     2400
ttccttattt tggtcgtcac gggtgcaaac aatttattcg gggaaagccc attcggtttg     2460
gctataagtt ttggtgtggt gccacctgtc tgggctacat tgctggtttt cagccgtatc     2520
agggtaaaaa cccaaatact aaacatgagg aatatggtgt cggtgcgtca cttgtccttc     2580
```

-continued

```
agtttagtga ggcacttaca gaggcacacc ctggacaata ccatttgta ttcaataact   2640
ttttcaccag tattgcactt cttgataagc tcagttcaat gggacatcag gcaacaggta   2700
cagtgagaaa ggatcacatt gacagagttc cactggaatc agatgtagct ttaaagaaaa   2760
aagaaagagg cacatttgat tatcgaattg atggcaaagg caatattgtc tgcagatgga   2820
atgataacag tgttgtcact gttgcctcat ctggtgctgg tatccatccc ctgtgtcttg   2880
tcagtcgtta ctcccagaaa ctgaaaaaga agatacaagt tcagcagcca aacatgatca   2940
aagtgtataa ccagttcatg ggaggcgtag acagagctga tgaaaacatt gataagtatc   3000
gggcatcaat ccgtggaaag aaatggtatt caagccctct tttgttctgt ttcgaactgg   3060
tcttacaaaa tgcttggcaa ttgcataaaa catatgatga gaaaccagtg gattttctgg   3120
agtttcgtcg acgtgtggta tgccattatc tggagaccca tggtcatcct ccagaacctg   3180
gccaaaaagg aagacctcag aagcgtaaca ttgactcacg ttatgatggc ataaatcatg   3240
tgatagtcaa acagggaaag caaacgcgat gcgctgaatg tcataagaac acaacttttc   3300
gatgtgaaaa atgtgatgtt gccttacatg tgaagtgttc cgttaatat cacactgaat    3360
agcaggtgtc accacctcct gagataagaa acatagtttt atacattatg tacagtgtag   3420
cagtggtttt gcctagtgtt ccaattttgg aacgtcacat aacaatggaa cataataaat   3480
ttttttttct cttcaaattt ttgttccttg aattttttcta ggtaacatat atgaatttca   3540
tgcaaaaatt caaaaaattg taacctcaga cataaatggg ttaaagatgt              3590
```

<210> SEQ ID NO 4
<211> LENGTH: 1493
<212> TYPE: PRT
<213> ORGANISM: Homo sapiens

<400> SEQUENCE: 4

```
Met Pro Asn Glu Gly Ile Pro His Ser Ser Gln Thr Gln Glu Gln Asp
1               5                   10                  15

Cys Leu Gln Ser Gln Pro Val Ser Asn Asn Glu Glu Met Ala Ile Lys
            20                  25                  30

Gln Glu Ser Gly Gly Asp Gly Glu Val Glu Glu Tyr Leu Ser Phe Arg
        35                  40                  45

Ser Val Gly Asp Gly Leu Ser Thr Ser Ala Val Gly Cys Ala Ser Ala
    50                  55                  60

Ala Pro Arg Arg Gly Pro Ala Leu Leu His Ile Asp Arg His Gln Ile
65                  70                  75                  80

Gln Ala Val Glu Pro Ser Ala Gln Ala Leu Glu Leu Gln Gly Leu Gly
                85                  90                  95

Val Asp Val Tyr Asp Gln Asp Val Leu Glu Gln Gly Val Leu Gln Gln
            100                 105                 110

Val Asp Asn Ala Ile His Glu Ala Ser Arg Ala Ser Gln Leu Val Asp
        115                 120                 125

Val Glu Lys Glu Tyr Arg Ser Val Leu Asp Asp Leu Thr Ser Cys Thr
    130                 135                 140

Thr Ser Leu Arg Gln Ile Asn Lys Ile Ile Glu Gln Leu Ser Pro Gln
145                 150                 155                 160

Ala Ala Thr Ser Arg Asp Ile Asn Arg Lys Leu Asp Ser Val Lys Arg
                165                 170                 175

Gln Lys Tyr Asn Lys Glu Gln Gln Leu Lys Lys Ile Thr Ala Lys Gln
            180                 185                 190

Lys His Leu Gln Ala Ile Leu Gly Gly Ala Glu Val Lys Ile Glu Leu
```

-continued

```
            195                 200                 205
Asp His Ala Ser Leu Glu Glu Asp Ala Glu Pro Gly Pro Ser Ser Leu
    210                 215                 220

Gly Ser Met Leu Met Pro Val Gln Glu Thr Ala Trp Glu Glu Leu Ile
225                 230                 235                 240

Arg Thr Gly Gln Met Thr Pro Phe Gly Thr Gln Ile Pro Gln Lys Gln
                245                 250                 255

Glu Lys Lys Pro Arg Lys Ile Met Leu Asn Glu Ala Ser Gly Phe Glu
                260                 265                 270

Lys Tyr Leu Ala Asp Gln Ala Lys Leu Ser Phe Glu Arg Lys Lys Gln
            275                 280                 285

Gly Cys Asn Lys Arg Ala Ala Arg Lys Ala Pro Ala Pro Val Thr Pro
    290                 295                 300

Pro Ala Pro Val Gln Asn Lys Asn Lys Pro Asn Lys Lys Ala Arg Val
305                 310                 315                 320

Leu Ser Lys Lys Glu Arg Leu Lys Lys His Ile Lys Lys Leu Gln
                325                 330                 335

Lys Arg Ala Leu Gln Phe Gln Gly Lys Val Gly Leu Pro Lys Ala Arg
            340                 345                 350

Arg Pro Trp Glu Ser Asp Met Arg Pro Glu Ala Glu Gly Asp Ser Glu
                355                 360                 365

Gly Glu Glu Ser Glu Tyr Phe Pro Thr Glu Glu Glu Glu Glu Glu Glu
370                 375                 380

Asp Asp Glu Val Glu Gly Ala Glu Ala Asp Leu Ser Gly Asp Gly Thr
385                 390                 395                 400

Asp Tyr Glu Leu Lys Pro Leu Pro Lys Gly Gly Lys Arg Gln Lys Lys
                405                 410                 415

Val Pro Val Gln Glu Ile Asp Asp Phe Phe Pro Ser Ser Gly Glu
                420                 425                 430

Glu Ala Glu Ala Ala Ser Val Gly Glu Gly Gly Gly Gly Arg Lys
            435                 440                 445

Val Gly Arg Tyr Arg Asp Asp Gly Asp Glu Asp Tyr Tyr Lys Gln Arg
    450                 455                 460

Leu Arg Arg Trp Asn Lys Leu Arg Leu Gln Asp Lys Glu Lys Arg Leu
465                 470                 475                 480

Lys Leu Glu Asp Asp Ser Glu Glu Ser Asp Ala Glu Phe Asp Glu Gly
                485                 490                 495

Phe Lys Val Pro Gly Phe Leu Phe Lys Lys Leu Phe Lys Tyr Gln Gln
                500                 505                 510

Thr Gly Val Arg Trp Leu Trp Glu Leu His Cys Gln Gln Ala Gly Gly
            515                 520                 525

Ile Leu Gly Asp Glu Met Gly Leu Gly Lys Thr Ile Gln Ile Ile Ala
    530                 535                 540

Phe Leu Ala Gly Leu Ser Tyr Ser Lys Ile Arg Thr Arg Gly Ser Asn
545                 550                 555                 560

Tyr Arg Phe Glu Gly Leu Gly Pro Thr Val Ile Val Cys Pro Thr Thr
                565                 570                 575

Val Met His Gln Trp Val Lys Glu Phe His Thr Trp Trp Pro Pro Phe
            580                 585                 590

Arg Val Ala Ile Leu His Glu Thr Gly Ser Tyr Thr His Lys Lys Glu
            595                 600                 605

Lys Leu Ile Arg Asp Val Ala His Cys His Gly Ile Leu Ile Thr Ser
            610                 615                 620
```

-continued

Tyr Ser Tyr Ile Arg Leu Met Gln Asp Asp Ile Ser Arg Tyr Asp Trp
625                 630                 635                 640

His Tyr Val Ile Leu Asp Glu Gly His Lys Ile Arg Asn Pro Asn Ala
            645                 650                 655

Ala Val Thr Leu Ala Cys Lys Gln Phe Arg Thr Pro His Arg Ile Ile
            660                 665                 670

Leu Ser Gly Ser Pro Met Gln Asn Asn Leu Arg Glu Leu Trp Ser Leu
            675                 680                 685

Phe Asp Phe Ile Phe Pro Gly Lys Leu Gly Thr Leu Pro Val Phe Met
690                 695                 700

Glu Gln Phe Ser Val Pro Ile Thr Met Gly Gly Tyr Ser Asn Ala Ser
705                 710                 715                 720

Pro Val Gln Val Lys Thr Ala Tyr Lys Cys Ala Cys Val Leu Arg Asp
            725                 730                 735

Thr Ile Asn Pro Tyr Leu Leu Arg Arg Met Lys Ser Asp Val Lys Met
            740                 745                 750

Ser Leu Ser Leu Pro Asp Lys Asn Glu Gln Val Leu Phe Cys Arg Leu
            755                 760                 765

Thr Asp Glu Gln His Lys Val Tyr Gln Asn Phe Val Asp Ser Lys Glu
770                 775                 780

Val Tyr Arg Ile Leu Asn Gly Glu Met Gln Ile Phe Ser Gly Leu Ile
785                 790                 795                 800

Ala Leu Arg Lys Ile Cys Asn His Pro Asp Leu Phe Ser Gly Pro
            805                 810                 815

Lys Asn Leu Lys Gly Leu Pro Asp Glu Leu Glu Glu Asp Gln Phe
            820                 825                 830

Gly Tyr Trp Lys Arg Ser Gly Lys Met Ile Val Val Glu Ser Leu Leu
            835                 840                 845

Lys Ile Trp His Lys Gly Gln Arg Val Leu Leu Phe Ser Gln Ser
850                 855                 860

Arg Gln Met Leu Asp Ile Leu Glu Val Phe Leu Arg Ala Gln Lys Tyr
865                 870                 875                 880

Thr Tyr Leu Lys Met Asp Gly Thr Thr Thr Ile Ala Ser Arg Gln Pro
            885                 890                 895

Leu Ile Thr Arg Tyr Asn Glu Asp Thr Ser Ile Phe Val Phe Leu Leu
            900                 905                 910

Thr Thr Arg Val Gly Gly Leu Gly Val Asn Leu Thr Gly Ala Asn Arg
            915                 920                 925

Val Val Ile Tyr Asp Pro Asp Trp Asn Pro Ser Thr Asp Thr Gln Ala
            930                 935                 940

Arg Glu Arg Ala Trp Arg Ile Gly Gln Lys Lys Gln Val Thr Val Tyr
945                 950                 955                 960

Arg Leu Leu Thr Ala Gly Thr Ile Glu Glu Lys Ile Tyr His Arg Gln
            965                 970                 975

Ile Phe Lys Gln Phe Leu Thr Asn Arg Val Leu Lys Asp Pro Lys Gln
            980                 985                 990

Arg Arg Phe Phe Lys Ser Asn Asp Leu Tyr Glu Leu Phe Thr Leu Thr
            995                 1000                1005

Ser Pro Asp Ala Ser Gln Ser Thr Glu Thr Ser Ala Ile Phe Ala
    1010                1015                1020

Gly Thr Gly Ser Asp Val Gln Thr Pro Lys Cys His Leu Lys Arg
    1025                1030                1035

```
Arg Ile Gln Pro Ala Phe Gly Ala Asp His Asp Val Pro Lys Arg
    1040                1045                1050

Lys Lys Phe Pro Ala Ser Asn Ile Ser Val Asn Asp Ala Thr Ser
    1055                1060                1065

Ser Glu Glu Lys Ser Glu Ala Lys Gly Ala Glu Val Asn Ala Val
    1070                1075                1080

Thr Ser Asn Arg Ser Asp Pro Leu Lys Asp Pro His Met Ser
    1085                1090                1095

Ser Asn Val Thr Ser Asn Asp Arg Leu Gly Glu Glu Thr Asn Ala
    1100                1105                1110

Val Ser Gly Pro Glu Glu Leu Ser Val Ile Ser Gly Asn Gly Glu
    1115                1120                1125

Cys Ser Asn Ser Ser Gly Thr Gly Lys Thr Ser Met Pro Ser Gly
    1130                1135                1140

Asp Glu Ser Ile Asp Glu Lys Leu Gly Leu Ser Tyr Lys Arg Glu
    1145                1150                1155

Arg Pro Ser Gln Ala Gln Thr Glu Ala Phe Trp Glu Asn Lys Gln
    1160                1165                1170

Met Glu Asn Asn Phe Tyr Lys His Lys Ser Lys Thr Lys His His
    1175                1180                1185

Ser Val Ala Glu Glu Glu Thr Leu Glu Lys His Leu Arg Pro Lys
    1190                1195                1200

Gln Lys Pro Lys Asn Ser Lys His Cys Arg Asp Ala Lys Phe Glu
    1205                1210                1215

Gly Thr Arg Ile Pro His Leu Val Lys Lys Arg Arg Tyr Gln Lys
    1220                1225                1230

Gln Asp Ser Glu Asn Lys Ser Glu Ala Lys Glu Gln Ser Asn Asp
    1235                1240                1245

Asp Tyr Val Leu Glu Lys Leu Phe Lys Lys Ser Val Gly Val His
    1250                1255                1260

Ser Val Met Lys His Asp Ala Ile Met Asp Gly Ala Ser Pro Asp
    1265                1270                1275

Tyr Val Leu Val Glu Ala Glu Ala Asn Arg Val Ala Gln Asp Ala
    1280                1285                1290

Leu Lys Ala Leu Arg Leu Ser Arg Gln Arg Cys Leu Gly Ala Val
    1295                1300                1305

Ser Gly Val Pro Thr Trp Thr Gly His Arg Gly Ile Ser Gly Ala
    1310                1315                1320

Pro Ala Gly Lys Lys Ser Arg Phe Gly Lys Arg Asn Ser Asn
    1325                1330                1335

Phe Ser Val Gln His Pro Ser Ser Thr Ser Pro Thr Glu Lys Cys
    1340                1345                1350

Gln Asp Gly Ile Met Lys Lys Glu Gly Lys Asp Asn Val Pro Glu
    1355                1360                1365

His Phe Ser Gly Arg Ala Glu Asp Ala Asp Ser Ser Ser Gly Pro
    1370                1375                1380

Leu Ala Ser Ser Ser Leu Leu Ala Lys Met Arg Ala Arg Asn His
    1385                1390                1395

Leu Ile Leu Pro Glu Arg Leu Glu Ser Glu Ser Gly His Leu Gln
    1400                1405                1410

Glu Ala Ser Ala Leu Leu Pro Thr Thr Glu His Asp Asp Leu Leu
    1415                1420                1425

Val Glu Met Arg Asn Phe Ile Ala Phe Gln Ala His Thr Asp Gly
```

| | | | | | | | | | | |
|---|---|---|---|---|---|---|---|---|---|---|
| | 1430 | | | | 1435 | | | | 1440 | |
| Gln | Ala | Ser | Thr | Arg | Glu | Ile | Leu | Gln | Glu | Phe | Glu | Ser | Lys | Leu |
| | | | 1445 | | | | | 1450 | | | | | 1455 | |
| Ser | Ala | Ser | Gln | Ser | Cys | Val | Phe | Arg | Glu | Leu | Leu | Arg | Asn | Leu |
| | | | 1460 | | | | | 1465 | | | | | 1470 | |
| Cys | Thr | Phe | His | Arg | Thr | Ser | Gly | Gly | Glu | Gly | Ile | Trp | Lys | Leu |
| | | | 1475 | | | | | 1480 | | | | | 1485 | |
| Lys | Pro | Glu | Tyr | Cys | | | | | | | | | | |
| | | | 1490 | | | | | | | | | | | |

<210> SEQ ID NO 5
<211> LENGTH: 3515
<212> TYPE: DNA
<213> ORGANISM: Homo sapiens

<400> SEQUENCE: 5

```
ctccttccgc gtggtccctc ccctcaggc cgcggtcgcg attacgctct ctacggcctg      60
cgaccgcagg gccgttgcgg gctggagaca cggcgccgac tggaaccgga ggagctctag     120
gccaaatggt tgggccagcc aggatcccag daccettege cgctegagac cggagagagg     180
aaacgaaaca gcgggaacc cgtggggag ggagggaact agcggaaggt gtcatggcgg       240
ccgcgctctt gagtcacgtg cccagggccc gccttgctac ttccggtcac gtgccctcag    300
actcctcgca gccagcgatg gaggcagac cccctagtaa cagaggcggt ggctactgct    360
gcggccactg ggtttcggcc tcttcccagc agcggctcta agaagcgcag cggaactcga    420
ccggatccaa cccagttagt tacttcctgt ctagagttgt agcttccacc tgagttctcc    480
tgggaagaag tgtttgccac tcaaggaata cactcaagaa aaacctggaa atcacagaag    540
gcattgtaag atagctacag tgattctgtt aaacctcctg aaattggtcc ttgaacaatt    600
aagaggtgct acagatgacc aggaaaattt accaggcaaa ttagctgtga acaattgac     660
catttgtgcc aatgttcgc accttctagc caccatggca acctcatctg aagaagtttt    720
gctgattgta agaaagtgc gtcaaaagaa gcaggatgga gctctgtacc tcatggcaga    780
aagaattgct tgggcacctg aaggcaaaga tagatttaca atcagccata tgtatgcaga   840
tattaaatgc cagaaaatta gtccagaagg aaaagctaaa attcagcttc agctggtcct    900
acatgcaggg gacacaacta acttccattt tccaatgaa agcacagcag tgaaagagcg    960
agatgcagta aaagaccttc ttcagcagct gctgcccaaa ttcaagagga agcaaataa   1020
agaactggaa gagaagaaca gaatgctgca gagatcct gttttgttc agctttataa   1080
agaccttgtt gtgagtcaag tgatcagtgc tgaggaattc tgggccaatc gtttaaatgt    1140
gaatgcaaca gatagttctt ccacatccaa tcataagcag gatgttggca tttctgctgc   1200
atttctggct gatgtccggc cccaaactga tggctgtaac ggtctaagat ataattaac    1260
ttctgatatc attgagtcca tatttaggac ctatccagca gtaaaaatga aatatgcaga   1320
aaatgttccc cacaacatga cagagaagga attctggaca cgttttttcc agtcccatta   1380
ttttcacagg gatcggctga atacagggtc aaaggatctc tttgcagaat gtgccaaaat   1440
agatgaaaaa ggcctaaaaa caatggtttc attaggagtg aaaaacccac tactagattt   1500
aacagctttg gaagataaac cattagatga gggctatggc atttcctctg tgccatctgc   1560
ttccaattct aaatccataa aagagaatag taatgctgcc atcatcaaga gatttaacca   1620
tcacagtgcc atggtcctgg cagctggact cagaaaacaa gaagcacaaa atgaacaaac   1680
tagtgagccc agcaacatgg atggaaattc cggagatgca gactgctttc agccagcagt   1740
```

```
caaaagggcg aaattacaag agtccattga atatgaagac ttggggaaaa ataattctgt    1800
aaaaacgatt gcactaaacc tcaagaagtc agataggtat tatcatggtc caactccaat    1860
ccagtcacta cagtatgcaa caagtcagga cattattaat tcttttcaaa gtattagaca    1920
agaaatggaa gcttatacac ccaagttaac tcaggttctc tcaagtagtg ctgccagtag    1980
taccatcaca gcactgtcac ctggagggc  acttatgcag ggaggaacac agcaagccat    2040
aaaccagatg gtgccaaatg atattcaatc tgaattgaaa cacttatatg tagctgttgg    2100
agaacttcta cgacatttct ggtcctgctt tcctgttaat acgccattcc tagaagaaaa    2160
ggtagtgaaa atgaaaagta atttggaacg attccaagtt acgaagctct gtccattcca    2220
agaaaagatt cggagacagt atttaagcac aaatttggta agtcacatag aagagatgct    2280
ccagacagcc tacaacaagc tccacacatg gcagtcacgg cgtctgatga agaaaacgtg    2340
aggtggccat gatgcttaca ggttttgtga gattgagaga actatgacct gcagcaactc    2400
tggaaacctg gcctgacaga caagcagatg acctcacagg agtgataaga acatctgct    2460 ccacgccaac tcccagagct gatgctattg tacttgcaca ttggagactg aaaggaaaga    2520
agggactaaa tgctggggag gtaaattaag acagaaccaa atgagctaag ttgcaaatat    2580
atatatatac acacacacac atatatgtac atgtgtatgt acatatatat tttaaaagac    2640
tgtttactgc agttgctcag gaactgcttt tgattcacat taagctgctt tcagaaatta    2700
aaaaaacact ttttaagggg tgcattgata aaatctgagg ttttttggtt gtcgtttttt    2760
tctgtgtaca tttttttcct aagtttatgg cacagggtag accttaagta ttcctcctcc    2820
atccttcatt cttcacccct cattggatcc tcaagtttta atgaattcca attatacctt    2880
acatcagcaa gttaaaaaaa gtactttaaa ataaagcaaa gggagactgt tgctcaacca    2940
tcaggaaaca gttgtcagaa gacatcattg gttctgtgtt tcctacggaa ataagaaacg    3000
ataaatattg cactgaatgt ttgtggtttg gagtccctga ataataaaga gggaatatat    3060
ttgcagaaag tcgcataggg tttttaatg  cagaattttg tcagaagaca atggcgctgc    3120
atgtttttct ttgagtgcaa atgtacattg ctaagatttt tttaagatgg catgtgcttt    3180
gaaaagaaga tattgcattt ttaagagttt aaaaatctta tgagtgagaa atattaaaaa    3240
aatcttattt tcacctcttt agaagaaata aaagatgttt ctcctatctc cttttctcta    3300
gtatttgact gttactgtcc ttggcgaatc gataatcatt gcatagtgac tgaaaagcct    3360
aagtgcaaaa aaaaaaaaaa aagatgttct tgtttctgaa cttcgtgcca tattttgttc    3420
ctgatgggat caacttaatg tttaagactt tagatgtctt gtattaaaaa ttacacaaaa    3480
aaagtaaaac tttttatact tacccttta actct                                3515
```

<210> SEQ ID NO 6
<211> LENGTH: 548
<212> TYPE: PRT
<213> ORGANISM: Homo sapiens

<400> SEQUENCE: 6

Met Ala Thr Ser Ser Glu Glu Val Leu Leu Ile Val Lys Lys Val Arg
1               5                   10                  15

Gln Lys Lys Gln Asp Gly Ala Leu Tyr Leu Met Ala Glu Arg Ile Ala
            20                  25                  30

Trp Ala Pro Glu Gly Lys Asp Arg Phe Thr Ile Ser His Met Tyr Ala
        35                  40                  45

Asp Ile Lys Cys Gln Lys Ile Ser Pro Glu Gly Lys Ala Lys Ile Gln

```
               50                  55                  60
Leu Gln Leu Val Leu His Ala Gly Asp Thr Thr Asn Phe His Phe Ser
 65                  70                  75                  80

Asn Glu Ser Thr Ala Val Lys Glu Arg Asp Ala Val Lys Asp Leu Leu
                 85                  90                  95

Gln Gln Leu Leu Pro Lys Phe Lys Arg Lys Ala Asn Lys Glu Leu Glu
                100                 105                 110

Glu Lys Asn Arg Met Leu Gln Glu Asp Pro Val Leu Phe Gln Leu Tyr
                115                 120                 125

Lys Asp Leu Val Val Ser Gln Val Ile Ser Ala Glu Glu Phe Trp Ala
                130                 135                 140

Asn Arg Leu Asn Val Asn Ala Thr Asp Ser Ser Ser Thr Ser Asn His
145                 150                 155                 160

Lys Gln Asp Val Gly Ile Ser Ala Ala Phe Leu Ala Asp Val Arg Pro
                165                 170                 175

Gln Thr Asp Gly Cys Asn Gly Leu Arg Tyr Asn Leu Thr Ser Asp Ile
                180                 185                 190

Ile Glu Ser Ile Phe Arg Thr Tyr Pro Ala Val Lys Met Lys Tyr Ala
                195                 200                 205

Glu Asn Val Pro His Asn Met Thr Glu Lys Glu Phe Trp Thr Arg Phe
                210                 215                 220

Phe Gln Ser His Tyr Phe His Arg Asp Arg Leu Asn Thr Gly Ser Lys
225                 230                 235                 240

Asp Leu Phe Ala Glu Cys Ala Lys Ile Asp Glu Lys Gly Leu Lys Thr
                245                 250                 255

Met Val Ser Leu Gly Val Lys Asn Pro Leu Leu Asp Leu Thr Ala Leu
                260                 265                 270

Glu Asp Lys Pro Leu Asp Glu Gly Tyr Gly Ile Ser Ser Val Pro Ser
                275                 280                 285

Ala Ser Asn Ser Lys Ser Ile Lys Glu Asn Ser Asn Ala Ala Ile Ile
                290                 295                 300

Lys Arg Phe Asn His His Ser Ala Met Val Leu Ala Ala Gly Leu Arg
305                 310                 315                 320

Lys Gln Glu Ala Gln Asn Glu Gln Thr Ser Glu Pro Ser Asn Met Asp
                325                 330                 335

Gly Asn Ser Gly Asp Ala Asp Cys Phe Gln Pro Ala Val Lys Arg Ala
                340                 345                 350

Lys Leu Gln Glu Ser Ile Glu Tyr Glu Asp Leu Gly Lys Asn Asn Ser
                355                 360                 365

Val Lys Thr Ile Ala Leu Asn Leu Lys Lys Ser Asp Arg Tyr Tyr His
                370                 375                 380

Gly Pro Thr Pro Ile Gln Ser Leu Gln Tyr Ala Thr Ser Gln Asp Ile
385                 390                 395                 400

Ile Asn Ser Phe Gln Ser Ile Arg Gln Glu Met Glu Ala Tyr Thr Pro
                405                 410                 415

Lys Leu Thr Gln Val Leu Ser Ser Ala Ala Ser Ser Thr Ile Thr
                420                 425                 430

Ala Leu Ser Pro Gly Gly Ala Leu Met Gln Gly Thr Gln Gln Ala
                435                 440                 445

Ile Asn Gln Met Val Pro Asn Asp Ile Gln Ser Glu Leu Lys His Leu
                450                 455                 460

Tyr Val Ala Val Gly Glu Leu Leu Arg His Phe Trp Ser Cys Phe Pro
465                 470                 475                 480
```

```
Val Asn Thr Pro Phe Leu Glu Glu Lys Val Val Lys Met Lys Ser Asn
            485                 490                 495
Leu Glu Arg Phe Gln Val Thr Lys Leu Cys Pro Phe Gln Glu Lys Ile
            500                 505                 510
Arg Arg Gln Tyr Leu Ser Thr Asn Leu Val Ser His Ile Glu Glu Met
            515                 520                 525
Leu Gln Thr Ala Tyr Asn Lys Leu His Thr Trp Gln Ser Arg Arg Leu
            530                 535                 540
Met Lys Lys Thr
545

<210> SEQ ID NO 7
<211> LENGTH: 1951
<212> TYPE: DNA
<213> ORGANISM: Homo sapiens

<400> SEQUENCE: 7
```

| | | | | | |
|---|---|---|---|---|---|
| ccttctagcg | gcgccggtga | gtccgcgtgt | ggaagtctgt | gaggcgcaga | ggtggggcag | 60 |
| gccgtctggc | tagctaggcg | gctgggagcg | ttttcgtggc | ggggaacgga | ggttgaattg | 120 |
| ccctgcctgg | gctcataggg | aaggaggatg | tgaaggagct | tgtgaaggca | gaggaagatt | 180 |
| attgaataat | aaaatacagt | tttgaaaaaa | atggatgaag | aacctgaaag | aactaagcga | 240 |
| tgggaaggag | gctatgaaag | aacatgggag | attcttaaag | aagatgaatc | tggatcactt | 300 |
| aaagctacaa | tagaagacat | tctattcaag | gcaaagagaa | aaagagtatt | tgagcaccat | 360 |
| ggacaagttc | gacttggaat | gatgcgccac | ctttatgtgg | tagtagatgg | atcaagaaca | 420 |
| atggaagacc | aagatttaaa | gcctaataga | ctgacgtgta | ctttaaagtt | gttggaatac | 480 |
| tttgtagagg | aatattttga | tcaaaatcct | attagtcaga | ttggaataat | tgtaactaag | 540 |
| agtaaaagag | ctgaaaaatt | gactgaactt | tcaggaaacc | caagaaaaca | tataacgtct | 600 |
| ttgaagaaag | ctgtggatat | gacctgccat | ggagagccat | ctctttataa | ttccctaagc | 660 |
| atagctatgc | agactctaaa | acacatgcct | ggacatacaa | gtcgagaagt | actaatcatc | 720 |
| tttagcagcc | ttacaacttg | cgatccatct | aatatttatg | atctaatcaa | gaccctaaag | 780 |
| gcagctaaaa | ttagagtatc | tgttattgga | ttgtctgcag | aagttcgcgt | ttgcactgta | 840 |
| cttgctcgtg | aaactggtgg | cacgtaccat | gttattttag | atgaaagcca | ttacaaagag | 900 |
| ttgctcacac | atcatgttag | tcctcctcct | gctagctcaa | gttctgaatg | ctcacttatt | 960 |
| cgtatgggat | ttcctcagca | caccattgct | tctttatctg | accaggatgc | aaaaccctct | 1020 |
| ttcagcatgg | cgcatttgga | tggcaatact | gagccagggc | ttacattagg | aggctatttc | 1080 |
| tgcccacagt | gtcgggcaaa | gtactgtgag | ctacctgttg | agtgtaaaat | ctgtggtctt | 1140 |
| actttggtgt | ctgctcccca | cttggcacgg | tcttaccatc | atttgtttcc | tttggatgct | 1200 |
| tttcaagaaa | ttcccctaga | agaatataat | ggagaaagat | tttgttatgg | atgtcagggg | 1260 |
| gaattgaaag | accaacatgt | ttatgtttgt | gctgtgtgcc | aaaatgtttt | ctgtgtggac | 1320 |
| tgtgatgttt | ttgttcatga | ttctctacac | tgttgccctg | gctgtattca | taagattcca | 1380 |
| gctccttcag | gtgtttgatt | ccagcatgta | gtatacattg | tatgtgttaa | aaagaaattt | 1440 |
| gcaactgtga | ataaaaggac | ttctttagaa | gaagcttcat | ttaaaacatg | aaaggataat | 1500 |
| ctgacttaag | aaacttttttg | ctaagaaaag | gtaatatttt | attaaatttt | aaatttgtgt | 1560 |
| tgtcacagaa | atacctgaaa | ttcagtagta | cttcattcaa | ttaattttgt | tttctattat | 1620 |
| tttgagttat | actgttttca | aagtcattat | gcagtatgta | taaacttata | agaattaaat | 1680 |

-continued

```
tgatgtgata attttatgtt tttataatta aatatagaat ctttatgatt tatgttaatt    1740
cattaattta gtgtaagaag aaagttaagt ctgaatgtaa attcagtgta agatgaaaat    1800
ttatcaatac ttatgaaatt aggctgggcg ctgtggctca cacctgtaat cccaacactt    1860
tgggaggctg aggtgggcag atcacctgag gtcaggagtt cgagaccagc ctggccaaca    1920
tggtgaaacc ccgtcactac taaaaataca a                                   1951
```

<210> SEQ ID NO 8
<211> LENGTH: 395
<212> TYPE: PRT
<213> ORGANISM: Homo sapiens

<400> SEQUENCE: 8

```
Met Asp Glu Glu Pro Glu Arg Thr Lys Arg Trp Glu Gly Gly Tyr Glu
1               5                   10                  15

Arg Thr Trp Glu Ile Leu Lys Glu Asp Glu Ser Gly Ser Leu Lys Ala
            20                  25                  30

Thr Ile Glu Asp Ile Leu Phe Lys Ala Lys Arg Lys Arg Val Phe Glu
        35                  40                  45

His His Gly Gln Val Arg Leu Gly Met Met Arg His Leu Tyr Val Val
    50                  55                  60

Val Asp Gly Ser Arg Thr Met Glu Asp Gln Asp Leu Lys Pro Asn Arg
65                  70                  75                  80

Leu Thr Cys Thr Leu Lys Leu Leu Glu Tyr Phe Val Glu Glu Tyr Phe
                85                  90                  95

Asp Gln Asn Pro Ile Ser Gln Ile Gly Ile Ile Val Thr Lys Ser Lys
            100                 105                 110

Arg Ala Glu Lys Leu Thr Glu Leu Ser Gly Asn Pro Arg Lys His Ile
        115                 120                 125

Thr Ser Leu Lys Lys Ala Val Asp Met Thr Cys His Gly Glu Pro Ser
    130                 135                 140

Leu Tyr Asn Ser Leu Ser Ile Ala Met Gln Thr Leu Lys His Met Pro
145                 150                 155                 160

Gly His Thr Ser Arg Glu Val Leu Ile Ile Phe Ser Ser Leu Thr Thr
                165                 170                 175

Cys Asp Pro Ser Asn Ile Tyr Asp Leu Ile Lys Thr Leu Lys Ala Ala
            180                 185                 190

Lys Ile Arg Val Ser Val Ile Gly Leu Ser Ala Glu Val Arg Val Cys
        195                 200                 205

Thr Val Leu Ala Arg Glu Thr Gly Gly Thr Tyr His Val Ile Leu Asp
    210                 215                 220

Glu Ser His Tyr Lys Glu Leu Leu Thr His His Val Ser Pro Pro
225                 230                 235                 240

Ala Ser Ser Ser Glu Cys Ser Leu Ile Arg Met Gly Phe Pro Gln
                245                 250                 255

His Thr Ile Ala Ser Leu Ser Asp Gln Asp Ala Lys Pro Ser Phe Ser
            260                 265                 270

Met Ala His Leu Asp Gly Asn Thr Glu Pro Gly Leu Thr Leu Gly Gly
        275                 280                 285

Tyr Phe Cys Pro Gln Cys Arg Ala Lys Tyr Cys Glu Leu Pro Val Glu
    290                 295                 300

Cys Lys Ile Cys Gly Leu Thr Leu Val Ser Ala Pro His Leu Ala Arg
305                 310                 315                 320
```

```
Ser Tyr His His Leu Phe Pro Leu Asp Ala Phe Gln Glu Ile Pro Leu
                325                 330                 335

Glu Glu Tyr Asn Gly Glu Arg Phe Cys Tyr Gly Cys Gln Gly Glu Leu
            340                 345                 350

Lys Asp Gln His Val Tyr Val Cys Ala Val Cys Gln Asn Val Phe Cys
        355                 360                 365

Val Asp Cys Asp Val Phe Val His Asp Ser Leu His Cys Cys Pro Gly
    370                 375                 380

Cys Ile His Lys Ile Pro Ala Pro Ser Gly Val
385                 390                 395

<210> SEQ ID NO 9
<211> LENGTH: 3434
<212> TYPE: DNA
<213> ORGANISM: Homo sapiens

<400> SEQUENCE: 9
```

| | | | | | |
|---|---|---|---|---|---|
| gggggctggc | acgagtcaca | gcacctcgtg | cgtcacttgg | cggcgccgga | cgttgggctg | 60 |
| cgcaggattt | gagacgctcc | cctgaccacc | acttgctctg | cgctgaggtg | ctgggacagc | 120 |
| catggtttca | gacgaagatg | aattgaatct | tctggttatt | gtagttgatg | ccaacccaat | 180 |
| ttggtgggga | aagcaagcat | taaaggaatc | tcagttcact | ttatccaaat | gcatagatgc | 240 |
| cgtgatggtg | ctgggaaatt | cgcatttatt | catgaatcgt | tccaacaaac | ttgctgtgat | 300 |
| agcaagtcac | attcaagaaa | gccgattctt | atatcctgga | agaatggca | gacttggaga | 360 |
| cttcttcgga | gaccctggca | accctcctga | atttaatccc | tctgggagta | agatggaaa | 420 |
| atacgaactt | ttaacctcag | caaatgaagt | tattgttgaa | gagattaaag | atctaatgac | 480 |
| caaaagtgac | ataaagggtc | aacatacaga | aactttgctg | gcaggatccc | tggccaaagc | 540 |
| cctttgctac | attcatagaa | tgaacaagga | agttaaagac | aatcaggaaa | tgaaatcaag | 600 |
| gatattggtg | attaaggctg | cagaagacag | tgcgttgcag | tatatgaact | tcatgaatgt | 660 |
| catctttgca | gcacagaaac | agaatatttt | gattgatgcc | tgtgttttag | actccgactc | 720 |
| agggctcctc | caacaggctt | gtgacatcac | gggaggactg | tacctgaagg | tgcctcagat | 780 |
| gccttctctt | ctgcagtatt | tgctgtgggt | gtttcttccc | gatcaagatc | agagatctca | 840 |
| gttaatcctc | ccaccccag | ttcatgttga | ctacagggct | gcttgcttct | gtcatcgaaa | 900 |
| tctcattgaa | attggttatg | tctgttctgt | gtgtttgtca | atattctgca | atttcagccc | 960 |
| catttgtact | acgtgcgaga | cagccttta a | aatttctctg | cctccagtgc | tgaaagccaa | 1020 |
| gaaaagaaa | ctgaaagtgt | ctgcctgagg | ataaaatatt | ttccccatct | tttagagctg | 1080 |
| ttaatagaaa | ttatatagca | gattctttgt | tgggaagact | gaaaaaaata | aagataggta | 1140 |
| taggataatt | tttaatatgg | tgaccttaca | gaaaatattt | cccaaacatc | cttttcatcc | 1200 |
| tgtgcttctg | gaggactgat | ttgtttgagg | gaatcattct | atgcattata | tcctaaaata | 1260 |
| ttctatgact | ggtttctgtc | catgtttgtg | gctttcattt | ttttaatggg | atgactatta | 1320 |
| gtcaaagtca | gcttgtcatg | actcatcata | ggctttctaa | cctactccct | gaatccgggt | 1380 |
| cctcattgtg | aaatgcatgc | catacgaaat | ttgaacgtag | ctttggaaaa | agggactatt | 1440 |
| tgtggagtaa | tggcattaat | caacatagaa | catcttattt | gaatcaacag | ttaacttcag | 1500 |
| tagtcatgtg | aataaaattc | ttattgtcta | aattgagaca | gcctcagata | tttgcagata | 1560 |
| tttactttt | gtctgatatc | agtacatatt | tggacaaagt | catctaaata | atagtttgtc | 1620 |
| accaaataac | tacaaaatct | catttttaaat | gagtaaggag | aacgtgtaca | gaagcaaatt | 1680 |

```
ttcttcaaaa tagttgtggg aagagcttat atgtgaaagc ttatgactgg ttttgaggga    1740
gaacttactg gagaaaatgg actctatgtt aagtatggtt ttcagataga attctttcct    1800
tttttaatga ggaaaaaaaa tccacattaa tattgaaact gcacctgtaa tcccagcact    1860 tgggaggct gaggacagag gattgcttga gcccaggagt tcgagagcag cctgggcagc     1920
aaagtgagac cccatctcta ctaaaaattt aaatgtattt attaaaactg ttctctagaa    1980
gctttggact gaatcccaaa agtgtttata agttcaaaag caaagtatt tgtaatttca     2040 acaacaaaaa atgtatttct ttatgtaatc ttgaaattat taaaagtcct tttagcttct    2100
agcacatatt tgtacaaaga gtttaaggaa tggtggctgg tttggtttgt tttttaaaaa    2160
tgtttactga cgaggccggg cgtggtggct caccctgca atcccagcac tttgggaggc     2220
cgaggcaggc agatcacaag gtcaggagtt caagatcagc ctggccagta tggtgaaacc    2280
ctgtctctac taaaaataga aaattagcc atgcgaagta gcaggtgcct gtagttccag     2340
ctactcggga ggctgaggca agagaattgc ttgaatccag gaggcagagg ttgcagtgag    2400
ccaagatagc gcctctgtac tccagcctgg gtgacagage gagactctgt atcaaaaaaa    2460
aaaaagatcg ggcacgttgg ctcacgcctg taatcccagc actttgggag gccaaggtgg    2520
gtggatcacg aggtcaggag tgatcaggct gggtttctgt tttgttttgt tttgtgagac    2580
agagtctcgc tctgttgccc aggctggggt gcagtggtgc aagctcggct ctctgcaagc    2640
tctgtctcct gggttcacgc cattctcctg cctcagcctc ccaagtagct gggattacta    2700
ctctactgaa cccatgaggc agaaatttga gaccatcctg cccaacgtgg tgaaaacatg    2760
gtgaaaccct gtctctacta aaaatacaaa aattagctgg gcgtggtggc aggtgcctgt    2820
aatcccagct actcaggaga ctgaggcagg agaattgctt gaacccagga ggtggaggtt    2880
gcagtgagcc aagatcaaga ttgcgccatt gcactccagc ctgggcgaca gaacaaaac    2940 tctgtctcaa aaaaaaaaa aaaaaaaag tctgtactga taaaacccat tgtgtacaaa      3000
actttgtatg taaggaagat tttaattttc tctttataca agctgagtca tatttaaata   3060
atttgatgtt ggcttagata atttcagata gattttatat tctggatttg tgttttgtt    3120 aacaaatata caaagacttt ggtgatcact ttgcaaatat ttgttaatcc ttgagtttga   3180
gaacctgtct tttaaaaata atattttgta tactaattaa gtgtaatgga aatcacaatt   3240
ttaagtctag gaaataaagt attatatata ctttcaaaca agctagcaag gcttttatta   3300
ttactttttt atttgaaata tcttatatat ttggttagtt ctgtttaact tgtttttaac   3360
tgttgccctt atgagttatt ttatataaat ttttacaata aataatttg attttcaaaa    3420 aaaaaaaaaa aaaa                                                      3434
```

<210> SEQ ID NO 10
<211> LENGTH: 308
<212> TYPE: PRT
<213> ORGANISM: Homo sapiens

<400> SEQUENCE: 10

```
Met Val Ser Asp Glu Asp Glu Leu Asn Leu Leu Val Ile Val Val Asp
1               5                   10                  15

Ala Asn Pro Ile Trp Trp Gly Lys Gln Ala Leu Lys Glu Ser Gln Phe
            20                  25                  30

Thr Leu Ser Lys Cys Ile Asp Ala Val Met Val Leu Gly Asn Ser His
        35                  40                  45

Leu Phe Met Asn Arg Ser Asn Lys Leu Ala Val Ile Ala Ser His Ile
    50                  55                  60
```

```
Gln Glu Ser Arg Phe Leu Tyr Pro Gly Lys Asn Gly Arg Leu Gly Asp
 65                  70                  75                  80

Phe Phe Gly Asp Pro Gly Asn Pro Pro Glu Phe Asn Pro Ser Gly Ser
                 85                  90                  95

Lys Asp Gly Lys Tyr Glu Leu Leu Thr Ser Ala Asn Glu Val Ile Val
            100                 105                 110

Glu Glu Ile Lys Asp Leu Met Thr Lys Ser Asp Ile Lys Gly Gln His
        115                 120                 125

Thr Glu Thr Leu Leu Ala Gly Ser Leu Ala Lys Ala Leu Cys Tyr Ile
130                 135                 140

His Arg Met Asn Lys Glu Val Lys Asp Asn Gln Glu Met Lys Ser Arg
145                 150                 155                 160

Ile Leu Val Ile Lys Ala Ala Glu Asp Ser Ala Leu Gln Tyr Met Asn
                165                 170                 175

Phe Met Asn Val Ile Phe Ala Ala Gln Lys Gln Asn Ile Leu Ile Asp
            180                 185                 190

Ala Cys Val Leu Asp Ser Asp Ser Gly Leu Leu Gln Gln Ala Cys Asp
        195                 200                 205

Ile Thr Gly Gly Leu Tyr Leu Lys Val Pro Gln Met Pro Ser Leu Leu
    210                 215                 220

Gln Tyr Leu Leu Trp Val Phe Leu Pro Asp Gln Asp Gln Arg Ser Gln
225                 230                 235                 240

Leu Ile Leu Pro Pro Pro Val His Val Asp Tyr Arg Ala Ala Cys Phe
                245                 250                 255

Cys His Arg Asn Leu Ile Glu Ile Gly Tyr Val Cys Ser Val Cys Leu
            260                 265                 270

Ser Ile Phe Cys Asn Phe Ser Pro Ile Cys Thr Thr Cys Glu Thr Ala
        275                 280                 285

Phe Lys Ile Ser Leu Pro Pro Val Leu Lys Ala Lys Lys Lys Lys Leu
    290                 295                 300

Lys Val Ser Ala
305

<210> SEQ ID NO 11
<211> LENGTH: 1736
<212> TYPE: DNA
<213> ORGANISM: Homo sapiens

<400> SEQUENCE: 11
cttttccact cctcccctta cctcccttct cttctgaatt ctccattctg ggctcttgcc      60
tgtgaaatct ttctttgctt tccccatctt ttcctcgcat tttttcacca tctttccctc     120
aatctccagg agccaatgcg agactttggc tccgattaag cgacggcccg agactcgggg     180
tgcgcgagga ggatcgacag agtggtgatg gagagcaccc cttcaagggg actgaaccga     240
gtacacctac aatgcaggaa tctgcaggaa ttcttagggg cctgagccc tggggtattg      300 gaccgattgt atgggcaccc tgccacatgt ctggctgtct tcagggagct cccatccttg     360
gctaagaact gggtgatgcg gatgctcttt ctggagcagc ctttgccaca ggctgctgta     420
gctctgtggg taaagaagga attcagcaag gctcaggagg aaagtacagg gctgctgagc     480
ggcctccgga tctggcacac acagctgctc ccaggcgggc tccagggcct catcctcaac     540
cccatttccc gccagaacct ccgcattgcc cttctgggtg gggggaaggc ctggtctgat     600
gacacaagtc agctgggacc agacaagcat gcccgggacg ttccctccct tgacaagtac     660
```

```
gccgaggagc gatgggaggt ggtcttgcac ttcatggtgg gctcccccag tgcagctgtc    720
agccaggact tggctcagct cctcagccag gctgggctca tgaagagtac tgaacctgga    780
gagccgccct gcattacttc cgctggcttc cagttcctgt tgctggacac cccggctcag    840
ctctggtact ttatgttgca gtatttgcag acagcccaga gccggggcat ggacctggta    900
gagattctct ccttcctctt ccagctcagc ttctctactc tgggcaagga ttactctgtg    960
gaaggtatga gtgattctct gttgaacttc ctgcaacatc tgcgtgagtt tgggcttgtt   1020
ttccagagga agaggaaatc tcggcgttac taccccacac gcctggccat caatctctca   1080
tcaggtgtct ctggagctgg gggcactgtg catcagccag gtttcattgt cgtggaaacc   1140
aattaccgac tgtatgccta cacggagtcg gagctgcaga ttgccctcat tgccctcttc   1200
tctgagatgc tctatcggtt ccccaacatg gtggtggcgc aggtgacccg ggagagtgtg   1260
cagcaggcaa tcgccagtgg catcacagcc agcagataa  tccatttcct aaggacaaga   1320
gcccacccag tgatgctcaa acagacacct gtgctgcccc ccaccatcac cgaccagatc   1380
cggctctggg agctggaaag ggacagactc cggttcactg agggtgtcct gtataaccag   1440
ttcctgtcgc aagtggactt tgagctgctg ctggcccacg cgcgggagct gggcgtgctc   1500
gtgttcgaga actcggccaa gcggctcatg gtggtgaccc cggccgggca cagcgacgtc   1560
aagcgctttt ggaagcggca gaaacatagc tcctgagagc gcgggacttg gacacggacc   1620
tcggcgggcg ggactgggcg gggcggggca tcagaactca ggtgttttt  atttacgcgt   1680 cagggctttt cttgtttaat aaagttatga tagctaaaaa aaaaaaaaaa aaaaaa       1736
```

<210> SEQ ID NO 12
<211> LENGTH: 462
<212> TYPE: PRT
<213> ORGANISM: Homo sapiens

<400> SEQUENCE: 12

```
Met Glu Ser Thr Pro Ser Arg Gly Leu Asn Arg Val His Leu Gln Cys
1               5                   10                  15

Arg Asn Leu Gln Glu Phe Leu Gly Gly Leu Ser Pro Gly Val Leu Asp
            20                  25                  30

Arg Leu Tyr Gly His Pro Ala Thr Cys Leu Ala Val Phe Arg Glu Leu
        35                  40                  45

Pro Ser Leu Ala Lys Asn Trp Val Met Arg Met Leu Phe Leu Glu Gln
    50                  55                  60

Pro Leu Pro Gln Ala Ala Val Ala Leu Trp Val Lys Lys Glu Phe Ser
65                  70                  75                  80

Lys Ala Gln Glu Glu Ser Thr Gly Leu Leu Ser Gly Leu Arg Ile Trp
                85                  90                  95

His Thr Gln Leu Leu Pro Gly Gly Leu Gln Gly Leu Ile Leu Asn Pro
            100                 105                 110

Ile Phe Arg Gln Asn Leu Arg Ile Ala Leu Leu Gly Gly Gly Lys Ala
        115                 120                 125

Trp Ser Asp Asp Thr Ser Gln Leu Gly Pro Asp Lys His Ala Arg Asp
    130                 135                 140

Val Pro Ser Leu Asp Lys Tyr Ala Glu Glu Arg Trp Glu Val Val Leu
145                 150                 155                 160

His Phe Met Val Gly Ser Pro Ser Ala Ala Val Ser Gln Asp Leu Ala
                165                 170                 175

Gln Leu Leu Ser Gln Ala Gly Leu Met Lys Ser Thr Glu Pro Gly Glu
            180                 185                 190
```

```
Pro Pro Cys Ile Thr Ser Ala Gly Phe Gln Phe Leu Leu Leu Asp Thr
            195                 200                 205

Pro Ala Gln Leu Trp Tyr Phe Met Leu Gln Tyr Leu Gln Thr Ala Gln
        210                 215                 220

Ser Arg Gly Met Asp Leu Val Glu Ile Leu Ser Phe Leu Phe Gln Leu
225                 230                 235                 240

Ser Phe Ser Thr Leu Gly Lys Asp Tyr Ser Val Glu Gly Met Ser Asp
                245                 250                 255

Ser Leu Leu Asn Phe Leu Gln His Leu Arg Glu Phe Gly Leu Val Phe
            260                 265                 270

Gln Arg Lys Arg Lys Ser Arg Arg Tyr Tyr Pro Thr Arg Leu Ala Ile
        275                 280                 285

Asn Leu Ser Ser Gly Val Ser Gly Ala Gly Gly Thr Val His Gln Pro
    290                 295                 300

Gly Phe Ile Val Val Glu Thr Asn Tyr Arg Leu Tyr Ala Tyr Thr Glu
305                 310                 315                 320

Ser Glu Leu Gln Ile Ala Leu Ile Ala Leu Phe Ser Glu Met Leu Tyr
                325                 330                 335

Arg Phe Pro Asn Met Val Val Ala Gln Val Thr Arg Glu Ser Val Gln
            340                 345                 350

Gln Ala Ile Ala Ser Gly Ile Thr Ala Gln Gln Ile Ile His Phe Leu
        355                 360                 365

Arg Thr Arg Ala His Pro Val Met Leu Lys Gln Thr Pro Val Leu Pro
    370                 375                 380

Pro Thr Ile Thr Asp Gln Ile Arg Leu Trp Glu Leu Glu Arg Asp Arg
385                 390                 395                 400

Leu Arg Phe Thr Glu Gly Val Leu Tyr Asn Gln Phe Leu Ser Gln Val
                405                 410                 415

Asp Phe Glu Leu Leu Leu Ala His Ala Arg Glu Leu Gly Val Leu Val
            420                 425                 430

Phe Glu Asn Ser Ala Lys Arg Leu Met Val Val Thr Pro Ala Gly His
        435                 440                 445

Ser Asp Val Lys Arg Phe Trp Lys Arg Gln Lys His Ser Ser
450                 455                 460

<210> SEQ ID NO 13
<211> LENGTH: 7503
<212> TYPE: DNA
<213> ORGANISM: Homo sapiens

<400> SEQUENCE: 13
ggcgcactct gccggcaacg ccgaggcgct tctgcatctg tgggccgagc attcttcagg    60
tcatctgaac cttctgagaa acatggtca acgtcttgaa aggagtgctt atagaatgtg    120
atcctgccat gaagcagttt ctgctgtact tggatgagtc caatgccctg gggaagaagt   180
tcatcattca agacattgat gacactcacg tctttgtaat agcagaattg gttaatgtcc   240
tccaggagcg agtgggtgaa ttaatggacc aaaatgcttt ttcccttacc cagaaatgaa   300
aatactcaat atggaccatt taggaattat aagcagcaac tgtgaaagac ttgccactca   360
atatcttagg tgactgatta gacatagagg gttgttttag gagcatgcca cgggaaagac   420
tgagggatca tgatcatttg ttcagaaaaa aagcccctga actgattttg ttaccataga   480
atttaaaaaa aaaaaagct taacagttg gctgtaattt ggcttttatt atccttatt     540 aaaatacaaa tgtcaatgct tttcctgcct ttttaatacc atgtcagtgt aacataggta   600
```

-continued

```
tttattttgc tcatccctgt gatctgtgca tttttgctgc gtggatgtga ttgtttggtt    660
tcagttagaa acgtcataga tttgctgttt gaatatgcca aggtggggac ttagacatta    720
tgtacgtctc acaaatccta cctgcatacc agtcagctct attgaggaag acaatgtaaa    780
actaatgtaa actacagttt gcatttccct gaaaacagaa tattgttttt aagagggtta    840
gaaacaacca gtgggaaagg cacatgctgc tttgtttagt ttttccttgt tcaaactttg    900
ttggtcacat tttcccatct gtattctttt ttattaagaa acagcttag ggaggctgag     960 gtgggaggat tgcttgagcc caggagtccg aggttgctac aaaaacacca ttgcactctg    1020
gcctggacaa cagagagacc ctgcctcaaa aaaaaaaaa aaaaaaaaaa aaattctact     1080
tgtaccttat tccctatgag aatacttatc aaacttatct aaaaagaaa aataggaaca     1140 gccatatgca aagtcagccc aacaggaaag gacatattag attaaaatac attgcggcct    1200
gggcttagtg gctcacacct gtaatcccag cactttggga ggctgaggca ggcagatcgc    1260
ttgagtccag gagtcgaaac cctgtctcta caaaaaaaaa aatacaaaaa tctgcctgtt    1320
gtcccagcca ctggggaggc tgaggtagga ggtcaaggct gcagtgaacc ttgatcattg    1380
ctactgccac tccagcctag gtgacagagt gagaccctgt ctccaaaaaa aaagtgtat    1440 atgtatgtgt gtatatatag caagagagag ttctgtgatc aattgaaggc aaaaacagta    1500
acactgagag gggctttgct tcccttcctg aagatcatgt cattggggtg ggttcctgta    1560
aagggaattt tccaagagaa aagagaattt tcatgacctg tagactctta caaatccatt    1620
ttacctgctt ccttatggta tgtttattca aagcacctgt gtaccatatt tattcactta    1680
cacagcatta ctgaatctgg aaattttcag ttaggtatat tttacataat tcccacccat    1740
ataactcagt ccatacagtt cacagttttc attccctcat agcaatgcaa aaaattttga    1800
tgagttacta ctactaaaac tagttaagta aaagatgatt cttaagaatt tccaggctgg    1860
gcacggtggc tcacgcctgt aatcccagca ctttgggagg ctgaggcagg cagctcacga    1920
ggtcaggaga tcgagaccat cctgctcggt gaaacccat ctctattaaa aatacaaaaa     1980
attagccggg cctggtggcg ggtgcctgta gtcccatcta ctcaggaggc tgaggcagga    2040
gaatggcgtg aacccgggag gcggagcttg cagtaagctg agattgtgcc actgcactcc    2100
agcctgggcg acagagggag actccatctc aaaaaaaaaa aaaaaaaaaa atgaatttcc    2160
agctatacca aaatgttact aatgtatctt atatttcagg catgtctaaa tcaacttta     2220 gtatgcctca ggcatttgtc accaacctttt tatattaaca tgaaacttag aaaattttg     2280 atagaatccc agagttcaaa aggtattagg attttttgcca ctgaagtaaa aaagagaaaa    2340
aaagatattt atgagaaaac tattgaacag tgactgtgtt gtacccgagc aagttagagg    2400
aacgccacac tttgagacga atttaaaagt cctttattta gctggcagcc aagaggtggc    2460
tcacacttgg aattctctca gctccgagga aggggcttga ttttccttta cttttggtt     2520 taggaagggg acgggagctc agttgcaaca attctacaga agtaaaaaca tgcaaaaaat    2580
taaaaagaca aatggttaca gagaaacaaa cagttccagg tgcagggggct ctaaatctat   2640 cataagatgt caggtgtggg ggctctgcca gacacaaact caaggcttta tggtgtatct    2700
cttgagcgaa atcctgggaa cttcgtacat tgcttgcttc agtaccttat gagttaattg    2760
gactctttga tatgttgaga gtcagcttac acaagttaac tccttgagga aaggggtgg     2820 gtaaggagtc cttgatgtcc tgtaaatgaa ggaaccaaat ggagttcctc cggctttctc    2880
agctaaggga gagcttattc acatggaaac aaggctaggt gattaaggga gaaagggaca    2940
```

```
gtctgaaaac aaggttagta aaaacaaggt taggtattag aactgcaaag agtattaagt    3000
gaaataagtg aaggaaaata tgagctctta ttttaaaaa gttgtgttgg ggcaaatgtt    3060
aaatatcttt ctttctctgg acattattaa gaaagataga gtgatgtgaa tgataggaag    3120
cccacctgta accacttagc tgacatgtcc aactatgggt gaacaggaaa taagcgacat    3180
tcacctaggc tgtttattgg aatctgacta gcattatttg atttggcata ctttacatgt    3240
ccagaacaag gctgttggtg cttggcacca agaaatttat gactttttt tttttttaa    3300 ataaagtcct aaaggtagca ttaaaatgac ttaactggag gcaggaggat cactgaagcc    3360
caggagtttg aagctgcagt aagctaagaa ggtgccactg cactgcagcc tggatgacag    3420
agtgaaactt tgtctcttaa tagaactatg gactgaagtt gtgatattga gtgttatatt    3480
tctcaataaa ggttttttct tttaatactg tattaggtca aattcaaggt cttaattcct    3540
tgaattccaa tttccttgtg aaatttcatg tgattaattt aaaattccag ggatcctatc    3600
taacatcaca gttgatggat ataacaatgt attttgagaa atcagttttg gtgaacagta    3660
acagcattac tgataatagg caacaaacac tactgcattt tatttctgat aggcattata    3720
ggtggtaatc caaatgatta atgatttat tgctctttac attttctaga acaggtgatt    3780
tgacataatt gtactttttt ctgagaagtt ggtagtgtac ttactactct attttgcagt    3840
tatacaataa atcttactta gctgacaact aggagtaaaa gctctgacaa aaagcctctg    3900
ctgtaactaa aatactgaga tcattctatc ttaacaaact taacagatgg ggaagggta    3960 tattttaaag atggagaaat gatgcagttt gcaaatatag tcaataaata ttctcaagtg    4020
tacgtagctc aatttcattt gcagcaaaga taacactgaa atgtctatgg atgagattat    4080
tggataaact tttttaaaaa cactgttctc aagataggca agtgattaag agcactgact    4140
gggccgggcg cggtggctca cgtctataat cctagcactt tgggaggccg aggcgggcaa    4200
atcacaaggt caggagatca aaacaatcct ggctaacaag gtgaaacccc gtctctacta    4260
aaaatacaaa aaaattagct gggcatggtg gtggacgcct gtagtcccag ctactcggga    4320
ggctgaggca ggagaatggt gtaatcccgg gaggtggagg ttgcagtgag ccgagatcgt    4380
gccactgcac tccagccggg gtgacagagc gagactccca cccatctcaa aaaaataaa    4440 aatgaaaagc actgattgaa tctagattcc ttgagtccaa gtgtcagatc tctgcttact    4500
agctctggga tctcagatgt ttcgttgatt ggatttcttt gtgctcattt gtgtaaacag    4560
gaatgcccgt cttaaagac tattaaaatg aatgtgagtt aacacacaag aggtcttcaa    4620
aaagttgatg gaaaatgcat attatgaaaa aaattatgca tagatttcaa aaatctttgc    4680
agcaaaataa actcatcatt ataacatgtc tgaacaggat ctagtttgag gcactaagaa    4740
ggatatcagt ttaaatagag cccctgtcag aacaatatga attctgctaa aactgaagca    4800
agaacaaaca tcaaatttat ggcaaagctt aggtggaaga atggtgcaat cattgatgct    4860
ttgcaaaaag tttatgggaa caacgcccca aggaaatcag tttacaaatg gataattcat    4920
tttaagaaag gacaagacaa tgttgaagat gaaacctaca gcagcagacc atgccacttc    4980
gtgaggaaaa aattatctca ttcatgcct acttgaagag gaccaatgat taacagcaga    5040
aacgatagcc aacacaatat gctcctcagt tggttcagct tttataaatc tgactgaaaa    5100
attaaagttg agcacacttt ccactcaatg gataccaaaa ccatccagcc caggtcagct    5160
gcagacaaaa gcagagcttt cgatggaaat gtcaaacaag tgagatcaag atcctgaagc    5220
atttcttcaa agaattgtag caaaaacaga cttttaaaac cttgaattca gagacaggta    5280
taaagactgc ttggtgattt tgaaaggact gagatcattt tgggagagat catcttcaga    5340
```

```
aaatgaccag atacaacaag aatttaacat ggcagccaaa ccaacccact aacacacatt      5400
taaataagat acccaaatgc agaaagaaaa gcacagtcgt catgcaaaat agtcactact      5460
cattcaaaaa ctctatagtt gtctgagtcg ttatgctcaa aatatccaat aatatttctt      5520
ttgctgagct gtaaaataat tattttgcaa acataaaaga aaaaaaaaag aattgtaaca      5580
gaaacatggc tttaccagta tgaccctcaa gacaaaatac aaaacaatgg ctaccaagag      5640
gtggaagtgg cccagtcaca gcaagagcag attgatcaag agcaaaggtc atggtaacag      5700
ttttttggat cctcaagtca ttttgcttgt tgactttttg gagggccaaa taaagatatc      5760
atctgcttat tatgagagtg tttcgagaga aatccaaagc ttagcagaga aacgcctggg      5820
aaagcttcac cagagggtct tccaccgtga cagttcccct gcgcattcct ctcataaagc      5880
aagggcagtt tagctagaat ttctatcaaa aatcattagg tatccatctc ccagtcctga      5940
tttggctcct tctgacttct ttttgtttcc caatcttaaa aaaatccctg aagggcacct      6000 gttttcttc agctaataaa aaagacatgg ttaatttccc aggaccctca gttcttagg       6060 gatagactga atggctggta tcattgcttg aacttaatgg agcttatgtt gagaaataaa      6120
agaaattata ttttattttt atcttttaat tctattttc catgaacttt ttgaagtccc       6180
ctcagatata aagcagaacg ttatgaaact gagttacctt gaatctagaa gagtacaatg     6240
ataaagggga agatagaaac acacacatat gcgttgtttt ccccactttc acaatgccgt     6300
gcagaaacta acagatgaag gaggagaatc cctaaaaaca gagcattggg tagctagtcc     6360
accagcggtc tgatgctttc attgatctca aaactgtctc tgagtaactc taccaggaaa     6420
gttgtctgga gggttaacat ttctgaaacc attttatct ttgccttcat tcttgaatga      6480
taattagtct cgaatgtttg gatcacaatc cattgaaaga ctaggctatt ttttcactgt     6540
cctcagacat ttactgagtc cagtttggac tttatttat tttatttttt ttgaaacaag      6600
atctcgctct gttgctcagg ctgaagtgca atagcgcaaa ctcggctcac tgcaacctcc     6660
caggttcaag caattctcgt gcctcagcca tccctatagg catgcgccac cacactttgc     6720
taatcttgta ttttggtag agacggggtt tgcaccatgt tggccaggct ggtctcgaac      6780
tcccaacctc aagtaatctg gcctcccaaa gtggtgggat tacaggcgtg agccagcgcg     6840
cccggcctgg acttaacttc tgaagaactc tttctgttta gattgcagga gcgttctctc     6900
ggctcatctc ttgttttctc acccagctgt tcttcttcta gttggccatc attcttcatc    6960
cctccctccc tttcctgcag ttaattattt ctttgaaatt ttaaaacttc ttaatgttgc     7020
ctggaataca tgagtcttcc tgatctcttc aaacgggggtt tgttttgttt tgctttgggg   7080
agaattcttt tgacgttttt gaataagctg ttaacaactt taatacctgt cttgtttgtt    7140
ttcttcagaa atttgttaat tctccatgat tagcacctt atgtggttat ctcattattt      7200
tcattccttt ttaattctct gtttaggaa tgcttgtcaa attcgtcact aaaattgatt      7260
tactttcttg aaaacctgtt tctgctgctc ccaacatgat ttaatcttgg ctactgagct     7320
tttggttacg ttgcactccc tttaaaatta ctccgtttaa gtacagtgtt cactctttgg    7380
gtaatgtgta caatagaagc ccaatcccca cctatacccc atatatccat gggacaagca     7440
tgtacatgca cccctgagt ctaaaataaa aattttaaaa aaactaaaaa aaaaaaaaa       7500 aaa                                                                  7503
```

<210> SEQ ID NO 14
<211> LENGTH: 71
<212> TYPE: PRT

<213> ORGANISM: Homo sapiens

<400> SEQUENCE: 14

| Met | Val | Asn | Val | Leu | Lys | Gly | Val | Leu | Ile | Glu | Cys | Asp | Pro | Ala | Met |
| --- | --- | --- | --- | --- | --- | --- | --- | --- | --- | --- | --- | --- | --- | --- | --- |
| 1 | | | | 5 | | | | | 10 | | | | | 15 | |

| Lys | Gln | Phe | Leu | Leu | Tyr | Leu | Asp | Glu | Ser | Asn | Ala | Leu | Gly | Lys | Lys |
| --- | --- | --- | --- | --- | --- | --- | --- | --- | --- | --- | --- | --- | --- | --- | --- |
| | | | 20 | | | | | 25 | | | | | 30 | | |

| Phe | Ile | Ile | Gln | Asp | Ile | Asp | Asp | Thr | His | Val | Phe | Val | Ile | Ala | Glu |
| --- | --- | --- | --- | --- | --- | --- | --- | --- | --- | --- | --- | --- | --- | --- | --- |
| | | | | 35 | | | | | 40 | | | | | 45 | |

| Leu | Val | Asn | Val | Leu | Gln | Glu | Arg | Val | Gly | Glu | Leu | Met | Asp | Gln | Asn |
| --- | --- | --- | --- | --- | --- | --- | --- | --- | --- | --- | --- | --- | --- | --- | --- |
| | 50 | | | | | 55 | | | | | 60 | | | | |

| Ala | Phe | Ser | Leu | Thr | Gln | Lys |
| --- | --- | --- | --- | --- | --- | --- |
| 65 | | | | | 70 | |

<210> SEQ ID NO 15
<211> LENGTH: 5831
<212> TYPE: DNA
<213> ORGANISM: Homo sapiens

<400> SEQUENCE: 15

```
gacatttcac gccgccgcca ttttgagagc gagccgagcc gagctgccgg gcgccgcgtc      60
cgctgccgga gccccgacga cgacgccgag gaggcggagg ccgcggctct cggaacgcgg     120
ccggcccgtc gcccgcccgc tccgccgctc ccgccggccc cagggcccgc aggcccgccg     180
cggccggcca ggcctcccgt ccgccgcgcc cggcccgagg cggggctgac tccgcggccc     240
ccgaccggcc gccctccgcc cccggccggc ccgcggcccc gcagccccgg ccccggcccc     300
ggcggcggga ggcgggcccc gcggcggcgg cggcggcggc cgcagcgagc gacgaggccg     360
cccgccccgg cccgccggcc gcccgcccgc ctcggcgccg agattgggcg aatcgcgagc     420
aagtacgtgc gcgtctccct gccgccgccg ccgcccgccg cgggccgccc cggggccgcc     480
gtcgccgacg acgcgcggga ggaggaggag gaggccgccc cgccgccgcc gccgccgccg     540
ccgccccggc tcgccgccgc ccgcccgccg ggctcgcagc cccggccccc ggccgcaggc     600
gaggcccagg ccgcggccga catgaaccac cagcagcagc agcagcagca gaaagcgggc     660
gagcagcagt tgagcgagcc cgaggacatg gagatggaag cgggagatac agatgaccca     720
ccaagaatta ctcagaaccc tgtgatcaat gggaatgtgg ccctgagtga tggacacaac     780
accgcggagg aggacatgga ggatgacacc agttggcgct ccgaggcaac ctttcagttc     840
actgtggagc gcttcagcag actgagtgag tcggtcctta gccctccgtg ttttgtgcga     900
aatctgccat ggaagattat ggtgatgcca cgctttatc cagacagacc acaccaaaaa     960
agcgtaggat tctttctcca gtgcaatgct gaatctgatt ccacgtcatg gtcttgccat    1020
gcacaagcag tgctgaagat aataaattac agagatgatg aaaagtcgtt cagtcgtcgt    1080
attagtcatt tgttcttcca taagaaaat gattggggat tttccaattt tatggcctgg    1140
agtgaagtga ccgatcctga gaaggattt atagatgatg acaaagttac ctttgaagtc    1200
tttgtacagg cggatgctcc ccatggagtt gcgtgggatt caaagaagca cacaggctac    1260
gtcggcttaa agaatcaggg agcgacttgt tacatgaaca gcctgctaca gacgttattt    1320
ttcacgaatc agctacgaaa ggctgtgtac atgatgccaa ccgaggggga tgattcgtct    1380
aaaagcgtcc ctttagcatt acaaagagtg ttctatgaat tacagcatag tgataaacct    1440
gtaggaacaa aaagttaac aaagtcattt gggtgggaaa ctttagatag cttcatgcaa    1500
catgatgttc aggagctttg tcgagtgttg ctcgataatg tggaaaataa gatgaaaggc    1560
```

```
acctgtgtag agggcaccat acccaaatta ttccgcggca aaatggtgtc ctatatccag    1620
tgtaaagaag tagactatcg gtctgataga agagaagatt attatgatat ccagctaagt    1680
atcaaaggaa agaaaaatat atttgaatca tttgtggatt atgtggcagt agaacagctc    1740
gatgggggaca ataaatacga cgctggggaa catggcttac aggaagcaga gaaaggtgtg   1800
aaattcctaa cattgccacc agtgttacat ctacaactga tgagatttat gtatgaccct    1860
cagacggacc aaaatatcaa gatcaatgat aggtttgaat cccagagca gttaccactt     1920
gatgaatttt tgcaaaaaac agatcctaag gaccctgcaa attatattct tcatgcagtc    1980
ctggttcata gtggagataa tcatggtgga cattatgtgg tttatctaaa ccccaaaggg    2040
gatggcaaat ggtgtaaatt tgatgacgac gtggtgtcaa ggtgtactaa agaggaagca    2100
attgagcaca attatggggg tcacgatgac gacctgtctg ttcgacactg cactaatgct    2160
tacatgttag tctacatcag ggaatcaaaa ctgagtgaag ttttacaggc ggtcaccgac    2220
catgatattc ctcagcagtt ggtggagcga ttacaagaag agaaaaggat cgaggctcag    2280
aagcggaagg agcggcagga agcccatctc tatatgcaag tgcagatagt cgcagaggac    2340
cagttttgtg gccaccaagg gaatgacatg tacgatgaag aaaaagtgaa atacactgtg    2400
ttcaaagtat tgaagaactc ctcgcttgct gagtttgttc agagcctctc tcagaccatg    2460
ggatttccac aagatcaaat tcgattgtgg cccatgcaag caaggagtaa tggaacaaaa    2520
cgaccagcaa tgttagataa tgaagccgac ggcaataaaa caatgattga gctcagtgat    2580
aatgaaaacc cttggacaat attcctggaa acagttgatc ccgagctggc tgctagtgga    2640
gcgaccttac ccaagtttga taaagatcat gatgtaatgt tattttgaa gatgtatgat     2700
cccaaaacgc ggagcttgaa ttactgtggg catatctaca caccaatatc ctgtaaaata    2760
cgtgacttgc tcccagttat gtgtgacaga gcaggattta ttcaagatac tagcctttac    2820
ctctatgagg aagttaaacc gaatttaaca gagagaattc aggactatga cgtgtctctt    2880
gataaagccc ttgatgaact aatggatggt gacatcatag tatttcagaa ggatgaccct    2940
gaaaatgata acagtgaatt acccaccgca aaggagtatt tccgagatct ctaccaccgc    3000
gttgatgtca ttttctgtga taaaacaatc cctaatgatc ctggatttgt ggttacgtta    3060
tcaaatagaa tgaattattt tcaggttgca aagacagttg cacagaggct caacacagat    3120
ccaatgttgc tgcagttttt caagtctcaa ggttataggg atggcccagg taatcctctt    3180
agacataatt atgaaggtac tttaagagat cttctacagt tcttcaagcc tagacaacct    3240
aagaaacttt actatcagca gcttaagatg aaaatcacag actttgagaa caggcgaagt    3300
tttaaatgta tatggttaaa cagccaattt agggaagagg aaataacact atatccagac    3360
aagcatgggt gtgtccggga cctgttagaa gaatgtaaaa aggccgtgga gcttggggag    3420
aaagcatcag ggaaacttag gctgctagaa attgtaagct acaaaatcat tggtgttcat    3480
caagaagatg aactattaga atgtttatct cctgcaacga gccggacgtt tcgaatagag    3540
gaaatccctt tggaccaggt ggacatagac aaagagaatg atgatgcttgt cacagtggcg   3600
catttccaca aagaggtctt cggaacgttc ggaatcccgt ttttgctgag gatacaccag    3660
ggcgagcatt tcgagaagt gatgaagcga atccagagcc tgctggacat ccaggagaag     3720
gagtttgaga gtttaaatt tgcaattgta atgatgggcc gacaccagta cataaatgaa      3780
gacgagtatg aagtaaattt gaaagacttt gagccacagc ccggtaatat gtctcatcct    3840
cggccttggc tagggctcga ccacttcaac aaagcccccaa agaggagtcg ctacacttac    3900
cttgaaaagg ccattaaaat ccataactga tttccaagct ggtgtgttca aggcgaggac    3960
```

```
ggtgtgtggg tggcccctta acagcctaga actttggtgc acgtgccctc tagccgaagt    4020
cttcagcaag aggattcgct gctggtgtta atttattttt attgaggctg ttcagtttgg    4080
cttctctgta tctattgact gcccttttg agcaaaatga agatgttttt ataaagcttg     4140
gatgccaatg agagttattt tatggtaacc acagtgcaag gcaactgtca gcgcaatggg    4200
ggagaagagg ttagtggatc gggggtccct ggctcaaggt ctctgggctg tccctagtgg    4260
gcacgagtgg ctcggctgcc ttcctggggt cccgtgcacc agccctgcag ctagcaagtc    4320
ttgtgtttag gctcgtctga cctatttcct tcagttatac tttcaatgac cttttgtgca    4380
tctgttaagg caaacagag aaactcacaa cctaataaat agcgctcttc ccttcattgt     4440
gtgcattgtc ggcccttcct cgggttctcc tcctccagct gcctggggc ttttaataa      4500 acttgtctca cctcgtcagc cactactgtc tgcagcccct ttgcaaagtg gatgcactga    4560
atacagtccg gacagacatt gtgggggtct ttttattaaa tcaagaacat tgttaaattc    4620
aattaaggtt tactctgctg ccttggcaga cttacgatct caacagttca tacgagcagg    4680
tgaaaggatt ataaatagaa tttcgttaaa gtggaacaga cgacaagaaa gccttttagc    4740
aagagggcat gctcactagt ggttagtaag ctgtcgactt tgtaaaaaag ttaaaaatga    4800
aaaaaaaagg aaaaatgaat tgtatattta atgaatgaac atgtacaatt tgccactggg    4860
aggaggttcc ttttgttgg gtgagtctgc aagtgaattt cactgatgtt gatattcatt      4920
gtgtgtagtt ttatttcggt cccagccccg tttccttta ttttggagct aatgccagct      4980
gcgtgtctag ttttgagtgc agtaaaatag aatcagcaaa tcactcttat ttttcatcct    5040
tttccggtat tttttgggtt gtttctgtgg gagcagtgta caccaactct tcctgtatat    5100 tgccttttg ctggaaaatg ttgtatgttg aataaaattt tctataaaaa ttataattca     5160
gtgagttacg tggaagtgga ggaagatttc tactctccct ggaaacaggc ctgggaaacc    5220
ttggcatttg taacaaggtt tcactgagat gtacttttcc ttctaattcc gttttgcggg    5280
ggcagggtct cttgtttctt ttttttttt tttttttttt tagcctctaa ctagtcacat     5340
ttactcttaa gaaatgaaag gttttccagg agagaactgt gtacaaataa ggtgactgga    5400
gatgtgacct gatgtgtcac gaggcccttc ggggcggcag gcgctatcgt gggcgtggtc    5460
cttgcaccgt cccatcggcc ttgccttcca gctccgtggc acggtttcct ggtctttggg    5520
ccagtgtgta ccttggagtg acttcctttc tcaacttcca ctgcagtgtg tgtgccttct    5580
gctctgagag ctgccttgtg acccgtgtga tagaaagcag ggagtgaggg tccccgcgga    5640 cctggcccctt ccctccttcc tcccccagaa agaggagtta gagcaggggt gcgagagccg    5700
ttcgctgtgg gtttgtcttt gaacaaacat taaggtgtct tgttttttgtt ctgggctggg    5760 ggttggctgt agtcttaggt aactgaaagt tcctactctc ccttaaggta ttaaatgact    5820 cttttttccaa a                                                        5831
```

<210> SEQ ID NO 16
<211> LENGTH: 1102
<212> TYPE: PRT
<213> ORGANISM: Homo sapiens

<400> SEQUENCE: 16

Met Asn His Gln Gln Gln Gln Gln Gln Lys Ala Gly Glu Gln Gln
1               5                   10                  15

Leu Ser Glu Pro Glu Asp Met Glu Met Glu Ala Gly Asp Thr Asp Asp
            20                  25                  30

-continued

Pro Pro Arg Ile Thr Gln Asn Pro Val Ile Asn Gly Asn Val Ala Leu
         35                  40                  45

Ser Asp Gly His Asn Thr Ala Glu Glu Asp Met Glu Asp Asp Thr Ser
 50                  55                  60

Trp Arg Ser Glu Ala Thr Phe Gln Phe Thr Val Glu Arg Phe Ser Arg
 65                  70                  75                  80

Leu Ser Glu Ser Val Leu Ser Pro Pro Cys Phe Val Arg Asn Leu Pro
                 85                  90                  95

Trp Lys Ile Met Val Met Pro Arg Phe Tyr Pro Asp Arg Pro His Gln
            100                 105                 110

Lys Ser Val Gly Phe Phe Leu Gln Cys Asn Ala Glu Ser Asp Ser Thr
            115                 120                 125

Ser Trp Ser Cys His Ala Gln Ala Val Leu Lys Ile Ile Asn Tyr Arg
130                 135                 140

Asp Asp Glu Lys Ser Phe Ser Arg Arg Ile Ser His Leu Phe Phe His
145                 150                 155                 160

Lys Glu Asn Asp Trp Gly Phe Ser Asn Phe Met Ala Trp Ser Glu Val
                165                 170                 175

Thr Asp Pro Glu Lys Gly Phe Ile Asp Asp Lys Val Thr Phe Glu
            180                 185                 190

Val Phe Val Gln Ala Asp Ala Pro His Gly Val Ala Trp Asp Ser Lys
        195                 200                 205

Lys His Thr Gly Tyr Val Gly Leu Lys Asn Gln Gly Ala Thr Cys Tyr
        210                 215                 220

Met Asn Ser Leu Leu Gln Thr Leu Phe Phe Thr Asn Gln Leu Arg Lys
225                 230                 235                 240

Ala Val Tyr Met Met Pro Thr Glu Gly Asp Asp Ser Ser Lys Ser Val
                245                 250                 255

Pro Leu Ala Leu Gln Arg Val Phe Tyr Glu Leu Gln His Ser Asp Lys
            260                 265                 270

Pro Val Gly Thr Lys Lys Leu Thr Lys Ser Phe Gly Trp Glu Thr Leu
            275                 280                 285

Asp Ser Phe Met Gln His Asp Val Gln Glu Leu Cys Arg Val Leu Leu
290                 295                 300

Asp Asn Val Glu Asn Lys Met Lys Gly Thr Cys Val Glu Gly Thr Ile
305                 310                 315                 320

Pro Lys Leu Phe Arg Gly Lys Met Val Ser Tyr Ile Gln Cys Lys Glu
                325                 330                 335

Val Asp Tyr Arg Ser Asp Arg Arg Glu Asp Tyr Tyr Asp Ile Gln Leu
            340                 345                 350

Ser Ile Lys Gly Lys Lys Asn Ile Phe Glu Ser Phe Val Asp Tyr Val
            355                 360                 365

Ala Val Glu Gln Leu Asp Gly Asp Asn Lys Tyr Asp Ala Gly Glu His
        370                 375                 380

Gly Leu Gln Glu Ala Glu Lys Gly Val Lys Phe Leu Thr Leu Pro Pro
385                 390                 395                 400

Val Leu His Leu Gln Leu Met Arg Phe Met Tyr Asp Pro Gln Thr Asp
                405                 410                 415

Gln Asn Ile Lys Ile Asn Asp Arg Phe Glu Phe Pro Glu Gln Leu Pro
            420                 425                 430

Leu Asp Glu Phe Leu Gln Lys Thr Asp Pro Lys Asp Pro Ala Asn Tyr
            435                 440                 445

Ile Leu His Ala Val Leu Val His Ser Gly Asp Asn His Gly Gly His

```
            450                 455                 460
Tyr Val Tyr Leu Asn Pro Lys Gly Asp Gly Lys Trp Cys Lys Phe
465                 470                 475                 480

Asp Asp Asp Val Val Ser Arg Cys Thr Lys Glu Glu Ala Ile Glu His
                        485                 490                 495

Asn Tyr Gly Gly His Asp Asp Leu Ser Val Arg His Cys Thr Asn
                500                 505                 510

Ala Tyr Met Leu Val Tyr Ile Arg Glu Ser Lys Leu Ser Glu Val Leu
                515                 520                 525

Gln Ala Val Thr Asp His Asp Ile Pro Gln Gln Leu Val Glu Arg Leu
530                 535                 540

Gln Glu Glu Lys Arg Ile Glu Ala Gln Lys Arg Lys Glu Arg Gln Glu
545                 550                 555                 560

Ala His Leu Tyr Met Gln Val Gln Ile Val Ala Glu Asp Gln Phe Cys
                565                 570                 575

Gly His Gln Gly Asn Asp Met Tyr Asp Glu Glu Lys Val Lys Tyr Thr
                580                 585                 590

Val Phe Lys Val Leu Lys Asn Ser Ser Leu Ala Glu Phe Val Gln Ser
                595                 600                 605

Leu Ser Gln Thr Met Gly Phe Pro Gln Asp Gln Ile Arg Leu Trp Pro
            610                 615                 620

Met Gln Ala Arg Ser Asn Gly Thr Lys Arg Pro Ala Met Leu Asp Asn
625                 630                 635                 640

Glu Ala Asp Gly Asn Lys Thr Met Ile Glu Leu Ser Asp Asn Glu Asn
                        645                 650                 655

Pro Trp Thr Ile Phe Leu Glu Thr Val Asp Pro Glu Leu Ala Ala Ser
                660                 665                 670

Gly Ala Thr Leu Pro Lys Phe Asp Lys Asp His Asp Val Met Leu Phe
                675                 680                 685

Leu Lys Met Tyr Asp Pro Lys Thr Arg Ser Leu Asn Tyr Cys Gly His
                690                 695                 700

Ile Tyr Thr Pro Ile Ser Cys Lys Ile Arg Asp Leu Leu Pro Val Met
705                 710                 715                 720

Cys Asp Arg Ala Gly Phe Ile Gln Asp Thr Ser Leu Ile Leu Tyr Glu
                        725                 730                 735

Glu Val Lys Pro Asn Leu Thr Glu Arg Ile Gln Asp Tyr Asp Val Ser
                740                 745                 750

Leu Asp Lys Ala Leu Asp Glu Leu Met Asp Gly Asp Ile Ile Val Phe
                755                 760                 765

Gln Lys Asp Asp Pro Glu Asn Asp Asn Ser Glu Leu Pro Thr Ala Lys
                770                 775                 780

Glu Tyr Phe Arg Asp Leu Tyr His Arg Val Asp Val Ile Phe Cys Asp
785                 790                 795                 800

Lys Thr Ile Pro Asn Asp Pro Gly Phe Val Val Thr Leu Ser Asn Arg
                        805                 810                 815

Met Asn Tyr Phe Gln Val Ala Lys Thr Val Ala Gln Arg Leu Asn Thr
                820                 825                 830

Asp Pro Met Leu Leu Gln Phe Phe Lys Ser Gln Gly Tyr Arg Asp Gly
                835                 840                 845

Pro Gly Asn Pro Leu Arg His Asn Tyr Glu Gly Thr Leu Arg Asp Leu
                850                 855                 860

Leu Gln Phe Phe Lys Pro Arg Gln Pro Lys Lys Leu Tyr Tyr Gln Gln
865                 870                 875                 880
```

```
Leu Lys Met Lys Ile Thr Asp Phe Glu Asn Arg Arg Ser Phe Lys Cys
            885                 890                 895
Ile Trp Leu Asn Ser Gln Phe Arg Glu Glu Ile Thr Leu Tyr Pro
        900                 905                 910
Asp Lys His Gly Cys Val Arg Asp Leu Leu Glu Cys Lys Lys Ala
        915                 920                 925
Val Glu Leu Gly Glu Lys Ala Ser Gly Lys Leu Arg Leu Leu Glu Ile
        930                 935                 940
Val Ser Tyr Lys Ile Ile Gly Val His Gln Glu Asp Glu Leu Leu Glu
945                 950                 955                 960
Cys Leu Ser Pro Ala Thr Ser Arg Thr Phe Arg Ile Glu Glu Ile Pro
            965                 970                 975
Leu Asp Gln Val Asp Ile Asp Lys Glu Asn Glu Met Leu Val Thr Val
            980                 985                 990
Ala His Phe His Lys Glu Val Phe Gly Thr Phe Gly Ile Pro Phe Leu
            995                1000                1005
Leu Arg Ile His Gln Gly Glu His Phe Arg Glu Val Met Lys Arg
       1010                1015                1020
Ile Gln Ser Leu Leu Asp Ile Gln Glu Lys Glu Phe Glu Lys Phe
       1025                1030                1035
Lys Phe Ala Ile Val Met Met Gly Arg His Gln Tyr Ile Asn Glu
       1040                1045                1050
Asp Glu Tyr Glu Val Asn Leu Lys Asp Phe Glu Pro Gln Pro Gly
       1055                1060                1065
Asn Met Ser His Pro Arg Pro Trp Leu Gly Leu Asp His Phe Asn
       1070                1075                1080
Lys Ala Pro Lys Arg Ser Arg Tyr Thr Tyr Leu Glu Lys Ala Ile
       1085                1090                1095
Lys Ile His Asn
       1100

<210> SEQ ID NO 17
<211> LENGTH: 4674
<212> TYPE: DNA
<213> ORGANISM: Homo sapiens

<400> SEQUENCE: 17
gccagggcgt gtcccgtgtg cccgagagcg ccggcggcgg ggccggaggg cgggccctgg       60
gccgagtgac aggccgcagc cccccgagca ccgtcgaagc cggcgcgccc gcccggtgca      120
gccgctgtgc gagagcgacc ccgcggtcca agcctcgcgt ggccctgccg ggccccttct      180
ttccccgagt agggcgcagc ttcccagcct ccgccccggc ctcgcctggc gcttccttcc      240
gggtccttcg gcctttccct ggcggtgcgg caggccctcg cctcatccca ccaggcacgc      300
cgcggtgctc ggccctgggt atccgggcag gctgcctccg ttagggccgc ccctgctctc      360
cggacgcgac ttttcattgg tctcagaatt tcttggctcc tcttggcctc tgcagccttg      420
ctggaggctg ccctgcggaa tctgaatatg gatcagaaac tttcgaagtt ggtagaagag      480
ctcacaactt caggagaacc ccgactaaat cctgagaaaa tgaaggaact gaagaaaatt      540
tgcaagtctt cagaggagca gctgagccgc gcctaccgcc tgctgatagc acagctgacc      600
caggagcacg ccgagatccg tctctcagcc ttccagattg tggaggaact cttcgtcagg      660
tctcaccagt tccggatgct ggttgtttcc aacttccagg agttcctgga gctcacgctg      720
ggcacagacc ccgcacagcc tctgccgccc cccagggagg cggcacagag gctgaggcag      780
```

| | |
|---|---|
| gcgaccaccc gggccgtgga agggtggaat gagaagtttg gggaggccta caagaagctt | 840 |
| gccttgggct accacttctt aagacacaac aaaaaggtgg attttcaaga cacgaatgct | 900 |
| cggagtctgg cagaaaggaa gagagaagag gagaagcaga agcacttgga taaaatttat | 960 |
| caagaaagag ccagccaggc ggagagggag atgcaagaaa tgtctggaga aattgaatcc | 1020 |
| tgcttgacgg aggtagagag ctgctttagg ctgctggtgc cttttgactt tgacccgaac | 1080 |
| ccggagacgg aatcccttgg catggcttct ggcatgtccg atgcccttcg ctcctcctgc | 1140 |
| gcgggccagg tgggcccctg ccggtctggc acccctgacc cccgggacgg ggagcagccc | 1200 |
| tgctgcagta gagacctgcc tgcctctgca ggccacccca gagcgggcgg cggggcacag | 1260 |
| ccatcccaga cagccacagg tgaccctca gatgaggacg aggacagcga cctcgaggag | 1320 |
| tttgtgcgga gccacgggct gggctcgcac aagtacacgc tggatgtgga gctctgctca | 1380 |
| gagggcctga aggtgcagga gaacgaggac aaccttgctc tcatccacgc cgcccgcgac | 1440 |
| acactcaagc tcatccggaa caagttcctg ccggctgtgt gctcgtggat ccagcgcttc | 1500 |
| acccgcgtcg ggacccacgg tggatgttta agcgtgcca ttgacctgaa ggctgaattg | 1560 |
| gagctcgtac tgagaaaata caaggagctg gacatcgagc ctgagggagg ggaaaggcgc | 1620 |
| aggacagaag ccctggggga tgcggaggaa gatgaggacg atgaggactt tgtggaggtc | 1680 |
| cctgagaagg aggggtatga gccacacatc cccgaccact tgcggcctga gtatgggctg | 1740 |
| gaggcagcac cagagaaaga cacagttgtg cggtgcttgc ggacgaggac gaggatggac | 1800 |
| gaggaggtgt cggaccccac ctctgcggct gctcagctgc ggcagctccg ggaccacttg | 1860 |
| cctccaccct catctgccag cccctccaga gcgttgccag agccacagga ggcccagaag | 1920 |
| ctggcagcag agcgggcccg ggcgcctgtg gtgccctacg gcgtggacct gcactactgg | 1980 |
| ggccaggagc tccccacagc cgggaagatt gtcaagtctg actcccagca ccgcttctgg | 2040 |
| aagcccagcg aggtggagga ggaagtggtc aatgccgaca tctccgagat gctccggagc | 2100 |
| cgccacatca cttttgccgg gaagtttgag cctgtgcagc actggtgccg tgccccgagg | 2160 |
| ccagacggcc ggctctgtga gcgccaagac cggctgaagt gcccttttcca tgggaagatt | 2220 |
| gttccacggg acgacgaagg acggccgctc gacccggaag acagggctcg tgagcagcgg | 2280 |
| cggcagctgc agaagcagga gcgccccgaa tggcaggacc ctgagttgat gagagacgtg | 2340 |
| gaagcagcca cagggcagga tctcggctca tccaggtaca gcgggaaagg caggggaag | 2400 |
| aagaggaggt accccagcct caccaacctg aaggctcagg ctgataccgc ccgcgctcgc | 2460 |
| attgggagaa aagtcttcgc caaggcagct gtgcggaggg tagtggcagc catgaaccgg | 2520 |
| atggaccaga agaagcacga gaagttttca aaccagttta actacgcact gaactagaga | 2580 |
| gcggggccca gtgcactggc catcagcact ttctccctct gccagtgtct caggacagca | 2640 |
| gagtgggcgt gggtctgggc agtaaccatg ctttgtctat tactgtgttt gatgtaaaga | 2700 |
| aatggtgtgt tgcaatgccc tgaaggtacg gccgctctgc tgctacaggg ttcggcatcg | 2760 |
| tctggtgatg ggtctggcct cgcagaagag gccctcgggc ctggagatgt gaacacaggc | 2820 |
| agcgaccctg ttccagaggg cttctgcgag tcctcgtgag accagtgctt gtcgtggtgt | 2880 |
| ggggttcagc acggacggaa tgtgtgtgca gctcagcctt cagagcgtgc attccccagc | 2940 |
| caggaggcga ccactcagag gaactctggg aaacccactt tgtgcaaat gctgttttta | 3000 |
| acacaaacac aaaggctagt gaaccgttca gtcatctgct ttctgtttct ggatgtgcct | 3060 |
| tttcatacat gtgtcctctt gtccctggct tcttacactt ggcgttgttt ttaaggttta | 3120 |

```
tccatgcagt tcccctccaa tgtataaaac aaaggaggtg aaaacctgtc catgcggaag      3180
cttgtgcacc catgttcaca gcagcattgg agaaggatac cgaacatctt ctcgtgggct      3240
tactggccat ttgtgtatct cctttggaga ggagtctatt caaacctctt gcctattttt      3300
aattgaatga tttatcttga gttgtaacag ttgttttttt tgttttttcct tttagagatg      3360 ggcttttgct cttacccagg ctgagtgcag tggcagaatc atagctcagt gcagcctcaa      3420
actcctgggc tcaagccatc cttccacgtc agcctcccag gtagctggga ctacaggcac      3480
acaccacaac acctggctaa ttttttaaat ttttgtaga gatgaggtct cactgtgttg      3540
cccacggtga tctcgaactc ctagcctcaa gcgatcctcc tgcttcggtc tcccaaagtg      3600
ttgggattac aggcatgagc caccactcct ggccaggagt ttatatgtat actgtggata      3660
ctagatcctc atgtgatttg caaaaacttt atttatttat ttatttattt ttgaaatgga      3720
atcttgctct gtcgccaggc tggagtgcaa tggcgtgatc tcggctcact gcaactacca      3780
cctcctgggt tcaagcgatt cgcctgcgtc agcgtcctga gtagctggga ctacaggcgc      3840
gcaccaccac gcccagctaa ttttttgtatt tttagtagag acgggatttc actgtgttgg      3900
ctgggatggt cttgatctct tgacctcgtg atccacccac ctcggcctcc catagtgctg      3960
ggattacagg tgtgagccac cgcactcagc tgatttgcaa aaactttctt ccatactgtt      4020
gtttcacttt ctggatagtg tcctctgaag cacaaaagtt aattttgatg aagtacagca      4080
atttatctgt ttttttcttt tgttgctat gcttttgctg tcacatttca gaagccatca      4140
cctaatccaa gatcacagag atttacacct agtttctaat aagcatttta taatttcagc      4200
tcttatgtgt agatctttga tccattgtga attaagtttt gtgtgtggtg taagagccca      4260
cattcttttg catgtggata tccagttgtc ccagcaccat ttgttgaaaa cattatttt      4320 ccccattgaa ttatcttcgc accattattg ataatcagtt gaccaaaaat gtacaggctt      4380
atttctgggc acttgactct attccattga cctgtttaac cttatgccag tgccacagtg      4440
ccttgatcag tgctgctttg ttgtgagaag ttttactttg ttctgcttca aggctgtttt      4500
gactcttctg catctcttgc atttccaaat gaattttagg atccactcat cagtttcttc      4560
aaaaaaaaaa aaaagcagc tgagattttt gataggaatt acattaaatc tagagattgc      4620
tttggaatgt attaccgtct taatattaaa tcttctgagt catgaaaaaa aaaa            4674
```

<210> SEQ ID NO 18
<211> LENGTH: 709
<212> TYPE: PRT
<213> ORGANISM: Homo sapiens

<400> SEQUENCE: 18

```
Met Asp Gln Lys Leu Ser Lys Leu Val Glu Glu Leu Thr Thr Ser Gly
1               5                   10                  15

Glu Pro Arg Leu Asn Pro Glu Lys Met Lys Glu Leu Lys Lys Ile Cys
            20                  25                  30

Lys Ser Ser Glu Glu Gln Leu Ser Arg Ala Tyr Arg Leu Leu Ile Ala
        35                  40                  45

Gln Leu Thr Gln Glu His Ala Glu Ile Arg Leu Ser Ala Phe Gln Ile
    50                  55                  60

Val Glu Glu Leu Phe Val Arg Ser His Gln Phe Arg Met Leu Val Val
65                  70                  75                  80

Ser Asn Phe Gln Glu Phe Leu Glu Leu Thr Leu Gly Thr Asp Pro Ala
                85                  90                  95

Gln Pro Leu Pro Pro Pro Arg Glu Ala Ala Gln Arg Leu Arg Gln Ala
```

```
                100                 105                 110
Thr Thr Arg Ala Val Glu Gly Trp Asn Glu Lys Phe Gly Glu Ala Tyr
            115                 120                 125
Lys Lys Leu Ala Leu Gly Tyr His Phe Leu Arg His Asn Lys Lys Val
            130                 135                 140
Asp Phe Gln Asp Thr Asn Ala Arg Ser Leu Ala Glu Arg Lys Arg Glu
145                 150                 155                 160
Glu Glu Lys Gln Lys His Leu Asp Lys Ile Tyr Gln Glu Arg Ala Ser
                165                 170                 175
Gln Ala Glu Arg Glu Met Gln Glu Met Ser Gly Glu Ile Glu Ser Cys
                180                 185                 190
Leu Thr Glu Val Glu Ser Cys Phe Arg Leu Leu Val Pro Phe Asp Phe
            195                 200                 205
Asp Pro Asn Pro Glu Thr Glu Ser Leu Gly Met Ala Ser Gly Met Ser
            210                 215                 220
Asp Ala Leu Arg Ser Ser Cys Ala Gly Gln Val Gly Pro Cys Arg Ser
225                 230                 235                 240
Gly Thr Pro Asp Pro Arg Asp Gly Glu Gln Pro Cys Cys Ser Arg Asp
                245                 250                 255
Leu Pro Ala Ser Ala Gly His Pro Arg Ala Gly Gly Ala Gln Pro
                260                 265                 270
Ser Gln Thr Ala Thr Gly Asp Pro Ser Asp Glu Asp Glu Asp Ser Asp
            275                 280                 285
Leu Glu Glu Phe Val Arg Ser His Gly Leu Gly Ser His Lys Tyr Thr
            290                 295                 300
Leu Asp Val Glu Leu Cys Ser Glu Gly Leu Lys Val Gln Glu Asn Glu
305                 310                 315                 320
Asp Asn Leu Ala Leu Ile His Ala Ala Arg Asp Thr Leu Lys Leu Ile
                325                 330                 335
Arg Asn Lys Phe Leu Pro Ala Val Cys Ser Trp Ile Gln Arg Phe Thr
            340                 345                 350
Arg Val Gly Thr His Gly Gly Cys Leu Lys Arg Ala Ile Asp Leu Lys
            355                 360                 365
Ala Glu Leu Glu Leu Val Leu Arg Lys Tyr Lys Glu Leu Asp Ile Glu
            370                 375                 380
Pro Glu Gly Gly Glu Arg Arg Arg Thr Glu Ala Leu Gly Asp Ala Glu
385                 390                 395                 400
Glu Asp Glu Asp Glu Asp Phe Val Glu Val Pro Glu Lys Glu Gly
                405                 410                 415
Tyr Glu Pro His Ile Pro Asp His Leu Arg Pro Glu Tyr Gly Leu Glu
                420                 425                 430
Ala Ala Pro Glu Lys Asp Thr Val Val Arg Cys Leu Arg Thr Arg Thr
            435                 440                 445
Arg Met Asp Glu Glu Val Ser Asp Pro Thr Ser Ala Ala Ala Gln Leu
450                 455                 460
Arg Gln Leu Arg Asp His Leu Pro Pro Ser Ser Ala Ser Pro Ser
465                 470                 475                 480
Arg Ala Leu Pro Glu Pro Gln Glu Ala Gln Lys Leu Ala Ala Glu Arg
                485                 490                 495
Ala Arg Ala Pro Val Val Pro Tyr Gly Val Asp Leu His Tyr Trp Gly
                500                 505                 510
Gln Glu Leu Pro Thr Ala Gly Lys Ile Val Lys Ser Asp Ser Gln His
            515                 520                 525
```

```
Arg Phe Trp Lys Pro Ser Glu Val Glu Glu Val Val Asn Ala Asp
    530                 535                 540
Ile Ser Glu Met Leu Arg Ser Arg His Ile Thr Phe Ala Gly Lys Phe
545                 550                 555                 560
Glu Pro Val Gln His Trp Cys Arg Ala Pro Arg Pro Asp Gly Arg Leu
                565                 570                 575
Cys Glu Arg Gln Asp Arg Leu Lys Cys Pro Phe His Gly Lys Ile Val
            580                 585                 590
Pro Arg Asp Asp Glu Gly Arg Pro Leu Asp Pro Glu Asp Arg Ala Arg
        595                 600                 605
Glu Gln Arg Arg Gln Leu Gln Lys Gln Glu Arg Pro Glu Trp Gln Asp
    610                 615                 620
Pro Glu Leu Met Arg Asp Val Glu Ala Ala Thr Gly Gln Asp Leu Gly
625                 630                 635                 640
Ser Ser Arg Tyr Ser Gly Lys Gly Arg Gly Lys Lys Arg Arg Tyr Pro
                645                 650                 655
Ser Leu Thr Asn Leu Lys Ala Gln Ala Asp Thr Ala Arg Ala Arg Ile
            660                 665                 670
Gly Arg Lys Val Phe Ala Lys Ala Ala Val Arg Val Val Ala Ala
        675                 680                 685
Met Asn Arg Met Asp Gln Lys Lys His Glu Lys Phe Ser Asn Gln Phe
    690                 695                 700
Asn Tyr Ala Leu Asn
705

<210> SEQ ID NO 19
<211> LENGTH: 2947
<212> TYPE: DNA
<213> ORGANISM: Homo sapiens

<400> SEQUENCE: 19
tgctgtagct gccatgggca aaagagaccg agcggaccgc ggtgagacgt tgcgcgggca      60
cgctcagcca cgactgccct tgccggcect gcccccgct ctgcctcgga gctgctccgg     120
gcctctgcgc cggccgaccc tgctggccct cccgcgcgca ccccgttggg acaggccttt     180
gggcgggaga gatgctggac ctgggcgcag cccagcgaac tcggcctagg ggagacgggt     240
gaggggcgca acgcctgcgg gatgcaggtg gctcttagct aggagtttgc ggcggcgcag     300
acaagaagaa atccaggaag cggcactatg aggatgaaga ggatgatgaa gaggacgccc     360
cggggaacga ccctcaggaa gcggttccct cggcggcggg gaagcaggtg gatgagtcag     420
gcaccaaagt ggatgaatat ggagccaagg actacaggct gcaaatgccg ctgaaggacg     480
accacacctc caggcccctc tgggtggctc ccgatggcca tatcttcttg gaagccttct     540
ctccagttta caaatatgcc caagacttct tggtggctat tgcagagcca gtgtgccgac     600
caacccatgt gcatgagtac aaactaactg cctactcctt gtatgcagct gtcagcgttg     660
ggctgcaaac cagtgacatc accgagtacc tcaggaagct cagcaagact ggagtccctg     720
atggaattat gcagtttatt aagttgtgta ctgtcagcta tggaaaagtc aagctggtct     780
tgaagcacaa cagatacttc gttgaaagtt gccaccctga tgtaatccag catcttctcc     840
aggaccccgt gatccgagaa tgccgcttaa gaaactctga gggggaggcc actgagctca     900
tcacagagac tttcacaagc aaatctgcca tttctaagac tgctgaaagc agtggtgggc     960
cctccacttc ccgagtgaca gatccacagg gtaaatctga catccccatg gacctgtttg    1020
```

| acttctatga gcaaatggac aaggatgaag aagaagaaga agagacacag acagtgtctt | 1080 |
| ttgaagtcaa gcaggaaatg attgaggaac tccagaaacg ttgcatccac ctggagtacc | 1140 |
| ctctgttggc agaatatgac ttccggaatg attctgtcaa ccctgatatc aacattgacc | 1200 |
| taaagcccac agctgtcctc agaccctatc aggagaagag cttgcgaaag atgtttggaa | 1260 |
| acgggcgtgc acgttcgggg gtcattgttc ttccctgcgg tgctggaaag tccctggttg | 1320 |
| gtgtgactgc tgcatgcact gtcagaaaac gctgtctggt gctgggcaac tcagctgttt | 1380 |
| ctgtggagca gtggaaagcc cagttcaaga tgtggtccac cattgacgac agccagatct | 1440 |
| gccggttcac ctccgatgcc aaggacaagc ccatcggctg ctccgttgcc attagcaccct | 1500 |
| actccatgct gggccacacc accaaaaggt cctgggaggc cgagcgagtc atggagtggc | 1560 |
| tcaagaccca ggagtggggc ctcatgatcc tggatgaagt gcacaccata ccagccaaga | 1620 |
| tgttccgaag ggtgctcacc atcgtgcagg cccactgtaa gctgggtttg actgcgaccc | 1680 |
| tcgtccgcga agatgacaaa attgtggatt taaattttct gattgggcct aagctctacg | 1740 |
| aagccaactg gatggagctg cagaataatg ctacatcgc caaagtccag tgtgctgagg | 1800 |
| tctggtgccc tatgtctcct gaattttacc gggaatatgt ggcaatcaaa accaagaaac | 1860 |
| gaatcttgct gtacaccatg aaccccaaca aatttagagc ttgccagttt ctgatcaagt | 1920 |
| ttcatgaaag gaggaatgac aagattattg tctttgctga caatgtgttt gccctaaagg | 1980 |
| aatatgccat tcgactgaac aaaccctata tctacgacc tacgtctcag ggggaaagga | 2040 |
| tgcaaattct ccagaatttc aagcacaacc ccaaaattaa caccatcttc atatccaagg | 2100 |
| taggtgacac ttcgtttgat ctgccggaag caaatgtcct cattcagatc tcatcccatg | 2160 |
| gtggctccag gcgtcaggaa gcccaaaggc tagggcgggt gcttcgagct aaaaaaggga | 2220 |
| tggttgcaga agagtacaat gccttttct actcactggt atcccaggac acacaggaaa | 2280 |
| tggcttactc aaccaagcgg cagagattct tggtagatca aggttatagc ttcaaggtga | 2340 |
| tcacgaaact cgctggcatg gaggaggaag acttggcgtt ttcgacaaaa gaagagcaac | 2400 |
| agcagctctt acagaaagtc ctggcagcca ctgacctgga tgccgaggag gaggtggtgg | 2460 |
| ctggggaatt tggctccaga tccagccagg catctcggcg ctttggcacc atgagttcta | 2520 |
| tgtctggggc cgacgacact gtgtacatgg agtaccactc atcgcggagc aaggcgccca | 2580 |
| gcaaacatgt acacccgctc ttcaagcgct ttaggaaatg atgcttaggc agggtacttc | 2640 |
| gttcaagacc ggcgcttggc acccttgttg gaaagggatt ttcagcataa catttctctt | 2700 |
| ccacctcttt gaccttccct ccagcgttgg ccaaattgtg ctgaggaaga tgcatcaagg | 2760 |
| gcttggctgt gccttcatag gtcatctagg gttttataaa ggaggaggag acaatatttt | 2820 |
| ttcaaacttt ttgggggagtg gggtcatttc tgtatataaa aaatgttaat atttaaggtg | 2880 |
| tatttatgtt accgttctga ataaacagaa tggaccattg aaccagtaaa aaaaaaaaaa | 2940 |
| aaaaaaa | 2947 |

<210> SEQ ID NO 20
<211> LENGTH: 718
<212> TYPE: PRT
<213> ORGANISM: Homo sapiens

<400> SEQUENCE: 20

Met Pro Leu Lys Asp Asp His Thr Ser Arg Pro Leu Trp Val Ala Pro
1               5                   10                  15

Asp Gly His Ile Phe Leu Glu Ala Phe Ser Pro Val Tyr Lys Tyr Ala
                20                  25                  30

-continued

```
Gln Asp Phe Leu Val Ala Ile Ala Glu Pro Val Cys Arg Pro Thr His
         35                  40                  45
Val His Glu Tyr Lys Leu Thr Ala Tyr Ser Leu Tyr Ala Ala Val Ser
 50                  55                  60
Val Gly Leu Gln Thr Ser Asp Ile Thr Glu Tyr Leu Arg Lys Leu Ser
 65                  70                  75                  80
Lys Thr Gly Val Pro Asp Gly Ile Met Gln Phe Ile Lys Leu Cys Thr
                 85                  90                  95
Val Ser Tyr Gly Lys Val Lys Leu Val Leu Lys His Asn Arg Tyr Phe
                100                 105                 110
Val Glu Ser Cys His Pro Asp Val Ile Gln His Leu Leu Gln Asp Pro
                115                 120                 125
Val Ile Arg Glu Cys Arg Leu Arg Asn Ser Glu Gly Glu Ala Thr Glu
        130                 135                 140
Leu Ile Thr Glu Thr Phe Thr Ser Lys Ser Ala Ile Ser Lys Thr Ala
145                 150                 155                 160
Glu Ser Ser Gly Gly Pro Ser Thr Ser Arg Val Thr Asp Pro Gln Gly
                165                 170                 175
Lys Ser Asp Ile Pro Met Asp Leu Phe Asp Phe Tyr Glu Gln Met Asp
                180                 185                 190
Lys Asp Glu Glu Glu Glu Thr Gln Thr Val Ser Phe Glu Val
                195                 200                 205
Lys Gln Glu Met Ile Glu Glu Leu Gln Lys Arg Cys Ile His Leu Glu
        210                 215                 220
Tyr Pro Leu Leu Ala Glu Tyr Asp Phe Arg Asn Asp Ser Val Asn Pro
225                 230                 235                 240
Asp Ile Asn Ile Asp Leu Lys Pro Thr Ala Val Leu Arg Pro Tyr Gln
                245                 250                 255
Glu Lys Ser Leu Arg Lys Met Phe Gly Asn Gly Arg Ala Arg Ser Gly
                260                 265                 270
Val Ile Val Leu Pro Cys Gly Ala Gly Lys Ser Leu Val Gly Val Thr
        275                 280                 285
Ala Ala Cys Thr Val Arg Lys Arg Cys Leu Val Leu Gly Asn Ser Ala
        290                 295                 300
Val Ser Val Glu Gln Trp Lys Ala Gln Phe Lys Met Trp Ser Thr Ile
305                 310                 315                 320
Asp Asp Ser Gln Ile Cys Arg Phe Thr Ser Asp Ala Lys Asp Lys Pro
                325                 330                 335
Ile Gly Cys Ser Val Ala Ile Ser Thr Tyr Ser Met Leu Gly His Thr
                340                 345                 350
Thr Lys Arg Ser Trp Glu Ala Glu Arg Val Met Glu Trp Leu Lys Thr
        355                 360                 365
Gln Glu Trp Gly Leu Met Ile Leu Asp Glu Val His Thr Ile Pro Ala
        370                 375                 380
Lys Met Phe Arg Arg Val Leu Thr Ile Val Gln Ala His Cys Lys Leu
385                 390                 395                 400
Gly Leu Thr Ala Thr Leu Val Arg Glu Asp Asp Lys Ile Val Asp Leu
                405                 410                 415
Asn Phe Leu Ile Gly Pro Lys Leu Tyr Glu Ala Asn Trp Met Glu Leu
                420                 425                 430
Gln Asn Asn Gly Tyr Ile Ala Lys Val Gln Cys Ala Glu Val Trp Cys
        435                 440                 445
```

```
Pro Met Ser Pro Glu Phe Tyr Arg Glu Tyr Val Ala Ile Lys Thr Lys
    450                 455                 460

Lys Arg Ile Leu Leu Tyr Thr Met Asn Pro Asn Lys Phe Arg Ala Cys
465                 470                 475                 480

Gln Phe Leu Ile Lys Phe His Glu Arg Arg Asn Asp Lys Ile Ile Val
                485                 490                 495

Phe Ala Asp Asn Val Phe Ala Leu Lys Glu Tyr Ala Ile Arg Leu Asn
            500                 505                 510

Lys Pro Tyr Ile Tyr Gly Pro Thr Ser Gln Gly Glu Arg Met Gln Ile
        515                 520                 525

Leu Gln Asn Phe Lys His Asn Pro Lys Ile Asn Thr Ile Phe Ile Ser
    530                 535                 540

Lys Val Gly Asp Thr Ser Phe Asp Leu Pro Glu Ala Asn Val Leu Ile
545                 550                 555                 560

Gln Ile Ser Ser His Gly Gly Ser Arg Arg Gln Ala Gln Arg Leu
                565                 570                 575

Gly Arg Val Leu Arg Ala Lys Lys Gly Met Val Ala Glu Glu Tyr Asn
            580                 585                 590

Ala Phe Phe Tyr Ser Leu Val Ser Gln Asp Thr Gln Glu Met Ala Tyr
        595                 600                 605

Ser Thr Lys Arg Gln Arg Phe Leu Val Asp Gln Gly Tyr Ser Phe Lys
    610                 615                 620

Val Ile Thr Lys Leu Ala Gly Met Glu Glu Glu Asp Leu Ala Phe Ser
625                 630                 635                 640

Thr Lys Glu Glu Gln Gln Gln Leu Leu Gln Lys Val Leu Ala Ala Thr
                645                 650                 655

Asp Leu Asp Ala Glu Glu Val Val Ala Gly Glu Phe Gly Ser Arg
            660                 665                 670

Ser Ser Gln Ala Ser Arg Arg Phe Gly Thr Met Ser Ser Met Ser Gly
        675                 680                 685

Ala Asp Asp Thr Val Tyr Met Glu Tyr His Ser Arg Ser Lys Ala
    690                 695                 700

Pro Ser Lys His Val His Pro Leu Phe Lys Arg Phe Arg Lys
705                 710                 715

<210> SEQ ID NO 21
<211> LENGTH: 2568
<212> TYPE: DNA
<213> ORGANISM: Homo sapiens

<400> SEQUENCE: 21
ttcatgaggg aggcgggtcg accccgctgc acagtccggc cggcgccatg aagctcaacg      60
tggacgggct cctggtctac ttcccgtacg actacatcta ccccgagcag ttctcctaca     120
tgcgggagct caaacgcacg ctggacgcca agggtcatgg agtcctggag atgccctcag     180
gcaccgggaa gacagtatcc ctgttggccc tgatcatggc ataccagaga gcatatccgc     240
tggaggtgac caaactcatc tactgctcaa gaactgtgcc agagattgag aaggtgattg     300
aagagcttcg aaagttgctc aacttctatg agaagcagga gggcgagaag ctgccgtttc     360
tgggactggc tctgagctcc cgcaaaaact tgtgtattca ccctgaggtg acacccctgc     420
gctttgggaa ggacgtcgat gggaaatgcc acagcctcac agcctcctat gtgcgggcgc     480
agtaccagca tgacaccagc ctgccccact gccgattcta tgaggaattt gatgcccatg     540
ggcgtgaggt gccctccccc gctggcatct acaacctgga tgacctgaag gccctggggc     600
```

```
ggcgccaggg ctggtgccca tacttccttg ctcgatactc aatcctgcat gccaatgtgg    660
tggtttatag ctaccactac ctcctggacc ccaagattgc agacctggtg tccaaggaac    720
tggcccgcaa ggccgtcgtg gtcttcgacg aggcccacaa cattgacaac gtctgcatcg    780
actccatgag cgtcaacctc acccgccgga cccttgaccg gtgccagggc aacctggaga    840
ccctgcagaa gacggtgctc aggatcaaag agacagacga gcagcgcctg cgggacgagt    900
accggcgtct ggtggagggg ctgcgggagg ccagcgccgc ccgggagacg gacgcccacc    960
tggccaaccc cgtgctgccc gacgaagtgc tgcaggaggc agtgcctggc tccatccgca   1020
cggccgagca tttcctgggc ttcctgaggc ggctgctgga gtacgtgaag tggcggctgc   1080
gtgtgcagca tgtggtgcag gagagcccgc ccgccttcct gagcggcctg cccagcgcg   1140 tgtgcatcca gcgcaagccc ctcagattct gtgctgaacg cctccggtcc ctgctgcata   1200
ctctggagat caccgacctt gctgacttct ccccgctcac cctccttgct aactttgcca   1260
cccttgtcag cacctacgcc aaaggcttca ccatcatcat cgagcccttt gacgacagaa   1320
ccccgaccat tgccaacccc atcctgcact tcagctgcat ggacgcctcg ctggccatca   1380
aacccgtatt tgagcgtttc cagtctgtca tcatcacatc tgggacactg tccccgctgg   1440
acatctaccc caagatcctg gacttccacc ccgtcaccat ggcaaccttc accatgacgc   1500
tggcacgggt ctgcctctgc cctatgatca tcggccgtgg caatgaccag gtggccatca   1560
gctccaaatt tgagacccgg gaggatattg ctgtgatccg gaactatggg aacctcctgc   1620
tggagatgtc cgctgtggtc cctgatggca tcgtggcctt cttcaccagc taccagtaca   1680
tggagagcac cgtggcctcc tggtatgagc aggggatcct tgagaacatc cagaggaaca   1740
agctgctctt tattgagacc caggatggtg ccgaaaccag tgtcgccctg gagaagtacc   1800
aggaggcctg cgagaatggc cgcggggcca tcctgctgtc agtggcccgg ggcaaagtgt   1860
ccgagggaat cgactttgtg caccactacg gcgggccgt catcatgttt ggcgtcccct   1920
acgtctacac acagagccgc attctcaagg cgcggctgga atacctgcgg gaccagttcc   1980
agattcgtga gaatgacttt cttaccttcg atgccatgcg ccacgcggcc cagtgtgtgg   2040
gtcgggccat caggggcaag acggactacg gcctcatggt cttttgccgac aagcggtttg   2100 cccgtgggga caagcggggg aagctgcccc gctggatcca ggagcacctc acagatgcca   2160 acctcaaccct gaccgtggac gagggtgtcc aggtggccaa gtacttcctg cggcagatgg   2220 cacagcccctt ccaccgggag atcagctggg gcctgtccct gctcagcctg gagcagctag   2280
aatcagagga gacgctgaag aggatagagc agattgctca gcagctctga gtggggcggg   2340 tggggcccata aacggttcct ggtgactcct gagtcttgcc tggccctggt tcccagcggc   2400
ggtggtgcta gaaggtctta tgaagtcagg tgacatttct cactgtcacg tccacagcct   2460
ttaatcgcag gagaaggcag ctatccacca ggtacccaga ggcaagggg ggccaggaga   2520 tgatagaccc cctctcaccc caccagccca tccctcctgc actgttcc                2568
```

<210> SEQ ID NO 22
<211> LENGTH: 760
<212> TYPE: PRT
<213> ORGANISM: Homo sapiens

<400> SEQUENCE: 22

Met Lys Leu Asn Val Asp Gly Leu Leu Val Tyr Phe Pro Tyr Asp Tyr
1               5                   10                  15

Ile Tyr Pro Glu Gln Phe Ser Tyr Met Arg Glu Leu Lys Arg Thr Leu
            20                  25                  30

-continued

```
Asp Ala Lys Gly His Gly Val Leu Glu Met Pro Ser Gly Thr Gly Lys
         35                  40                  45

Thr Val Ser Leu Leu Ala Leu Ile Met Ala Tyr Gln Arg Ala Tyr Pro
 50                  55                  60

Leu Glu Val Thr Lys Leu Ile Tyr Cys Ser Arg Thr Val Pro Glu Ile
 65                  70                  75                  80

Glu Lys Val Ile Glu Glu Leu Arg Lys Leu Leu Asn Phe Tyr Glu Lys
                 85                  90                  95

Gln Glu Gly Glu Lys Leu Pro Phe Leu Gly Leu Ala Leu Ser Ser Arg
                100                 105                 110

Lys Asn Leu Cys Ile His Pro Glu Val Thr Pro Leu Arg Phe Gly Lys
            115                 120                 125

Asp Val Asp Gly Lys Cys His Ser Leu Thr Ala Ser Tyr Val Arg Ala
130                 135                 140

Gln Tyr Gln His Asp Thr Ser Leu Pro His Cys Arg Phe Tyr Glu Glu
145                 150                 155                 160

Phe Asp Ala His Gly Arg Glu Val Pro Leu Pro Ala Gly Ile Tyr Asn
                165                 170                 175

Leu Asp Asp Leu Lys Ala Leu Gly Arg Arg Gln Gly Trp Cys Pro Tyr
            180                 185                 190

Phe Leu Ala Arg Tyr Ser Ile Leu His Ala Asn Val Val Tyr Ser
            195                 200                 205

Tyr His Tyr Leu Leu Asp Pro Lys Ile Ala Asp Leu Val Ser Lys Glu
        210                 215                 220

Leu Ala Arg Lys Ala Val Val Phe Asp Glu Ala His Asn Ile Asp
225                 230                 235                 240

Asn Val Cys Ile Asp Ser Met Ser Val Asn Leu Thr Arg Arg Thr Leu
                245                 250                 255

Asp Arg Cys Gln Gly Asn Leu Glu Thr Leu Gln Lys Thr Val Leu Arg
            260                 265                 270

Ile Lys Glu Thr Asp Glu Gln Arg Leu Arg Asp Glu Tyr Arg Arg Leu
        275                 280                 285

Val Glu Gly Leu Arg Glu Ala Ser Ala Ala Arg Glu Thr Asp Ala His
290                 295                 300

Leu Ala Asn Pro Val Leu Pro Asp Glu Val Leu Gln Glu Ala Val Pro
305                 310                 315                 320

Gly Ser Ile Arg Thr Ala Glu His Phe Leu Gly Phe Leu Arg Arg Leu
                325                 330                 335

Leu Glu Tyr Val Lys Trp Arg Leu Arg Val Gln His Val Val Gln Glu
            340                 345                 350

Ser Pro Pro Ala Phe Leu Ser Gly Leu Ala Gln Arg Val Cys Ile Gln
        355                 360                 365

Arg Lys Pro Leu Arg Phe Cys Ala Glu Arg Leu Arg Ser Leu Leu His
370                 375                 380

Thr Leu Glu Ile Thr Asp Leu Ala Asp Phe Ser Pro Leu Thr Leu Leu
385                 390                 395                 400

Ala Asn Phe Ala Thr Leu Val Ser Thr Tyr Ala Lys Gly Phe Thr Ile
                405                 410                 415

Ile Ile Glu Pro Phe Asp Asp Arg Thr Pro Thr Ile Ala Asn Pro Ile
            420                 425                 430

Leu His Phe Ser Cys Met Asp Ala Ser Leu Ala Ile Lys Pro Val Phe
        435                 440                 445
```

```
Glu Arg Phe Gln Ser Val Ile Ile Thr Ser Gly Thr Leu Ser Pro Leu
    450                 455                 460
Asp Ile Tyr Pro Lys Ile Leu Asp Phe His Pro Val Thr Met Ala Thr
465                 470                 475                 480
Phe Thr Met Thr Leu Ala Arg Val Cys Leu Cys Pro Met Ile Ile Gly
                485                 490                 495
Arg Gly Asn Asp Gln Val Ala Ile Ser Ser Lys Phe Glu Thr Arg Glu
            500                 505                 510
Asp Ile Ala Val Ile Arg Asn Tyr Gly Asn Leu Leu Leu Glu Met Ser
        515                 520                 525
Ala Val Val Pro Asp Gly Ile Val Ala Phe Phe Thr Ser Tyr Gln Tyr
530                 535                 540
Met Glu Ser Thr Val Ala Ser Trp Tyr Glu Gln Gly Ile Leu Glu Asn
545                 550                 555                 560
Ile Gln Arg Asn Lys Leu Leu Phe Ile Glu Thr Gln Asp Gly Ala Glu
                565                 570                 575
Thr Ser Val Ala Leu Glu Lys Tyr Gln Glu Ala Cys Glu Asn Gly Arg
            580                 585                 590
Gly Ala Ile Leu Leu Ser Val Ala Arg Gly Lys Val Ser Glu Gly Ile
        595                 600                 605
Asp Phe Val His His Tyr Gly Arg Ala Val Ile Met Phe Gly Val Pro
    610                 615                 620
Tyr Val Tyr Thr Gln Ser Arg Ile Leu Lys Ala Arg Leu Glu Tyr Leu
625                 630                 635                 640
Arg Asp Gln Phe Gln Ile Arg Glu Asn Asp Phe Leu Thr Phe Asp Ala
                645                 650                 655
Met Arg His Ala Ala Gln Cys Val Gly Arg Ala Ile Arg Gly Lys Thr
            660                 665                 670
Asp Tyr Gly Leu Met Val Phe Ala Asp Lys Arg Phe Ala Arg Gly Asp
        675                 680                 685
Lys Arg Gly Lys Leu Pro Arg Trp Ile Gln Glu His Leu Thr Asp Ala
    690                 695                 700
Asn Leu Asn Leu Thr Val Asp Glu Gly Val Gln Val Ala Lys Tyr Phe
705                 710                 715                 720
Leu Arg Gln Met Ala Gln Pro Phe His Arg Glu Asp Gln Leu Gly Leu
                725                 730                 735
Ser Leu Leu Ser Leu Glu Gln Leu Glu Ser Glu Thr Leu Lys Arg
            740                 745                 750
Ile Glu Gln Ile Ala Gln Gln Leu
        755                 760

<210> SEQ ID NO 23
<211> LENGTH: 6765
<212> TYPE: DNA
<213> ORGANISM: Homo sapiens

<400> SEQUENCE: 23
agagcttcca tggagtcagg gcagccggct cgacggattg ccatggcgcc gctgctggag      60
tacgagcgac agctggtgct ggaactgctc gacactgacg ggctagtagt gtgcgcccgc     120
gggctcggcg cggaccggct cctctaccac tttctccagc tgcactgcca cccagcctgc     180
ctggtgctgg tgctcaacac gcagccggcc gaggaggagt attttatcaa tcagctgaag     240
atagaaggag ttgaacacct ccctcgccgt gtaacaaatg aaatcacaag caacagtcgc     300
tatgaagttt acacacaagg tggtgttata tttgcgacaa gtaggatact tgtggttgac     360
```

```
ttcttgactg atagaatacc ttcagattta attactggca tcttggtgta tagagcccac    420
agaataatcg agtcttgtca agaagcattc atcttgcgcc tctttcgcca gaaaaacaaa    480
cgtggtttta ttaaagcttt cacagacaat gctgttgcct ttgatactgg tttttgtcat    540
gtggaaagag tgatgagaaa tcttttttgtg aggaaactgt atctgtggcc aaggttccat    600
gtagcagtaa actcattttt agaacagcac aaacctgaag ttgtagaaat ccatgtttct    660
atgcacccta ccatgcttgc tatacagact gctatactgg acattttaaa tgcatgtcta    720
aaggaactaa aatgccataa cccatcgctt gaagtggaag attttatcttt agaaaatgct    780 attggaaaac cttttgacaa gacaatccgc cattatctgg atcctttgtg gcaccagctt    840
ggagccaaga ctaaatcctt agttcaggat ttgaagatat tacgaacttt gctgcagtat    900
ctctctcagt atgattgtgt cacatttctt aatcttctgg aatctctgag agcaacggaa    960
aaagcttttg gtcagaattc aggttggctg tttcttgact ccagcacctc gatgtttata   1020
aatgctcgag caagggttta tcatcttcca gatgccaaaa tgagtaaaaa agaaaaaata   1080
tctgaaaaaa tggaaattaa agaaggggaa gaaacaaaaa aggaactggt cctagaaagc   1140
aacccaaagt gggaggcact gactgaagta ttaaaagaaa ttgaggcaga aaataaggag   1200
agtgaagctc ttggtggtcc aggtcaagta ctgatttgtg caagtgatga ccgaacatgt   1260
tcccagctga gagactatat cactcttgga gcggaggcct tcttattgag gctctacagg   1320
aaaacctttg agaaggatag caaagctgaa gaagtctgga tgaaatttag gaaggaagac   1380
agttcaaaga gaattaggaa atctcacaaa agacctaaag accccaaaa caaagaacgg   1440 gcttctacca agaaagaac cctcaaaaag aaaaaacgga gttgaccctt aactcaaatg   1500
gtaggaaaac ctgaagaact ggaagaggaa ggagatgtcg aggaaggata tcgtcgagaa   1560
ataagcagta gcccagaaag ctgcccggaa gaaattaagc atgaagaatt tgatgtaaat   1620
ttgtcatcgg atgctgcttt cggaatcctg aaagaacccc tcactatcat ccatccgctt   1680
ctgggttgca gcgacccta tgctctgaca agggtactac atgaagtgga gccaagatac   1740
gtggttcttt atgacgcaga gctaaccttt gttcggcagc ttgaaattta cagggcgagt   1800
aggcctggga aacctctgag ggtttacttt cttatatacg gaggttcaac tgaggaacaa   1860
cgctatctca ctgcttttgcg gaaagaaaag gaagcttttg aaaaactcat aagggaaaaa   1920
gcaagcatgg ttgtccctga agaaagaaa ggcagagatg aaacaaactt agacctagta   1980
agaggcacag catctgcaga tgtttccact gacactcgga aagccggtgg ccaggaacag   2040
aatggtacac agcaaagcat agttgtggat atgcgtgaat tcgaagtga gcttccatct   2100 ctgatccatc gtcggggcat tgacattgaa cccgtgactt tagaggttgg agattacatc   2160
ctcactccag aaatgtgcgt ggagcgcaag agtatcagtg atttaatcgg ctctttaaat   2220
aacggccgcc tctacagcca gtgcatctcc atgtcccgct actacaagcg tcccgtgctt   2280
ctgattgagt ttgaccctag caagcctttc tctctcactt cccgaggtgc cttgtttcag   2340
gagatctcca gcaatgacat tagttccaaa ctcactcttc ttacacttca cttccccaga   2400
ctacggattc tctggtgccc ctctcctcat gcaacggcgg agttgtttga ggagctgaaa   2460
caaagcaagc cacagcctga tgcggcgaca gcactggcca ttacagcaga ttctgaaacc   2520
cttcccgagt cagagaagta taatcctggt ccccaagact tcttgttaaa aatgccaggg   2580
gtgaatgcca aaaactgccg ctccttgatg caccacgtta agaacatcgc agaattagca   2640
gccctgtcac aagacgagct cacgagtatt ctggggaatg ctgcaaatgc caaacagctt   2700
```

```
tatgatttca ttcacacctc ttttgcagaa gtcgtatcaa aaggaaaagg gaaaaagtga    2760
acagtgatgg ctgttttctt atcccatgcc tgtacttttc agcggctcct tgccagacat    2820
cataggtcat tattaattat tggtttgcta tttcattctt ttccaatgct cttaatgatt    2880
gtacggtgga ccagaagcca ggattcctct ctgaactctg cagttaggca tcacttgaac    2940
ttgcctgtgc ctgctctttt tcctccctgc accgtctatg ccgggcttag catgtttctt    3000
tttaaatgag gtttgtcagg atcaggtaaa gttcctacaa gtgattacag aaggtagaaa    3060
ctttacctga tcctaacaga tctcatttag aaaggaatat gctaagcctg gcatggacgg    3120
tgcagggagg gaaaagagca ggcacaagaa agctaccatt tttaacagtc cttgttatct    3180
agtgcaacat aaataacagt cttaattgca cttatacccca tgtcctgtgg ctctccaaat    3240
ctggtctttg ctgttgtgtc tgctggacgc ttgaactgat gtttgtgtag gaaatcatgt    3300 tctgacccctt tgtctacaaa ggagccttct ggaacactga gaagaaacat ctctttgcca    3360
ttcctgacca gttctctcta ccacattttc ttcagctcca tacttctgcc tgtctgctct    3420
aaggaaattt catggagcct tcctactact aattcaagac agtctcctca aaaactggtt    3480
gactagtctt ctaatgaccc taacatatgt agcatatact ataatttcat tgttccaaat    3540 tagtatttt aaagcaaaat gaattacctg tttgcaaaag ttaatgatga aggagctctt    3600
agaattctca atttttgcac atattcagtc tcctaatatc agagatccct aagtccagct    3660
ggctagttac agagtttttt cagacttcct cgtttctcag ctcttatatc ctaagacacc    3720
agcatcatat cctctagaaa tacaacctaa ttggcagtga gccgagatcg caccactgca    3780
cccctgcctg ggcgacagag tgagactttg tctctattac aaaagaaaaa gaaagaaat    3840 acaacctaag ctcacctgcc tgtgattcct catttctcac catcctgtgc cagggtggct    3900
acttctctct gtgaggactc aaatacaagc caatgagtgg cccactaagc ttttaagatt    3960 tgatttttcct gccttgagat aaaaggagt gtaggtaaat gaaagatcaa tgtatggaat    4020
atataaaaat acgaaagaaa tatatacgtt taaaaatcca taaagaaaaa aatctcattc    4080
taaacctgat taagttggct ttttacgtaa gtgtacaaat aggatattca cagcatcttt    4140
gtgcagtttt taaacttta tatttaaaca ttattaagtt ggcttttgtt cacatgttga    4200
gtaatgggta gtaaattttc tacctcagga gctgatatag acatcagttc tgctagccat    4260
atcacatatt ttaatgtttc atcaacatca gctgtttttt tgtttgctac actatttgaa    4320
ctaatagaca gtggatcatg taacacaaaa ttgtcttcaa ctttaacaaa attgtcattg    4380
ttattttttt ttgagacaga gtctccctct gttgcccagg ctggagtgca gtggcgcaat    4440
ctcggctcac tgcaacctcg cctgctgggt tcaagcagtt ctcccacctc agcctcccaa    4500
gtagctggga ttataggtgt gcaccaccag acccggctaa ttttttgtatt tttagtagag    4560 acggggtttc accatgttgg ccaggctggt ctcaaactac tgacctcagg tgatccaccc    4620
accttggcct cccaaagtgc tgagataaca ggcgtgagcc accgcaccca cccaacaaaa    4680
ttatttttaa ctgtcgtttc tgaactgaac ctctcacatt ggcatcttga tttattggta    4740
cttaacagta tatatggatt ttgaactcta cacaagggta taaccagaat gaattgaggg    4800
gtatcaagaa ccagattggt tacagtagaa ctctgtaaga tgatgtggag agtaaggaaa    4860
aggagaagaa ataaaaatta gtttaagatg gaataaagat ttgggctgct aattttttcc    4920
caggattcaa aatatacccg ctagaatgga aacaaaaat ttgaatgatt acaacattat    4980
cgttaacatt caatttttgta tttattgttt tattgaatat agttcagagt atattaaaat    5040
agacctacca cttcaaatga taatgattat tataatgtct cttcacccta ttctagcact    5100
```

-continued

```
tctgcttgca gtatgtggtt tctatttttt tcctcttgta taattccact tgcttttaat    5160
tgttgtttca ttatataaaa ggaacatctt cccatagcat attctatgaa aggggtttca    5220
ttccaagttg agttttcaaa aaaaaggtct tcctaaagct accattttca accgtccttg    5280
ttatctagta caacataaat aacagtctta aaaattgcac taataccagt gccccctgg     5340
ctctccaaat ctgttctttg ctcttgtatc tgctggacgc ttgaagacag gtgcactgtc    5400
tcgtatgtat ttgaattatg aacagtaatt ctaatgaat tctaaaatgg tcattgtaag    5460
tgaaagcctc tcgctaccac ttcctcttcc aactacataa atatatttca atgtatttcc    5520
agttttggaa agttttcaat acatacatca agtgttact tagattttta taaaaatttt    5580
ttttacaatc taataatctt tggtaaagga actagagatg catgcagttg caaaattaat    5640
gtatttattt tccagcataa ttttattaac ttcactttt ttctctctag taaatatcca    5700
gtgtacttat gaactcatgt ttggctcttt taaaacctt tctaaaagct agatcagcat    5760
ttttctattt tacaagtttt ttgtataaaa aggtgaacat atgagatatt gtgagaaatc    5820
attttaagtt tcatttaaat catggtgcct cttttgatac tttcttaaaa ttgtgcaaga    5880
agaaatcatt tttagtagtg gtcataaata ttatcctttt ggcagtaagc tattactaat    5940
tcagcctgaa gctcggtaga caatatgtct acatgtgttt gagtacatcc tggatacagt    6000
ttcccagctc atgagggact gaaaatagtc ttattcatca acccactagg atgtgaaggg    6060
ttaagtctag atttggtcgc attgaaaccc cacaatatag aattaataaa tggccttcag    6120
taggaaaacc tacactaaag caaatccgaa gaagtggggc aggggaaag aggcattact    6180
ggtctttcct tttgttttgc aagcataatt tgattttcct ttggctcaga aaactcattt    6240
ggggaaattc tcttttgtgt tcagtttaac ctagaaaggt cctcttgaaa accaacatt     6300
ttaggaaagt tcttttttca ggatggagta tattaaaatt aagccaggct ttgacgtgaa    6360
ttatcacttt tctttattat tttgttttct atttggtttt atagctatt  ctggttcagt    6420
tctgaacttc agcacttaat catccttatc aaccaggctt ttggtagcct aaaccgctat    6480
gctgttgttt tttaattta aagatgtata agccaaaatt tggatgggag tgagacataa    6540
ctgatttata tgaattttaa cagagttgta tttgtgtgtg tttaataaaa tatatattta    6600
ttcagtactt tcctcagtat tttatgggca aagtaaaaat aacaatgcat agtgaaaggg    6660
catatattac cagcagtaat aattcaaaat cctgaaaatg tttcattttt tttgttttg    6720
ttatgcagaa taaacaaggc agaaatgctc tttgaaccac taaaa                  6765
```

<210> SEQ ID NO 24
<211> LENGTH: 916
<212> TYPE: PRT
<213> ORGANISM: Homo sapiens

<400> SEQUENCE: 24

```
Met Glu Ser Gly Gln Pro Ala Arg Arg Ile Ala Met Ala Pro Leu Leu
1               5                   10                  15

Glu Tyr Glu Arg Gln Leu Val Leu Glu Leu Leu Asp Thr Asp Gly Leu
            20                  25                  30

Val Val Cys Ala Arg Gly Leu Gly Ala Asp Arg Leu Leu Tyr His Phe
        35                  40                  45

Leu Gln Leu His Cys His Pro Ala Cys Leu Val Leu Val Leu Asn Thr
    50                  55                  60

Gln Pro Ala Glu Glu Glu Tyr Phe Ile Asn Gln Leu Lys Ile Glu Gly
65                  70                  75                  80
```

-continued

```
Val Glu His Leu Pro Arg Arg Val Thr Asn Glu Ile Thr Ser Asn Ser
                 85                  90                  95

Arg Tyr Glu Val Tyr Thr Gln Gly Gly Val Ile Phe Ala Thr Ser Arg
                100                 105                 110

Ile Leu Val Val Asp Phe Leu Thr Asp Arg Ile Pro Ser Asp Leu Ile
                115                 120                 125

Thr Gly Ile Leu Val Tyr Arg Ala His Arg Ile Ile Glu Ser Cys Gln
            130                 135                 140

Glu Ala Phe Ile Leu Arg Leu Phe Arg Gln Lys Asn Lys Arg Gly Phe
145                 150                 155                 160

Ile Lys Ala Phe Thr Asp Asn Ala Val Ala Phe Asp Thr Gly Phe Cys
                165                 170                 175

His Val Glu Arg Val Met Arg Asn Leu Phe Val Arg Lys Leu Tyr Leu
                180                 185                 190

Trp Pro Arg Phe His Val Ala Val Asn Ser Phe Leu Glu Gln His Lys
                195                 200                 205

Pro Glu Val Val Glu Ile His Val Ser Met Thr Pro Thr Met Leu Ala
                210                 215                 220

Ile Gln Thr Ala Ile Leu Asp Ile Leu Asn Ala Cys Leu Lys Glu Leu
225                 230                 235                 240

Lys Cys His Asn Pro Ser Leu Glu Val Glu Asp Leu Ser Leu Glu Asn
                245                 250                 255

Ala Ile Gly Lys Pro Phe Asp Lys Thr Ile Arg His Tyr Leu Asp Pro
                260                 265                 270

Leu Trp His Gln Leu Gly Ala Lys Thr Lys Ser Leu Val Gln Asp Leu
            275                 280                 285

Lys Ile Leu Arg Thr Leu Leu Gln Tyr Leu Ser Gln Tyr Asp Cys Val
290                 295                 300

Thr Phe Leu Asn Leu Leu Glu Ser Leu Arg Ala Thr Glu Lys Ala Phe
305                 310                 315                 320

Gly Gln Asn Ser Gly Trp Leu Phe Leu Asp Ser Ser Thr Ser Met Phe
                325                 330                 335

Ile Asn Ala Arg Ala Arg Val Tyr His Leu Pro Asp Ala Lys Met Ser
                340                 345                 350

Lys Lys Glu Lys Ile Ser Glu Lys Met Glu Ile Lys Glu Gly Glu Glu
                355                 360                 365

Thr Lys Lys Glu Leu Val Leu Glu Ser Asn Pro Lys Trp Glu Ala Leu
            370                 375                 380

Thr Glu Val Leu Lys Glu Ile Glu Ala Glu Asn Lys Glu Ser Glu Ala
385                 390                 395                 400

Leu Gly Gly Pro Gly Gln Val Leu Ile Cys Ala Ser Asp Asp Arg Thr
                405                 410                 415

Cys Ser Gln Leu Arg Asp Tyr Ile Thr Leu Gly Ala Glu Ala Phe Leu
                420                 425                 430

Leu Arg Leu Tyr Arg Lys Thr Phe Glu Lys Asp Ser Lys Ala Glu Glu
            435                 440                 445

Val Trp Met Lys Phe Arg Lys Glu Asp Ser Ser Lys Arg Ile Arg Lys
450                 455                 460

Ser His Lys Arg Pro Lys Asp Pro Gln Asn Lys Glu Arg Ala Ser Thr
465                 470                 475                 480

Lys Glu Arg Thr Leu Lys Lys Lys Arg Lys Leu Thr Leu Thr Gln
                485                 490                 495
```

```
Met Val Gly Lys Pro Glu Glu Leu Glu Glu Gly Asp Val Glu Glu
            500                 505                 510

Gly Tyr Arg Arg Glu Ile Ser Ser Pro Glu Ser Cys Pro Glu Glu
            515                 520                 525

Ile Lys His Glu Glu Phe Asp Val Asn Leu Ser Ser Asp Ala Ala Phe
            530                 535                 540

Gly Ile Leu Lys Glu Pro Leu Thr Ile Ile His Pro Leu Leu Gly Cys
545                 550                 555                 560

Ser Asp Pro Tyr Ala Leu Thr Arg Val Leu His Glu Val Glu Pro Arg
                565                 570                 575

Tyr Val Val Leu Tyr Asp Ala Glu Leu Thr Phe Val Arg Gln Leu Glu
            580                 585                 590

Ile Tyr Arg Ala Ser Arg Pro Gly Lys Pro Leu Arg Val Tyr Phe Leu
            595                 600                 605

Ile Tyr Gly Gly Ser Thr Glu Glu Gln Arg Tyr Leu Thr Ala Leu Arg
            610                 615                 620

Lys Glu Lys Glu Ala Phe Glu Lys Leu Ile Arg Glu Lys Ala Ser Met
625                 630                 635                 640

Val Val Pro Glu Glu Arg Glu Gly Arg Asp Glu Thr Asn Leu Asp Leu
                645                 650                 655

Val Arg Gly Thr Ala Ser Ala Asp Val Ser Thr Asp Thr Arg Lys Ala
                660                 665                 670

Gly Gly Gln Glu Gln Asn Gly Thr Gln Gln Ser Ile Val Val Asp Met
                675                 680                 685

Arg Glu Phe Arg Ser Glu Leu Pro Ser Leu Ile His Arg Arg Gly Ile
            690                 695                 700

Asp Ile Glu Pro Val Thr Leu Glu Val Gly Asp Tyr Ile Leu Thr Pro
705                 710                 715                 720

Glu Met Cys Val Glu Arg Lys Ser Ile Ser Asp Leu Ile Gly Ser Leu
                725                 730                 735

Asn Asn Gly Arg Leu Tyr Ser Gln Cys Ile Ser Met Ser Arg Tyr Tyr
            740                 745                 750

Lys Arg Pro Val Leu Leu Ile Glu Phe Asp Pro Ser Lys Pro Phe Ser
            755                 760                 765

Leu Thr Ser Arg Gly Ala Leu Phe Gln Glu Ile Ser Ser Asn Asp Ile
            770                 775                 780

Ser Ser Lys Leu Thr Leu Leu Thr Leu His Phe Pro Arg Leu Arg Ile
785                 790                 795                 800

Leu Trp Cys Pro Ser Pro His Ala Thr Ala Glu Leu Phe Glu Glu Leu
            805                 810                 815

Lys Gln Ser Lys Pro Gln Pro Asp Ala Ala Thr Ala Leu Ala Ile Thr
            820                 825                 830

Ala Asp Ser Glu Thr Leu Pro Glu Ser Glu Lys Tyr Asn Pro Gly Pro
            835                 840                 845

Gln Asp Phe Leu Leu Lys Met Pro Gly Val Asn Ala Lys Asn Cys Arg
            850                 855                 860

Ser Leu Met His His Val Lys Asn Ile Ala Glu Leu Ala Ala Leu Ser
865                 870                 875                 880

Gln Asp Glu Leu Thr Ser Ile Leu Gly Asn Ala Ala Asn Ala Lys Gln
                885                 890                 895

Leu Tyr Asp Phe Ile His Thr Ser Phe Ala Glu Val Val Ser Lys Gly
            900                 905                 910

Lys Gly Lys Lys
```

915

<210> SEQ ID NO 25
<211> LENGTH: 4091
<212> TYPE: DNA
<213> ORGANISM: Homo sapiens

<400> SEQUENCE: 25

```
attttcatg ggtttgcgga cccaccagcg aaggcgggag gtgtcgcagg gacatcttct      60
ggctgtttcc gtcgcctgcg tggcccttgc accccggtct tccattagcg gcgcagacgt     120
ttgggcctaa gcgctgggcg aggcgaggcc ctgcccctcc ccgccaacgg ccattctctg     180
gacctgtctt tcttccggga ggcggtgaca gctgctgaga cgtgttgcag ccagagtctc     240
tccgctttaa tgcgctccca ttagtgccgt cccccactgg aaaaccgtgg cttctgtatt     300
atttgccatc tttgttgtgt aggagcaggg agggcttcct cccggggtcc taggcggcgg     360
tgcagtccgt cgtagaagaa ttagagtaga agttgtcggg gtccgctctt aggacgcagc     420
cgcctcatgg gggtccaggg gctctggaag ctgctggagt gctccgggcg gcaggtcagc     480
cccgaagcgc tggaagggaa gatcctggct gttgatatta gcatttggtt aaaccaagca     540
cttaaaggag tccgggatcg ccatgggaac tcaatagaaa atcctcatct tctcactttg     600
tttcatcggc tctgcaaact cttattttt cgaattcgtc ctattttgt gtttgatggg       660
gatgctccac tattgaagaa acagactttg gtgaagagaa ggcagagaaa ggacttagcg     720
tccagtgact ccaggaaaac gacagagaag cttctgaaaa catttttgaa aagacaagcc     780
atcaaaactg ccttcagaag caaaagagat gaagcactac ccagtcttac ccaagttcga     840
agagaaaacg acctctatgt tttgcctcct ttacaagagg aagaaaaaca cagttcagaa     900
gaggaagatg aaaaagaatg gcaagaagag atgaatcaaa acaagcatt acaggaagag      960
ttctttcata atcctcaagc gatagatatt gagtctgagg acttcagcag cctgccccct    1020
gaagtaaagc atgaaatctt gactgatatg aaagagttca ccaagcgcag aagaacatta    1080
tttgaagcaa tgccagagga gtctgatgac ttttcacagt accaactcaa aggcttgctt    1140
aaaaagaact atctgaacca gcatatagaa catgtccaaa aggaaatgaa tcagcaacat    1200
tcaggacaca tccgaaggca gtatgaagat gaagggggct ttctgaagga ggtagagtca    1260
aggagagtgg tctctgaaga cacttcacat tacatcttga taaaaggtat tcaagctaag    1320
acagttgcag aagtggattc agagtctctt ccttcttcca gcaaaatgca cggcatgtct    1380
tttgacgtga agtcatctcc atgtgaaaaa ctgaagacag agaaagagcc tgatgctacc    1440
cctccttctc caagaacttt actagctatg caagctgccc tgctgggaag tagctcagaa    1500
gaggagctgg agagtgaaaa tcgaaggcag gcccgtggga ggaacgcacc tgctgctgta    1560
gacgaaggct ccatatcacc ccggactctt tcagccatta agagagctct tgacgatgac    1620
gaagatgtaa agtgtgtgc tgggatgat gtgcagacgg gagggccagg agcagaagaa      1680
atgcgtataa acagctccac cgagaacagt gatgaaggac ttaaagtgag agatggaaaa    1740
ggaataccgt ttactgcaac acttgcgtca tctagtgtga actctgcaga ggagcacgta    1800
gccagcacta atgaggggag agagcccaca gactcagttc caaaagaaca aatgtcactt    1860
gttcacgtgg ggactgaagc ctttccgata agtgatgagt ctatgattaa ggacagaaaa    1920
gatcggctgc ctctggagag tgcagtggtt agacatagtg acgcacctgg gctcccgaat    1980
ggaagggaac tgacaccggc atctccaact tgtacaaatt ctgtgtcaaa gaatgaaaca    2040
catgctgaag tgcttgagca gcagaacgaa cttttgcccat atgagagtaa attcgattct    2100
```

-continued

```
tctcttcttt caagtgatga tgaaacaaaa tgtaaaccga attctgcttc tgaagtcatt    2160
ggccctgtca gtttgcaaga acaagtagc atagtaagtg tcccttcaga ggcagtagat    2220
aatgtggaaa atgtggtgtc atttaatgct aaagagcatg agaattttct ggaaaccatc   2280
caagaacagc agaccactga atctgcaggc caggatttaa tttccattcc aaaggccgtg   2340
gaaccaatgg aaattgactc ggaagaaagt gaatctgatg gaagtttcat tgaagtgcaa   2400
agtgtgatta gtgatgagga acttcaagca gaattccctg aaacttccaa acctccctca   2460
gaacaaggcg aagaggaact ggtaggaact agggagggag aagcccctgc tgagtccgag   2520
agcctcctga gggacaactc tgagagggac gacgtggatg gtgagccaca ggaagctgag   2580
aaagatgcgg aagattcgct ccatgaatgg caagatatta atttggagga gttggaaact   2640
ctggagagca acctcttagc acagcagaat tcactgaaag ctcaaaaaca gcagcaagaa   2700
cggatcgctg ctactgtcac cggacagatg ttcctggaaa gccaggaact cctgcgcctg   2760
ttcggcattc cctacatcca ggctcccatg gaagcagagg cgcagtgcgc catcctggac   2820
ctgactgatc agacttccgg aaccatcact gatgacagtg atatctggct gtttggagcg   2880
cggcatgtct atagaaactt ttttaataaa aacaagtttg tagaatatta tcaatatgtg   2940
gactttcaca atcaattggg attggaccgg aataagttaa taaatttggc ttatttgctt   3000
ggaagtgatt ataccgaagg aataccaact gtgggttgtg taaccgccat ggaaattctc   3060
aatgaattcc ctgggcatgg cctggaacct ctcctaaaat tctcagaatg gtggcatgaa   3120
gctcaaaaaa atccaaagat aagacctaat cctcatgaca ccaaagtgaa aaaaaaatta   3180
cggacattgc aactcacccc tggctttcct aacccagctg ttgccgaggc ctacctcaaa   3240
cccgtggtgg atgactcgaa gggatccttt ctgtggggga acctgatct cgacaaaatt   3300 agagaatttt gtcagcggta tttcggctgg aacagaacga agacagatga atctctgttt   3360
cctgtattaa agcaactcga tgcccagcag acacagctcc gaattgattc cttctttaga   3420
ttagcacaac aggagaaaga agatgctaaa cgtattaaga gccagagact aaacagagct   3480
gtgacatgta tgctaaggaa agagaaagaa gcagcagcca gcgaaataga agcagtttct   3540
gttgccatgg agaaagaatt tgagctactt gataaggcaa acgaaaaac ccagaagaga   3600 ggcataacaa ataccttaga agagtcatca agcctgaaaa gaaagaggct ttcagattct   3660
aaacgaaaga atacatgcgg tggattttg ggggagacct gcctctcaga atcatctgat   3720
ggatcttcaa gtgaagatgc tgaaagttca tctttaatga atgtacaaag gagaacagct   3780
gcgaaagagc caaaaccag tgcttcagat tcgcagaact cagtgaagga agctcccgtg   3840
aagaatggag gtgcgaccac cagcagctct agtgatagtg atgacgatgg agggaaagag   3900
aagatggtcc tcgtgaccgc cagatctgtg tttgggaaga aagaaggaa actaagacgt   3960 gcgaggggaa gaaaaaggaa aacctaatta aaaaatatgt atcctctata attagttatg   4020
acagccattt gtaatgaatt tgtcgcaaag acgtaataaa attaactggt ggcacggtct   4080
ttgtaaaaaa a                                                       4091
```

<210> SEQ ID NO 26
<211> LENGTH: 1186
<212> TYPE: PRT
<213> ORGANISM: Homo sapiens

<400> SEQUENCE: 26

```
Met Gly Val Gln Gly Leu Trp Lys Leu Leu Glu Cys Ser Gly Arg Gln
1               5                   10                  15
```

```
Val Ser Pro Glu Ala Leu Glu Gly Lys Ile Leu Ala Val Asp Ile Ser
         20                  25                  30

Ile Trp Leu Asn Gln Ala Leu Lys Gly Val Arg Asp Arg His Gly Asn
     35                  40                  45

Ser Ile Glu Asn Pro His Leu Leu Thr Leu Phe His Arg Leu Cys Lys
 50                  55                  60

Leu Leu Phe Phe Arg Ile Arg Pro Ile Phe Val Phe Asp Gly Asp Ala
65                   70                  75                  80

Pro Leu Leu Lys Lys Gln Thr Leu Val Lys Arg Arg Gln Arg Lys Asp
             85                  90                  95

Leu Ala Ser Ser Asp Ser Arg Lys Thr Thr Glu Lys Leu Leu Lys Thr
            100                 105                 110

Phe Leu Lys Arg Gln Ala Ile Lys Thr Ala Phe Arg Ser Lys Arg Asp
            115                 120                 125

Glu Ala Leu Pro Ser Leu Thr Gln Val Arg Arg Glu Asn Asp Leu Tyr
    130                 135                 140

Val Leu Pro Pro Leu Gln Glu Glu Lys His Ser Ser Glu Glu Glu
145                 150                 155                 160

Asp Glu Lys Glu Trp Gln Glu Arg Met Asn Gln Lys Gln Ala Leu Gln
                165                 170                 175

Glu Glu Phe Phe His Asn Pro Gln Ala Ile Asp Ile Glu Ser Glu Asp
            180                 185                 190

Phe Ser Ser Leu Pro Pro Glu Val Lys His Glu Ile Leu Thr Asp Met
        195                 200                 205

Lys Glu Phe Thr Lys Arg Arg Arg Thr Leu Phe Glu Ala Met Pro Glu
210                 215                 220

Glu Ser Asp Asp Phe Ser Gln Tyr Gln Leu Lys Gly Leu Leu Lys Lys
225                 230                 235                 240

Asn Tyr Leu Asn Gln His Ile Glu His Val Gln Lys Glu Met Asn Gln
                245                 250                 255

Gln His Ser Gly His Ile Arg Arg Gln Tyr Glu Asp Glu Gly Gly Phe
            260                 265                 270

Leu Lys Glu Val Glu Ser Arg Arg Val Val Ser Glu Asp Thr Ser His
        275                 280                 285

Tyr Ile Leu Ile Lys Gly Ile Gln Ala Lys Thr Val Ala Glu Val Asp
    290                 295                 300

Ser Glu Ser Leu Pro Ser Ser Lys Met His Gly Met Ser Phe Asp
305                 310                 315                 320

Val Lys Ser Ser Pro Cys Glu Lys Leu Lys Thr Glu Lys Glu Pro Asp
                325                 330                 335

Ala Thr Pro Pro Ser Pro Arg Thr Leu Leu Ala Met Gln Ala Ala Leu
            340                 345                 350

Leu Gly Ser Ser Ser Glu Glu Glu Leu Glu Ser Glu Asn Arg Arg Gln
        355                 360                 365

Ala Arg Gly Arg Asn Ala Pro Ala Ala Val Asp Glu Gly Ser Ile Ser
    370                 375                 380

Pro Arg Thr Leu Ser Ala Ile Lys Arg Ala Leu Asp Asp Asp Glu Asp
385                 390                 395                 400

Val Lys Val Cys Ala Gly Asp Asp Val Gln Thr Gly Gly Pro Gly Ala
                405                 410                 415

Glu Glu Met Arg Ile Asn Ser Ser Thr Glu Asn Ser Asp Glu Gly Leu
            420                 425                 430
```

```
Lys Val Arg Asp Gly Lys Gly Ile Pro Phe Thr Ala Thr Leu Ala Ser
            435                 440                 445

Ser Ser Val Asn Ser Ala Glu Glu His Val Ala Ser Thr Asn Glu Gly
        450                 455                 460

Arg Glu Pro Thr Asp Ser Val Pro Lys Glu Gln Met Ser Leu Val His
465                 470                 475                 480

Val Gly Thr Glu Ala Phe Pro Ile Ser Asp Glu Ser Met Ile Lys Asp
                485                 490                 495

Arg Lys Asp Arg Leu Pro Leu Glu Ser Ala Val Val Arg His Ser Asp
            500                 505                 510

Ala Pro Gly Leu Pro Asn Gly Arg Glu Leu Thr Pro Ala Ser Pro Thr
        515                 520                 525

Cys Thr Asn Ser Val Ser Lys Asn Glu Thr His Ala Glu Val Leu Glu
530                 535                 540

Gln Gln Asn Glu Leu Cys Pro Tyr Glu Ser Lys Phe Asp Ser Ser Leu
545                 550                 555                 560

Leu Ser Ser Asp Asp Glu Thr Lys Cys Lys Pro Asn Ser Ala Ser Glu
                565                 570                 575

Val Ile Gly Pro Val Ser Leu Gln Glu Thr Ser Ser Ile Val Ser Val
            580                 585                 590

Pro Ser Glu Ala Val Asp Asn Val Glu Asn Val Val Ser Phe Asn Ala
        595                 600                 605

Lys Glu His Glu Asn Phe Leu Glu Thr Ile Gln Glu Gln Gln Thr Thr
610                 615                 620

Glu Ser Ala Gly Gln Asp Leu Ile Ser Ile Pro Lys Ala Val Glu Pro
625                 630                 635                 640

Met Glu Ile Asp Ser Glu Glu Ser Glu Ser Asp Gly Ser Phe Ile Glu
                645                 650                 655

Val Gln Ser Val Ile Ser Asp Glu Glu Leu Gln Ala Glu Phe Pro Glu
            660                 665                 670

Thr Ser Lys Pro Pro Ser Glu Gln Gly Glu Glu Leu Val Gly Thr
        675                 680                 685

Arg Glu Gly Glu Ala Pro Ala Glu Ser Glu Ser Leu Leu Arg Asp Asn
690                 695                 700

Ser Glu Arg Asp Asp Val Asp Gly Glu Pro Gln Glu Ala Glu Lys Asp
705                 710                 715                 720

Ala Glu Asp Ser Leu His Glu Trp Gln Asp Ile Asn Leu Glu Glu Leu
                725                 730                 735

Glu Thr Leu Glu Ser Asn Leu Leu Ala Gln Gln Asn Ser Leu Lys Ala
            740                 745                 750

Gln Lys Gln Gln Glu Arg Ile Ala Ala Thr Val Thr Gly Gln Met
        755                 760                 765

Phe Leu Glu Ser Gln Glu Leu Leu Arg Leu Phe Gly Ile Pro Tyr Ile
770                 775                 780

Gln Ala Pro Met Glu Ala Glu Ala Gln Cys Ala Ile Leu Asp Leu Thr
785                 790                 795                 800

Asp Gln Thr Ser Gly Thr Ile Thr Asp Asp Ser Asp Ile Trp Leu Phe
                805                 810                 815

Gly Ala Arg His Val Tyr Arg Asn Phe Phe Asn Lys Asn Lys Phe Val
            820                 825                 830

Glu Tyr Tyr Gln Tyr Val Asp Phe His Asn Gln Leu Gly Leu Asp Arg
        835                 840                 845

Asn Lys Leu Ile Asn Leu Ala Tyr Leu Leu Gly Ser Asp Tyr Thr Glu
```

Gly Ile Pro Thr Val Gly Cys Val Thr Ala Met Glu Ile Leu Asn Glu
865                 870                 875                 880

Phe Pro Gly His Gly Leu Glu Pro Leu Leu Lys Phe Ser Glu Trp Trp
            885                 890                 895

His Glu Ala Gln Lys Asn Pro Lys Ile Arg Pro Asn Pro His Asp Thr
        900                 905                 910

Lys Val Lys Lys Lys Leu Arg Thr Leu Gln Leu Thr Pro Gly Phe Pro
            915                 920                 925

Asn Pro Ala Val Ala Glu Ala Tyr Leu Lys Pro Val Val Asp Asp Ser
        930                 935                 940

Lys Gly Ser Phe Leu Trp Gly Lys Pro Asp Leu Asp Lys Ile Arg Glu
945                 950                 955                 960

Phe Cys Gln Arg Tyr Phe Gly Trp Asn Arg Thr Lys Thr Asp Glu Ser
                965                 970                 975

Leu Phe Pro Val Leu Lys Gln Leu Asp Ala Gln Gln Thr Gln Leu Arg
            980                 985                 990

Ile Asp Ser Phe Phe Arg Leu Ala Gln Gln Glu Lys Glu Asp Ala Lys
        995                 1000                1005

Arg Ile Lys Ser Gln Arg Leu Asn Arg Ala Val Thr Cys Met Leu
    1010                1015                1020

Arg Lys Glu Lys Glu Ala Ala Ser Glu Ile Glu Ala Val Ser
    1025                1030                1035

Val Ala Met Glu Lys Glu Phe Glu Leu Leu Asp Lys Ala Lys Arg
    1040                1045                1050

Lys Thr Gln Lys Arg Gly Ile Thr Asn Thr Leu Glu Glu Ser Ser
    1055                1060                1065

Ser Leu Lys Arg Lys Arg Leu Ser Asp Ser Lys Arg Lys Asn Thr
    1070                1075                1080

Cys Gly Gly Phe Leu Gly Glu Thr Cys Leu Ser Glu Ser Ser Asp
    1085                1090                1095

Gly Ser Ser Ser Glu Asp Ala Glu Ser Ser Ser Leu Met Asn Val
    1100                1105                1110

Gln Arg Arg Thr Ala Ala Lys Glu Pro Lys Thr Ser Ala Ser Asp
    1115                1120                1125

Ser Gln Asn Ser Val Lys Glu Ala Pro Val Lys Asn Gly Gly Ala
    1130                1135                1140

Thr Thr Ser Ser Ser Ser Asp Ser Asp Asp Gly Gly Lys Glu
    1145                1150                1155

Lys Met Val Leu Val Thr Ala Arg Ser Val Phe Gly Lys Lys Arg
    1160                1165                1170

Arg Lys Leu Arg Arg Ala Arg Gly Arg Lys Arg Lys Thr
    1175                1180                1185

<210> SEQ ID NO 27
<211> LENGTH: 2492
<212> TYPE: DNA
<213> ORGANISM: Homo sapiens

<400> SEQUENCE: 27
cactcagaaa ggccgctggg tgcggggagc gcagaggcgg tgcagggcgg ctggctcgcc       60
tcggcgtgca gtgcgcgtgc gtggagctgg gagctaggtc ctcggagtgg gccagagatg      120
gcggcggccg acggggcttt gccggaggcg gcggctttag agcaaccgc ggagctgcct       180

-continued

```
gcctcggtgc gggcgagtat cgagcggaag cggcagcggg cactgatgct gcgccaggcc    240
cggctggctg cccggcccta ctcggcgacg gcggctgcgg ctactggagg tttgggccgc    300
gtccgcgctt tccccttccc tctccccgcc tccccggtcc ccagactggc tcgtgcaagc    360
cgagtcccgg ggcccggggg tcgcgtcaac tccgctggcg tatgtgtgca gattctcccc    420
gagtcggaga gggaatccgc ccagccagcc gccttgtcaa agcgtcctgt ccacgaccac    480
agagcgttcc tctgtcgcac gcgggcctcc tgaccccccag ccccgggcct tcttcgctgc    540
acctcggctg ctggcagctt cgattttcg tttagggatg cagccgcccc ggccgggagg    600
tgtcagccac tgccaggtgt cagggcctca gctgtcccgg aaagaggagt tagactagtt    660
cttgattctg gcctctatac ctagaactag ttgatggaag aggcagatct tggtgtttgt    720
tagggagagc tttcaacaat tagagttgcc aaaagtgcaa tggattgctt ctcatgagct    780
tcccgttact agaagcgctc aaataggaac tggaagaacg cttacttatg tggaggagag    840
gagattcagc aatcagaatc tcctactcag caatcagaag aagggactgg atagtaaacc    900
tttaagattc taatccatag attccatgag tctatttctt ggacatgtga cctctgcgat    960
ttcttggcaa aaactagttg ctcaaaacgt gtttattgat tgaagtaaat taaggactga   1020
tctctcattg cagattattc tcttatagaa tttgccactg gggtcaacta ataatcttta   1080
acaggatact taaatatag tttggttgac aggcagttct tcagggctgc ctctataaca   1140
tgaagtacat gtgttcctaa agctctatac tgccctttgt cgagcacagt ttagagctgt   1200
attactcttt tttatcagcc agatgtagtg agagtgagaa gagtctgagg ctggcagcat   1260
gtcttgatgt tcatactaac accgaaactg caaattccag ctactttga tggcatggct    1320
aatgtaaaag cagccccaaa gataattgac acaggaggag gcttcatttt agaagaggaa   1380
gaagaagaag aacagaaaat tggaaaagtt gttcatcaac caggacctgt tatggaattt   1440
gattatgtaa tatgcgaaga atgtgggaaa gaatttatgg attcttatct tatgaaccac   1500
tttgatttgc caacttgtga taactgcaga gatgctgatg ataaacacaa gcttataacc   1560
aaaacagagg caaaacaaga atatcttctg aaagactgtg atttagaaaa aagagagcca   1620
cctcttaaat ttattgtgaa gaagaatcca catcattcac aatggggtga tatgaaactc   1680
tacttaaagt tacagattgt gaagaggtct cttgaagttt ggggtagtca agaagcatta   1740
gaagaagcaa aggaagtccg acaggaaaac cgagaaaaaa tgaaacagaa gaaatttgat   1800
aaaaaagtaa aagaattgcg gcgagcagta agaagcagcg tgtggaaaag ggagacgatt   1860
gttcatcaac atgagtatgg accagaagaa aacctagaag atgacatgta ccgtaagact   1920
tgtactatgt gtggccatga actgacatat gaaaaaatgt gatttttag ttcagtgacc    1980
tgttttatag aattttatat ttaaataaag gaaatttaga ttggtccttt tcaaaattca   2040
aaaaaaaaag caacatcttc atagatgaat gaaaccttg tataagtaat acttcagtaa    2100
taattatgta tgttatggct aaaagcaag tttcagtgaa ggtcacctgg cctggttgtg    2160
tgcacaatgt catgtctgtg attgccttct tacaacagag atgggagctg agtgctagag   2220
taggtgcaga agtggtaggt cagctacaaa tttgaggaca agataccaag gcaaacccta   2280
gattggggta gagggaaaag ggttcaacaa aggctgaact ggattcttaa ccaagaaaca   2340
aataatagca atggtggtgc accactgtac cccaggttct agtcatgtgt tttttaggac   2400
gatttctgtc tccacgatgg tggaaacagt ggggaactac tgctggaaaa agccctaata   2460
gcagaaaataa acattgagtt gtacgagtct ga                                2492
```

-continued

<210> SEQ ID NO 28
<211> LENGTH: 273
<212> TYPE: PRT
<213> ORGANISM: Homo sapiens

<400> SEQUENCE: 28

Met Ala Ala Ala Asp Gly Ala Leu Pro Glu Ala Ala Leu Glu Gln
1               5                   10                  15

Pro Ala Glu Leu Pro Ala Ser Val Arg Ala Ser Ile Glu Arg Lys Arg
            20                  25                  30

Gln Arg Ala Leu Met Leu Arg Gln Ala Arg Leu Ala Ala Arg Pro Tyr
        35                  40                  45

Ser Ala Thr Ala Ala Ala Thr Gly Gly Met Ala Asn Val Lys Ala
    50                  55                  60

Ala Pro Lys Ile Ile Asp Thr Gly Gly Phe Ile Leu Glu Glu
65                  70                  75                  80

Glu Glu Glu Glu Gln Lys Ile Gly Lys Val Val His Gln Pro Gly Pro
                85                  90                  95

Val Met Glu Phe Asp Tyr Val Ile Cys Glu Cys Gly Lys Glu Phe
            100                 105                 110

Met Asp Ser Tyr Leu Met Asn His Phe Asp Leu Pro Thr Cys Asp Asn
        115                 120                 125

Cys Arg Asp Ala Asp Lys His Lys Leu Ile Thr Lys Thr Glu Ala
    130                 135                 140

Lys Gln Glu Tyr Leu Leu Lys Asp Cys Asp Leu Glu Lys Arg Glu Pro
145                 150                 155                 160

Pro Leu Lys Phe Ile Val Lys Lys Asn Pro His His Ser Gln Trp Gly
                165                 170                 175

Asp Met Lys Leu Tyr Leu Lys Leu Gln Ile Val Lys Arg Ser Leu Glu
            180                 185                 190

Val Trp Gly Ser Gln Glu Ala Leu Glu Ala Lys Glu Val Arg Gln
        195                 200                 205

Glu Asn Arg Glu Lys Met Lys Gln Lys Lys Phe Asp Lys Lys Val Lys
210                 215                 220

Glu Leu Arg Arg Ala Val Arg Ser Ser Val Trp Lys Arg Glu Thr Ile
225                 230                 235                 240

Val His Gln His Glu Tyr Gly Pro Glu Glu Asn Leu Glu Asp Asp Met
                245                 250                 255

Tyr Arg Lys Thr Cys Thr Met Cys Gly His Glu Leu Thr Tyr Glu Lys
            260                 265                 270

Met

<210> SEQ ID NO 29
<211> LENGTH: 5739
<212> TYPE: DNA
<213> ORGANISM: Homo sapiens

<400> SEQUENCE: 29
gacgtaatgc ggtagcgcgg ggaatttcga gtggtgttgg agcgccggag gctagtgggt      60
ggctgacccc cagcatcctc gggagcgacc atgactcccc tggccgagtc tcggtggcct    120
ccgggcctgg cagtcatgaa gacaatagat gatttgctgc ggtgtggaat ttgcttcgag    180
tatttcaaca ttgcaatgat aatacctcag tgttcacata actactgctc tctctgtata    240
agaaaatttc tgtcctataa aactcagtgt ccaacttgct gtgtgactgt cacagagccg    300
gatctgaaaa ataaccgcat attagatgaa ctggtaaaaa gcttgaattt tgcacggaat    360

-continued

```
catctgctgc agtttgcttt agagtcacca gccaaatctc ctgcttcttc ctcttcaaag       420
aatcttgctg tcaaagtata tactcctgta gcctccagac agtctttaaa gcaggggagc       480
aggttaatgg ataatttctt gatcagagaa atgagtggtt ctacatcaga gttgttgata       540
aaagaaaata aaagcaaatt cagccctcaa aagaggcga gccctgctgc aaagaccaaa        600
gagacacgtt ctgtagaaga gatcgctcca gatccctcag aggctaagcg tcctgagcca       660
ccctcgacat ccactttgaa acaagttact aaagtggatt gtcctgtttg cggggttaac      720
attccagaaa gtcacattaa taagcattta gacagctgtt tatcacgcga agagaagaag       780
gaaagcctca gaagttctgt tcacaaaagg aagccgctgc ccaaaactgt atataatttg      840
ctctctgatc gtgatttaaa gaaaagcta aagagcatg gattatctat tcaaggaaat         900
aaacaacagc tcattaaaag gcaccaagaa tttgtacaca tgtacaatgc caatgcgat        960 gctttgcatc ctaaatcagc tgctgaaata gttcgagaaa tcgaaaatat agagaagact       1020
aggatgcgtc ttgaagctag taaactcaat gaaagtgtaa tggttttttac aaaggaccaa     1080 acagaaaagg aaatagatga atccacagt aaatatcgta aaaacataa gagtgaattt         1140 cagcttctgg tggatcaggc tagaaaagga tacaagaaaa ttgctggaat gtcacaaaaa      1200
acagtaacaa taacaaaaga gatgaatct acagaaaagc tatcttctgt atgcatggga        1260
caggaagata atatgacctc agtaacaaac cacttttctc aatcaaagct ggactcccca      1320
gaggaattgg aacctgacag agaagaggat tcttctagct gtattgatat tcaagaagtt     1380 cttttcttcat cagaatcaga ttcatgcaat agttccagtt cagacatcat aagagatctt    1440
ttagaagaag aggaagcctg ggaagcatca cataaaaacg atcttcaaga cacagaaata     1500
agtccaagac agaatcgccg cacaagagcc gctgaaagtg ctgagattga accaagaaac       1560
aagcgtaata ggaattaatg tgggcttttg ctgactttc aaatgcattg attagaatac      1620 cgtactttg gttgccacag atagattttc tatttataa tgcccaagga agatgctaa         1680 attctaaata ttacggttag ctgatattca ttcttttctg cttttccaga ggggaaaaat      1740
gttacaaaat atccttactt ggtcagttgc ctcctgcctc taaacatct ctctctaaaa        1800 atactgacat ttcacacagg taccagcttt gcagaggagg tagactcttt ggcactttgg      1860
cacagggatt tggtttggtt tggtttggtt tgataattaa atttcagaat gtccttaggc      1920
cattctcctt ctcttccatg gagaatccag cctcacaaaa ggattctttc aacttcttta     1980
ttgcaagaaa cagttgagtt aaatgtttgt ttttggaaag gcgggatgtc agttcacatc     2040
cttggtgtgt gtaagtaccg atgcacgcca ccaccatgcc tgtgttacag cagctccatg     2100
atggttgttg cccgaggtta atgtagttgt ttgttagacc tgtgtcttac acatttctca      2160
gagtaggata ttagtattat aatttaaagc tacgacagtc acaaagtcac aataacttag      2220
aaacattgcg catattcttc tgaaatagca cttaaaaatg attagtgtca gtattttttc      2280
acttgggtca atcaaatctg taacactgaa tccaagctat aaacaaaaa gtatgcaatg       2340 aatgaatttt gtaaatgaat agagagtatc agtttacaat aatgttctta aaacagtatc     2400
ctctggatag ttgagtatgg gttagaaatc attgaaatgg attggtcaga aattgctatc     2460
tgtgtaaaat gtctaccagt agccagatgc ttccagagtt cttaatgcct ctctggcatt     2520
tcagagccag catcccccaa ctcccacccc tctgccatca cccaacccaa acacatcagc     2580
tttcaaatga gatgatagta aatgcggcaa tgttaagaca agaaattat gatttgccag       2640 attcaacatt tatgacctcc ccttccaaag actgtctccg ttgaccttgt cttttggta     2700
```

```
tgccttgggg tttctgataa tgtgtggagt ctcattatgg ctgagagttt agtgttttca    2760
cagtgaagtg cagacatttg atttctttat gagttccctg tgttagaaat ggctatagaa    2820
aaatttgtca taataatttc atttgcatga atcctgagg  ggtgcattaa ggaaactaaa    2880
agcaccactt accaaatcta tcggcagaac tgatgtgagg taagtgagca tgtcaaacaa    2940
aataggagct cacatggata tatttatgtc actgagttgt cagaaattat gtcaaaatga    3000
aaactgtttg tttcatgaca aattatatag tctataaatt aaactggaag taattattac    3060
tttaattgca gcaaaggag  tttgtgaggg agcggtgaga cccaagattg ggaaagtagg    3120
cacatgagtt cattcagcaa atatttggtt atctatgtct gtcactgtgc tgacactggg    3180
aatacaaagg tggccaaaga tcatctagaa caatggttcc cagtggggtg ggcagaaaga    3240
ttttgccccc caggagacag ctggcaatgt gtggagacac ttttggaggt ggagggtggt    3300
gaggggtact accagtatca atgggtggag gccagggatg aggctaaaca cccaacccte    3360 atggattagt ttgccagggc tgccgtcaca agatactgca gacggggaag cttacacaac    3420
agaaatgtgt attctcagaa ttctggaggc tggaagtcca agatcagtag ggtttcttct    3480
tcggcctctc tccttggctt ccactcatgg tgtccttgca tggtctttc  tctgtgtgca    3540 catgactgtg caggactggt gtcccgattt cttgtaggga cagcagtcat tggatcaggg    3600
cccatgcgta tggcctcatt ttacttcagt tacctctttt ttagatagag ggccctatct    3660
ctaaatactg tcacattctg agataccggc agttaagact tccaacatat ttagtggtag    3720
gggttaaggg gcacgcttta gactacaaca ctccacagta agaattatc  cagtctaaca    3780 tgtcagttgt gccaagactg agaaacctgt aatgtaaagg aactcccaag tctacctgaa    3840
aagtaaggtc taaagagcat ttattgagca ctatctgtta gcacttagca tatgtttaat    3900
attcatacat tgaaagaaat gtatgttcat atccatctga caaagattaa ggaacttaga    3960
gtaagtaata gatccaaaat tgaaactgat aaacttctgg ttctaaaatt caccttttag    4020
tgaaaataca gtttctcacc aaacttacag taattcagag ttattaactc tttctacctc    4080
ctcactcccc tcaaagttat aacatctccc atcaacatca gctcagaatg cagtgatgc    4140 ttatggtttg tggggtgca  ggtgagctgc tggatgcact ttagatggcc tagtatgcca    4200
ggccgtcctt tcatcctcta ctctcgtctt tcttttcga  cctcatgttg aggattactg    4260
gtctagttga aaaagaatt  catacacata agaccatgta tataatagag ggaggtatgc    4320
ctttaaaaac aaaattacat ggtaaagact gatgtgtcaa cagggataga caacatagag    4380
aaggctagaa ctgtttctgg aaaaaaaccc aaaaacaatg gatttcaaac ttcttagcat    4440
ccgataaaag aaagtagcaa ttattcaaat gagaaacact tctgtctgtt atgtacatat    4500
tatgaaagta tgaacataag agggaaaacc acaaccatta cattttttac catttcagta    4560 atttttttt  ggtttttagt ctgtttttag acatccttaa gaacaactat ctgaggctgt    4620
aaacaagtat ttacattaac acccatgata ctgactttat actccctacc tgcattgaga    4680
ccttaaaggg ggcatttctc cattccttct gtgtatttct gggtatcccc aggttcagat    4740
attcagaata cagatacaag tccatgcttg catatgttgc tgctccccc  gacagacttc    4800 taccagcatc tgccctcctc accgctgctc tgtcacgtgc actgcggctg gcctgctgg    4860 aaagtcctac cttgcctagg acgccatccc cgatatagcc ccaagatgca aacctgccaa    4920
gtgctagggc agccctgcct tcctgtccat ttcagtctct tggccttgct tgttccaag    4980 tggaaatggg agtgtgcttt cctggttgc  tagtgtacta tcacccggac cacagcgtcc    5040
tgtgcaaaaa tttgcttcct ctctcttccc ctttcactct ttctcttttc tcttccccac    5100
```

```
cccctttttt ttctctttcc ccttaccttt ctttccttc cactcttcct gtccttcctt   5160
ccttcaacta ttaggactat atgtcaagta atgtgcaaaa caaagacagt tcctgccctg   5220
atggagcttg tagatcagaa gggaagatga gcattaagta attatataga ttaatgtaca   5280
actgtgatga gtgcaacaaa agagaggttc atggcactat caaacatgca atggacggat   5340 tttgttttg cctataaact cttgccatag aaagcttgaa atcagtcca gggggacagc     5400 attaatcacc atgttctttc cttatccctg tcttccccaa aattcatgtg ttgaaactta   5460
acaagaggtg ggaactttag gatgtgatta agtcgtgagg gcacagctct tatagatggg   5520
gtcacggtcc ttctaaaagg gcttgaggga gtggttttgt ttccttccat cccttccgcc   5580
acatgaggac acagtcttcg ttccctctgg aggactcagc aacaacacac catcttggaa   5640
gcagagagca gtcctcacca gacacggaat ctgccagtgc cttgatcttg gacttaccag   5700
cctccatacc tgtgagaaat aaatttctat tgtctataa                          5739
```

<210> SEQ ID NO 30
<211> LENGTH: 495
<212> TYPE: PRT
<213> ORGANISM: Homo sapiens

<400> SEQUENCE: 30

```
Met Asp Ser Leu Ala Glu Ser Arg Trp Pro Pro Gly Leu Ala Val Met
1               5                   10                  15

Lys Thr Ile Asp Asp Leu Leu Arg Cys Gly Ile Cys Phe Glu Tyr Phe
            20                  25                  30

Asn Ile Ala Met Ile Ile Pro Gln Cys Ser His Asn Tyr Cys Ser Leu
        35                  40                  45

Cys Ile Arg Lys Phe Leu Ser Tyr Lys Thr Gln Cys Pro Thr Cys Cys
    50                  55                  60

Val Thr Val Thr Glu Pro Asp Leu Lys Asn Asn Arg Ile Leu Asp Glu
65                  70                  75                  80

Leu Val Lys Ser Leu Asn Phe Ala Arg Asn His Leu Leu Gln Phe Ala
                85                  90                  95

Leu Glu Ser Pro Ala Lys Ser Pro Ala Ser Ser Ser Lys Asn Leu
            100                 105                 110

Ala Val Lys Val Tyr Thr Pro Val Ala Ser Arg Gln Ser Leu Lys Gln
        115                 120                 125

Gly Ser Arg Leu Met Asp Asn Phe Leu Ile Arg Glu Met Ser Gly Ser
    130                 135                 140

Thr Ser Glu Leu Leu Ile Lys Glu Asn Lys Ser Lys Phe Ser Pro Gln
145                 150                 155                 160

Lys Glu Ala Ser Pro Ala Ala Lys Thr Lys Glu Thr Arg Ser Val Glu
                165                 170                 175

Glu Ile Ala Pro Asp Pro Ser Glu Ala Lys Arg Pro Glu Pro Pro Ser
            180                 185                 190

Thr Ser Thr Leu Lys Gln Val Thr Lys Val Asp Cys Pro Val Cys Gly
        195                 200                 205

Val Asn Ile Pro Glu Ser His Ile Asn Lys His Leu Asp Ser Cys Leu
    210                 215                 220

Ser Arg Glu Glu Lys Lys Glu Ser Leu Arg Ser Ser Val His Lys Arg
225                 230                 235                 240

Lys Pro Leu Pro Lys Thr Val Tyr Asn Leu Leu Ser Asp Arg Asp Leu
                245                 250                 255
```

-continued

```
Lys Lys Lys Leu Lys Glu His Gly Leu Ser Ile Gln Gly Asn Lys Gln
            260                 265                 270

Gln Leu Ile Lys Arg His Gln Glu Phe Val His Met Tyr Asn Ala Gln
        275                 280                 285

Cys Asp Ala Leu His Pro Lys Ser Ala Ala Glu Ile Val Arg Glu Ile
            290                 295                 300

Glu Asn Ile Glu Lys Thr Arg Met Arg Leu Gly Ala Ser Lys Leu Asn
305                 310                 315                 320

Glu Ser Val Met Val Phe Thr Lys Asp Gln Thr Glu Lys Glu Ile Asp
                325                 330                 335

Glu Ile His Ser Lys Tyr Arg Lys Lys His Lys Ser Glu Phe Gln Leu
            340                 345                 350

Leu Val Asp Gln Ala Arg Lys Gly Tyr Lys Lys Ile Ala Gly Met Ser
        355                 360                 365

Gln Lys Thr Val Thr Ile Thr Lys Glu Asp Glu Ser Thr Glu Lys Leu
    370                 375                 380

Ser Ser Val Cys Met Gly Gln Glu Asp Asn Met Thr Ser Val Thr Asn
385                 390                 395                 400

His Phe Ser Gln Ser Lys Leu Asp Ser Pro Glu Glu Leu Glu Pro Asp
                405                 410                 415

Arg Glu Glu Asp Ser Ser Ser Cys Ile Asp Ile Gln Glu Val Leu Ser
            420                 425                 430

Ser Ser Glu Ser Asp Ser Cys Asn Ser Ser Ser Asp Ile Ile Arg
        435                 440                 445

Asp Leu Leu Glu Glu Glu Ala Trp Glu Ala Ser His Lys Asn Asp
    450                 455                 460

Leu Gln Asp Thr Glu Ile Ser Pro Arg Gln Asn Arg Arg Thr Arg Ala
465                 470                 475                 480

Ala Glu Ser Ala Glu Ile Glu Pro Arg Asn Lys Arg Asn Arg Asn
                485                 490                 495

<210> SEQ ID NO 31
<211> LENGTH: 4263
<212> TYPE: DNA
<213> ORGANISM: Homo sapiens

<400> SEQUENCE: 31
ctctccacgg cgcacagagc atgcgcgggg cgggagtgag cgaaattcaa gctccaaact    60
ctaagctcca agctccaagc tccaagctcc aagctccaaa ctcccgccgg ggtaactgga   120
acccaatccg agggtcatgg aggcatcccg aaggtttccg gaagccgagg ccttgagccc   180
agagcaggct gctcattacc taagatatgt gaaagaggcc aaagaagcaa ctaagaatgg   240
agacctggaa gaagcattta aacttttcaa tttggcaaag acattttttc ccaatgaaaa   300
agtgctgagc agaatccaaa aaatacagga agccttggag gagttggcag aacagggaga   360
tgatgaattt acagatgtgt gcaactctgg cttgctactt tatcgagaac tgcacaacca   420
actctttgag caccagaagg aaggcatagc tttcctctat agcctgtata gggatggaag   480
aaaaggtggt atattggctg atgatatggg attagggaag actgttcaaa tcattgcttt   540
cctttccggt atgtttgatg catcacttgt gaatcatgtg ctgctgatca tgccaaccaa   600
tcttattaac acatgggtaa agaattcat caagtggact ccaggaatga gagtcaaaac   660
ctttcatggt cctagcaagg atgaacggac cagaaacctc aatcggattc agcaaaggaa   720
tggtgttatt atcactacat accaaatgtt aatcaataac tggcagcaac tttcaagctt   780
```

```
tagggggccaa gagtttgtgt gggactatgt catcctcgat gaagcacata aaataaaaac    840
ctcatctact aagtcagcaa tatgtgctcg tgctattcct gcaagtaatc gcctcctcct    900
cacaggaacc ccaatccaga ataatttaca agaactatgg tccctatttg attttgcttg    960
tcaagggtcc ctgctgggaa cattaaaaac ttttaagatg gagtatgaaa atcctattac   1020
tagagcaaga gagaaggatg ctaccccagg agaaaaagcc ttgggattta aaatatctga   1080
aaacttaatg gcaatcataa aaccctattt tctcaggagg actaaagaag acgtacagaa   1140
gaaaaagtca agcaacccag aggccagact taatgaaaag aatccagatg ttgatgccat   1200
ttgtgaaatg ccttcccttt ccaggaaaaa tgatttaatt atttggatac gacttgtgcc   1260
tttacaagaa gaaatataca ggaaatttgt gtctttagat catatcaagg agttgctaat   1320
ggagacgcgc tcacctttgg ctgagctagg tgtcttaaag aagctgtgtg atcatcctag   1380
gctgctgtct gcacgggctt gttgtttgct aaatcttggg acattctctg ctcaagatgg   1440
aaatgagggg gaagattccc cagatgtgga ccatattgat caagtaactg atgacacatt   1500 gatgaagaa tctggaaaaa tgatattcct aatggaccta cttaagaggc tgcgagatga   1560
gggacatcaa actctggtgt tttctcaatc gaggcaaatt ctaaacatca ttgaacgcct   1620
cttaaagaat aggcactta agacattgcg aatcgatggg acagttactc atcttttgga   1680
acgagaaaaa agaattaact tattccagca aaataaagat tactctgttt ttctgcttac   1740
cactcaagta ggtggtgtcg gtttaacatt aactgcagca actagagtgg tcattttga   1800 ccctagctgg aatcctgcaa ctgatgctca agctgtggat agagtttacc gaattggaca   1860
aaaagagaat gttgtggttt ataggctaat cacttgtggg actgtagagg aaaaaatata   1920
cagaagacag gttttcaagg actcattaat aagacaaact actggtgaaa aaagaaccc   1980 tttccgatat tttagtaaac aagaattaag agagctcttt acaatcgagg atcttcagaa   2040
ctctgtaacc cagctgcagc ttcagtcttt gcatgctgct cagaggaaat ctgatataaa   2100
actagatgaa catattgcct acctgcagtc tttggggata gctggaatct cagaccatga   2160
tttgatgtac acatgtgatc tgtctgttaa agaagagctt gatgtggtag aagaatctca   2220
ctatattcaa caagggttc agaaagctca attcctcgtt gaattcgagt ctcaaaataa   2280
agagttcctg atggaacaac aaagaactag aaatgagggg gcctggctaa gagaacctgt   2340
atttccttct tcaacaaaga agaaatgccc taaattgaat aaaccacagc ctcagccttc   2400
acctcttcta agtactcatc atactcagga agaagatatc agttccaaaa tggcaagtgt   2460
agtcattgat gatctgccca agagggtgga gaaacaagat ctctccagta taaaggtgaa   2520
tgttaccacc ttgcaagatg gtaaaggtac aggtagtgct gactctatag ctactttacc   2580
aaagggtttt ggaagtgtag aagaactttg tactaactct tcattgggaa tggaaaaaag   2640
ctttgcaact aaaaatgaag ctgtacaaaa agagacatta caagaggggc taagcaaga   2700 ggcactgcaa gaggatcctc tggaaagttt taattatgta cttagcaaat caaccaaagc   2760
tgatattggg ccaaatttag atcaactaaa ggatgatgag attttacgtc attgcaatcc   2820
ttggcccatt atttccataa caaatgaaag tcaaaatgca gaatcaaatg tatccattat   2880
tgaaatagct gatgacctt cagcatccca tagtgcactg caggatgctc aagcaagtga   2940
ggccaagttg gaagaggaac cttcagcatc ttcaccacag tatgcatgtg atttcaatct   3000
tttcttggaa gactcagcag acaacagaca aaatttttcc agtcagtctt tagagcatgt   3060
tgagaaagaa aatagcttgt gtggctctgc acctaattcc agagcagggt ttgtgcatag   3120
caaaacatgt ctcagttggg agttttctga gaaagacgat gaaccagaag aagtagtagt   3180
```

```
taaagcaaaa atcagaagta aagctagaag gattgtttca gatggcgaag atgaagatga   3240 ttctttaaa  gatacctcaa gcataaatcc attcaacaca tctctctttc aattctcatc   3300
tgtgaaacaa tttgatgctt caactcccaa aaatgacatc agtccaccag gaaggttctt   3360
ttcatctcaa atacccagta gtgtaaataa gtctatgaac tctagaagat ctctggcttc   3420
taggaggtct cttattaata tggttttaga ccacgtggag gacatggagg aaagacttga   3480
cgacagcagt gaagcaaagg gtcctgaaga ttatccagaa gaaggggtgg aggaaagcag   3540
tggcgaagcc tccaagtata cagaagagga tccttccgga gaaacactgt cttcagaaaa   3600
caagtccagc tggttaatga cgtctaagcc tagtgctcta gctcaagaga cctctcttgg   3660
tgcccctgag cctttgtctg gtgaacagtt ggttggttct ccccaggata aggcggcaga   3720
ggctacaaat gactatgaga ctcttgtaaa gcgtggaaaa gaactaaaag agtgtggaaa   3780
aatccaggag gccctaaact gcttagttaa agcgcttgac ataaaagtg cagatcctga    3840 agttatgctc ttgactttaa gtttgtataa gcaacttaat aacaattgag aatgtaacct   3900
gtttattgta ttttaaagtg aaactgaata tgagggaatt tttgttccca taattggatt   3960
ctttgggaac atgaagcatt caggcttaag gcaagaaaga tctcaaaaag caacttctgc   4020
cctgcaacgc cccccactcc atagtctggt attctgagca ctagcttaat atttcttcac   4080
ttgaatattc ttatatttta ggcatattct ataaatttaa ctgtgttgtt tcttggaaag   4140
ttttgtaaaa ttattctggt cattcttaat tttactctga aagtgatcat ctttgtatat   4200
aacagttcag ataagaaaat taagttact  tttctcaagt gttttccaaa aaaaaaaaa    4260 aaa                                                                 4263
```

<210> SEQ ID NO 32
<211> LENGTH: 1250
<212> TYPE: PRT
<213> ORGANISM: Homo sapiens

<400> SEQUENCE: 32

```
Met Glu Ala Ser Arg Arg Phe Pro Glu Ala Glu Ala Leu Ser Pro Glu
1               5                   10                  15

Gln Ala Ala His Tyr Leu Arg Tyr Val Lys Glu Ala Lys Glu Ala Thr
            20                  25                  30

Lys Asn Gly Asp Leu Glu Glu Ala Phe Lys Leu Phe Asn Leu Ala Lys
        35                  40                  45

Asp Ile Phe Pro Asn Glu Lys Val Leu Ser Arg Ile Gln Lys Ile Gln
    50                  55                  60

Glu Ala Leu Glu Glu Leu Ala Glu Gln Gly Asp Asp Glu Phe Thr Asp
65                  70                  75                  80

Val Cys Asn Ser Gly Leu Leu Leu Tyr Arg Glu Leu His Asn Gln Leu
                85                  90                  95

Phe Glu His Gln Lys Glu Gly Ile Ala Phe Leu Tyr Ser Leu Tyr Arg
            100                 105                 110

Asp Gly Arg Lys Gly Gly Ile Leu Ala Asp Asp Met Gly Leu Gly Lys
        115                 120                 125

Thr Val Gln Ile Ile Ala Phe Leu Ser Gly Met Phe Asp Ala Ser Leu
    130                 135                 140

Val Asn His Val Leu Leu Ile Met Pro Thr Asn Leu Ile Asn Thr Trp
145                 150                 155                 160

Val Lys Glu Phe Ile Lys Trp Thr Pro Gly Met Arg Val Lys Thr Phe
                165                 170                 175
```

```
His Gly Pro Ser Lys Asp Glu Arg Thr Arg Asn Leu Asn Arg Ile Gln
            180                 185                 190

Gln Arg Asn Gly Val Ile Ile Thr Thr Tyr Gln Met Leu Ile Asn Asn
            195                 200                 205

Trp Gln Gln Leu Ser Ser Phe Arg Gly Gln Glu Phe Val Trp Asp Tyr
210                 215                 220

Val Ile Leu Asp Glu Ala His Lys Ile Lys Thr Ser Ser Thr Lys Ser
225                 230                 235                 240

Ala Ile Cys Ala Arg Ala Ile Pro Ala Ser Asn Arg Leu Leu Leu Thr
                245                 250                 255

Gly Thr Pro Ile Gln Asn Asn Leu Gln Glu Leu Trp Ser Leu Phe Asp
                260                 265                 270

Phe Ala Cys Gln Gly Ser Leu Leu Gly Thr Leu Lys Thr Phe Lys Met
            275                 280                 285

Glu Tyr Glu Asn Pro Ile Thr Arg Ala Arg Glu Lys Asp Ala Thr Pro
            290                 295                 300

Gly Glu Lys Ala Leu Gly Phe Lys Ile Ser Glu Asn Leu Met Ala Ile
305                 310                 315                 320

Ile Lys Pro Tyr Phe Leu Arg Arg Thr Lys Glu Asp Val Gln Lys Lys
                325                 330                 335

Lys Ser Ser Asn Pro Glu Ala Arg Leu Asn Glu Lys Asn Pro Asp Val
                340                 345                 350

Asp Ala Ile Cys Glu Met Pro Ser Leu Ser Arg Lys Asn Asp Leu Ile
            355                 360                 365

Ile Trp Ile Arg Leu Val Pro Leu Gln Glu Glu Ile Tyr Arg Lys Phe
            370                 375                 380

Val Ser Leu Asp His Ile Lys Glu Leu Leu Met Glu Thr Arg Ser Pro
385                 390                 395                 400

Leu Ala Glu Leu Gly Val Leu Lys Lys Leu Cys Asp His Pro Arg Leu
                405                 410                 415

Leu Ser Ala Arg Ala Cys Cys Leu Leu Asn Leu Gly Thr Phe Ser Ala
                420                 425                 430

Gln Asp Gly Asn Glu Gly Glu Asp Ser Pro Asp Val Asp His Ile Asp
            435                 440                 445

Gln Val Thr Asp Thr Leu Met Glu Glu Ser Gly Lys Met Ile Phe
            450                 455                 460

Leu Met Asp Leu Leu Lys Arg Leu Arg Asp Glu Gly His Gln Thr Leu
465                 470                 475                 480

Val Phe Ser Gln Ser Arg Gln Ile Leu Asn Ile Ile Glu Arg Leu Leu
                485                 490                 495

Lys Asn Arg His Phe Lys Thr Leu Arg Ile Asp Gly Thr Val Thr His
            500                 505                 510

Leu Leu Glu Arg Glu Lys Arg Ile Asn Leu Phe Gln Gln Asn Lys Asp
            515                 520                 525

Tyr Ser Val Phe Leu Leu Thr Thr Gln Val Gly Val Gly Leu Thr
            530                 535                 540

Leu Thr Ala Ala Thr Arg Val Val Ile Phe Asp Pro Ser Trp Asn Pro
545                 550                 555                 560

Ala Thr Asp Ala Gln Ala Val Asp Arg Val Tyr Arg Ile Gly Gln Lys
                565                 570                 575

Glu Asn Val Val Val Tyr Arg Leu Ile Thr Cys Gly Thr Val Glu Glu
            580                 585                 590
```

```
Lys Ile Tyr Arg Arg Gln Val Phe Lys Asp Ser Leu Ile Arg Gln Thr
            595                 600                 605

Thr Gly Glu Lys Lys Asn Pro Phe Arg Tyr Phe Ser Lys Gln Glu Leu
610                 615                 620

Arg Glu Leu Phe Thr Ile Glu Asp Leu Gln Asn Ser Val Thr Gln Leu
625                 630                 635                 640

Gln Leu Gln Ser Leu His Ala Ala Gln Arg Lys Ser Asp Ile Lys Leu
                645                 650                 655

Asp Glu His Ile Ala Tyr Leu Gln Ser Leu Gly Ile Ala Gly Ile Ser
                660                 665                 670

Asp His Asp Leu Met Tyr Thr Cys Asp Leu Ser Val Lys Glu Glu Leu
                675                 680                 685

Asp Val Val Glu Glu Ser His Tyr Ile Gln Gln Arg Val Gln Lys Ala
            690                 695                 700

Gln Phe Leu Val Glu Phe Glu Ser Gln Asn Lys Glu Phe Leu Met Glu
705                 710                 715                 720

Gln Gln Arg Thr Arg Asn Glu Gly Ala Trp Leu Arg Glu Pro Val Phe
                725                 730                 735

Pro Ser Ser Thr Lys Lys Lys Cys Pro Lys Leu Asn Lys Pro Gln Pro
                740                 745                 750

Gln Pro Ser Pro Leu Leu Ser Thr His His Thr Gln Glu Glu Asp Ile
            755                 760                 765

Ser Ser Lys Met Ala Ser Val Val Ile Asp Asp Leu Pro Lys Glu Gly
            770                 775                 780

Glu Lys Gln Asp Leu Ser Ser Ile Lys Val Asn Val Thr Thr Leu Gln
785                 790                 795                 800

Asp Gly Lys Gly Thr Gly Ser Ala Asp Ser Ile Ala Thr Leu Pro Lys
                805                 810                 815

Gly Phe Gly Ser Val Glu Leu Cys Thr Asn Ser Ser Leu Gly Met
                820                 825                 830

Glu Lys Ser Phe Ala Thr Lys Asn Glu Ala Val Gln Lys Glu Thr Leu
                835                 840                 845

Gln Glu Gly Pro Lys Gln Glu Ala Leu Gln Glu Asp Pro Leu Glu Ser
850                 855                 860

Phe Asn Tyr Val Leu Ser Lys Ser Thr Lys Ala Asp Ile Gly Pro Asn
865                 870                 875                 880

Leu Asp Gln Leu Lys Asp Asp Glu Ile Leu Arg His Cys Asn Pro Trp
                885                 890                 895

Pro Ile Ile Ser Ile Thr Asn Glu Ser Gln Asn Ala Glu Ser Asn Val
                900                 905                 910

Ser Ile Ile Glu Ile Ala Asp Asp Leu Ser Ala Ser His Ser Ala Leu
                915                 920                 925

Gln Asp Ala Gln Ala Ser Glu Ala Lys Leu Glu Glu Pro Ser Ala
                930                 935                 940

Ser Ser Pro Gln Tyr Ala Cys Asp Phe Asn Leu Phe Leu Glu Asp Ser
945                 950                 955                 960

Ala Asp Asn Arg Gln Asn Phe Ser Ser Gln Ser Leu Glu His Val Glu
                965                 970                 975

Lys Glu Asn Ser Leu Cys Gly Ser Ala Pro Asn Ser Arg Ala Gly Phe
                980                 985                 990

Val His Ser Lys Thr Cys Leu Ser Trp Glu Phe Ser Glu Lys Asp Asp
            995                 1000                1005

Glu Pro Glu Glu Val Val Val Lys Ala Lys Ile Arg Ser Lys Ala
```

| | | | | | | | | | |
|---|---|---|---|---|---|---|---|---|---|
| | | 1010 | | | 1015 | | | 1020 | |
| Arg | Arg | Ile | Val | Ser | Asp | Gly | Glu | Asp | Glu Asp Ser Phe Lys |
| | 1025 | | | | 1030 | | | | 1035 |
| Asp | Thr | Ser | Ser | Ile | Asn | Pro | Phe | Asn | Thr Ser Leu Phe Gln Phe |
| | 1040 | | | | 1045 | | | | 1050 |
| Ser | Ser | Val | Lys | Gln | Phe | Asp | Ala | Ser | Thr Pro Lys Asn Asp Ile |
| | 1055 | | | | 1060 | | | | 1065 |
| Ser | Pro | Pro | Gly | Arg | Phe | Phe | Ser | Ser | Gln Ile Pro Ser Ser Val |
| | 1070 | | | | 1075 | | | | 1080 |
| Asn | Lys | Ser | Met | Asn | Ser | Arg | Arg | Ser | Leu Ala Ser Arg Arg Ser |
| | 1085 | | | | 1090 | | | | 1095 |
| Leu | Ile | Asn | Met | Val | Leu | Asp | His | Val | Glu Asp Met Glu Glu Arg |
| | 1100 | | | | 1105 | | | | 1110 |
| Leu | Asp | Asp | Ser | Ser | Glu | Ala | Lys | Gly | Pro Glu Asp Tyr Pro Glu |
| | 1115 | | | | 1120 | | | | 1125 |
| Glu | Gly | Val | Glu | Glu | Ser | Ser | Gly | Glu | Ala Ser Lys Tyr Thr Glu |
| | 1130 | | | | 1135 | | | | 1140 |
| Glu | Asp | Pro | Ser | Gly | Glu | Thr | Leu | Ser | Ser Glu Asn Lys Ser Ser |
| | 1145 | | | | 1150 | | | | 1155 |
| Trp | Leu | Met | Thr | Ser | Lys | Pro | Ser | Ala | Leu Ala Gln Glu Thr Ser |
| | 1160 | | | | 1165 | | | | 1170 |
| Leu | Gly | Ala | Pro | Glu | Pro | Leu | Ser | Gly | Glu Gln Leu Val Gly Ser |
| | 1175 | | | | 1180 | | | | 1185 |
| Pro | Gln | Asp | Lys | Ala | Ala | Glu | Ala | Thr | Asn Asp Tyr Glu Thr Leu |
| | 1190 | | | | 1195 | | | | 1200 |
| Val | Lys | Arg | Gly | Lys | Glu | Leu | Lys | Glu | Cys Gly Lys Ile Gln Glu |
| | 1205 | | | | 1210 | | | | 1215 |
| Ala | Leu | Asn | Cys | Leu | Val | Lys | Ala | Leu | Asp Ile Lys Ser Ala Asp |
| | 1220 | | | | 1225 | | | | 1230 |
| Pro | Glu | Val | Met | Leu | Leu | Thr | Leu | Ser | Leu Tyr Lys Gln Leu Asn |
| | 1235 | | | | 1240 | | | | 1245 |
| Asn | Asn | | | | | | | | |
| | 1250 | | | | | | | | |

<210> SEQ ID NO 33
<211> LENGTH: 10324
<212> TYPE: DNA
<213> ORGANISM: Homo sapiens

<400> SEQUENCE: 33

```
caattcggga gcccgttctc gcgggatttt ccaagaccgg gttggaattt gcggggggtta      60
ggagacggaa gtcagagcct aggaagattt gggggtcgcc ttgccggcct cctgtcctcc     120
tccggcggcg gcggagcccg agagaactag gtgaacaccg ctttgccagc ctcacacagc     180
gtccctggc tctgccgccg ctccggacgt cgccctcccg ttctgcttgg gtccccttag      240
tcgctacctt tgctgggatc ccctcctcc atcctgtggc ttcgggttgc cgaagagcga      300
tgctcggagg gcggccggaa gtggcgttgg ccgccattgg cctgccggcc agccaccttg     360
ctgtcctccg ccgccttccg ggtgttacat gcagccgggc tcggccctc ccctggccg       420
gatggatccg tcggcgccac agccccgcgc ggaaacctca ggcaaagaca tatggcatcc     480
aggagaaaga tgtcttgccc cttctccaga taatggaaaa ctttgtgaag caagcataaa     540
atctatcaca gtggatgaaa atggcaagtc atttgcagtc gtcttatatg cagatttttca    600
agaaaggaaa ataccctctta aacagcttca agaagtgaaa tttgttaaag attgccctag    660
```

```
gaatcttata tttgatgatg aagatttaga aaaaccttat ttcccaaacc gaaaatttcc    720
atcatcttct gttgcttttg aattatctga caatggagac tctattcctt ataccatcaa    780
taggtatttg agagactacc aaagagaagg aacccggttt ctttatggac actacatcca    840
tggaggaggg tgcattctgg gtgatgacat gggacttgga aaaacagtac aggttatttc    900
atttctggct gcagttttgc ataaaaaggg aactcgtgag gatattgaaa ataacatgcc    960
agagttttta ctaagaagta tgaaaaagga acccctttct tctacagcaa aaagatgtt   1020
cttaatagtt gctcctcttt ctgtcctcta caactggaag gatgaattgg acacctgggg   1080
atatttcaga gtcactgttt tacatggaaa cagaaaagat aatgaattaa ttcgtgtaaa   1140
gcagaggaaa tgtgaaattg ctctaacaac ttatgaaaca ctacgcttat gcctggatga   1200
acttaacagt ttggaatggt cagctgtcat tgtggatgaa gctcatagaa tcaagaatcc   1260
aaaagctaga gtaacagaag ttatgaaagc tttgaaatgt aatgtccgca ttggcctcac   1320
tggaaccatc cttcagaaca acatgaagga actgtggtgt gttatggact gggctgtgcc   1380
aggccttttg gggagtggga cctacttcaa gaagcagttt tctgacccag tagaacatgg   1440
tcagagacac acggcaacaa agagagaact agccactggc cgaaaggcca tgcaaagact   1500
tgccaaaaag atgtctggct ggtttctcag gcgcaccaag actcttatca aggatcagtt   1560
gcctaagaag gaagaccgga tggtgtattg ttctttgaca gatttccaga aagctgtcta   1620
tcaaacagtg ttagaaacag aggacgtgac tttgatactt caatcttctg agccttgtac   1680
ctgtaggagt ggccaaaaaa ggagaaattg ttgttataag accaattctc atggtgaaac   1740
agtgaaaacc ttgtatctca gttaccttac agtccttcag aaggtagcta accatgtcgc   1800
gctactgcaa gctgctagta cttccaaaca acaggaaaca cttatcaaaa ggatatgtga   1860
tcaggtatttt ccagattcc cagattttgt gcagaaaagc aaagatgcag cctttgaaac   1920
actttctgac cctaaataca gtggaaaaat gaaggtcctt cagcagcttt taaatcattg   1980
caggaaaaac agagataaag ttcttctctt ttctttttcc accaagttgc ttgacgtgct   2040
acagcagtac tgtatggcgt ctgggcttga ttaccgacga cttgatggaa gtacaaaatc   2100
agaggaaaga ctcaagattg taaaagagtt caacagtaca caagatgtta acatttgcct   2160
tgtctctaca atggctggtg gactaggcct caattttgtc ggtgccaatg ttgttgtatt   2220
atttgatcct acttggaatc cagccaatga tcttcaagcc attgacagag catataggat   2280
tggacaatgt agagatgtca aagtgcttag gctgatatcc ttgggaactg tggaggaaat   2340
catgtatttg cgacagatat acaagcagca acttcactgt gtggtggttg aagtgaaaaa   2400
tgccaaacga tattttgaag cagttcaagg atctaaagag catcaaggag agcttttttgg   2460
gatccataac ctcttcaaat ttaggtccca agggtcttgt cttacgaagg catcctggaa   2520
gagagaaggc caagtagaag cagggatcat gacagccaca acatggttga agagggacc   2580
tccagcacac aaactggaaa tgcctagaca gcctgactgt caggaatgca gaggtacaga   2640
acaagctgca gagccactgg caaaggaagc atgtgatctc tgcagtgact tcagtgatga   2700
agagccagtg ggagccacag gaataaagac tgccaaaaac aaagcacccg attcaagtaa   2760
agcttccagc tctccaggac agcttacctt actccagtgt ggtttctcga aattgcttga   2820
aacaaaatgt aaagcagttg aggatagtga tggaaatact gcctctgatg atgaaagttc   2880
tgatgagcag cccacatgcc tttcaacaga gccaaagat gctggttgtg agaaaaatca   2940
ggactctctt ggtacttcaa aacatcagaa attagataac atcctaaatc caaagaaaa   3000
```

```
gcatatttttt tataaaagtg agaagatttt agaacagaat atttcttcca agtctgacga    3060
gaaaaaaatt aaaaatacag ataaacattg cattttacag aatgtcacag aatcagaaga    3120
tagtgatgtc atctgtccta cacaatacac aactgagaga ttccccgaca atagtataag    3180
gtttaagcca cccttggaag gatctgagga ttctgaaaca gaacacactg taaaaacaag    3240
aaataatgat aatagtcgaa acactgatga caaaagaaat ggaataattt caaaaaagtt    3300
aagtcctgag aacacaaccc tgaaatctat tttgaaaaga aaaggcacca gtgatatcag    3360
tgatgaatct gatgacattg aaatttcttc caagtcaaga gtaagaaaga gagctagttc    3420
attgaggttt aagagaataa aagaaaccaa aaaagaactt cacaattctc ccaaaacaat    3480
gaacaaaaca aaccaagtgt atgcagcaaa tgaggatcat aactctcagt ttattgatga    3540
ttattcatcc tcagatgaga gtttatccgt cagccacttc agtttctcta acagagccaa    3600
cagaccaaga actataagag acagaactag ttttttcttc aaaattgccta gccataataa    3660
gaaaaatagc acttttattc caagaaaacc aatgaaatgt tcaaatgaga aagttgttaa    3720
tcaagagcag tcgtatgaat caatggataa attttttagat ggcgttcagg aagtggctta    3780
tattcactca aaccagaatg taattggatc gagcaaagct gaaaatcaca tgagccgatg    3840
ggcagcacat gacgtatttg agttgaagca gttttctcag ctgcctgcta acatagctgt    3900
ttgcagttct aagacatata agaaaaaagt ggatgcagat acattgccac acacaaagaa    3960
aggccagcaa ccgagtgaag gcagcatttc acttcctctt tacatttcaa atcctgtaaa    4020
ccagaagaag aaaaaagtct accatacaaa ccagaccacc ttcataattg gagaaacacc    4080
aaaaggaatc gcagaaaac aatttgaaga atggcctctc tattttaact cgtcttctgt    4140
aaacgaattt gctaaacata taaccaatgc cacatcagaa gaacgacaga aaatgctaag    4200
agacttttat gcttctcaat atccagaggt aaaagaattt tttgtggatt ctgtgtcaca    4260
attcaacaat tcttcctttg agaaggaga gcagcgcacc cggaagaaat ctgataaaag    4320
agaatctctt ataaaaccaa ggctgtcaga ttctgaaacc ttgtcatttta aagattctac    4380
caacaaaatt tctcaagttt gcagcctaaa acatataaaa agaaaatcag ttaagtttca    4440
gaatcatatt tcctatagag aagaggtgtt ttttaatgat gcagaaacta agaaatcacc    4500
tgttagttct actcaagaga ttgacagtgg gaaaaacagc caggcatccg aagatactgt    4560
gacatcccgt tctctgaaca gtgagtctga aacacgtgag agaaggttag aaaataccat    4620
gaaagaccaa caggacctca caagaacggg catttcaaga aaagaacccc ttctcaaatt    4680
ggaaaacaaa aagatagaaa atccagtgct ggaaaatact tctgtgataa gcttacttgg    4740
tgatacctct attcttgatg accttttaa aagtcatggg aacagtccca cacaactgcc    4800
aaagaaagtt ctttcagggc ccatggaaaa agcaaacag agaccaaaag atttctggga    4860
catcttgaat gagcagaatg atgagagtct tagtaaactc acagacttgg cagtaataga    4920
gactctgtgt gaaaaagcac ctctagcagc acccttaaaa aggagagaag agccagcaac    4980
ttctctcttgg aaatcaaatg agaaattttt atggaagaaa tttagcccaa gtgatacaga    5040
tgaaaacgca accaatacac agagtaccac ataagcatat aaatgaatta ctgcaccagt    5100
aaactgctgc catcactgtt tacggcactg gattccacac tgattctatt atcttgaaca    5160
cagttgttga catatatttt tattaaatta ttgctttagg attttttgaa gtctaaagta    5220
ttgtcatgga tctgtttttc ttgatatttg atttgatctt tcaagaatat gattgtattt    5280
atagtataaa cctctgttat gaattagaaa agattctagg tttgttaata ggagacctgg    5340
gacatctttc ttactatatt acataatgat gtgacacttg ccccggtgag cattgtttcc    5400
```

```
cagtatgaaa gatgaagagt ctgtaccgaa tcagcatgag tgtccttcca gtttaaaaaa    5460
gctttgcttc gctctcctaa tggctcatag gctgaatcat gtctgcccct caaatcaggt    5520
gtataccaat gtgtttttta ctagcacttg ggaaagttat taagtatttt ctttttccct    5580
gggcatcatg ttctattatt attttagaaa aaagtcataa ttggtactga atatatggta    5640
tatataatat taaaatggta attttgcaac agctcaaaat taaaaggtta atgttataca    5700
ctttactata tgagctgtga ttactaccat tagccacaga taccagtgcc tcaacttttt    5760
atgtacctat tgtgatttaa tgtaaataaa ggtttgtata gtacttttgt agttcttaag    5820
tatgaagaaa tgggtaaact ttttatttttg ttagaaactg ttatattttg agtgtaatat    5880
ttatggttta tagcaaaatg aatgtgctta ttgttgaatg catgtattta gaagccttta    5940
ctcagcccct gtgttctgtg ctaggagctt gagctctaca ggtaaggcag agctaccggt    6000
gaatgaaagg aaatcatgtc agtgaaaaat catggtggaa agccctggc atcacatgtg      6060 catgctgtag gcaggacctg agctgcctcc gctgcaggtt cagatgcacc gctgcagctg    6120
tccttcagtt agttcacagg gctgcaagag gaggacacat ccctccagaa aacagcctga   6180
gccgggaact ggctgtgcta aagagcactg ctatcaagtt gaggagagag ggcttccgtg    6240
tactcaggat gtagagtcat tgctcagaag tgaacaaaaa atcaaaaaca aaagtcttct    6300
caagggactg atcggccaag tatgcttttc tttagagcaa tgttttgccc tagagaattg    6360
taaaatttat gtcatgactc agtacatatg tgttcgtaca tatatgattg gaataaaatg    6420
tttatgaaat atttactcat aagccatgta acatactttg acattttct cttctaggat    6480 tgtgtttggt agggcagtgg gtttgtgtgt gtgttaatcc tctcacaacc cactgaattg    6540
aatttcatgg cccatggtta agatccacag tgtgaaaacg ctgttttaaa ttatatgagt    6600
tcgtcatttg tttgctctgt gcagctgagt tgtgtccaga cttaccagat ggtatgtttt    6660
gccattgagg ggccttctac acaatgagtg catgatatgg tccttgatag acttgacttg    6720
tagatgtttt cagcctacaa tgtgatcagc tatctgagga actccagtaa gtagatacca    6780
cttcatttca gtttatatac aagacaatgt agttcaaaca ttttaatacc ttgtaaatta    6840
tgatattcat ataaatatta gctctatagt cttcatatat gtacagtttt ttttttttt    6900 ttttttttt tgagattgag tctcactctg tcacccaggc tggagtacag tggcatgatc    6960
ttggctcact gcaacctcca cctccctccc aaacaactct tatgcctcag cctcctgagt    7020
agctaggatt acaggtgtgt accaccacac tcagctaaac atttttttt tttttgaga    7080 cggagtctca ctctgtcgcc aggctggagt gcagtggctc gatcttggct cactgcagcc    7140 tccgccccc gagtcaagca attctcctgc ctcagcctcc cgagtagctg ggactacagg    7200
tgcgtgccac cacgcccagc taattttttt gtgtttttag tagggatggg gtttcaccat    7260
gttggccagg ctggtctcaa tctcctggct gcaagcgatc cacctgcctt gtcctcccaa    7320
agtgctggga ttacaggtgt gagccaccat gcccagccaa taatgctat taagaaact      7380 tttaggccgg gcacagtggc tcacgcctgt aatcccagca ctttgggagg ccgaggcagg    7440
cggatcacaa ggtcatgaga tcgagactat cctggctaac gcggtgaaac cccgtctcta    7500
ctaaaaaaaa aaaaaataca aaaattagcc aggcgtggtg gtgggcgcct gtagtcccag    7560
ctactcggga ggctgaggca ggagaatggc gtgaacctgg gaggcagagc ttgcagtgag    7620
ccaggattgt gcccctgcac cccagcctgg gtgacagagc aagactccat ctcaaaaaag    7680 gaaacttta tcaatagtag tcaaaatggg agcaaaaatg cagaactgga gtttaaaaat    7740
```

```
tagtttccaa cagttgtcag tgaaatattt atcactatta tgtaggaaag tgtgtcaggt    7800
ggaatgcaga gtccagtatg aaaaggagcc tgtttcagaa cggaaactgt caggtggagt    7860
ggactccctg caatggagtg atggaaagat ttggtacaac cattgatgac ctgagaacag    7920
acactaggaa ggtttgacaa gatccttcct accccactc cactggtgat gtgtcaccaa     7980
gttctgctaa ctaaatgggt ggcctcaagc aaatccctta cctccttta gccttagttt     8040 cccctttaaa ttggtgatgg attagatcag tggtggtcag ccattttctt aaagcaactg    8100
aactgtatct taatcagaaa cttaactagt aaaacaatta aaatgcaagt ctgttgcttc    8160
aagcaacacc actgtggctc catggagcac taatttgaaa accacagaga tgagatcatt    8220
tctaagaaaa cctttcaact tgtttccat gatgctactt gccacaatct ttttacttta     8280
agcaatgata ccgtttctgg ctgaacactc accacacagc tattaatatt ggaaactgag    8340
gcaagatacc aagagatttt tgcacttgaa ttcctcaggg ttctcttaca gccctgaaaa    8400
cacctcttca aggaaataaa taacatctgc aaatggtgca gctgcccta agtattcaag     8460 gcaagaagc cttagtttgc agagatgatg ataaactttt catccttcca cagaaaatga     8520
gaaagccaca ggaaatacac ggttattttc taattaaagt tcaatgtgta cgcttttaaa    8580
ttctgaagtt atccttcttt tatgatatca aaatagccct ctttttttgaa atgatggtag   8640 atcataccttt tggtcttt tcattgtcct tacataaag ttggtaatca tatgtcagtc      8700
ccagaagttt tatttgacac ttactggtct ataaaatcca aaggaatggg gatcactgcc    8760
tgccttaaag gttttttgt gtgtttgttt gtttgtttgt ttgcatgtga aggatttta     8820 tgtcacaaat ccagctaaca gtggatctag gatctaggcc tcaccgagga tgtcactgaa    8880
cctgtcagcc ccaatgacag gcacacacct tcaaagagca agagtgccca tcactttcta   8940
ggctccttgc ctgctgctca ttccatcatc acggatacag acttgtttct ggtttcatct    9000
tccaccagag attgcaaagc atcctctgcc cagtgcttct aggaggcctt actgggatgg    9060
ttcataagcc actttcctct tggtgacagc ccctgtacac tgtggcatgt acggctggct    9120
ccacttggta tttgttgcag gagggaagaa catctcactt tgcttggct aaagggccac     9180 cccaggagag ctattttgcc tcagggtctt gcagggtttc tctaggaaaa cagtgcatct    9240
gatagttact ctctgcccct aggaggaaag acagattcgc ccttccttcc caagtcccag    9300
gctgtgtggt tcccagcccc aagggtagca agtcagaacc tccggagagg cttttaagca    9360
tgcacatgtc cagggtcctc atcaagagac tgaatcaggg ggtctagggc tcagcacagg   9420
cacccttttt gttttgcag tttcacagga attctgatgt gccagtgatt gtcaggtttg     9480
tccctgggca ggacccacct gcctgacctt ctgtccccct gggacacagt atttccagag    9540
aggtgcttca gttgccccac cacgacttcc agcgcccccc atctctgtat gcagctgagc    9600
tcatgatgga gcccactgtg tgctttttgt tgttgttaca ttcctataaa aatgtccacg    9660
catatttgaa catctgtgtt catagtggca ttattcacaa tggctacaac acgaagaaag    9720
cattccaagt acctatcgat gaataagcaa aatattacac acacaggaat attattcagc    9780
cttgaaagga aattcggaca cgtgctacaa catagatgaa tcttgaggac ggtatgcaaa    9840
gtgaaataaa tcagacacag aaggacaaat actgtatgat tccacttata taaagtacct    9900
agattagtca gattcataga gacaaagtag aatggtggtt gctagacgct ggagggaggg    9960
gagaaagggg agttattaat gggtgtagag tttctgttac acaggatgca aagtggcctg   10020
aagatggatg gtcgtgatgg ttgcacagca atgtgaattt aatgacactg aagtgtacac   10080
ttaaaagtca ttaaaatgct aaattttgta tgtgttttac aattttaaaa atggaaaaaa   10140
```

-continued

```
agtaagacca aaagcaacac ctctccagaa tgtgtgttat ataccaaatt ttgatgtatg    10200
tgagattgct gactatattt tacttatcaa tttgaaatta tattgttttt atgttgacac    10260
tccatataag ccattatttt gaaaaaaaca ttttccttat taaaagattg gaaaaaaatt    10320
caca                                                                 10324
```

<210> SEQ ID NO 34
<211> LENGTH: 1561
<212> TYPE: PRT
<213> ORGANISM: Homo sapiens

<400> SEQUENCE: 34

```
Met Gln Pro Gly Ser Ala Pro Pro Gly Arg Met Asp Pro Ser Ala
1               5                   10                  15

Pro Gln Pro Arg Ala Glu Thr Ser Gly Lys Asp Ile Trp His Pro Gly
            20                  25                  30

Glu Arg Cys Leu Ala Pro Ser Pro Asp Asn Gly Lys Leu Cys Glu Ala
        35                  40                  45

Ser Ile Lys Ser Ile Thr Val Asp Glu Asn Gly Lys Ser Phe Ala Val
    50                  55                  60

Val Leu Tyr Ala Asp Phe Gln Glu Arg Lys Ile Pro Leu Lys Gln Leu
65                  70                  75                  80

Gln Glu Val Lys Phe Val Lys Asp Cys Pro Arg Asn Leu Ile Phe Asp
                85                  90                  95

Asp Glu Asp Leu Glu Lys Pro Tyr Phe Pro Asn Arg Lys Phe Pro Ser
            100                 105                 110

Ser Ser Val Ala Phe Lys Leu Ser Asp Asn Gly Asp Ser Ile Pro Tyr
        115                 120                 125

Thr Ile Asn Arg Tyr Leu Arg Asp Tyr Gln Arg Glu Gly Thr Arg Phe
    130                 135                 140

Leu Tyr Gly His Tyr Ile His Gly Gly Gly Cys Ile Leu Gly Asp Asp
145                 150                 155                 160

Met Gly Leu Gly Lys Thr Val Gln Val Ile Ser Phe Leu Ala Ala Val
                165                 170                 175

Leu His Lys Lys Gly Thr Arg Glu Asp Ile Glu Asn Asn Met Pro Glu
            180                 185                 190

Phe Leu Leu Arg Ser Met Lys Lys Glu Pro Leu Ser Ser Thr Ala Lys
        195                 200                 205

Lys Met Phe Leu Ile Val Ala Pro Leu Ser Val Leu Tyr Asn Trp Lys
    210                 215                 220

Asp Glu Leu Asp Thr Trp Gly Tyr Phe Arg Val Thr Val Leu His Gly
225                 230                 235                 240

Asn Arg Lys Asp Asn Glu Leu Ile Arg Val Lys Gln Arg Lys Cys Glu
                245                 250                 255

Ile Ala Leu Thr Thr Tyr Glu Thr Leu Arg Leu Cys Leu Asp Glu Leu
            260                 265                 270

Asn Ser Leu Glu Trp Ser Ala Val Ile Val Asp Glu Ala His Arg Ile
        275                 280                 285

Lys Asn Pro Lys Ala Arg Val Thr Glu Val Met Lys Ala Leu Lys Cys
    290                 295                 300

Asn Val Arg Ile Gly Leu Thr Gly Thr Ile Leu Gln Asn Asn Met Lys
305                 310                 315                 320

Glu Leu Trp Cys Val Met Asp Trp Ala Val Pro Gly Leu Leu Gly Ser
                325                 330                 335
```

```
Gly Thr Tyr Phe Lys Lys Gln Phe Ser Asp Pro Val Glu His Gly Gln
                340                 345                 350

Arg His Thr Ala Thr Lys Arg Glu Leu Ala Thr Gly Arg Lys Ala Met
            355                 360                 365

Gln Arg Leu Ala Lys Lys Met Ser Gly Trp Phe Leu Arg Arg Thr Lys
370                 375                 380

Thr Leu Ile Lys Asp Gln Leu Pro Lys Glu Asp Arg Met Val Tyr
385                 390                 395                 400

Cys Ser Leu Thr Asp Phe Gln Lys Ala Val Tyr Gln Thr Val Leu Glu
                405                 410                 415

Thr Glu Asp Val Thr Leu Ile Leu Gln Ser Ser Glu Pro Cys Thr Cys
            420                 425                 430

Arg Ser Gly Gln Lys Arg Arg Asn Cys Cys Tyr Lys Thr Asn Ser His
            435                 440                 445

Gly Glu Thr Val Lys Thr Leu Tyr Leu Ser Tyr Leu Thr Val Leu Gln
        450                 455                 460

Lys Val Ala Asn His Val Ala Leu Leu Gln Ala Ala Ser Thr Ser Lys
465                 470                 475                 480

Gln Gln Glu Thr Leu Ile Lys Arg Ile Cys Asp Gln Val Phe Ser Arg
                485                 490                 495

Phe Pro Asp Phe Val Gln Lys Ser Lys Asp Ala Ala Phe Glu Thr Leu
                500                 505                 510

Ser Asp Pro Lys Tyr Ser Gly Lys Met Lys Val Leu Gln Gln Leu Leu
            515                 520                 525

Asn His Cys Arg Lys Asn Arg Asp Lys Val Leu Leu Phe Ser Phe Ser
            530                 535                 540

Thr Lys Leu Leu Asp Val Leu Gln Gln Tyr Cys Met Ala Ser Gly Leu
545                 550                 555                 560

Asp Tyr Arg Arg Leu Asp Gly Ser Thr Lys Ser Glu Glu Arg Leu Lys
                565                 570                 575

Ile Val Lys Glu Phe Asn Ser Thr Gln Asp Val Asn Ile Cys Leu Val
                580                 585                 590

Ser Thr Met Ala Gly Gly Leu Gly Leu Asn Phe Val Gly Ala Asn Val
            595                 600                 605

Val Val Leu Phe Asp Pro Thr Trp Asn Pro Ala Asn Asp Leu Gln Ala
        610                 615                 620

Ile Asp Arg Ala Tyr Arg Ile Gly Gln Cys Arg Asp Val Lys Val Leu
625                 630                 635                 640

Arg Leu Ile Ser Leu Gly Thr Val Glu Glu Ile Met Tyr Leu Arg Gln
                645                 650                 655

Ile Tyr Lys Gln Gln Leu His Cys Val Val Gly Ser Glu Asn Ala
                660                 665                 670

Lys Arg Tyr Phe Glu Ala Val Gln Gly Ser Lys Glu His Gln Gly Glu
            675                 680                 685

Leu Phe Gly Ile His Asn Leu Phe Lys Phe Arg Ser Gln Gly Ser Cys
            690                 695                 700

Leu Thr Lys Asp Ile Leu Glu Arg Glu Gly Gln Val Glu Ala Gly Ile
705                 710                 715                 720

Met Thr Ala Thr Thr Trp Leu Lys Glu Gly Pro Ala His Lys Leu
                725                 730                 735

Glu Met Pro Arg Gln Pro Asp Cys Gln Glu Cys Arg Gly Thr Glu Gln
                740                 745                 750
```

| | | | | | | | | | | | | |
|---|---|---|---|---|---|---|---|---|---|---|---|---|
| Ala | Ala | Glu | Pro | Leu | Ala | Lys | Glu | Ala | Cys | Asp | Leu | Cys | Ser | Asp | Phe |
| | | | 755 | | | | 760 | | | | 765 | | | | |
| Ser | Asp | Glu | Glu | Pro | Val | Gly | Ala | Thr | Gly | Ile | Lys | Thr | Ala | Lys | Asn |
| 770 | | | | | 775 | | | | | 780 | | | | | |
| Lys | Ala | Pro | Asp | Ser | Ser | Lys | Ala | Ser | Ser | Ser | Pro | Gly | Gln | Leu | Thr |
| 785 | | | | | 790 | | | | | 795 | | | | | 800 |
| Leu | Leu | Gln | Cys | Gly | Phe | Ser | Lys | Leu | Leu | Glu | Thr | Lys | Cys | Lys | Ala |
| | | | | 805 | | | | | 810 | | | | | 815 | |
| Val | Glu | Asp | Ser | Asp | Gly | Asn | Thr | Ala | Ser | Asp | Glu | Ser | Ser | Asp |
| | | 820 | | | | | 825 | | | | | 830 | | |
| Glu | Gln | Pro | Thr | Cys | Leu | Ser | Thr | Glu | Ala | Lys | Asp | Ala | Gly | Cys | Glu |
| | | 835 | | | | | 840 | | | | | 845 | | | |
| Lys | Asn | Gln | Asp | Ser | Leu | Gly | Thr | Ser | Lys | His | Gln | Lys | Leu | Asp | Asn |
| | 850 | | | | | 855 | | | | | 860 | | | | |
| Ile | Leu | Asn | Pro | Lys | Glu | Lys | His | Ile | Phe | Tyr | Lys | Ser | Glu | Lys | Ile |
| 865 | | | | | 870 | | | | | 875 | | | | | 880 |
| Leu | Glu | Gln | Asn | Ile | Ser | Ser | Lys | Ser | Asp | Glu | Lys | Lys | Ile | Lys | Asn |
| | | | | 885 | | | | | 890 | | | | | 895 | |
| Thr | Asp | Lys | His | Cys | Ile | Leu | Gln | Asn | Val | Thr | Glu | Ser | Glu | Asp | Ser |
| | | | 900 | | | | | 905 | | | | | 910 | | |
| Asp | Val | Ile | Cys | Pro | Thr | Gln | Tyr | Thr | Thr | Glu | Arg | Phe | Pro | Asp | Asn |
| | | 915 | | | | | 920 | | | | | 925 | | | |
| Ser | Ile | Arg | Phe | Lys | Pro | Pro | Leu | Glu | Gly | Ser | Glu | Asp | Ser | Glu | Thr |
| | 930 | | | | | 935 | | | | | 940 | | | | |
| Glu | His | Thr | Val | Lys | Thr | Arg | Asn | Asn | Asp | Asn | Ser | Arg | Asn | Thr | Asp |
| 945 | | | | | 950 | | | | | 955 | | | | | 960 |
| Asp | Lys | Arg | Asn | Gly | Ile | Ile | Ser | Lys | Lys | Leu | Ser | Pro | Glu | Asn | Thr |
| | | | | 965 | | | | | 970 | | | | | 975 | |
| Thr | Leu | Lys | Ser | Ile | Leu | Lys | Arg | Lys | Gly | Thr | Ser | Asp | Ile | Ser | Asp |
| | | | | 980 | | | | | 985 | | | | | 990 | |
| Glu | Ser | Asp | Asp | Ile | Glu | Ile | Ser | Ser | Lys | Ser | Arg | Val | Arg | Lys | Arg |
| | | 995 | | | | | 1000 | | | | | 1005 | | | |
| Ala | Ser | Ser | Leu | Arg | Phe | Lys | Arg | Ile | Lys | Glu | Thr | Lys | Lys | Glu |
| | 1010 | | | | | 1015 | | | | | 1020 | | | | |
| Leu | His | Asn | Ser | Pro | Lys | Thr | Met | Asn | Lys | Thr | Asn | Gln | Val | Tyr |
| | 1025 | | | | | 1030 | | | | | 1035 | | | | |
| Ala | Ala | Asn | Glu | Asp | His | Asn | Ser | Gln | Phe | Ile | Asp | Asp | Tyr | Ser |
| | 1040 | | | | | 1045 | | | | | 1050 | | | | |
| Ser | Ser | Asp | Glu | Ser | Leu | Ser | Val | Ser | His | Phe | Ser | Phe | Ser | Lys |
| | 1055 | | | | | 1060 | | | | | 1065 | | | | |
| Gln | Ser | His | Arg | Pro | Arg | Thr | Ile | Arg | Asp | Arg | Thr | Ser | Phe | Ser |
| | 1070 | | | | | 1075 | | | | | 1080 | | | | |
| Ser | Lys | Leu | Pro | Ser | His | Asn | Lys | Lys | Asn | Ser | Thr | Phe | Ile | Pro |
| | 1085 | | | | | 1090 | | | | | 1095 | | | | |
| Arg | Lys | Pro | Met | Lys | Cys | Ser | Asn | Glu | Lys | Val | Val | Asn | Gln | Glu |
| | 1100 | | | | | 1105 | | | | | 1110 | | | | |
| Gln | Ser | Tyr | Glu | Ser | Met | Asp | Lys | Phe | Leu | Asp | Gly | Val | Gln | Glu |
| | 1115 | | | | | 1120 | | | | | 1125 | | | | |
| Val | Ala | Tyr | Ile | His | Ser | Asn | Gln | Asn | Val | Ile | Gly | Ser | Ser | Lys |
| | 1130 | | | | | 1135 | | | | | 1140 | | | | |
| Ala | Glu | Asn | His | Met | Ser | Arg | Trp | Ala | Ala | His | Asp | Val | Phe | Glu |
| | 1145 | | | | | 1150 | | | | | 1155 | | | | |
| Leu | Lys | Gln | Phe | Ser | Gln | Leu | Pro | Ala | Asn | Ile | Ala | Val | Cys | Ser |

-continued

|   |   |   | 1160 |   |   | 1165 |   |   | 1170 |   |   |
|---|---|---|---|---|---|---|---|---|---|---|---|

Ser Lys Thr Tyr Lys Glu Lys Val Asp Ala Asp Thr Leu Pro His
1175                1180                1185

Thr Lys Lys Gly Gln Gln Pro Ser Glu Gly Ser Ile Ser Leu Pro
1190                1195                1200

Leu Tyr Ile Ser Asn Pro Val Asn Gln Lys Lys Lys Val Tyr
1205                1210                1215

His Thr Asn Gln Thr Thr Phe Ile Ile Gly Glu Thr Pro Lys Gly
1220                1225                1230

Ile Arg Arg Lys Gln Phe Glu Glu Met Ala Ser Tyr Phe Asn Ser
1235                1240                1245

Ser Ser Val Asn Glu Phe Ala Lys His Ile Thr Asn Ala Thr Ser
1250                1255                1260

Glu Glu Arg Gln Lys Met Leu Arg Asp Phe Tyr Ala Ser Gln Tyr
1265                1270                1275

Pro Glu Val Lys Glu Phe Val Asp Ser Val Ser Gln Phe Asn
1280                1285                1290

Asn Ser Ser Phe Glu Lys Gly Glu Gln Arg Thr Arg Lys Lys Ser
1295                1300                1305

Asp Lys Arg Glu Ser Leu Ile Lys Pro Arg Leu Ser Asp Ser Glu
1310                1315                1320

Thr Leu Ser Phe Lys Asp Ser Thr Asn Lys Ile Ser Gln Val Cys
1325                1330                1335

Ser Leu Lys Thr Tyr Lys Arg Lys Ser Val Lys Phe Gln Asn His
1340                1345                1350

Ile Ser Tyr Arg Glu Glu Val Phe Phe Asn Asp Ala Glu Thr Lys
1355                1360                1365

Lys Ser Pro Val Ser Ser Thr Gln Glu Ile Asp Ser Gly Lys Asn
1370                1375                1380

Ser Gln Ala Ser Glu Asp Thr Val Thr Ser Arg Ser Leu Asn Ser
1385                1390                1395

Glu Ser Glu Thr Arg Glu Arg Arg Leu Glu Asn Thr Met Lys Asp
1400                1405                1410

Gln Gln Asp Leu Thr Arg Thr Gly Ile Ser Arg Lys Glu Pro Leu
1415                1420                1425

Leu Lys Leu Glu Asn Lys Lys Ile Glu Asn Pro Val Leu Glu Asn
1430                1435                1440

Thr Ser Val Ile Ser Leu Leu Gly Asp Thr Ser Ile Leu Asp Asp
1445                1450                1455

Leu Phe Lys Ser His Gly Asn Ser Pro Thr Gln Leu Pro Lys Lys
1460                1465                1470

Val Leu Ser Gly Pro Met Glu Lys Ala Lys Gln Arg Pro Lys Asp
1475                1480                1485

Phe Trp Asp Ile Leu Asn Glu Gln Asn Asp Glu Ser Leu Ser Lys
1490                1495                1500

Leu Thr Asp Leu Ala Val Ile Glu Thr Leu Cys Glu Lys Ala Pro
1505                1510                1515

Leu Ala Ala Pro Phe Lys Arg Arg Glu Glu Pro Ala Thr Ser Leu
1520                1525                1530

Trp Lys Ser Asn Glu Lys Phe Leu Trp Lys Lys Phe Ser Pro Ser
1535                1540                1545

Asp Thr Asp Glu Asn Ala Thr Asn Thr Gln Ser Thr Thr
1550                1555                1560

<210> SEQ ID NO 35
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 35
ccttgatccc agatgttgtg gcctg                                              25

<210> SEQ ID NO 36
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 36
ctgggaaagc cctcattgct acagt                                              25

<210> SEQ ID NO 37
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 37
tacctcagtt gtgaccttca gcaga                                              25

<210> SEQ ID NO 38
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 38
gtggaggcca tcagtattga ctttc                                              25

<210> SEQ ID NO 39
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 39
tattgacttt ctcttacttg ctgta                                              25

<210> SEQ ID NO 40
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 40
cttgctgtac tatcagcctg ctcgt                                              25

<210> SEQ ID NO 41
<211> LENGTH: 24
<212> TYPE: DNA
<213> ORGANISM: Artificial Sequence
<220> FEATURE:

```
<223> OTHER INFORMATION: Synthetic polynucleotide

<400> SEQUENCE: 41
tgctcgtttc cacctttaag aatg                                          24

<210> SEQ ID NO 42
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 42
ctcaatgtct cctactatcc aaaat                                         25

<210> SEQ ID NO 43
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 43
atgtgcatca caggaggctc ttaac                                         25

<210> SEQ ID NO 44
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 44
ttgcgctaat gcttgaactc ttttt                                         25

<210> SEQ ID NO 45
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 45
gtatgaccaa atcctgcctc attaa                                         25

<210> SEQ ID NO 46
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 46
gctagaaacc acctgattct gccag                                         25

<210> SEQ ID NO 47
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 47
tgaaagcggg cacctgcagg aagct                                         25
```

```
<210> SEQ ID NO 48
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 48
gaacacgatg accttctggt ggaga                                  25

<210> SEQ ID NO 49
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 49
tgagaaactt catcgctttc caggc                                  25

<210> SEQ ID NO 50
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 50
tccaggccca cactgatggc caggc                                  25

<210> SEQ ID NO 51
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 51
caggccagca ccagggagat actgc                                  25

<210> SEQ ID NO 52
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 52
aagttatctg catcacagtc ttgtg                                  25

<210> SEQ ID NO 53
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 53
cagtcttgtg tcttccgaga actat                                  25

<210> SEQ ID NO 54
<211> LENGTH: 25
<212> TYPE: DNA
<213> ORGANISM: Artificial Sequence
<220> FEATURE:
<223> OTHER INFORMATION: Synthetic polynucleotide
```

<400> SEQUENCE: 54
atctgtgcac tttccataga acttc                                    25

<210> SEQ ID NO 55
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 55
aacaacattg cttcctaaac tttca                                    25

<210> SEQ ID NO 56
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 56
ggaagttggc tgcacttgat gtttg                                    25

<210> SEQ ID NO 57
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 57
gagactgttg ctcaaccatc aggaa                                    25

<210> SEQ ID NO 58
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 58
gagactgttg ctcaaccatc aggaa                                    25

<210> SEQ ID NO 59
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 59
gcagaaagtc gcatagggtt tttta                                    25

<210> SEQ ID NO 60
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 60
gacaatggcg ctgcatgttt ttctt                                    25

<210> SEQ ID NO 61
<211> LENGTH: 25

```
<212> TYPE: DNA
<213> ORGANISM: Artificial Sequence
<220> FEATURE:
<223> OTHER INFORMATION: Synthetic polynucleotide

<400> SEQUENCE: 61
tatctccttt tctctagtat ttgac                                           25

<210> SEQ ID NO 62
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 62
tttgactgtt actgtccttg gcgaa                                           25

<210> SEQ ID NO 63
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 63
gttactgtcc ttggcgaatc gataa                                           25

<210> SEQ ID NO 64
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 64
ggcgaatcga taatcattgc atagt                                           25

<210> SEQ ID NO 65
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 65
tagtgactga aaagcctaag tgcaa                                           25

<210> SEQ ID NO 66
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 66
ttcttgtttc tgaacttcgt gccat                                           25

<210> SEQ ID NO 67
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 67
```
acttcgtgcc atattttgtt cctga					25

<210> SEQ ID NO 68
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 68
tctattagag acttaccctc ctgac					25

<210> SEQ ID NO 69
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 69
cttaccctcc tgacctgata aaaag					25

<210> SEQ ID NO 70
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 70
aaagggatac ccatgtctct attaa					25

<210> SEQ ID NO 71
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 71
tacccatgtc tctattaaca gcttt					25

<210> SEQ ID NO 72
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 72
ttagttatgc ttaaggagga gttct					25

<210> SEQ ID NO 73
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 73
taatgtaaga cagttttggc cttta					25

<210> SEQ ID NO 74
<211> LENGTH: 25
<212> TYPE: DNA
<213> ORGANISM: Artificial Sequence

```
<220> FEATURE:
<223> OTHER INFORMATION: Synthetic polynucleotide

<400> SEQUENCE: 74
attatcatga gagatccttc tgaat                                              25

<210> SEQ ID NO 75
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 75
ccttctgaat aggatgtctt tctga                                              25

<210> SEQ ID NO 76
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 76
tctttctgag ttccactatt cagtt                                              25

<210> SEQ ID NO 77
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 77
cagttacaaa actccttaat gctta                                              25

<210> SEQ ID NO 78
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 78
tactgtgtac cttttatatt taata                                              25

<210> SEQ ID NO 79
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 79
aagtctgtac tgataaaacc cattg                                              25

<210> SEQ ID NO 80
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 80
actgataaaa cccattgtgt acaaa                                              25
```

```
<210> SEQ ID NO 81
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 81
ttctctttat acaagctgag tcata                                               25

<210> SEQ ID NO 82
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 82
gattttatat tctggatttg tgttt                                               25

<210> SEQ ID NO 83
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 83
agactttggt gatcactttg caaat                                               25

<210> SEQ ID NO 84
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 84
tggtgatcac tttgcaaata tttgt                                               25

<210> SEQ ID NO 85
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 85
atatttgtta atccttgagt ttgag                                               25

<210> SEQ ID NO 86
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 86
tgagtttgag aacctgtctt ttaaa                                               25

<210> SEQ ID NO 87
<211> LENGTH: 25
<212> TYPE: DNA
<213> ORGANISM: Artificial Sequence
<220> FEATURE:
<223> OTHER INFORMATION: Synthetic polynucleotide
```

<400> SEQUENCE: 87
atactttcaa acaagctagc aaggc                                            25

<210> SEQ ID NO 88
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 88
ttatatattt ggttagttct gttta                                            25

<210> SEQ ID NO 89
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 89
ctgttgccct tatgagttat tttat                                            25

<210> SEQ ID NO 90
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 90
attaccgact gtatgcctac acgga                                            25

<210> SEQ ID NO 91
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 91
tacacggagt cggagctgca gattg                                            25

<210> SEQ ID NO 92
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 92
ttccccaaca tggtggtggc gcagg                                            25

<210> SEQ ID NO 93
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 93
gcagcaggca atcgccagtg gcatc                                            25

<210> SEQ ID NO 94

-continued

```
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 94
cagcccagca gataatccat ttcct                                    25

<210> SEQ ID NO 95
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 95
cagactccgg ttcactgagg gtgtc                                    25

<210> SEQ ID NO 96
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 96
gagggtgtcc tgtataacca gttcc                                    25

<210> SEQ ID NO 97
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 97
aaccagttcc tgtcgcaagt ggact                                    25

<210> SEQ ID NO 98
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 98
ttcgagaact cggccaagcg gctca                                    25

<210> SEQ ID NO 99
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 99
ggcacagcga cgtcaagcgc ttttg                                    25

<210> SEQ ID NO 100
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 100
```

```
gctcctgaga gcgcgggact tggac                                               25

<210> SEQ ID NO 101
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 101
gagcattctt caggtcatct gaacc                                               25

<210> SEQ ID NO 102
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 102
gagaaaacat ggtcaacgtc ttgaa                                               25

<210> SEQ ID NO 103
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 103
gtgcttatag aatgtgatcc tgcca                                               25

<210> SEQ ID NO 104
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 104
cagtttctgc tgtacttgga tgagt                                               25

<210> SEQ ID NO 105
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 105
ttggatgagt ccaatgccct gggga                                               25

<210> SEQ ID NO 106
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 106
gatgacactc acgtctttgt aatag                                               25

<210> SEQ ID NO 107
<211> LENGTH: 25
<212> TYPE: DNA
```

```
<213> ORGANISM: Artificial Sequence
<220> FEATURE:
<223> OTHER INFORMATION: Synthetic polynucleotide

<400> SEQUENCE: 107
gcagaattgg ttaatgtcct ccagg                                              25

<210> SEQ ID NO 108
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 108
tgtcctccag gagcgagtgg gtgaa                                              25

<210> SEQ ID NO 109
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 109
aactgtgaaa gacttgccac tcaat                                              25

<210> SEQ ID NO 110
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 110
gccactcaat atcttaggtg actga                                              25

<210> SEQ ID NO 111
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 111
gggttgtttt aggagcatgc cacgg                                              25

<210> SEQ ID NO 112
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 112
agtccggaca gacattgtgg gggtc                                              25

<210> SEQ ID NO 113
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 113
attaaggttt actctgctgc cttgg                                              25
```

<210> SEQ ID NO 114
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 114
gccttggcag acttacgatc tcaac                                          25

<210> SEQ ID NO 115
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 115
cgatctcaac agttcatacg agcag                                          25

<210> SEQ ID NO 116
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 116
gagggcatgc tcactagtgg ttagt                                          25

<210> SEQ ID NO 117
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 117
gtggttagta agctgtcgac tttgt                                          25

<210> SEQ ID NO 118
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 118
gaacatgtac aatttgccac tggga                                          25

<210> SEQ ID NO 119
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 119
aatgccagct gcgtgtctag ttttg                                          25

<210> SEQ ID NO 120
<211> LENGTH: 25
<212> TYPE: DNA
<213> ORGANISM: Artificial Sequence
<220> FEATURE:

<223> OTHER INFORMATION: Synthetic polynucleotide

<400> SEQUENCE: 120
agcaaatcac tcttattttt catcc                                              25

<210> SEQ ID NO 121
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 121
gtgggagcag tgtacaccaa ctctt                                              25

<210> SEQ ID NO 122
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 122
aactcttcct gtatattgcc ttttt                                              25

<210> SEQ ID NO 123
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 123
taacagtaac tgactggccc actga                                              25

<210> SEQ ID NO 124
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 124
ccacctggga gagaaccacc cgagg                                              25

<210> SEQ ID NO 125
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 125
gtacccggct ctgacgggtg gtcat                                              25

<210> SEQ ID NO 126
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 126
ttgctgctgg acttttcgaa gggaa                                              25

```
<210> SEQ ID NO 127
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 127
gagcttgctg atgggcgagt tggtc                                          25

<210> SEQ ID NO 128
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 128
ggtccatcgc ctttagggta tgtcc                                          25

<210> SEQ ID NO 129
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 129
ctttagggta tgtccacctc tgttc                                          25

<210> SEQ ID NO 130
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 130
ctctgttcac ttcctccaag gaaaa                                          25

<210> SEQ ID NO 131
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 131
caccctcagg cagccagaga ttcat                                          25

<210> SEQ ID NO 132
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 132
aacttcccct cggagggtgg agcat                                          25

<210> SEQ ID NO 133
<211> LENGTH: 25
<212> TYPE: DNA
<213> ORGANISM: Artificial Sequence
<220> FEATURE:
<223> OTHER INFORMATION: Synthetic polynucleotide
```

```
<400> SEQUENCE: 133
gattattctg tatcctgtgt ttgta                                              25

<210> SEQ ID NO 134
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 134
ggtgatcacg aaactcgctg gcatg                                              25

<210> SEQ ID NO 135
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 135
ggaggaagac ttggcgtttt cgaca                                              25

<210> SEQ ID NO 136
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 136
ggctggggaa tttggctcca gatcc                                              25

<210> SEQ ID NO 137
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 137
gcgctttggc accatgagtt ctatg                                              25

<210> SEQ ID NO 138
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 138
ttctatgtct ggggccgacg acact                                              25

<210> SEQ ID NO 139
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 139
taccactcat cgcggagcaa ggcgc                                              25

<210> SEQ ID NO 140
<211> LENGTH: 25
```

```
<212> TYPE: DNA
<213> ORGANISM: Artificial Sequence
<220> FEATURE:
<223> OTHER INFORMATION: Synthetic polynucleotide

<400> SEQUENCE: 140
acccgctctt caagcgcttt aggaa                                              25

<210> SEQ ID NO 141
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 141
gcagggtact tcgttcaaga ccggc                                              25

<210> SEQ ID NO 142
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 142
cctccagcgt tggccaaatt gtgct                                              25

<210> SEQ ID NO 143
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 143
ggctgtgcct tcataggtca tctag                                              25

<210> SEQ ID NO 144
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 144
ggggagtggg gtcatttctg tatat                                              25

<210> SEQ ID NO 145
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 145
gaaaccagtg tcgccctgga gaagt                                              25

<210> SEQ ID NO 146
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 146
```
aggaggcctg cgagaatggc cgcgg                                              25

<210> SEQ ID NO 147
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 147
tgctgtcagt ggcccggggc aaagt                                              25

<210> SEQ ID NO 148
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 148
gagggaatcg actttgtgca ccact                                              25

<210> SEQ ID NO 149
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 149
tctacacaca gagccgcatt ctcaa                                              25

<210> SEQ ID NO 150
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 150
gcattctcaa ggcgcggctg gaata                                              25

<210> SEQ ID NO 151
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 151
gggaccagtt ccagattcgt gagaa                                              25

<210> SEQ ID NO 152
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 152
agaatgactt tcttaccttc gatgc                                              25

<210> SEQ ID NO 153
<211> LENGTH: 25
<212> TYPE: DNA
<213> ORGANISM: Artificial Sequence

```
<220> FEATURE:
<223> OTHER INFORMATION: Synthetic polynucleotide

<400> SEQUENCE: 153
gtcgggccat cagggggcaag acgga                                           25

<210> SEQ ID NO 154
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 154
ggtctttgcc gacaagcggt ttgcc                                            25

<210> SEQ ID NO 155
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 155
tcagcagctc tgagtggggc gggtg                                            25

<210> SEQ ID NO 156
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 156
ttagttccaa actcactctt cttac                                            25

<210> SEQ ID NO 157
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 157
cgacagcact ggccattaca gcaga                                            25

<210> SEQ ID NO 158
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 158
ttacagcaga ttccgaaacc cttcc                                            25

<210> SEQ ID NO 159
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 159
gagaagtata atcctggtcc ccaag                                            25
```

```
<210> SEQ ID NO 160
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 160
ggtgaatgcc aaaaactgcc gctcc                                          25

<210> SEQ ID NO 161
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 161
gctccttgat gcaccacgtt aagaa                                          25

<210> SEQ ID NO 162
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 162
tagcagccct gtcacaagac gagct                                          25

<210> SEQ ID NO 163
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 163
tatgatttca ttcacacctc ttttg                                          25

<210> SEQ ID NO 164
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 164
tgatggctgt tttcttatcc catgc                                          25

<210> SEQ ID NO 165
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 165
tcccatgcct gtactttca gcggc                                           25

<210> SEQ ID NO 166
<211> LENGTH: 25
<212> TYPE: DNA
<213> ORGANISM: Artificial Sequence
<220> FEATURE:
<223> OTHER INFORMATION: Synthetic polynucleotide
```

```
<400> SEQUENCE: 166
gctccttgcc agacatcata ggtca                                              25

<210> SEQ ID NO 167
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 167
gaagcagcag ccagcgaaat agaag                                              25

<210> SEQ ID NO 168
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 168
aagaggcttt cagattctaa acgaa                                              25

<210> SEQ ID NO 169
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 169
atacatgcgg tggatttttg gggga                                              25

<210> SEQ ID NO 170
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 170
tcatctgatg gatcttcaag tgaac                                              25

<210> SEQ ID NO 171
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 171
gccaaaaacc agtgcttcag attcg                                              25

<210> SEQ ID NO 172
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 172
gcttcagatt cgcagaactc agtga                                              25

<210> SEQ ID NO 173
```

```
<210> SEQ ID NO 173
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 173
gaatggaggt gcgaccacca gcagc                                       25

<210> SEQ ID NO 174
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 174
accagcagct ctagtgatag tgatg                                       25

<210> SEQ ID NO 175
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 175
agagaagatg gtcctcgtga ccgcc                                       25

<210> SEQ ID NO 176
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 176
gtgaccgcca gatctgtgtt tggga                                       25

<210> SEQ ID NO 177
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 177
gaaggaaact aagacgtgcg agggg                                       25

<210> SEQ ID NO 178
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 178
taagacttgt actatgtgtg gccat                                       25

<210> SEQ ID NO 179
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 179
```
gtgtggccat gaactgacat atgaa                                        25

<210> SEQ ID NO 180
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 180
tcagtgaagg tcacctggcc tggtt                                        25

<210> SEQ ID NO 181
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 181
gttgtgtgca caatgtcatg tctgt                                        25

<210> SEQ ID NO 182
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 182
atgtctgtga ttgccttctt acaac                                        25

<210> SEQ ID NO 183
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 183
aggtgcagaa gtggtaggtc agcta                                        25

<210> SEQ ID NO 184
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 184
ggacaagata ccaaggcaaa cccta                                        25

<210> SEQ ID NO 185
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 185
ggctgaactg gattcttaac caaga                                        25

<210> SEQ ID NO 186
<211> LENGTH: 25
<212> TYPE: DNA

<213> ORGANISM: Artificial Sequence
<220> FEATURE:
<223> OTHER INFORMATION: Synthetic polynucleotide

<400> SEQUENCE: 186
gcaatggtgg tgcaccactg taccc                                         25

<210> SEQ ID NO 187
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 187
actgtacccc aggttctagt catgt                                         25

<210> SEQ ID NO 188
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 188
ttaggacgat ttctgtctcc acgat                                         25

<210> SEQ ID NO 189
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 189
cccttccaaa gactgtctcc gttga                                         25

<210> SEQ ID NO 190
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 190
tccaaagact gtctccgttg acctt                                         25

<210> SEQ ID NO 191
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 191
tgaccttgtc ttttggtat gcctt                                          25

<210> SEQ ID NO 192
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 192
ccttgtcttt tggtatgcc ttggg                                          25

<210> SEQ ID NO 193
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 193
ttttggtatg ccttggggtt tctga                                   25

<210> SEQ ID NO 194
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 194
ggtatgcctt ggggtttctg ataat                                   25

<210> SEQ ID NO 195
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 195
gccttggggt ttctgataat gtgtg                                   25

<210> SEQ ID NO 196
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 196
aggtaagtga gcatgtcaaa caaaa                                   25

<210> SEQ ID NO 197
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 197
gtcaaacaaa ataggagctc acatg                                   25

<210> SEQ ID NO 198
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 198
aggagctcac atggatatat ttatg                                   25

<210> SEQ ID NO 199
<211> LENGTH: 25
<212> TYPE: DNA
<213> ORGANISM: Artificial Sequence
<220> FEATURE:

<223> OTHER INFORMATION: Synthetic polynucleotide

<400> SEQUENCE: 199
atggatatat ttatgtcact gagtt                                25

<210> SEQ ID NO 200
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 200
gagcctttgt ctggtgaaca gttgg                                25

<210> SEQ ID NO 201
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 201
tctccccagg ataaggcggc agagg                                25

<210> SEQ ID NO 202
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 202
ggcggcagag gctacaaatg actat                                25

<210> SEQ ID NO 203
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 203
aatccaggag gccctaaact gctta                                25

<210> SEQ ID NO 204
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 204
gcagatcctg aagttatgct cttga                                25

<210> SEQ ID NO 205
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 205
gttatgctct tgactttaag tttgt                                25

```
<210> SEQ ID NO 206
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 206
ggaatttttg ttcccataat tggat                                25

<210> SEQ ID NO 207
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 207
tcaaaaagca acttctgccc tgcaa                                25

<210> SEQ ID NO 208
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 208
ccccactcca tagtctggta ttctg                                25

<210> SEQ ID NO 209
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 209
gtctggtatt ctgagcacta gctta                                25

<210> SEQ ID NO 210
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 210
gagcactagc ttaatatttc ttcac                                25

<210> SEQ ID NO 211
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 211
tatttagaag cctttactca gcccc                                25

<210> SEQ ID NO 212
<211> LENGTH: 25
<212> TYPE: DNA
<213> ORGANISM: Artificial Sequence
<220> FEATURE:
<223> OTHER INFORMATION: Synthetic polynucleotide
```

```
<400> SEQUENCE: 212
ggagcttgag ctctacaggt aaggc                                              25

<210> SEQ ID NO 213
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 213
taaggcagag ctaccggtga atgaa                                              25

<210> SEQ ID NO 214
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 214
cccctggcat cacatgtgca tgctg                                              25

<210> SEQ ID NO 215
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 215
gcatgctgta ggcaggacct gagct                                              25

<210> SEQ ID NO 216
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 216
tccgctgcag gttcagatgc accgc                                              25

<210> SEQ ID NO 217
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 217
tgcagctgtc cttcagttag ttcac                                              25

<210> SEQ ID NO 218
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 218
agcctgagcc gggaactggc tgtgc                                              25

<210> SEQ ID NO 219
<211> LENGTH: 25
```

```
<212> TYPE: DNA
<213> ORGANISM: Artificial Sequence
<220> FEATURE:
<223> OTHER INFORMATION: Synthetic polynucleotide

<400> SEQUENCE: 219
agggcttccg tgtactcagc atgta                                          25

<210> SEQ ID NO 220
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 220
gtcttctcaa gggactgatc ggcca                                          25

<210> SEQ ID NO 221
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 221
gatcggccaa gtatgctttt cttta                                          25

<210> SEQ ID NO 222
<211> LENGTH: 4518
<212> TYPE: DNA
<213> ORGANISM: Homo sapiens

<400> SEQUENCE: 222
ggagtttatt cataacgcgc tctccaagta tacgtggcaa tgcgttgctg ggttatttta     60
atcattctag gcatcgtttt cctccttatg cctctatcat tcctcccta ctacactaac    120 atcccacgct ctgaacgcgc gcccattaat acccttcttt cctccactct ccctgggact    180
cttgatcaaa gcgcggccct ttccccagcc ttagcgaggc gccctgcagc ctggtacgcg    240
cgtggcgtgg cggtgggcgc gcagtgcgtt tcggtgtgg agggcagctg ttccgcctgc     300
gatgatttat actcacagga caaggatgcg gtttgtcaaa cagtactgct acggaggagc    360
agcagagaaa gggagagggt ttgagaggga gcaaaagaaa atggtaggcg cgcgtagtta    420
attcatgcgg ctctcttact ctgtttacat cctagagcta gagtgctcgg ctgcccggct    480
gagtctcctc cccaccttcc ccaccctccc caccctcccc ataagcgccc ctcccggtt     540 cccaaagcag agggcgtggg ggaaaagaaa aaagatcctc tctcgctaat ctccgcccac    600
cggcccttta taatgcgagg gtctggacgg ctgaggaccc ccgagctgtg ctgctcgcgg    660
ccgccaccgc cgggccccgg ccgtccctgg ctcccctcct gcctcgagaa gggcagggct    720
tctcagaggc ttggcgggaa aaagaacgga gggagggatc gcgctgagta taaaagccgg    780
ttttcggggc tttatctaac tcgctgtagt aattccagcg agaggcagag ggagcgagcg    840
ggcggccggc tagggtggaa gagccggggc agcagagctg cgctgcgggc gtcctgggaa    900
gggagatccg gagcgaatag ggggcttcgc tctggccca gccctcccgc tgatccccca     960
gccagcggtc cgcaacccct tgccgcatcca cgaaactttg cccatagcag cgggcgggca   1020
ctttgcactg gaacttacaa caccgagca aggacgcgac tctcccgacg cggggaggct    1080
attctgccca tttggggaca cttccccgcc gctgccagga cccgcttctc tgaaaggctc   1140
```

```
tccttgcagc tgcttagacg ctggattttt ttcgggtagt ggaaaaccag cagcctcccg    1200
cgacgatgcc cctcaacgtt agcttcacca acaggaacta tgacctcgac tacgactcgg    1260
tgcagccgta tttctactgc gacgaggagg agaacttcta ccagcagcag cagcagagcg    1320
agctgcagcc cccggcgccc agcgaggata tctggaagaa attcgagctg ctgcccaccc    1380 cgccctgtc ccctagccgc cgctccgggc tctgctcgcc ctcctacgtt gcggtcacac    1440
ccttctccct cggggagac aacgacgcg gtggcgggag cttctccacg gccgaccagc    1500
tggagatggt gaccgagctg ctgggaggag acatggtgaa ccagagtttc atctgcgacc    1560
cggacgacga gaccttcatc aaaaacatca tcatccagga ctgtatgtgg agcggcttct    1620
cggccgccgc caagctcgtc tcagagaagc tggcctccta ccaggctgcg cgcaaagaca    1680
gcggcagccc gaaccccgcc cgcggccaca gcgtctgctc cacctccagc ttgtacctgc    1740
aggatctgag cgccgccgcc tcagagtgca tcgacccctc ggtggtcttc ccctaccctc    1800
tcaacgacag cagctcgccc aagtcctgcg cctcgcaaga ctccagcgcc ttctctccgt    1860
cctcggattc tctgctctcc tcgacggagt cctccccgca gggcagcccc gagcccctgg    1920
tgctccatga ggagacaccg cccaccacca gcagcgactc tgaggaggaa caagaagatg    1980
aggaagaaat cgatgttgtt tctgtggaaa agaggcaggc tcctggcaaa aggtcagagt    2040
ctggatcacc ttctgctgga ggccacagca acctcctca cagcccactg gtcctcaaga    2100
ggtgccacgt ctccacacat cagcacaact acgcagcgcc tccctccact cggaaggact    2160
atcctgctgc caagagggtc aagttggaca gtgtcagagt cctgagacag atcagcaaca    2220
accgaaaatg caccagcccc aggtcctcgg acaccgagga gaatgtcaag aggcgaacac    2280
acaacgtctt ggagcgccag aggaggaacg agctaaaacg gagctttttt gccctgcgtg    2340
accagatccc ggagttggaa aacaatgaaa aggcccccaa ggtagttatc cttaaaaaag    2400
ccacagcata catcctgtcc gtccaagcag aggagcaaaa gctcatttct gaagaggact    2460
tgttgcggaa acgacgagaa cagttgaaac acaaacttga acagctacgg aactcttgtg    2520
cgtaaggaaa agtaaggaaa acgattcctt ctaacagaaa tgtcctgagc aatcacctat    2580
gaacttgttt caaatgcatg atcaaatgca acctcacaac cttggctgag tcttgagact    2640
gaaagattta gccataatgt aaactgcctc aaattggact ttgggcataa aagaactttt    2700
ttatgcttac catcttttttt ttttctttaa cagatttgta tttaagaatt gttttttaaaa    2760 aattttaaga tttacacaat gtttctctgt aaatattgcc attaaatgta aataacttta    2820
ataaaacgtt tatagcagtt acacagaatt tcaatcctag tatatagtac ctagtattat    2880
aggtactata acccctaatt tttttatttt aagtacattt tgcttttttaa agttgatttt    2940 tttctattgt ttttagaaaaa aataaaataa ctggcaaata tatcattgag ccaaatctta    3000
agttgtgaat gttttgtttc gtttcttccc cctcccaacc accaccatcc ctgtttgttt    3060
tcatcaattg cccccttcaga gggtggtctt aagaaaggca agagttttcc tctgttgaaa    3120
tgggtctggg ggccttaagg tctttaagtt cttggaggtt ctaagatgct tcctggagac    3180
tatgataaca gccagagttg acagttagaa ggaatggcag aaggcaggtg agaaggtgag    3240
aggtaggcaa aggagataca agaggtcaaa ggtagcagtt aagtacacaa agaggcataa    3300
ggactgggga gttgggagga aggtgaggaa gaaactcctg ttactttagt taaccagtgc    3360
cagtcccctg ctcactccaa acccaggaat tctgcccagt tgatggggac acggtgggaa    3420
ccagcttctg ctgccttcac aaccaggcgc cagtcctgtc catgggttat ctcgcaaacc    3480
ccagaggatc tctgggagga atgctactat taaccctatt tcacaaacaa ggaaatagaa    3540
```

-continued

```
gagctcaaag aggttatgta acttatctgt agccacgcag ataatacaaa gcagcaatct   3600
ggacccattc tgttcaaaac acttaaccct tcgctatcat gccttggttc atctgggtct   3660
aatgtgctga gatcaagaag gtttaggacc taatggacag actcaagtca taacaatgct   3720
aagctctatt tgtgtcccaa gcactcctaa gcattttatc cctaactcta catcaacccc   3780
atgaaggaga tactgttgat ttccccatat tagaagtaga gagggaagct gaggcacaca   3840
aagactcatc cacatgccca agattcactg atagggaaaa gtggaagcga gatttgaacc   3900
caggctgttt actcctaacc tgtccaagcc acctctcaga cgacggtagg aatcagctgg   3960
ctgcttgtga gtacaggagt tacagtccag tgggttatgt tttttaagtc tcaacatcta   4020
agcctggtca ggcatcagtt ccccttttt tgtgatttat tttgttttta ttttgttgtt   4080
cattgtttaa ttttccttt tacaatgaga aggtcaccat cttgactcct acctagcca   4140 tttgttgaat cagactcatg acggctcctg ggaagaagcc agttcagatc ataaaataaa   4200
acatatttat tctttgtcat gggagtcatt attttagaaa ctacaaactc tccttgcttc   4260 catcctttt tacatactca tgacacatgc tcatcctgag tccttgaaaa ggtattttg    4320 aacatgtgta ttaattataa gcctctgaaa acctatggcc caaaccagaa atgatgttga   4380 ttataggt aaatgaagga tgctattgct gttctaatta cctcattgtc tcagtctcaa     4440
agtaggtctt cagctccctg tactttggga ttttaatcta ccaccaccca taaatcaata   4500 ataattact ttctttga                                                  4518
```

<210> SEQ ID NO 223
<211> LENGTH: 454
<212> TYPE: PRT
<213> ORGANISM: Homo sapiens

<400> SEQUENCE: 223

```
Met Asp Phe Phe Arg Val Val Glu Asn Gln Gln Pro Pro Ala Thr Met
1               5                  10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190
```

Leu Gln Asp Leu Ser Ala Ala Ala Ser Glu Cys Ile Asp Pro Ser Val
            195                 200                 205

Val Phe Pro Tyr Pro Leu Asn Asp Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
            260                 265                 270

Asp Glu Glu Glu Ile Asp Val Val Ser Val Glu Lys Arg Gln Ala Pro
            275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450

<210> SEQ ID NO 224
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 224
gcaacaaccg aaaatgcacc agccc                                25

<210> SEQ ID NO 225
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 225
ccccaggtcc tcggacaccg aggag                                25

<210> SEQ ID NO 226
<211> LENGTH: 25
<212> TYPE: DNA

<213> ORGANISM: Artificial Sequence
<220> FEATURE:
<223> OTHER INFORMATION: Synthetic polynucleotide

<400> SEQUENCE: 226
cgaacacaca acgtcttgga gcgcc                                          25

<210> SEQ ID NO 227
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 227
ggagcgccag aggaggaacg agcta                                          25

<210> SEQ ID NO 228
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 228
gctaaaacgg agcttttttg ccctg                                          25

<210> SEQ ID NO 229
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 229
aaaagccaca gcatacatcc tgtcc                                          25

<210> SEQ ID NO 230
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 230
catcctgtcc gtccaagcag aggag                                          25

<210> SEQ ID NO 231
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 231
catcctgtcc gtccaagcag aggag                                          25

<210> SEQ ID NO 232
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 232
gaggacttgt tgcggaaacg acgag                                          25

<210> SEQ ID NO 233
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 233
gaacagctac ggaactcttg tgcgt                                      25

<210> SEQ ID NO 234
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 234
gaaatgtcct gagcaatcac ctatg                                      25

<210> SEQ ID NO 235
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 235
gcaacctcac aaccttggct gagtc                                      25

<210> SEQ ID NO 236
<211> LENGTH: 1291
<212> TYPE: DNA
<213> ORGANISM: Homo sapiens

<400> SEQUENCE: 236
gagccgaagg tggaggtcaa aggggcgtgg cgttacagag cctctagcgc tgggtgttgg    60
ggacctgacg ctatggagct ctcggagttt tgtgggggac ggctgtgagt gggggggttcc   120 tgctgcggga tgagaacgta gacgccagtg gctcactcgc tcctggcacc ttcccttca   180 ggctccagat ggaccctggg aaggacaaag aggggggtgcc ccagccctca gggccgccag   240
caaggaagaa atttgtgata ccccctcgacg aggatgaggt ccctcctgga gtggccaagc   300
ccttattccg atctacacag agccttccca ctgtggacac ctcggcccag gcggcccctc   360
agacctacgc cgaatatgcc atctcacagc tctggaagg gctgggggcc acgtgccca    420 cagggtcaga gccccctggca ggagagacgc ccaaccaggc cctgaaaccc ggggcaaaat   480
ccaacagcat cattgtgagc cctcggcaga ggggcaatcc cgtactgaag ttcgtgcgca   540
atgtgccctg ggaattggc gacgtaattc ccgactatgt gctgggccag agcacctgtg   600
ccctgttcct cagcctccgc taccacaacc tgcacccaga ctacatccat gggcggctgc   660
agagcctggg gaagaacttc gccttgcggg tcctgcttgt ccaggtggat gtgaaagatc   720
cccagcaggc cctcaaggag ctggctaaga tgtgtatcct ggccgactgc acattgatcc   780
tcgcctggag ccccgaggaa gctgggcggt acctggagac ctacaaggcc tatgagcaga   840
aaccagcgga cctcctgatg gagaagctag agcaggactt cgtctcccgg gtgactgaat   900
gtctgaccac cgtgaagtca gtcaacaaaa cggacagtca gacccctcctg accacatttg   960 gatctctgga acagctcatc gccgcatcaa gagaagatct ggcctttatgc ccaggcctgg  1020

-continued

```
gccctcagaa agtaagagct ctgggaaaga acccaaggag ttgggggaag gagagagccc    1080
caaataaaca caacctgaga ccccaaagtt ttaaggtgaa aaagaaccaa aagaccagac    1140
acagtggctt ccgcctgtaa tcccaacatt ttgggaggcc aaggcgggag gactgcttga    1200
ggccagaagt tggagaccag cctgggcaag tggacacctc atttttacta aaataaaaa     1260 aaactagctg ggcaaaaaaa aaaaaaaaaa a                                   1291
```

<210> SEQ ID NO 237
<211> LENGTH: 323
<212> TYPE: PRT
<213> ORGANISM: Homo sapiens

<400> SEQUENCE: 237

```
Met Asp Pro Gly Lys Asp Lys Glu Gly Val Pro Gln Pro Ser Gly Pro
1               5                   10                  15

Pro Ala Arg Lys Lys Phe Val Ile Pro Leu Asp Glu Asp Glu Val Pro
                20                  25                  30

Pro Gly Val Ala Lys Pro Leu Phe Arg Ser Thr Gln Ser Leu Pro Thr
            35                  40                  45

Val Asp Thr Ser Ala Gln Ala Ala Pro Gln Thr Tyr Ala Glu Tyr Ala
50                  55                  60

Ile Ser Gln Pro Leu Glu Gly Ala Gly Ala Thr Cys Pro Thr Gly Ser
65                  70                  75                  80

Glu Pro Leu Ala Gly Glu Thr Pro Asn Gln Ala Leu Lys Pro Gly Ala
                85                  90                  95

Lys Ser Asn Ser Ile Ile Val Ser Pro Arg Gln Arg Gly Asn Pro Val
            100                 105                 110

Leu Lys Phe Val Arg Asn Val Pro Trp Glu Phe Gly Asp Val Ile Pro
        115                 120                 125

Asp Tyr Val Leu Gly Gln Ser Thr Cys Ala Leu Phe Leu Ser Leu Arg
130                 135                 140

Tyr His Asn Leu His Pro Asp Tyr Ile His Gly Arg Leu Gln Ser Leu
145                 150                 155                 160

Gly Lys Asn Phe Ala Leu Arg Val Leu Leu Val Gln Val Asp Val Lys
                165                 170                 175

Asp Pro Gln Gln Ala Leu Lys Glu Leu Ala Lys Met Cys Ile Leu Ala
            180                 185                 190

Asp Cys Thr Leu Ile Leu Ala Trp Ser Pro Glu Glu Ala Gly Arg Tyr
        195                 200                 205

Leu Glu Thr Tyr Lys Ala Tyr Glu Gln Lys Pro Ala Asp Leu Leu Met
210                 215                 220

Glu Lys Leu Glu Gln Asp Phe Val Ser Arg Val Thr Glu Cys Leu Thr
225                 230                 235                 240

Thr Val Lys Ser Val Asn Lys Thr Asp Ser Gln Thr Leu Leu Thr Thr
                245                 250                 255

Phe Gly Ser Leu Glu Gln Leu Ile Ala Ala Ser Arg Glu Asp Leu Ala
            260                 265                 270

Leu Cys Pro Gly Leu Gly Pro Gln Lys Val Arg Ala Leu Gly Lys Asn
        275                 280                 285

Pro Arg Ser Trp Gly Lys Glu Arg Ala Pro Asn Lys His Asn Leu Arg
290                 295                 300

Pro Gln Ser Phe Lys Val Lys Lys Glu Pro Lys Thr Arg His Ser Gly
305                 310                 315                 320

Phe Arg Leu
```

<210> SEQ ID NO 238
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 238
aagatctggc cttatgccca ggcct                                        25

<210> SEQ ID NO 239
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 239
ccctcagaaa gcccggaggc tgttt                                        25

<210> SEQ ID NO 240
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 240
ctcagaaagc ccggaggctg tttga                                        25

<210> SEQ ID NO 241
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 241
gaaagcccgg aggctgtttg atgtc                                        25

<210> SEQ ID NO 242
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 242
aagcccggag gctgtttgat gtcct                                        25

<210> SEQ ID NO 243
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 243
ggctgtttga tgtcctgcac gagcc                                        25

<210> SEQ ID NO 244
<211> LENGTH: 25
<212> TYPE: DNA
<213> ORGANISM: Artificial Sequence
<220> FEATURE:

<223> OTHER INFORMATION: Synthetic polynucleotide

<400> SEQUENCE: 244
tgcacgagcc cttcttgaaa gtacc                                  25

<210> SEQ ID NO 245
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 245
gcccttcttg aaagtaccct gatga                                  25

<210> SEQ ID NO 246
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 246
ccttcttgaa agtaccctga tgacc                                  25

<210> SEQ ID NO 247
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 247
ttcttgaaag taccctgatg acccc                                  25

<210> SEQ ID NO 248
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 248
tcttgaaagt accctgatga cccca                                  25

<210> SEQ ID NO 249
<211> LENGTH: 1220
<212> TYPE: DNA
<213> ORGANISM: Homo sapiens

<400> SEQUENCE: 249
atgcacacat acgcgcgcgc acatgcacat aggcacacag agatacgcgc acacacacac    60
acaaacgcac tcagatttcc cggaccctgg ttttcctcct gtgacccttt cggggccggg   120
ctctcaccct aaagaagcag ccccgccctg ggtggcccc accctctctt gggacctgtc   180
ataagtcgga ccccgggcgc ccggctgcgc agtcccagcc gccttcccca ggcagtggaa   240
ccttcgggct cctgagcttc aggatggttc gtactaagac atggaccctg aagaagcact   300
ttgttggcta tcctactaat agtgactttg agttgaagac agctgagctc ccacccttaa   360
aaaatggaga ggtcctgctt gaagctttgt tcctcaccgt ggatccctac atgagagtgg   420
cagccaaaag attgaaggaa ggtgatacaa tgatggggca gcaagtggcc aaagttgtgg   480
aaagtaaaaa tgtagcccta ccaaaaggaa ctattgtact ggcttctcca ggctggacaa   540

```
cgcactccat ttctgatggg aaagatctgg aaaagctgct gacagagtgg ccagacacaa    600
taccactgtc tttggctctg gggacagttg gcatgccagg cctgactgcc tactttggcc    660
tacttgaaat ctgtggtgtg aagggtggag aaacagtgat ggttaatgca gcagctggag    720
ctgtgggctc agtcgtgggg cagattgcaa agctcaaggg ctgcaaagtt gttggagcag    780
tagggtctga tgaaaaggtt gcctaccttc aaaagcttgg atttgatgtc gtctttaact    840
acaagacggt agagtctttg gaagaaacct tgaagaaagc gtctcctgat ggttatgatt    900
gttattttga taatgtaggt ggagagtttt caaacactgt tatcggccag atgaagaaat    960
ttggaaggat tgccatatgt ggagccatct ctacatataa cagaaccggc ccacttcccc   1020
caggcccacc cccagagatt gttatctatc aggagcttcg catggaagct tttgtcgtct   1080
accgctggca aggagatgcc cgccaaaaag ctctgaagga cttgctgaaa tgggtcttag   1140
agatcaaaag agaaaatgaa gaagattgaa gcttcaaagc agaaaatgaa agggaatatg   1200
tatcattcac cattacctta                                               1220
```

<210> SEQ ID NO 250
<211> LENGTH: 301
<212> TYPE: PRT
<213> ORGANISM: Homo sapiens

<400> SEQUENCE: 250

```
Met Val Arg Thr Lys Thr Trp Thr Leu Lys Lys His Phe Val Gly Tyr
1               5                   10                  15

Pro Thr Asn Ser Asp Phe Glu Leu Lys Thr Ala Glu Leu Pro Pro Leu
            20                  25                  30

Lys Asn Gly Glu Val Leu Leu Glu Ala Leu Phe Leu Thr Val Asp Pro
        35                  40                  45

Tyr Met Arg Val Ala Ala Lys Arg Leu Lys Glu Gly Asp Thr Met Met
    50                  55                  60

Gly Gln Gln Val Ala Lys Val Val Glu Ser Lys Asn Val Ala Leu Pro
65                  70                  75                  80

Lys Gly Thr Ile Val Leu Ala Ser Pro Gly Trp Thr Thr His Ser Ile
                85                  90                  95

Ser Asp Gly Lys Asp Leu Glu Lys Leu Leu Thr Glu Trp Pro Asp Thr
            100                 105                 110

Ile Pro Leu Ser Leu Ala Leu Gly Thr Val Gly Met Pro Gly Leu Thr
        115                 120                 125

Ala Tyr Phe Gly Leu Leu Glu Ile Cys Gly Val Lys Gly Gly Glu Thr
    130                 135                 140

Val Met Val Asn Ala Ala Ala Gly Ala Val Gly Ser Val Val Gly Gln
145                 150                 155                 160

Ile Ala Lys Leu Lys Gly Cys Lys Val Val Gly Ala Val Gly Ser Asp
                165                 170                 175

Glu Lys Val Ala Tyr Leu Gln Lys Leu Gly Phe Asp Val Phe Asn
            180                 185                 190

Tyr Lys Thr Val Glu Ser Leu Glu Glu Thr Leu Lys Lys Ala Ser Pro
        195                 200                 205

Asp Gly Tyr Asp Cys Tyr Phe Asp Asn Val Gly Gly Glu Phe Ser Asn
    210                 215                 220

Thr Val Ile Gly Gln Met Lys Lys Phe Gly Arg Ile Ala Ile Cys Gly
225                 230                 235                 240

Ala Ile Ser Thr Tyr Asn Arg Thr Gly Pro Leu Pro Pro Gly Pro Pro
```

```
            245                 250                 255
Pro Glu Ile Val Ile Tyr Gln Glu Leu Arg Met Glu Ala Phe Val Val
        260                 265                 270

Tyr Arg Trp Gln Gly Asp Ala Arg Gln Lys Ala Leu Lys Asp Leu Leu
    275                 280                 285

Lys Trp Val Leu Glu Ile Lys Arg Glu Asn Glu Glu Asp
  290                 295                 300
```

<210> SEQ ID NO 251
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 251
gcttggattt gatgtcgtct ttaac                                       25

<210> SEQ ID NO 252
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 252
gaaagcgtct cctgatggtt atgat                                       25

<210> SEQ ID NO 253
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 253
ttcaaacact gttatcggcc agatg                                       25

<210> SEQ ID NO 254
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 254
atgtggagcc atctctacat ataac                                       25

<210> SEQ ID NO 255
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 255
tacatataac agaaccggcc cactt                                       25

<210> SEQ ID NO 256
<211> LENGTH: 25
<212> TYPE: DNA
<213> ORGANISM: Artificial Sequence
<220> FEATURE:
<223> OTHER INFORMATION: Synthetic polynucleotide

```
<400> SEQUENCE: 256
cccaccccca gagattgtta tctat                                              25

<210> SEQ ID NO 257
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 257
gttatctatc aggagcttcg catgg                                              25

<210> SEQ ID NO 258
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 258
catggaagct tttgtcgtct accgc                                              25

<210> SEQ ID NO 259
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 259
taccgctggc aaggagatgc ccgcc                                              25

<210> SEQ ID NO 260
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 260
aggatttgaa aacatgccag ctgca                                              25

<210> SEQ ID NO 261
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 261
gaggacacat ggaatctgga ggcca                                              25

<210> SEQ ID NO 262
<211> LENGTH: 2520
<212> TYPE: DNA
<213> ORGANISM: Homo sapiens

<400> SEQUENCE: 262
gcgcgcctgc gtactgcggt cagagggccg aggcctgggg gcgagctggg gtcgtgcagt        60
acagcctctt tccggcaaat cacgcgagat ttcgttcacc cgggctccac agggagtatt       120
ttatacagaa atcttgtgaa accactgccc aaccagagca atgattgttc aaagagtggt       180
attgaattct cgacctggaa aaaatggtaa tccagtggca gagaatttcc gaatggaaga       240
```

```
agtctattta ccagataata ttaatgaagg acaagtacaa gttagaactc tttatctttc    300
tgtggatcct tacatgcgtt gtagaatgaa tgaagacact ggcactgatt atataacacc    360
ttggcagcta tctcaagtcg ttgatggagg aggtattgga attatagaag aaagcaaaca    420
cacaaatttg actaaaggcg attttgtgac ttctttctat tggccctggc aaaccaaggt    480
tattctggat ggaaatagcc ttgaaaaggt agacccacaa cttgtggatg gacacctttc    540
atattttctt ggagctatag gtatgcctgg tttgacttcc ttgattggga tacaggaaaa    600
aggtcatata actgctggat ctaataagac aatggttgtc agtggggccg caggtgcctg    660
tggatctgtg gctgggcaga ttggccattt cttaggttgt tccagagtgg tgggaatttg    720
tggaacacat gagaaatgca tcctcttgac ctcagaactg ggctttgatg ctgcaattaa    780
ttataaaaaa gacaatgtgg cagaacagct ccgtgaatca tgcccagctg gagtggatgt    840
ttattttgac aatgttggtg gtaacatcag tgatacagtg ataagtcaga tgaatgagaa    900
cagccacatc atcctgtgtg gtcaaatttc tcagtacaac aaagatgtgc cttatcctcc    960
cccgctatcc cctgctatag aggcaatcca gaaagaaaga aacatcacaa gggaaagatt   1020
tctggtatta aattataaag acaaatttga gcctggcatt ctacagctga gtcagtggtt   1080
taaagaagga aagctaaaga ttaaagagac ggtaataaat gggttggaaa acatgggagc   1140
tgcattccag tccatgatga caggaggtaa cattggaaag cagatagttt gcatttcaga   1200
agaaatctct ttgtaattgc tgtaaatgtc atcaaggcaa tcatagattt cttttccatt   1260
ttgcatattt tcaaagatat gttaaaaaat ccttagacta tacatagctc ttgatttaaa   1320
tgtgatcata ggtgttattt ttagttgcat agggtatttg atacaatcat taatggatca   1380
tacacaatag gttttttaaaa attaataact tttagtaatt acttttatta atttaaaata   1440
gaacgcttga gaggcacttt gtaaagattt gttaaactgg aaacgttta catgatctga    1500 tacaaccatt aatgaatcat acacaatagg ttttttaaaa ttaatattaa taacttttat   1560
taatttaaaa tagaatgctt aaaataaaat agaatgcttg agaggcactg agtaaagatt   1620
tgttgaactg gaaatgtttt acatgattct taaactgaaa cttggtgtaa aaatagaatt   1680
gagatggcct tttttttcaca ttgtagactg aaaagagact taatggtatg atgtgtacat   1740
agggactggg ggcaggattg ggggtttcgg agcttgtgta acagttttg ggataggaga    1800 ccagcggttt tgggttggga ttagtatggg aagataaata acttaggttg gttaagttga   1860
caagatttac tccagaggat catctctttg tatttgccaa ataatttact gtatagccta   1920
aaaactccat atatattgag aaaagcatat gtttattttta ggttagcagg cacatactgt   1980
caagttgtaa agattgagag ggcaaacaga tgtaaacatc acttgtaggt gattaaaaag   2040
attgacagcc gggcctgatg tctcaagcct gtaatcctag cactttggga ggcagaggcg   2100
ggcagatcac ttgaggtcag gagttcaaga ccagcctggc caacacggtg aaaccccatc   2160
tctctaaaaa tacaaaaatt agctgggcgt ggtggcacac gcctgtaatc ccagctactc   2220
aggaggctga ggctggagaa tcatttgaac ctgggagggg gaggttgccg tgagctgagc   2280
ttgcaccatt gcactccagc ctgggcgaca agagtgaaat tccatctcaa aaacaaaaa    2340 cagattgaca acaagacag tttcagaaaa tgacaggact gggcaaatta acaaatgttt    2400
gtaaacatga atgttcagga actactgatg tacctcaaaa gtttgtttta ttaattgtac   2460
tcaaccctcg cagaacagta aaactgaaga ttattgtttc tgaaaaaaaa aaaaaaaaa    2520
```

<210> SEQ ID NO 263

<211> LENGTH: 351
<212> TYPE: PRT
<213> ORGANISM: Homo sapiens

<400> SEQUENCE: 263

```
Met Ile Val Gln Arg Val Val Leu Asn Ser Arg Pro Gly Lys Asn Gly
1               5                   10                  15

Asn Pro Val Ala Glu Asn Phe Arg Met Glu Glu Val Tyr Leu Pro Asp
            20                  25                  30

Asn Ile Asn Glu Gly Gln Val Gln Val Arg Thr Leu Tyr Leu Ser Val
        35                  40                  45

Asp Pro Tyr Met Arg Cys Arg Met Asn Glu Asp Thr Gly Thr Asp Tyr
    50                  55                  60

Ile Thr Pro Trp Gln Leu Ser Gln Val Val Asp Gly Gly Ile Gly
65                  70                  75                  80

Ile Ile Glu Glu Ser Lys His Thr Asn Leu Thr Lys Gly Asp Phe Val
                85                  90                  95

Thr Ser Phe Tyr Trp Pro Trp Gln Thr Lys Val Ile Leu Asp Gly Asn
            100                 105                 110

Ser Leu Glu Lys Val Asp Pro Gln Leu Val Asp Gly His Leu Ser Tyr
        115                 120                 125

Phe Leu Gly Ala Ile Gly Met Pro Gly Leu Thr Ser Leu Ile Gly Ile
    130                 135                 140

Gln Glu Lys Gly His Ile Thr Ala Gly Ser Asn Lys Thr Met Val Val
145                 150                 155                 160

Ser Gly Ala Ala Gly Ala Cys Gly Ser Val Ala Gly Gln Ile Gly His
                165                 170                 175

Phe Leu Gly Cys Ser Arg Val Val Gly Ile Cys Gly Thr His Glu Lys
            180                 185                 190

Cys Ile Leu Leu Thr Ser Glu Leu Gly Phe Asp Ala Ala Ile Asn Tyr
        195                 200                 205

Lys Lys Asp Asn Val Ala Glu Gln Leu Arg Glu Ser Cys Pro Ala Gly
    210                 215                 220

Val Asp Val Tyr Phe Asp Asn Val Gly Gly Asn Ile Ser Asp Thr Val
225                 230                 235                 240

Ile Ser Gln Met Asn Glu Asn Ser His Ile Ile Leu Cys Gly Gln Ile
                245                 250                 255

Ser Gln Tyr Asn Lys Asp Val Pro Tyr Pro Pro Leu Ser Pro Ala
            260                 265                 270

Ile Glu Ala Ile Gln Lys Glu Arg Asn Ile Thr Arg Glu Arg Phe Leu
        275                 280                 285

Val Leu Asn Tyr Lys Asp Lys Phe Glu Pro Gly Ile Leu Gln Leu Ser
    290                 295                 300

Gln Trp Phe Lys Glu Gly Lys Leu Lys Ile Lys Glu Thr Val Ile Asn
305                 310                 315                 320

Gly Leu Glu Asn Met Gly Ala Ala Phe Gln Ser Met Met Thr Gly Gly
                325                 330                 335

Asn Ile Gly Lys Gln Ile Val Cys Ile Ser Glu Glu Ile Ser Leu
            340                 345                 350
```

<210> SEQ ID NO 264
<211> LENGTH: 25
<212> TYPE: DNA
<213> ORGANISM: Artificial Sequence
<220> FEATURE:
<223> OTHER INFORMATION: Synthetic polynucleotide -continued

<400> SEQUENCE: 264
ggaaagcaga tagtttgcat ttcag                                              25

<210> SEQ ID NO 265
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 265
aaaatcctta gactatacat agctc                                              25

<210> SEQ ID NO 266
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 266
agactataca tagctcttga tttaa                                              25

<210> SEQ ID NO 267
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 267
gatcataggt gttatttta gttgc                                               25

<210> SEQ ID NO 268
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 268
ttagttgcat agggtatttg ataca                                              25

<210> SEQ ID NO 269
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 269
gatacaatca ttaatggatc ataca                                              25

<210> SEQ ID NO 270
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 270
ggatcataca caataggttt ttaaa                                              25

<210> SEQ ID NO 271

```
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 271
agaacgcttg agaggcactt tgtaa                                    25

<210> SEQ ID NO 272
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 272
ggaaacgttt tacatgatct gatac                                    25

<210> SEQ ID NO 273
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 273
tgatctgata caaccattaa tgaat                                    25

<210> SEQ ID NO 274
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 274
gaatcataca caataggttt tttaa                                    25

<210> SEQ ID NO 275
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 275
gcagtctttc ccttgaggct                                          20

<210> SEQ ID NO 276
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 276
tcgggaatta cgtcgccaaa                                          20

<210> SEQ ID NO 277
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 277
```

```
tacccccgagc agttctccta cat                                              23

<210> SEQ ID NO 278
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 278
gccagttcct tggacaccag gtctg                                             25

<210> SEQ ID NO 279
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 279
gcatccacct ggagtaccct                                                   20

<210> SEQ ID NO 280
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 280
tcccaggacc ttttggtggt                                                   20

<210> SEQ ID NO 281
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 281
tgaggcagaa ataaggaga gtgaa                                              25

<210> SEQ ID NO 282
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 282
tggggaagtg aagtgtaaga agagt                                             25

<210> SEQ ID NO 283
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 283
aggcagaaaa taaggagagt g                                                 21

<210> SEQ ID NO 284
<211> LENGTH: 21
<212> TYPE: DNA
```

<213> ORGANISM: Artificial Sequence
<220> FEATURE:
<223> OTHER INFORMATION: Synthetic polynucleotide

<400> SEQUENCE: 284
aagcggatgg atgatagtga g                                    21

<210> SEQ ID NO 285
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 285
gcgaggtaga gtcaaggaga gtggtct                              27

<210> SEQ ID NO 286
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 286
gcgcaaagtt cgttctgctg ctcaag                               26

<210> SEQ ID NO 287
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 287
gccgagatga tggagatgaa gatta                                25

<210> SEQ ID NO 288
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 288
gcgcagtagg tatggattta tgtga                                25

<210> SEQ ID NO 289
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 289
gtagtcattg atgatctgcc caaagag                              27

<210> SEQ ID NO 290
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 290
gagccacaca agctattttc tttctca                              27

<210> SEQ ID NO 291
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 291
gcagttcaag gatctaaaga gcatcaa                                        27

<210> SEQ ID NO 292
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 292
aacatctgta tgctgaggat gaacaca                                        27

<210> SEQ ID NO 293
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 293
tgatgatgag actaaaacaa aat                                            23

<210> SEQ ID NO 294
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 294
tgaagaagaa agaataaaat aat                                            23

<210> SEQ ID NO 295
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 295
ttttccagtc ccattatttt cacag                                          25

<210> SEQ ID NO 296
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 296
agtcccttct ttcctttcag tctcc                                          25

<210> SEQ ID NO 297
<211> LENGTH: 25
<212> TYPE: DNA
<213> ORGANISM: Artificial Sequence
<220> FEATURE:

<223> OTHER INFORMATION: Synthetic polynucleotide

<400> SEQUENCE: 297
tcaaggcaaa gagaaaaaga gtatt    25

<210> SEQ ID NO 298
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 298
agacaccaaa gtaagaccac agatt    25

<210> SEQ ID NO 299
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 299
agacttggag acttcttcgg agacc    25

<210> SEQ ID NO 300
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 300
taaaacacag gcatcaatca aaata    25

<210> SEQ ID NO 301
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 301
gaactgggtg atgcggatgc t    21

<210> SEQ ID NO 302
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 302
gctggaagag gaaggagaga a    21

<210> SEQ ID NO 303
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 303
acaaggtgaa accccgtctc tactaaa    27

```
<210> SEQ ID NO 304
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 304
ttcttccacc taagctttgc cataaat                                               27

<210> SEQ ID NO 305
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 305
atcaaaaaca tcatcatcca ggactgt                                               27

<210> SEQ ID NO 306
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 306
tctcaggact ctgacactgt ccaactt                                               27

<210> SEQ ID NO 307
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 307
caggatggtt cgtactaaga catggac                                               27

<210> SEQ ID NO 308
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 308
gctttcttca aggtttcttc caaagac                                               27

<210> SEQ ID NO 309
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 309
catgcgttgt agaatgaatg aagacac                                               27

<210> SEQ ID NO 310
<211> LENGTH: 27
<212> TYPE: DNA
<213> ORGANISM: Artificial Sequence
<220> FEATURE:
<223> OTHER INFORMATION: Synthetic polynucleotide
```

<400> SEQUENCE: 310
tgtactgaga aatttgacca cacagga 27

<210> SEQ ID NO 311
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 311
agcaggttaa tggataattt cttgat 26

<210> SEQ ID NO 312
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 312
ggtcctttgt aaaaccatt acactt 26

<210> SEQ ID NO 313
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 313
cgtttccttt tattttggag ctaatgc 27

<210> SEQ ID NO 314
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 314
aaggaagtca ctccaaggta cacactg 27

<210> SEQ ID NO 315
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 315
atgcaagaaa tgtctggaga aattgaa 27

<210> SEQ ID NO 316
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 316
ccttgtattt tctcagtacg agctcca 27

<210> SEQ ID NO 317
<211> LENGTH: 25

```
<212> TYPE: DNA
<213> ORGANISM: Artificial Sequence
<220> FEATURE:
<223> OTHER INFORMATION: Synthetic polynucleotide

<400> SEQUENCE: 317
gcgacggcgg ctgcggctac tggag                                  25

<210> SEQ ID NO 318
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 318
ttcttctaat gcttcttgac taccc                                  25

<210> SEQ ID NO 319
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 319
tgaaaggaag gagaaggaga aaaag                                  25

<210> SEQ ID NO 320
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 320
agaggcagtg agggcagcat tagta                                  25

<210> SEQ ID NO 321
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 321
taaatggaga ggaggtagaa gaaac                                  25

<210> SEQ ID NO 322
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 322
ggtggtagaa agagaacgaa aagtc                                  25

<210> SEQ ID NO 323
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 323
```
gcgtgacatt aaggagaagc tgt                                              23

<210> SEQ ID NO 324
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 324
cttgttttct gcgcaagtta ggt                                              23

<210> SEQ ID NO 325
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 325
aggagccagg agaggact                                                    18

<210> SEQ ID NO 326
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 326
gcagggacga aaggtatc                                                    18

<210> SEQ ID NO 327
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 327
gtatcgtgga aggactcatg acc                                              23

<210> SEQ ID NO 328
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 328
tctcttcctc ttgtgctctt gct                                              23

<210> SEQ ID NO 329
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 329
gcacacagaa gcgctcagta agggctttga aacttaacag tttgggagcc agatcctcag      60
gccacatctc tctcctccca cgacctccgc ggtcctccag aaccatagag agttgtacag     120

<210> SEQ ID NO 330
<211> LENGTH: 120

```
<212> TYPE: DNA
<213> ORGANISM: Artificial Sequence
<220> FEATURE:
<223> OTHER INFORMATION: Synthetic polynucleotide

<400> SEQUENCE: 330
agatcgccct gctctatgct ctactctcct ggggagcggg gccagagagg ccggaagtgc    60
tgcgagccct gggccacgct ggccgtgctg gcagtgggcc gcctcgatcc ctctgcagtc   120

<210> SEQ ID NO 331
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 331
tttcccttga ggctccaaga ccagcaggtg aggcctcgcg gcgctgaaac cgtgaggccc    60
ggaccacagg tgcgggaggc ggagactgcg ggtggagatt ggcgccgcgg aagccaatca   120

<210> SEQ ID NO 332
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 332
gcgatgggac ttgtggacct gtaaggggcg gggcgagccg aaggtggagg tcaaaggggc    60
gtggcgttac agagcctcta gcgctgggtg ttggggacct gacgctatgg agctctcgga   120

<210> SEQ ID NO 333
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 333
gttttgtggg ggacggctgt gagtgggggg ttcctgctgc gggatgagaa cgtagacgcc    60
agtggctcac tcgctcctgg caccttccct ttcaggctcc agatggaccc tgggaaggac   120

<210> SEQ ID NO 334
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 334
aaagaggggg tgcccagcc ctcagggccg ccagcaagga agaaatttgt gatacccctc    60
gacgaggatg aggtccctcc tggagtggta ggacaaggag atgcggggcc cctgggaggc   120

<210> SEQ ID NO 335
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 335
ttctccccac aggccaagcc cttattccga tctacacaga gccttccac tgtggacacc    60
```
tcggcccagg cggcccctca gacctacgcc gaatatgcca tctcacagcc tctggaaggg    120

<210> SEQ ID NO 336
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 336
gctggggcca cgtgcccccac agggtcagag cccctggcag gagagacgcc caaccaggcc    60
ctgaaacccg gggcaaaatc caacagcatc attgtgagcc ctcggcaggt gaggagggag    120

<210> SEQ ID NO 337
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 337
ctccccagag gggcaatccc gtactgaagt tcgtgcgcaa tgtgccctgg gaatttggcg    60
acgtaattcc cgactatgtg ctgggccaga gcacctgtgc cctgttcctc aggtgagctc    120

<210> SEQ ID NO 338
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 338
cccccaccag cctccgctac cacaacctgc acccagacta catccatggg cggctgcaga    60
gcctggggaa gaacttcgcc ttgcgggtcc tgcttgtcca ggtggatgtg gtaagcaggg    120

<210> SEQ ID NO 339
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 339
aattctgatt ttctcctcca gaaagatccc cagcaggccc tcaaggagct ggctaagatg    60
tgtatcctgg ccgactgcac attgatcctc gcctggaggt gagatgaggg cttccctgcc    120

<210> SEQ ID NO 340
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 340
gttatcccag ccccgaggaa gctgggcggt acctggagac ctacaaggcc tatgagcaga    60
aaccagcgga cctcctgatg gagaagctag agcaggactt cgtctcccgg gtgaggccac    120

<210> SEQ ID NO 341
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 341
cactcctgcc tccacccttt ccaggtgact gaatgtctga ccaccgtgaa gtcagtcaac    60
aaaacggaca gtcagaccct cctgaccaca tttggagtaa ggaatggctc ccctgcccca   120

<210> SEQ ID NO 342
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 342
ggaggctttt gtgctcaact gccctgaccc ctcgctttca cctttcagtc tctggaacag    60
ctcatcgccg catcaagaga agatctggcc ttatgcccag gcctgggccc tcagaaagta   120

<210> SEQ ID NO 343
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 343
agagctctgg gaaagaaccc aaggagttgg gggaaggaga gagccccaaa taaacacaac    60
ctgagacccc aaagttttaa ggtgaaaaaa gaaccaaaga ccagacacag tggcttccg    119

<210> SEQ ID NO 344
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 344
ggcgggtcga ccccgctgca cagtccggcc ggcgccatga agtgagaagg gggctggggg    60
tcgcgctcgc tagcgggcgc ggggggtctt gaagatgggg tcatcggtgg gcgcgcctgg   120

<210> SEQ ID NO 345
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 345
gtccccaagg gggcgagggg agggtgaagg ggtgggacgg gggcagccgc agggagcagc    60
agtgatagcg aggagacact gagggggccc cgaggctcct gaggacctga gggttaccgg   120

<210> SEQ ID NO 346
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 346
gggcgccggg cccgtcaccc ttctctgggc tcgacgaccg ggcactgtgg aggcgggaga    60
ggggctgagg ggacgggaac tgacccagca gcccctgccg ccaggctcaa cgtggacggg   120

<210> SEQ ID NO 347

```
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 347
ctcctggtct acttcccgta cgactacatc tacccccgagc agttctccta catgcgggag      60
ctcaaacgca cgctggacgc caaggtgggt ggccggtggg cccgaccccgc ccactcgacc     120

<210> SEQ ID NO 348
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 348
cctctggtcc ccaacatgca gggtcatgga gtcctggaga tgccctcagg caccgggaag      60
acagtatccc tgttggccct gatcatggca taccagagag tgagtgatgc gctgaacccg     120

<210> SEQ ID NO 349
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 349
agggactgag tccgcttgtt atcggcaggc atatccgctg gaggtgacca aactcatcta      60
ctgctcaaga actgtgccag agattgagaa ggtaagctgg gactcatcct ggtgctccag     120

<210> SEQ ID NO 350
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 350
agtaggtgat tgaagagctt cgaaagttgc tcaacttcta tgagaagcag gagggcgaga      60
agctgccgtt tctgggactg gctctgagct cccgcaaaaa cttgtgtatt caccctgagg     120

<210> SEQ ID NO 351
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 351
aggtgacacc cctgcgcttt gggaaggacg tcgatgggaa atgccacagc ctcacagcct      60
cctatgtgcg ggcgcagtac cagcatgaca ccagcctgcc ccactgccga ttctatgagg     120

<210> SEQ ID NO 352
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 352
aggaatttga tgcccatggg cgtgaggtgc ccctccccgc tggcatctac aacctggatg      60
```

```
acctgaaggc cctggggcgg cgccagggct ggtgcccata cttccttgct cgatactcag    120
```

<210> SEQ ID NO 353
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 353

```
ggtaggggta ggggttgggg tggcagggcc ctggtaaccc tgctccccgg ccccccagat    60
cctgcatgcc aatgtggtgg tttatagcta ccactacctc ctggacccca agattgcaga    120
```

<210> SEQ ID NO 354
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 354

```
cctggtgtcc aaggaactgg cccgcaaggc cgtcgtggtc ttcgacgagg cccacaacat    60
tggtgagggg ggcgccaggg gccaaaggga tgccagcccc tctgagtgag gcccctgcag    120
```

<210> SEQ ID NO 355
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 355

```
cccctctctcc agacaacgtc tgcatcgact ccatgagcgt caacctcacc cgccggaccc    60
ttgaccggtg ccagggcaac ctggagaccc tgcagaagac ggtgctcagg tggggccggg    120
```

<210> SEQ ID NO 356
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 356

```
acttgtcccc agggttgcca gcccctccc agcccagct catctctccg caggatcaaa    60
gagacagacg agcagcgcct gcgggacgag taccggcgtc tggtggaggg gctgcgggag    120
```

<210> SEQ ID NO 357
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 357

```
gccagcgccg cccgggagac ggacgcccac ctggccaacc ccgtgctgcc cgacgaagtg    60
ctgcagggtg agccccgacc ccccgctgcc ccccagtccc tttcccgcct ccccgtcgcc    120
```

<210> SEQ ID NO 358
<211> LENGTH: 120
<212> TYPE: DNA
<213> ORGANISM: Artificial Sequence
<220> FEATURE:

<223> OTHER INFORMATION: Synthetic polynucleotide

<400> SEQUENCE: 358

```
cgcctccccg tcgccgctga tagcgtctcc tcgcagaggc agtgcctggc tccatccgca    60
cggccgagca tttcctgggc ttcctgaggc ggctgctgga gtacgtgaag tggcggctgc   120
```

<210> SEQ ID NO 359
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 359

```
gtgtgcagca tgtggtgcag gagagcccgc ccgccttcct gagcggcctg gcccagcgcg    60
tgtgcatcca gcgcaagccc ctcaggtgcg gccccagaca gcgcgcgggg tgggggcccg   120
```

<210> SEQ ID NO 360
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 360

```
attctgtgct gaacgcctcc ggtccctgct gcatactctg gagatcaccg accttgctga    60
cttctccccg ctcaccctcc ttgctaactt tgccacccct gtcagcacct acgccaaagg   120
```

<210> SEQ ID NO 361
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 361

```
accccctcctt gcctgccctc tgcaggcttc accatcatca tcgagcccct tgacgacaga    60
accccgacca ttgccaaccc catcctgcac ttcaggtggg accctgcccg gtgagggtgt   120
```

<210> SEQ ID NO 362
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 362

```
cctcactgcc ctcatctctc tccagctgca tggacgcctc gctggccatc aaacccgtat    60
ttgagcgttt ccagtctgtc atcatcacat ctggggtaag gacccttccc cgtcccctcc   120
```

<210> SEQ ID NO 363
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 363

```
ccgccacaga cactgtcccc gctggacatc taccccaaga tcctggactt ccaccccgtc    60
accatggcaa ccttcaccat gacgctggca cgggtctgcc tctgccctat ggtgagtggg   120
```

<210> SEQ ID NO 364
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 364
gcttatcgtg acctctgttg ctctccagat catcggccgt ggcaatgacc aggtggccat    60
cagctccaaa tttgagaccc gggaggatat tggtatgctg ccagtggggc tggtttctgt   120

<210> SEQ ID NO 365
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 365
agacagagaa gggaggagga cctgggccag gagagggccc aacctctgac cccttgcagc    60
tgtgatccgg aactatggga acctcctgct ggagatgtcc gctgtggtcc ctgatggcat   120

<210> SEQ ID NO 366
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 366
cgtggccttc ttcaccagct accagtacat ggagagcacc gtggcctcct ggtatgagca    60
ggtacgcctg gccacccccct ccctgcacct gctctcctca gtccctggca ctgcaccgct   120

<210> SEQ ID NO 367
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 367
gggtccttcc ccaggggatc cttgagaaca tccagaggaa caagctgctc tttattgaga    60
cccaggatgg tgccgaaacc agtgtcgccc tggagaagta ccaggaggtg ggtgtgcgag   120

<210> SEQ ID NO 368
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 368
tgcgtctcgg tctccccacc tcaggcctgc gagaatggcc gcggggccat cctgctgtca    60
gtggcccggg gcaaagtgtc cgagggaatc gactttggtg agtggactgg gctcttcctc   120

<210> SEQ ID NO 369
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 369 cgcccctct cctctgccca ccagtgcacc actacgggcg ggccgtcatc atgtttggcg    60
tcccctacgt ctacacacag agccgcattc tcaaggtgag tagctctgtc tcccagggag   120

<210> SEQ ID NO 370
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 370
aggagtggct cccccacctc cccagcttct catcctccgt atctgcaggc gcggctggaa    60
tacctgcggg accagttcca gattcgtgag aatgactttc ttaccttcga tgccatgcgc   120

<210> SEQ ID NO 371
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 371
cacgcggccc agtgtgtggg tcgggccatc aggggcaaga cggactacgg cctcatggtc    60
tttgccgaca aggtgcagct tcaggggtgc ccctgtgctc ccatcccagg ctccaagaac   120

<210> SEQ ID NO 372
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 372
aggctccccg aatgaccttc tgtccctggc ctgcgcttct gcccacagcg gtttgcccgt    60
ggggacaagc gggggaagct gccccgctgg atccaggagc acctcacaga tgccaacctc   120

<210> SEQ ID NO 373
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 373
aacctgaccg tggacgaggg tgtccaggtg gccaagtact cctgcggca gatggcacag    60 cccttccacc gggtgaggcc tgcgtccccc tcccggcacc ctcccaggct gagcttctcc   120

<210> SEQ ID NO 374
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 374
tctgttctct gcaggaggat cagctgggcc tgtccctgct cagcctggag cagctagaat    60
cagaggagac gctgaagagg atagagcaga ttgctcagca gctctgagtg gggcgggtgg   120

<210> SEQ ID NO 375
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 375

```
gagcggggtc atcttctctc tgctgctgta gctgccatgg gcaaaagaga ccgagcggac    60
cgcggtgaga cgttgcgcgg gcacgctcag ccacgactgc ccttgccggc cctgccccc    120
```

<210> SEQ ID NO 376
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 376

```
gctctgcctc ggagctgctc cgggcctctg cgccggccga ccctgctggc cctcccgcgc    60 gcacccccgtt gggacaggcc tttgggcggg agagatgctg acctgggcg cagcccagcg    120
```

<210> SEQ ID NO 377
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 377

```
aactcggcct aggggagacg ggtgaggggc gcaacgcctg cgggatgcag gtggctctta    60
gctaggagtt tgcggcggcg caggtgaaat gctgccaagc ggtgcggagg gaaccctgaa    120
```

<210> SEQ ID NO 378
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 378

```
gtgttggtat cttgcagaca agaagaaatc caggaagcgg cactatgagg atgaagagga    60
tgatgaagag gacgccccgg ggaacgaccc tcaggaagcg gttccctcgg cggcggggaa    120
```

<210> SEQ ID NO 379
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 379

```
gcaggtggat gagtcaggca ccaaagtgga tgaatatgga gccaaggact acaggctgca    60
aatgccgctg aaggacgacc acacctccag gccctctgg gtggtaagca tgcccttagc    120
```

<210> SEQ ID NO 380
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 380

```
aggctcccga tggccatatc ttcttggaag ccttctctcc agtttacaaa tatgcccaag    60
acttcttggt ggctattgca gagccagtgt gccgaccaac ccatgtgcat gagtacaaac    120
```

<210> SEQ ID NO 381
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 381
taactgccta ctccttgtat gcagctgtca gcgttgggct gcaaaccagt gacatcaccg    60
agtacctcag gaagctcagc aagactggag tccctgatgg aattatgcag tttattaagg   120

<210> SEQ ID NO 382
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 382
cacatttacc tgttggatgt tatctgtatt tgcagttgtg tactgtcagc tatggaaaag    60
tcaagctggt cttgaagcac aacaggtaag agattccatg acaggcctgt cccaaggcac   120

<210> SEQ ID NO 383
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 383
tccaggaggt acctgctggt cagtagaccc cttcttcctc ccctgcttgc agatacttcg    60
ttgaaagttg ccaccctgat gtaatccagc atcttctcca ggacccgtg atccgagaat    120

<210> SEQ ID NO 384
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 384
gccgcttaag aaactctgaa ggggaggcca ctgagctcat cacagagact ttcacaagca    60
aatctgccgt atgtggactc ctgggccacc cttgggtggg ggcaggcatt taggatttca   120

<210> SEQ ID NO 385
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 385
aatgttgtgt gcacgttcag cacctacctc tctcacagat ttctaagact gctgaaagca    60
gtggtgggcc ctccacttcc cgagtgacag atccacaggg taaatctgac atccccatgg   120

<210> SEQ ID NO 386
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 386

```
acctgtttga cttctatgag caaatggaca aggatgaaga agaagaagaa gagacacaga    60
cagtgtcttt tgaagtcaag caggttagtg aatgtacctt cctcctggtt ccttcactga   120
```

<210> SEQ ID NO 387
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 387

```
tttgtgccct ctttccagga aatgattgag gaactccaga aacgttgcat ccacctggag    60
taccctctgt tggcagaata tgacttccgg aatgattctg tcaaccctga tatcaacatt   120
```

<210> SEQ ID NO 388
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 388

```
gacctaaagc ccacagctgt cctcagaccc tatcaggaga agagcttgcg aaagatgttt    60
ggaaacgggc gtgcacgttc gggggtcatt gttcttccct gcggtaagtg gtaccagagt   120
```

<210> SEQ ID NO 389
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 389

```
attgcactct tgtttcttgt aggtgctgga aagtccctgg ttggtgtgac tgctgcatgc    60
actgtcagaa aacgctgtct ggtgctgggc aactcagctg tttctgtgga gcagtggaaa   120
```

<210> SEQ ID NO 390
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 390

```
gcccagttca agatgtggtc caccattgac gacagccaga tctgccggtt cacctccgat    60
gccaaggaca agcccatcgg ctgctccgtt gccattagca cctactccat gctgggccac   120
```

<210> SEQ ID NO 391
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 391

```
accaccaaaa ggtcctggga ggccgagcga gtcatggagt ggctcaagac ccaggagtgg    60
ggcctcatga tcctggatga agtgcacacc ataccaggta agcaggctgg agctgagctg   120
```

<210> SEQ ID NO 392
<211> LENGTH: 120
<212> TYPE: DNA

```
<213> ORGANISM: Artificial Sequence
<220> FEATURE:
<223> OTHER INFORMATION: Synthetic polynucleotide

<400> SEQUENCE: 392
agtgtgaatg ctcccattgt ttcctcagcc aagatgttcc gaagggtgct caccatcgtg    60
caggcccact gtaagctggg tttgactgcg accctcgtcc gcgaagatga caaaattgtg   120

<210> SEQ ID NO 393
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 393
gatttaaatt ttctgattgg gcctaagctc tacgaagcca actggatgga gctgcagaat    60
aatggctaca tcgccaaagt ccagtgtgct gaggtagctg ggcctgggct ggggggcgtct  120

<210> SEQ ID NO 394
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 394
gttcttactg tattacaggt ctggtgccct atgtctcctg aattttaccg ggaatatgtg    60
gcaatcaaaa ccaagaaacg aatcttgctg tacaccatga accccaacaa atttagagct   120

<210> SEQ ID NO 395
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 395
tgccagtttc tgatcaagtt tcatgaaagg aggaatgaca agattattgt ctttgctgac    60
aatgtgtttg ccctaaagga atatgccatt cgactgaaca agtaagaatt gaaaacttgg   120

<210> SEQ ID NO 396
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 396
attcttctct agaccctata tctacggacc tacgtctcag ggggaaagga tgcaaattct    60
ccagaatttc aagcacaacc ccaaaattaa caccatcttc atatccaagg tttgtgtggc   120

<210> SEQ ID NO 397
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 397
ggtaggtgac acttcgtttg atctgccgga agcaaatgtc ctcattcaga tctcatccca    60
tggtggctcc aggcgtcagg aagcccaaag gctagggcgg gtgcttcgag ctaaaaaagg   120
```

<210> SEQ ID NO 398
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 398
ggatggttgc agaagagtac aatgccttt tctactcact ggtatcccag gacacacagg      60
aaatggctta ctcaaccaag cggcagagat tcttggtaga tcaaggttat agcttcaagg    120

<210> SEQ ID NO 399
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 399
agagagagca gaaaggggca tgtctgctgg cttgggcttt gcaggtgatc acgaaactcg      60
ctggcatgga ggaggaagac ttggcgtttt cgacaaaaga gagcaacag cagctcttac     120

<210> SEQ ID NO 400
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 400
agaaagtcct ggcagccact gacctggatg ccgaggagga ggtggtggct ggggaatttg      60
gctccagatc cagccaggtg agtaaatggg tgaggaggtt ccaggtgtca gtgctctcac    120

<210> SEQ ID NO 401
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 401
aggagtatct tttcttctgg agactaacat gggctggttc cccttcccg gcaggcatct      60 cggcgctttg gcaccatgag ttctatgtct ggggccgacg acactgtgta catggagtac    120

<210> SEQ ID NO 402
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 402
cactcatcgc ggagcaaggc gcccagcaaa catgtacacc cgctcttcaa gcgctttagg      60
aaatgatgct taggcagggt acttcgttca agaccggcgc ttggcaccct tgttggaaag    120

<210> SEQ ID NO 403
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 403
acccggaaga gcttccatgg agtcagggca gccggctcga cggattgcca tggcgccgct    60
gctggagtac gagcgacagc tggtgctgga actgctcgac actgacgggc tagtagtgtg   120

<210> SEQ ID NO 404
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 404
cgcccgcggg ctcggcgcgg accggctcct ctaccacttt ctccagctgc actgccaccc    60
agcctgcctg gtgctggtgc tcaacacgca gccggccgag gaggtgcggc gcgctggcg   120

<210> SEQ ID NO 405
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 405
agcctactaa tcaagtttga tttgatttag gagtatttta tcaatcagct gaagatagaa    60
ggagttgaac acctccctcg ccgtgtaaca atgaaatca caagcaacag tcgctatgaa   120

<210> SEQ ID NO 406
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 406
gtttacacac aaggtggtgt tatatttgcg acaagtagga tacttgtggt tgacttcttg    60
actgatagaa taccttcaga tttaattact ggtaagaatt tgaaatctta ttattagtat   120

<210> SEQ ID NO 407
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 407
aaattatgtt tctcccctc aggcatcttg gtgtatagag cccacagaat aatcgagtct    60
tgtcaagaag cattcatctt gcgcctcttt cgccagaaaa acaaacgtgg ttttattaaa   120

<210> SEQ ID NO 408
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 408
gctttcacag acaatgctgt tgcctttgat actggttttt gtcatgtgga aagagtgatg    60
agaaatcttt ttgtgaggaa actgtatctg tggccaaggt aaagaacatt atgtgacaaa   120

<210> SEQ ID NO 409
<211> LENGTH: 120

```
<212> TYPE: DNA
<213> ORGANISM: Artificial Sequence
<220> FEATURE:
<223> OTHER INFORMATION: Synthetic polynucleotide

<400> SEQUENCE: 409
atatttgtct ctttaggttc catgtagcag taaactcatt tttagaacag cacaaacctg    60
aagttgtaga aatccatgtt tctatgacac ctaccatgct tgctatacag actgctatac   120

<210> SEQ ID NO 410
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 410
tggacatttt aaatgcatgt ctaaaggaac taaaatgcca taccccatcg cttgaagtgg    60
aagatttatc tttagaaaat gctattggaa aacctttga caaggtactc ttttccttt    120

<210> SEQ ID NO 411
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 411
tagcaatacc aaattttatt cttgttttag acaatccgcc attatctgga tcctttgtgg    60
caccagcttg gagccaagac taaatcctta gttcaggatt tgaagatatt acgaactttg   120

<210> SEQ ID NO 412
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 412
ctgcagtatc tctctcagta tgattgtgtc acatttctta atcttctgga atctctgaga    60
gcaacggaaa aagcttttgg tcagaattca ggtgggagat taaaatacta ataatattct   120

<210> SEQ ID NO 413
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 413
ctgttttaaa ttaaccataa attgatggca cttttttcttt taacttttcg tattaggttg    60
gctgtttctt gactccagca cctcgatgtt tataaatgct cgagcaaggg tttatcatct   120

<210> SEQ ID NO 414
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 414
tccagatgcc aaaatgagta aaaagaaaa aatatctgaa aaaatggaaa ttaaagaagg    60
```
ggaaggtatc ttgtggggtt aagtctttaa atgtgttttt tatttcggta tttggtatgg    120

<210> SEQ ID NO 415
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 415
acagaaacaa aaaggaact ggtcctagaa agcaacccaa agtgggaggc actgactgaa    60
gtattaaaag aaattgaggc agaaaataag gagagtgaag ctcttggtgg tccaggtagg    120

<210> SEQ ID NO 416
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 416
ggtcaagtac tgatttgtgc aagtgatgac cgaacatgtt cccagctgag agactatatc    60
actcttggag cggaggcctt cttattgagg ctctacagga aaacctttga aaggatagc    120

<210> SEQ ID NO 417
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 417
aaagctgaag aagtctggat gaaatttagg aaggaagaca gttcaaagag aattaggaaa    60
tctcacaaaa gacctaaaga cccccaaaac aaagaacggg cttctaccaa agaaagaacc    120

<210> SEQ ID NO 418
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 418
ctcaaaaaga aaaacggaa gttgaccttaa actcaaatgg taggaaaacc tgaagaactg    60
gaagaggaag gagatgtcga ggaaggatat cgtcgagaaa taagcagtag cccagaaagc    120

<210> SEQ ID NO 419
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 419
tgcccggaag aaattaagca tgaagaattt gatgtaaatt tgtcatcgga tgctgctttc    60
ggaatcctga aagaacccct cactatcatc catccgcttc tgggttgcag cgaccccat    120

<210> SEQ ID NO 420
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 420
gctctgacaa gggtactaca tgaagtggag ccaagatacg tggttcttta tgacgcagag       60
ctaacctttg ttcggcagct tgaaatttac agggcgagta ggcctgggaa acctctgagg      120

<210> SEQ ID NO 421
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 421
gtcttaacat gcagggttta ctttcttata tacggaggtt caactgagga acaacgctat       60
ctcactgctt tgcggaaaga aaggaagct tttgaaaaac tcataaggta atacatagaa      120

<210> SEQ ID NO 422
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 422
acagggaaaa agcaagcatg gttgtccctg aagaaagaga aggcagagat gaaacaaact       60
tagacctagt aagaggcaca gcatctgcag atgtttccac tgacactcgg aaagccggtg      120

<210> SEQ ID NO 423
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 423
attccttctt tgagagttct tccccagtga cattacttac ttttctctg taggtggcca       60 ggaacagaat ggtacacagc aaagcatagt tgtggatatg cgtgaatttc gaagtgagct      120

<210> SEQ ID NO 424
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 424
tccatctctg atccatcgtc ggggcattga cattgaaccc gtgactttag aggttggaga       60
ttacatcctc actccagaaa tgtgcgtgga gcgcaagagt atcagtgatt taatcggctc      120

<210> SEQ ID NO 425
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 425
tttaaataac ggccgcctct acagccagtg catctccatg tcccgctact acaagcgtcc       60
cgtgcttctg attgagtttg accctagcaa gcctttctct ctcacttccc gaggtgcctt      120

<210> SEQ ID NO 426

```
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 426
gtttcaggag atctccagca atgacattag ttccaaactc actcttctta cacttcactt      60
ccccagacta cggattctct ggtgcccctc tcctcatgca acggcggagt tgtttgagga     120

<210> SEQ ID NO 427
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 427
gctgaaacaa agcaagccac agcctgatgc ggcgacagca ctggccatta cagcagattc      60
tgaaaccctt cccgagtcag agaagtataa tcctggtccc caagacttct tgttaaaaat     120

<210> SEQ ID NO 428
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 428
gccaggggtg aatgccaaaa actgccgctc cttgatgcac cacgttaaga acatcgcaga      60
attagcagcc ctgtcacaag acgagctcac gagtattctg gggaatgctg caaatgccaa     120

<210> SEQ ID NO 429
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 429
acagctttat gatttcattc acacctcttt tgcagaagtc gtatcaaaag gaaaagggaa      60
aaagtgaaca gtgatggctg ttttcttatc ccatgcctgt acttttcagc ggctccttgc     120

<210> SEQ ID NO 430
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 430
aggacgcagc cgcctcatgg gggtccaggg gctctggaag ctgctggagt gctccgggcg      60
gcaggtcagc cccgaagcgc tggaagggaa gatcctggct gttggtatcc ttaacgccgc     120

<210> SEQ ID NO 431
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 431
cccggagttt tttccattaa caattctccc agatattagc atttggttaa accaagcact      60
```

```
taaaggagtc cgggatcgcc atgggaactc aatagaaaat cctcatcttc tcactttgtt    120
```

```
<210> SEQ ID NO 432
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 432
tcatcggctc tgcaaactct tattttttcg aattcgtcct attttttgtgt ttgatgggga    60 tgctccacta ttgaagaaac agactttggt aagtgtcgta tagtttttag taagtgtcaa    120
```

```
<210> SEQ ID NO 433
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 433
aggtgaagag aaggcagaga aaggacttag cgtccagtga ctccaggaaa acgacagaga    60
agcttctgaa aacattttg aaaagacaag ccatcaaaac tgccttcaga agcaaaaggc    120
```

```
<210> SEQ ID NO 434
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 434
tttgtgtact ttccagagat gaagcactac ccagtcttac ccaagttcga agagaaaacg    60
acctctatgt tttgcctcct ttacaagagg aagaaaaaca caggtaaatg tttaactatt    120
```

```
<210> SEQ ID NO 435
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 435
agatatcgta aaagtatgtt tgactttcag ttcagaagag gaagatgaaa aagaatggca    60
agaaagaatg aatcaaaaac aagcattaca ggtatttaga tcattttga attcagaatg    120
```

```
<210> SEQ ID NO 436
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 436
aagtgtatga aatgtaaatt tcatggtgct gtgattttat ctttacagga agagttctttt    60 cataatcctc aagcgataga tattgagtct gaggacttca gcagcctgcc ccctgaagta    120
```

```
<210> SEQ ID NO 437
<211> LENGTH: 120
<212> TYPE: DNA
<213> ORGANISM: Artificial Sequence
<220> FEATURE:
```

<223> OTHER INFORMATION: Synthetic polynucleotide

<400> SEQUENCE: 437

```
aagcatgaaa tcttgactga tatgaaagag ttcaccaagc gcagaagaac attatttgaa    60
gcaatgccag aggtgaaata tgcaacagta cattcatgct tagaattaag aacttcagca   120
```

<210> SEQ ID NO 438
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 438

```
tttattttgc ctttaggagt ctgatgactt ttcacagtac caactcaaag gcttgcttaa    60
aaagaactat ctgaaccagc atatagaaca tgtccaaaag gaaatgaatc agcaacattc   120
```

<210> SEQ ID NO 439
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 439

```
aggacacatc cgaaggcagt atgaagatga aggggctttt ctgaaggagg tagagtcaag    60
gagagtggtc tctgaagaca cttcacatta catcttgata aaaggtatca ggcaccatca   120
```

<210> SEQ ID NO 440
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 440

```
aaggtattca agctaagaca gttgcagaag tggattcaga gtctcttcct tcttccagca    60
aaatgcacgg catgtctttt gacgtgaagt catctccatg tgaaaaactg aagacagaga   120
```

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

```
<210> SEQ ID NO 445
<400> SEQUENCE: 445
000

<210> SEQ ID NO 446
<400> SEQUENCE: 446
000

<210> SEQ ID NO 447
<400> SEQUENCE: 447
000

<210> SEQ ID NO 448
<400> SEQUENCE: 448
000

<210> SEQ ID NO 449
<400> SEQUENCE: 449
000

<210> SEQ ID NO 450
<400> SEQUENCE: 450
000

<210> SEQ ID NO 451
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 451
aagagcctga tgctaccccct ccttctccaa gaactttact agctatgcaa gctgccctgc    60
tgggaagtag ctcagaagag gagctggaga gtgaaaatcg aaggcaggcc cgtgggagga   120

<210> SEQ ID NO 452
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 452
acgcacctgc tgctgtagac gaaggctcca tatcaccccg gactctttca gccattaaga    60
gagctcttga cgatgacgaa gatgtaaaag tgtgtgctgg ggatgatgtg cagacgggag   120

<210> SEQ ID NO 453
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 453
```

```
ggccaggagc agaagaaatg cgtataaaca gctccaccga gaacagtgat gaaggactta    60
aagtgagaga tggaaaagga ataccgttta ctgcaacact tgcgtcatct agtgtgaact   120
```

<210> SEQ ID NO 454
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 454

```
ctgcagagga gcacgtagcc agcactaatg aggggagaga gcccacagac tcagttccaa    60
aagaacaaat gtcacttgtt cacgtgggga ctgaagcctt ccgataagt gatgagtcta   120
```

<210> SEQ ID NO 455
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 455

```
tgattaagga cagaaaagat cggctgcctc tggagagtgc agtggttaga catagtgacg    60
cacctgggct cccgaatgga agggaactga caccggcatc tccaacttgt acaaattctg   120
```

<210> SEQ ID NO 456
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 456

```
tgtcaaagaa tgaaacacat gctgaagtgc ttgagcagca gaacgaactt tgcccatatg    60
agagtaaatt cgattcttct cttctttcaa gtgatgatga acaaaatgt aaaccgaatt   120
```

<210> SEQ ID NO 457
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 457

```
ctgcttctga agtcattggc cctgtcagtt tgcaagaaac aagtagcata gtaagtgtcc    60
cttcagaggc agtagataat gtggaaaatg tggtgtcatt taatgctaaa gagcatgaga   120
```

<210> SEQ ID NO 458
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 458

```
attttctgga aaccatccaa gaacagcaga ccactgaatc tgcaggccag gatttaattt    60
ccattccaaa ggccgtggaa ccaatggaaa ttgactcgga agaaagtgaa tctgatggta   120
```

<210> SEQ ID NO 459
<211> LENGTH: 120
<212> TYPE: DNA
<213> ORGANISM: Artificial Sequence

```
<220> FEATURE:
<223> OTHER INFORMATION: Synthetic polynucleotide

<400> SEQUENCE: 459
tgcaggatca ttttaatgtt ttgattgtag atgaagtgac cttttaattt tggtacagga    60
agtttcattg aagtgcaaag tgtgattagt gatgaggaac ttcaagcaga attccctgaa   120

<210> SEQ ID NO 460
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 460
acttccaaac ctccctcaga acaaggcgaa gaggaactgg taggaactag ggagggagaa    60
gccgctgctg agtccgagag cctcctgagg gacaactctg agagggacga cgtggatggt   120

<210> SEQ ID NO 461
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 461
gagccacagg aagctgagaa agatgcggaa gattcgctcc atgaatggca agatattaat    60
ttggtaatac cgtaacattg tgtttcgact tcttgctgag gaagccaggt taagtaggtt   120

<210> SEQ ID NO 462
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 462
tgtaaacaaa actcatttgg attattaata taaatctata aatgaaaaaa cattttatag    60
gaggagttgg aaactctgga gagcaacctc ttagcacagc agaattcact gaaagctcaa   120

<210> SEQ ID NO 463
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 463
aaacagcagc aagaacggat cgctgctact gtcaccggac agatgttcct ggaaagccag    60
gtgggtgcag gcagcttggg tttccttac caccttcttc agacccctgg gggaatgcac   120

<210> SEQ ID NO 464
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 464
cctcactctg caggaactcc tgcgcctgtt cggcattccc tacatccagg ctcccatgga    60
agcagaggcg cagtgcgcca tcctggacct gactgatcag acttccggaa ccatcactga   120
```

<210> SEQ ID NO 465
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 465
tgacagtgat atctggctgt ttggagcgcg gcatgtctat agaaactttt ttaataaaaa    60
caagtttgta gaatattatc aatatgtgga ctttcacaat caattgggta agacttcaga   120

<210> SEQ ID NO 466
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 466
tcatataaga aatcttgata aaaattaaaa aatattgtta ctctttagga ttggaccgga    60
ataagttaat aaatttggct tatttgcttg gaagtgatta taccgaagga ataccaactg   120

<210> SEQ ID NO 467
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 467
tgggttgtgt aaccgccatg gaaattctca atgaattccc tgggcatggc ctggaacctc    60
tcctaaaatt ctcgtaaggt cttttatttc tttaatttgg ataattgtgt aaatacccaa   120

<210> SEQ ID NO 468
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 468
ttgtttcctt tattttacag agaatggtgg catgaagctc aaaaaaatcc aaagataaga    60
cctaatcctc atgacaccaa agtgaaaaaa aaattacgga cattgcaact caccccctggc  120

<210> SEQ ID NO 469
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 469
tttcctaacc cagctgttgc cgaggcctac ctcaaacccg tggtggatga ctcgaaggga    60
tcctttctgt gggggaaacc tgatctcgac aaaattagag aatatccttt gcttcttaaa   120

<210> SEQ ID NO 470
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 470

```
agtcttaact gcatgcatat tttgtcagcg gtatttcggc tggaacagaa cgaagacaga    60
tgaatctctg tttcctgtat taaagcaact cgatgcccag caggtaatca tggtggaccc   120
```

<210> SEQ ID NO 471
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 471

```
agacacagct ccgaattgat tccttcttta gattagcaca acaggagaaa gaagatgcta    60
aacgtattaa gagccagaga ctaaacagag ctgtgacatg tatgctaagg aaagagaaag   120
```

<210> SEQ ID NO 472
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 472

```
aagcagcagc cagcgaaata gaagcagttt ctgttgccat ggagaaagaa tttgagctac    60
ttgataaggc aaaaggaaaa acccagaaga gaggcataac aaatacctta gaagagtcat   120
```

<210> SEQ ID NO 473
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 473

```
caagcctgaa aagaaagagg ctttcagatt ctaaaggaaa gaatacatgc ggtggatttt    60
tgggggagac ctgcctctca gaatcatctg atggatcttc aagtgaagat gctgaaagtt   120
```

<210> SEQ ID NO 474
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 474

```
catctttaat gaatgtacaa aggagaacag ctgcgaaaga gccaaaaacc agtgcttcag    60
attcgcagaa ctcagtgaag gaagctcccg tgaagaatgg aggtgcgacc accagcagct   120
```

<210> SEQ ID NO 475
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 475

```
ctagtgatag tgatgacgat ggagggaaag agaagatggt cctcgtgacc gccagatctg    60
tgtttgggaa gaaagaagg aaactaagac gtgcgagggg aagaaaaagg aaaacctaat   120
```

<210> SEQ ID NO 476
<211> LENGTH: 120
<212> TYPE: DNA

```
<213> ORGANISM: Artificial Sequence
<220> FEATURE:
<223> OTHER INFORMATION: Synthetic polynucleotide

<400> SEQUENCE: 476 ttttttcct tttaggtagt ctgtagagaa tgccaaatga gggaatcccc cactcaagtc      60
aaactcagga gcaagactgt ttacagagtc aacctgtcag taataatgaa gaaatggcaa    120

<210> SEQ ID NO 477
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 477
tcaagcaaga aagtggtggt gatggggagg tggaggagta cctctccttt cgttctgtgg    60
gtgacgggct gtccacctct gctgtggggt gcgcatcagc agctccgagg agagggccag    120

<210> SEQ ID NO 478
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 478
ccctgctgca catcgaccga catcagatcc aggcagtaga gcctagcgcc caggcccttg    60
agctgcaggg tttgggtgtg gacgtctatg accaggacgt gctggaacag ggagtgcttc    120

<210> SEQ ID NO 479
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 479
agcaggtgga caatgccatc catgaggcca gccgtgcctc ccagctcgtt gacgtggaga    60
aggagtatcg gtcggtcctg gatgacctca cgtgagtgca gcccatcttc ttcctttcaa    120

<210> SEQ ID NO 480
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 480
tatattatgc tataaaaatg ttatcagagt gcaaaataga caatttatct tatttttcag    60
gtcatgtacg acatccctaa ggcaaatcaa taaaattatt gaacagctta gccctcaagc    120

<210> SEQ ID NO 481
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 481
tgccaccagc agagacatca acaggaaact agattctgta aaacgacaga agtataataa    60
ggtgattcag aataacattc agtattgcat ttttgaaaaa gtcatcattt aggggcactt    120
```

<210> SEQ ID NO 482
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 482
ttcaaggaac aacagctaaa aaagatcact gcaaaacaaa agcatctcca ggccatcctt    60
ggaggagcag aggtgaaaat tgaactagat cacgccagtc tggaggagga tgcaggtgag   120

<210> SEQ ID NO 483
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 483
ggtggagggg gcagaggcgg acctgtctgg agatggtact gactatgagc tgaagcctct    60
gcccaagggc gggaaacggc agaagaaagt gccagtgcag gagattgatg atgactttt   120

<210> SEQ ID NO 484
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 484
cccaagttct ggggaagaag ctgaagctgc ttctgtagga gaaggaggag gaggaggtcg    60
gaaagtggga agataccgag atgatggaga tgaagattat tataagcagc ggttaaggtc   120

<210> SEQ ID NO 485
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 485
atttgtagct gcctaatatt tcttgaaaga gtgagcattt cttttgtacc ctcggaaagt    60
ttcatgctag tgcgaaacgc attgctattg ttctttcaga gccggggcca tccagtcttg   120

<210> SEQ ID NO 486
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 486
gcagcatgct catgcctgtc caggagactg cctgggaaga gctcatccgc actggccaga    60
tgacaccttt tggtacccag atccctcaga acaggagaa aaagcccaga aaatcatgc    120

<210> SEQ ID NO 487
<211> LENGTH: 120
<212> TYPE: DNA
<213> ORGANISM: Artificial Sequence
<220> FEATURE:
<223> OTHER INFORMATION: Synthetic polynucleotide

```
<400> SEQUENCE: 487
ttaatgaagc atcaggcttc gaaaagtatt tggcagatca agcaaaactg tcttttgaaa      60
ggaagaagca aggttgtaat aaaagagcag ctagaaaagc tccagcccca gtcacgcctc     120

<210> SEQ ID NO 488
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 488
cagccccagt gcaaaataaa acaaaccaa acaagaaagc cagagttctg tccaaaaaag       60
aggagcgttt gaaaagcac atcaagaaac tccagaagag ggctttgcag ttccagggga     120

<210> SEQ ID NO 489
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 489
aagtgggatt gccaaaggca aggagacctt gggagtcaga catgaggcca gaggcagagg       60
gagactctga gggtgaagag tctgagtatt tccccacaga ggaggaggaa gaggaggaa      119

<210> SEQ ID NO 490
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 490
tggaacacta ggcaaaacca ctaccactag gactaataat accttttttc cgttttagtc       60
ccaagatgcc tcgaacacta agtttacatg aaataactga ccttttagag acagatgaca     120

<210> SEQ ID NO 491
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 491
ttacagaggc acaccctgga caataccatt ttgtattcaa taacttttc accagtattg       60 cacttcttga taagctcagt tcaatgggac atcaggcaac aggtacagtg agaaaggatc     120

<210> SEQ ID NO 492
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 492
acattgacag agttccactg gaatcagatg tagctttaaa gaaaaagaa agaggcacat        60 ttgattatcg aattgatggc aaaggcaata ttgtctgcag atggaatgat aacagtgttg      120

<210> SEQ ID NO 493
<211> LENGTH: 120
```

```
<212> TYPE: DNA
<213> ORGANISM: Artificial Sequence
<220> FEATURE:
<223> OTHER INFORMATION: Synthetic polynucleotide

<400> SEQUENCE: 493
tcactgttgc ctcatctggt gctggtatcc atccctgtg tcttgtcagt cgttactccc    60
agaaactgaa aaagaagata caagttcagc agccaaacat gatcaaagtg tataaccagt  120

<210> SEQ ID NO 494
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 494
tcatgggagg cgtagacaga gctgatgaaa acattgataa gtatcgggca tcaatccgtg    60
gaaagaaatg gtattcaagc cctcttttgt tctgtttcga actggtctta caaaatgctt  120

<210> SEQ ID NO 495
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 495
ggcaattgca taaaacatat gatgagaaac cagtggattt tctggagttt cgtcgacgtg    60
tggtatgcca ttatctggag acccatggtc atcctccaga acctggccaa aaaggaagac  120

<210> SEQ ID NO 496
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 496
ctcagaagcg taacattgac tcacgttatg atggcataaa tcatgtgata gtcaaacagg    60
gaaagcaaac gcgatgcgct gaatgtcata agaacacaac ttttcgatgt gaaaaatgtg  120

<210> SEQ ID NO 497
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 497
atgttgcctt acatgtgaag tgttccgttg aatatcacac tgaatagcag gtgtcaccac    60
ctcctgagat aagaaacata gttttataca ttatgtacag tgtagcagtg gttttgccta  120

<210> SEQ ID NO 498
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 498
gtgttccaat tttggaacgt cacataacaa tggaacataa taaatttttt tttctcttca    60
```
aatttttgtt ccttgaattt ttctaggtaa catatatgaa tttcatgcaa aaattcaaaa    120

<210> SEQ ID NO 499
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 499
gcatagaagc aagtgctata gtgatacaac cacctgaaaa tgctacagca cctgtttctg    60
atgaggaatc aggagatgaa gaaggtggaa caataaataa tctgccaggt tctttgttgc    120

<210> SEQ ID NO 500
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 500
acacagctgc gtatcttatt caagatggct ctgatgctga gtctgactca gatgatccct    60
catacgcacc taaagatgac tctcctgatg aagttccatc tacgtttact gtgcagcaac    120

<210> SEQ ID NO 501
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 501
ctccaccatc aaggaggagg aaaatgacaa aaattctttg caaatggaaa aaagccgacc    60
taactgtaca acccgtagca ggtagagtta cagcaccacc aaacgatttc ttcaccgtaa    120

<210> SEQ ID NO 502
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 502
tgagaactcc cacagaaatt cttgaacttt ttcttgatga cgaggtcatt gaactcattg    60
tcaagtactc caacttatat gcttgcagta aaggtgtaca tcttggcttg actagctctg    120

<210> SEQ ID NO 503
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 503
aattcaaatg ttttctggga attattttc tgagtggtta tgtctcagtt cctagaaggc    60
gtatgttttg ggaacaaaga acagatgtgc ataatgtact ggttagtgct gccatgagac    120

<210> SEQ ID NO 504
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 504
gtgaccggtt tgaaactata ttttctaatt tgcatgttgc tgacaatgca aatttggatc    60
cagtggacaa attttccaaa ttgcgacctc tcataagcaa acttaatgag agatgcatga   120

<210> SEQ ID NO 505
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 505
aatttgttcc aaatgaaaca tatttcagct ttgatgaatt catggttcct tatttggtc    60 gtcacgggtg caaacaattt attcggggaa agcccattcg gtttggctat aagttttggt   120

<210> SEQ ID NO 506
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 506
gtggtgccac ctgtctgggc tacatttgct ggtttcagcc gtatcagggt aaaaacccaa    60
atactaaaca tgaggaatat ggtgtcggtg cgtcacttgt ccttcagttt agtgaggcac   120

<210> SEQ ID NO 507
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 507
tttaaatctg tcttgtgatc aaaataatgg aaatgtgatt tttattttca tggtaggaga    60
tggaataaac tgagactgca ggacaaagag aaacgtctga agctggagga cgattctgag   120

<210> SEQ ID NO 508
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 508
gaaagtgatg ctgaatttga cgaaggtttt aaagtgccag gttttctgtt caaaaagctt    60
tttaagtatg taccatatgt tctttccttt ctatttgcta tcaagccatt atgtacaaat   120

<210> SEQ ID NO 509
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 509
ttgccatttt ctctttctt gttggtgttt gttgtcatag gtaccagcag acaggtgtta    60
ggtggctgtg ggaattgcac tgccagcagg caggaggaat tctgggagat gaaatgggat   120

<210> SEQ ID NO 510

<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 510
tgggcaagac catccagata attgccttct tggcaggtct gagctacagc aagatcagga    60
ctcgtggttc aaattacagg caagtgctcc tctgcagact gtcagtctgt ggagctcaat   120

<210> SEQ ID NO 511
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 511
tgactgtata tgctctttca tggttgtttt cttcttggac gtttggatgc aggtttgagg    60
ggttgggtcc aactgtaatt gtctgtccaa caacagtgat gcatcagtgg gtgaaggaat   120

<210> SEQ ID NO 512
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 512
ttcacacgtg gtggcctccg ttcagagtgg caattctaca tgaaaccggt tcctataccc    60
acaaaaaggt aacacaatat ttcagtacct ttttgttttg ttttaatgcc ctccatttta   120

<210> SEQ ID NO 513
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 513
taaaactgac tttaccattt tattgtggtc tcaggagaaa ctaattcgag atgttgctca    60
ttgtcatgga attttgatca catcttactc ctacattcga ttgatgcagg atgacattag   120

<210> SEQ ID NO 514
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 514
caggtatgac tggcactatg tgatcttgga cgaaggacac aaaattcgaa atccaaatgc    60
tgctgtcacc cttgcttgca aacaggtatg acctcttta acagggaga tttccaagtg   120

<210> SEQ ID NO 515
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 515
ttaataaaaa ggtgcttcct ttcctcaaat agtttcgcac ccctcatcgg atcattctgt    60
ctggctcacc gatgcaaaat aacctccgag agctgtggtc gctctttgac ttcatcttcc    120

<210> SEQ ID NO 516
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 516
cgggaaagtt aggcacgttg cctgtgttta tggagcagtt ctccgtcccc atcaccatgg    60
ggggatattc aaatgcttcc ccagtacagg taaaatatta ggatgataat acttttggca   120

<210> SEQ ID NO 517
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 517
aggtcaaaac tgcttacaag tgtgcatgtg tcttacgaga taccataaat ccatacctac    60
tgcggagaat gaagtcagat gtcaagatga gcctttcttt gccagataaa aatgaacagg   120

<210> SEQ ID NO 518
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 518
tcccgtccgt aggtcttatt ttgccgtctt acagatgagc agcataaagt ctaccaaaat    60
ttcgttgatt ccaaagaagt ttacaggatt ctcaatggag agatgcaggt cagctaaaaa   120

<210> SEQ ID NO 519
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 519
ttcttaccac agattttctc cggacttata gccctaagaa aaatttgcaa ccaccctgat    60
ctcttttctg gaggtcccaa gaatctcaaa ggtcttcctg atgatgaact agaagaagat   120

<210> SEQ ID NO 520
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 520
cagtttgggt actggaaacg ttctgggaaa atgattgttg ttgagtcttt gttgaaaata    60
tggcacaagc agggtcagcg agtattgctg ttttctcagt caaggcaggt gagtgcacag   120

<210> SEQ ID NO 521
<211> LENGTH: 120
<212> TYPE: DNA
<213> ORGANISM: Artificial Sequence
<220> FEATURE:

-continued

<223> OTHER INFORMATION: Synthetic polynucleotide

<400> SEQUENCE: 521
acagatgctg gacatacttg aagtattcct tagagcccaa aagtatacct atctcaagat     60
ggatggtacc actacaatag cttcaagaca gccactgatt acgagataca atgaggtaac    120

<210> SEQ ID NO 522
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 522
ggctgagaac tgtaactggt cttaagtgtg tgtgctcagt gttgtgtgtc ttacctctag     60
gacacatcca tatttgtgtt tcttctgacc acgcgggtgg gcggcttagg tgtcaacctg    120

<210> SEQ ID NO 523
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 523
acgggggcaa acagagttgt catctatgac ccagactgga acccaagcac ggacacgcag     60
gtttgttttt attttttttt taaaagaatg tattagtaga aatatagttt catggttagc    120

<210> SEQ ID NO 524
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 524
tctctgttgc aggcccggga gcgagcatgg agaataggcc agaagaagca agtgactgtg     60
tacaggctcc tgactgcggg caccattgaa gaaaagatct accaccggtc agtgcacaca    120

<210> SEQ ID NO 525
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 525
gtagagctac acattgtttt ataccagctt atctttatt tttttagaca aatcttcaag     60 cagttttga caaatagagt gctaaaagac ccaaaacaaa ggcggttttt caaatccaat    120

<210> SEQ ID NO 526
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 526
gatctctatg agctatttac tctgactagt cctgatgcat cccagagcac tgaaacaagt     60 gcaattttg caggtattac ataaaatcat ttaatttaaa gtaatcaatt gcacaagatg    120

```
<210> SEQ ID NO 527
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 527
ttacaggaac tggatcagat gttcagacac ccaaatgcca tctaaaaaga aggattcaac      60
cagcctttgg agcagaccat gatgttccaa aacgcaagaa gttccctgct tctaacatat    120

<210> SEQ ID NO 528
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 528
ctgtaaatga tgccacatca tctgaagaga aatctgaggc taaaggagct gaagtaaatg      60
cagtaacttc taatcgaagt gatcctttga aagatgaccc tcacatgagt agtaatgtaa    120

<210> SEQ ID NO 529
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 529
ctagcaatga taggcttgga gaagagacaa atgcagtatc tggaccagaa gagttgtcag      60
tgattagtgg aaatggggaa tgttcaaatt cttcaggaac aggcaaaact tctatgccat    120

<210> SEQ ID NO 530
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 530
ctggtgatga aagcattgat gaaaagttag gtctttctta caaaagagaa agacccagcc      60
aggctcaaac agaagctttt tgggagaata acaaatggaa aataattttt tataagcaca    120

<210> SEQ ID NO 531
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 531
agtcaaaaac aaaacatcat agtgtggcag aagaagagac cctggagaaa catctgagac      60
caaagcaaaa gcctaagaac tctaagcatt gcagagacgc caagtttgaa ggaactcgaa    120

<210> SEQ ID NO 532
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 532
```
ttccacacct ggtgaagaaa aggcgttacc agaagcaaga cagtgaaaac aagagtgagg 60
ccaaggaaca gagcaatgac gattatgttt tggaaaagct tttcaaaaaa tcaggtaatc 120

<210> SEQ ID NO 533
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 533
tatttctttt cttgctagtt ggcgtgcaca gtgtcatgaa gcacgatgcc atcatggatg 60
gagccagccc agattatgta ctggtggagg cagaagccaa ccgagtggcc caggatgccc 120

<210> SEQ ID NO 534
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 534
tgaaagcact gaggctctct cgtcagcggt gtctgggagc agtgtctggt gttcccacct 60
ggactggcca caggggatt tctggtgcac cagcaggaaa aaagtaagag attgctgcat 120

<210> SEQ ID NO 535
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 535
tgatgctttt cctttttag gagtagattt ggtaagaaaa ggaattctaa cttctctgtg 60
cagcatcctt catcaacatc tccaacagag aagtgccagg taatatagat aaccttttg 120

<210> SEQ ID NO 536
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 536
tatatcagta tagtggtctt cttttatag gatggcatca tgaaaaagga gggaaaagat 60
aatgtccctg agcattttag tggaagagca gaagatgcag actcttcatc cgggcccctc 120

<210> SEQ ID NO 537
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 537
gcttcctcct cactcttggc taaaatgaga gctagaaacc acctgattct gccagagcgt 60
ttagaaagtg aaagcgggca cctgcaggaa gcttctgccc tgctgcccac cacagaacac 120

<210> SEQ ID NO 538
<211> LENGTH: 120
<212> TYPE: DNA
<213> ORGANISM: Artificial Sequence

```
<220> FEATURE:
<223> OTHER INFORMATION: Synthetic polynucleotide

<400> SEQUENCE: 538
gatgaccttc tggtggagat gagaaacttc atcgctttcc aggcccacac tgatggccag      60
gccagcacca gggagatact gcaggagttt gaatccaagt tatctgcatc acagtcttgt     120

<210> SEQ ID NO 539
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 539
gtcttccgag aactattgag aaatctgtgc actttccata gaacttctgg tggtgaagga      60
atttggaaac tcaagccaga atactgctaa acaacattgc ttcctaaact ttcaagtccc     120

<210> SEQ ID NO 540
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 540
ggtaactgga acccaatccg agggtcatgg aggcatcccg aaggtttccg gaagccgagg      60
ccttgagccc agagcaggct gctcattacc taaggtatgt ctggaccgct gggcgggtct     120

<210> SEQ ID NO 541
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 541 tcttttttt tctatagata tgtgaaagag gccaaagaag caactaagaa tggagacctg      60
gaagaagcat ttaaactttt caatttggca aaggacattt ttcccaatga aaaagtgctg     120

<210> SEQ ID NO 542
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 542
gaagaaatat acaggaaatt tgtgtcttta gatcatatca aggagttgct aatggagacg      60
cgctcacctt tggctgagct aggtgtctta aagaagctgt gtgatcatcc taggctgctg     120

<210> SEQ ID NO 543
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 543
tctgcacggg cttgttgttt gctaaatctt gggacattct ctgctcaaga tggaaatgag      60
ggggaagatt ccccagatgt ggaccatatt gatcaagtaa ctgatgacac attgatggaa     120
```

<210> SEQ ID NO 544
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 544
gaatctggaa aaatgatatt cctaatggac ctacttaaga ggctgcgaga tgagggacat    60
caaactctgg tgttttctca atcgaggcaa attctaaaca tcattgaacg cctcttaaag   120

<210> SEQ ID NO 545
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 545
aataggcact ttaagacatt gcgaatcgat gggacagtta ctcatctttt ggaacgagaa    60
aaaagaatta acttattcca gcaaaataaa gattactctg tttttctgct taccactcaa   120

<210> SEQ ID NO 546
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 546
gtaggtggtg tcggtttaac attaactgca gcaactagag tggtcatttt tgaccctagc    60
tggaatcctg caactgatgc tcaagctgtg gatagagttt accgaattgg acaaaaagag   120

<210> SEQ ID NO 547
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 547
aatgttgtgg tttataggct aatcacttgt gggactgtag aggaaaaaat atacagaaga    60
caggttttca aggactcatt aataagacaa actactggtg aaaaaaagaa ccctttccga   120

<210> SEQ ID NO 548
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 548
tattttagta aacaagaatt aagagagctc tttacaatcg aggatcttca gaactctgta    60
acccagctgc agcttcagtc tttgcatgct gctcagagga aatctgatat aaaactagat   120

<210> SEQ ID NO 549
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 549

```
gaacatattg cctacctgca gtctttgggg atagctggaa tctcagacca tgatttgatg    60
tacacatgtg atctgtctgt taaagaagag cttgatgtgg tagaagaatc tcactatatt   120
```

<210> SEQ ID NO 550
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 550

```
caacaaaggg ttcagaaagc tcaattcctc gttgaattcg agtctcaaaa taaagagttc    60
ctgatggaac aacaaagaac tagaaatgag ggggcctggc taagagaacc tgtatttcct   120
```

<210> SEQ ID NO 551
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 551

```
tcttcaacaa agaagaaatg ccctaaattg aataaaccac agcctcagcc ttcacctctt    60
ctaagtactc atcatactca ggaagaagat atcagttcca aaatggcaag tgtagtcatt   120
```

<210> SEQ ID NO 552
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 552

```
agcagaatcc aaaaaataca ggaagccttg gaggagttgg cagaacaggg agatgatgaa    60
tttacagatg tgtgcaactc tggcttgcta ctttatcgag aactgcacaa ccaactcttt   120
```

<210> SEQ ID NO 553
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 553

```
gatgatctgc ccaaagaggg tgagaaacaa gatctctcca gtataaaggt gaatgttacc    60
accttgcaag atggtaaagg tacaggtagt gctgactcta tagctacttt accaaagggg   120
```

<210> SEQ ID NO 554
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 554

```
tttggaagtg tagaagaact tgtactaac tcttcattgg gaatggaaaa aagctttgca    60
actaaaaatg aagctgtaca aaaagagaca ttacaagagg ggcctaagca agaggcactg   120
```

<210> SEQ ID NO 555
<211> LENGTH: 120
<212> TYPE: DNA

```
<213> ORGANISM: Artificial Sequence
<220> FEATURE:
<223> OTHER INFORMATION: Synthetic polynucleotide

<400> SEQUENCE: 555
caagaggatc ctctggaaag ttttaattat gtacttagca aatcaaccaa agctgatatt    60
gggccaaatt tagatcaact aaaggatgat gagattttac gtcattgcaa tccttggccc   120

<210> SEQ ID NO 556
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 556
attatttcca taacaaatga agtcaaaat gcagaatcaa atgtatccat tattgaaata     60
gctgatgacc tttcagcatc ccatagtgca ctgcaggatg ctcaagcaag tgaggccaag   120

<210> SEQ ID NO 557
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 557
ttggaagagg aaccttcagc atcttcacca cagtatgcat gtgatttcaa tcttttcttg    60
gaagactcag cagacaacag acaaaatttt tccagtcagt ctttagagca tgttgagaaa   120

<210> SEQ ID NO 558
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 558
gaaaatagct tgtgtggctc tgcacctaat tccagagcag ggtttgtgca tagcaaaaca    60
tgtctcagtt gggagttttc tgagaaagac gatgaaccag aagaagtagt agttaaagca   120

<210> SEQ ID NO 559
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 559
aaaatcagaa gtaaagctag aaggattgtt tcagatggcg aagatgaaga tgattctttt    60
aaagatacct caagcataaa tccattcaac acatctctct ttcaattctc atctgtgaaa   120

<210> SEQ ID NO 560
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 560
caatttgatg cttcaactcc caaaaatgac atcagtccac caggaaggtt cttttcatct    60
caaataccca gtagtgtaaa taagtctatg aactctagaa gatctctggc ttctaggagg   120
```

<210> SEQ ID NO 561
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 561
tctcttatta atatggtttt agaccacgtg gaggacatgg aggaaagact tgacgacagc    60
agtgaagcaa agggtcctga agattatcca aagaagggg tggaggaaag cagtggcgaa   120

<210> SEQ ID NO 562
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 562
gcctccaagt atacagaaga ggatccttcc ggagaaacac tgtcttcaga aaacaagtcc    60
agctggttaa tgacgtctaa gcctagtgct ctagctcaag agacctctct tggtgcccct   120

<210> SEQ ID NO 563
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 563
gagcaccaga aggaaggcat agctttcctc tatagcctgt atagggatgg aagaaaaggt    60
ggtatattgg ctgatgatat gggattaggg aagactgttc aaatcattgc tttcctttcc   120

<210> SEQ ID NO 564
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 564
gagcctttgt ctggtgaaca gttggttggt tctccccagg ataaggcggc agaggctaca    60
aatgactatg agactcttgt aaagcgtgga aaagaactaa aagagtgtgg aaaaatccag   120

<210> SEQ ID NO 565
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 565
gaggccctaa actgcttagt taaagcgctt gacataaaaa gtgcagatcc tgaagttatg    60
ctcttgactt taagtttgta taagcaactt aataacaatt gagaatgtaa cctgtttatt   120

<210> SEQ ID NO 566
<211> LENGTH: 120
<212> TYPE: DNA
<213> ORGANISM: Artificial Sequence
<220> FEATURE:
<223> OTHER INFORMATION: Synthetic polynucleotide

```
<400> SEQUENCE: 566
ggtatgtttg atgcatcact tgtgaatcat gtgctgctga tcatgccaac caatcttatt     60
aacacatggg taaagaatt catcaagtgg actccaggaa tgagagtcaa aacctttcat     120

<210> SEQ ID NO 567
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 567
ggtcctagca aggatgaacg gaccagaaac ctcaatcgga ttcagcaaag gaatggtgtt     60
attatcacta cataccaaat gttaatcaat aactggcagc aactttcaag ctttaggggc    120

<210> SEQ ID NO 568
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 568
caagagtttg tgtgggacta tgtcatcctc gatgaagcac ataaaataaa aacctcatct     60
actaagtcag caatatgtgc tcgtgctatt cctgcaagta atcgcctcct cctcacagga    120

<210> SEQ ID NO 569
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 569
accccaatcc agaataattt acaagaacta tggtccctat ttgattttgc ttgtcaaggg     60
tccctgctgg gaacattaaa aactttaag atggagtatg aaaatcctat tactagagca    120

<210> SEQ ID NO 570
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 570
agagagaagg atgctacccc aggagaaaaa gccttgggat ttaaaatatc tgaaaactta     60
atggcaatca taaaccccta ttttctcagg aggactaaag aagacgtaca gaagaaaaag    120

<210> SEQ ID NO 571
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 571
tcaagcaacc cagaggccag acttaatgaa aagaatccag atgttgatgc catttgtgaa     60
atgccttccc tttccaggaa aaatgattta attatttgga tacgacttgt gcctttacaa    120

<210> SEQ ID NO 572
<211> LENGTH: 120
```

<212> TYPE: DNA
<213> ORGANISM: Artificial Sequence
<220> FEATURE:
<223> OTHER INFORMATION: Synthetic polynucleotide

<400> SEQUENCE: 572
cgccgccttc cgggtgttac atgcagccgg gctcggcccc tccccctggc cggatggatc    60
cgtcggcgcc acagccccgc gcggaaacct caggcaaagg taccagctcc gcgctcgccc   120

<210> SEQ ID NO 573
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 573
ggaaacttta ttttctttat tcttgcagac atatggcatc caggagaaag atgtcttgcc    60
ccttctccag ataatggaaa actttgtgaa gcaagcataa aatctatcac agtggatgaa   120

<210> SEQ ID NO 574
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 574
aatggcaagt catttgcagt cgtcttatat gcagattttc aagaaaggaa aatacctctt    60
aaacagcttc aagaagtgaa atttgttaaa gattgcccta ggaatcttat atttgatgat   120

<210> SEQ ID NO 575
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 575
gaagatttag aaaaacctta tttcccaaac cgaaaatttc catcatcttc tgttgctttt    60
aaattatctg acaatggaga ctctattcct tataccatca ataggtattt gagagactac   120

<210> SEQ ID NO 576
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 576
caaagagaag gaacccggtt tctttatgga cactacatcc atggaggagg gtgcattctg    60
ggtgatgaca tgggacttgg aaaaacagta caggtattta attatgttat aacagtaaag   120

<210> SEQ ID NO 577
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 577 aaatttgta cgtcatgata cattatacac agtgattgaa aaagtctttt ttccccaggt    60

```
tatttcattt ctggctgcag ttttgcataa aaagggaact cgtgaggata ttgaaaataa    120

<210> SEQ ID NO 578
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 578
catgccagag ttttactaa gaagtatgaa aaggaaccc ctttcttcta cagcaaaaaa      60
ggtaaaatct ctagacaatg tatattctac tcatgatgct ggtattacaa aagcatatag   120

<210> SEQ ID NO 579
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 579
aaattttttt attcttgttt tagatgttct taatagttgc tcctctttct gtcctctaca    60
actggaagga tgaattggac acctggggat atttcagagt cactgtttta catggaaaca   120

<210> SEQ ID NO 580
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 580
gaaaagataa tgaattaatt cgtgtaaagc agaggaaatg tgaaattgct ctaacaactt    60
atgaaacact acgcttatgc ctggatgaac ttaacaggta atgggaataa taggaatagg   120

<210> SEQ ID NO 581
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 581
gttttctcaa cctcacccct ctttttttctt actttatagt ttggaatggt cagctgtcat   60
tgtggatgaa gctcatagaa tcaagaatcc aaaagctaga gtaacagaag ttatgaaagc   120

<210> SEQ ID NO 582
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 582
tttgaaatgt aatgtccgca ttggcctcac tggaaccatc cttcagaaca acatgaagga    60
actgtggtgt gttatggact ggtgagagaa aacacttttt aaaaaattgt ttaatagttc   120

<210> SEQ ID NO 583
<211> LENGTH: 120
<212> TYPE: DNA
<213> ORGANISM: Artificial Sequence
<220> FEATURE:
<223> OTHER INFORMATION: Synthetic polynucleotide
```

<400> SEQUENCE: 583
tattgtcttt ataaagggct gtgccaggcc ttttagggag tgggacctac ttcaagaagc    60
agttttctga cccagtagaa catggtcaga gacacacggc aacaaagaga gaactagcca   120

<210> SEQ ID NO 584
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 584
ctggccgaaa ggccatgcaa agacttgcca aaaagatgtc tggctggttt ctcaggcgca    60
ccaagactct tatcaaggat cagttgccta agaaggaaga ccgggtaaga accgcatttg   120

<210> SEQ ID NO 585
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 585
tattgttata aacaaaatac taataactac cttgtatttt atcttggcag atggtgtatt    60
gttctttgac agatttccag aaagctgtct atcaaacagt gttagaaaca gaggacgtga   120

<210> SEQ ID NO 586
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 586
ctttgatact tcaatcttct gagccttgta cctgtaggag tggccaaaaa aggagaaatt    60
gttgttataa ggcaagcatt tcaatatatc tttataatca tgcttttgat tacatagtac   120

<210> SEQ ID NO 587
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 587
cagaccaatt ctcatggtga aacagtgaaa accttgtatc tcagttacct tacagtcctt    60
cagaaggtag ctaaccatgt cgcgctactg caagctgcta gtacttccaa acaacaggtt   120

<210> SEQ ID NO 588
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 588
attatttcaa tttatacagg tttgaatgtg ttaagtggaa atatcttttc ttctgccttt    60
tcccttcaag gaaacactta tcaaaaggat atgtgatcag gtattttcca gattcccaga   120

<210> SEQ ID NO 589

```
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 589
ttttgtgcag aaaagcaaag atgcagcctt tgaaacactt tctgacccta aatacagtgg      60
aaaaatgaag gtaagtgctc ctctttcagg ttgcatacag acatgataca caaatatt      119

<210> SEQ ID NO 590
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 590
tgattttctg tggttcattt tcaggtcctt cagcagcttt taaatcattg caggaaaaac      60
agagataaag ttcttctctt ttcttttttcc accaaggtga gttcatctaa agtatatcct    120

<210> SEQ ID NO 591
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 591
tacttaacca agattcatgt ttgcccatct tcatacctct cgtctagttg cttgacgtgc      60
tacagcagta ctgtatggcg tctgggcttg attaccgacg acttgatgga agtacaaaat    120

<210> SEQ ID NO 592
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 592
cagaggaaag actcaagatt gtaaaagagt tcaacagtac acaagatgtt aacatttgcc      60
ttgtctctac aatgtaagaa aattaaattt ataactaga tttttatcca attgttttg      120

<210> SEQ ID NO 593
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 593
tctttcctcc agggctggtg gactaggcct caattttgtc ggtgccaatg ttgttgtatt      60
atttgatcct acttggaatc cagccaatga tcttcaagcc attgacaggt ataatactga    120

<210> SEQ ID NO 594
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 594 cctttttacag agcatatagg attggacaat gtagagatgt caaagtgctt aggctgatat     60
```

```
ccttgggaac tgtggaggaa atcatgtatt tacgacagat atacaagcag gtaaatatgt    120
```

<210> SEQ ID NO 595
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 595

```
gcaaacactt caaaaatgtc ttgtgttttt tctgttttag caacttcact gtgtggtggt    60
tggaagtgaa aatgccaaac gatatttga agcagttcaa ggatctaaag agcatcaagg    120
```

<210> SEQ ID NO 596
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 596

```
agagcttttt gggatccata acctcttcaa atttaggtcc caagggtctt gtcttacgaa    60
ggacatcctg gaggtgtgaa cttcttctct gaccttttca ataatatttt aaatacagtt    120
```

<210> SEQ ID NO 597
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 597

```
tttttcttcat cttttttttc tctcttagca ccttctagcc accatggcaa cctcatctga    60
agaagttttg ctgattgtaa agaaagtgcg tcaaaagaag caggatggag ctctgtacct    120
```

<210> SEQ ID NO 598
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 598

```
catggcagaa agaattgctt gggcacctga aggcaaagat agatttacaa tcagccatat    60
gtatgcagat attaaatgta agtcagctat actaagttct gatgtatttg tatgtcatag    120
```

<210> SEQ ID NO 599
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 599

```
aactgccctc atgcttcttt ttaggccaga aaattagtcc agaaggaaaa gctaaaattc    60
agcttcagct ggtcctacat gcaggggaca caactaactt ccattttcc aatgaaagca    120
```

<210> SEQ ID NO 600
<211> LENGTH: 120
<212> TYPE: DNA
<213> ORGANISM: Artificial Sequence
<220> FEATURE:

<223> OTHER INFORMATION: Synthetic polynucleotide

<400> SEQUENCE: 600
cagcagtgaa agagcgagat gcagtaaaag accttcttca gcagctgctg cccaaattca    60
agaggaaagc aaataaagaa ctggaagaga agaacaggtg ggaggaaaag aatagccttt   120

<210> SEQ ID NO 601
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 601
agaagttcag ttatattcag tatattctgc tttacagaat gctgcaagaa gatcctgttt    60
tgtttcagct ttataaagac cttgttgtga gtcaagtgat cagtgctgag gaattctggg   120

<210> SEQ ID NO 602
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 602
ccaatcgttt aaatgtgaat gcaacagata gttcttccac atccaatcat aagcaggatg    60
ttggcatttc tgctgcattt ctggtatgtg agccttctag atttctgaag aaaataaaaa   120

<210> SEQ ID NO 603
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 603
ggctttgttt taggctgatg tccggcccca aactgatggc tgtaacggtc taagatataa    60
tttaacttct gatatcattg agtccatatt taggacctat ccagcaggta agaagaatca   120

<210> SEQ ID NO 604
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 604
aaaatggaaa ttcagtatat aatatttgtg ggttttttc cacagtaaaa atgaaatatg    60
cagaaaatgt tccccacaac atgacagaga aggaattctg gacacgtttt ttccagtccc   120

<210> SEQ ID NO 605
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 605
attattttca cagggatcgg ctgaatacag ggtcaaagga tctctttgca gaatgtgcca    60
aaatagatga aaaggtaac tgtttatctc tgatagacac tggtatttaa cttgccaccc   120

```
<210> SEQ ID NO 606
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 606
ttattttgtt gattttctag gcctaaaaac aatggtttca ttaggagtga aaaacccact      60
actagattta acagctttgg aagataaacc attagatgag gtaagaagca ataaaagaag    120

<210> SEQ ID NO 607
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 607
tataataaga aaagcagaac cttttaaaaa aattttaat ctattatttc tcacagggct       60
atggcatttc ctctgtgcca tctgcttcca attctaaatc cataaaagag aatagtaatg    120

<210> SEQ ID NO 608
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 608
ctgccatcat caagagattt aaccatcaca gtgccatggt cctggcagct ggactcagaa      60
aacagttaag tataaatgca gaggtgcagt aactgggctt ttcaggatat ccagatggag    120

<210> SEQ ID NO 609
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 609 tccccttat tttaagagaa gcacaaaatg aacaaactag tgagcccagc aacatggatg       60
gaaattccgg agatgcagac tgctttcagc cagcagtcaa aagggtatgg gcaaaaaaat    120

<210> SEQ ID NO 610
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 610
gtgttaataa ttataggcga aattacaaga gtccattgaa tatgaagact tggggaaaaa      60
taattctgta aaaacgattg cactaaacct caagaagtca gataggtaag tttggtcaat    120

<210> SEQ ID NO 611
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 611
```

```
ggtattatca tggtccaact ccaatccagt cactacagta tgcaacaagt caggacatta    60
ttaattcttt tcaaagtatt agacaagaaa tggaagctta tacacccaag ttaactcagg   120
```

<210> SEQ ID NO 612
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 612

```
ttcattttt tcaggttctc tcaagtagtg ctgccagtag taccatcaca gcactgtcac    60
ctggaggggc acttatgcag ggaggaacac agcaagccat aaaccgtatg tgccgggcca   120
```

<210> SEQ ID NO 613
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 613

```
agagatggtg ccaaatgata ttcaatctga attgaaacac ttatatgtag ctgttggaga    60
acttctacga catttctggt cctgctttcc tgttaatacg ccattcctag aagaaaggt    120
```

<210> SEQ ID NO 614
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 614

```
ctcatctttt ttaggtagtg aaaatgaaaa gtaatttgga acgattccaa gttacgaagc    60
tctgtccatt ccaagaaaag attcggagac agtatttaag cacaaatgta aggcagcaat   120
```

<210> SEQ ID NO 615
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 615

```
ttgctgtgtt tttcagttgg taagtcacat agaagagatg ctccagacag cctacaacaa    60
gctccacaca tggcagtcac ggcgtctgat gaagaaaacg tgaggtggcc atgatgctta   120
```

<210> SEQ ID NO 616
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 616

```
ttttacagat tattgaataa taaaatacag ttttgaaaaa aatggatgaa gaacctgaaa    60
gaactaagcg atgggaagga ggctatgaaa gaacatggta aggagagctt tattgccctg   120
```

<210> SEQ ID NO 617
<211> LENGTH: 120
<212> TYPE: DNA
<213> ORGANISM: Artificial Sequence

```
<220> FEATURE:
<223> OTHER INFORMATION: Synthetic polynucleotide

<400> SEQUENCE: 617
aacaaataat tatgacttat agggagattc ttaaagaaga tgaatctgga tcacttaaag      60
ctacaataga agacattcta ttcaaggcaa agagaaaaag gtatgtaacc ttcctatgta     120

<210> SEQ ID NO 618
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 618
agtatatgga attacattaa aatgtttgta taattttaac agagtatttg agcaccatgg      60
acaagttcga cttggaatgg tatgtcatta tttttttcttt tactagtaca gaactagttt    120

<210> SEQ ID NO 619
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 619 ttctttttttc cgatagatgc gccacctttta tgtggtagta gatggatcaa gaacaatgga   60
agaccaagat ttaaagccta atagactgac gtgtacttta aaggtaaaat ttaagtttat    120

<210> SEQ ID NO 620
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 620
cctttatcta gtatgtcttt ttttgtttaa acagttgttg gaatactttg tagaggaata     60
ttttgatcaa aatcctatta gtcaggtacg tatctaagtg atagaattca gaattagatt    120

<210> SEQ ID NO 621
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 621
atattaataa taattttttgt ttttatttca agattggaat aattgtaact aagagtaaaa    60
gagctgaaaa attgactgaa ctttcaggta tgcataaaat tacctttaca tgactcaagg   120

<210> SEQ ID NO 622
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 622
attttaggaa acccaagaaa acatataacg tctttgaaga aagctgtgga tatgacctgc     60
catggagagc catctcttta taattcccta agcatagcta tgcagactct aaagttagta   120
```

<210> SEQ ID NO 623
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 623

```
atctttcttt taagacacat gcctggacat acaagtcgag aagtactaat catctttagc    60
agccttacaa cttgcgatcc atctaatatt tatgatctaa tcaaggtaga ccaaaaaatc   120
```

<210> SEQ ID NO 624
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 624

```
cttggatttt atgaagaccc taaaggcagc taaaattaga gtatctgtta ttggattgtc    60
tgcagaagtt cgcgtttgca ctgtacttgc tcgtgaaact ggtggtatat ataaattta   120
```

<210> SEQ ID NO 625
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 625

```
tgttaggcac gtaccatgtt attttagatg aaagccatta caaagagttg ctcacacatc    60
atgttagtcc tcctcctgct agctcaagtt ctgaatgctc acttattcgt atgggtaagt   120
```

<210> SEQ ID NO 626
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 626

```
agaaagtaat acatttcctt ctatgaagga tttcctcagc acaccattgc ttctttatct    60
gaccaggatg caaaccctc tttcagcatg gcgtaagtaa agaccttgaa aatatcagtg   120
```

<210> SEQ ID NO 627
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 627

```
ccctacaggc atttggatgg caatactgag ccagggctta cattaggagg ctatttctgc    60
ccacagtgtc gggcaaagta ctgtgagcta cctgttgagt gtaaaatctg tggtaagaaa   120
```

<210> SEQ ID NO 628
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 628

```
tgtgttaggt cttactttgg tgtctgctcc ccacttggca cggtcttacc atcatttgtt    60
tcctttggat gcttttcaag aaattcccct agaagaatat aatggagaaa ggtatttcag   120
```

<210> SEQ ID NO 629
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 629

```
gtaaattcta agaaaaaaca ttgttaaact ttttttcag attttgttat ggatgtcagg    60
gggaattgaa agaccaacat gtaagttctt tggctttcta aatattaagt aatgtacaag   120
```

<210> SEQ ID NO 630
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 630

```
tagctgtgct gtaattaact tttggaaact agtttatcac ttttcttctt ttcactacag    60
gtttatgttt gtgctgtgtg ccaaaatgtt ttctgtgtgg actgtgatgt ttttgttcat   120
```

<210> SEQ ID NO 631
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 631

```
gattctctac actgttgccc tggctgtatt cataagattc cagctccttc aggtgtttga    60
ttccagcatg tagtatacat tgtatgtgtt aaaaagaaat ttgcaactgt gaataaaagg   120
```

<210> SEQ ID NO 632
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 632

```
tttgagacgc tccctgacc accacttgct ctgcgctgag gtgctgggac agccatggtt    60
tcagacggtg aggaccctgc agggcgggac ttcgactccg gggctcggct gtctcggtcc   120
```

<210> SEQ ID NO 633
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 633

```
tttcttgtta atattttcag aagatgaatt gaatcttctg gttattgtag ttgatgccaa    60
cccaatttgg tggggaaagc aagcattaaa ggaatctcag gtaagactgc ttgaggaggc   120
```

<210> SEQ ID NO 634
<211> LENGTH: 120
<212> TYPE: DNA

```
<213> ORGANISM: Artificial Sequence
<220> FEATURE:
<223> OTHER INFORMATION: Synthetic polynucleotide

<400> SEQUENCE: 634
caacagttca ctttatccaa atgcatagat gccgtgatgg tgctgggaaa ttcgcattta    60
ttcatgaatc gttccaacaa acttgctgtg atagcaagtc acattcaaga aaggtatgac   120

<210> SEQ ID NO 635
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 635
ggcctggtgt aaccaggttt tttcccctgc tgtttcagcc gattcttata tcctggaaag    60
aatggcagac ttggagactt cttcggagac cctggcaacc ctcctgaatt taatccctct   120

<210> SEQ ID NO 636
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 636
gggagtaaag atggaaaata cgaacttta acctcagcaa atgaagttat tgttgaagag    60
attaaagatc taatgaccaa aagtaacaac ttttaaacat tgttattttg caaatagtgt   120

<210> SEQ ID NO 637
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 637 ccctttaat gttttctgtt atttgcaggt gacataaagg gtcaacatac agaaactttg    60
ctggcaggat ccctggccaa agcccttgc tgtatccttg gtgtctgaat catttagaag   120

<210> SEQ ID NO 638
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 638
ttatgaagca aaataatatt tttgtattcc ttaatgttaa gaaattaaga cattcataga    60
atgaacaagg aagttaaagg taagagccta cgttttccta tgagaactgt aatcctactt   120

<210> SEQ ID NO 639
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 639
ttagtaagat ttagttaaat tttttctgc tttttctct tgtagacaa tcaggaaatg    60 aaatcaagga tattggtaag ataaaaaaat cattactttt ttatatgaca actataatta   120
```

<210> SEQ ID NO 640
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 640
ttaacatgac tgtgattttt aggtgattaa ggctgcagaa gacagtgcgt tgcagtatat    60
gaacttcatg aatgtcatct ttgcagcaca gaaacaggtg aactgagagc ctgccgttta   120

<210> SEQ ID NO 641
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 641
attcctgtaa tattttcaaa atgtttcttt tagaatattt tgattgatgc ctgtgtttta    60
gactccgact cagggctcct ccaacaggta tgttttaaaa ccatgctttg tgtcggtggt   120

<210> SEQ ID NO 642
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 642
ggcagcaagc cgcctgtgtc ttgcaggctt gtgacatcac gggaggactg tacctgaagg    60
tgcctcagat gccttctctt ctgcagtatt tgctggtaag gagacagcag cggcgaccct   120

<210> SEQ ID NO 643
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 643
atttttttcc catgttttaa ataaaagttt cttttgtttg tttgtttac agtgggtgtt    60 tcttcccgat caagatcaga gatctcagtt aatcctccca cccccagttc atgttgacta   120

<210> SEQ ID NO 644
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 644
cagggctgct tgcttctgtc atcgaaatct cattgaaatt ggttatgtct gttctgtgtg    60
tttgtcaagt aagttaatgt acctagtttt tcttttttt ctatgttggg gggcaggaaa   120

<210> SEQ ID NO 645
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 645
ttttcagcca ccctattgtt tcttttttt tttaatttac agtattctgc aatttcagcc    60
ccatttgtac tacgtgcgag taagtatctt tgagattgtg tgggtggcta atacttcaca   120

<210> SEQ ID NO 646
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 646
aatgttttcc tctctgtaat ttcaggacag cctttaaaat ttctctgcct ccagtgctga    60
aagccaagaa aaagaaactg aaagtgtctg cctgaggata aaatattttc cccatctttt   120

<210> SEQ ID NO 647
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 647
acactggcat ggatggtgag gttgcacttc tgacgtttgc attcctcagg tgatggagag    60
caccccttca aggggactga accgagtaca cctacaatgc aggaatctgc aggaattctt   120

<210> SEQ ID NO 648
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 648 aggggcctg agccctgggg tattggaccg attgtatggg caccctgcca catgtctggc    60
tgtcttcagg tgagaagccc cttcatggca gggaaatgta atggggtctg cggagtggaa   120

<210> SEQ ID NO 649
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 649
ctgtacaggg agctcccatc cttggctaag aactgggtga tgcggatgct ctttctggag    60
cagcctttgc cacaggctgc tgtagctctg tgggtaaaga aggaattcag caagtaagtc   120

<210> SEQ ID NO 650
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 650
gggcctcctt tttgttttcc aaatacccta ctcacctctc tgcttctgtt ccagggctca    60
ggaggaaagt acagggctgc tgagcggcct ccggatctgg cacacacagc tgctcccagg   120

<210> SEQ ID NO 651
<211> LENGTH: 120

<212> TYPE: DNA
<213> ORGANISM: Artificial Sequence
<220> FEATURE:
<223> OTHER INFORMATION: Synthetic polynucleotide

<400> SEQUENCE: 651
cgggctccag ggcctcatcc tcaaccccat tttccgccag aacctccgca ttgcccttct     60
gggtgggtat gtcacttctc tctcttccta agctagggca ggggaactgc tgcttattaa    120

<210> SEQ ID NO 652
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 652
cctggccgta gggggaaggc ctggtctgat gacacaagtc agctgggacc agacaagcat     60
gcccgggacg ttccctccct tgacaagtac gccgaggagc gatgggaggt aagcacttgg    120

<210> SEQ ID NO 653
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 653
ctcttctgtt cttcaggtgg tcttgcactt catggtgggc tcccccagtg cagctgtcag     60
ccaggacttg gctcagctcc tcagccaggc tgggctcatg aagaggtgag gaagccggag    120

<210> SEQ ID NO 654
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 654
ctagtactga acctggagag ccgccctgca ttacttccgc tggcttccag ttcctgttgc     60
tggacacccc ggctcagctc tggtacttta tgttgcagta tttgcagaca gcccaggtga    120

<210> SEQ ID NO 655
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 655
tttgtctctg cctctttctc cctagagccg gggcatggac ctggtagaga ttctctcctt     60
cctcttccag ctcagcttct ctactctggg caaggtaagc aggggctga aaggtataga    120

<210> SEQ ID NO 656
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 656
gaaacctctg ttcctcagga ttactctgtg gaaggtatga gtgattctct gttgaacttc     60

```
ctgcaacatc tgcgtgagtt tgggcttgtt ttccagagga aggtatgagc gcctagataa    120
```

<210> SEQ ID NO 657
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 657

```
agatgtaagg cagtgacttc tgagacaagg catctgcctt tctattcttt tcagaggaaa    60
tctcggcgtt actacccccac acgcctggcc atcaatctct catcaggtgt ctctggagct   120
```

<210> SEQ ID NO 658
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 658

```
gggggcactg tgcatcagcc aggtttcatt gtcgtggaaa ccaattaccg actgtatgcc    60
tacacgggtg aggcgggaca gagggcccct ggaagaggag gttggggggtg agggaatgcc   120
```

<210> SEQ ID NO 659
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 659

```
agggagtctg ggtgtggggg tggcctcctc atcctctttc tatccctggc tcagagtcgg    60
agctgcagat tgccctcatt gccctcttct ctgagatgct ctatcggttc cccaacatgg   120
```

<210> SEQ ID NO 660
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 660

```
tggtggcgca ggtgacccgg gagagtgtgc agcaggcaat cgccagtggc atcacagccc    60
agcaggtatt cccacttggg agaggtggag caggaagaca ggctgcactt gggctgcggg   120
```

<210> SEQ ID NO 661
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 661

```
tcttgctgga gccctcatgc cattcttgtc tgttttccta gataatccat ttcctaagga    60
caagagccca cccagtgatg ctcaaacagg tatagacagg ctccaagatg tcagaggctg   120
```

<210> SEQ ID NO 662
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 662
gcagctggtg atgacatgat ggaaaagaaa aagggcatc caaatctggg gaagaaacag    60
agggccgggt tgtctggggc agtattctga gtccctacag tcaacccttg ctccttgcag   120

<210> SEQ ID NO 663
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 663
acacctgtgc tgccccccac catcaccgac cagatccggc tctgggagct ggaaagggac    60
agactccggt tcactgaggg tgagtagctt ctggtggcca agtcttggtc attggccaga   120

<210> SEQ ID NO 664
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 664
tctccccgcg cccctcccgt cctgccgacc ccaggtgtcc tgtataacca gttcctgtcg    60
caagtggact ttgagctgct gctggcccac gcgcgggagc tgggcgtgct cgtgttcgag   120

<210> SEQ ID NO 665
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 665
aactcggcca agcggctcat ggtggtgacc ccggccgggc acagcgacgt caagcgcttt    60
tggaagcggc agaaacatag ctcctgagag cgcgggactt ggacacggac ctcggcgggc   120

<210> SEQ ID NO 666
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 666
tttattagca ttcttcaggt catctgaacc ttctgagaaa acatggtcaa cgtcttgaaa    60
ggagtgctta tagaatggtt agtagttttg atactgcatg agttttaagt ttaaatattg   120

<210> SEQ ID NO 667
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 667
tgtcttacaa tcatgtgttt gtctttacag tgatcctgcc atgaagcagt ttctgctgta    60
cttggatgag tccaatgccc tggggaagaa gttcatcatt caagacattg atgacactca   120

<210> SEQ ID NO 668

```
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 668
cgtctttgta atagcagaat tggttaatgt cctccaggag cgagtgggtg aattaatgga      60
ccaaaatgct ttttcccttta cccagaaatg aaaatactca atatggacca tttaggaatt     120

<210> SEQ ID NO 669
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 669
caggacccgc ttctctgaaa ggctctcctt gcagctgctt agacgctgga ttttttcgg      60 gtagtggaaa accaggtaag caccgaagtc cacttgcctt ttaatttatt tttttatcac     120

<210> SEQ ID NO 670
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 670
aagactgcct cccgctttgt gtgccccgct ccagcagcct cccgcgacga tgcccctcaa      60
cgttagcttc accaacagga actatgacct cgactacgac tcggtgcagc cgtatttcta     120

<210> SEQ ID NO 671
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 671
ctgcgacgag gaggagaact tctaccagca gcagcagcag agcgagctgc agccccggc      60 gcccagcgag gatatctgga agaaattcga gctgctgccc accccgcccc tgtcccctag     120

<210> SEQ ID NO 672
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 672
ccgccgctcc gggctctgct cgccctccta cgttgcggtc acaccttct cccttcgggg      60 agacaacgac ggcggtggcg ggagcttctc cacggccgac cagctggaga tggtgaccga     120

<210> SEQ ID NO 673
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 673
gctgctggga ggagacatgg tgaaccagag tttcatctgc gacccggacg acgagacctt      60
```

```
catcaaaaac atcatcatcc aggactgtat gtggagcggc ttctcggccg ccgccaagct    120
```

<210> SEQ ID NO 674
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 674

```
cgtctcagag aagctggcct cctaccaggc tgcgcgcaaa gacagcggca gcccgaaccc    60
cgcccgcggc cacagcgtct gctccacctc cagcttgtac ctgcaggatc tgagcgccgc    120
```

<210> SEQ ID NO 675
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 675

```
cgcctcagag tgcatcgacc cctcggtggt cttcccctac cctctcaacg acagcagctc    60
gcccaagtcc tgcgcctcgc aagactccag cgccttctct ccgtcctcgg attctctgct    120
```

<210> SEQ ID NO 676
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 676

```
ctcctcgacg gagtcctccc cgcagggcag ccccgagccc ctggtgctcc atgaggagac    60
accgcccacc accagcagcg actctggtaa gcgaagcccg cccaggcctg tcaaaagtgg    120
```

<210> SEQ ID NO 677
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 677

```
ctatttcctt tcttaaagag gaggaacaag aagatgagga agaaatcgat gttgtttctg    60
tggaaaagag gcaggctcct ggcaaaaggt cagagtctgg atcaccttct gctggaggcc    120
```

<210> SEQ ID NO 678
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 678

```
acagcaaacc tcctcacagc ccactggtcc tcaagaggtg ccacgtctcc acacatcagc    60
acaactacgc agcgcctccc tccactcgga aggactatcc tgctgccaag agggtcaagt    120
```

<210> SEQ ID NO 679
<211> LENGTH: 120
<212> TYPE: DNA
<213> ORGANISM: Artificial Sequence
<220> FEATURE:

-continued

<223> OTHER INFORMATION: Synthetic polynucleotide

<400> SEQUENCE: 679
tggacagtgt cagagtcctg agacagatca gcaacaaccg aaaatgcacc agccccaggt    60
cctcggacac cgaggagaat gtcaagaggc gaacacacaa cgtcttggag cgccagagga   120

<210> SEQ ID NO 680
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 680
ggaacgagct aaaacggagc ttttttgccc tgcgtgacca gatcccggag ttggaaaaca    60
atgaaaaggc ccccaaggta gttatcctta aaaaagccac agcatacatc ctgtccgtcc   120

<210> SEQ ID NO 681
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 681
aagcagagga gcaaaagctc atttctgaag aggacttgtt gcggaaacga cgagaacagt    60
tgaaacacaa acttgaacag ctacggaact cttgtgcgta aggaaaagta aggaaaacga   120

<210> SEQ ID NO 682
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 682
cttcaggatg gttcgtacta agacatggac cctgaagaag cactttgttg gctatcctac    60
taatagtgac tttgagttga agacagctga gctcccaccc ttaaaaaatg gaggtaagtc   120

<210> SEQ ID NO 683
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 683
gagtttctaa ttgcctatgg aatgctttat tttgtagagg tcctgcttga agctttgttc    60
ctcaccgtgg atccctacat gaggtattat ttatttcgcc cctcaaaatg ctaatgctgt   120

<210> SEQ ID NO 684
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 684
tttttttttt tttttttttt tgcagagtgg cagccaaaag attgaaggaa ggtgatacaa    60
tgatggggca gcaagtggcc aagtaattat ttccatttgt cccagtgctt ggaaaatatg   120

<210> SEQ ID NO 685
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 685
tctcttaaaa aaaccaaaca tctcattctt tattttttta aattttgtgt ctcaatgact     60
agccagttat tataatacca ttggtagaaa tcgtctatgg atctttactg gaatttcag    119

<210> SEQ ID NO 686
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 686
acatgcctta atgccttaat gtgctttatc tttcagagtt gtggaaagta aaaatgtagc     60
cctaccaaaa ggaactattg tactggcttc tccaggctgg acaacgcact ccatttctga    120

<210> SEQ ID NO 687
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 687
tgggaaagat ctggaaaagc tgctgacaga gtggccagac acaataccac tgtctttggc     60
tctggggaca gttggcatgc cagggtgagt tcatggata tattccattt gtttgaatgt    120

<210> SEQ ID NO 688
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 688
gcctgactgc ctactttggc ctacttgaaa tctgtggtgt gaagggtgga gaaacagtga     60
tggttaatgc agcagctgga gctgtgggct cagtcgtggg gcagattgca aagctcaagg    120

<210> SEQ ID NO 689
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 689
tgacttattc atggtttcct ttttttttt ttttctactt agggctgcaa agttgttgga     60
gcagtagggt ctgatgaaaa ggttgcctac cttcaaaagc ttggatttga tgtcgtcttt    120

<210> SEQ ID NO 690
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 690

```
aactacaaga cggtagagtc tttggaagaa accttgaaga aagcgtctcc tgatggttat      60
gattgttatt ttgataatgt aagtacaaac tggacttaat atctaattta ttatggaagt     120
```

<210> SEQ ID NO 691
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 691

```
gtttaggtag gtggagagtt ttcaaacact gttatcggcc agatgaagaa atttggaagg      60
attgccatat gtggagccat ctctacatat aacagaaccg gcccacttcc cccaggtaat     120
```

<210> SEQ ID NO 692
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 692

```
gcccaccccc agagattgtt atctatcagg agcttcgcat ggaagctttt gtcgtctacc      60
gctggcaagg agatgcccgc caaaaagctc tgaaggactt gctgaaatgg gtcttagagg     120
```

<210> SEQ ID NO 693
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 693

```
ttgagaatat taaattaagt tttaaaattt gttgttgctt tgatacaggg taaaatccag      60
tacaaggaat atatcattga aggatttgaa acatgccag ctgcatttat gggaatgctg     120
```

<210> SEQ ID NO 694
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 694

```
aaaggagata atttggggaa gacaatagtg aaagcatgaa aaagaggaca catggaatct      60
ggaggccatt tagatgatta gttaatttgt ttttcaccat ttagcaaaaa tgtatactac     120
```

<210> SEQ ID NO 695
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 695

```
cttaaatgtc ttaagaaata gtactcataa tgagtttgag ctacttaata aaatacattt      60
aagtggtatg taattagtga tggaggatgg aagtttcaaa gtcaacaaca accagtcacc     120
```

<210> SEQ ID NO 696
<211> LENGTH: 120
<212> TYPE: DNA
<213> ORGANISM: Artificial Sequence

```
<220> FEATURE:
<223> OTHER INFORMATION: Synthetic polynucleotide

<400> SEQUENCE: 696
gatcaaaaga gaaaatgaag aagattgaag cttcaaagca gaaaaatgaa gggaatatgt      60
atcattcacc attaccttag aaggcaaggg tccactttac aaaaggacta caaacattta    120

<210> SEQ ID NO 697
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 697
gggtggctga cccccagcat cctcgggagc gaccatggac tccctggccg agtctcggtg      60
gcctccgggc ctggcagtca tgaaggtgag tgcttcgggg agtttgggag ctcccgggtg    120

<210> SEQ ID NO 698
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 698
atgcatattt gcatttcaga caatagatga tttgctgcgg tgtggaattt gcttcgagta      60
tttcaacatt gcaatgataa tacctcagtg ttcacataac tgtaagtatg ttttgttcct    120

<210> SEQ ID NO 699
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 699
aacattatgt tgcactttgt gttttgcaga ctgctctctc tgtataagaa aatttctgtc      60
ctataaaact cagtgtccaa cttgctgtgt ggtgagtttt tgtttccttt ttttaaaact    120

<210> SEQ ID NO 700
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 700
ccatctgttg tttgttttt ctagactgtc acagagccgg atctgaaaaa taaccgcata      60
ttagatgaac tggtaaaaag cttgaatttt gcacggtatg atttaatttt gtgactaacc    120

<210> SEQ ID NO 701
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 701
tgtgcttcaa ggaatcatct gctgcagttt gctttagagt caccagccaa atctcctgct      60
tcttcctctt caaagaatct tgctgtcaaa gtatatactc ctgtagcctc cagacagtct    120
```

<210> SEQ ID NO 702
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 702
ttaaagcagg ggagcaggtt aatggataat ttcttgatca gagaaatgag tggttctaca      60
tcagagttgt tgataaaaga aaataaaagc aaattcagcc ctcaaaaaga ggcgagccct     120

<210> SEQ ID NO 703
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 703
gctgcaaaga ccaaagagac acgttctgta gaagagatcg ctccagatcc ctcagaggct      60
aagcgtcctg agccaccctc gacatccact ttgaaacaag ttactaaagg taggaagtta     120

<210> SEQ ID NO 704
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 704
aaaaatacag tggattgtcc tgtttgcggg gttaacattc agaaagtca cattaataag      60 catttagaca gctgtttatc acgcgaagag aagaaggaaa gcctcagaag gtaaggaagt     120

<210> SEQ ID NO 705
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 705
atcatcaggt atcttcccccc cttttcagtt ctgttcacaa aaggaagccg ctgcccaaaa      60
ctgtatataa tttgctctct gatcgtgatt taaagaaaaa gctaaagag catggattat     120

<210> SEQ ID NO 706
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 706
ctattcaagg aaataaacaa cagctcatta aaaggcacca agaatttgta cacatgtaca      60
atgcccaatg cgatgctttg catcctaaat caggtaaagt aataaaacag tgagttatgc     120

<210> SEQ ID NO 707
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 707

```
gttattttct tatttaaca gctgctgaaa tagttcgaga aatcgaaaat atagagaaga        60
ctaggatgcg tcttgaagct agtaaactca atgaaagtgt atgttaatgg gctatttcag       120
```

<210> SEQ ID NO 708
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 708

```
tttattaagg tctttttttg attatttag gtaatggttt ttacaaagga ccaaacagaa        60
aaggaaatag atgaaatcca cagtaaatat cgtaagttgc acgactttat ttaatttgta      120
```

<210> SEQ ID NO 709
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 709

```
ggttaacttt catagtccta gctttactga aagatctttt tgaatttcag gtaaaaaaca       60
taagagtgaa tttcagcttc tggtggatca ggctagaaaa ggatacaaga aaattgctgg      120
```

<210> SEQ ID NO 710
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 710

```
aatgtcacaa aaaacagtaa caataacaaa agaagatgaa tctacagaaa agctatcttc      60
tgtatgcatg ggtaagagac tataattaaa aacagacata tgtcgaattt cattatttac     120
```

<210> SEQ ID NO 711
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 711

```
aagttgtaga ttttaaggta ctcttaaatt tatttttcc taggacagga agataatatg        60
acctcagtaa caaaccactt ttctcaatca aagctggact ccccagagga attggaacct     120
```

<210> SEQ ID NO 712
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 712

```
gacagagaag aggattcttc tagctgtatt gatattcaag aagttctttc ttcatcagaa       60
tcagattcat gcaataggta agaaacatgc agtagttgat tatttaaat atctacttca      120
```

<210> SEQ ID NO 713
<211> LENGTH: 120
<212> TYPE: DNA

```
<213> ORGANISM: Artificial Sequence
<220> FEATURE:
<223> OTHER INFORMATION: Synthetic polynucleotide

<400> SEQUENCE: 713
tgtcaatact gatgtacata tccttttagt tccagttcag acatcataag agatctttta      60
gaagaagagg aagcctggga agcatcacat aagtgagttc tcataatcat gaaataagca     120

<210> SEQ ID NO 714
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 714
gtcttcagaa acgatcttca agacacagaa ataagtccaa gacagaatcg ccgcacaaga      60
gccgctgaaa gtgctgagat tgaaccaaga acaagcgta ataggaatta atgtgggctt     120

<210> SEQ ID NO 715
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 715
ttttatacag aaatcttgtg aaaccactgc ccaaccagag caatgattgt tcaaagagtg      60
gtattgaatt ctcgacctgg tatgtatttg cgatgaatga acaactctga tctttgataa     120

<210> SEQ ID NO 716
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 716
gaaaaaatgg taatccagtg gcagagaatt tccgaatgga agaagtctat ttaccagata      60
atattaatga aggacaagta caagttagaa ctctttatct ttctgtggat ccttacatgg     120

<210> SEQ ID NO 717
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 717
tatcttaatg ttttcttttt tcagcgttgt agaatgaatg aagacactgg cactgattat      60
ataacacctt ggcagctatc tcaagtcgtt gatggaggag gtattggaat tatagaagaa     120

<210> SEQ ID NO 718
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 718
agcaaacaca caaatttgac taaaggcgat tttgtgactt ctttctattg gccctggcaa      60
accaaggtta ttctggatgg aaatagcctt gaaaaggtga tatatatatg aacatatctg     120
```

<210> SEQ ID NO 719
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 719
cctagtattt ttaaagggta tatattttat tttaggtaga cccacaactt gtggatggac    60
acctttcata ttttcttgga gctataggta tgcctggttt gacttccttg attgggatac   120

<210> SEQ ID NO 720
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 720
aggaaaaagg tcatataact gctggatcta ataagacaat ggttgtcagt ggggccgcag    60
gtgcctgtgg atctgtggct gggcaggtaa actttctgag aattatttga ttttctgatt   120

<210> SEQ ID NO 721
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 721
aaatttcccc cctagattgg ccatttctta ggttgttcca gagtggtggg aatttgtgga    60
acacatgaga aatgcatcct cttgacctca gaactgggct tgatgctgc aattaattat    120

<210> SEQ ID NO 722
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 722
aaaaaagaca atgtggcaga acagctccgt gaatcatgcc cagctggagt ggatgtttat    60
tttgacaatg ttggtggtaa catcagtgat acagtgataa gtcaggttgt ttgctgattt   120

<210> SEQ ID NO 723
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 723
agccataaaa tcagtaaaca taggaaaggg atattttatc attattttc tctgtgcaga    60 tgaatgagaa cagccacatc atcctgtgtg gtcaaatttc tcagtacaac aaagatgtgc   120

<210> SEQ ID NO 724
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 724
cttatcctcc cccgctatcc cctgctatag aggcaatcca gaaagaaaga aacatcacaa    60
ggtgtgttct tcctctttgc ccttattacc aggttcatgg ggttttaaat atcatagatg   120

<210> SEQ ID NO 725
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 725
ttcttcctca ctgcagggaa agatttctgg tattaaatta taaagacaaa tttgagcctg    60
gcattctaca gctgagtcag tggtttaaag aaggaaagct aaaggtagaa cttctattct   120

<210> SEQ ID NO 726
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 726
aagtttaaag actattaaat ctagctattt tgatttacag attaaagaga cggtaataaa    60
tgggttggaa acatgggag gtaagatgaa tgtagactta ttatatacac atgctcagca   120

<210> SEQ ID NO 727
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 727
aacctacttt ctcttttcc agctgcattc cagtccatga tgacaggagg taacattgga    60
aagcagatag tttgcatttc agaagaaatc tctttgtaat tgctgtaaat gtcatcaagg   120

<210> SEQ ID NO 728
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 728
gagctgggag ctaggtcctc ggagtgggcc agagatggcg gcggccgacg gggctttgcc    60
ggaggcggcg gctttagagc aacccgcgga gctgcctgcc tcggtgcggg cgagtatcga   120

<210> SEQ ID NO 729
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 729
gcggaagcgg cagcgggcac tgatgctgcg ccaggcccgg ctggctgccc ggccctactc    60
ggcgacggcg gctgcggcta ctggaggttt gggccgcgtc cgcgctttcc ccttccctct   120

<210> SEQ ID NO 730
<211> LENGTH: 120

```
<212> TYPE: DNA
<213> ORGANISM: Artificial Sequence
<220> FEATURE:
<223> OTHER INFORMATION: Synthetic polynucleotide

<400> SEQUENCE: 730
gtaggcatgg ctaatgtaaa agcagcccca aagataattg acacaggagg aggcttcatt    60
ttagaagagg aagaagaaga agaacagaaa attggaaaag ttgttcatca accaggtaaa   120

<210> SEQ ID NO 731
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 731
ttcttaggac ctgttatgga atttgattat gtaatatgcg aagaatgtgg gaaagaattt    60
atggattctt atcttatgaa ccactttgat ttgccaactt gtgataactg caggtactta   120

<210> SEQ ID NO 732
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 732
ataactaatt tatataatgg acttaatctg ttttcagaga tgctgatgat aaacacaagc    60
ttataaccaa aacagaggca aaacaagaat atcttctgaa agactgtgat ttagaaaaaa   120

<210> SEQ ID NO 733
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 733
gagagccacc tcttaaattt attgtgaaga agaatccaca tcattcacaa tggggtgata    60
tgaaactcta cttaaagtta caggtctcta ataagttgta tttattattt ttcactctgg   120

<210> SEQ ID NO 734
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 734
gattgtgaag aggtctcttg aagtttgggg tagtcaagaa gcattagaag aagcaaagga    60
agtccgacag gaaaaccgag aaaaaatgaa acagaagaaa tttgataaaa agtaaaagg    120

<210> SEQ ID NO 735
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 735
cctgaatagc accactgaaa agatgacttt aaaatttttt tttcagaatt gcggcgagca    60
```

```
gtaagaagca gcgtgtggaa aagggagacg attgttcatc aacatgagta tggaccagaa     120

<210> SEQ ID NO 736
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 736
gaaaacctag aagatgacat gtaccgtaag acttgtacta tgtgtggcca tgaactgaca     60
tatgaaaaaa tgtgattttt tagttcagtg acctgtttta tagaatttta tatttaaata    120

<210> SEQ ID NO 737
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 737
caagcaacat ggctcggaaa cgcgcggccg gcggggagcc gcgggacgc gaactgcgca      60 gccagaaatc caaggccaag agcaaggccc ggcgtgagga ggaggaggag ggtgagagcg    120

<210> SEQ ID NO 738
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 738
tatgttctgt gttgtcacct agatgccttt gaagatgaga acccccaaa gaagagcctt      60 ctctccaaag tttcacaagg aaagaggaaa agaggctgca gtcatcctgg gggttcagca    120

<210> SEQ ID NO 739
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 739
gatggtccag caaaaaagaa agtggccaag gtgactgtta aatctgaaaa cctcaaggtt     60
ataaaggatg aagccctcag cgatggggat gacctcaggt gagatgtctg caaagctttg    120

<210> SEQ ID NO 740
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 740
acagggactt tccaagtgac ctcaagaagg cacaccatct gaagagaggg gctaccatga     60
atgaagacag caatgaagaa gaggaagaaa gtgaaaatga ttgggaagag gttgaaggtg    120

<210> SEQ ID NO 741
<211> LENGTH: 120
<212> TYPE: DNA
<213> ORGANISM: Artificial Sequence
<220> FEATURE:
<223> OTHER INFORMATION: Synthetic polynucleotide
```

<400> SEQUENCE: 741
acagtagcta ttattattgt tattactatt actgattttt aaaaatgctt gttgatagaa    60
cttagtgagc ctgtgctggg tgacgtgaga gaaagtacag ccttctctcg atctcttctg   120

<210> SEQ ID NO 742
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 742
cctgtgaagc cagtggagat agagattgaa acgccagagc aggcgaagac aagagaaaga    60
aggtaagctt aggcccttgc ttctaggctc ctgtcacatg cagtaggcaa cagctgctgc   120

<210> SEQ ID NO 743
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 743
tttcactatt tgttgcagtg aaaagataaa actggagttt gagacatatc ttcggagggc    60
gatgaaacgt ttcaataaag gggtccatga ggacacacac aaggtaaggg caaggaatga   120

<210> SEQ ID NO 744
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 744
ccttccttcc atgctgcccc ttcctccttt cctcttcaca ggttcacctt ctctgcctgc    60
tagcaaatgg cttctatcga aataacatct gcagccagcc agatctgcat gctattggcc   120

<210> SEQ ID NO 745
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 745
tgtccatcat cccagcccgc tttaccagag tgctgcctcg agatgtggac acctactacc    60
tctcaaacct ggtgaagtgg taaggccctc cgcttgtcct gcagagctgg ggagtgtagg   120

<210> SEQ ID NO 746
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 746
gaaatgaaaa ttcccctttg ccctgacctc tgacacaagg aatgcctgct ttctccccag    60
gttcattgga acatttacag ttaatgcaga actttcagcc agtgaacaag ataacctgca   120

<210> SEQ ID NO 747

```
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 747
gactacattg gaaaggagat ttgctattta ctctgctcga gatgatgagg aattggtcca     60
tgtaagtgat cctcccggat cactgttttt tatcagtact gttaactaat gataatggca    120

<210> SEQ ID NO 748
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 748
tccttttcat catagatatt cttactgatt ctccgggctc tgcagctctt gacccggctg     60
gtattgtctc tacagccaat tcctctgaag tcagcaacag caaaggtgag gtgcgcaggg    120

<210> SEQ ID NO 749
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 749
gggggagaaa aaaagcaaa atttcttatt ctgtttaagg gaaagaaacc ttccaaggaa      60
agattgactg cggatccagg aggctcctca gaaacttcca gccaagttct agaaaaccac    120

<210> SEQ ID NO 750
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 750
accaaaccaa agaccagcaa aggaaccaaa caagaggaaa cctttgctaa gggcacctgc     60
aggccaagtg ccaaagggaa gaggaacaag ggaggcagaa agaaacggag caagccctcc    120

<210> SEQ ID NO 751
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 751
tccagcgagg aagatgaggg cccaggagac aagcaggaga aggcaaccca gcgacgtccg     60
catggccggg agcggcgggt ggcctccagg gtgtcttata aagaggagag tgggagtgat    120

<210> SEQ ID NO 752
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 752
gaggctggca gcggctctga ttttgagctc tccagtggag aagcctctga tccctctgat     60
```

```
gaggattccg aacctggccc tccaaagcag aggaaagccc ccgctcctca gaggacaaag    120
```

<210> SEQ ID NO 753
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 753

```
gctgggtcca agagtgcctc caggacccat cgtgggagcc atcgtaagga cccaagcttg     60
ccagcggcat cctcaagctc ttcaagcagt aaaagaggca agaaaatgtg cagcgatggt    120
```

<210> SEQ ID NO 754
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 754

```
gagaaggcag aaaaaagaag catagctggt atagaccagt ggctagaggt gttctgtgag     60
caggaggaaa agtgggtatg tgtagactgt gtgcacggtg tggtgggcca gcctctgacc    120
```

<210> SEQ ID NO 755
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 755

```
tgttacaagt acgccaccaa gcccatgacc tatgtggtgg gcattgacag tgacggctgg     60
gtccgagatg tcacacagag gtacgaccca gtctggatga cagtgacccg caagtgccgg    120
```

<210> SEQ ID NO 756
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 756

```
gttgatgctg agtggtgggc cgagaccttg agaccatacc agagcccatt tatggacagg     60
gagaagaaag aagacttgga ggtaaggcct tggctgccag gggctccaag acacagtcag    120
```

<210> SEQ ID NO 757
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 757

```
ctaaataaca tgctcaacct tgtctgtctg gcctttgcag tttcaggcta aacacatgga     60
ccagcctttg cccactgcca ttggcttata taagaaccac cctctgtatg ccctgaagcg    120
```

<210> SEQ ID NO 758
<211> LENGTH: 120
<212> TYPE: DNA
<213> ORGANISM: Artificial Sequence
<220> FEATURE:

<223> OTHER INFORMATION: Synthetic polynucleotide

<400> SEQUENCE: 758
gcatctcctg aaatatgagg ccatctatcc cgagacagct gccatccttg ggtattgtcg    60
tggagaagcg gtctactcca ggtgcgtgag gcagcctggt tggcctcagg ggcttcctga   120

<210> SEQ ID NO 759
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 759
tcctgtgttg gttccacagg gattgtgtgc acactctgca ttccagggac acgtggctga    60
agaaagcaag agtggtgagg cttggagaag taccctacaa ggtaactgga gctgggggt   120

<210> SEQ ID NO 760
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 760
ctgaggaact ggatgccttt gttgtaaacg gtggccgtgt cctctggtgc agatggtgaa    60 aggctttttct aaccgtgctc ggaaagcccg acttgctgag ccccagctgc gggaagaaaa   120

<210> SEQ ID NO 761
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 761
tgacctgggc ctgtttggct actggcagac agaggagtat cagcccccag tggccgtgga    60
cgggaaggta agggcagcat cagaagggct caggaccagg ccgccttgtt cccctgctgg   120

<210> SEQ ID NO 762
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 762
tgctggccaa atgctgactt gctcacccga cacaggtgcc ccggaacgag tttgggaatg    60
tgtacctctt cctgcccagc atgatgccta ttggctgtgt ccagctgaac ctgcccaatc   120

<210> SEQ ID NO 763
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 763
tacaccgcgt ggccccgcaag ctggacatcg actgtgtcca ggccatcact ggctttgatt    60
tccatggcgg ctactcccat cccgtgtgcg tgaggggcct tcgatggagg ctaaacacag   120

```
<210> SEQ ID NO 764
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 764
tgtgtcccca caggactgat ggatacatcg tctgcgagga attcaaagac gtgctcctga      60
ctgcctggga aaatgagcag gcagtcattg aaaggaagga gaaggaggta agcgcatatg     120

<210> SEQ ID NO 765
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 765 cattttgcc tgcagaaaaa ggagaagcgg gctctaggga actggaagtt gctggccaaa       60
ggtctgctca tcagggagag gctgaagcgt cgctacgggc ccaaggtcag tgcaggttct     120

<210> SEQ ID NO 766
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 766
acctgtccag agtgaggcag cagctcccca cacagatgca ggaggtggac tctcttctga      60
tgaagaggag gggaccagct ctcaagcaga agcggccagg atactggctg cctcctggcc     120

<210> SEQ ID NO 767
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 767
tcaaaaccga gaagatgaag aaaagcagaa gctgaagggt gggcccaaga agaccaaaag      60
ggaaaagaaa gcagcagctt cccacctgtt cccatttgag cagctgtgag ctgagcgccc     120

<210> SEQ ID NO 768
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 768
cagaaagcgg gcgagcagca gttgagcgag cccgaggaca tggagatgga aggtgaggcc      60
cgagggccgg ccgcggcggg gccgggggc gcctttcatt gtggccgggg gagccgcggg     120

<210> SEQ ID NO 769
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 769
```
tgaatgtttc tggtcctaaa gacaaggctt ctgtgggatg ctttaaaaaa taaaaagaa    60 tgctgaggta gagctcctag agattctatg cagtcactct gatgtgggtg agagaacctc   120

<210> SEQ ID NO 770
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 770
ccccatcccc cagcagaggc cactgcagag ccatgcagag atggctggga accacaggct    60
tgggctggaa ggtgagtcag gttttcaggt tgagctcctt atgctggtga tggatggaga   120

<210> SEQ ID NO 771
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 771
ctttaaagcg ggagatacag atgacccacc aagaattact cagaaccctg tgatcaatgg    60
gaatgtggcc ctgagtgatg gacacaacac cgcggaggag gacatggagg atggtaagtg   120

<210> SEQ ID NO 772
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 772
atgatgtgtt tttttgcag acaccagttg gcgctccgag gcaacctttc agttcactgt     60
ggagcgcttc agcagactga gtgagtcggt ccttagccct ccgtgttttg tgcgaaatct   120

<210> SEQ ID NO 773
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 773
gccatggaag attatggtga tgccacgctt ttatccagac agaccacacc aaaaaagcgt    60
aggattcttt ctccagtgca atgctgaatc tgattccacg taagacagta tttcattact   120

<210> SEQ ID NO 774
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 774
aacatctggt aaataatgtc aactaaggct cagattattc ttttaaacag gtcatggtct    60
tgccatgcac aagcagtgct gaagataata aattacagag atgatgaaaa gtcgttcagt   120

<210> SEQ ID NO 775
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 775

```
cgtcgtatta gtcatttgtt cttccataaa gaaaatgatt ggggattttc caattttatg    60
gcctggagtg taagtaacag tgtatttagt ctgaacaatt ggtgcattac tgcttgttgt   120
```

<210> SEQ ID NO 776
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 776

```
tatttatgtt ttataggaag tgaccgatcc tgagaaagga tttatagatg atgacaaagt    60
tacctttgaa gtctttgtac aggcggatgc tccccatgga gttgcgtaag ttttctttta   120
```

<210> SEQ ID NO 777
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 777

```
tttcaggtgg gattcaaaga agcacacagg ctacgtcggc ttaaagaatc agggagcgac    60
ttgttacatg aacagcctgc tacagacgtt atttttcacg aatcagctac gaaaggtaaa   120
```

<210> SEQ ID NO 778
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 778

```
taaattcccc tgcatcttct cagagtaaaa attcttattt cttaattgtt tcaggctgtg    60
tacatgatgc caaccgaggg ggatgattcg tctaaaagcg tcccttta gc attacaaaga  120
```

<210> SEQ ID NO 779
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 779

```
gtgttctatg aattacagca tagtgataaa cctgtaggaa caaaaaagtt aacaaagtca    60
tttgggtatg tattagacat ctgcctttgc cattctgctt cctcttttt tttttttttt   120
```

<210> SEQ ID NO 780
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 780

```
ttaaatggag ttgtttgttt tatctttgaa aggtgggaaa ctttagatag cttcatgcaa    60
catgatgttc aggagctttg tcgagtggta agtttcaagc aatacttgta tatttcttac   120
```

<210> SEQ ID NO 781
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 781
gccaaaacat tcttttttcag ttgctcgata atgtggaaaa taagatgaaa ggcacctgtg   60
tagagggcac catacccaaa ttattccgcg gcaaaatggt ggtatgtggc taccagttct  120

<210> SEQ ID NO 782
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 782
ttccttattt gcagtcctat atccagtgta aagaagtaga ctatcggtct gatagaagag   60
aagattatta tgatatccag ctaagtatca aaggaaagaa aaatagtaag tgttgtgtgt  120

<210> SEQ ID NO 783
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 783
ctctctctct ctttaaagta tttgaatcat tgtggatta tgtggcagta gaacagctcg    60
atggggacaa taaatacgac gctggggaac atggcttaca ggtaaattga gtgttttgtg  120

<210> SEQ ID NO 784
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 784
tttaggaagc agagaaaggt gtgaaattcc taacattgcc accagtgtta catctacaac   60
tgatgagatt tatgtatgac cctcagacgg accaaaatat caagatcaat gataggtaat  120

<210> SEQ ID NO 785
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 785
tgtaaattaa tactgaattt cttttaaaat gttttctaat aggtttgaat tcccagagca   60
gttaccactt gatgaatttt tgcaaaaaac agatcctaag gaccctgcaa attatattct  120

<210> SEQ ID NO 786
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 786
tcatgcagtc ctggttcata gtggagataa tcatggtgga cattatgtgg tttatctaaa    60
ccccaaaggg gatggcaaag taagtggtgg gacccagggc tgaatgcaag ctcatcagaa    120

<210> SEQ ID NO 787
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 787
cttgtcacag tgcttgatcg ctgctggtgt gtgttgtttt ccttgcagtg gtgtaaattt    60
gatgacgacg tggtgtcaag gtgtactaaa gaggaagcaa ttgagcacaa ttatggggt    120

<210> SEQ ID NO 788
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 788
cacgatgacg acctgtctgt tcgacactgc actaatgctt acatgttagt ctacatcagg    60
gaatcaaaac tgagtgagta gtgttcactt ttgttctgtt ctttactgtg gtggacttgg    120

<210> SEQ ID NO 789
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 789
ctaagagggg aaagtccatc tgcaggggtc aaagaggatg cctttgtcct gcaggtgaag    60
ttttacaggc ggtcaccgac catgatattc ctcagcagtt ggtggagcga ttacaagaag    120

<210> SEQ ID NO 790
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 790
agaaaaggat cgaggctcag aagcggaagg agcggcagga agcccatctc tatatgcaag    60
tgcaggtcag cccccgccct tctgggactc cgggtcacca tgcagccggg cacccatctc    120

<210> SEQ ID NO 791
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 791
tcattttttg tcagttgtca agtcttttct gtgctttcat acatattttc agatagtcgc    60
agaggaccag ttttgtggcc accaagggaa tgacatgtac gatgaagaaa aagtgaaata    120

<210> SEQ ID NO 792
<211> LENGTH: 120
<212> TYPE: DNA

```
<213> ORGANISM: Artificial Sequence
<220> FEATURE:
<223> OTHER INFORMATION: Synthetic polynucleotide

<400> SEQUENCE: 792
cactgtgttc aaagtattga agaactcctc gcttgctgag tttgttcaga gcctctctca      60
gaccatggtg cgtaccggtc ccgtggatat accccaccgt ggctcccaac gtccaccttc     120

<210> SEQ ID NO 793
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 793 tttttttcagg gatttccaca agatcaaatt cgattgtggc ccatgcaagc aaggagtaat     60
ggaacaaaac gaccagcaat gttagataat gaagccgacg gcaataaaac agtaaatatt    120

<210> SEQ ID NO 794
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 794
gaaatagatg attgagctca gtgataatga aaacccttgg acaatattcc tggaaacagt     60
tgatcccgag ctggctgcta gtggagcgac cttacccaag tttgataaag atcgtaagtg    120

<210> SEQ ID NO 795
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 795
tattaacctt gtagatgatg taatgttatt tttgaagatg tatgatccca aaacgcggag     60
cttgaattac tgtgggcata tctacacacc aatatcctgt aaaatacgta agtccttcgt    120

<210> SEQ ID NO 796
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 796
catttaaaat atcttctttc tcctaggtga cttgctccca gttatgtgtg acagagcagg     60
atttattcaa gatactagcc ttatcctcta tgaggtttgg atggtttatt tttccataat    120

<210> SEQ ID NO 797
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 797
ttcactgtag gaagttaaac cgaatttaac agagagaatt caggactatg acgtgtctct     60
tgataaagcc cttgatgaac taatggatgg tgacatcata gtatttcaga agtatgtact    120
```

<210> SEQ ID NO 798
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 798
ccatggactt tgattcagac tgcaaacttt ctccctccac cagggatgac cctgaaaatg      60
ataacagtga attacccacc gcaaaggagt atttccgaga tctctaccac cgcgttgatg     120

<210> SEQ ID NO 799
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 799 tcatttctg tgataaaaca atccctaatg atcctggatt tgtggttacg ttatcaaata      60
gaatgaatta ttttcaggta tttaataaat gctcctttcc tcttcagatc ccactccaga     120

<210> SEQ ID NO 800
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 800
tgtgaacctt cctttctgtg tcttaggttg caaagacagt tgcacagagg ctcaacacag      60
atccaatgtt gctgcagttt ttcaagtctc aagggtaggt cacatgtgtg gacacttgct     120

<210> SEQ ID NO 801
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 801
gtgtagttat agggatggcc caggtaatcc tcttagacat aattatgaag gtactttaag      60
agatcttcta cagttcttca agcctagaca acctaagaaa ctttactatc agcaggtatg     120

<210> SEQ ID NO 802
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 802
gaatctttct tttcttaata gcttaagatg aaaatcacag actttgagaa caggcgaagt      60
tttaaatgta tatggttaaa cagccaattt agggaagagg taagttttt taatactatg      120

<210> SEQ ID NO 803
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 803
cattacttag gaaataacac tatatccaga caagcatggg tgtgtccggg acctgttaga    60
agaatgtaaa aaggccgtgg agcttgggga gaaagcatca gggaaactta ggcaagtatt   120

<210> SEQ ID NO 804
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 804
ctctgttcag gctgctagaa attgtaagct acaaaatcat tggtgttcat caagaagatg    60
aactattaga atgtttatct cctgcaacga gccggacgtt tcgaatagag gtatctgtcc   120

<210> SEQ ID NO 805
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 805
tggacacttt gaccacatca cttgcactta cagaactgtg tctgttgtcc gtgtcccag     60 gaaatccctt tggaccaggt ggacatagac aaagagaatg agatgcttgt cacagtggcg   120

<210> SEQ ID NO 806
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 806
catttccaca aagaggtctt cggaacgttc ggaatcccgt ttttgctgag gatacaccag    60
gtatgctgtt gtggttggcc gagtggctca cgtcaaaacc tggagccttt gagtggccgc   120

<210> SEQ ID NO 807
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 807
agcacatgtc ctttgccatt ctagggcgag cattttcgag aagtgatgaa gcgaatccag    60
agcctgctgg acatccagga gaaggagttt gagaaggtgt gcagctgggg cctcctgggg   120

<210> SEQ ID NO 808
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 808
gtttaaattt gcaattgtaa tgatgggccg acaccagtac ataaatgaag acgagtatga    60
agtaaatttg aaagactttg agccacagcc cggtaagggt tctcccccc ccgggggctg    120

<210> SEQ ID NO 809
<211> LENGTH: 120

```
<212> TYPE: DNA
<213> ORGANISM: Artificial Sequence
<220> FEATURE:
<223> OTHER INFORMATION: Synthetic polynucleotide

<400> SEQUENCE: 809
caccaggtaa tatgtctcat cctcggcctt ggctagggct cgaccacttc aacaaagccc      60
caaagaggag tcgctacact taccttgaaa aggccattaa aatccataac tgatttccaa     120

<210> SEQ ID NO 810
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 810
tatttctaga tatggatcag aaactttcga agttggtaga agagctcaca acttcaggag      60
aaccccgact aaatcctgag aaaatgaagg aactgaagaa aatttgcaag tatgtcttag     120

<210> SEQ ID NO 811
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 811
gctcgcatcc ccaggtcttc agaggagcag ctgagccgcg cctaccgcct gctgatagca      60
cagctgaccc aggagcacgc cgagatccgt ctctcagcct tccagattgt ggaggaactc     120

<210> SEQ ID NO 812
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 812
ttcgtcaggt ctcaccagtt ccggatgctg gttgtttcca acttccagga gttcctggag      60
ctcacgctgg gcacagaccc cgcacagcct ctgccgcccc caggggaggc ggcacagagg     120

<210> SEQ ID NO 813
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 813
ctgaggcagg cgaccacccg ggccgtggaa gggtggaatg agaagtttgg ggaggcctac      60
aagaagcttg ccttgggcta ccacttctta agacacaaca aaaaggtagg tgggcctggc     120

<210> SEQ ID NO 814
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 814
gtgagccacc gcgcctgtcc cctagtcttt attttcaatt gctcaggtgg attttcaaga      60
```
cacgaatgct cggagtctgg cagaaaggaa gagagaagag gagaagcaga agcacttgga    120

<210> SEQ ID NO 815
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 815
taaaatttat caagaaagag ccagccaggc ggagagggag atgcaaggca agtgtccagg    60
acggagggag gggcccacgc ctctgagggt tgcccgtggt ccagcagttc atcctcctgg    120

<210> SEQ ID NO 816
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 816
cttttgctcc acatagcgca gcaaacaggt gtcttgatct tccggcagaa atgtctggag    60
aaattgaatc ctgcttgacg gaggtagaga gctgctttag gctgctggtg ccttttgact    120

<210> SEQ ID NO 817
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 817
ttgacccgaa cccggagacg gaatcccttg gcatggcttc tggcatgtcc gatgcccttc    60
gctcctcctg cgcgggccag gtgggcccct gccggtctgg caccccctgac ccccgggacg    120

<210> SEQ ID NO 818
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 818
gggagcagcc ctgctgcagt agagacctgc ctgcctctgc aggccacccc agagcgggcg    60
gcggggcaca gccatcccag acagccacag gtgacccctc agatgaggac gaggacagcg    120

<210> SEQ ID NO 819
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 819
acctcgagga gtttgtgcgg agccacgggc tgggctcgca caagtacacg ctggatgtgg    60
agctctgctc aggtaactgc cttcgcgggg tctctgtggc gccaccctgc cccggctccc    120

<210> SEQ ID NO 820
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 820
ccagagggcc tgaaggtgca ggagaacgag acaaccttg ctctcatcca cgccgcccgc     60
gacacactca agctcatccg gaacaagttc ctgccggctg tgtgctcgtg gatccaggtg    120

<210> SEQ ID NO 821
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 821
gtgtgccagg gaccccccgg gccagtggac ctggcatgtg cctcccagca ggacagcttc     60
ccaggtcctg cccggccggc ccctgagctg ttcgcacccc cgtttcgcag cgcttcaccc    120

<210> SEQ ID NO 822
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 822
gcgtcgggac ccacggtgga tgtttaaagc gtgccattga cctgaaggct gaattggagc     60
tcgtactgag aaaatacaag gagctggaca tcgagcctga gggaggggaa aggcgcaggg    120

<210> SEQ ID NO 823
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 823
acagacagaa gccctggggg atgcggagga agatgaggac gatgaggact tgtgtggaggt    60 ccctgagaag gaggggtatg agccacacat ccccgaccac ttgcggcctg agtatggtga   120

<210> SEQ ID NO 824
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 824
ggcgggttgt gggagtggtg gcagggagtg gacacgtgtc tgtttcaggg ctggaggcag     60
caccagagaa agacacagtt gtgcggtgct tgcggacgag gacgaggatg gacgaggagg    120

<210> SEQ ID NO 825
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 825
tgtcggaccc cacctctgcg gctgctcagc tgcggcagct ccgggaccac ttgcctccac     60
cctcatctgc caggtgactc ccagtgtcct gtgtgctgag cccctgccc ggcgctgcca    120

<210> SEQ ID NO 826

```
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 826
gctgtgggtg gcaccagcag caccgtcagg ctgtcccact ctgctcctgt agcccctcca    60
gagcgttgcc agagccacag gaggcccaga agctggcagc agagcgggcc cgggcgcctg   120

<210> SEQ ID NO 827
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 827
tggtgcccta cggcgtggac ctgcactact ggggccagga gctccccaca gccgggaaga    60
ttgtcaagtg agtccccatg tgtctgaagt cggccagggc acacaaccag ggtcccagcc   120

<210> SEQ ID NO 828
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 828
ctatgagggc ctctggctgt gtctgcaggt ctgactccca gcaccgcttc tggaagccca    60
gcgaggtgga ggaggaagtg gtcaatgccg acatctccga gatgctccgg agccgccaca   120

<210> SEQ ID NO 829
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 829
tcacttttgc cgggaagttt gagcctgtgc agcactggtg ccgtgccccg aggccagacg    60
gccggctctg tgagcgccaa gaccggctga aggtgaggcc gtggcccgag ggcggggtg   120

<210> SEQ ID NO 830
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 830
gactttccac agctgcccaa gaccttccgg ctccagagga gggacggagc catccccacg    60
tccctgtggc tctcaggacg ccctcctctg aggggcgcgt gattccaggt tgtgtacact   120

<210> SEQ ID NO 831
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 831
ttggctctgt gataccaccc accctggtcg ctgtttgtgc ccaagtcgtg gtggtggggg    60
```

```
gaggtggtca aggcaagcgg acccctcccc gccatcagcc accgtgtcct cgctgtgcag    120
```

<210> SEQ ID NO 832
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 832

```
tgccctttcc atgggaagat tgttccacgg gacgacgaag gacggccgct cgacccggaa    60
gacagggctc gtgagcagcg gcggcagctg cagaagcagg agcgcccggg taggtctggg   120
```

<210> SEQ ID NO 833
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 833

```
cgtctcctga agtgcttgag ttttgtttgc agaatggcag gaccctgagt tgatgagaga    60
cgtggaagca gccacagggc aggatctcgg ctcatccagg tacagcggga aaggcagggg   120
```

<210> SEQ ID NO 834
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 834

```
gaagaagagg aggtacccca gcctcaccaa cctgaaggct caggctgata ccgcccgcgc    60
tcgcattggg agaaaagtct tcgccaagta agagtggctg ctgggtcacc tcccaccgcg   120
```

<210> SEQ ID NO 835
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 835

```
tgtttcccca cagggcagct gtgcggaggg tagtggcagc catgaaccgg atggaccaga    60
agaagcacga gaagttttca aaccagttta actacgcact gaactagaga gcggggccca   120
```

<210> SEQ ID NO 836
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 836

```
tttttcttta tcttttttt ttttagacta caacaaaatc acaattaaat ccggcctttg    60
aagatgcctg gagcagcagt gatgaagaag gatgaatatc atctttagta cctttttgtc   120
```

<210> SEQ ID NO 837
<211> LENGTH: 120
<212> TYPE: DNA
<213> ORGANISM: Artificial Sequence
<220> FEATURE:

<223> OTHER INFORMATION: Synthetic polynucleotide

<400> SEQUENCE: 837

```
ctttgccttc tatgttatag aactttata gtggtagcag agactgcaac attctggctt      60
gggttccatc cttatatgaa ccagttcctg atgatgatga ggtaaatatt attttcacaa    120
```

<210> SEQ ID NO 838
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 838

```
accattgctg tttatacagt ttactcagga gaacagataa ctatgcttaa gggacattat      60
aaaactgttg actgctgtgt atttcagtca aatttccagg taagagtgat acaggaattt    120
```

<210> SEQ ID NO 839
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 839

```
cttattattt taatcctaca ggtgaactat ggaaaagttt gtaataacag taaaaaagga      60
ttgaaattca ctgtctcctg tggctgcagt tcagaatttg tttttgtacc atatggtagc    120
```

<210> SEQ ID NO 840
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 840

```
ctcactgttg gtacagataa tcgaatgagg ctctggaata gttccaatgg agaaaacaca      60
cttgtaagag atttttaagt atatatttgg gtataaatta agaaatggat ctgtgacata    120
```

<210> SEQ ID NO 841
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 841

```
acattaaata tgtcctgaat acaagaacag ataaactgaa ctatgttttt cattgcagca      60
aacactgctc ataatgggaa agttaatggc ttatgtttta caagtgatgg acttcacctc    120
```

<210> SEQ ID NO 842
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 842

```
ttcttctcag tgctgacagt agagtaaaat tatgggatgt gagaagagca tcaggatgtt      60
tgattactct tgatcaacat aatgggaaaa agtcacaagc tgttgaatca ggtaaggaag    120
```

<210> SEQ ID NO 843
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 843
gacttttcat atagttgtat ttgcaggtca cagacaagaa atattagcag tttcctggtc    60
tccacgttat gactatatct tggcaacagc aaggtaaaat ttaacttatt tgcttttgaa   120

<210> SEQ ID NO 844
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 844
aatgtctttt gattaccaga ctgcagatgt atttaatttt gaggaaacag tttatagtca    60
tcatatgtct ccagtctcca ccaagcactg tttggtagca ggtttgtaag tgtattcttt   120

<210> SEQ ID NO 845
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 845 tttatttta agagttttgg gactggaatt aaataaagac agagatgttg aaagaatcca    60
cggcggtgga attaacaccc ttgacattga acctgttgaa gggagatagt aagtttatta   120

<210> SEQ ID NO 846
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 846
ccagccggtg tgaggacacg atatgctggg gttttgtcc gcacgccaaa cgggtttgga    60
ggaccctctt cgccttcgga gagcagagtc aacacggagg taaagaaaac cttacttttt   120

<210> SEQ ID NO 847
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 847
gcatgttcac atcaagctca tttgataaaa ctctgaaagt atgggataca aatacattac    60
aagtaagtac attaaaacat ttgcagattg ctttgtagga taaggagaa tttaatccta   120

<210> SEQ ID NO 848
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 848

```
taccagtttt gaaactcaca taagtcagtt aatgtaaatt ttgattgctg ttttgtagag    60
atcatcctga tgttcacaga tacagtgtgg agactgtaca gtggtatcct catgacactg   120
```

<210> SEQ ID NO 849
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 849

```
tattatcagc atgttatcag gtggttcaga tggtgtgatt gtactttatg accttgagaa    60
ctccagcaga caatcttatt acacatgtaa agcagtgtgt tccattggca ggtatgtatt   120
```

<210> SEQ ID NO 850
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 850

```
ggtatttta ttttatttca aacggcaact actttgagta aacgattcaa taaaaagaaa    60
cgttactaac agtgtattct ttgtaagtga catgactaat gtactttgtg ctggttgttg   120
```

<210> SEQ ID NO 851
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 851

```
ttttgatgat gacttatgat aaaattatct taaaccggtt ctgttttac agttggtact    60 agaggaccca agtacaact ttgtgacttg aagtctggat cctgttctca cattctacag   120
```

<210> SEQ ID NO 852
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 852

```
aatttgtgat acccctcgac g                                              21
```

<210> SEQ ID NO 853
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 853

```
tgggaaggct ctgtgtagat cgga                                           24
```

<210> SEQ ID NO 854
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 854
tgtgagatgg catattcggc                                           20

<210> SEQ ID NO 855
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 855
tccttgctaa ctttgccacc                                           20

<210> SEQ ID NO 856
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 856
tgcttccaca gtgctgagcc t                                         21

<210> SEQ ID NO 857
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 857
catctttgct actggttttc cc                                        22

<210> SEQ ID NO 858
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 858
gtccgcgaag atgacaaaat tg                                        22

<210> SEQ ID NO 859
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 859
agcacactgg actttggcga tgta                                      24

<210> SEQ ID NO 860
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 860
aattcaggag acatagggca c                                         21

<210> SEQ ID NO 861
<211> LENGTH: 22
<212> TYPE: DNA

```
<213> ORGANISM: Artificial Sequence
<220> FEATURE:
<223> OTHER INFORMATION: Synthetic polynucleotide

<400> SEQUENCE: 861
tctttatgac gcagagctaa cc                                              22

<210> SEQ ID NO 862
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 862
ttcggcagct tgaaatttac agggc                                           25

<210> SEQ ID NO 863
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 863
tccgcaaagc agtgagatag                                                 20

<210> SEQ ID NO 864
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 864
gactccagga aaacgacaga g                                               21

<210> SEQ ID NO 865
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 865
agcaaaagag atgaagcact acccagtc                                        28

<210> SEQ ID NO 866
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 866
ggaggcaaaa catagaggtc g                                               21

<210> SEQ ID NO 867
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 867
ggaaagtggg aagataccga g                                               21
```

```
<210> SEQ ID NO 868
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 868
tgcaggacaa agagaaacgt ctgaagc                                27

<210> SEQ ID NO 869
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 869
ccttcgtcaa attcagcatc ac                                     22

<210> SEQ ID NO 870
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 870
agtagaaata cggctgcacc                                        20

<210> SEQ ID NO 871
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 871
tccggaaggc cgaggccttg                                        20

<210> SEQ ID NO 872
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 872
ccaggtctcc attcttagtt gc                                     22

<210> SEQ ID NO 873
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 873
agccattgac agagcatata gg                                     22

<210> SEQ ID NO 874
<211> LENGTH: 26
<212> TYPE: DNA
<213> ORGANISM: Artificial Sequence
<220> FEATURE:
```

<223> OTHER INFORMATION: Synthetic polynucleotide

<400> SEQUENCE: 874
cctccacagt tcccaaggat atcagc                                          26

<210> SEQ ID NO 875
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 875
ggcattttca cttccaacca c                                               21

<210> SEQ ID NO 876
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 876
gtgaggacac gatatgctgg                                                 20

<210> SEQ ID NO 877
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 877
aacacggaga gttttgggac tggaat                                          26

<210> SEQ ID NO 878
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 878
gccgtggatt ctttcaacat c                                               21

<210> SEQ ID NO 879
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 879
tccacatcca atcataagca gg                                              22

<210> SEQ ID NO 880
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 880
cggacatcag ccagaaatgc agc                                             23

```
<210> SEQ ID NO 881
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 881
cttagaccgt tacagccatc ag                                              22

<210> SEQ ID NO 882
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 882
caaaaccctc tttcagcatg g                                               21

<210> SEQ ID NO 883
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 883
tggctcagtg ttgctatcca gatgc                                           25

<210> SEQ ID NO 884
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 884
agcagacacc aaagtaagac c                                               21

<210> SEQ ID NO 885
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 885
agccatggtt tcagacgaag                                                 20

<210> SEQ ID NO 886
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 886
ttcctttaat gcttgctttc cccacc                                          26

<210> SEQ ID NO 887
<211> LENGTH: 18
<212> TYPE: DNA
<213> ORGANISM: Artificial Sequence
<220> FEATURE:
<223> OTHER INFORMATION: Synthetic polynucleotide
```

```
<400> SEQUENCE: 887
tttcccagca ccatcacg                                                  18

<210> SEQ ID NO 888
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 888
ccatctttcc ctcaatctcc ag                                             22

<210> SEQ ID NO 889
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 889
cgtcgcttaa tcggagccaa agtct                                          25

<210> SEQ ID NO 890
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 890
ctgcattgta ggtgtactcg g                                              21

<210> SEQ ID NO 891
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 891
tggtcaacgt cttgaaagga g                                              21

<210> SEQ ID NO 892
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 892
tgaatgatga acttcttccc cagggc                                         26

<210> SEQ ID NO 893
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 893
aaccaattct gctattacaa agacg                                          25

<210> SEQ ID NO 894
<211> LENGTH: 20
```

```
<212> TYPE: DNA
<213> ORGANISM: Artificial Sequence
<220> FEATURE:
<223> OTHER INFORMATION: Synthetic polynucleotide

<400> SEQUENCE: 894
ttcgggtagt ggaaaaccag                                            20

<210> SEQ ID NO 895
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 895
cccctcaacg ttagcttcac caaca                                      25

<210> SEQ ID NO 896
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 896
agtagaaata cggctgcacc                                            20

<210> SEQ ID NO 897
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 897
atataacaga accggcccac                                            20

<210> SEQ ID NO 898
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 898
catctccttg ccagcggtag acg                                        23

<210> SEQ ID NO 899
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 899
ccctctaaga cccatttcag c                                          21

<210> SEQ ID NO 900
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 900
```

```
ccctctaaga cccatttcag c                                    21
```

<210> SEQ ID NO 901
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 901

```
tcttgtgaaa ccactgccca acca                                 24
```

<210> SEQ ID NO 902
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 902

```
attctctgcc actggattac c                                    21
```

<210> SEQ ID NO 903
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 903

```
gcaaagacca aagagacacg                                      20
```

<210> SEQ ID NO 904
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 904

```
tcaaagtgga tgtcgagggt ggc                                  23
```

<210> SEQ ID NO 905
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 905

```
ggaatgttaa ccccgcaaac                                      20
```

<210> SEQ ID NO 906
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 906

```
ccaggagaag gagtttgaga ag                                   22
```

<210> SEQ ID NO 907
<211> LENGTH: 25
<212> TYPE: DNA
<213> ORGANISM: Artificial Sequence

```
<220> FEATURE:
<223> OTHER INFORMATION: Synthetic polynucleotide

<400> SEQUENCE: 907
tttgaaagac tttgagccac agccc                                   25

<210> SEQ ID NO 908
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 908
ggccgaggat gagacatatt ac                                      22

<210> SEQ ID NO 909
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 909
gatgaggacg atgaggactt tg                                      22

<210> SEQ ID NO 910
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 910
cgaccacttg cggcctgagt atg                                     23

<210> SEQ ID NO 911
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 911
tgtgtctttc tctggtgctg                                         20

<210> SEQ ID NO 912
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 912
gagtatcgag cggaagcg                                           18

<210> SEQ ID NO 913
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 913
attagccatg cctccagtag ccg                                     23
```

<210> SEQ ID NO 914
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 914
ctcctgtgtc aattatcttt ggg                                              23

<210> SEQ ID NO 915
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 915
gtctctacag ccaattcctc tg                                               22

<210> SEQ ID NO 916
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 916
tggatccgca gtcaatcttt ccttgg                                           26

<210> SEQ ID NO 917
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 917
cctttgctgg tctttggttt g                                                21

<210> SEQ ID NO 918
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 918
accttctaca atgagctgcg                                                  20

<210> SEQ ID NO 919
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 919
atctgggtca tcttctcgcg gttg                                             24

<210> SEQ ID NO 920
<211> LENGTH: 21
<212> TYPE: DNA
<213> ORGANISM: Artificial Sequence
<220> FEATURE:
<223> OTHER INFORMATION: Synthetic polynucleotide

```
<400> SEQUENCE: 920
cctggatagc aacgtacatg g                                               21

<210> SEQ ID NO 921
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 921
acttgcccag atgttctcag                                                 20

<210> SEQ ID NO 922
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 922
accaaccgat ccaaagtctc cagc                                            24

<210> SEQ ID NO 923
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 923
gtatccctct agccattcag tg                                              22

<210> SEQ ID NO 924
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 924
acatcgctca gacaccatg                                                  19

<210> SEQ ID NO 925
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 925
aaggtcggag tcaacggatt tggtc                                           25

<210> SEQ ID NO 926
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 926
tgtagttgag gtcaatgaag gg                                              22
```

METHODS, COMPOSITIONS AND DEVICES FOR TREATING CANCER WITH ILLUDOFULVENES

PRIORITY CLAIM

This application claims priority to (i) U.S. Provisional Application No. 62/777,774 entitled "METHODS, COMPOSITIONS AND DEVICES FOR TREATING CANCER WITH ILLUDOFULVENES", inventor: Michael Kelner et al. filed Dec. 11, 2018, (ii) U.S. Provisional Application No. 62/796,409 entitled "METHODS, COMPOSITIONS AND DEVICES FOR TREATING CANCER WITH ILLUDOFULVENES", inventor: Michael Kelner et al. filed Jan. 24, 2019, and (ii) U.S. Provisional Application No. 62/796,409 entitled "METHODS, COMPOSITIONS AND DEVICES FOR TREATING CANCER WITH ILLUDOFULVENES", inventor: Michael Kelner et al. filed Nov. 25, 2019 which applications (i)-(iii) are herein expressly incorporated by reference in their entireties and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file MKEL-01048US3_ST25.TXT, created on Nov. 29, 2019, 447,093 bytes, machine format IBM-PC, MS-Windows operating system, is hereby incorporated by reference.

TECHNICAL FIELD

The present invention relates to compositions, methods and devices for treating cancer with illudofulvenes including methods to detect the expression levels of genes encoding biomarkers in cancer patients and to predict the responsiveness of cancer patients to illudofulvenes.

BACKGROUND ART

DNA microarrays have been used to measure gene expression in samples from patients and to facilitate diagnosis of disease. Gene expression can reveal the presence of cancer in a patient in addition to the type, stage, and origin of the cancer. Gene expression may even have a role in predicting the efficacy of cancer therapies. In recent decades, the National Cancer Institute (NCI) has tested cancer therapeutics for their effect in limiting the growth of 60 human cancer cell lines. The NCI has also measured gene expression in those 60 cancer cell lines using DNA microarrays. Various studies have explored the relationship between gene expression and therapeutic effect using the NCI datasets.

Illudofulvenes have been proposed as medicants for Affinity Drug Conjugates in U.S. Pat. No. 10,285,955 issued May 14, 2019 to M. J. Kelner entitled Affinity Medicant Conjugates, which is incorporated by reference herein in its entirety and for all purposes.

SUMMARY OF INVENTION

There exists a continuing need for delivery of chemotherapeutic agents for which tumors do not have a medicant resistant phenotype and which inhibit tumor growth, especially solid tumor growth, and which have an adequate therapeutic index to be effective for in vivo treatment. The illudofulvenes of the present invention have shown efficacy in humans and animals for a wide range of therapeutic applications including: cancer, adenocarcinoma, carcinoma, breast cancer, prostate cancer, ovarian cancer, endometrial cancer, and neuroendocrine tumors. For example, veterinary and agricultural applications can include treatment of cancer, adenocarcinoma, carcinoma, ovarian cancer, endometrial cancer, and neuroendocrine tumors in farmyard and/or companion animals.

The invention features methods for detecting expression of a biomarker (e.g., one, two, three, four, five, ten, or all of the biomarkers shown in Tables 1-8, such as Excision Repair Cross-Complementation (ERCC) e.g., ERCC2 (SEQ ID NO:21)) in a patient having cancer, such as a human patient having cancer that is resistant to one or more cancer therapies other than an Illudofulvene Analog (e.g., a patient with prostate cancer, ovarian cancer, or hepatocellular carcinoma (HCC) that is resistant to one or more cancer therapies including radiation therapy and/or chemotherapy based on Other Drugs as set forth herein), and for determining responsiveness of a cancer patient (e.g., a patient with prostate cancer, ovarian cancer, or HCC) to treatment with an Illudofulvene Analog. The invention also features methods of treating cancer in a patient in need thereof (e.g., a patient with prostate cancer, ovarian cancer, or HCC or a treatment resistant form thereof) that include administering an Illudofulvene Analog to the patient, in which the patient is or has been determined to be responsive to an Illudofulvene Analog according to the diagnostic methods described herein. Without wishing to be bound by any theory, it is believed that sensitivity to Illudofulvene Analog treatment in patients can be caused by a deficiency in a component of the transcription-coupled repair (TCR) pathway or the post-replication repair pathway (e.g. ERCC or RAD18 E3 Ubiquitin Protein Ligase (RAD18)), or alternatively sensitivity to Illudofulvene Analogs can be caused by an upregulation or increase in a gene product (i.e., protein, e.g., MYC Proto-Oncogene (MYC), and/or Prostaglandin Reductase (PTGR), e.g., PTGR1, and/or PTGR2). A Southern blot, a northern blot, mRNA/RNA microarray, protein array, gene sequencing, immunohistochemical staining requiring additional tissue sampling and a readout by a competent pathologist can be utilized to identify the patient population.

The methods of this invention include predicting the sensitivity of illudofulvenes, preferably in the form of a pharmaceutical composition, to an animal in need thereof. In a further embodiment, pharmaceutical compositions are disclosed containing illudofulvenes of the present invention in combination with a pharmaceutically acceptable carrier.

In an embodiment of the present invention, an illudofulvenes can target cancer cells with reduced toxicity to normal cells. In an embodiment of the present invention, these compounds are useful in treatment of tumors in which a marker is expressed. In various embodiments of the present invention, pharmaceutical compositions comprising the illudofulvene compounds are used in the treatment of tumors in which the marker is expressed. In various embodiments of the present invention, methods of using the pharmaceutical compositions comprise these compounds to treat tumors in which the marker is expressed. In various embodiments of the present invention, pharmaceutical compositions comprising these compounds are used in the treatment of one or more of the following diseases: cancer, adenocarcinoma, carcinoma, breast cancer, prostate cancer, ovarian cancer, endometrial cancer.

BRIEF DESCRIPTION OF THE DRAWINGS

This invention is described with respect to specific embodiments thereof. Additional features can be appreciated from the Figures in which:

FIG. 4A shows that MYC expression causes cells to become sensitive to Illudofulvene Analog 002, according to an embodiment of the invention;

FIG. 4B shows that MYC expression is not sensitive to Mithramycin;

FIG. 4C shows that MYC expression is not sensitive to Mitomycin C;

FIG. 4D shows that MYC expression is not sensitive to Topotecan; and

DETAILED DESCRIPTION OF THE INVENTION

Figure 1:
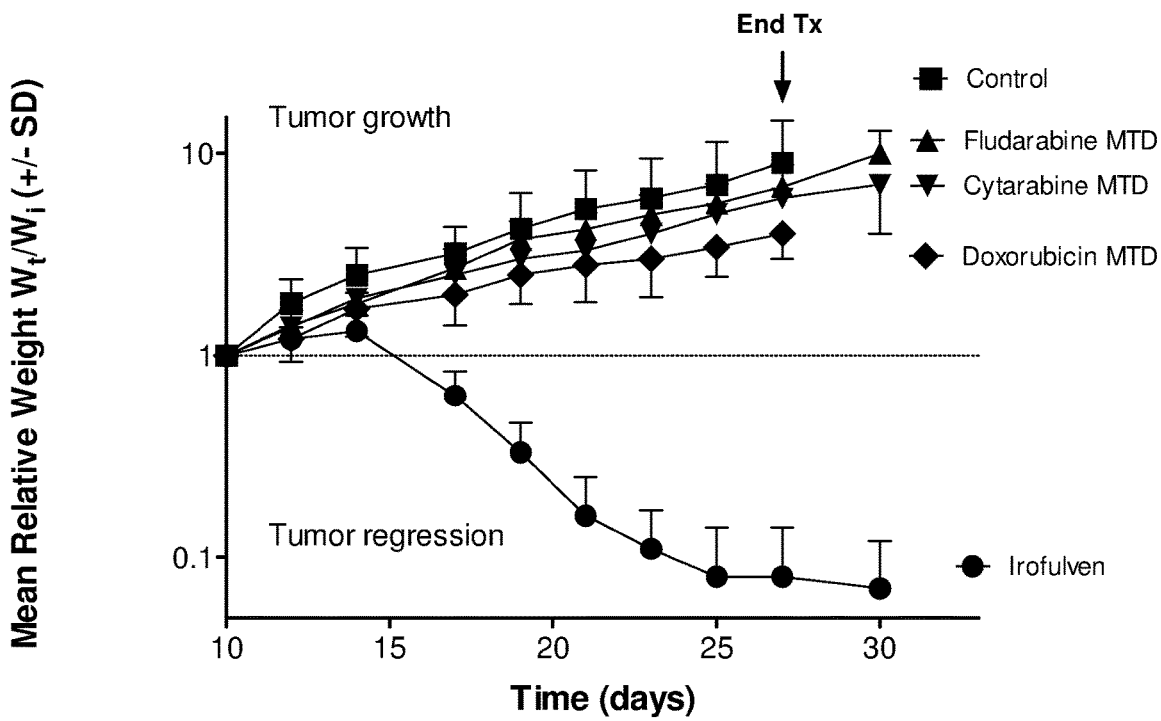
FIG. 1 shows the tumor regression produced by administration of an Illudofulvene Analog 002, according to an embodiment of the invention.

The term 'upregulated' means that the messenger RNA and/or the gene product (protein) is increased above basal level of a housekeeping gene by at least approximately one point nine (1.9) standard deviations which corresponds with ninety (90) percent confidence assuming a normal distribution. The phrase 'increased expression' means that the messenger RNA and/or the gene product (protein) is increased above a basal level of a housekeeping gene by at least approximately one point nine (1.9) standard deviations which corresponds with ninety (90) percent confidence assuming a normal distribution. The term 'downregulated.' means that the messenger RNA and/or the gene product (protein) is decreased below basal levels of a housekeeping gene by at least approximately one point nine (1.9) standard deviations which corresponds with ninety (90) percent confidence assuming a normal distribution. The phrase 'decreased expression' means that the messenger RNA and/or the gene product (protein) is decreased below a basal level of a housekeeping gene by at least approximately one point nine (1.9) standard deviations which corresponds with ninety (90) percent confidence assuming a normal distribution. In relation to upregulation and/or downregulation, approximately means plus or minus ten (10) percent.

The phrase 'not upregulated' means that the messenger RNA and/or the gene product (protein) are within the normal range of the basal level of a housekeeping gene. A basal expression level is the expression level of an mRNA or a protein under normal circumstances. The phrase 'determining if a cancerous tumor is sensitive to an illudofulvene analog' means that the indicated gene is either upregulated or downregulated as specified. The phrase 'using a selected technique' means a technique selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

The phrase 'determining the regulation of expression of a PTGR gene' means probing the level of expression of the PTGR gene in the (tissue) sample using a selected technique. The phrase 'determining the regulation of expression of a MYC gene' means probing the level of expression of the MYC gene in the (tissue) sample using a selected technique. The phrase 'determining the regulation of expression of a TCR gene' means probing the level of expression of the TCR gene in the (tissue) sample using a selected technique. The phrase 'determining the regulation of expression of a Housekeeping gene' means probing the level of expression of the Housekeeping gene in the (tissue) sample using a selected technique. The phrase 'determining a relative ratio of expression of a gene is high' means calculating that the determined regulation of the gene is 1.9 standard deviations above the determined regulation of a housekeeping gene. The phrase 'determining a relative ratio of expression of a gene is deficient' means calculating that the determined regulation of the gene is 1.9 standard deviations below the determined regulation of a housekeeping gene.

The phrase 'Other Drugs' means docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, cisplatin, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab.

'Acylfulvene' means an Illudofulvene subgroup with the following structural molecular formula:

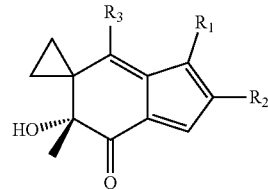

where $R_1$, $R_2$, $R_3$, $R_8$, $R_9$, $R_{10}$, $R_{11}$, are as set forth in Formula P1, as given herein.

'Formula P1' means $R_1$ represents —H, —$CR_9R_8OH$, —$CHR_9CHR_8OH$, —$CHR_{10}CHR_9CHR_8OH$, —$CH_2CHR_{10}CHR_9CHR_8OH$, —$CR_9R_8OH$, —$CHR_9CHR_8OH$, —$CHR_{10}CHR_9CHR_8OH$, —$CH_2CHR_{10}CHR_9CHR_8OH$, —C(=O)H, —$CH_2$(C=O)H, —$CH_2CH_2$(C=O)H, —$CH_2CH_2CH_2$(C=O)H, —$CH_2CH_2CH_2CH_2$(C=O)H, —$CR_9R_8$(C=O)H, —$CHR_9CHR_8$(C=O)H, —$CH_2CHR_9CHR_8$(C=O)H, —$CR_9R_8$(C=O)$R_{10}$, —$CHR_9CHR_8$(C=O)$R_{10}$, —$CH_2CHR_9CHR_8$(C=O)$R_{10}$, —$CH_2CH_2CHR_9CHR_8$(C=O)$R_{10}$, —$CO_2H$, —$CHR_9CO_2H$, —$CHR_8CHR_9CO_2H$, —$CHR_{10}CHR_8CHR_9CO_2H$, —$CO_2R_{10}$, —$CHR_9CO_2R_{10}$, —$CHR_8CHR_9CO_2R_{10}$, —$CH_2CHR_8CHR_9CO_2R_{10}$, —$CHR_9CH_2CH_2CHR_8CO_2H$, —CHR$_9$CH$_2$CH$_2$CHR$_8$CO$_2$R$_{10}$, —CR$_8$=CH$_2$, —CHR$_8$CH=CH$_2$, —CH$_2$CHR$_8$CH=CH$_2$, —CH$_2$CH$_2$CHR$_8$CH=CH$_2$, —CR$_8$=CHR$_9$, —CHR$_8$CR$_9$=CH$_2$, —CH$_2$CHR$_8$CR$_9$=CH$_2$, —CH$_2$CH$_2$CHR$_8$CR$_9$=CH$_2$, —CR$_8$=CR$_9$R$_{10}$, —CHR$_8$CH=CR$_9$R$_{10}$, —CH$_2$CHR$_8$CH=CHR$_9$R$_{10}$, —CH$_2$CH$_2$CHR$_8$CH=CHR$_9$R$_{10}$, —Cl, —Br, —I, —F, —NO$_2$, —NR$_8$R$_9$, —CH$_2$Cl, —CH$_2$Br, —CH$_2$I, —CH$_2$F, —CR$_8$Cl$_2$, —CR$_8$Br$_2$, —CR$_8$I$_2$, —CR$_8$F$_2$, —CCl$_3$, —CBr$_3$, —CI$_3$, —CF$_3$, —CHR$_8$Cl, —CR$_8$R$_9$Cl, —CHR$_8$CHR$_9$Cl, —CHR$_{10}$CHR$_8$CHR$_9$Cl, —CH$_2$CHR$_{10}$CHR$_8$CHR$_9$Cl, —CHR$_8$Br, —CR$_8$R$_9$Br, —CHR$_8$CHR$_9$Br, —CHR$_{10}$CHR$_8$CHR$_9$Br, —CH$_2$CHR$_{10}$CHR$_8$CHR$_9$Br, —CHR$_8$I, —CR$_8$R$_9$I, —CHR$_8$CHR$_9$Br, —CHR$_{10}$CHR$_8$CHR$_9$I, —CH$_2$CHR$_{10}$CHR$_8$CHR$_9$I, —CR$_8$R$_9$NH$_2$, —CHR$_8$CHR$_9$NH$_2$, —CHR$_{10}$CHR$_8$CHR$_9$NH$_2$, —CH$_2$CHR$_{10}$CHR$_8$CHR$_9$NH$_2$, —CR$_9$R$_{10}$NHR$_8$, —CHR$_9$CHR$_{10}$NHR$_8$, —CH$_2$CHR$_9$CHR$_{10}$NHR$_8$, —CH$_2$CH$_2$CHR$_9$CHR$_{10}$NHR$_8$, —CHR$_9$NHR$_8$R$_{10}$, —CHR$_9$CH$_2$NHR$_8$R$_{10}$, —CH$_2$CH$_2$CHR$_9$NR$_{10}$R$_8$, —CH$_2$CH$_2$CH$_2$CH$_2$NHR$_8$, —CR$_9$R$_8$OR$_{10}$, —CH$_2$CR$_8$R$_9$OR$_{10}$, —CH$_2$CH$_2$CR$_8$R$_9$OR$_{10}$, —CH$_2$CH$_2$CH$_2$R$_8$R$_9$OR$_{10}$, —CH$_2$CH$_2$CH$_2$R$_8$R$_9$OR$_{10}$, —CHR$_8$OC(=O)CHR$_9$R$_{10}$, —CHR$_8$OC(=O)CHR$_9$R$_{10}$, —CH$_2$CH$_2$OC(=O)CHR$_9$R$_{10}$, —CH$_2$CH$_2$CHR$_8$OC(=O)CHR$_9$R$_{10}$, —CH$_2$CH$_2$CH$_2$OC(=O)CHR$_9$R$_{10}$, —CHR$_8$(=O)OCHR$_9$R$_{10}$, —CHR$_8$(=O)OCHR$_9$R$_{10}$, —CH$_2$CHR$_8$(=O)OCHR$_9$R$_{10}$, —CH$_2$CH$_2$CHR$_8$(=O)OCHR$_9$R$_{10}$, —CH$_2$CH$_2$CH$_2$CHR$_8$(=O)OCHR$_9$R$_{10}$, —R$_{12}$C=CR$_9$CH$_2$OH, —R$_{12}$C=CR$_9$C(=O)H, —R$_{12}$C=CR$_9$CH$_2$OR$_{10}$, —R$_{12}$C=CR$_9$C(=O) R$_{10}$, —CH$_3$, —CH$_2$CH$_2$, —CHR$_8$CH$_2$, —CHR$_8$CH$_2$CH$_2$, —CHR$_8$CHR$_9$CH$_3$, —OCH$_3$, —OCR$_8$R$_9$R$_{10}$, —OCH$_2$CR$_8$R$_9$R$_{10}$, —OCR$_9$R$_8$CHR$_{10}$, —OCHR$_8$CH$_2$CH$_3$, —OCHR$_8$CHR$_9$CH$_3$, —NR$_8$CH$_3$, —NR$_8$CH$_2$CH$_3$, —NR$_9$CHR$_8$CH$_3$, —NR$_9$CHR$_8$CH$_2$CH$_3$, —NR$_{10}$CHR$_8$CHR$_9$CH$_3$, —OCH$_2$OR$_8$, —OCHR$_8$OR$_9$, —OCHR$_8$CH$_2$OR$_9$, —OCHR$_8$CHR$_9$OR$_{10}$, —OC(=O)OR$_8$, —OCH$_2$C(=O)OR$_8$, —OCHR$_9$C(=O)OR$_8$, —CR$_8$(=N)H, —CH$_2$CR$_8$(=N)H, —CH$_2$CR$_8$(=N)H, —CH$_2$CH$_2$CR$_8$(=N)H, —CH$_2$CH$_2$CH$_2$CR$_8$(=N)H, —CH$_2$CH$_2$CH$_2$CH$_2$CR$_8$(=N)H, —CR$_8$(=N)OH, —CH$_2$CR$_8$(=N)OH, —CH$_2$CR$_8$(=N)OH, —CH$_2$CH$_2$CR$_8$(=N)OH, —CH$_2$CH$_2$CR$_8$(=N)OH, —CH$_2$CH$_2$CH$_2$CR$_8$(=N)OH, —CH$_2$CH$_2$CH$_2$CH$_2$CR$_8$(=N)OH, —CR$_8$(=N)R$_9$, —CH$_2$CR$_8$(=N) R$_9$, —CH$_2$CR$_8$(=N) R$_9$, —CH$_2$CH$_2$CR$_8$(=N) R$_9$, —CH$_2$CH$_2$CR$_8$(=N)R$_9$, —CH$_2$CH$_2$CH$_2$CR$_8$(=N)R$_9$, —CH$_2$CH$_2$CH$_2$CH$_2$CR$_8$(=N)R$_9$, —CR$_8$(=N)OR$_9$, —CH$_2$CR$_8$(=N)OR$_9$, —CH$_2$CR$_8$(=N)O R$_9$, —CH$_2$CH$_2$CR$_8$(=N)OR$_9$, —CH$_2$CH$_2$CR$_8$(=N)OR$_9$, —CH$_2$CH$_2$CH$_2$CR$_8$(=N(OR$_9$), —CR$_8$(=N)NR$_9$, —CH$_2$CR$_8$(=N)NR$_9$, —CH$_2$CR$_8$(=N)NR$_9$, —CH$_2$CH$_2$CR$_8$(=N)NR$_9$, —CH$_2$CH$_2$CH$_2$—CR$_8$(=N)NR$_9$, —CH$_2$CH$_2$CH$_2$CH$_2$CR$_8$(=N)NR$_9$, —CR$_8$(=N)NR$_9$S(=O)$_2$R$_{10}$, —CH$_2$C(R$_8$)(=N)NR$_9$S(=O)$_2$R$_{10}$, —CH$_2$CH$_2$C(R$_8$)(=N)NR$_9$S(=O)$_2$R$_{10}$, —CH$_2$CH$_2$CH$_2$C(R$_8$)(=N)NR$_9$S(=O)$_2$R$_{10}$, CH$_2$CH$_2$CH$_2$CH$_2$C(R$_8$)(=N)NR$_9$S(=O)$_2$R$_{10}$, —R$_{12}$N(R$_8$)C(=O)NR$_9$R$_{10}$, —R$_{12}$N(R$_8$)C(=S)NR$_9$R$_{10}$, —R$_{12}$N(OR$_8$)C(=O)NR$_9$R$_{10}$, —R$_{12}$N(OR$_8$)C(=S)NR$_9$R$_{10}$, —R$_{12}$OS(O$_2$)NH$_2$, —R$_{12}$NHS(O$_2$)NH$_2$, —R$_{12}$OS(O$_2$)NR$_8$R$_9$, —R$_{12}$NHS(O$_2$)NR$_8$R$_9$, —CH$_2$N(R$_8$)S(O2)NR$_9$R$_{10}$, —CH$_2$CH$_2$N(R$_8$)S(O2) NR$_9$R$_{10}$, —CH$_2$CH$_2$N(R$_8$)S(O2)NR$_9$R$_{10}$, —CH$_2$N(R$_8$)S(O2)CR$_9$R$_{10}$R$_{11}$, —CH$_2$CH$_2$N(R$_8$)S(O2) CR$_9$R$_{10}$R$_{11}$, —CH$_2$CH$_2$CH$_2$N(R$_8$)S(O2) CR$_9$R$_{10}$R$_{11}$, —N(R$_8$)C(=O)R$_9$, —CH$_2$N(R$_8$)C(=O)R$_9$, —CH$_2$CH$_2$N(R$_8$)C(=O)R$_9$, —CH$_2$CH$_2$CH$_2$N(R$_8$)C(=O)R9, —CH$_2$N(R$_8$)(C=O)NR$_9$R$_{10}$, —CH$_2$CH$_2$N(R$_8$)(C=O)NR$_9$R$_{10}$, —CH$_2$CH$_2$N(R$_8$)(C=O)NR$_9$R$_{10}$, —CH$_2$N(R$_8$)(C=O)CR$_9$R$_{10}$R$_{11}$, —CH$_2$CH$_2$N(R$_8$)(C=O) CR$_9$R$_{10}$R$_{11}$, —CH$_2$CH$_2$N(R$_8$)(C=O) CR$_9$R$_{10}$R$_{11}$, —R$_{12}$N(OH)C(=O)NHOH, —R$_{12}$N(OH)C(=S)NHOH, —R$_{12}$N(OR$_8$)C(=O)NHOR$_9$, —R$_{12}$N(OR$_8$)C(=S)NHOR$_9$, —R$_{12}$OS(O$_2$)NHOH, —R$_{12}$NHS(O$_2$)NHOH, —R$_{12}$OS(O$_2$)NHOR$_9$, —R$_{12}$OS(O$_2$)N(R$_8$)OR$_9$, —R$_{12}$NR$_8$S(O$_2$)NHOR$_9$, —CR$_9$(=N)OR$_8$, —NH(OR$_8$), —C(C=O)NHR$_8$, —C(C=O)NR$_9$R$_8$, —NR$_{10}$(OR$_8$)C(=O)R9, —N(OR$_8$)C(=O)NR$_9$, —NR$_8$(R$_9$)S—, —N(R$_8$)S(=O)R$_9$, —NR(R$_8$)S(=O)$_2$R$_9$, —OC(=O)NR$_8$, —N(OR$_8$)C(=O)OR$_9$, —N(R$_8$)C(=S)R$_9$, —O(S(=O)$_2$R$_8$, —R$_{12}$O(S(=O)$_2$R$_8$, —O(S(=O)$_2$NR$_8$, —R$_{12}$O(S(=O)$_2$NR$_8$, —S(=O)R$_8$, —R$_{12}$S(=O)R$_8$, —S(=O)$_2$R$_8$, —R$_{12}$S(=O)$_2$R$_8$, —NR$_{10}$(R$_9$)S(=O)$_2$NHR$_8$, —NR$_9$(C=O)R$_8$, —NR$_9$(C=O)OR$_8$, —NR$_9$O(C=O)OR$_8$, —NR$_9$(C=O)NR$_8$R to, —R$_{12}$N(R$_9$)S(=O)$_2$NHR$_8$, —R$_{12}$N(R$_9$)(C=O)R$_8$, —R$_{12}$N(R$_9$)(C=O)OR$_8$, —R$_{12}$N(R$_9$)(C=O)NR$_8$, —N(=NR$_{10}$)R$_8$, —R$_{12}$—N(=NR$_{10}$)R$_8$, —C(R$_{10}$)(=N—N=)CR$_8$R$_9$; —N$_3$, —CH$_2$N$_3$, —CH$_2$CH$_2$N$_3$, —CH$_2$CH$_2$CH$_2$N$_3$, —CH$_2$CH$_2$CH$_2$CH$_2$N$_3$, —CHR$_8$N$_3$, —CR$_9$R$_8$N$_3$, —CHR$_9$CHR$_8$N$_3$, —CH$_2$CHR$_9$CHR$_8$N$_3$, —CH$_2$CH$_2$CHR$_8$N$_3$, —C(R$_8$)=N—R$_9$, —CH$_2$C(R$_8$) =N—R$_9$, —CH$_2$C(R$_8$)=N—R$_9$, —CH$_2$CH$_2$C(R$_8$)=N—R$_9$, —N$_3$, —CH$_2$N$_3$, —CH$_2$CH$_2$N$_3$, —CH$_2$CH$_2$CH$_2$N$_3$; and R2 and R3 each independently represent —H, —OH, —CH$_3$, —OCH$_3$, —C(=O)CH$_3$, —OC(=O)CH$_3$, —C(=O)OCH$_3$, —C(=O)CH$_2$CH$_3$, —OC(=O)CH$_2$CH$_3$, —C(=O)OCH$_2$CH$_3$, —CH$_2$CH$_3$, —CH(CH$_3$)$_2$, —C(CH$_3$)$_3$, —CH$_2$CH$_2$CH$_3$, —CH$_2$CH(CH$_3$)$_2$, —CHC(CH$_3$)$_3$, —CH$_2$OH, —NH$_2$, —CH$_2$NH$_2$, —N$_3$, and (C1-C4)alkyl; where R$_8$, R$_9$, R$_{10}$, R$_{11}$ each independently represent —H, —OH, —CH$_3$, —CH$_2$CH$_3$, —CH$_2$=CH$_2$, —CH$_2$CH$_2$=CH$_2$, —CH$_2$CH$_2$CH$_2$=CH$_2$, —C(H)=O, —CH$_2$C(H)=O, —CH$_2$CH$_2$C(H)=O, —CH(CH$_3$)CH$_3$, —CH$_2$CH$_2$CH$_3$, —CH$_2$CH(CH$_3$)CH$_3$, —CHC(CH$_3$)$_2$CH$_3$, —C(=O)CH$_3$, —C(=O)CH$_2$CH$_3$, —C(=O)NH$_2$, —CH$_2$OH, —CH$_2$CH$_2$OH, —C(H)(OH)C(H$_2$)(OH), —OCH$_3$, —OC(CH$_3$)$_3$, —OCH$_2$CH$_3$, —OCH(CH$_3$)$_2$, —CO$_2$H, —C(=O)OCH$_3$, —C(=O)OCH$_2$CH$_3$, —OC(=O)CH$_3$, —OC(=O)CH$_2$CH$_3$, —OC(=O)OCH$_3$, —OC(=O)OCH$_2$CH$_3$, —C(CH$_3$)$_3$, —CH$_2$CH$_2$(CH$_3$)$_2$, —CHC(CH$_3$)$_3$, —CH$_2$CH$_2$OH, CH$_2$CH$_2$CH$_2$OH, —Cl, —Br, —I, —F, —CH$_2$Cl, —CH$_2$Br, —CH$_2$F, —CHCl$_2$, —CHBr$_2$, —CHI$_2$, —CHF$_2$, —CCl$_3$, —CBr$_3$, —CI$_3$, —CF$_3$, —NH$_2$, —CH$_2$NH$_2$, —NH(OH), —CH$_2$N(OH), —NH(OCH$_3$), —N(OCH$_2$CH$_3$), —CH$_2$NH(OCH$_3$), —CH$_2$N(OCH$_2$CH$_3$), —N$_3$, —CH$_2$N$_3$, —CH$_2$CH$_2$N$_3$, —CH=NH, —CH=NOH, —CH=NOCH$_3$, —SH, —SCH$_3$, —SCH$_2$CH$_3$, —NO$_2$, —CN, cyclopropane ring, saturated or unsaturated cyclobutane ring, saturated or unsaturated cyclopentane ring, saturated or unsaturated cyclohexane ring, benzene ring, phenolic ring, xylene ring, an amino acid(s), (C$_1$-C$_4$)alkyl, and R$_{12}$ represents —CH$_2$—, —CH$_2$CH$_2$—, —CH(CH$_3$)CH$_2$—, —C(CH$_3$)CH$_2$—, —CH=CH—, —O—, —S—, —O(C=O)—, —(C=O)O—, —NH—, —N(R$_8$)—, —N(OH)—, —CH2-O—, —O—CH$_2$—, —CH$_2$CH$_2$—O—, —O—CH$_2$CH$_2$—, —S(=O)—, —(S=O)$_2$—, —NH(S=O)$_2$—, —N(OH)S(=O)$_2$—, —S(=O)$_2$NH—, —S(=O)$_2$N(OH)—, —NHS(=O)$_2$—, —N(OH)S(=O)$_2$—, —CH$_2$NH—, —CH$_2$N(R$_8$)—, —CH$_2$N(OH)—, —NHCH$_2$—, —N(R$_8$)CH$_2$—, —N(OH)CH$_2$—, —OC(C=O)O—, —OC(=O)NR$_8$—, —NR$_8$C(=O)O—.

An 'Illudin', which includes illudin M (where R$_1$, and R$_3$ are CH$_3$, and R$_2$ is OH), illudin S (where R$_1$ is CH$_2$OH, R$_2$ is OH, and R₃ is CH₃) and syn-illudins (which include an illudin ring derivative (where R₂ is the site of derivatization) or an illudin alkyl derivative (where R₁ is the site of derivatization) means an Illudofulvene subgroup with the following structural molecular formula:

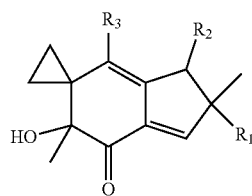

where R₁, R₂, R₃, are as set forth in Formula P2, as given herein.

'Formula P2' means where R₁, R₂, and R₃ each independently represent —H, —OH, —CH₃, —OCH₃, —C(═O)CH₃, —OC(═O)CH₃, —C(═O)OCH₃, —C(═O)CH₂CH₃, —OC(═O)CH₂CH₃, —C(═O)OCH₂CH₃, —CH₂CH₃, —CH(CH₃)₂, —C(CH₃)₃, —CH₂CH₂CH₃, —CH₂CH(CH₃)₂, —CHC(CH₃)₃, —CH₂OH, —NH₂, —NHOH, —CH₂NH₂, —CH₂NHOH, —N₃, and (C1-C4) alkyl.

Syn-Illudins are semi-synthetic derivatives of Illudins. Acylfulvenes are also semi-synthetic derivatives of Illudins. Syn-Illudins and Acylfulvenes have each been chemically modified at select sites to allow their use as medicants. The modifications in the Syn-Illudins do not alter any of the cyclic rings (cyclopropane, cyclopentane, cyclohexane) of the basic Illudin chemical structure. The modifications of Acylfulvenes differ from Syn-Illudins in that an additional double bond (an unsaturated bond) has been created in the 5 membered (cyclopentane) ring. Table 14 is a listing of IUPAC names of the Illudofulvene Analog according to various embodiments of the present invention.

During cancer treatment, critical time is often lost due to a trial and error approach to finding an effective therapy. In addition, cancer cells often develop resistance to a previously effective therapy. In such situations, patient outcome can be greatly improved by early detection of such resistance. Thus, there exists a need in the art for methods and devices that can predict the responsiveness of cancer patients to a medical treatment.

Exemplary types of cancer that can be diagnosed or treated with the methods include, e.g., prostate cancer, ovarian cancer (e.g., ovarian adenocarcinoma or embryonal carcinoma), liver cancer (e.g., HCC or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma, and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, or neoplasms of the central nervous system. For example, the cancer may be a solid tumor or a hematological cancer.

A first aspect of the invention features a method for detecting expression of a biomarker (e.g., one, two, three, four, five, ten, or all of the biomarkers shown in Tables 1-8, such as ERCC2 (SEQ ID NO:21)) in a patient having cancer (e.g., prostate cancer, ovarian cancer, or HCC), such as a patient having cancer that is resistant to one or more cancer therapies other than an illudofulvene (e.g., a patient with prostate cancer, ovarian cancer, or HCC that is resistant to one or more cancer therapies other than an illudofulvene). The method includes (a) contacting a sample (e.g., a tumor sample) from the patient including one or more nucleic acid molecules with a device (e.g., a microarray) including: i) one or more single-stranded nucleic acid molecules capable of specifically hybridizing with the nucleotides of one or more biomarkers of sensitivity selected from the biomarkers of Tables 1-8 (e.g., ERCC2 (SEQ ID NO:21)); and (b) detecting a level of expression of one or more of the biomarker(s) of sensitivity by performing microarray analysis or quantitative reverse transcriptase polymerase chain reaction (qRT-PCR). Expression of the biomarker(s) may be detected by determining the level of a messenger RNA (mRNA) transcribed from a nucleic acid molecule corresponding to a gene of the biomarker (e.g., a mRNA expressed from the ERCC2 (SEQ ID NO:21)) or a complementary DNA (cDNA) thereof.

A second aspect of the invention features a method of determining responsiveness of a patient having cancer (e.g., one of the cancers noted above, such as prostate cancer, ovarian cancer, or HCC) to an illudofulvene. In particular, the patient may have a cancer that is resistant to one or more cancer therapies other than an illudofulvene, such as prostate cancer, ovarian cancer, or HCC that is resistant to one or more cancer therapies other than an illudofulvene. The method includes a) contacting a sample (e.g., a tumor sample) from the patient including one or more nucleic acid molecules with a device (e.g., a microarray or a device for performing a qRT-PCR reaction) including: i) one or more single-stranded nucleic acid molecules capable of specifically hybridizing with the nucleotides of one or more biomarkers of sensitivity selected from the biomarkers of Tables 1-8 (e.g., ERCC2 (SEQ ID NO:21)); and b) measuring hybridization, or an amplification product resulting from hybridization, between the one or more nucleic acid molecules from the patient and the single-stranded nucleic acid molecules of the device to detect a level of expression of one or more of the biomarkers of sensitivity. The patient is determined to be responsive to an illudofulvene if: i) the level of expression of the biomarkers of sensitivity is substantially similar to the level of expression of the biomarkers of sensitivity (e.g., ERCC2 (SEQ ID NO:21)) in a cell (e.g., a cancer cell) or tissue (e.g., a tumor tissue) known to be sensitive to an illudofulvene.

The method of the second aspect can further include administering an illudofulvene to the patient if: i) the level of expression of the biomarkers of sensitivity (e.g., ERCC2 (SEQ ID NO:21)) is substantially similar to the level of expression of the biomarkers of sensitivity in a cell (e.g., a cancer cell) or tissue (e.g., a tumor tissue) known to be sensitive to an illudofulvene. The method can further include administering one or more cancer therapies other than an illudofulvene to the patient if: i) the level of expression of the biomarkers of sensitivity (e.g., ERCC2 (SEQ ID NO:21)) is substantially dissimilar to the level of expression of the biomarkers of sensitivity in a cell (e.g., a cancer cell) or tissue (e.g., a tumor tissue) known to be sensitive to an illudofulvene.

In particular, the one or more of the cancer therapies includes surgery, radiation, or a therapeutic agent, such as Other Drugs as set forth herein.

The invention also features a method of treating cancer in a patient in need thereof (e.g., one of the cancers noted above, such as prostate cancer, ovarian cancer, or HCC) that includes administering an illudofulvene to the patient, in which the patient has been determined to be responsive to an illudofulvene according to the method of the first or second aspect of the invention. In particular, the patient may have a cancer that is resistant to one or more cancer therapies other than an Illudofulvene Analog selected from Table 14 (e.g., a patient with prostate cancer, ovarian cancer, or HCC that is resistant to one or more cancer therapies other than an illudofulvene).

A third aspect of the invention features a method of treating a patient having cancer (e.g., one of the cancers noted above, such as prostate cancer, ovarian cancer, or HCC). In particular, the patient may have a cancer that is resistant to one or more cancer therapies which use other than an Illudofulvene Analog selected from Table 14 (e.g., a patient with prostate cancer, ovarian cancer, or HCC that is resistant to one or more cancer therapies other than an illudofulvene). The method includes a) contacting a sample (e.g., a tumor sample) from the patient including one or more nucleic acid molecules with a device (e.g., a microarray or a device for performing a qRT-PCR reaction) including: i) one or more single-stranded nucleic acid molecules capable of specifically hybridizing with the nucleotides of one or more biomarkers of sensitivity selected from the biomarkers of Tables 1-8 (e.g., ERCC2 (SEQ ID NO:21)); and b) measuring hybridization, or an amplification product resulting from hybridization, between the one or more nucleic acid molecules from the patient and the single-stranded nucleic acid molecules of the device to detect a level of expression of one or more of the biomarkers of sensitivity and c) administering an Illudofulvene Analog selected from Table 14 to the patient if: i) the level of expression of the biomarkers of sensitivity is substantially similar to the level of expression of the biomarkers of sensitivity in a cell (e.g., a cancer cell) or tissue (e.g., a tumor tissue) known to be sensitive to an illudofulvene.

The method of the third aspect of the invention may further include administering one or more additional therapies (e.g., surgery, radiation, or a therapeutic agent) to the patient prior to, concurrently with, or after administration of an Illudofulvene Analog selected from Table 14. In particular, the therapeutic agent may be selected from the group consisting of Other Drugs as set forth herein. The therapeutic agent can be administered parenterally (e.g. intravenously, intramuscularly, transdermally, intradermally, intraarterially, intracranially, subcutaneously, intraorbitally, intraventricularly, intraspinally, intraperitoneally, or intranasally), enterally, or topically.

In the second or third aspect of the invention, an illudofulvene may be administered parenterally (e.g. intravenously, intramuscularly, transdermally, intradermally, intraarterially, intracranially, subcutaneously, intraorbitally, intraventricularly, intraspinally, intraperitoneally, or intranasally), enterally, or topically. Preferably, an illudofulvene is administered by intravenous injection. An illudofulvene analog selected from Table 14 may be administered to the patient two or more times, such as one or more times daily, weekly, every two weeks, every three weeks, or monthly (e.g., one or more times per week for two weeks or more). Additionally, a second dose of an illudofulvene analog selected from Table 14 may be administered to the patient two weeks, three weeks, four weeks, or five weeks after administration of a prior dose of an illudofulvene. In particular, an illudofulvene analog selected from Table 14 is administered in a 3 week treatment regimen in which the illudofulvene analog selected from Table 14 is administered on day 1 an day 8. The treatment regimen may be repeated two to twenty times or more, as needed.

In particular, an illudofulvene analog selected from Table 14 may be administered to the patient at a dose of about 0.05 mg/kg to 6 mg/kg, such as at a dose of about 0.1 mg/kg to 1 mg/kg. For example, an illudofulvene may be administered at a dose of about 0.15 mg/kg, 0.20 mg/kg, 0.25 mg/kg, 0.30 mg/kg, 0.35 mg/kg, 0.40 mg/kg, 0.45 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, or 0.95 mg/kg. An illudofulvene may be administered to the patient in a treatment regimen at least once per week for at least two weeks and/or on day 1 and day 8 of a 3 week treatment regimen, in which the treatment regimen occurs one or more times (e.g., the treatment regimen is repeated two to twenty times). In particular, an illudofulvene is administered to the patient at a dose of about 0.1 mg/kg to 1 mg/kg, such as a dose of about 0.2 mg/kg to about 0.6 mg/kg (e.g., a dose of about 0.45 mg/kg). This dosage of an illudofulvene can be administered in a 3 week treatment regimen, in which an illudofulvene is administered on day 1 and day 8.

In the second or third aspect of the invention, the contacting step (a) and the measuring step (b) may occur prior to, concurrent with, or after administration of an illudofulvene analog selected from Table 14 to the patient. Additionally, the contacting step (a) and the measuring step (b) may occur two or more times, e.g., during treatment with an illudofulvene. For example, the contacting step (a) and the measuring step (b) may occur two or more times to assess the continued sensitivity of the patient to the Illudofulvene Analog selected from Table 14.

In any of the above aspects of the invention, the device can include at least two, at least three, at least four, at least five, at least six, at least seven, at least eight, at least nine, at least ten, or more single-stranded nucleic acid molecules capable of specifically hybridizing with the nucleotides of one or more biomarkers of sensitivity selected from the biomarkers of Tables 1-8 (e.g., ERCC2 (SEQ ID NO:21)). Any of these aspects can be used individually or in any combination with other aspects. In particular, one or more of the single-stranded nucleic acid molecules of the device have a length in the range of 10 to 100 nucleotides in length (e.g., a length in the range of 20 to 60 nucleotides).

In any of the above aspects of the invention, the method may include converting the level of expression of one or more of the biomarkers of sensitivity (e.g., one, two, three, four, five, ten, or all of the biomarkers shown in Tables 1-8, such as ERCC2 (SEQ ID NO:21)) into a mean score, in which the mean score indicates the responsiveness of the patient to an Illudofulvene Analog selected from Table 14. In particular, the mean score and/or the difference score above a cutoff value indicates that the patient is responsive to an illudofulvene, such as if the cutoff value is above a specific numeric value.

In any of the above aspects of the invention, the biomarker of sensitivity may be selected from one or more of the 'Select Sensitive Genes', where the Select Sensitive Genes means 'ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18), ERCC3 (SEQ ID NOS:19-20), ERCC2 (SEQ ID NOS:21-22), ERCC4 (SEQ ID NOS:23-24), ERCC5 (SEQ ID NOS:25-26), XPA (SEQ ID NOS:27-28), RAD18 (SEQ ID NOS:29-30), ERCC6L (SEQ ID NOS:31-32), ERCC6L2 (SEQ ID NOS:33-34), MYC (SEQ ID NOS:222-223), ERCC1 (SEQ ID NOS:236-237), PTGR1 (SEQ ID NOS:249-250), and/or PTGR2 (SEQ ID NOS:262-263)'.

For example, the biomarkers of sensitivity may include ERCC8 (SEQ ID NOS:1-2) and ERCC6 (SEQ ID NOS:3-4). For example, the biomarkers of sensitivity may include ERCC8 (SEQ ID NOS:1-2), ERCC6 (SEQ ID NOS:3-4), and GTF2H1 (SEQ ID NOS:5-6). For example, the biomarkers of sensitivity may include ERCC8 (SEQ ID NOS:1-2), ERCC6 (SEQ ID NOS:3-4), GTF2H1 (SEQ ID NOS:5-6), and GTF2H2 (SEQ ID NOS:7-8). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8) and GTF2H3 (SEQ ID NOS:9-10). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10) and GTF2H4 (SEQ ID NOS:11-12). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12) and GTF2H5 (SEQ ID NOS:13-14). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), and USP7 (SEQ ID NOS:15-16). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), and UVSSA (SEQ ID NOS:17-18). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18) and ERCC3 (SEQ ID NOS:19-20). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NO:13 or SEQ ID NO:14 or SEQ ID NO:101-111), USP7 (SEQ ID NOS:15-16), UVSSA (SEQ ID NOS:17-18), ERCC3 (SEQ ID NOS:19-20), and ERCC2 (SEQ ID NOS:21-22). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18), ERCC3 (SEQ ID NOS:19-20), ERCC2 (SEQ ID NOS:21-22), and ERCC4 (SEQ ID NOS:23-24). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18), ERCC3 (SEQ ID NOS:19-20), ERCC2 (SEQ ID NOS:21-22), ERCC4 (SEQ ID NOS:23-24) and ERCC5 (SEQ ID NOS:25-26). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18), ERCC3 (SEQ ID NOS:19-20), ERCC2 (SEQ ID NOS:21-22), ERCC4 (SEQ ID NOS:23-24), ERCC5 (SEQ ID NOS:25-26) and XPA (SEQ ID NOS:27-28). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18), ERCC3 (SEQ ID NOS:19-20), ERCC2 (SEQ ID NOS:21-22), ERCC4 (SEQ ID NOS:23-24), ERCC5 (SEQ ID NOS:25-26), XPA (SEQ ID NOS:27-28) and RAD18 (SEQ ID NOS:29-30). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18), ERCC3 (SEQ ID NOS:19-20), ERCC2 (SEQ ID NOS:21-22), ERCC4 (SEQ ID NOS:23-24), ERCC5 (SEQ ID NOS:25-26), XPA (SEQ ID NOS:27-28), RAD18 (SEQ ID NOS:29-30) and ERCC6L (SEQ ID NOS:31-32). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18), ERCC3 (SEQ ID NOS:19-20), ERCC2 (SEQ ID NOS:21-22), ERCC4 (SEQ ID NOS:23-24), ERCC5 (SEQ ID NOS:25-26), XPA (SEQ ID NOS:27-28), RAD18 (SEQ ID NOS:29-30), ERCC6L (SEQ ID NOS:31-32) and ERCC6L2 (SEQ ID NOS:33-34). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18), ERCC3 (SEQ ID NOS:19-20), ERCC2 (SEQ ID NOS:21-22), ERCC4 (SEQ ID NOS:23-24), ERCC5 (SEQ ID NOS:25-26), XPA (SEQ ID NOS:27-28), RAD18 (SEQ 11) NOS:29-30), ERCC6L (SEQ ID NOS:31-32), ERCC6L2 (SEQ ID NOS:33-34) and/or MYC (SEQ ID NOS:222-223). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18), ERCC3 (SEQ ID NOS:19-20), ERCC2 (SEQ ID NOS:21-22), ERCC4 (SEQ ID NOS:23-24), ERCC5 (SEQ ID NOS:25-26), XPA (SEQ ID NOS:27-28), RAD18 (SEQ ID NOS:29-30), ERCC6L (SEQ ID NOS:31-32), ERCC6L2 (SEQ ID NOS:33-34), MYC (SEQ ID NOS:222-223), and/or ERCC1 (SEQ ID NOS:236-237). For example, the biomarkers of sensitivity may include ERCC8 (SEQ ID NOS:1-2), ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18), ERCC3 (SEQ ID NOS:19-20), ERCC2 (SEQ ID NOS:21-22), ERCC4 (SEQ ID NOS:23-24), ERCC5 (SEQ ID NOS:25-26), XPA (SEQ ID NOS:27-28), RAD18 (SEQ ID NOS:29-30), ERCC6L (SEQ ID NOS:31-32), ERCC6L2 (SEQ ID NOS:33-34), MYC (SEQ ID NOS:222-223), ERCC1 (SEQ ID NOS:236-237) and/or PTGR1 (SEQ ID NOS:249-250). For example, the biomarkers of sensitivity may include the Select Sensitive Genes.

In any of the above aspects of the invention, the device can be a microarray, such as a deoxyribonucleic acid (DNA)-based platform. Alternatively, the device can be for performing a qRT-PCR reaction (e.g., the device is used with a system for detecting the amplification product, for example, by fluorescence or by another method). The methods may also utilize both a microarray and a qRT-PCR. Thus, the expression level of the biomarkers of sensitivity (e.g., one, two, three, four, five, ten, or all of the biomarkers shown in Tables 1-8, such as ERCC2 (SEQ ID NO:21)) can be measured using qRT-PCR (Table 4). In particular, the level of expression of one or more of the biomarkers of sensitivity is determined by detecting the level of mRNA transcribed from one or more genes encoding one or more of the biomarkers of Tables 1-8.

In any of the above aspects of the invention, the cancer is selected from a solid tumor cancer and a hematological cancer. For example, the cancer is prostate cancer, ovarian cancer, HCC, multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, or squamous cell carcinoma of the head and neck (SCCHN). In particular, the cancer is prostate cancer, such as prostate cancer that is resistant to one or more cancer therapies other than an illudofulvene. The cancer may also be ovarian cancer, such as ovarian cancer that is resistant to one or more cancer therapies other than an illudofulvene. Alternatively, the cancer may be HCC, such as HCC that is resistant to one or more cancer therapies other than an illudofulvene.

In any of the above aspects of the invention, the patient may exhibit cancer relapse (e.g., relapse of prostate cancer, ovarian cancer, or HCC), such as relapse after treatment with a therapeutic agent other than an illudofulvene. In particular, the patient may exhibit cancer relapse prior to treatment with an illudofulvene. Alternatively, the patient may have not been administered a treatment for cancer.

Described Methods

The expression levels of the biomarkers shown in Tables 1-8 in a patient having cancer are useful for predicting the responsiveness of the patient to an illudofulvene. These patients may already be determined to be resistance to a therapy other than an illudofulvene, such as Other Drugs as set forth herein.

A device, such as a microarray, with one or more single-stranded oligonucleotide probes that have substantial identity (e.g., at least 85%, 90%, 95%, 99%, or 100% sequence identity) to a sequence that is complementary or identical to the nucleic acid sequence of one or more biomarkers shown in Tables 1-8 can be used according to the methods described herein to assess the responsiveness of a cancer patient to treatment with an illudofulvene. For example, the probes can be used to detect one or more (e.g., two, three, four, five, ten, or all of the biomarkers shown in Tables 1-8, such as ERCC2 (SEQ ID NO:21) or ERCC3 (SEQ ID NO:19) in a sample (e.g., a tumor sample) from a patient having cancer (e.g., prostate cancer, ovarian cancer, or hepatocellular carcinoma (HCC)).

Accordingly, the invention features individual biomarkers (e.g. ERCC2 (SEQ ID NO:21) or ERCC3 (SEQ ID NO:19)) and sets of biomarkers shown in Tables 1-8 that can be used to determine the responsiveness of a cancer patient to an illudofulvene at various stages of disease progression (e.g., patients diagnosed with cancer or patients after cancer recurrence) and at different times during the treatment process (e.g., prior to administration of any cancer treatment, after administration of one or more cancer treatments other than an illudofulvene, prior to administration of an illudofulvene, or during administration of an illudofulvene). Additionally, the methods can be used to determine the an illudofulvene responsiveness of a patient with cancer that is resistant to one or more cancer therapies other than an illudofulvene, such as Other Drugs as set forth herein.

The invention provides methods of determination for assessing whether a patient with a cancer may be responsive to treatment with illudofulvenes by detecting the expression magnitude of either mRNA, or the corresponding protein produced from this mRNA, of one or more of the biomarkers shown in Table 6 (e.g. ERCC2 (SEQ ID NO:21) in a biological sample (e.g. a direct tumor biopsy or alternatively collection of free circulating tumor cells in peripheral blood) obtained from the patient using a device (e.g. a cDNA/mRNA microarray or protein array). Table 6 also contains components of the TCR post-replication repair pathway, PTGR1, PTGR2, and Myc. The expression level of one or more of these biomarkers can be compared to the expression level of the same biomarker(s) in a cell or tissue known to be sensitive to illudofulvenes based on a known defect in the TCR-NER pathway. The patient may be responsive to illudofulvene treatment if the expression level of one or more of the biomarkers (e.g. the Select Sensitive Genes) are similar to the expression levels of the corresponding biomarker in a cell or tissue known to be sensitive to an Illudofulvene Analog.

The invention features methods for identifying biomarkers (e.g., one or more of the biomarkers of Tables 1-8) for determining the responsiveness of a cancer patient to a cancer treatment, such as an Illudofulvene Analog selected from Table 14. Such methods can involve, for example, an algorithm based on growth inhibition (GI50), tumor growth inhibition (TGI), and lethal concentration (LD50) values derived from an In vitro Cancer Growth Inhibition Screen that was performed using a tumor obtained from a patient that was subjected to treatment with an Illudofulvene. In addition, or alternatively, the expression of genes associated with the TCR-NER pathway in this tumor can be measured (e.g., using a microarray (e.g., an Affymetrix HG-U133A or HG-U133_Plus_2 array)) and their expression compared to expression of a control or housekeeping gene (e.g. beta actin (ACTB), transferrin receptor (TFRC), glyceraldehyde-3-phosphate dehydrogenase (GAPD), or ubiquitin) to determine the responsiveness of a cancer patient to a cancer treatment, such as an Illudofulvene.

The invention also features methods of treating a patient having cancer that is resistant to one or more cancer therapies other than treatment including an illudofulvene, by detecting the expression levels of one or more of the biomarkers shown in Table 6 (e.g. ERCC2 (SEQ ID NO:21) in a sample (e.g. a direct tumor biopsy or alternatively collection of free circulating tumor cells in peripheral blood) obtained from the patient and then administering an illudofulvene based on the expression levels of these biomarkers. In summary, a patient having cancer may be administered an illudofulvene if the expression level of one or more of the biomarkers of sensitivity are similar to the expression levels of the biomarker of sensitivity in a cell or tissue known to be sensitive to illudofulvenes. Thus, the methods described can be used to identify cancer patients who can be predicted to respond to illudofulvenes, such as patients having, e.g., prostate cancer, ovarian cancer, hepatocellular carcinoma (HCC), cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, squamous cell carcinoma of the head and neck (SCCHN), acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), and Hodgkin's lymphoma. Alternatively, a patient having cancer would not be administered an illudofulvene if the expression levels of sensitivity of all biomarkers were substantially dissimilar to the expression level of biomarkers of sensitivity in a cell or tissue known to be sensitive to illudofulvenes.

Methods are described herein for identifying biomarkers of drug responsiveness, detecting this biomarker gene expression in samples from cancer patients, determining the responsiveness of a cancer patient to treatment with an illudofulvene, and treating cancer patients with an illudofulvene.

Methods of Determining the Responsiveness of a Patient to an Illudofulvene.

The invention features diagnostic methods for the detection and screening of cancer patients (e.g., a patient having cancer that is resistant to one or more cancer therapies other than an illudofulvene) that may be responsive to an illudofulvene analog selected from Table 14 using one or more of the biomarkers shown in Tables 1-8 (e.g. ERCC2 (SEQ ID NO:21) or ERCC3 (SEQ ID NO:19)). The methods of the invention may be used for predicting a patient's responsiveness to an illudofulvene, and optionally, treating the cancer patient throughout the progression of cancer and/or in cases of recurrence (e.g., after a first line treatment, a second line treatment, and/or a third line treatment).

The invention provides individual biomarkers (e.g. ERCC2 (SEQ ID NO:21) and sets of biomarkers (e.g., two or more of the biomarkers listed in Tables 1-8), the expression levels of which, as detected in a biological sample (e.g., a tumor sample, such as a biopsy) obtained from a cancer patient (e.g., a human with cancer), are indicative of responsiveness to an Illudofulvene Analog. The biomarkers were identified using methods similar to those previously described in, e.g., W Yang, et al. Genomics of drug sensitivity in cancer (GDSC): a resource for therapeutic biomarker discovery in cancer cells. Nucleic Acids Research, 41(D1): D955, 2013, which is incorporated by reference herein in its entirety for all purposes.

In particular, an algorithm based on the obtained in vitro cell culture values (i.e. growth inhibition values (GI50), or the total growth inhibition (TGI), or the lethal concentration (LC50)) of cell lines (e.g., NCI60 cells) subjected to treatment with an illudofulvene, and gene expression is determined in these same cell lines (e.g., by microarray analysis, reverse transcriptase polymerase chain reaction (RT-PCR), quantitative real-time PCR (qPCR), or next generation sequencing). After normalization, genes with, e.g., a Pearson correlation coefficient greater than about 0.5 or below about −0.5 to one of the obtained in vitro cell culture values, can be classified as biomarkers of sensitivity or resistance, respectively. A probability or significance value can also be calculated for the correlation between the obtained in vitro cell culture values (i.e. growth inhibition values (GI50), or the total growth inhibition (TGI), or the lethal concentration (LC50)) and the normalized expression of a specific gene.

In particular, a probability value of <0.05 is a statistically significant cut-off value as known in the art for establishing whether the expression level of A GENE, e.g., the genes shown in Tables 1-8, correlate with the likelihood of cancer treatment sensitivity, such as sensitivity to an illudofulvene. Thus, a probability value of <0.05 can be used to estimate the statistical significance of the expression level of the genes of Tables 1-8 for predicting patient responsiveness to treatment with an illudofulvene according to the methods described herein.

Biomarkers of Sensitivity.

The expression levels of one or more biomarkers of Tables 1-8 can be used to determine cancer patient responsiveness to treatment with an illudofulvene. Once determined to be responsive, the patient can be treated with an illudofulvene. In particular, the biomarker ERCC8 (SEQ ID NO:1) may be used to assess a cancer patient's (e.g., a patient having cancer that is resistant to one or more cancer therapies other than an illudofulvene) responsiveness to an illudofulvene. The expression level of the biomarker ERCC8 (SEQ ID NO:1) may be assessed using nucleic acid amplification methods (e.g., PCR) or a device (e.g., a microarray). As is described above, the expression level of ERCC8 (SEQ ID NO:1) in the patient sample may then be compared, e.g., to the expression level of ERCC8 (SEQ ID NO:1) in a cell (e.g., a cancer cell) or tissue (e.g., a tumor tissue) known to be sensitive or resistant to treatment with an illudofulvene and used to determine the cancer patient's responsiveness to an illudofulvene. The biomarker ERCC8 (SEQ ID NO:1) may be used alone to predict cancer patient responsiveness to treatment with an illudofulvene or in combination with one or more additional biomarkers (e.g., one, two, three, four, five, ten, or all of the biomarkers shown in Tables 1-8), such as ERCC6 (SEQ ID NOS:3-4), GTF2H1 (SEQ ID NOS:5-6), GTF2H2 (SEQ ID NOS:7-8), GTF2H3 (SEQ ID NOS:9-10), GTF2H4 (SEQ ID NOS:11-12), GTF2H5 (SEQ ID NOS:13-14), USP7 (SEQ ID NOS:15-16), UVSSA (SEQ ID NOS:17-18), ERCC3 (SEQ ID NOS: 19-20), ERCC2 (SEQ ID NOS:21-22), ERCC4 (SEQ ID NOS:23-24), ERCC5 (SEQ ID NOS:25-26), XPA (SEQ ID NOS:27-28), RAD18 (SEQ ID NOS:29-30), ERCC6L (SEQ ID NOS:31-32), ERCC6L2 (SEQ ID NOS:33-34), MYC (SEQ ID NOS:222-223), ERCC1 (SEQ ID NOS:236-237), PTGR1 (SEQ ID NOS:249-50), and/or PTGR2 (SEQ ID NOS:262-263). The expression level of the biomarker(s) may be determined using, e.g., a microarray, PCR, or other techniques described herein, for example, using a nucleic acid probe sequence based on the target sequences shown in Tables 1-8.

The expression level of the biomarker ERCC6 (SEQ ID NO:3) may be assessed using nucleic acid amplification methods (e.g., PCR) or a device (e.g., a microarray). As is described above, the expression level of ERCC6 (SEQ ID NO:3) in the patient sample may then be compared, e.g., to the expression level of ERCC6 (SEQ ID NO:3) in a cell (e.g., a cancer cell) or tissue (e.g., a tumor tissue) known to be sensitive or resistant to treatment with an illudofulvene and used to determine the cancer patient's responsiveness to an illudofulvene. The biomarker ERCC6 (SEQ ID NO:3) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker GTF2H1 (SEQ ID NO:5) may be used to assess a cancer patient's (e.g., a patient having cancer that is resistant to one or more cancer therapies other than an illudofulvene) responsiveness to an illudofulvene. The expression level of the biomarker GTF2H1 (SEQ ID NO:5) may be assessed using nucleic acid amplification methods (e.g., PCR) or a device (e.g., a microarray). As is described above, the expression level of GTF2H1 (SEQ ID NO:5) in the patient sample may then be compared, e.g., to the expression level of GTF2H1 (SEQ ID NO:5) in a cell (e.g., a cancer cell) or tissue (e.g., a tumor tissue) known to be sensitive or resistant to treatment with an illudofulvene and used to determine the cancer patient's responsiveness to an illudofulvene. The biomarker GTF2H1 (SEQ ID NO:5) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker GTF2H2 (SEQ ID NO:7) may be used to assess a cancer patient's (e.g., a patient having cancer that is resistant to one or more cancer therapies other than an illudofulvene) responsiveness to an illudofulvene. The expression level of the biomarker GTF2H2 (SEQ ID NO:7) may be assessed using nucleic acid amplification methods (e.g., PCR) or a device (e.g., a microarray). As is described above, the expression level of GTF2H2 (SEQ ID NO:7) in the patient sample may then be compared, e.g., to the expression level of GTF2H2 (SEQ ID NO:7) in a cell (e.g., a cancer cell) or tissue (e.g., a tumor tissue) known to be sensitive or resistant to treatment with an illudofulvene and used to determine the cancer patient's responsiveness to an illudofulvene. The biomarker GTF2H2 (SEQ ID NO:7) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker GTF2H3 (SEQ ID NO:9) may be used to assess a cancer patient's (e.g., a patient having cancer that is resistant to one or more cancer therapies other than an illudofulvene) responsiveness to an illudofulvene. The expression level of the biomarker GTF2H3 (SEQ ID NO:9) may be assessed using nucleic acid amplification methods (e.g., PCR) or a device (e.g., a microarray). As is described above, the expression level of GTF2H3 (SEQ ID NO:9) in the patient sample may then be compared, e.g., to the expression level of GTF2H3 (SEQ ID NO:9) in a cell (e.g., a cancer cell) or tissue (e.g., a tumor tissue) known to be sensitive or resistant to treatment with an illudofulvene and used to determine the cancer patient's responsiveness to an illudofulvene. The biomarker GTF2H3 (SEQ ID NO:9) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker GTF2H4 (SEQ ID NO:11) may be used to assess a cancer patient's (e.g., a patient having cancer that is resistant to one or more cancer therapies other than an illudofulvene) responsiveness to an illudofulvene. The expression level of the biomarker GTF2H4 (SEQ ID NO:11) may be assessed using nucleic acid amplification methods (e.g., PCR) or a device (e.g., a microarray). As is described above, the expression level of GTF2H4 (SEQ ID NO:11) in the patient sample may then be compared, e.g., to the expression level of GTF2H4 (SEQ ID NO:11) in a cell (e.g., a cancer cell) or tissue (e.g., a tumor tissue) known to be sensitive or resistant to treatment with an illudofulvene and used to determine the cancer patient's responsiveness to an illudofulvene. The biomarker GTF2H4 (SEQ ID NO:11) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker GTF2H5 (SEQ ID NO:13) may be used to assess a cancer patient's (e.g., a patient having cancer that is resistant to one or more cancer therapies other than an illudofulvene) responsiveness to an illudofulvene. The expression level of the biomarker GTF2H5 (SEQ ID NO:13) may be assessed using nucleic acid amplification methods (e.g., PCR) or a device (e.g., a microarray). As is described above, the expression level of GTF2H5 (SEQ ID NO:13) in the patient sample may then be compared, e.g., to the expression level of GTF2H5 (SEQ ID NO:13) in a cell (e.g., a cancer cell) or tissue (e.g., a tumor tissue) known to be sensitive or resistant to treatment with an illudofulvene and used to determine the cancer patient's responsiveness to an illudofulvene. The biomarker GTF2H5 (SEQ ID NO:13) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker USP7 (SEQ ID NO:15) may be used to assess a cancer patient's (e.g., a patient having cancer that is resistant to one or more cancer therapies other than an illudofulvene) responsiveness to an illudofulvene. The expression level of the biomarker USP7 (SEQ ID NO:15) may be assessed using nucleic acid amplification methods (e.g., PCR) or a device (e.g., a microarray). As is described above, the expression level of USP7 (SEQ ID NO:15) in the patient sample may then be compared, e.g., to the expression level of USP7 (SEQ ID NO:15) in a cell (e.g., a cancer cell) or tissue (e.g., a tumor tissue) known to be sensitive or resistant to treatment with an illudofulvene and used to determine the cancer patient's responsiveness to an illudofulvene. The biomarker USP7 (SEQ ID NO:15) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker UVSSA (SEQ ID NO:17) may be used to assess a cancer patient's (e.g., a patient having cancer that is resistant to one or more cancer therapies other than an illudofulvene) responsiveness to an illudofulvene. The expression level of the biomarker UVSSA (SEQ ID NO:17) may be assessed using nucleic acid amplification methods (e.g., PCR) or a device (e.g., a microarray). As is described above, the expression level of UVSSA (SEQ ID NO:17) in the patient sample may then be compared, e.g., to the expression level of UVSSA (SEQ ID NO:17) in a cell (e.g., a cancer cell) or tissue (e.g., a tumor tissue) known to be sensitive or resistant to treatment with an illudofulvene and used to determine the cancer patient's responsiveness to an illudofulvene. The biomarker UVSSA (SEQ ID NO:17) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker ERCC3 (SEQ ID NO:19) may be used to assess a cancer patient's (e.g., a patient having cancer that is resistant to one or more cancer therapies other than an illudofulvene) responsiveness to an illudofulvene. The expression level of the biomarker ERCC3 (SEQ ID NO:19) may be assessed using nucleic acid amplification methods (e.g., PCR) or a device (e.g., a microarray). As is described above, the expression level of ERCC3 (SEQ ID NO:19) in the patient sample may then be compared, e.g., to the expression level of ERCC3 (SEQ ID NO:19) in a cell (e.g., a cancer cell) or tissue (e.g., a tumor tissue) known to be sensitive or resistant to treatment with an illudofulvene and used to determine the cancer patient's responsiveness to an illudofulvene. The biomarker ERCC3 (SEQ ID NO:19) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker ERCC2 (SEQ ID NO:21) may be used to assess a cancer patient's (e.g., a patient having cancer that is resistant to one or more cancer therapies other than an illudofulvene) responsiveness to an illudofulvene. The expression level of the biomarker ERCC2 (SEQ ID NO:21) may be assessed using nucleic acid amplification methods (e.g., PCR) or a device (e.g., a microarray). As is described above, the expression level of ERCC2 (SEQ ID NO:21) in the patient sample may then be compared, e.g., to the expression level of ERCC2 (SEQ ID NO:21) in a cell (e.g., a cancer cell) or tissue (e.g., a tumor tissue) known to be sensitive or resistant to treatment with an illudofulvene and used to determine the cancer patient's responsiveness to an illudofulvene. The biomarker ERCC2 (SEQ ID NO:21) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker ERCC4 (SEQ ID NO:23) may be used to assess a cancer patient's (e.g., a patient having cancer that is resistant to one or more cancer therapies other than an illudofulvene) responsiveness to an illudofulvene. The expression level of the biomarker ERCC4 (SEQ ID NO:23) may be assessed using nucleic acid amplification methods (e.g., PCR) or a device (e.g., a microarray). As is described above, the expression level of ERCC4 (SEQ ID NO:23) in the patient sample may then be compared, e.g., to the expression level of ERCC4 (SEQ ID NO:23) in a cell (e.g., a cancer cell) or tissue (e.g., a tumor tissue) known to be sensitive or resistant to treatment with an illudofulvene and used to determine the cancer patient's responsiveness to an illudofulvene. The biomarker ERCC4 (SEQ ID NO:23) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker ERCC5 (SEQ ID NO:25) may be used to assess a cancer patient's (e.g., a patient having cancer that is resistant to one or more cancer therapies other than an illudofulvene) responsiveness to an illudofulvene. The expression level of the biomarker ERCC5 (SEQ ID NO:25) may be assessed using nucleic acid amplification methods (e.g., PCR) or a device (e.g., a microarray). As is described above, the expression level of ERCC5 (SEQ ID NO:25) in the patient sample may then be compared, e.g., to the expression level of ERCC5 (SEQ ID NO:25) in a cell (e.g., a cancer cell) or tissue (e.g., a tumor tissue) known to be sensitive or resistant to treatment with an illudofulvene and used to determine the cancer patient's responsiveness to an illudofulvene. The biomarker ERCC5 (SEQ ID NO:25) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker XPA (SEQ ID NO:27) may be used to assess a cancer patient's (e.g., a patient having cancer that is resistant to one or more cancer therapies other than an illudofulvene) responsiveness to an illudofulvene. The expression level of the biomarker XPA (SEQ ID NO:27) may be assessed using nucleic acid amplification methods (e.g., PCR) or a device (e.g., a microarray). As is described above, the expression level of XPA (SEQ ID NO:27) in the patient sample may then be compared, e.g., to the expression level of XPA (SEQ ID NO:27) in a cell (e.g., a cancer cell) or tissue (e.g., a tumor tissue) known to be sensitive or resistant to treatment with an illudofulvene and used to determine the cancer patient's responsiveness to an illudofulvene. The biomarker XPA (SEQ ID NO:27) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker RAD18 (SEQ ID NO:29) may be used to assess a cancer patient's (e.g., a patient having cancer that is resistant to one or more cancer therapies other than an illudofulvene) responsiveness to an illudofulvene. The expression level of the biomarker RAD18 (SEQ ID NO:29) may be assessed using nucleic acid amplification methods (e.g., PCR) or a device (e.g., a microarray). As is described above, the expression level of RAD18 (SEQ ID NO:29) in the patient sample may then be compared, e.g., to the expression level of RAD18 (SEQ ID NO:29) in a cell (e.g., a cancer cell) or tissue (e.g., a tumor tissue) known to be sensitive or resistant to treatment with an illudofulvene and used to determine the cancer patient's responsiveness to an illudofulvene. The biomarker RAD18 (SEQ ID NO:29) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker ERCC6/L (SEQ ID NO:31) may be used to assess a cancer patient's (e.g., a patient having cancer that is resistant to one or more cancer therapies other than an illudofulvene) responsiveness to an illudofulvene. The expression level of the biomarker ERCC6/L (SEQ ID NO:31) may be assessed using nucleic acid amplification methods (e.g., PCR) or a device (e.g., a microarray). As is described above, the expression level of ERCC6/L (SEQ ID NO:31) in the patient sample may then be compared, e.g., to the expression level of ERCC6/L (SEQ ID NO:31) in a cell (e.g., a cancer cell) or tissue (e.g., a tumor tissue) known to be sensitive or resistant to treatment with an illudofulvene and used to determine the cancer patient's responsiveness to an illudofulvene. The biomarker ERCC6/L (SEQ ID NO:31) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker ERCC6/L2 (SEQ ID NO:33) may be used to assess a cancer patient's (e.g., a patient having cancer that is resistant to one or more cancer therapies other than an illudofulvene) responsiveness to an illudofulvene. The expression level of the biomarker ERCC6/L2 (SEQ ID NO:33) may be assessed using nucleic acid amplification methods (e.g., PCR) or a device (e.g., a microarray). As is described above, the expression level of ERCC6/L2 (SEQ ID NO:33) in the patient sample may then be compared, e.g., to the expression level of ERCC6/L2 (SEQ ID NO:33) in a cell (e.g., a cancer cell) or tissue (e.g., a tumor tissue) known to be sensitive or resistant to treatment with an illudofulvene and used to determine the cancer patient's responsiveness to an illudofulvene. The biomarker ERCC6/L2 (SEQ ID NO:33) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker MYC (SEQ ID NO:222) may be used to assess a cancer patient's (e.g., a patient having cancer that is resistant to one or more cancer therapies other than an illudofulvene) responsiveness to an illudofulvene. The expression level of the biomarker MYC (SEQ ID NO:222) may be assessed using nucleic acid amplification methods (e.g., PCR) or a device (e.g., a microarray). As is described above, the expression level of MYC (SEQ ID NO:22) in the patient sample may then be compared, e.g., to the expression level of MYC (SEQ ID NO:222) in a cell (e.g., a cancer cell) or tissue (e.g., a tumor tissue) known to be sensitive or resistant to treatment with an illudofulvene and used to determine the cancer patient's responsiveness to an illudofulvene. The biomarker MYC (SEQ ID NO:222) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker ERCC1 (SEQ ID NO:236) may be used to assess a cancer patient's (e.g., a patient having cancer that is resistant to one or more cancer therapies other than an illudofulvene) responsiveness to an illudofulvene. The expression level of the biomarker ERCC1 (SEQ ID NO:236) may be assessed using nucleic acid amplification methods (e.g., PCR) or a device (e.g., a microarray). As is described above, the expression level of ERCC1 (SEQ ID NO:236) in the patient sample may then be compared, e.g., to the expression level of ERCC1 (SEQ ID NO:236) in a cell (e.g., a cancer cell) or tissue (e.g., a tumor tissue) known to be sensitive or resistant to treatment with an illudofulvene and used to determine the cancer patient's responsiveness to an illudofulvene. The biomarker ERCC1 (SEQ ID NO:236) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker PTGR1 (SEQ ID NO:249) may be used to assess a cancer patient's (e.g., a patient having cancer that is resistant to one or more cancer therapies other than an illudofulvene) responsiveness to an illudofulvene. The expression level of the biomarker PTGR1 (SEQ ID NO:249) may be assessed using nucleic acid amplification methods (e.g., PCR) or a device (e.g., a microarray). As is described above, the expression level of PTGR1 (SEQ ID NO:249) in the patient sample may then be compared, e.g., to the expression level of PTGR1 (SEQ ID NO:249) in a cell (e.g., a cancer cell) or tissue (e.g., a tumor tissue) known to be sensitive or resistant to treatment with an illudofulvene and used to determine the cancer patient's responsiveness to an illudofulvene. The biomarker PTGR1 (SEQ ID NO:249) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The biomarker PTGR2 (SEQ ID NO:262) may be used to assess a cancer patient's (e.g., a patient having cancer that is resistant to one or more cancer therapies other than an illudofulvene) responsiveness to an illudofulvene. The expression level of the biomarker PTGR2 (SEQ ID NO:262) may be assessed using nucleic acid amplification methods (e.g., PCR) or a device (e.g., a microarray). As is described above, the expression level of PTGR2 (SEQ ID NO:262) in the patient sample may then be compared, e.g., to the expression level of PTGR2 (SEQ ID NO:262) in a cell (e.g., a cancer cell) or tissue (e.g., a tumor tissue) known to be sensitive or resistant to treatment with an illudofulvene and used to determine the cancer patient's responsiveness to an illudofulvene. The biomarker MYC (SEQ ID NO:222) may be used alone to predict cancer patient responsiveness to treatment with an illudofulvene or in combination with one or more additional biomarkers (e.g., one, two, three, four, five, ten, or all of the biomarkers shown in Tables 1-8), such as the Select Sensitive Genes. The expression level of the biomarker(s) may be determined using, e.g., a microarray, PCR, or other techniques described herein, for example, using a nucleic acid probe sequence based on the target sequences shown in Tables 1-8.

The following Examples 1-4, are intended to illustrate, rather than limit, the invention.

Example 1

Identification of Biomarkers of Sensitivity to an Illudofulvene using cell lines deficient in a specific DNA repair gene. Cell growth inhibition assays were performed using Illudofulvene against a bank of cell lines which are deficient in DNA repair based on lack of expression of a specific DNA repair gene (Table 21).

TABLE 21

Sensitivity of DNA repair Deficient Cells to Illudofulvene Analog

| Cell line | DNA-repair Gene Deficient | GI50 value (nM) Mean +/SD (N = 3) | Corresponding GENE SEQ ID NOS: |
|---|---|---|---|
| AA8 | None (wild type) | 1440 ± 70 | None |
| UV20 | ERCC1 | 144 ± 4 | 236-237 |
| UV5 | ERCC2 | 60 ± 7 | 21, 22, 145-155 |
| UV24 | ERCC3 | 127 ± 13 | 19, 20, 134-144 |
| UV41 | ERCC4 | 167 ± 10 | 23, 24, 156-166 |
| UV135 | ERCC5 | 174 ± 22 | 25, 26, 167-177 |
| UV61 | ERCC6 | 366 ± 18 | 3, 4, 46-56 |
| EM9 | XRCC1 | 1197 ± 44 | None |

Studies clearly identified that a cell which is deficient in Transcription-coupled repair (TCR) (e.g. ERCC2 or ERCC3) is sensitive to Illudofulvene as compared to its parental line (AA8) whereas cells deficient in other DNA repair components, such as homologous recombination (e.g. XRCC1). These results are consistent with the finding that Illudofulvene Analogs produce a damage that is repaired only by the TCR genes and that other DNA-repair pathways (e.g. homologous recombination, Base-excision, etc.) are not involved (Kelner, et al. Cancer Research, 55:4936-40, 1995; and Jaspers, et al. DNA Repair 1:1027-38, 2002, both of which are herein expressly incorporated by reference in their entireties and for all purposes). TCR genes means Excision Repair Cross-Complementation (ERCC) 1 (ERCC1), ERCC2, ERCC3, ERCC4, ERCC5, ERCC6, ERCC6L, ERCC6L2, DNA Damage Recognition and Repair Factor (XPA), Ubiquitin Specific Peptidase? (USP7), UV Stimulated Scaffold Protein A (UVSSA), E3 ubiquitin-protein ligase RAD18 (RAD18), General Transcription Factor IIH (GTF2H) Subunit 1 (GTF2H1), GTF2H2, GTF2H2, GTF2H3, GTF2H4, GTF2H5 genes.

Example 2

Identification of Biomarkers of Sensitivity to An Illudofulvene Using Gene Expression data derived by DNA chip analysis of the 60 cancer cell lines of the NCI60 data set.

The expression of thousands of genes in each of the cell lines composing the NCI DTP 60 cell line has been analyzed using a variety of different DNA chips (or microarrays) and is publicly available at website dtp.cancer.gov/compare-web-public_compare/SearchAndDisplay/SearchAndDisplay.

Data has been generated using a variety of Affymetrix DNA chips including HG-U133A array (GENELOGIC_133 data set), HG-U133 Plus 2.0 array (GENELOGIC_133PLUS2 data set), the HG-95 (GENELOGIC_U95 data set), as well as others. Results from DNA microchips produced by other companies, e.g. Novartis, are also available. The data from these array experiments has been logit normalized to allow a direct comparison of a genes expression between different cell lines. For each array, the logit transformation was performed followed by a Z-transformation to mean zero and SD.

One can determine the growth inhibition (GI50), total growth inhibition (TGI), or lethal concentration (LC50) for a drug for each of the cell lines in the NCI DTP 60 cell line panel. One can use these 3 values to search for correlations against all gene expressions in all cell lines using the NCI's publicly available CELL MINER Software. Alternatively, one can down load for a specific gene its relative expression in each of the 60 cell lines using the NCI's publicly available COMPARE Software, and performs the expression for a specific gene.

Figure 2:
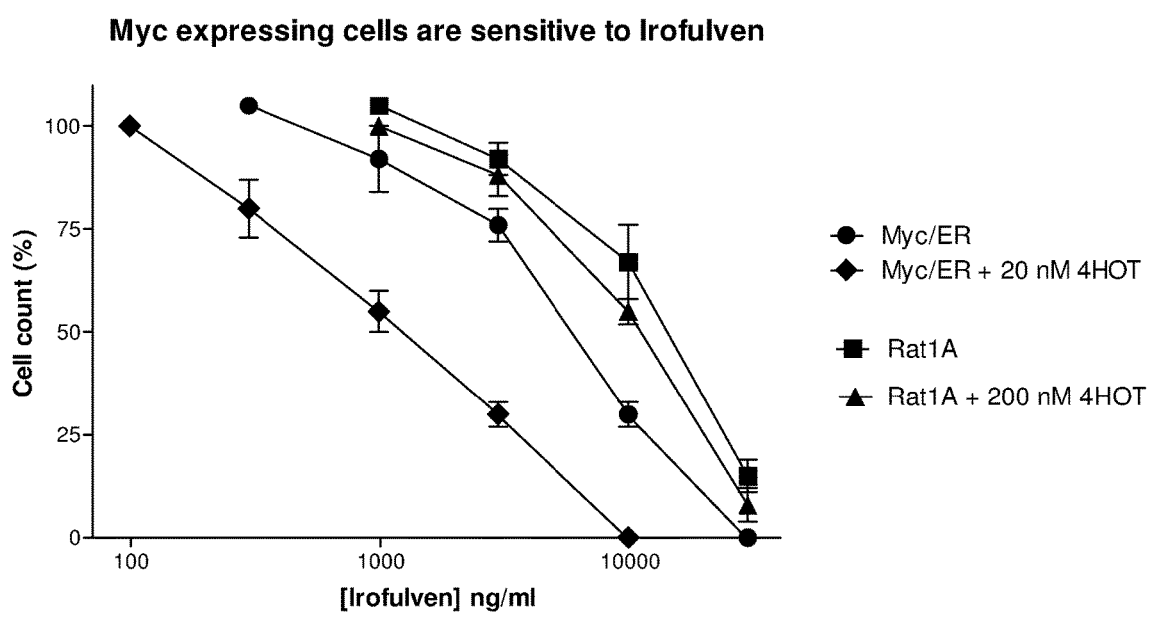
FIG. 2 shows that expression of MYC causes cancer cells to become sensitive to the illudofulvene (Analog 002), according to an embodiment of the invention.

A gene's expression in each cell line can then be correlated to the ability of an illudofulvene to hinder cell growth (GI50, TGI, or LC50 value) and a correlation coefficient determined to identify genes positively and negatively correlated to sensitivity to an Illudofulvene Analog. Positively correlated genes can be those in which as the expression of the gene increase, the tumor cells become sensitive to the drug. Negatively correlated genes can be those that as the expression of the gene decreases, the tumor cells become sensitive to the drug.

Analysis of the cell growth inhibition values for the Illudofulvene Analog 002, to specific gene expression values retrieved by COMPARE from data generated by the Affymetrix HG-U133 Plus 2.0 array again confirms that a deficiency in expression of components of TCR-pathway confers sensitivity to Illudofulvene Analog 002 (Table 16) including ERCC2, ERCC8, GTF2H1, USP7, and XPC. However, there was no correlation with components of other DNA repair pathways such as double strand repair (RAD50), NER (XPC), X-ray repair (XRCC1), etc.

Similar results are obtained with illudofulvene Analogs 142, 176, 184, (see Tables 17-20).

Example 3

Identification of Biomarkers whose expression causing sensitivity to Illudofulvene Analog 002 followed by confirmation using Gene Expression data derived by DNA chip analysis of the 60 cancer cell lines of the NCI60 data set (see, Example 2 above) and also confirmed using cell lines deficient in a specific GENE (see, Example 1 above).

To further explore the mechanism(s) of action of Illudofulvene Analog 002, we used phage display technology to identify peptides capable of binding to the drug and utilized this information to identify potential target proteins for Illudofulvene Analog 002 binding. The proto-oncogene c-myc (Gene Symbol MYC) was identified as a putative target, and its role in sensitizing tumor cells to an Illudofulvene Analog was confirmed using Gene Expression data derived by DNA chip analysis of the 60 cancer cell lines of the NCI60 data set (see, Example 2 above) and then confirmed in vitro using cell lines deficient in a specific GENE (see, Example 1 above).

Three different ER2537-derived phage libraries (New England Biolabs, Beverly, Mass.) were used for biopanning studies; 7-mer, 12-mer, and C7C. The latter consisted of a 7-mer library flanked by two cysteines to allow disulfide formation. The aldehyde derivative of Illudofulvene Analog 002 was prepared by reacting Illudofulvene Analog 001 with acrolein, and then linked to biotin using Biotin-LC-hydrazide (Pierce). A 96 well avidin coated plate was coated with 75 μg of the target molecule (Illudofulvene Analog 001-biotin conjugate) in 150 μl of PBS, and rocked gently overnight at 4° C. The desired phage library was added to the wells and the plate gently rocked for 60 minutes at room temperature. Wells were rinsed ten times with TBST (50 mM Tris-HCl, pH 7.5, 150 mM NaCl, 0.1% v/v tween-20). Bound phage was eluted by applying excess target molecule (Illudofulvene Analog 001) and increasing salt concentration. One μl of the eluate was used for titering and the remaining eluate was amplified using standard techniques.

Using phage display panning we isolated 157 nonredundant sequences capable of binding to Illudofulvene Analog 002. Two algorithms were used to predict a sequence and 3D structure of a protein capable of binding to Illudofulvene Analog 002; "peptide elongation without substitution" and "peptide elongation with substitution". Each of the 157 sequences was initially aligned using a FASTA program to proteins in the PIR database followed by the desired peptide elongation process. A complete description of the process has been published (Tsigelny I, Sharikov Y, Kelner MJ, and Ten Eyck LF., Protein structure prediction on the basis of combinatorial peptide libraries screening. In: Protein Structure Prediction: A Bioinformatics Approach. Ed: I Tsigelny. International University Line Publishing, 2001, which is herein expressly incorporated by reference in its entirety for all purposes). The algorithm of elongation without substitution identified c-myc as a potential target of Illudofulvene Analog 002 and docking studies revealed a potential binding site for Illudofulvene Analog 002 that matched the peptides recovered by phage panning.

To determine if the MYC gene had clinical significance in regards to the therapeutic activity of Illudofulvene Analog 002, we inputted the in vitro cell culture values (i.e. growth inhibition values (GI50), or the total growth inhibition (TGI), or the lethal concentration (LC50) obtained for Illudofulvene Analog 002 from cell lines contained in the NCI 60 cell line panel and used CELLMINER to screen for correlation against the normalized expression of genes in cell lines in the NCI 60 cell line panel.

Using CELLMINER, after normalization, genes with, e.g., a Pearson correlation coefficient greater than about 0.2 or below about −0.2 can be classified as biomarkers of sensitivity or resistance, respectively. In particular, a correlation coefficient of about 0.2 or greater is a statistically significant cut-off known in the art for establishing whether the expression level of A GENE, e.g., the genes shown in Tables 1-8, correlate with the likelihood of cancer treatment sensitivity, such as sensitivity to Illudofulvene Analog 002. Thus, a correlation coefficient of about 0.2 or greater or about −0.2 or lower can be used to estimate the statistical significance of the expression level of the genes of Tables 1-8 for predicting patient responsiveness to treatment with an Illudofulvene Analog according to the methods described herein.

Using CELLMINER the correlation of MYC expression to Illudofulvene Analog 002 activity was identified at 0.42, and a p value of 0.000941 (highly significant) indicating MYC expression in a patient's tumor can be predictive of response to treatment with Illudofulvene Analog 002. A similar significant correlation between MYC expression and GI50 values for CAP-0142 ($P<0.001$) and CAP-0241 ($P<0.001$). To confirm the role of c-myc in Illudofulvene Analog 002 cytotoxicity, studies were conducted using the c-myc negative Rat 1A line, and c-myc positive daughter line Myc/Rat1A. The expression of c-myc in this cell line is under the control of a modified receptor that responds to 4-hydroxytamoxifen (4HOT). FIG. 2 shows that the presence of 4HOT expresses c-myc and induces sensitivity to expression of MYC causing cancer cells to become sensitive to illudofulvene (Analog 002) in the Myc/ER daughter, but not the Rat 1A parental cell line.

Figure 3:
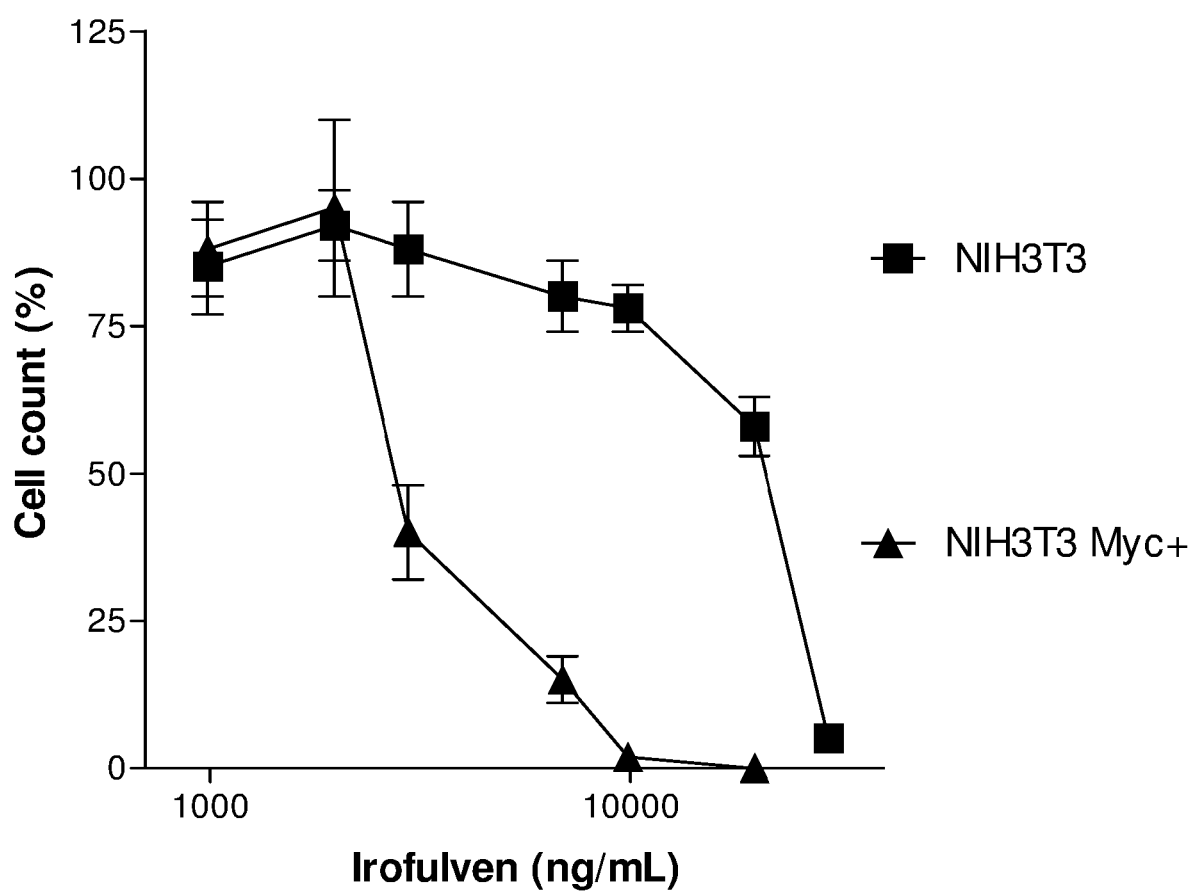
FIG. 3 shows a comparison of Cell Count (%) as a function of the Illudofulvene Analog 002 concentration for two cell types (NIH3T3 MYC+ and NIH3T3 MYC-null), according to an embodiment of the invention.

FIG. 3 shows the influence of c-myc expression on Illudofulvene Analog 002 cytotoxicity in a comparison of Cell Count (%) as a function of Analog 002 concentration for a paired c-myc expressing (NIH3T3 MYC+) cell line and a c-myc nonexpressing (NIH3T3) or null cell line. Expression of cellular c-myc conferred a greater than 10 fold increase in sensitivity to illudofulvene Analog 002 to the daughter NIH3T3 MYC+ cell line as compared to the parental c-myc null or nonexpressing NIH3T3 cell line, based on the decrease in cell count. The ability of c-myc expression to alter cellular sensitivity to other agents was also studied. The expression of c-myc, however, did not alter cellular sensitivity towards a variety of other anticancer agents (including mithramycin, mitomycin C, topotecan (as shown in FIG. 4B—FIG. 4D) or cisplatin (data not shown) as compared to Illudofulvene Analog 002 (see FIG. 4A).

Example 4

Most relevant to clinical applications, Illudofulvene Analog 002 activity is independent of common resistance mechanisms such as the multi-medicant resistance phenotype, anti-apoptotic B-cell lymphoma 2 (Bcl-2) over expression, as well as tumor protein 53 (p53) and cyclin dependent kinase inhibitor 1 (p21/WAF1) mutations (see Tables 7 and 11).

Growth factors, including peptides and proteins are critical mediators of a wide range of cell-cell communication. They are important endocrine, paracrine and autocrine messengers. Growth factors function as neurotransmitters and neuromodulators, regulate chemotaxis, immune function, development, cell growth, and can influence tumor cells. The receptors that recognize growth factors are highly selective and define specific cell populations. As a result, growth factor receptors are a large and important class of medicant (including drug) targets. In addition to physiologic noncancerous cell populations, these receptors can also be expressed in various cancer cell populations.

FIG. 1 shows the ability of the illudofulvene Analog 002 to induce tumor regression in the MV522 cell line (a lung-derived adenocarcinoma cell line) compared with other alternative compounds (i.e., Fludarabine, Cytarabine and Doxorubicin). In various embodiments of the invention, the MV522 cell line represents a "target" cell line. That is an illudofulvene analog that exhibits toxicity against this solid tumor cell line shows a desirable result. The 8392B cell line represents a hematopoietic cell line. In various embodiments of the invention, the 8392B cell line is considered a "nontarget" cell line. The two hour toxicity data represents the concentration of a given analog for which a two hour exposure will inhibit 50% of the DNA synthesis activity in a given cell line. The 48 hour exposure data represents the concentration at which a given analog with a 48 hour exposure will inhibit the growth or viability in a given cell line as defined by the standard Trypan Blue Exclusion assay. As an example, Illudofulvene Analog 002 will inhibit the target MV522 cell line at 110 nM with only a 2 hour exposure but has no inhibitory effect on the nontarget 8392B cell line at 26,000 nM (26 µM), see Table 13. Illudofulvene Analog 002 with a prolonged exposure period (e.g. 48 hours) can eventually inhibit the 8392B nontarget cell line, see Table 13. In contrast, Illudofulvene Analog 201 will inhibit the target MV522 cell line with only a 2 hour exposure (IC50=360 nM) but has minimal effect on the 8392B cell nontarget line with even a 48 hour exposure (IC50=26,000 nM) indicating superior anticancer activity as a monotherapeutic agent, see Table 13. In contrast to these two analogs, Illudofulvene Analog 224 displayed minimal toxicity as well as no differential toxicity between the target and nontarget cell line indicating it can have minimal properties as a monotherapeutic anticancer agent, see Table 13. Table 10 indicates that Illudofulvene Analog 001 or Illudofulvene Analog 002 have a novel mechanism of action versus chemotherapeutic agents including Other Drugs as set forth herein.

Compositions and Methods of Administration.

In other embodiments, described is a pharmaceutical composition including an effective amount of an illudofulvene and a pharmaceutically acceptable carrier or vehicle. The compositions are suitable for veterinary or human administration.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or infrasternal injection or infusion techniques. In one aspect, the compositions are administered parenterally. In a specific embodiment, the compositions are administered intravenously.

Pharmaceutical compositions can be formulated so as to allow an illudofulvene to be bioavailable upon administration of the composition to a patient. Compositions can take the form of one or more dosage units, where for example, a tablet can be a single dosage unit, and a container of an illudofulvene in liquid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the illudofulvene, the manner of administration, and the composition employed.

The pharmaceutically acceptable carrier or vehicle can be solid or particulate, so that the compositions are, for example, in tablet or powder form. The carrier(s) can be liquid. In addition, the carrier(s) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben;

antioxidants such as ascorbic acid or sodium bisulfite; chelating agents such as ethylenediamine tetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the illudofulvene that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and can be decided according to the judgment of the practitioner and each patient's circumstances.

The compositions comprise an effective amount of an illudofulvene such that a suitable dosage will be obtained. Typically, this amount can be at least about 0.01% of an illudofulvene by weight of the composition. In an exemplary embodiment, pharmaceutical compositions are prepared so that a parenteral dosage unit (actual powder) dissolved and used to inject the patient was 98% drug by weight, although once diluted in an IV the dose contains from about 0.01% to about 2% by weight).

For intravenous administration, the composition can comprise from about 0.01 to about 100 mg of an illudofulvene per kg of the patient's body weight. In one aspect, the composition can include from about 1 to about 100 mg of an illudofulvene per kg of the patient's body weight. In another aspect, the amount administered will be in the range from about 0.1 to about 25 mg/kg of body weight of the illudofulvene.

Generally, the dosage of an illudofulvene administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

The illudofulvene can be administered by any convenient route, for example by infusion or bolus injection. Administration can be systemic or local. Various delivery systems are known, e.g., encapsulation in liposomes, micro-particles, microcapsules, capsules, etc., and can be used to administer an illudofulvene. In certain embodiments, more than one illudofulvene can be administered to a patient.

In specific embodiments, it can be desirable to administer one or more illudofulvene locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the illudofulvene can be delivered in a controlled release system, such as but not limited to, a pump or various polymeric materials can be used. In yet another embodiment, a controlled-release system can be placed in proximity of the target of the illudofulvene, e.g., the liver, thus requiring only a fraction of the systemic dose.

The present compositions can take the form of solutions, pellets, powders, sustained-release formulations, or any other form suitable for use.

In an embodiment, the illudofulvenes are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where an illudofulvene is to be administered by infusion, it can be dispensed, for example, with an infusion bottle containing sterile pharmaceutical grade water or saline. Where the illudofulvene can be administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer, an autoimmune disease or an infectious disease.

The illudofulvene can also be used in an in vitro or ex vivo fashion, such as for the treatment of certain cancers, including, but not limited to leukemia and lymphomas, such treatment involving autologous stem cell transplants. This can involve a multi-step process in which the animal's autologous hematopoietic stem cells are harvested and purged of all cancer cells, the animal's remaining bone-marrow cell population can then eradicated via the administration of a high dose of an illudofulvenes with or without accompanying high dose radiation therapy, and the stem cell graft can be infused back into the animal. Supportive care can then be provided while bone marrow function is restored and the patient recovers.

A method of ablating cancer cells comprising the steps of selecting an illudofulvene which is cytotoxic to the cancer cell and treating the cancer cells with the illudofulvene.

Figure 5:
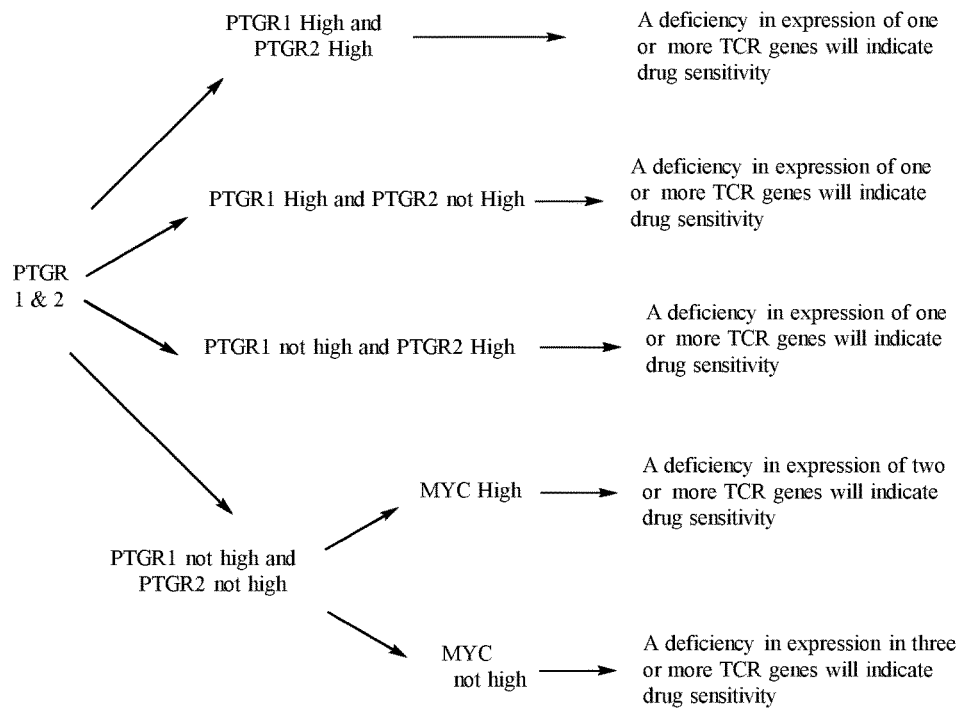
FIG. 5 shows a scheme relating the responsiveness of the cancer patient to treatment with Illudofulvenes based on the relative expression of the biomarkers.

In an embodiment of the present invention, a tumor sample from a patient can be harvested and processed to identify the relative expression of genes encoding the biomarkers described in this application that predict the responsiveness of the patient to Illudofulvenes. Once the relative expression of the biomarkers has been determined, the responsiveness of the cancer patient to treatment with Illudofulvenes, can be determined as outlined in the FIG. 5.

In an embodiment of the present invention, a cancer patient who has an upregulated expression of either PTGR1 or PTGR2 will display responsiveness to treatment with an Illudofulvene if there is a deficiency in any one (or more) of the TCR genes. In an embodiment of the present invention, a cancer patient who has an upregulated expression of either PTGR1 or PTGR2 or an upregulated expression of Myc will display responsiveness to treatment with an Illudofulvene if there is a deficiency in any one (or more) of the TCR genes.

In an embodiment of the present invention, a cancer patient who has an upregulated expression of Myc and does not have an upregulated expression either PTGR1 or PTGR2 will display responsiveness to treatment with an Illudofulvene if there is a deficiency in any two (or more) of the TCR genes. In an embodiment of the present invention, a cancer patient who does not have upregulated expression of PTGR1 and PTGR2 but has an upregulated expression of Myc will display responsiveness to treatment with an Illudofulvene if there is a deficiency in any two (or more) of the TCR genes.

In an embodiment of the present invention, a cancer patient who does not have an upregulated expression of PTGR1 and PTGR2 and does not have an upregulated expression of Myc will display responsiveness to treatment with an Illudofulvene if there is a deficiency in any three (or more) of the TCR genes. In an embodiment of the present invention, a cancer patient who does not have an upregulated expression of Myc and does not have an upregulated expression of PTGR1 and PTGR2 will display responsiveness to treatment with an Illudofulvene if there is a deficiency in any three (or more) of the TCR genes. In an embodiment of the present invention, a cancer patient who does not have an upregulated expression of PTGR1, PTGR2, and Myc will display responsiveness to treatment with an Illudofulvene if there is a deficiency in any three (or more) of the TCR genes.

Quantification of Gene mRNA Expression by Probe Analysis.

Tumor tissue can be harvested and total RNA can be purified using Trizol Reagent (Invitrogen Life Technology, 15596-018, Waltham, Mass.) and the RNeasy Mini Kit (Qiagen, 74104, Germantown, Md.). The mRNA can then be purified (from the total RNA) using an Oliogotex mRNA kit (Qiagen, 70022, Germantown, Md.). The isolated tissue mRNA can then be fixed to a nylon membrane (ThermoFisher, AM10102, Waltham, Mass.), by UV crosslinking (Stratagene, UC Crosslinker 2400, La Jolla, Calif.), for subsequent analysis of the relative quantity expressed by a specific gene. Probes can then be prepared by PCR labeling. Probes can be labeled with a radioactive isotope, e.g. P32 or P33, but the preferred approach is use of a nonradioactive label such as Digoxigen-11-dUTP (Sigma Aldrich, 1157315290, St Louis, Mo.). Other potential nonradioactive probe labeling methods include the use of Biotin-16-UTP, Biotin-11-CTP or Fluoroscein-12-UTP. In PCR labeling, a thermostable polymerase (Agilent, 600195, Santa Clara, Calif.) incorporates the Digoxigen-11-dUTP as it amplifies a specific region of template DNA that is often contained in a plasmid. The specificity of the probe (or gene under study) can be determined by the two PCR primers utilized. The result can be a highly labeled, highly specific and sensitive hybridization probe for quantifying the amount of corresponding mRNA in a tissue sample. The hybridization of the probe to the membrane can be performed normally in roller bottles in a hybridization oven, followed by high stringency washes at elevated temperatures up to 70° C., to remove nonspecific binding and background signal. The digoxigen labeled probes are detected using labeled anti-digoxigen antibody (Abcam product number 420) or Fab fragments (Sigma Aldrich, 11207733910, St Louis, Mo.). If another label is utilized for probe labeling, such as biotin, then an anti-biotin labeled antibody can be used. Visualization and quantification of signal can be performed using a phosphoimager (Storm, 860 imager, Ramsey, Minn.) or a fluoroimager, depending upon the type of label used in the detection antibody.

In an embodiment of the invention, the tumor tissue is harvested and mRNA purified from the tumor. The mRNA is processed, subjected to electrophoresis and then analyzed with the desired probe for individual gene products, as well as for the three "housekeeping" genes (ACTB, TFRC, and GAPD). The required probes specific for detecting a gene product are prepared using PCR with the stated primers specific for that gene (Table 1) and labeled with a detection product as described in this application. The raw expression of each gene product is then determined using a densitometer appropriate for the label used (fluorescent, visible, photometer, radioisotope, etc.) Next a "relative ratio of expression" is determined for each of the gene products under investigation versus the individual "housekeeping genes" as described above in the Microarray section. These ratios are then compared to ratios obtained for a cell known to be sensitive to an Illudofulvene as well as to ratios for a cell know to be resistant to an Illudofulvene. One can then determine whether (i) a PTGR gene is upregulated, and/or (ii) the MYC gene is upregulated and (iii) there is a deficiency in a specific TCR gene. The tumor can then be classified as either sensitive, or resistant, to Illudofulvenes based on this analysis.

TABLE 1

Primers for use with gene mRNA expression, according to embodiments of the invention.

| GENE | Upper Primer SEQ ID NOS: | Lower Primer SEQ ID NOS: | Probe (bp) | Primer Annealing Temp (° C.) |
|---|---|---|---|---|
| ERCC1 | 275 | 276 | 467 | 59 |
| ERCC2 | 277 | 278 | 601 | 60 |
| ERCC3 | 279 | 280 | 415 | 59 |
| ERCC4 (set 1) | 281 | 282 | 1217 | 56 |
| ERCC4 (set 2) | 283 | 284 | 500 | 58 |
| ERRC5 | 285 | 286 | 872 | 56 |
| ERCC6 | 287 | 288 | 876 | 55 |
| ERCC6L | 289 | 290 | 629 | 62 |
| ERCC6L2 | 291 | 292 | 594 | 63 |
| ERCC8 | 293 | 294 | 534 | 50 |
| GTF2H1 | 295 | 296 | 1139 | 66 |
| GTF2H2 | 297 | 298 | 802 | 64 |
| GTF2H3 | 299 | 300 | 344 | 62 |
| GTF2H4 | 301 | 302 | 560 | 62 |
| GTF2H5 | 303 | 304 | 606 | 63 |
| MYC | 305 | 306 | 630 | 63 |
| PTGR1 | 307 | 308 | 621 | 61 |
| PTGR2 | 309 | 310 | 626 | 63 |
| RAD18 | 311 | 312 | 601 | 58 |
| USP7 | 313 | 314 | 600 | 62 |
| UVSSA | 315 | 316 | 595 | 62 |
| XPA | 317 | 318 | 459 | 64 |
| XPC | 319 | 320 | 855 | 62 |
| XPE | 321 | 322 | 629 | 62 |
| Controls | | | | |
| ACTB β-Actin | 323 | 324 | 566 | 59 |
| TFRC | 325 | 326 | 1096 | 53 |
| GAPD | 327 | 328 | 547 | 60 |

The cDNA genes under investigation were isolated internally (by applicant) from a lambda gt11 expression vector using primers above, then cloned into a plasmid. All sequences were confirmed by nucleotide sequencing. The genes at the time were not available from commercial sources.

Microarray Analysis.

Tumor tissue can be harvested and total RNA can be purified using Trizol Reagent (Invitrogen Life Technology, 15596-018, Waltham, Mass.) and the RNeasy Mini Kit (Qiagen, 74104, Germantown, Md.). The mRNA can then be purified (from the total RNA) using an Oliogotex mRNA kit (Qiagen, 70022, Germantown, Md.). The Oliogotex mRNA kit (Qiagen, 70022, Germantown, Md.) is the preferred method for preparing mRNA for Genechip® analysis such as the Affymetrix® platform. Prior to use in a Microarray analysis, the purified mRNA (~1 to 2 µg) can be first reverse transcribed using a T7-Oligo(dT) Promoter Primer (Affymetrix GeneChip T7-Oligo(dT) Promoter Primer Kit 900375, Waltham, Mass.) in the first-strand cDNA synthesis reaction. Alternatively, total RNA (10 µg to 15 µg) can be used if of high quality.

Next an RNase H-mediated second-strand cDNA synthesis can be performed, the double-stranded cDNA can be purified, and this double-strand cDNA serves as the template in a subsequent in vitro transcription (IVT) reaction (Affymetrix GeneChip IVT kit 900688, Waltham, Mass.). The IVT reaction can be carried out in the presence of provided T7 RNA Polymerase and a biotinylated nucleotide analog/ribonucleotide mix for complementary RNA (cRNA) amplification and biotin labeling. The biotinylated cRNA targets are then cleaned up and fragmented using the buffer provided in the kit.

Next the cRNA under study and a control oligonucleotide are prepared in a hybridization solution (Affymetrix, 900454, Waltham, Mass.) and added to the Affymetrix HG-U133 Plus 2 array cartridge, then placed in the hybridization oven at 45 C.° with rotation at 60 RPM, for 16 hours. The HG-U133 cartridge can be then washed and stained using the appropriate Fluidics station per manufacturer's protocol. The array can then be scanned using an appropriate device such as the Affymetrix GeneChip scanner or a generic scanner such as the Agilent GeneArray scanner. Normalization and analysis of data can be accomplished using the NetAffx Software (Thermo Fisher, Waltham, Mass.), the Gene Spring GX 9 software (Agilent, Santa Clara, Calif.) or open source academic software such as R/Bioconductor.

The specific probe sequences and corresponding Affymetrix IDs, for the biomarkers involved, for the Human Genome U133 Plus 2.0 array (HG-U133 Plus 2) are provided in Tables 2 and 3.

In an embodiment of the invention, the tumor tissue is harvested and the relative expression of the individual gene products, as well as the mRNA expression for the three "housekeeping" genes (ACTB, TFRC, GAPD), is quantified by a microarray apparatus using the specific probes for each gene product (see Tables 2 and 3). Next a "relative ratio of expression" is determined for each of the gene products under s investigation versus the individual "housekeeping genes" (e.g. ERCC6 expression/ACTB expression). This is accomplished by dividing the raw value of expression for each gene product under study by the raw value of expression for the desired "housekeeping gene". As an example the ERCC6/ACTB, ERCC6/TFRC, and the ERRC6/GAPD expression ratios for the tumor under study are calculated. Next an analysis is performed by comparing each relative ratio for each gene using each housekeeping gene, and comparing the ratio to the same ratio for a cell known to be sensitive to an Illudofulvene as well as a cell know to be resistant to an Illudofulvene. As an example the ERCC6/ACTB, ERCC6/TFRC, and the ERRC6/GAPD expression ratios for the tumor under study are compared to the same ratios in a cell known to be sensitive to an Illudofulvene as well as a cell know to be resistant to an Illudofulvene. Note that only one of the many gene ratios could be similar to a ratio derived from a cell known to be sensitive to an Illudofulvene in order to classify the tumor as TCR deficient. If any single component of the TCR pathway is deficient then that single deficiency is sufficient to render a tumor sensitive to Illudofulvenes (see Table 10). Similarly, the ratios for the individual expression of PTGR1, PTGR2, and MYC to the three "housekeeping" genes can be derived and each ratio can be compared to the same ratio in a cell known to be sensitive to an Illudofulvene as well as a cell know to be resistant to an Illudofulvene. This allows a classification as to whether PTGR1, PTGR2, or MYC are either upregulated or not upregulated and which specific gene(s) are upregulated for that individual tumor. The classification also allows determination of the specific TCR genes that are deficient.

TABLE 2

Probe Sequences to analyze not upregulated gene products that confer sensitivity to Illudofulvenes.

| Gene | Affymetrix ID | SEQ ID NOS: |
|---|---|---|
| ERCC8 | 201562_at | 35-45 |
| ERCC6 | 207347_at | 46-56 |
| GTF2H1 | 202451_at | 57-67 |
| GTF2H2 | 230177_at | 68-78 |
| GTF2H3 | 239346_at | 79-89 |
| GTF2H4 | 203577_at | 90-100 |
| GTF2H5 | 213357_at | 101-111 |
| USP7 | 2014498_at | 112-122 |
| UVSSA | 241201_at | 123-133 |
| ERCC3 | 202176_at | 134-144 |
| ERCC2 | 213468_at | 145-155 |
| ERCC4 | 210158_at | 156-166 |
| ERCC5 | 202414_at | 167-177 |
| XPA | 205672_at | 178-188 |
| RAD18 | 223417_at | 189-199 |
| ERCC6/L | 219650_at | 200-210 |
| ERCC6/L2 | 228211_at | 211-221 |
| ERCC1 | 203719_t | 238-248 |

Affymetrix IDs refer to the array type Human Genome U133 Plus 2.0 (HG-U133 Plus 2)

TABLE 3

Probe Sequences to analyze upregulated gene products that confer sensitivity to Illudofulvenes

| Gene | Affymetrix ID | SEQ ID NOS: |
|---|---|---|
| MYC | 20243_s_at | 224-235 |
| PTGR1 | 231897_at | 251-261 |
| PTGR2 | 230774_at | 264-274 |

Affymetrix IDs refer to the array type Human Genome U133 Plus 2.0 (HG-U133 Plus 2)

RT-PCR Analysis.

In an embodiment of the invention, the RT-PCR Analysis can be carried out using the Hydrolysis Taqman Fluorescent probe approach. Tumor tissue can be harvested and total RNA can be purified using Trizol Reagent (Invitrogen Life Technology, 15596-018, Waltham, Mass.) and the RNeasy Mini Kit (Qiagen, 74104, Germantown, Md.). The mRNA can then be purified (from the total RNA) using an Oliogotex mRNA kit (Qiagen, 70022, Germantown, Md.). Then reverse transcription can be performed using oligo(dT) and random hexamers and SuperScript® H (ThermoFisher, #18064014, Waltham, Mass.) to produce cDNA. Each reaction mixture contains approximately 50 ng of tumor-derived cDNA.

The desired gene primers, and associated hydrolysis oligonucleotide probe (see Table 4) with a 5' fluorescent reporter and a 3' quencher, are obtained from Integrated DNA Technologies. RT-PCR reaction conditions are an initial denaturation for 2 minutes at 95° C. and 45 cycles of 94° C. for 15 seconds, annealing at 56° C. for 15 seconds and 72° C. for 30 seconds, with final extension at 72° C. for 10 minutes. The hydrolysis probe for the gene under study can be labeled at the 5' end with the fluorophore FAM (fluorescein). A control gene can be amplified as an internal control to check the specificity of the reaction. The hydrolysis probe can be labeled at the 5' end with the fluorophore HEX (555) to allow for differentiation of fluorescence arising from the biomarker hydrolysis probe and the internal control probe. All RT-PCR assays are run in triplicate using TaqMan® Gene Expression Master Mix (ThermoFisher, #4369016, Waltham, Mass.).

Quantitative results are obtained by monitoring the increase in fluorescence (which occurs upon release of the fluorescent reporter molecule from the hydrolysis probe and the associated quencher) and can be proportional to the amount of amplified product produced, using a Roche Light cycle Model 2.0 (or later version).

In an embodiment of the invention, the tumor tissue is harvested and the relative expression of the individual gene products, as well as the mRNA expression for the three "housekeeping" genes (ACTB, TFRC, GAPD), is quantified by RT-PCR using the desired primers (Table 4) specific for each gene product or "housekeeping gene". Next a "relative ratio of expression" is determined for each of the gene products under s investigation versus the individual "housekeeping genes" as described above in the Microarray Analysis section. These ratios are then compared to ratios obtained for a cell known to be sensitive to an Illudofulvene as well as to ratios for a cell know to be resistant to an Illudofulvene. It can then be determined whether (i) a PTGR gene is upregulated, or (ii) the MYC gene is upregulated and (iii) there is a deficiency in at least one specific TCR gene. The tumor can then be classified as either sensitive, or resistant, to Illudofulvenes based on this analysis.

TABLE 4

Required RT-PCR primers and hydrolysis probe for each Biomarker.

| GENE | Upper Primer SEQ ID NOS: | Hydrolysis Probe SEQ ID NOS: | Lower Primer SEQ ID NOS: | Probe (bp) | Temp (° C.) |
| --- | --- | --- | --- | --- | --- |
| ERCC1 | 852 | 853 | 854 | 139 | 61 |
| ERCC2 | 855 | 856 | 857 | 141 | 60 |
| ERCC3 | 858 | 859 | 860 | 143 | 60 |
| ERCC4 | 861 | 862 | 863 | 137 | 60 |
| ERRC5 | 864 | 865 | 866 | 143 | 60 |
| ERCC6 | 867 | 868 | 869 | 148 | 60 |
| ERCC6L | 870 | 871 | 872 | 137 | 61 |
| ERCC6L2 | 873 | 874 | 875 | 148 | 60 |
| ERCC8 | 876 | 877 | 878 | 142 | 60 |
| GTF2H1 | 879 | 880 | 881 | 89 | 61 |
| GTF2H2 | 882 | 883 | 884 | 146 | 60 |
| GTF2H3 | 885 | 886 | 887 | 141 | 61 |
| GTF2H4 | 888 | 889 | 890 | 150 | 61 |
| GTF2H5 | 891 | 892 | 893 | 149 | 61 |
| MYC | 894 | 895 | 896 | 108 | 60 |
| PT'GR1 | 897 | 898 | 899 | 150 | 60 |

TABLE 4-continued

Required RT-PCR primers and hydrolysis probe for each Biomarker.

| GENE | Upper Primer SEQ ID NOS: | Hydrolysis Probe SEQ ID NOS: | Lower Primer SEQ ID NOS: | Probe (bp) | Temp (° C.) |
| --- | --- | --- | --- | --- | --- |
| PTGR2 | 900 | 901 | 902 | 148 | 60 |
| RAD18 | 903 | 904 | 905 | 137 | 60 |
| USP7 | 906 | 907 | 908 | 135 | 60 |
| UVSSA | 909 | 910 | 911 | 114 | 61 |
| XPA | 912 | 913 | 914 | 140 | 60 |
| XPC | 915 | 916 | 917 | 144 | 61 |
| ACTB β-Actin (control) | 918 | 919 | 920 | 148 | 61 |
| TFRC (control) | 921 | 922 | 923 | 127 | 60 |
| GAPD (control) | 924 | 925 | 926 | 143 | 60 |

TCR Tumor Mutation Panel (22 Genes) Analysis.

The TCR Tumor Mutation Panel targets a total of 22 clinically relevant genes. Specifically, the panel interrogates all exons of 22 genes known to be associated with sensitivity to Illudofulvenes.

The TCR Tumor Mutation Panel (see Table 5) is a highly multiplexed targeted re-sequencing assay for detecting somatic variants across key genes in cancer genomes [see (i) Illumina HiSeq® 2500 System User Guide. Illumina Proprietary Part #15035786 Rev. D, November 2014; (ii) HiSeq Rapid SBS Kit v2 Reagent Prep Guide. Illumina Proprietary Part #15058772 Rev. A, November 2014; (iii) HiSeq Rapid Cluster Kit v2 Reagent Prep Guide. Illumina Proprietary Part #15059131 Rev. A, November 2014; (iv) Sequencing Analysis Viewer Software User Guide. Illumina Proprietary Part #15020619 Rev. F, October 2014; of which (i)-(iv) are herein expressly incorporated by reference in their entireties for all purposes]. The analysis entails hybridization-based capture of 513 probes (custom mix synthesis from Integrative DNA Technologies) covering 47,848 base pairs that encompass the 281 exons and regulatory regions of these 22 genes. The generation of a library of multiplexed, enriched genomic regions can be followed by a sequencing-by-synthesis assay using massively parallel 100 base pair sequence reads. Once data are generated, a series of bioinformatics tools are used to align the reads to the genome, call variants, and annotate variants with respect to somatic status and functional predictions. This analysis can detect single nucleotide variants, short insertion/deletions, and splice variants predicted to be deleterious. In addition, the analysis can detect a set of targeted fusions or rearrangement.

Genomic DNA extracted from tumor tissue can be sheared, end repaired, A-tailed, adapter ligated, amplified, hybridized to the capture (bait) library primers, then re-amplified per the HiSeq Reagent Pre Guides (Illumina #15058772 and #15059131). The subsequent sample pool can then be sequenced to a depth of 300× on an Illumina HiSeq 2500 workstation per the user guide (Illumina #15035786). The primary data analysis can be accomplished by the on-board software (Real Time Analysis). Secondary analysis can be accomplished by uploading base call files (*.bcl) to a genomics server designed to generate reads and read alignments, followed by comparison to the DNA sequence for the 22 genes as listed in the latest version of the Genomic Reference Consortium Human (current build 37). This allows identification of tumors that are deficient in TCR capacity, on the basis of a deficiency in one (or more) of the components of the TCR pathways, and which can be responsive to treatment with an Illudofulvene. In addition, tumors that are deficient in PTGR metabolic activity (either PTGR1 or PTGR2) can also be identified, and such tumors excluded from treatment based on the expected lack of response to therapy.

In an embodiment of the invention, a tumor sample is obtained from a patient, prepared, and the genomic DNA isolated and processed as described in this application. The TCR 22 gene mutation panel (Table 5) is then obtained by sequencing in entirety these genes, and results analyzed versus the latest version of the Genomic Reference Consortium Human (current build 37, Table 6), as described in this application. Tumors deficient in TCR capacity, on the basis of a deficiency in one (or more) of the components of the TCR pathways due to a mutation, and which can be responsive to treatment with an Illudofulvene, can then be identified. Tumors that are deficient in PTGR metabolic activity (either PTGR1 or PTGR2) can also be identified, and such tumors excluded from treatment based on the expected lack of response to therapy, subject to the flow chart of FIG. 5. It can also be determined whether MYC is upregulated or downregulated.

TABLE 5

The twenty two (22) Gene TCR Tumor Mutation Panel

| GENE | SEQ ID NOS: |
|---|---|
| ERCC1 | 329-343 |
| ERCC2 | 344-374 |
| ERCC3 | 375-402 |
| ERCC4 | 403-429 |
| ERCC5 | 430-440 and 451-475 |
| ERCC6 | 476-539 |
| ERCC6L | 540-571 |
| ERCC6L2 | 572-596 |
| GTF2H1 | 597-615 |
| GTF2H2 | 616-631 |
| GTF2H3 | 632-646 |
| GTF2H4 | 647-665 |
| GTF2H5 | 666-668 |
| MYC | 669-681 |
| PTGR1 | 682-696 |
| RAD18 | 697-714 |
| PTGR2 | 715-727 |
| XPA | 728-736 |
| XPC | 737-777 |
| USP7 | 768-809 |
| UVSSA | 810-835 |
| ERCC8 | 836-851 |

TABLE 6

A list of genes comprising components of the TCR-NER pathway, post-replication repair pathway, or bio activation of Illudofulvenes of which an alteration of one or more of the components will confer sensitivity to illudofulvenes, according to various embodiments of the invention.

| Gene (HGNC Symbol) | Gene Aliases | Representative mRNA Sequence | SEQ ID NO | Representative Protein Sequence | SEQ ID NO |
|---|---|---|---|---|---|
| ERCC8 | CSA, CKN1, UVSS2 | NM_001290285 | 1 | NP_000073 | 2 |
| ERCC6 | CSB, ARMD5, CKN2, COFS, COFS1, RAD26 POF11, UVSS1 | NM_001277058.1 | 3 | NP_000115.1 | 4 |
| GTF2H1 | P62, BTF2P62, T'FB1, TFIIH SUBUNIT 1 | NM_001142307.1 | 5 | NP_005307.1 | 6 |
| GTF2H2 | BTF2P44. P44 | NM_001515.3 | 7 | NP_001506.1 | 8 |
| G1P2H3 | P34, TFB4 | NM_001516.4 | 9 | NP_001507.2 | 10 |
| GTF2H4 | P52, TFB2 | NM_001517.4 | 11 | NP_001508.1 | 12 |
| GTF2H5 | TTDA, TFB5, TGF2H5, TTD3, C6orf175, bA120J8.2 | NM_207118.2 | 13 | NP_997001.1 | 14 |
| USP7 | HAUSP, TEF1 | NM_003470.3 | 15 | NP_003461.2 | 16 |
| UVSSA | KIAA1530, UVSS3 | NM_020894.3 | 17 | NP_001304863.1 | 18 |
| ERCC3 | XPB, RAD25, TTD2, BFT2 | NM_001303418.1 | 19 | NP_001290347.1 | 20 |
| ERCC2 | XPD, COFS2, EM9, TTD1 | NM_000400.3 | 21 | NP_000391.1 | 22 |
| ERCC4 | XPF, ERCC11, FANCQ, RAD1, XFEPS | NM_005236.2 | 23 | NP_005227.1 | 24 |

TABLE 6-continued

A list of genes comprising components of the TCR-NER pathway, post-replication repair pathway, or bio activation of Illudofulvenes of which an alteration of one or more of the components will confer sensitivity to illudofulvenes, according to various embodiments of the invention.

| Gene (HGNC Symbol) | Gene Aliases | Representative mRNA Sequence | SEQ ID NO | Representative Protein Sequence | SEQ ID NO |
|---|---|---|---|---|---|
| ERCC5 | XPG, COFS3, ERCM2, UVDR, XPGC | NM_000123.3 | 25 | NP_000114.2 | 26 |
| XPA | XP1, XPAC | NM_001354975.1 | 27 | NP_000371.1 | 29 |
| RAD18 | RNF73 | NM_020165.3 | 29 | NP_064550.3 | 30 |
| ERCC6L | PICH, RAD26L | NM_017669.3 | 31 | NP_060139.2 | 32 |
| ERCC6/L2 | BMFS2, C9orf102, RAD26L, SR278 | NM_020207.4 | 33 | NP_064592.2 | 34 |
| MYC | v-myc, c-myc, bHLHe39, MYCC | NM_002467.5 | 222 | NP_002458 | 223 |
| ERCC1 | COFS4, UV20, RAD10 | NM_202001.2 | 236 | NP_973730.1 | 237 |
| PTGR1 | PGR1, PRG-1, LTBD4H, ZADH3 | NM_001146109.1 | 249 | NP_001139581 | 250 |
| PTGR2 | PGR2, ZADH1, HEL-S-298 | NM_001146154.1 | 262 | NP_001139626.1 | 263 |

TABLE 7

A list of biomarkers that when downregulated (expression decreased) confer sensitivity to illudofulvenes, according to various embodiments of the invention.

| Gene | Affymetrix ID | SEQ ID NO |
|---|---|---|
| ERCC8 | 201562_at | 35-45 |
| ERCC6 | 207347_at | 46-56 |
| GTF2H1 | 202451_at | 57-67 |
| GTF2H2 | 230177_at | 68-78 |
| GTF2H3 | 239346_at | 79-89 |
| GTF2H4 | 203577_at | 90-100 |
| GTF2H5 | 213357_at | 101-111 |
| USP7 | 2014498_at | 112-122 |
| UVSSA | 241201_at | 123-133 |
| ERCC3 | 202176_at | 134-144 |
| ERCC2 | 213468_at | 145-155 |
| ERCC4 | 210158_at | 156-166 |
| ERCC5 | 202414_at | 167-177 |
| XPA | 205672_at | 178-188 |
| RAD18 | 223417_at | 189-199 |
| ERCC6/L | 219650_at | 200-210 |
| ERCC6/L2 | 228211_at | 211-221 |
| ERCC1 | 203719_t | 238-248 |

Affymetrix IDs refer to the array type Human Genome U133 Plus 2.0 (HG-U133 Plus 2)

TABLE 8

A list of biomarkers that when upregulated (expression increased) confer sensitivity to illudofulvenes, according to various embodiments of the invention.

| Gene | Affymetrix ID | SEQ ID NO |
|---|---|---|
| MYC | 20243_s_at | 224-235 |
| PTGR1 | 231897_at | 251-261 |
| PTGR2 | 230774_at | 264-274 |

Affymetrix IDs refer to the array type Human Genome U133 Plus 2.0 (HG-U133 Plus 2).

TABLE 9

The toxicity of Illudofulven Analog 001/Analog 002 to either 2 hour or 48 hour incubation, according to various embodiments of the invention.

| | Cytotoxicity? | |
|---|---|---|
| Tumor cell line | 2 hr incubation | 48 hr incubation |
| Myeloid leukemias | Yes | Yes |
| Breast carcinomas | Yes | Yes |
| Epidermoid | Yes | Yes |
| Ovarian | Yes | Yes |
| Lung carcinomas | Yes | Yes |
| Prostate carcinomas | Yes | Yes |
| B cell leukemias | No | Yes |
| T cell leukemias | No | Yes |
| Fibroblasts (normal) | No | Yes |

TABLE 10

A comparison of the DNA damage profile of Illudofulven Analog 001/Analog 002 with Other Drugs and UV irradiation, according to embodiments of the invention.

| Gene | Other Drugs* | UV | Illudofulvene Analog 001/002 |
|---|---|---|---|
| XP-A | + | + | + |
| XP-B | 0 | + | + |
| XP-C | + | + | 0 |
| XP-D | 0 | + | + |
| XP-E | + | + | 0 |
| XP-F | + | + | + |
| CS-A | +/− | + | ++ |
| CS-B | +/− | + | ++ |
| ERCC1 | + | + | + |
| ERCC5 | + | + | + |

*as defined herein.

TABLE 11

The multidrug resistance of Illudofulvene Analog 001/Analog 002, according to various embodiment of the invention.

| Mechanism of Multi-drug Resistance | Resistance to Mudofulvene Analog 001/Analog 002 |
|---|---|
| Gp170/MDR1 | No |
| Gp180/MRP | No |
| Topoisomerase I | No |
| Topoisomerase II | No |
| MVP/LRP (vault) | No |
| Thiol content/GST pi | No |
| DNA repair | No |
| Myc expression | No |
| Bcl-2 expression | No |
| BRCA status | No |
| P53 status | No |
| P21 status | No |
| MGMT expression | No |
| Microtubulin alteration | No |

TABLE 12

The cytotoxic $IC_{50}$ values (micromolar, 2 hour exposure, N = 3, mean ± SD) for illudin M, Illudofulvene Analog 108 and Illudofulvene Analog 110 for cells expressing the estrogen receptor (ER) (MCF7) and cells not expressing the ER (HT29), according to embodiments of the invention.

| Analog | HT29 (ER Negative) | MCF7 (ER positive) |
|---|---|---|
| Illudin M | 0.52 ± 0.10 | 0.48 ± 0.13 |
| 108 | >55 | 14.1 ± 2.8 |
| 110 | >19 | 2.0 ± 0.1 |

TABLE 13

The ability of Illudofulvene analogs to inhibit tumor cell growth, according to various embodiments of the invention.

| Illudofulvene Analog | MV522 Target Cell Line 2 hr exposure | MV522 Target Cell Line 48 hr exposure | 8392B Nontarget Cell Line 2 hr exposure | 8392B Nontarget Cell Line 48 hr exposure |
|---|---|---|---|---|
| 001 | 2200 ± 100 | 350 ± 20 |  | 830 ± 100 |
| 002 | 110 ± 40 | 70 ± 10 | 26000 ± 4500 | 800 ± 100 |
| 004 | 4200 | 600 |  |  |
| 008 | 870 ± 90 | 630 ± 80 | 12200 ± 700 | 15100 ± 2200 |
| 009 | 500 ± 30 | 850 ± 180 | 47100 ± 11000 | 43200 ± 2300 |
| 010 | 8900 ± 1500 | 170 ± 60 | 29400 ± 1600 | 14500 ± 1700 |
| 011 | 4900 ± 900 | 1200 (N = 2) | >100000 | 40400 ± 6700 |
| 012 | 5150 ± 1350 | 320 ± 90 | 42200 ± 5000 | 18800 ± 2800 |
| 013 | 5100 ± 700 | 270 ± 130 | 11900 ± 1300 | 4200 ± 400 |
| 014 | 115 ± 30 | 460 ± 120 | 9650 ± 200 | 1100 ± 300 |
| 015 | 1800 ± 200 | 480 ± 110 | 810 ± 260 | 1300 ± 150 |
| 016 | 490 ± 130 | 440 ± 90 | >100000 | 870 ± 60 |
| 017 | 2400 ± 360 | 320 ± 60 | 14700 ± 900 |  |
| 018 | 8800 ± 2900 |  | 4200 ± 1300 |  |
| 019 | 470 ± 60 | 660 ± 80 | >75000 |  |
| 020 | 530 ± 140 | 230 ± 10 | 25000 ± 3100 |  |
| 021 | 2400 ± 1000 | 930 ± 250 | 34400 ± 9400 |  |
| 022 | 700 ± 200 | 680 ± 180 | 31700 ± 1400 |  |
| 023 | 2900 ± 1140 | 2750 ± 500 | >138000 |  |
| 024 | 1800 ± 200 | 1200 ± 300 | 12800 ± 2100 |  |
| 025 | 1300 ± 310 | 1200 ± 100 | >25000 |  |
| 030 |  | >3000 |  |  |
| 031 |  | >3000 |  |  |
| 032 | 600 ± 190 | 210 ± 30 | >30000 |  |
| 033 | 10000 ± 1100 | 4600 ± 200 | 29900 ± 3300 |  |
| 034 | 1400 ± 170 | 490 ± 40 | >100000 | 4400 ± 200 |
| 035 | 5600 ± 600 |  | >150000 |  |
| 037 | 26000 ± 5000 | 29200 ± 2300 | >85000 |  |
| 038 | 750 ± 60 |  | 24900 ± 8000 |  |
| 039 | 1500 ± 240 | 600 ± 40 | 24600 ± 2400 | 820 ± 250 |
| 040 | 3400 ± 360 | 700 ± 90 | 24000 ± 3300 | 5200 ± 470 |
| 060 | 19400 ± 1800 |  | 27600 ± 3000 |  |
| 062 | 2600 ± 300 | 660 ± 200 | 37100 ± 2300 |  |
| 063 | 43000 ± 5700 | 580 ± 250 |  |  |
| 064 | 28000 ± 4600 | 1200 ± 300 |  |  |
| 065 | 6200 ± 1100 | 2500 ± 1200 |  |  |
| 075 | 19600 ± 9700 |  | 62000 ± 3600 |  |
| 076 | 24000 ± 6100 |  | 39500 ± 7200 |  |

TABLE 13-continued

The ability of Illudofulvene analogs to inhibit tumor cell growth, according to various embodiments of the invention.

| | Mean IC50 value (nM) ± SD, N = 3 unless otherwise indicated | | | |
|---|---|---|---|---|
| Illudofulvene | MV522 Target Cell Line | | 8392B Nontarget Cell Line | |
| Analog | 2 hr exposure | 48 hr exposure | 2 hr exposure | 48 hr exposure |
| 077 | 9200 ± 1200 | | | |
| 078 | 20400 ± 6300 | | >100000 | |
| 079 | 7700 ± 3500 | | >100000 | |
| 080 | 8800 ± 2400 | | >100000 | |
| 081 | >80000 | | >80000 | |
| 082 | 50600 ± 7100 | | >100000 | |
| 083 | | 37200 ± 2900 | | >42000 |
| 084 | | 28200 ± 1400 | | >42000 |
| 085 | >40000 | >40000 | | |
| 087 | >40000 | 24700 ± 3900 | >40000 | |
| 089 | 19300 ± 5700 | 15500 ± 2800 | >60000 | |
| 090 | 2500 ± 400 | 2900 ± 400 | 1600 ± 200 | 3800 ± 300 |
| 094 | 800 ± 100 | 210 ± 20 | 9000 ± 1700 | 110 ± 10 |
| 096 | 2700 ± 400 | 6200 ± 600 | >88000 | >3000 |
| 097 | 2900 ± 100 | | >82000 | |
| 098 | 18800 ± 2500 | 4600 ± 250 | >65000 | 11700 ± 1800 |
| 099 | 8400 ± 1100 | 1800 ± 200 | 4000 ± 400 | 300 ± 20 |
| 100 | >10000 | 1700 ± 500 | | |
| 101 | >8000 | >7500 | | |
| 102 | >13000 | 1300 ± 100 | | |
| 103 | 31800 ± 4900 | 5900 ± 400 | 12100 ± 2000 | 2300 ± 200 |
| 104 | 6300 ± 400 | 6000 ± 500 | 36400 ± 6500 | 2700 ± 600 |
| 105 | 7300 ± 1200 | 2100 ± 400 | >100000 | |
| 106 | 5200 ± 1000 | | >83000 | |
| 107 | >50000 | 1600 ± 100 | >50000 | |
| 108 | 12300 ± 2300 | 520 ± 50 | >55000 | 6000 ± 1600 |
| 109 | >50000 | | >50000 | |
| 110 | >55000 | 1400 ± 100 | >55000 | 25300 ± 2100 |
| 111 | 16700 ± 2100 | 11900 ± 2800 | 34600 ± 2100 | 10200 ± 1000 |
| 112 | 10000 ± 2000 | 6700 ± 1200 | 14900 ± 100 | 5200 ± 300 |
| 113 | 85000 ± 700 | 14100 ± 3000 | >93000 | 7800 ± 1000 |
| 114 | 1500 ± 100 | 260 ± 70 | 25100 ± 1000 | 700 ± 100 |
| 115 | 1500 ± 100 | 70 ± 5 | 1600 ± 700 | 630 ± 60 |
| 116 | 400 ± 100 | 1000 ± 50 | 7000 ± 400 | 170 ± 30 |
| 117 | 1100 ± 100 | 100 ± 30 | 7900 ± 1600 | 10 ± 2 |
| 118 | 14000 ± 2000 | 740 ± 120 | 24500 ± 4500 | 2000 ± 400 |
| 119 | 1100 ± 70 | 270 ± 40 | >33000 | >10000 |
| 120 | 2800 ± 900 | 600 ± 100 | 19100 ± 4600 | 510 ± 110 |
| 121 | 300 ± 10 | 90 ± 10 | 15200 ± 6000 | 1300 ± 500 |
| 122 | 6400 ± 300 | 2400 ± 300 | 14500 ± 1200 | 1100 ± 300 |
| 123 | 1900 ± 400 | 600 ± 60 | 450 ± 30 | 2400 ± 500 |
| 124 | 2800 ± 700 | 870 ± 350 | >30000 | 2400 ± 550 |
| 125 | 3700 ± 600 | 1200 ± 200 | 15500 ± 1400 | 600 ± 100 |
| 126 | 2100 ± 500 | 900 ± 100 | >30000 | 330 ± 80 |
| 127 | 870 ± 30 | 340 ± 90 | >30000 | 100 ± 40 |
| 128 | 840 ± 230 | 370 ± 50 | >35000 | 800 ± 70 |
| 129 | >136000 | 19700 ± 1900 | >136000 | 39400 ± 9200 |
| 130 | 700 ± 100 | 130 ± 40 | 27,000 ± 7000 | 4400 ± 500 |
| 133 | 58800 ± 6600 | 15800 ± 2600 | 12200 ± 2300 | 2700 ± 400 |
| 134 | 50000 ± 6000 | 28000 ± 4000 | 43900 ± 5100 | 8500 ± 2000 |
| 135 | 1600 ± 300 | 22 ± 4 | 70 ± 20 | 22 ± 2 |
| 136 | 430 ± 10 | 130 ± 10 | >6200 | 25 ± 2 |
| 137 | 850 ± 110 | 1200 ± 100 | 8500 ± 1200 | 710 ± 60 |
| 138 | 2100 ± 200 | 1000 ± 200 | 5400 ± 200 | 820 ± 230 |
| 139 | 6400 ± 900 | 3400 ± 500 | 11600 ± 900 | 2600 ± 1000 |
| 140 | 17100 ± 5100 | >14000 | 12700 ± 300 | >14000 |
| 141 | 11400 ± 1000 | 3700 ± 800 | 13700 ± 1900 | 1100 ± 140 |
| 142 | 90 ± 10 | 24 ± 7 | 6400 ± 1100 | 80 ± 6 |
| 143 | 43500 ± 11300 | 11400 ± 1800 | 56500 ± 20000 | 3600 ± 700 |
| 146 | 2500 ± 400 | 740 ± 280 | 13,000 ± 1200 | |
| 147 | >76000 | 26100 ± 12900 | >76000 | 43800 ± 3000 |
| 148 | 17100 ± 1100 | 6800 ± 1100 | 61000 ± 11600 | 6700 ± 1600 |
| 149 | 2900 ± 1000 | 1500 500 | 44600 ± 1400 | 4100 ± 900 |
| 150 | 9500 ± 1600 | 1400 ± 400 | 59000 ± 5500 | 10600 ± 800 |
| 151 | 7900 ± 400 | 4200 ± 1600 | 25500 ± 1200 | 6600 ± 2300 |
| 152 | | 6400 ± 1200 | 49000 ± 7700 | 9100 ± 100 |
| 153 | 8700 ± 2700 | 10900 ± 3400 | >90000 | 15800 ± 9600 |
| 154 | >70000 | 61300 ± 10000 | >70000 | 46,700 ± 13100 |
| 155 | 8200 ± 1200 | 3600 ± 400 | 17,000 ± 4000 | 9100 ± 1100 |
| 156 | 7200 ± 500 | 3100 ± 100 | 32,300 ± 9,400 | 5500 ± 1200 |
| 157 | >400,000 | >123,000 | >350,000 | 13100 ± 1600 |

TABLE 13-continued

The ability of Illudofulvene analogs to inhibit tumor cell growth, according to various embodiments of the invention.

| | Mean IC50 value (nM) ± SD, N = 3 unless otherwise indicated | | | |
|---|---|---|---|---|
| Illudofulvene | MV522 Target Cell Line | | 8392B Nontarget Cell Line | |
| Analog | 2 hr exposure | 48 hr exposure | 2 hr exposure | 48 hr exposure |
| 158 | >175,000 | >175,000 | >200,000 | 61,000 ± 9,000 |
| 159 | 2700 ± 400 | 120 ± 10 | 13,700 ± 4,200 | <10 nM |
| 160 | 1900 ± 200 | 500 ± 200 | 52,400 ± 17,800 | 3200 ± 1100 |
| 161 | 2800 ± 500 | 3300 ± 700 | 13,800 ± 3,400 | >10,000 |
| 163 | 3500 ± 800 | 820 ± 40 | 18600 ± 800 | 910 ± 100 |
| 164 | | 70 ± 10 | 3500 ± 1600 | 130 ± 40 |
| 165 | 7700 ± 1100 | 290 ± 40 | 11000 ± 3300 | 11000 ± 1000 |
| 166 | 6500 ± 600 | 7200 ± 1900 | 6500 ± 2100 | 6000 ± 1500 |
| 167 | 14800 ± 2200 | | 18500 ± 2300 | |
| 169 | 7100 ± 600 | | 2300 ± 600 | |
| 177 | 7500 ± 800 | 1900 ± 800 | 73000 ± 5000 | 4100 ± 1300 |
| 178 | 21000 ± 4000 | 1000 ± 100 | 32000 ± 9000 | >8000 |
| 180 | 19900 ± 300 | >4000 | 5200 ± 1800 | 660 ± 50 |
| 182 | 99000 ± 12000 | 38000 ± 8200 | 39000 ± 7000 | 18700 ± 2700 |
| 183 | >120,000 | >275,000 | >120,000 | >235,000 |
| 184 | 800 ± 300 | 210 ± 20 | >100,000 | >10000 |
| 185 | 1700 ± 600 | 1900 ± 100 | | |
| 186 | 144000 ± 32000 | 70000 ± 16000 | 79000 ± 24000 | 48000 ± 2000 |
| 187 | 1300 ± 400 | 900 ± 200 | 3200 ± 800 | 3200 ± 700 |
| 189 | 8900 ± 2500 | 6100 ± 2600 | 41,000 ± 3700 | |
| 190 | 19,000 ± 4000 | >9,000 | 56,000 ± 2000 | >9,000 |
| 191 | >140,000 | 49,000 ± 13000 | >140,000 | 15000 ± 4000 |
| 192 | 1,600 ± 200 | 700 ± 100 | 8700 ± 1700 | 200 ± 30 |
| 193 | 1400 ± 400 | 2500 ± 600 | 48,000 ± 7000 | >11,000 |
| 195 | 1400 ± 200 | 390 ± 120 | 21,000 ± 6000 | 4300 ± 1200 |
| 196 | 840 ± 100 | 450 ± 120 | 80,000 ± 5000 | >9,200 |
| 197 | 950 ± 70 | 500 ± 100 | 9500 ± 400 | 11,300 ± 100 |
| 198 | 700 ± 100 | 2800 ± 600 | >8,200 | >82,000 |
| 199 | 4700 ± 600 | 2500 ± 1100 | >93,000 | >9,300 |
| 201 | 360 ± 110 | 260 ± 70 | 13,000 ± 1700 | 26,000 ± 7000 |
| 202 | 1200 ± 100 | 650 ± 100 | >62,000 | >6200 |
| 203 | 760 ± 170 | 940 ± 330 | 48,000 ± 6000 | >5500 |
| 204 | 220 ± 40 | 1600 ± 300 | 4100 ± 800 | 8600 ± 800 |
| 205 | 8400 ± 2200 | 1200 ± 400 | >185,000 | >2,600 |
| 206 | 610 ± 40 | 230 ± 20 | 20,000 ± 1000 | 8200 ± 200 |
| 207 | 570 ± 60 | 410 ± 60 | | |
| 208 | 1200 ± 100 | 930 ± 160 | 25,000 ± 3000 | |
| 209 | 3900 ± 1100 | 610 ± 100 | >90,000 | |
| 210 | 40,000 ± 4000 | 5500 ± 600 | | |
| 211 | 470 ± 120 | 430 ± 100 | 59,000 ± 9000 | |
| 212 | 80 ± 10 | 55 ± 5 | | |
| 213 | 2300 ± 700 | 1700 ± 700 | | |
| 214 | 2900 ± 800 | 360 ± 30 | | |
| 215 | 26,000 ± 3000 | 490 ± 120 | | |
| 216 | 460 ± 60 | 150 ± 40 | | |
| 217 | 2,200 ± 100 | 2,200 ± 100 | 43,000 ± 4,000 | >7,000 |
| 218 | 10,000 ± 3,000 | 600 ± 200 | 15,000 ± 6,000 | 600 ± 100 |
| 219 | >52,000 | >52,00 | >52,000 | >52,000 |
| 220 | 90 ± 10 | 130 ± 10 | 101,000 ± 18,000 | 40,000 ± 3,000 |
| 221 | >21,000 | 2,500 ± 200 | >21,000 | >21,000 |
| 222 | 5,000 ± 100 | 1,100 ± 100 | 9,300 ± 200 | 330 ± 60 |
| 223 | 20,000 ± 3,700 | 2,700 ± 300 | >185,000 | >55,000 |
| 224 | >200,000 | >130,000 | >200,000 | >130,000 |
| 225 | 47,000 ± 4,000 | 55,000 ± 11,000 | >350,000 | 33,000 ± 13,000 |
| 226 | >59,000 | >59,000 | >59,000 | >59,000 |
| 227 | >57,000 | 4,400 ± 700 | >57,000 | 16,000 ± 4,000 |
| 228 | >38,000 | >38,000 | 24,000 ± 3,000 | >38,000 |
| 229 | >56,000 | >2,000 | >56,000 | >2,000 |
| 230 | 620 ± 80 | 100 ± 10 | 38,000 ± 5,000 | 1,000 ± 200 |
| 231 | 1,500 ± 100 | 280 ± 10 | 14,000 ± 4,000 | |
| 232 | 700 ± 100 | 460 ± 60 | 42,000 ± 6,000 | 3,300 ± 600 |
| 233 | 3,200 ± 300 | 350 ± 80 | >150,000 | 2,400 ± 700 |
| 234 | 3,000 ± 300 | 1,100 ± 400 | 24,000 ± 6,000 | 9,000 ± 1,000 |
| 235 | 3,500 ± 400 | 2,200 ± 400 | 49,000 ± 6,000 | 6,500 ± 1,600 |
| 236 | 49,000 ± 11,000 | 29,000 ± 5,000 | 48,000 ± 10,000 | |
| 237 | 1,200 ± 300 | 730 ± 140 | 22,000 ± 1,000 | 6,600 ± 900 |
| 238 | 780 ± 190 | 57 ± 8 | 23,000 ± 2,000 | 4,700 ± 1,200 |
| 239 | 420 ± 60 | 70 ± 20 | 39,000 ± 3,000 | 28,000 ± 4,000 |
| 240 | 2,900 ± 100 | 1,300 ± 200 | >24,000 | 1,300 ± 100 |
| 241 | 560 ± 90 | 110 ± 20 | >28,000 | 18,000 ± 4,000 |
| 242 | 2,400 ± 400 | 580 ± 150 | 18,000 ± 2,000 | 2,900 ± 600 |

TABLE 13-continued

The ability of Illudofulvene analogs to inhibit tumor cell growth, according to various embodiments of the invention.

| | Mean IC50 value (nM) ± SD, N = 3 unless otherwise indicated | | | |
|---|---|---|---|---|
| Illudofulvene | MV522 Target Cell Line | | 8392B Nontarget Cell Line | |
| Analog | 2 hr exposure | 48 hr exposure | 2 hr exposure | 48 hr exposure |
| 243 | 2,200 ± 500 | 670 ± 240 | 64,000 ± 10,000 | 26,000 ± 6,000 |
| 244 | 1,600 ± 400 | 150 ± 10 | 87,000 ± 11,000 | 35,000 ± 7,000 |
| 245 | 3,400 ± 1000 | 440 ± 90 | 79,000 ± 7,000 | 14,000 ± 1,700 |
| 246 | 2,800 ± 260 | 1,900 ± 450 | 14,000 ± 2,000 | 6,200 ± 1,300 |
| 247 | 6,100 ± 2,000 | 1,200 ± 250 | 10,000 ± 1,400 | 7,100 ± 1,700 |
| 248 | 830 ± 100 | 200 ± 25 | 23,000 ± 1,000 | 610 ± 120 |
| 249 | 4,100 ± 820 | 420 ± 100 | 18,000 ± 3,500 | 19,000 ± 3,800 |
| 250 | 99,000 ± 21,000 | 137,000 ± 14,000 | >275,000 | 137,000 ± 10,000 |
| 251 | 128,000 ± 4,000 | 51,000 ± 1,000 | >275,000 | 82,000 ± 8,000 |
| 252 | >380,000 | 33,000 ± 3,000 | >380,000 | >380,000 |
| 253 | >380,000 | >38,000 | >380,000 | >380,000 |
| 254 | 2,700 ± 800 | 1,100 ± 100 | 43,000 ± 6,000 | >65,000 |
| 255 | 2,900 ± 500 | 55 ± 2 | 119,000 ± 15,000 | 99,000 ± 4,000 |
| 256 | 1,500 ± 200 | 880 ± 200 | 7,500 ± 800 | 7,100 ± 300 |
| 257 | 2,800 ± 600 | 320 ± 30 | 25,000 ± 2,000 | 26,000 ± 3,000 |
| 258 | >45,000 | >45,000 | >45,000 | >45,000 |
| 259 | 16000 ± 3000 | 2400 ± 200 | >85,000 | 4700 ± 400 |
| 260 | 1600 ± 500 | 150 ± 20 | >64,000 | 19000 ± 4500 |
| 261 | 6300 ± 1100 | 1000 ± 150 | 64000 ± 2000 | 38000 ± 2100 |
| 262 | 8700 ± 1300 | 3900 ± 570 | 287000 ± 14000 | 73000 ± 17000 |
| 263 | 2000 ± 300 | 1400 ± 200 | 124000 ± 18000 | 39000 ± 7000 |
| 264 | 1400 ± 100 | 76 ± 17 | >85,000 | 54000 ± 20000 |
| 265 | 810 ± 20 | 8 ± 1 | 1100 ± 200 | 250 ± 80 |
| 266 | 140 ± 20 | 70 ± 18 | 56000 ± 15000 | 32000 ± 7000 |
| 267 | 900 ± 160 | 160 ± 20 | >90,000 | 28000 ± 8000 |
| 268 | 2100 ± 200 | 330 ± 90 | 54,000 ± 16000 | >8,000 |
| 269 | 11000 ± 3000 | 850 ± 320 | 52000 ± 4000 | >7,000 |
| 270 | 8000 ± 1500 | 1300 ± 100 | >84,000 | 7100 ± 700 |
| 271 | 1700 ± 200 | 200 ± 90 | >93,000 | >9,300 |
| 272 | >46,000 | >4,700 | >47,000 | >4,700 |
| 273 | 30000 ± 5000 | >1,500 | >45,000 | >4,500 |
| 274 | 39000 ± 3000 | 1200 ± 300 | >46,000 | >4,500 |
| 275 | 1500 ± 300 | 370 ± 40 | >62,000 | >6,200 |
| 276 | 1500 ± 200 | 760 ± 100 | >61,000 | >6,100 |
| 277 | 760 ± 70 | 190 ± 20 | 31,000 ± 6000 | 9,800 ± 1000 |
| 278 | 1000 ± 100 | 270 ± 10 | >94000 | >9,400 |
| 279 | 1700 ± 400 | 190 ± 20 | >90000 | >9,000 |
| 280 | 2400 ± 800 | +2180 | >83000 | >2,800 |
| 281 | 1800 ± 700 | 170 ± 10 | 27000 ± 2000 | 5000 ± 700 |
| 282 | 680 ± 60 | 110 ± 10 | >85000 | >8,500 |
| 283 | 2900 ± 1200 | 300 ± 20 | 40000 ± 4000 | >9,300 |
| 284 | 13,600 (N = 2) | 340 ± 20 | | >8,800 |
| 285 | 3800 ± 1100 | 310 ± 20 | 84000 ± 9000 | 2000 ± 100 |
| 286 | 48000 ± 10000 | 6300 ± 200 | 51000 ± 1700 | >8,800 |
| 287 | 455000 ± 22000 | 1100 ± 100 | 567000 ± 17000 | 4700 ± 400 |
| 288 | 1800 ± 600 | 150 ± 20 | 11000 ± 3200 | ~9,000 |
| 289 | 51 ± 4 | 530 ± 150 | >290000 | >8,800 |
| 294 | 960 ± 170 | | | |
| 295 | 200 ± 44 | | | |
| 296 | 250 (N = 2) | | | |
| 297 | 2200 (N = 1) | | | |
| 298 | >7000 | | | |

TABLE 14

The IUPAC name of Illudofulvene Analogs.

| Entry # | Illudofulvene Analog | IUPAC Name of Illudofulvene Analog |
|---|---|---|
| 1 | 001 | (R)-6'-hydroxy-2',4',6'-trimethylspiro[cyclopropane-1,5'-inden]-7'(6'H)-one |
| 2 | 002 | (6'R)-6'-hydroxy-3'-(hydroxymethyl)-2',4',6'-trimethylspiro[cyclopropane-1,5'-inden]-7'(6-H)-one |
| 3 | 003 | (6'R,6'''R)-3',3'''-methylenebis(6'-hydroxy-2',4',6'-trimethylspiro[cyclopropane-1,5'-inden]-7'(6'H)-one) |
| 4 | 004 | (R)-3'-bromo-6'-hydroxy-2',4',6'-trimethylspiro[cyclopropane-1,5'-inden]-7'(6'H)-one |

TABLE 14-continued

The IUPAC name of Illudofulvene Analogs.

| Entry # | Illudofulvene Analog | IUPAC Name of Illudofulvene Analog |
|---|---|---|
| 5 | 005 | (R)-6'-hydroxy-3'-iodo-2',4',6'-trimethylspiro[cyclopropane-1,5'-inden]-7'(6'H)-one |
| 6 | 006 | (R)-6'-hydroxy-3'-(4-hydroxybenzyl)-2',4',6'-trimethylspiro[cyclopropane-1,5'-inden]-7'(6'H)-one |
| 7 | 007 | (R)-6'-hydroxy-3'-(4-methoxybenzyl)-2',4',6'-trimethylspiro[cyclopropane-1,5'-inden]-7'(6'H)-one |
| 8 | 008 | (R)-((6'-hydroxy-2',4',6'-trimethyl-7'-oxo-6',7'-dihydrospiro[cyclopropane-1,5'-inden]-3'-yl)methoxy)methyl acetate |
| 9 | 009 | (R)-6'-hydroxy-3'-(3-hydroxypropyl)-2',4',6'-trimethylspiro[cyclopropane-1,5'-inden]-7'(6'H)-one |
| 10 | 010 | (R)-3-(6'-hydroxy-2',4',6'-trimethyl-7'-oxo-6',7'-dihydrospiro[cyclopropane-1,5'-inden]-3'-yl)propanal |
| 11 | 011 | (R)-6'-hydroxy-2',4',6'-trimethyl-7'-oxo-6',7'-dihydrospiro[cyclopropane-1,5'-indene]-3'-carbaldehyde |
| 12 | 012 | (R)-6'-hydroxy-2',4',6'-trimethyl-3'-nitrospiro[cyclopropane-1,5'-inden]-7'(6'H)-one |
| 13 | 013 | 4-hydroxy-5-(((R)-6'-hydroxy-2',4',6'-trimethyl-7'-oxo-6',7'-dihydrospiro[cyclopropane-1,5'-inden]-3'-yl)methyl)cyclohexane-1,3-dicarbaldehyde |
| 14 | 014 | (4a'S,7'R,9b'S)-7'-hydroxy-4a',7',9'-trimethyl-4a',9b'-dihydro-4'H-spiro[cyclopropane-1,8'-indeno[1,2-d][1,3]dioxin]-6'(7'H)-one |
| 15 | 015 | (R)-3'-(hydroxymethyl)-2',4',6'-trimethyl-7'-oxo-6',7'-dihydrospiro[cyclopropane-1,5'-inden]-6'-yl acetate |
| 16 | 016 | (R)-3'-(ethoxymethyl)-6'-hydroxy-2',4',6'-trimethylspiro[cyclopropane-1,5'-inden]-7'(6'H)-one |
| 17 | 017 | (6'R,6'''R)-3',3'''1-(oxybis(methylene))bis(6'-hydroxy-2',4',6'-trimethylspiro[cyclopropane-1,5'-inden]-7'(6'H)-one) |
| 18 | 018 | (R)-6'-hydroxy-2',4',6'-trimethyl-3'-((((2R,3S,4R,5R,6S)-3,4,5-trihydroxy-6-(hydroxymethyl)tetrahydro-2H-pyran-2-yl)oxy)methyl)spiro[cyclopropane-1,5'-inden]-7'(6'H)-one |
| 19 | 019 | (6'R)-3'-((2,3-dihydroxypropoxy)methyl)-6'-hydroxy-2',4',6'-trimethylspiro[cyclopropane-1,5'-inden]-7'(6'H)-one |
| 20 | 020 | (R)-3'-((2-bromoethoxy)methyl)-6'-hydroxy-2',4',6'-trimethylspiro[cyclopropane-1,5'-inden]-7'(6'H)-one |
| 21 | 021 | (R)-6'-hydroxy-3'-(((2-methoxypropan-2-yl)oxy)methyl)-2',4',6'-trimethylspiro[cyclopropane-1,5'-inden]-7'(6'H)-one |
| 22 | 022 | (R)-6'-hydroxy-3'-((2-hydroxyethoxy)methyl)-2',4',6'-trimethylspiro[cyclopropane-1,5'-inden]-7'(6'H)-one |
| 23 | 023 | (R)-6'-hydroxy-3'-(((4-hydroxyphenyl)thio)methyl)-2',4',6'-trimethylspiro[cyclopropane-1,5'-inden]-7'(6'H)-one |
| 24 | 024 | (R)-3'-((benzylthio)methyl)-6'-hydroxy-2',4',6'-trimethylspiro[cyclopropane-1,5'-inden]-7'(6'H)-one |
| 25 | 025 | methyl (R)-2-(((6'-hydroxy-2',4',6'-trimethyl-7'-oxo-6',7'-dihydrospiro[cyclopropane-1,5'-inden]-3'-yl)methyl)thio)acetate |
| 26 | 026 | (R)-6'-hydroxy-2',4',6'-trimethyl-3'-((p-tolylthio)methyl)spiro[cyclopropane-1,5'-inden]-7'(6'H)-one |
| 27 | 027 | (R)-(6'-hydroxy-2',4',6'-trimethyl-7'-oxo-6',7'-dihydrospiro[cyclopropane-1,5'-inden]-3'-yl)methyl phenyl carbonate |
| 28 | 028 | (R)-(6'-hydroxy-2',4',6'-trimethyl-7'-oxo-6',7'-dihydrospiro[cyclopropane-1,5'-inden]-3'-yl)methyl benzoate |
| 29 | 029 | (R)-2-(((6'-hydroxy-2',4',6'-trimethyl-7'-oxo-6',7'-dihydrospiro[cyclopropane-1,5'-inden]-3'-yl)methyl)thio)acetic acid |
| 30 | 030 | methyl (R)-2-(((6'-hydroxy-1'-((2-methoxy-2-oxoethyl)thio)-2',4',6'-trimethyl-7'-oxo-6',7'-dihydrospiro[cyclopropane-1,5'-inden]-3'-yl)methyl)thio)acetate |
| 31 | 031 | methyl 2-((((6'R)-6',7a'-dihydroxy-1'-((2-methoxy-2-oxoethyl)thio)-2',4',6'-trimethyl-7'-oxo-1',6',7',7a'-tetrahydrospiro[cyclopropane-1,5'-inden]-3'-yl)methyl)thio)acetate |
| 32 | 032 | (6'R)-3'-(((2,3-dihydroxypropyl)thio)methyl)-6'-hydroxy-2',4',6'-trimethylspiro[cyclopropane-1,5'-inden]-7'(6'H)-one |
| 33 | 033 | 7'-methyl-4'H-dispiro[cyclopropane-1,6'-indene-5',2'''-[1,3]dioxolan]-4'-one |
| 34 | 034 | (R)-(6'-hydroxy-2',4',6'-trimethyl-7'-oxo-6',7'-dihydrospiro[cyclopropane-1,5'-inden]-3'-yl)methyl acetate |
| 35 | 035 | 6'-hydroxy-4'-methylspiro[cyclopropane-1,5'-inden]-7'(6'H)-one |
| 36 | 036 | (R)-3'-((1H-imidazol-1-yl)methyl)-6'-hydroxy-2',4',6'-trimethylspiro[cyclopropane-1,5'-inden]-7'(6'H)-one |
| 37 | 037 | 1-carboxy-2-((((R)-6'-hydroxy-2',4',6'-trimethyl-7'-oxo-6',7'-dihydrospiro[cyclopropane-1,5'-inden]-3'-yl)methyl)thio)ethan-1-aminium |
| 38 | 038 | (R)-3-(6'-hydroxy-2',4',6'-trimethyl-7'-oxo-6',7'-dihydrospiro[cyclopropane-1,5'-inden]-3'-yl)propanoic acid |

TABLE 14-continued

The IUPAC name of Illudofulvene Analogs.

| Entry # | Illudofulvene Analog | IUPAC Name of Illudofulvene Analog |
|---|---|---|
| 39 | 039 | (R)-3'-(3,3-dimethoxypropyl)-6'-hydroxy-2',4',6'-trimethylspiro[cyclopropane-1,5'-inden]-7'(6'H)-one |
| 40 | 040 | (R)-3'-(3,3-diethoxypropyl)-6'-hydroxy-2',4',6'-trimethylspiro[cyclopropane-1,5'-inden]-7'(6'H)-one |
| 41 | 041 | (R,Z)-3-(6'-hydroxy-2',4',6'-trimethyl-7'-oxo-6',7'-dihydrospiro[cyclopropane-1,5'-inden]-3'-yl)acrylaldehyde |
| 42 | 042 | (R)-3'-(hydroxymethyl)-4',6'-dimethyl-6'-(((triethylsilyl)oxy)spiro[cyclopropane-1,5'-inden]-7'(6'H)-one |
| 43 | 043 | (R)-6'-hydroxy-2',4',6'-trimethyl-3'-((((triethylsilyl)oxy)methyl)spiro[cyclopropane-1,5'-inden]-7'(6'H)-one |
| 44 | 044 | (R)-2',4',6'-trimethyl-6'-((triethylsilyl)oxy)-3'-((((triethylsilyl)oxy)methyl)spiro[cyclopropane-1,5'-inden]-7'(6'H)-one |
| 45 | 045 | methyl 2-(7-hydroxy-5-(2-hydroxyethyl)-3-(hydroxymethyl)-2,4,6-trimethyl-1H-inden-1-yl)thio)acetate |
| 46 | 046 | (R)-3-(6'-hydroxy-2',4',6'-trimethyl-7'-oxo-6',7'-dihydrospiro[cyclopropane-1,5'-inden]-3'-yl)propyl acetate |
| 47 | 047 | (6'R)-3'-(2-(1,7-dihydroxy-2,4,6-trimethyl-1H-inden-5-yl)ethyl)-6'-hydroxy-2',4',6'-trimethylspiro[cyclopropane-1,5'-inden]-7'(6'H)-one |
| 48 | 048 | (R)-6'-hydroxy-2',4',6'-trimethyl-1'-(p-tolylthio)-3'-((p-tolylthio)methyl)spiro[cyclopropane-1,5'-inden]-7'(6'H)-one |
| 49 | 049 | (R)-6'-hydroxy-2',4',6'-trimethyl-3'-(p-tolylthio)spiro[cyclopropane-1,5'-inden]-7'(6'H)-one |
| 50 | 050 | (R)-6'-hydroxy-2',4',6'-trimethyl-1',3'-bis(p-tolylthio)spiro[cyclopropane-1,5'-inden]-7'(6'H)-one |
| 51 | 051 | (R)-2-(2-((((6'-hydroxy-2',4',6'-trimethyl-7'-oxo-6',7'-dihydrospiro[cyclopropane-1,5'-inden]-3'-yl)methyl)thio)acetoxy)ethyl 2-mercaptoacetate |
| 52 | 052 | ethane-1,2-diyl bis(2-((((R)-6'-hydroxy-2',4',6'-trimethyl-7'-oxo-6',7'-dihydrospiro[cyclopropane-1,5'-inden]-3'-yl)methyl)thio)acetate) |
| 53 | 053 | (R)-3'-((2-(2-bromoethoxy)ethoxy)methyl)-6'-hydroxy-2',4',6'-trimethylspiro[cyclopropane-1,5'-inden]-7'(6'H)-one |
| 54 | 054 | (R)-6'-hydroxy-1'-(((R)-6'-hydroxy-2',4',6'-trimethyl-7'-oxo-6',7'-dihydrospiro[cyclopropane-1,5'-inden]-3'-yl)methyl)-3'-(hydroxymethyl)-2',4',6'-trimethylspiro[cyclopropane-1,5'-inden]-7'(6'H)-one |
| 55 | 055 | 5-(2-hydroxyethyl)-1-((4-hydroxyphenyl)thio)-3-(((4-hydroxyphenyl)thio)methyl)-2,4,6-trimethyl-1H-inden-7-ol |
| 56 | 056 | (R)-6'-hydroxy-3'-((4-hydroxyphenyl)thio)-2',4',6'-trimethylspiro[cyclopropane-1,5'-inden]-7'(6'H)-one |
| 57 | 057 | (R)-6'-hydroxy-1'-((4-hydroxyphenyl)thio)-2',4',6'-trimethylspiro[cyclopropane-1,5'-inden]-7'(6'H)-one |
| 58 | 058 | (R)-6'-hydroxy-1',3'-bis((4-hydroxyphenyl)thio)-2',4',6'-trimethylspiro[cyclopropane-1,5'-inden]-7'(6'H)-one |
| 59 | 059 | (6'S,7'R)-4'-methyl-6'-((triethylsilyl)oxy)-6',7'-dihydrospiro[cyclopropane-1,5'-inden]-7'-ol |
| 60 | 060 | (R)-7'-methyl-4'H-dispiro[cyclopropane-1,6'-indene-5',2''-[1,3]dioxolan]-4'-ol |
| 61 | 061 | (S)-4'-methyl-6'-((triethylsilyl)oxy)spiro[cyclopropane-1,5'-inden]-7'(6'H)-one |
| 62 | 062 | (R)-6'-hydroxy-2'-(hydroxymethyl)-4',6'-dimethylspiro[cyclopropane-1,5'-inden]-7'(6'H)-one |
| 63 | 063 | (R)-6'-hydroxy-2',3'-bis(hydroxymethyl)-4',6'-dimethylspiro[cyclopropane-1,5'-inden]-7'(6'H)-one |
| 64 | 064 | N-acetyl-S-(((R)-6'-hydroxy-2',4',6'-trimethyl-7'-oxo-6',7'-dihydrospiro[cyclopropane-1,5'-inden]-3'-yl)methyl)-L-cysteine |
| 65 | 065 | (R)-2-acetamido-3-((((R)-6'-hydroxy-4',6'-dimethyl-7'-oxo-6',7'-dihydrospiro[cyclopropane-1,5'-inden]-3'-yl)methyl)thio)-N-((S)-1-phenylethyl)propanamide |
| 66 | 066 | (S)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-((S)-1-phenylethyl)propanamide |
| 67 | 067 | 4-methyl-2,3-dihydro-5H-indeno[5,6-b]furan-5-one |
| 68 | 068 | 5-hydroxy-6-(2-hydroxyethyl)-7-methyl-1H-inden-1-one |
| 69 | 069 | 5-(2-hydroxyethoxy)-6-(2-hydroxyethyl)-7-methyl-1H-inden-1-one |
| 70 | 070 | (3a'R,4'R)-4'-hydroxy-7'-methyl-3a',4'-dihydro-1'H-dispiro[cyclopropane-1,6'-indene-5',2''-[1,3]dioxolan]-1'-one |
| 71 | 071 | (3a'R,4'R)-7'-methyl-4'-((triethylsilyl)oxy)-3a',4'-dihydro-1'H-dispiro[cyclopropane-1,6'-indene-5',2''-[1,3]dioxolan]-1'-one |
| 72 | 072 | (7'R,7a'R)-7'-hydroxy-4'-methyl-7',7a'-dihydrospiro[cyclopropane-1,5'-indene]-3',6'-dione |
| 73 | 073 | (7'R,7a'R)-4'-methyl-7'-((triethylsilyl)oxy)-7',7a'-dihydrospiro[cyclopropane-1,5'-indene]-3',6'-dione |

TABLE 14-continued

The IUPAC name of Illudofulvene Analogs.

| Entry # | Illudofulvene Analog | IUPAC Name of Illudofulvene Analog |
|---|---|---|
| 74 | 074 | (6'R)-3'-((((2,2-dimethyl-1,3-dioxolan-4-yl)methyl)thio)methyl)-6'-hydroxy-2',4',6'-trimethylspiro[cyclopropane-1,5'-inden]-7'(6'H)-one |
| 75 | 075 | (R)-(6'-hydroxy-4',6'-dimethyl-7'-oxo-6',7'-dihydrospiro[cyclopropane-1,5'-inden]-2'-yl)methyl acetate |
| 76 | 076 | (R)-(6'-hydroxy-4',6'-dimethyl-7'-oxo-6',7'-dihydrospiro[cyclopropane-1,5'-indene]-2',3'-diyl)bis(methylene) diacetate |
| 77 | 077 | (R)-(6'-hydroxy-3'-(hydroxymethyl)-4',6'-dimethyl-7'-oxo-6',7'-dihydrospiro[cyclopropane-1,5'-inden]-2'-yl)methyl acetate |
| 78 | 078 | (R)-(6'-hydroxy-2'-(hydroxymethyl)-4',6'-dimethyl-7'-oxo-6',7'-dihydrospiro[cyclopropane-1,5'-inden]-3'-yl)methyl acetate |
| 79 | 079 | (R)-6'-hydroxy-2'-(methoxymethyl)-4',6'-dimethylspiro[cyclopropane-1,5'-inden]-7'(6'H)-one |
| 80 | 080 | (R)-6'-hydroxy-3'-(methoxymethyl)-2',4',6'-trimethylspiro[cyclopropane-1,5'-inden]-7'(6'H)-one |
| 81 | 081 | (R)-6'-hydroxy-2'-(hydroxymethyl)-3'-(methoxymethyl)-4',6'-dimethylspiro[cyclopropane-1,5'-inden]-7'(6'H)-one |
| 82 | 082 | (R)-6'-hydroxy-2',3'-bis(methoxymethyl)-4',6'-dimethylspiro[cyclopropane-1,5'-inden]-7'(6'H)-one |
| 83 | 083 | (R)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-((S)-1-((2-(((S)-4-methyl-1-oxopentan-2-yl)amino)-2-oxoethyl)amino)-1-oxo-3-phenylpropan-2-yl)propanamide |
| 84 | 084 | (S)-2-(R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-(2-oxo-2-(((R)-1-oxo-3-phenylpropan-2-yl)amino)ethyl)pentanamide |
| 85 | 085 | (S)-2-(R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-((S)-4-methyl-1-oxo-1-(((R)-1-oxo-3-phenylpropan-2-yl)amino)pentan-2-yl)pentanamide |
| 86 | 086 | (R)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-(2-oxo-2-(((R)-1-oxo-3-phenylpropan-2-yl)amino)ethyl)propanamide |
| 87 | 087 | (S)-2-(R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-aR)-4-methyl-1-(((S)-4-methyl-1-oxopentan-2-yl)amino)-1-oxopentan-2-yl)pentanamide |
| 88 | 088 | (R)-(6'-acetoxy-2',4',6'-trimethyl-7'-oxo-6',7'-dihydrospiro[cyclopropane-1,5'-inden]-3'-yl)methyl acetate |
| 89 | 089 | N5-((R)-1-((carboxymethyl)amino)-3-((((R)-6'-hydroxy-2',4',6'-trimethyl-7'-oxo-6',7'-dihydrospiro[cyclopropane-1,5'-inden]-3'-yl)methyl)thio)-1-oxopropan-2-yl)-D-glutamine |
| 90 | 090 | (R)-2'-(hydroxymethyl)-4',6'-dimethyl-7'-oxo-6',7'-dihydrospiro[cyclopropane-1,5'-inden]-6'-yl acetate |
| 91 | 091 | (R)-3-(6'-hydroxy-2',4',6'-trimethyl-7'-oxo-6',7'-dihydrospiro[cyclopropane-1,5'-inden]-3'-yl)propanoic acid |
| 92 | 092 | (R)-6'-hydroxy-3'-(3-methoxypropyl)-2',4',6'-trimethylspiro[cyclopropane-1,5'-inden]-7'(6'H)-one |
| 93 | 093 | (R)-3'-(3,3-diethoxypropyl)-6'-hydroxy-2',4',6'-trimethylspiro[cyclopropane-1,5'-inden]-7'(6'H)-one |
| 94 | 094 | (R)-3-(6'-hydroxy-2',4',6'-trimethyl-7'-oxo-6',7'-dihydrospiro[cyclopropane-1,5'-inden]-3'-yl)propyl acetate |
| 95 | 095 | (R)-6'-hydroxy-3'-(3-methoxypropyl)-2',4',6'-trimethylspiro[cyclopropane-1,5'-inden]-7'(6'H)-one |
| 96 | 096 | (R)-6'-hydroxy-2',4',6'-trimethyl-3'-(((1-methyl-1H-imidazol-2-yl)thio)methyl)spiro[cyclopropane-1,5'-inden]-7'(6'H)-one |
| 97 | 097 | S-(((R)-6'-hydroxy-2',4',6'-trimethyl-7'-oxo-6',7'-dihydrospiro[cyclopropane-1,5'-inden]-3'-yl)methyl)homocysteine |
| 98 | 098 | ((S)-3-((((R)-6'-hydroxy-2',4',6'-trimethyl-7'-oxo-6',7'-dihydrospiro[cyclopropane-1,5'-inden]-3'-yl)methyl)thio)-2-methylpropanoyl)proline |
| 99 | 099 | (2'S,6'R)-6'-hydroxy-2'-(hydroxymethyl)-2',4',6'-trimethylspiro[cyclopropane-1,5'-indene]-3',7'(2-H,6'H)-dione |
| 100 | 100 | S-(((R)-6'-hydroxy-2',4',6'-trimethyl-7'-oxo-6',7'-dihydrospiro[cyclopropane-1,5'-inden]-3'-yl)methyl)-N-S-(((R)-6'-hydroxy-2',4',6'-trimethyl-7'-oxo-6',7'-dihydrospiro[cyclopropane-1,5'-inden]-3'-yl)methyl)cysteinyl-L-asparaginylglycyl-L-arginylcysteine |
| 101 | 101 | S-(((R)-6'-hydroxy-2',4',6'-trimethyl-7'-oxo-6',7'-dihydrospiro[cyclopropane-1,5'-inden]-3'-yl)methyl)-N-S-(((R)-6'-hydroxy-2',4',6'-trimethyl-7'-oxo-6',7'-dihydrospiro[cyclopropane-1,5'-inden]-3'-yl)methyl)cysteinyl-L-arginylglycyl-L-asparaginylcysteine |

TABLE 14-continued

The IUPAC name of Illudofulvene Analogs.

| Entry # | Illudofulvene Analog | IUPAC Name of Illudofulvene Analog |
|---|---|---|
| 102 | 102 | S-(((R)-6'-hydroxy-2',4',6'-trimethyl-7'-oxo-6',7'-dihydrospiro[cyclopropane-1,5'-inden]-3'-yl)methyl)cysteinyl-L-asparaginylglycyl-L-arginylcysteine |
| 103 | 103 | (R)-(6'-acetoxy-2'-(hydroxymethyl)-4',6'-dimethyl-7'-oxo-6',7'-dihydrospiro[cyclopropane-1,5'-inden]-3'-yl)methyl acetate |
| 104 | 104 | (R)-8'-hydroxy-6',8'-dimethyl-1',5'-dihydrospiro[cyclopropane-1,7'-indeno[1,2-e][1,3]dioxepin]-9'(8'H)-one |
| 105 | 105 | (E)-2-((2R,4S)-4-hydroxy-2-((1R,2S)-2-hydroxy-4,4-dimethylcyclopentyl)-2-methylcyclobutylidene)propanal |
| 106 | 106 | 5-(((3'S,6'R)-6'-hydroxy-2',2',4',6'-tetramethyl-7'-oxo-2',3',6',7'-tetrahydrospiro[cyclopropane-1,5'-inden]-3'-yl)oxy)-5-oxopentanoic acid |
| 107 | 107 | (3'S,6'R)-6'-hydroxy-2',2',4',6'-tetramethyl-7'-oxo-2',3',6',7'-tetrahydrospiro[cyclopropane-1,5'-inden]-3'-yl ((13S)-13-methyl-17-oxo-7,8,9,11,12,13,14,15,16,17-decahydro-6H-cyclopenta[a]phenanthren-3-yl) glutarate |
| 108 | 108 | (13S)-17-hydroxy-13-methyl-7,8,9,11,12,13,14,15,16,17-decahydro-6H-cyclopenta[a]phenanthren-3-yl 3-((R)-6'-hydroxy-2',4',6'-trimethyl-7'-oxo-6',7'-dihydrospiro[cyclopropane-1,5'-inden]-3'-yl)propanoate |
| 109 | 109 | (13S)-17-hydroxy-13-methyl-7,8,9,11,12,13,14,15,16,17-decahydro-6H-cyclopenta[a]phenanthren-3-yl ((3'S,6'R)-6'-hydroxy-2',2',4',6'-tetramethyl-7'-oxo-2',3',6',7'-tetrahydrospiro[cyclopropane-1,5'-inden]-3'-yl) glutarate |
| 110 | 110 | (13S)-13-methyl-17-oxo-7,8,9,11,12,13,14,15,16,17-decahydro-6H-cyclopenta[a]phenanthren-3-yl 3-((R)-6'-hydroxy-2',4',6'-trimethyl-7'-oxo-6',7'-dihydrospiro[cyclopropane-1,5'-inden]-3'-yl)propanoate |
| 111 | 111 | (10R,13S)-10,13-dimethyl-3-oxo-2,3,6,7,8,9,10,11,12,13,14,15,16,17-tetradecahydro-1H-cyclopenta[a]phenanthren-17-yl 3-(6'-hydroxy-2',4'-dimethyl-7'-oxo-6',7'-dihydrospiro[cyclopropane-1,5'-inden]-3'-yl)propanoate |
| 112 | 112 | (13S)-10,13-dimethyl-17-oxohexadecahydro-1H-cyclopenta[a]phenanthren-3-yl 3-((R)-6'-hydroxy-2',4',6'-trimethyl-7'-oxo-6',7'-dihydrospiro[cyclopropane-1,5'-inden]-3'-yl)propanoate |
| 113 | 113 | (R)-3'-(but-3-en-1-yl)-6'-hydroxy-2',4',6'-trimethylspiro[cyclopropane-1,5'-inden]-7'(6'H)-one |
| 114 | 114 | (6'R)-6'-hydroxy-2',4',6'-trimethyl-3'-(2-(oxiran-2-yl)ethyl)spiro[cyclopropane-1,5'-inden]-7'(6E)-one |
| 115 | 115 | (R)-3-(6'-hydroxy-2',4',6'-trimethyl-7'-oxo-6',7'-dihydrospiro[cyclopropane-1,5'-inden]-3'-yl)propanal oxime |
| 116 | 116 | (R)-3'-(tert-butoxymethyl)-6'-hydroxy-2',4',6'-trimethylspiro[cyclopropane-1,5'-inden]-7'(6'H)-one |
| 117 | 117 | 5-(((2'S,6'R)-3'-((4-carboxybutanoyl)oxy)-6'-hydroxy-2',4',6'-trimethyl-7'-oxo-2',3',6',7'-tetrahydrospiro[cyclopropane-1,5'-inden]-2'-yl)methoxy)-5-oxopentanoic acid |
| 118 | 118 | 5-(((2'S,6'R)-2'-(((3,5-dinitrobenzoyl)oxy)methyl)-6'-hydroxy-2',4',6'-trimethyl-7'-oxo-2',3',6',7'-tetrahydrospiro[cyclopropane-1,5'-inden]-3'-yl)oxy)-5-oxopentanoic acid |
| 119 | 119 | (6'R)-3'-(3,4-dihydroxybutyl)-6'-hydroxy-2',4',6'-trimethylspiro[cyclopropane-1,5'-inden]-7'(6'H)-one |
| 120 | 120 | (R)-6'-hydroxy-3'-(3-((3-((S)-6'-hydroxy-2',4',6'-trimethyl-7'-oxo-6',7'-dihydrospiro[cyclopropane-1,5'-inden]-3'-yl)propylidene)hydrazineylidene)propyl)-2',4',6'-trimethylspiro[cyclopropane-1,5'-inden]-7'(6'H)-one |
| 121 | 121 | (R)-2-(3-(6'-hydroxy-2',4',6'-trimethyl-7'-oxo-6',7'-dihydrospiro[cyclopropane-1,5'-inden]-3'-yl)propylidene)hydrazine-1-carboxamide |
| 122 | 122 | (R)-6'-hydroxy-2',4',6'-trimethyl-3'-(3-(2-phenylhydrazineylidene)propyl)spiro[cyclopropane-1,5'-inden]-7'(6'H)-one |
| 123 | 123 | (R)-N'-(3-(6'-hydroxy-2',4',6'-trimethyl-7'-oxo-6',7'-dihydrospiro[cyclopropane-1,5'-inden]-3'-yl)propylidene)-4-methylbenzenesulfonohydrazide |
| 124 | 124 | (R)-3-(6'-hydroxy-2',4',6'-trimethyl-7'-oxo-6',7'-dihydrospiro[cyclopropane-1,5'-inden]-3'-yl)propanal O-acetyl oxime |
| 125 | 125 | (R)-3'-(3-(2-(2,4-dinitirophenyl)hydrazineylidene)propyl)-6'-hydroxy-2',4',6'-trimethylspiro[cyclopropane-1,5'-inden]-7'(6'H)-one |
| 126 | 126 | (R)-6'-hydroxy-2',4',6'-trimethyl-7'-oxo-6',7'-dihydrospiro[cyclopropane-1,5'-indene]-3'-carbaldehyde oxime |
| 127 | 127 | 2-hydroxy-4-((R)-6'-hydroxy-2',4',6'-trimethyl-7'-oxo-6',7'-dihydrospiro[cyclopropane-1,5'-inden]-3'-yl)butanenitrile |

TABLE 14-continued

The IUPAC name of Illudofulvene Analogs.

| Entry # | Illudofulvene Analog | IUPAC Name of Illudofulvene Analog |
|---|---|---|
| 128 | 128 | (6'R)-6'-hydroxy-3'-(3-hydroxybutyl)-2',4',6'-trimethylspiro[cyclopropane-1,5'-inden]-7'(6'H)-one |
| 129 | 129 | (6'R)-2',4',6'-trimethyl-6',7'-dihydrospiro[cyclopropane-1,5'-indene]-6',7'-diol |
| 130 | 130 | (R)-6'-hydroxy-3'-(3-(hydroxyamino)propyl)-2',4',6'-trimethylspiro[cyclopropane-1,5'-inden]-7'(6'H)-one |
| 131 | 131 | (R)-N-benzyl-3-(6'-hydroxy-2',4',6'-trimethyl-7'-oxo-6',7'-dihydrospiro[cyclopropane-1,5'-inden]-3'-yl)propanamide |
| 132 | 133 | (E)-7-(chloromethylene)-5-hydroxy-5,9-dimethylspiro[3.5]non-8-en-6-one |
| 133 | 134 | (E)-6-(chloromethylene)-4-hydroxy-4,8-dimethylspiro[2.5]oct-7-en-5-one |
| 134 | 135 | ((2'S,6'R)-3',6'-dihydroxy-2',4',6'-trimethyl-7'-oxo-2',3',6',7'-tetrahydrospiro[cyclopropane-1,5'-inden]-2'-yl)methyl 4-nitrobenzoate |
| 135 | 136 | ((2'S,6'R)-3',6'-dihydroxy-2',4',6'-trimethyl-7'-oxo-2',3',6',7'-tetrahydrospiro[cyclopropane-1,5'-inden]-2'-yl)methyl 4-(N-acetoxyacetamido)benzoate |
| 136 | 137 | ((2'S,6'R)-6'-hydroxy-2',4',6'-trimethyl-3',7'-dioxo-2',3',6',7'-tetrahydrospiro[cyclopropane-1,5'-inden]-2'-yl)methyl 4-nitrobenzoate |
| 137 | 138 | ((2'S,6'R)-6'-hydroxy-2',4',6'-trimethyl-3',7'-dioxo-2',3',6',7'-tetrahydrospiro[cyclopropane-1,5'-inden]-2'-yl)methyl 4-(N-acetoxyacetamido)benzoate |
| 138 | 139 | (2'S,6'R)-6'-hydroxy-2',4',6'-trimethyl-2'-(((4-nitrobenzoyl)oxy)methyl)-7'-oxo-2',3',6',7'-tetrahydrospiro[cyclopropane-1,5'-inden]-3'-yl 4-nitrobenzoate |
| 139 | 140 | ((2'S,6'R)-3'-((4-(N-acetoxyacetamido)benzoyl)oxy)-6'-hydroxy-2',4',6'-trimethyl-7'-oxo-2',3',6',7'-tetrahydrospiro[cyclopropane-1,5'-inden]-2'-yl)methyl 4-(N-acetoxyacetamido)benzoate |
| 140 | 141 | dimethyl (5'R)-4',5'-dihydroxy-5',7',9'-trimethyl-4',5'-dihydro-1'H-spiro[cyclopropane-1,6'-[1,3a]ethenoindene]-2',3'-dicarboxylate |
| 141 | 142 | dimethyl (5'R)-5'-hydroxy-5',7',9'-trimethyl-4'-oxo-4',5'-dihydro-1'H-spiro[cyclopropane-1,6'-[1,3alethenoindene]-2',3'-dicarboxylate |
| 142 | 143 | (R)-6'-hydroxy-1',2',4',6'-tetramethylspiro[cyclopropane-1,5'-inden]-7'(6'H)-one |
| 143 | 144 | (R)-2-(2'-ethyl-6'-hydroxy-4',6'-dimethyl-7'-oxo-6',7'-dihydrospiro[cyclopropane-1,5'-inden]-3'-yl)methoxy)ethyl acetate |
| 144 | 145 | (R)-5-((6'-hydroxy-2',4',6'-trimethyl-7'-oxo-6',7'-dihydrospiro[cyclopropane-1,5'-inden]-3'-yl)methoxy)-5-oxopentanoic acid |
| 145 | 146 | (R)-4-(6'-hydroxy-2',4',6'-trimethyl-7'-oxo-6',7'-dihydrospiro[cyclopropane-1,5'-inden]-3'-yl)butanenitrile |
| 146 | 147 | (R)-3'-((benzo[d]thiazol-2-ylthio)methyl)-6'-hydroxy-2',4',6'-trimethylspiro[cyclopropane-1,5'-inden]-7'(6'H)-one |
| 147 | 148 | (R)-3'-((benzo[d]oxazol-2-ylthio)methyl)-6'-hydroxy-2',4',6'-trimethylspiro[cyclopropane-1,5'-inden]-7'(6'H)-one |
| 148 | 149 | (R)-6'-hydroxy-2',4',6'-trimethyl-3'-(((1-methyl-1H-tetrazol-5-yl)thio)methyl)spiro[cyclopropane-1,5'-inden]-7'(6'H)-one |
| 149 | 150 | (R)-6'-hydroxy-2',4',6'-trimethyl-3'-(((5-methyl-1H-benzo[dlmidazol-2-yl)thio)methyl)spiro[cyclopropane-1,5'-inden]-7'(6'H)-one |
| 150 | 151 | (R)-6'-hydroxy-2',4',6'-trimethyl-3'-(((1-phenyl-1H-tetrazol-5-yl)thio)methyl)spiro[cyclopropane-1,5'-inden]-7'(6'H)-one |
| 151 | 152 | (R)-6'-hydroxy-2',4',6'-trimethyl-3'-(((5-nitro-1H-benzo[d]imidazol-2-yl)thio)methyl)spiro[cyclopropane-1,5'-inden]-7'(6'H)-one |
| 152 | 153 | (R)-3'-(((1H-1,2,4-triazol-3-yl)thio)methyl)-6'-hydroxy-2',4',6'-trimethylspiro [cyclopropane-1,5'-inden]-7'(6'H)-one |
| 153 | 154 | (R)-6'-hydroxy-3'-(((4-hydroxypteridin-2-yl)thio)methyl)-2',4',6'-trimethylspiro[cyclopropane-1,5'-inden]-7'(6'H)-one |
| 154 | 155 | (R)-6'-hydroxy-3'-(((1-(4-hydroxyphenyl)-1H-tetrazol-5-yl)thio)methyl)-2',4',6'-trimethylspiro[cyclopropane-1,5'-inden]-7'(6'H)-one |
| 155 | 156 | (R)-4-(5-(((6'-hydroxy-2',4',6'-trimethyl-7'-oxo-6',7'-dihydrospiro[cyclopropane-1,5'-inden]-3'-yl)methyl)thio)-1H-tetrazol-1-yl)phenyl acetate |
| 156 | 157 | 7'-methyl-4'H-dispiro[cyclobutane-1,6'-indene-5',2''-[1,3]dioxolan]-4'-one |
| 157 | 158 | 5-hydroxy-2,2,6,8a-tetramethyl-2,3,3a,8,8a,8b-hexahydro-1H-cyclobuta[d]cyclopenta[b]oxepin-7(5H)-one |

TABLE 14-continued

The IUPAC name of Illudofulvene Analogs.

| Entry # | Illudofulvene Analog | IUPAC Name of Illudofulvene Analog |
|---|---|---|
| 158 | 159 | ((6'R)-3',6'-dihydroxy-2',4',6'-trimethyl-7'-oxo-2',3',6',7'-tetrahydrospiro[cyclopropane-1,5'-inden]-2'-yl)methyl acetate |
| 159 | 160 | 5-(((6'R)-2'-(acetoxymethyl)-6'-hydroxy-2',4',6'-trimethyl-7'-oxo-2',3',6',7'-tetrahydrospiro[cyclopropane-1,5'-inden]-3'-yl)oxy)-5-oxopentanoic acid |
| 160 | 161 | ((6'R)-6'-hydroxy-2',4',6'-trimethyl-3',7'-dioxo-2',3',6',7'-tetrahydrospiro[cyclopropane-1,5'-inden]-2'-yl)methyl acetate |
| 161 | 162 | 5-(((6'R)-6'-hydroxy-2',4',6'-trimethyl-3',7'-dioxo-2',3',6',7'-tetrahydrospiro[cyclopropane-1,5'-inden]-2'-yl)methoxy)-5-oxopentanoic acid |
| 162 | 163 | (6'R)-2'-(acetoxymethyl)-6'-hydroxy-2',4',6'-trimethyl-7'-oxo-2',3',6',7'-tetrahydrospiro[cyclopropane-1,5'-inden]-3'-yl 2-chloroacetate |
| 163 | 164 | (R)-(6'-hydroxy-2',4',6'-trimethyl-7'-oxo-6',7'-dihydrospiro[cyclopropane-1,5'-inden]-3'-yl)methyl 2-chloroacetate |
| 164 | 165 | (R)-(6'-hydroxy-2',4',6'-trimethyl-7'-oxo-6',7'-dihydrospiro[cyclopropane-1,5'-inden]-3'-yl)methyl 2-morpholinoacetate |
| 165 | 166 | (6'R)-2'-(acetoxymethyl)-6'-hydroxy-2',4',6'-trimethyl-7'-oxo-2',3',6',7'-tetrahydrospiro[cyclopropane-1,5'-inden]-3'-yl methyl glutarate |
| 166 | 167 | (6'R)-6'-hydroxy-2'-(hydroxymethyl)-2',4',6'-trimethyl-7'-oxo-2',3',6',7'-tetrahydrospiro[cyclopropane-1,5'-inden]-3'-yl methyl glutarate |
| 167 | 168 | ((6'R)-6'-hydroxy-2',4',6'-trimethyl-3',7'-dioxo-2',3',6',7'-tetrahydrospiro[cyclopropane-1,5'-inden]-2'-yl)methyl methyl glutarate |
| 168 | 169 | ((6'R)-6'-hydroxy-2',4',6'-trimethyl-3',7'-dioxo-2',3',6',7'-tetrahydrospiro[cyclopropane-1,5'-inden]-2'-yl)methyl 2-chloroacetate |
| 169 | 170 | 5-(2-hydroxyethyl)-3-(hydroxymethyl)-2,4,6-trimethyl-1H-inden-7-ol |
| 170 | 171 | 6-(2-hydroxyethyl)-2,5,7-trimethyl-1-methylene-1H-inden-4-ol |
| 171 | 172 | 6-ethyl-2,5,7-trimethyl-1-methylene-1H-inden-4-ol |
| 172 | 173 | 2-(4-hydroxy-2,5,7-ttimethyl-1-methylene-1H-inden-6-yl)ethyl acetate |
| 173 | 174 | 5-(2-hydroxyethyl)-3-(hydroxymethyl)-2,4,6-trimethyl-1H-indene-1,7-diol |
| 174 | 175 | (2S,3S,4R,5S,6R)-2-(acetoxymethyl)-6-(((R)-6'-hydroxy-2',4',6'-trimethyl-7'-oxo-6',7'-dihydrospiro[cyclopropane-1,5'-inden[-3'-yl)methoxy)tetrahydro-2H-pyran-3,4,5-triyltriacetate |
| 175 | 176 | 3-((R)-6'-hydroxy-2',4',6'-trimethyl-7'-oxo-6',7'-dihydrospiro[cyclopropane-1,5'-inden]-3'-yl)propyl leucinate |
| 176 | 177 | (R)-5-(3-(6'-hydroxy-2',4',6'-trimethyl-7'-oxo-6',7'-dihydrospiro[cyclopropane-1,5'-inden]-3'-yl)propoxy)-5-oxopentanoic acid |
| 177 | 178 | (R)-4-(3-(6'-hydroxy-2',4',6'-trimethyl-7'-oxo-6',7'-dihydrospiro[cyclopropane-1,5'-inden]-3'-yl)propoxy)-4-oxobutanoic acid |
| 178 | 179 | (R)-3-(6'-hydroxy-2',4',6'-trimethyl-7'-oxo-6',7'-dihydrospiro[cyclopropane-1,5'-inden]-3'-yl)propyl glycinate |
| 179 | 180 | (1a'R,3'R,7'S,7a'R)-3',7'-dihydroxy-1a',3',6',6'-tetramethyl-6',7'-dihydro-1a'H-spiro[cyclopropane-1,2'-indeno[3a,4-b]oxiren]-4'(3'H)-one |
| 180 | 181 | ((1a'R,3'R,6'S,7'S,7a'R)-3',7'-dihydroxy-1a',3',6'-trimethyl-4'-oxo-3',4',6',7'-tetrahydro-1a'H-spiro[cyclopropane-1,2'-indeno[3a,4-b]oxiren]-6'-yl)methyl acetate |
| 181 | 182 | (2'R,7'S,7a'S)-2'-chloro-7'-hydroxy-2',4'-dimethyl-1',2',7',7a'-tetrahydrospiro[cyclopropane-1,5'-indene]-3',6'-dione |
| 182 | 183 | (2'S,7'S,7a'S)-7'-hydroxy-2'-isopropoxy-2',4'-dimethyl-1',2',7',7a'-tetrahydrospiro[cyclopropane-1,5'-indene]-3',6'-dione |
| 183 | 184 | (R)-1-hydroxy-1-((6'-hydroxy-2',4',6'-trimethyl-7'-oxo-6',7'-dihydrospiro[cyclopropane-1,5'-inden]-3'-yl)methyl)urea |
| 184 | 185 | (S)-6'-hydroxy-2',4',6'-trimethylspiro[cyclopropane-1,5'-inden]-7'(6'H)-one |
| 185 | 186 | (6'S,7'R)-6',7'-dihydroxy-2',4',6'-trimethyl-7',7a'-dihydrospiro[cyclopropane-1,5'-inden]-3'(6'H)-one |
| 186 | 187 | (S)-6'-hydroxy-3'-(hydroxymethyl)-2',4',6'-trimethylspiro[cyclopropane-1,5'-inden]-7'(6'H)-one |
| 187 | 188 | (6'S,6''S)-3',3''-methylenebis(6'-hydroxy-2',4',6'-trimethylspiro[cyclopropane-1,5'-inden]-7'(6'H)-one) |

TABLE 14-continued

The IUPAC name of Illudofulvene Analogs.

| Entry # | Illudofulvene Analog | IUPAC Name of Illudofulvene Analog |
|---|---|---|
| 188 | 189 | (R)-1-((6'-hydroxy-2',4',6'-trimethyl-7'-oxo-6',7'-dihydrospiro[cyclopropane-1,5'-inden]-3'-yl)methyl)-1H-pyrrole-2,5-dione |
| 189 | 190 | (R)-1-(3-(6'-hydroxy-2',4',6'-trimethyl-7'-oxo-6',7'-dihydrospiro[cyclopropane-1,5'-inden]-3'-yl)propyl)-1H-pyrrole-2,5-dione |
| 190 | 191 | 6'-hydroxy-4',6'-dimethylspiro[cyclobutane-1,5'-inden]-7'(6'H)-one |
| 191 | 192 | (R)-2-((6'-hydroxy-2',4',6'-trimethyl-7'-oxo-6',7'-dihydrospiro[cyclopropane-1,5'-inden]-3'-yl)methyl)isoindoline-1,3-dione |
| 192 | 193 | (R)-3'-(azidomethyl)-6'-hydroxy-2',4',6'-trimethylspiro[cyclopropane-1,5'-inden]-7'(6'H)-one |
| 193 | 194 | (R)-3'-(((R)-3'-(azidomethyl)-6'-hydroxy-2',4',6'-trimethyl-7'-oxo-6',7'-dihydrospiro[c yclopropane-1,5'-inden]-1'-yl)methyl)-6'-hydroxy-2',4',6'-trimethylspiro[cyclopropane-1,5'-inden]-7'(6'H)-one |
| 194 | 195 | (R)-3'-(3-azidopropyl)-6'-hydroxy-4',6'-dimethylspiro[cyclopropane-1,5'-inden]-7'(6'H)-one |
| 195 | 196 | 3-((R)-6'-hydroxy-2',4',6'-trimethyl-7'-oxo-6',7'-dihydrospiro[cyclopropane-1,5'-inden]-3'-yl)propyl L-prolinate |
| 196 | 197 | (R)-2-(3-(6'-hydroxy-2',4',6'-trimethyl-7'-oxo-6',7'-dihydrospiro[cyclopropane-1,5'-inden]-3'-yl)propyl)isoindoline-1,3-dione |
| 197 | 198 | (R)-6'-hydroxy-2',4',6'-trimethyl-3'-((4-nitrophenoxy)methyl)spiro[cyclopropane-1,5'-inden]-7'(6E)-one |
| 198 | 199 | (R)-6'-hydroxy-2',4',6'-trimethyl-3'-(phenoxymethyl)spiro[cyclopropane-1,5'-inden]-7'(6'H)-one |
| 199 | 200 | (R)-6'-hydroxy-3'-(2-hydroxybenzyl)-2',4',6'-trimethylspiro[cyclopropane-1,5'-inden]-7'(6'H)-one |
| 200 | 201 | (R)-N-(3-(6'-hydroxy-2',4',6'-trimethyl-7'-oxo-6',7'-dihydrospiro[cyclopropane-1,5'-inden]-3'-yl)propyl)acetamide |
| 201 | 202 | (S)-N-(3-((R)-6'-hydroxy-2',4',6'-trimethyl-7'-oxo-6',7'-dihydrospiro[cyclopropane-1,5'-inden]-3'-yl)propyl)pyrrolidine-2-carboxamide |
| 202 | 203 | 3-((R)-6'-hydroxy-2',4',6'-trimethyl-7'-oxo-6',7'-dihydrospiro[cyclopropane-1,5'-inden]-3'-yl)propyl L-seryl-L-prolinate |
| 203 | 204 | 2'-(((tert-butyldimethylsilyl)oxy)methyl)-3',6'-dihydroxy-2',4',6'-trimethyl-2',3'-dihydrospiro[cyclopropane-1,5'-inden]-7'(6'H)-one |
| 204 | 205 | (2'R,3'S,6'R)-3'-amino-2'-(((tert-butyldimethylsilyl)oxy)methyl)-6'-hydroxy-2',4',6'-trimethyl-2',3'-dihydrospiro[cyclopropane-1,5'-inden]-7'(6'H)-one |
| 205 | 206 | (2'R,3'S,6'R)-3'-amino-6'-hydroxy-2'-(hydroxymethyl)-2',4',6'-trimethyl-2',3'-dihydrospiro[cyclopropane-1,5'-inden]-7'(6'H)-one |
| 206 | 207 | (S)-2-amino-N-(3-((R)-6'-hydroxy-2',4',6'-trimethyl-7'-oxo-6',7'-dihydrospiro[cyclopropane-1,5'-inden]-3'-yl)propyl)-4-methylpentanamide |
| 207 | 208 | 3-((R)-6'-hydroxy-2',4',6'-trimethyl-7'-oxo-6',7'-dihydrospiro[cyclopropane-1,5'-inden]-3'-yl)propyl (tert-butoxycarbonyl)-L-seryl-L-prolinate |
| 208 | 209 | 3-((R)-6'-hydroxy-2',4',6'-trimethyl-7'-oxo-6',7'-dihydrospiro[cyclopropane-1,5'-inden]-3'-yl)propyl L-seryl-L-seryl-L-prolinate |
| 209 | 210 | 3-((R)-6'-hydroxy-2',4',6'-trimethyl-7'-oxo-6',7'-dihydrospiro[cyclopropane-1,5'-inden]-3'-yl)propyl ((S)-2-((S)-2-((S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |
| 210 | 211 | (R)-3'-(3-aminopropyl)-6'-hydroxy-2',4',6'-trimethylspiro[cyclopropane-1,5'-inden]-7'(6'H)-one |
| 211 | 212 | (3'S,6'R)-6'-hydroxy-2',2',4',6'-tetramethyl-7'-oxo-2',3',6',7'-tetrahydrospiro[cyclopropane-1,5'-inden]-3'-yl L-prolinate |
| 212 | 213 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl L-prolinate |
| 213 | 214 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl L-seryl-L-seryl-L-prolinate |
| 214 | 215 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl ((S)-2-(S)-2-(S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |

TABLE 14-continued

The IUPAC name of Illudofulvene Analogs.

| Entry # | Illudofulvene Analog | IUPAC Name of Illudofulvene Analog |
|---|---|---|
| 215 | 216 | (3'S,6'R)-6'-hydroxy-2',2',4',6'-tetramethyl-7'-oxo-2',3',6',7'-tetrahydrospiro[cyclopropane-1,5'-inden]-3'-yl ((S)-2-((S)-2-((S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |
| 216 | 217 | (R)-(6'-hydroxy-2',4',6'-trimethyl-7'-oxo-6',7'-dihydrospiro[cyclopropane-1,5'-inden]-3'-yl)methyl 6-(2,5-dioxo-2,5-dihydro-1H-pyrrol-1-yl)hexanoate |
| 217 | 218 | (3'S,6'R)-6'-hydroxy-2',2',4',6'-tetramethyl-7'-oxo-2',3',6',7'-tetrahydrospiro[cyclopropane-1,5'-inden]-3'-yl 6-(2,5-dioxo-2,5-dihydro-1H-pyrrol-1-yl)hexanoate |
| 218 | 219 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl 4-(fluorosulfonyl)benzoate |
| 219 | 220 | (R)-1-acetoxy-1-((6'-hydroxy-2',4',6'-trimethyl-7'-oxo-6',7'-dihydrospiro[cyclopropane-1,5'-inden]-3'-yl)methyl)urea |
| 220 | 221 | (S)-2-((3S,6S,9S,12S,15S)-3-((1H-imidazol-4-yl)methyl)-12-(4-aminobutyl)-6,9-bis(hydroxymethyl)-15-isobutyl-1-morpholino-1,4,7,10,13-pentaoxo-2,5,8,11,14-pentaazahexadecan-16-amido)-N1-((S)-1-((3-((R)-6'-hydroxy-2',4',6'-trimethyl-7'-oxo-6',7'-dihydrospiro[cyclopropane-1,5'-inden]-3'-yl)propyl)amino)-4-methyl-1-oxopentan-2-yl)pentanediamide |
| 221 | 222 | (3'S,6'R)-6'-hydroxy-2',2',4',6'-tetramethyl-7'-oxo-2',3',6',7'-tetrahydrospiro[cyclopropane-1,5'-inden]-3'-yl 4-(fluorosulfonyl)benzoate |
| 222 | 223 | 3-((R)-6'-hydroxy-2',4',6'-trimethyl-7'-oxo-6',7'-dihydrospiro[cyclopropane-1,5'-inden]-3'-yl)propyl ((4R,7S,13S)-13-(2-amino-2-oxoethyl)-7-(3-guanidinopropyl)-6,9,12,15-tetraoxo-1,2-dithia-5,8,14-triazacycloheptadecane-4-carbonyl)glycinate |
| 223 | 224 | (R,E)-6'-hydroxy-2',4',6'-trimethylspiro[cyclopropane-1,5'-inden]-7'(6'H)-one oxime |
| 224 | 225 | (2'R,3'R,6'R,E)-2',3',6'-trihydroxy-2',4',6'-trimethyl-2',3'-dihydrospiro[cyclopropane-1,5'-inden]-7'(6'H)-one oxime |
| 225 | 226 | (R)-(6'-hydroxy-2',4',6'-trimethyl-7'-oxo-6',7'-dihydrospiro[cyclopropane-1,5'-inden]-3'-yl)methyl (E)-octadec-9-enoate |
| 226 | 227 | (R)-3-(6'-hydroxy-2',4',6'-trimethyl-7'-oxo-6',7'-dihydrospiro[cyclopropane-1,5'-inden]-3'-yl)propyl (E)-octadec-9-enoate |
| 227 | 228 | (2'S,6'R)-6'-hydroxy-2',4',6'-trimethyl-2'-((((E)-octadec-9-enoyl)oxy)methyl)-7'-oxo-2',3',6',7'-tetrahydrospiro[cyclopropane-1,5'-inden]-3'-yl (E)-octadec-9-enoate |
| 228 | 229 | (R,E)-N-(3-(6'-hydroxy-2',4',6'-trimethyl-7'-oxo-6',7'-dihydrospiro[cyclopropane-1,5'-inden]-3'-yl)propyl)octadec-9-enamide |
| 229 | 230 | N-((3'R,6'R)-6'-hydroxy-2',2',4',6'-tetramethyl-7'-oxo-2',3',6',7'-tetrahydrospiro[cyclopropane-1,5'-inden]-3'-yl)methanesulfonamide |
| 230 | 231 | N-((3'R,6'R)-6'-hydroxy-2',2',4',6'-tetramethyl-7'-oxo-2',3',6',7'-tetrahydrospiro[cyclopropane-1,5'-inden]-3'-yl)-4-methylbenzenesulfonamide |
| 231 | 232 | (R)-3-(6'-hydroxy-2',4',6'-trimethyl-7'-oxo-6',7'-dihydrospiro[cyclopropane-1,5'-inden]-3'-yl)propyl hydroxycarbamate |
| 232 | 233 | ethyl (R)-hydroxy((6'-hydroxy-2',4',6'-trimethyl-7'-oxo-6',7'-dihydrospiro[cyclopropane-1,5'-inden]-3'-yl)methyl)carbamate |
| 233 | 234 | benzyl (R)-hydroxy((6'-hydroxy-2',4',6'-trimethyl-7'-oxo-6',7'-dihydrospiro[cyclopropane-1,5'-inden]-3'-yl)methyl)carbamate |
| 234 | 235 | tert-butyl (R)-hydroxy((6'-hydroxy-2',4',6'-trimethyl-7'-oxo-6',7'-dihydrospiro[cyclopropane-1,5'-inden]-3'-yl)methyl)carbamate |
| 235 | 236 | (R)-6'-hydroxy-3'-(hydroxymethyl)-1',2',4',6'-tetramethylspiro[cyclopropane-1,5'-inden]-7'(6'H)-one |
| 236 | 237 | (R)-3-(6'-hydroxy-2',4',6'-trimethyl-7'-oxo-6',7'-dihydrospiro[cyclopropane-1,5'-inden]-3'-yl)propyl (2-bromoethyl)carbamate |
| 237 | 238 | (R)-3-(6'-hydroxy-2',4',6'-trimethyl-7'-oxo-6',7'-dihydrospiro[cyclopropane-1,5'-inden]-3'-yl)propyl (2-chloroethyl)carbamate |
| 238 | 239 | (R)-3-(6'-hydroxy-2',4',6'-trimethyl-7'-oxo-6',7'-dihydrospiro[cyclopropane-1,5'-inden]-3'-yl)propyl (2-hydroxyethyl)carbamate |
| 239 | 240 | (R)-3-(6'-hydroxy-2',4',6'-trimethyl-7'-oxo-6',7'-dihydrospiro[cyclopropane-1,5'-inden]-3'-yl)propyl acetoxy(acetyl)carbamate |

TABLE 14-continued

The IUPAC name of Illudofulvene Analogs.

| Entry # | Illudofulvene Analog | IUPAC Name of Illudofulvene Analog |
|---|---|---|
| 240 | 241 | (R)-N-(3-(6'-hydroxy-2',4',6'-trimethyl-7'-oxo-6',7'-dihydrospiro[cyclopropane-1,5'-inden]-3'-yl)propyl)methanesulfonamide |
| 241 | 242 | (R)-N-(3-(6'-hydroxy-2',4',6'-uimethyl-7'-oxo-6',7'-dihydrospiro[cyclopropane-1,5'-inden]-3'-yl)propyl)-4-methylbenzenesulfonamide |
| 242 | 243 | (R)-3-(6'-hydroxy-2',4',6'-trimethyl-7'-oxo-6',7'-dihydrospiro[cyclopropane-1,5'-inden]-3'-yl)propyl (2-fluoroethyl)carbamate |
| 243 | 244 | (R)-1-hydroxy-1-(3-(6'-hydroxy-2',4',6'-trimethyl-7'-oxo-6',7'-dihydrospiro[cyclopropane-1,5'-inden]-3'-yl)propyl)urea |
| 244 | 245 | (R)-1-hydroxy-1-(3-(6'-hydroxy-2',4',6'-trimethyl-7'-oxo-6',7'-dihydrospiro[cyclopropane-1,5'-inden]-3'-yl)propyl)thiourea |
| 245 | 246 | (R)-3-(6'-hydroxy-2',4',6'-trimethyl-7'-oxo-6',7'-dihydrospiro[cyclopropane-1,5'-inden]-3'-yl)propyl morpholine-4-carboxylate |
| 246 | 247 | (R)-3-(6'-hydroxy-2',4',6'-trimethyl-7'-oxo-6',7'-dihydrospiro[cyclopropane-1,5'-inden]-3'-yl)propyl morpholine-4-carboxylate |
| 247 | 248 | (R)-3-(6'-hydroxy-2',4',6'-trimethyl-7'-oxo-6',7'-dihydrospiro[cyclopropane-1,5'-inden]-3'-yl)propyl [1,4'-bipiperidine]-1'-carboxylate |
| 248 | 249 | (R)-6'-hydroxy-2'-(hydroxymethyl)-3',4',6'-trimethylspiro[cyclopropane-1,5'-inden]-7'(6'H)-one |
| 249 | 250 | ((1a'R,2'S,3'R,6'R,7a'S)-3'-acetoxy-6'-hydroxy-2',4',6'-trimethyl-7'-oxo-1',1a',2',3',6',7'-hexahydrospiro[cyclopropane-1,5'-cyclopropa[c]inden]-2'-yl)methyl acetate |
| 250 | 251 | ((1a'S,2'S,3'R,6'R,7a'R)-3'-acetoxy-6'-hydroxy-2',4',6'-trimethyl-7'-oxo-1',1a',2',3',6',7'-hexahydrospiro[cyclopropane-1,5'-cyclopropa[c]inden]-2'-yl)methyl acetate |
| 251 | 252 | (1a'R,3'S,6'R,7a'S)-3',6'-dihydroxy-2',2',4',6'-tetramethyl-1',1a',2',3'-tetrahydrospiro[cyclopropane-1,5'-cyclopropa[c]inden]-7'(6'H)-one |
| 252 | 253 | (1a'S,3'S,6'R,7a'R)-3',6'-dihydroxy-2',2',4',6'-tetramethyl-1',1a',2',3'-tetrahydrospiro[cyclopropane-1,5'-cyclopropa[c]inden]-7'(6'H)-one |
| 253 | 254 | (R)-3-(6'-hydroxy-2',4',6'-trimethyl-7'-oxo-6',7'-dihydrospiro[cyclopropane-1,5'-inden]-3'-yl)propyl 4-sulfamoylbenzoate |
| 254 | 255 | (R)-3-(6'-hydroxy-2',4',6'-trimethyl-7'-oxo-6',7'-dihydrospiro[cyclopropane-1,5'-inden]-3'-yl)propyl sulfamate |
| 255 | 256 | 3-((R)-6'-hydroxy-2',4',6'-trimethyl-7'-oxo-6',7'-dihydrospiro[cyclopropane-1,5'-inden]-3'-yl)propyl 1-(3-((R)-6'-hydroxy-2',4',6'-trimethyl-7'-oxo-6',7'-dihydrospiro[cyclopropane-1,5'-inden]-3'-yl)propyl)-1H-1,2,3-triazole-4-carboxylate |
| 256 | 257 | 3-((R)-6'-hydroxy-2',4',6'-trimethyl-7'-oxo-6',7'-dihydrospiro[cyclopropane-1,5'-inden]-3'-yl)propyl 1-(((R)-6'-hydroxy-2',4',6'-trimethyl-7'-oxo-6',7'-dihydrospiro[cyclopropane-1,5 '-ind en]-3'- yl)methyl)-1H-1,2,3-triazole-4-carboxylate |
| 257 | 258 | (4-carboxy-4-(4-carboxy-4-((3-((R)-6'-hydroxy-2',4',6'-trimethyl-7'-oxo-6',7'-dihydrospiro[cyclopropane-1,5'-inden]-3'-yl)propyl)amino)butanamido)butanoyl)glutamic acid |
| 258 | 259 | (R)-3'-((S)-2,2-dioxido-1,2,3-oxathiazinan-4-yl)-6'-hydroxy-2',4',6'-trimethylspiro[cyclopropane-1,5'-inden]-7'(6'H)-one |
| 259 | 260 | (R)-N-(3-(6'-hydroxy-2',4',6'-trimethyl-7'-oxo-6',7'-dihydrospiro[cyclopropane-1,5'-inden]-3'-yl)propyl)-[1,4'-bipiperidine]-1'-carboxamide |
| 260 | 261 | (R)-3-(6'-hydroxy-2',4',6'-trimethyl-7'-oxo-6',7'-dihydrospiro[cyclopropane-1,5'-inden]-3'-yl)propyl 1H-imidazole-l-carboxylate |
| 261 | 262 | methyl (R)-2-(((6'-hydroxy-2',4',6'-trimethyl-7'-oxo-6',7'-dihydrospiro[cyclopropane-1,5'-inden]-3'-yl)methyl)sulfonyl)acetate |
| 262 | 263 | methyl 2-((((R)-6'-hydroxy-2',4',6'-trimethyl-7'-oxo-6',7'-dihydrospiro[cyclopropane-1,5'-inden]-3'-yl)methyl)sulfinyl)acetate |
| 263 | 264 | N-[3-(6'-hydroxy-2',6'-dimethyl-7'-oxo-6',7'-dihydrospiro[cyclopropane-1,5'-inden]-3'-yl)propyl]sulfuric diamide |
| 264 | 265 | N-hydroxy-N'-[3-(6'-hydroxy-2',6'-dimethyl-7'-oxo-6',7'-dihydrospiro[cyclopropane-1,5'-inden]-3'-yl)propylisulfuric diamide |
| 265 | 266 | N-[3-(6'-hydroxy-2',6'-dimethyl-7'-oxo-6',7'-dihydrospiro[cyclopropane-1,5'-inden]-3'-yl)propyl]-N-methoxysulfuric diamide |
| 266 | 267 | (R)-2-amino-N-((6'-hydroxy-2',4',6'-trimethyl-7'-oxo-6',7'-dihydrospiro[cyclopropane-1,5'-inden]-3'-yl)methyl)-N-methoxyacetamide |

TABLE 14-continued

The IUPAC name of Illudofulvene Analogs.

| Entry # | Illudofulvene Analog | IUPAC Name of Illudofulvene Analog |
|---|---|---|
| 267 | 268 | (R)-2,2,2-trifluoro-N-(3-(6'-hydroxy-2',4',6'-trimethyl-7'-oxo-6',7'-dihydrospiro[cyclopropane-1,5'-inden]-3'-yl)propyl)acetamide |
| 268 | 269 | (R)-(6'-hydroxy-2',4',6'-trimethyl-7'-oxo-6',7'-dihydrospiro[cyclopropane-1,5'-inden]-3'-yl)methyl (4-methoxyphenyl)sulfamate |
| 269 | 270 | (R)-3'-(aminomethyl)-6'-hydroxy-2',4',6'-trimethylspiro[cyclopropane-1,5'-inden]-7'(6'H)-one |
| 270 | 271 | (R)-N-((6'-hydroxy-2',4',6'-trimethyl-7'-oxo-6',7'-dihydrospiro[cyclopropane-1,5'-inden]-3'-yl)methyl)methanesulfonamide |
| 271 | 272 | (5S,6S,7S)-3-(((3-((R)-6'-hydroxy-2',4',6'-trimethyl-7'-oxo-6',7'-dihydrospiro[cyclopropane-1,5'-inden]-3'-yl)propanoyl)oxy)methyl)-8-oxo-7-(2-(thiophen-2-yl)acetamido)-5-thia-1-azabicyclo[4.2.0]oct-2-ene-2-carboxylic acid 5-oxide |
| 272 | 273 | (5S,6S,7S)-3-((((3-((R)-6'-hydroxy-2',4',6'-trimethyl-7'-oxo-6',7'-dihydrospiro[cyclopropane-1,5'-inden]-3'-yl)propyl)carbamoyl)oxy)methyl)-8-oxo-7-(2-(thiophen-2-yl)acetamido)-5-thia-1-azabicyclo[4.2.0]oct-2-ene-2-carboxylic acid 5-oxide |
| 273 | 274 | (6S,7S)-3-((((3-((R)-6'-hydroxy-2',4',6'-trimethyl-7'-oxo-6',7'-dihydrospiro[cyclopropane-1,5'-inden]-3'-yl)propyl)carbamoyl)oxy)methyl)-8-oxo-7-(2-(thiophen-2-yl)acetamido)-5-thia-1-azabicyclo[4.2.0]oct-2-ene-2-carboxylic acid 5,5-dioxide |
| 274 | 275 | N-(((R)-6'-hydroxy-2',4',6'-trimethyl-7'-oxo-6',7'-dihydrospiro[cyclopropane-1,5'-inden]-3'-yl)methyl)pyrrolidine-2-carboxamide |
| 275 | 276 | 2-amino-N-(((R)-6'-hydroxy-2',4',6'-trimethyl-7'-oxo-6',7'-dihydrospiro[cyclopropane-1,5'-inden]-3'-yl)methyl)-4-methylpentanamide |
| 276 | 277 | (R)-1-hydroxy-3-((6'-hydroxy-2',4',6'-trimethyl-7'-oxo-6',7'-dihydrospiro[cyclopropane-1,5'-inden]-3'-yl)methyl)urea |
| 277 | 278 | (R)-1-((6'-hydroxy-2',4',6'-trimethyl-7'-oxo-6',7'-dihydrospiro[cyclopropane-1,5'-inden]-3'-yl)methyl)-3-methoxyurea |
| 278 | 279 | (R)-1-((6'-hydroxy-2',4',6'-trimethyl-7'-oxo-6',7'-dihydrospiro[cyclopropane-1,5'-inden]-3'-yl)methyl)-3-(2-hydroxyethyl)urea |
| 279 | 280 | (R)-1-(3-(6'-hydroxy-2',4',6'-trimethyl-7'-oxo-6',7'-dihydrospiro[cyclopropane-1,5'-inden]-3'-yl)propyl)-3-(2-hydroxyethyl)urea |
| 280 | 281 | (R)-1-(2-chloroethyl)-3-(3-(6'-hydroxy-2',4',6'-trimethyl-7'-oxo-6',7'-dihydrospiro[cyclopropane-1,5'-inden]-3'-yl)propyl)urea |
| 281 | 282 | (R)-1-(2-chloroethyl)-3-((6'-hydroxy-2',4',6'-trimethyl-7'-oxo-6',7'-dihydrospiro[cyclopropane-1,5'-inden]-3'-yl)methyl)urea |
| 282 | 283 | N-[(6'-hydroxy-2',6'-dimethyl-7'-oxo-6',7'-dihydrospiro[cyclopropane-1,5'-inden]-3'-yl)methyl]sulfuric diamide |
| 283 | 284 | (R)-3-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 284 | 285 | N-hydroxy-N-R6'-hydroxy-2',6'-dimethyl-7'-oxo-6',7'-dihydrospiro[cyclopropane-1,5'-inden]-3'-yl)methyl]sulfuric diamide |
| 285 | 286 | (R)-5-fluoro-1-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 286 | 287 | (R)-5-fluoro-3-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 287 | 288 | (R)-1-hydroxy-3-(3-(6'-hydroxy-2',4',6'-trimethyl-7'-oxo-6',7'-dihydrospiro[cyclopropane-1,5'-inden]-3'-yl)propyl)urea |
| 288 | 289 | (R)-1-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 289 | 290 | ((S)-6'-hydroxy-2',4',6'-trimethyl-7'-oxo-6',7'-dihydrospiro[cyclopropane-1,5'-inden]-3'-yl)methyl 5-oxo-5-(((S)-1,2,3,10-tetramethoxy-9-oxo-5,6,7,9-tetrahydrobenzo[a]heptalen-7-yl)amino)pentanoate |
| 290 | 291 | 3-((S)-6'-hydroxy-2',4',6'-trimethyl-7'-oxo-6',7'-dihydrospiro[cyclopropane-1,5'-inden]-3'-yl)propyl 5-oxo-5-(((S)-1,2,3,10-tetramethoxy-9-oxo-5,6,7,9-tetrahydrobenzo[a]heptalen-7-yl)amino)pentanoate |

TABLE 14-continued

The IUPAC name of Illudofulvene Analogs.

| Entry # | Illudofulvene Analog | IUPAC Name of Illudofulvene Analog |
|---|---|---|
| 291 | 292 | N1-(((S)-6'-hydroxy-2',4',6'-trimethyl-7'-oxo-6',7'-dihydrospiro[cyclopropane-1,5'-inden]-3'-yl)methyl)-N5-((S)-1,2,3,10-tetramethoxy-9-oxo-5,6,7,9-tetrahydrobenzo[a]heptalen-7-yl)glutaramide |
| 292 | 293 | 3-((S)-6'-hydroxy-2',4',6'-trimethyl-7'-oxo-6',7'-dihydrospiro[cyclopropane-1,5'-inden]-3'-yl)-N-((S)-1,2,3,10-tetramethoxy-9-oxo-5,6,7,9-tetrahydrobenzo[a]heptalen-7-yl)propanamide |
| 293 | 294 | 2-amino-N-(aR)-6'-hydroxy-2',4',6'-trimethyl-7'-oxo-6',7'-dihydrospiro[cyclopropane-1,5'-inden]-3'-yl)methyl)-N-methoxypropanamide |
| 294 | 295 | 2-amino-N-MR)-6'-hydroxy-2',4',6'-trimethyl-7'-oxo-6',7'-dihydrospiro[cyclopropane-1,5'-inden]-3'-yl)methyl)-N-methoxy-4-methylpentanamide |
| 295 | 296 | 2-amino-N-(((R)-6'-hydroxy-2',4',6'-trimethyl-7'-oxo-6',7'-dihydrospiro[cyclopropane-1,5'-inden]-3'-yl)methyl)-N-methoxy-4-(methylthio)butanamide |
| 296 | 297 | 2-amino-N-(((R)-6'-hydroxy-2',4',6'-trimethyl-7'-oxo-6',7'-dihydrospiro[cyclopropane-1,5'-inden]-3'-yl)methyl)-3-(1H-indol-3-yl)-N-methoxypropanamide |
| 297 | 298 | (R)-3-(6'-hydroxy-2',4',6'-trimethyl-7'-oxo-6',7'-dihydrospiro[cyclopropane-1,5'-inden]-3'-yl)propyl (tert-butoxycarbonyl)glycinate |
| 298 | 299 | (2'S,3'R,6'R)-2'-(azidomethyl)-3',6'-dihydroxy-2',4',6'-trimethyl-2',3'-dihydrospiro[cyclopropane-1,5'-inden]-7'(6'H)-one |
| 299 | 300 | (2'R,3'R,6'R)-3'-azido-6'-hydroxy-2'-(hydroxymethyl)-2',4',6'-trimethyl-2',3'-dihydrospiro[cyclopropane-1,5'-inden]-7'(6'H)-one |
| 300 | 301 | (R)-6'-hydroxy-2',4',6'-trimethyl-7'-oxo-6',7'-dihydrospiro[cyclopropane-1,5'-inden]-3'-yl 6-oxo-6-phenylhexanoate |
| 301 | 302 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 3,5-dinitrobenzoate |
| 302 | 303 | (2'S,3'R,6'R)-2'-(((3,5-dinitrocyclohexa-2,4-diene-1-carbonyl)oxy)methyl)-6'-hydroxy-2',4',6'-trimethyl-7'-oxo-2',3',6',7'-tetrahydrospiro[cyclopropane-1,5'-inden]-3'-yl 3,5-dinitrobenzoate |
| 303 | 304 | (R)-3-(6'-hydroxy-2',4',6'-trimethyl-7'-oxo-6',7'-dihydrospiro[cyclopropane-1,5'-indeiA-3'-yl)propyl propiolate |
| 304 | 305 | (R)-3-(6'-hydroxy-2',4',6'-trimethyl-7'-oxo-6',7'-dihydrospiro[cyclopropane-1,5'-inden]-3'-yl)propyl (4-nitrophenyl) carbonate |
| 305 | 306 | (R)-3-(6'-hydroxy-2',4',6'-trimethyl-7'-oxo-6',7'-dihydrospiro[cyclopropane-1,5'-inden]-3'-yl)propyl 4-methylbenzenesulfonate |
| 306 | 307 | (3'R,6'R)-3'-azido-6'-hydroxy-2',2',4',6'-tetramethyl-2',3'-dihydrospiro[cyclopropane-1,5'-inden]-7'(6'H)-one |
| 307 | 308 | (3'R,6'R)-3'-amino-6'-hydroxy-2',2',4',6'-tetramethyl-2',3'-dihydrospiro[cyclopropane-1,5'-inden]-7'(6'H)-one |
| 308 | 309 | (2'R,3'S,6'R)-3'-azido-2'-(((tert-butyldimethylsilyl)oxy)methyl)-6'-hydroxy-2',4',6'-trimethyl-2',3'-dihydrospiro[cyclopropane-1,5'-inden]-7'(6'H)-one |
| 309 | 310 | (R)-(6'-hydroxy-2',4',6'-trimethyl-7'-oxo-6',7'-dihydrospiro[cyclopropane-1,5'-inden]-3'-yl)methy 4-sulfamoylbenzoate |
| 310 | 311 | (3'S,6'R)-6'-hydroxy-2',2',4',6'-tetramethyl-7'-oxo-2',3',6',7'-tetrahydrospiro[cyclopropane-1,5'-inden]-3'-yl 4-sulfamoylbenzoate |
| 311 | 312 | (R)-(6'-hydroxy-2',4',6'-trimethyl-7'-oxo-6',7'-dihydrospiro[cyclopropane-1,5'-inden]-3'-yl)methyl 4-methylbenzenesulfonate |
| 312 | 313 | 2,3,4,5,6-pentafluoro-N-((3'R,6'R)-6'-hydroxy-2',2',4',6'-tetramethyl-7'-oxo-2',3',6',7'-tetrahydrospiro[cyclopropane-1,5'-inden]-3'-yl)benzenesulfonamide |
| 313 | 314 | (R)-3-(6'-hydroxy-2',4',6'-trimethyl-7'-oxo-6',7'-dihydrospiro[cyclopropane-1,5'-inden]-3'-yl)propyl 4-methylbenzenesulfonate |
| 314 | 315 | (R)-3'-((2,5-dimethyl-1H-pyrrol-3-yl)methyl)-6'-hydroxy-2',4',6'-trimethylspiro[cyclopropane-1,5'-inden]-7'(6'H)-one |
| 315 | 316 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-(fluorosulfonyl)benzoate |
| 316 | 317 | (2'S,3'R,6'R)-6'-hydroxy-2'-(hydroxymethyl)-2',4',6'-trimethyl-7'-oxo-2',31,6',7'-tetrahydrospiro[cyclopropane-1,5'-inden]-3'-yl 4-(fluorosulfonyl)benzoate |

TABLE 14-continued

The IUPAC name of Illudofulvene Analogs.

| Entry # | Illudofulvene Analog | IUPAC Name of Illudofulvene Analog |
|---|---|---|
| 317 | 318 | ((2'S,3'R,6'R)-3'-((4-(fluorosulfonyl)benzoyl)oxy)-6'-hydroxy-2',4',6'-trimethyl-7'-oxo-2',3',6',7'-tetrahydrospiro[cyclopropane-1,5'-inden]-2'-yl)methyl 4-(fluorosulfonyl)benzoate |
| 318 | 332 | (R)-6'-hydroxy-3'-((methoxyamino)methyl)-2',4',6'-trimethylspiro[cyclopropane-1,5'-inden]-7'(6'H)-one |
| 319 | 333 | ((2'S,3'R,6'R)-6'-hydroxy-2',4',6'-trimethyl-3'-(((4-nitrophenoxy)carbonyl)oxy)-7'-oxo-2',3',6',7'-tetrahydrospiro[cyclopropane-1,5'-inden]-2'-yl)methyl acetate |
| 320 | 334 | ((2'S,3'R,6'R)-3'-(((2-((tert-butoxycarbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 321 | 335 | tert-butyl ((2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate) |
| 322 | 337 | 4-nitrophenyl (R)-((6'-hydroxy-2',4',6'-trimethyl-7'-oxo-6',7'-dihydrospiro[cyclopropane-1,5'-inden]-3'-yl)methyl)carbamate |
| 323 | 338 | 4-nitrophenyl (R)-(3-(6'-hydroxy-2',4',6'-trimethyl-7'-oxo-6',7'-dihydrospiro[cyclopropane-1,5'-inden]-3'-yl)propyl)carbamate |
| 324 | 339 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-methylbenzenesulfonate |
| 325 | 340 | (R)-N-((6'-hydroxy-2',4',6'-tritnethyl-7'-oxo-6',7'-dihydrospiro[cyclopropane-1,5'-inden]-3'-yl)methyl)methanesulfonamide |
| 326 | 345 | (2'S,3'R,6'R)-2'-(acetoxymethyl)-6'-hydroxy-2',4',6'-trimethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate |
| 327 | 346 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-(N-(2-(2-(2-(2-aminoacetamido)acetamido)acetamido)ethyl)-N-methylsulfamoyl)benzoate |
| 328 | 347 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-sulfamoylbenzoate |
| 330 | 348 | (3'S,6'R)-6'-hydroxy-2',2',4',6'-tetramethyl-7'-oxo-2',3',6',7'-tetrahydrospiro[cyclopropane-1,5'-inden]-3'-yl 4-sulfamoylbenzoate |
| 331 | 351 | (3'S,6'R)-6'-hydroxy-2',2',4',6'-tetramethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate |
| 332 | 353 | ((6'R)-3'-(((2-(((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 333 | 354 | 4-((S)-2-((S)-2-(6-(2,5-dioxo-2,5-dihydro-1H-pyrrol-1-yl)hexanamido)-3-methylbutanamido)-5-ureidopentanamido)benzyl (2-(3-((S)-6'-hydroxy-2',4',6'-trimethyl-7'-oxo-6',7'-dihydrospiro[cyclopropane-1,5'-inden]-3'-yl)propylidene)hydrazine-1-carbonyl)carbamate |
| 334 | 356 | ((2'S,3'S,6'R)-3'-(((1-(9H-fluoren-9-yl)-13-methyl-3,6,9,12-tetraoxo-2-oxa-4,7,10,13-tetraazapentadecan-15-yl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 335 | 357 | ((2'S,3'S,6'R)-3'-(((2-(2-(2-(2-aminoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 336 | 359 | ((2'S,3'S,6'R)-6'-hydroxy-2',4',6'-trimethyl-3'-((methyl(2,2,14-trimethyl-4,7,10,13-tetraoxo-3-oxa-5,8,11,14-tetraazahexadecan-16-yl)carbamoyl)oxy)-7'-oxo-2',3',6',7'-tetrahydrospiro[cyclopropane-1,5'-inden]-2'-yl)methyl acetate |
| 337 | 361 | ((2'S,3'R,6'R)-3'-((((2,5-dioxopyrrolidin-1-yl)oxy)carbonyl)oxy)-6'-hydroxy-2',4',6'-trimethyl-7'-oxo-2',3',6',7'-tetrahydrospiro[cyclopropane-1,5'-inden]-2'-yl)methyl acetate |
| 338 | 362 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl methanesulfonate |
| 339 | 363 | (2'S,3'R,6'R)-2'-(aminomethyl)-3',6'-dihydroxy-2',4',6'-trimethyl-2',3'-dihydrospiro[cyclopropane-1,5'-inden]-7'(6'H)-one |

TABLE 14-continued

The IUPAC name of Illudofulvene Analogs.

| Entry # | Illudofulvene Analog | IUPAC Name of Illudofulvene Analog |
|---|---|---|
| 340 | 364 | (2'R,3'R,6'R)-3'-amino-6'-hydroxy-2'-(hydroxymethyl)-2',4',6'-trimethyl-2',3'-dihydrospiro[cyclopropane-1,5'-inden]-7'(6'H)-one |
| 341 | 366 | tert-butyl (R)-((6'-hydroxy-2',4',6'-trimethyl-7'-oxo-6',7'-dihydrospiro[cyclopropane-1,5'-inden]-3'-yl)methyl)carbamate |
| 342 | 367 | tert-butyl (R)-(3-(6'-hydroxy-2',4',6'-trimethyl-7'-oxo-6',7'-dihydrospiro[cyclopropane-1,5'-inden]-3'-yl)propyl)carbamate |
| 343 | 368 | ((2'S,3'R,6'R)-3'-acetoxy-6'-hydroxy-2',4',6'-trimethyl-7'-oxo-2',3',6',7'-tetrahydrospiro[cyclopropane-1,5'-inden]-2'-yl)methyl acetate |
| 344 | 369 | (2'S,3'R,6'R)-2'-(((tert-butyldimethylsilyl)oxy)methyl)-3',6'-dihydroxy-2',4',6'-trimethyl-2',3'-dihydrospiro[cyclopropane-1,5'-inden]-7'(6'H)-one |
| 345 | 370 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl acetate |
| 346 | 371 | (2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl acetate |
| 347 | 372 | (2'R,3'R,6'R)-2'-formyl-6'-hydroxy-2',4',6'-trimethyl-7'-oxo-2',3',6',7'-tetrahydrospiro[cyclopropane-1,5'-inden]-3'-yl acetate |
| 348 | 373 | (2'S,3'R,6'R)-2'-(((((9H-fluoren-9-yl)methoxy)carbonyl)amino)methyl)-6'-hydroxy-2',4',6'-trimethyl-7'-oxo-2',3',6',7'-tetrahydrospiro[cyclopropane-1,5'-inden]-3'-yl acetate |
| 349 | 374 | (2'S,3'R,6'R)-2'-(aminomethyl)-6'-hydroxy-2',4',6'-trimethyl-7'-oxo-2',3',6',7'-tetrahydrospiro[cyclopropane-1,5'-inden]-3'-yl acetate |
| 350 | 377 | ((2'S,3'R,6'R)-6'-hydroxy-2',4',6'-trimethyl-7'-oxo-3'-((tributylsilyl)oxy)-2',3',6',7'-tetrahydrospiro[cyclopropane-1,5'-inden]-2'-yl)methyl acetate |
| 351 | 378 | (2'S,3'R,6'R)-2'-(((tert-butoxycarbonyl)amino)methyl)-6'-hydroxy-2',4',6'-trimethyl-7'-oxo-2',3',6',7'-tetrahydrospiro[cyclopropane-1,5'-inden]-3'-yl acetate |
| 352 | 379 | ((2'S,3'R,6'R)-3'-(((2-(((((4-((14S,17S)-1-(9H-fluoren-9-yl)-14-isopropyl-3,6,9,12,15-pentaoxo-17-(3-ureidopropyl)-2-oxa-4,7,10,13,16-pentaazaoctadecan-18-amido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 353 | 380 | ((2'S,3'R,6'R)-3'-(((2-(((((4-((2S,5S)-14-amino-5-isopropyl-4,7,10,13-tetraoxo-2-(3-ureidopropyl)-3,6,9,12-tetraazatetradecanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 354 | 381 | (2'S,3'R,6'R)-6'-hydroxy-2'-(hydroxymethyl)-2',4',6'-trimethyl-3'-((tributylsilyl)oxy)-2',3'-dihydrospiro[cyclopropane-1,5'-inden]-7'(6'H)-one |
| 355 | 382 | (2'R,3'R,6'R)-6'-hydroxy-2',4',6'-trimethyl-7'-oxo-3'-((tributylsilyl)oxy)-2',3',6',7'-tetrahydrospiro[cyclopropane-1,5'-indene]-2'-carbaldehyde |
| 356 | 383 | (2'R,3'R,6'R)-3',6'-dihydroxy-2',4',6'-trimethyl-7'-oxo-2',3',6',7'-tetrahydrospiro[cyclopropane-1,5'-indene]-2'-carbaldehyde |
| 357 | 384 | tert-butyl (((2'S,3'R,6'R)-6'-hydroxy-2',4',6'-tlimethyl-7'-oxo-3'-((tributylsilyl)oxy)-2',3',6',7'-tetrahydrospiro[cyclopropane-1,5'-inden]-2'-yl)methyl)carbamate |
| 358 | 389 | tert-butyl (((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl)carbamate |
| 359 | 392 | ((2'S,3'S,6'R)-3'-(((2-(2-(2-(2-azidoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 360 | 393 | ((2'S,3'R,6'R)-3'-(((2-(2,5-dioxo-2,5-dihydro-1H-pyrrol-1-yl)ethyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 361 | 394 | (R)-6'-hydroxy((hydroxyamino)methyl)-2',4',6'-trimethylspiro[cyclopropane-1,5'-inden]-7'(6'H)-one |

TABLE 15

A summary NCI DTP 60 Cell Line showing Growth Inhibition (GI), Total Growth Inhibition (TGI, the concentration of test drug where 100 × (T − T0)/(C − T0) = 0, i.e. TGI signifies a cytostatic effect) and Lethal Concentration Dose (a cytotoxic effect, LD) Data for selected Other Drugs, naturally occurring illudins, and Illudofulvene Analogs.

| NAME/NSC | Mean GI50 inhibition | Mean TGI cytostatic | Mean LD50 cytotoxic |
|---|---|---|---|
| Pyrrolobenzo-diazepines 694501 | 7 nM | 302 nM | >23,000 nM |
| Maytansine 153858 | 19 nM | 318 nM | 49,200 nM |
| Fumagillol 642492 | 6,130 nM | 9,850 nM | >50,000 nM |
| Dolstatin-10 376128 | 17 nM | 2,680 nM | >50,000 nM |
| Auristatins 654663 | 1.4 nM | 902 nM | >5,000 nM |
| Enadiyne 157365 | 2,900 nM | >100,000 nM | >100,000 nM |
| Halichondrin B 609395 | 1.2 nM | 199 nM | >1,000 nM |
| Tubulysin A | 12 nM | 1,318 nM | >10,000 nM |
| Illudin S | 10 nM | 64 nM | 511 nM |
| Illudin M | 3 nM | 20 nM | 291 nM |
| Illudofulvene Analog 0016 | 102 nM | 1,070 nM | 4,270 nM |
| Illudofulvene Analog 0142 | 447 nM | 4,667 nM | 53,700 nM |
| Illudofulvene Analog 0159 | 117 nM | 2,090 nM | 14,790 nM |

TABLE 16

A comparison of Illudofulvene Analog 002 growth inhibition values obtained from cells in the NCI DTP 60 cell line panel to expression of various DNA repair genes, according to an embodiment of the invention.

| GENE | GENE SEQ ID Nos | P value |
|---|---|---|
| ERCC2 | 21, 22, 145 through 155 | P = 0.0246 |
| ERCC8 | 1, 2, 35 through 45 | P = 0.007 |
| GTF2H1 | 5, 6, 57 through 67 | P = 0.0007 |
| PTGR1 | 249, 250, 251 through 261 | P < 0.0001 |
| USP7 | 1, 16, 112 through 122 | P < 0.0001 |
| XPC | none | P > 0.20 |
| XRCC1 | none | P > 0.20 |
| RAD50 | none | P > 0.20 |

TABLE 17

A comparison of Illudofulvene Analog 142 growth inhibition values obtained from cells in the NCI DTP 60 cell line panel to expression of various DNA repair genes, according to an embodiment of the invention.

| GENE | GENE SEQ ID Nos | P value |
|---|---|---|
| ERCC2 | 21, 22, 145 through 155 | P = 0.029 |
| ERCC3 | 19, 20, 134 through 144 | P = 0.0167 |
| ERCC6 | 3, 4, 46 through 56 | P = 0.0297 |
| ERCC8 | 1, 2, 35 through 45 | P = 0.0159 |
| PTGR1 | 249, 250, 251 through 261 | P < 0.0001 |
| USP7 | 1, 16, 112 through 122 | P < 0.0001 |
| XPC | none | P > 0.20 |
| XRCC1 | none | P > 0.20 |
| RAD50 | none | P > 0.20 |

TABLE 18

A comparison of Illudofulvene Analog 184 growth inhibition values obtained from cells in the NCI DTP 60 cell line panel to expression of various DNA repair genes, according to an embodiment of the invention.

| GENE | GENE SEQ ID Nos | P value |
|---|---|---|
| ERCC3 | 19, 20, 134 through 144 | P = 0.0252 |
| ERCC8 | 1, 2, 35 through 45 | P = 0.0125 |
| GTF2H2 | 5, 6, 68 through 78 | P = 0.0107 |
| PTGR1 | 249, 250, 251 through 261 | P < 0.0001 |
| USP7 | 15, 16, 112 through 122 | P < 0.0001 |
| MYC | 222, 223, 224 through 235 | P < 0.005 |
| XPA | 27, 28, 178 through 188 | P = 0.0219 |
| XPC | none | P > 0.20 |
| XRCC1 | none | P > 0.20 |
| RAD50 | none | P > 0.20 |

TABLE 19

A comparison of Illudofulvene Analog 176 growth inhibition values obtained from cells in the NCI DTP 60 cell line panel to expression of various DNA repair genes, according to an embodiment of the invention.

| GENE | GENE SEQ ID Nos | P value |
|---|---|---|
| ERCC3 | 19, 20, 134 through 144 | P = 0.0258 |
| ERCC8 | 1, 2, 35 through 45 | P = 0.042 |
| RAD18 | 29, 30, 189 through 199 | P = 0.0147 |
| GTF2H3 | 9, 10, 79 through 89 | P = 0.0037 |
| GTF2H5 | 13, 14 101 through 111 | P = 0.0387 |
| PTGR1 | 249, 250, 251 through 261 | P < 0.0001 |
| USP7 | 15, 16, 112 through 122 | P < 0.0001 |
| MYC | 222, 223, 224 through 235 | P < 0.002 |
| XPC | none | P > 0.20 |
| XRCC1 | none | P > 0.20 |
| RAD50 | none | P > 0.20 |

TABLE 20

A comparison of the Illudin S growth inhibition values obtained from cells in the NCI DTP 60 cell line panel to expression of various DNA repair genes.

| GENE | GENE SEQ ID Nos. | P value |
|---|---|---|
| ERCC3 | 19, 20, 134 through 144 | P = 0.032 |
| ERCCI | 236, 237, 238 through 248 | P = 0.0102 |
| GTF2H1 | 5, 6, 57 through 67 | P = 0.0003 |
| PTGRI | 249, 250, 251 through 261 | P < 0.0244 |
| PTGR2 | 262, 263, 264 through 274 | P = 0.0382 |
| PTGR1 + 2* | 249 through 274 | P = 0.0031 |
| USP7 | 15, 16, 112 through 122 | P < 0.0103 |
| MYC | 222, 223, 224 through 235 | P < 0.0134 |
| XPC | none | P > 0.20 |
| XRCC1 | none | P > 0.20 |
| RAD50 | none | P > 0.20 |

*PTGR1 + 2 refers to the sum of the activity of PTGR1 gene and the PTGR2 gene.

Analysis of Primary Tumor Cell Sensitivity.

Visible residues of healthy tissue are removed from the tumor sample excised from the patient or obtained from peripheral blood or other fluids. The tumor can be washed with PBS, placed in a petri dish and 2 ml of Primary Cancer Cell Medium D-ACF (PromoCell #C-2081) added and the tumor dissected into small pieces, then homogenized to 1 mm³ particles. The tissue can be pelleted, washed, suspended then plated into NCDD-treated tissue culture vessels (PromoCell #C-43080) containing Primary Cancer Cell Medium D-ACF. After 7 days the adherent cells are harvested, split, and plated into NCDD-treated tissue culture vessels (PromoCell #C-43080) containing Primary Cancer Cell Medium D-ACF. A portion of the harvested adherent tumor cells are plated into 6 well tissue culture plates containing Primary Cancer Cell Medium D-ACF. Cells are allowed to adhere overnight. An illudofulvene is then added at: 0 ng/mL (control), 30 ng/mL, 100 ng/mL, 300 ng/mL, 1000 ng/mL, 3000 ng/mL. Cell viability at each concentration can then be determined and compared to the control population at 48 hours later by using a viability dye such as MTT, trypan blue or Sulforhodamine B. Tumor cell populations with an IC50 less than 300 ng/mL can be considered sensitive to the illudofulvene, whereas those with an IC50 greater than 3,000 ng/mL can be considered resistant. The illudofulvene can be administered to the patient based on the sensitivity. For example, in an embodiment of the invention, the tumor sample can be exposed to the desired Illudofulvene Analog under study at half-log internal concentrations from 1 ng/mL to 10,000 ng/mL, and cell viability determined using a viability dye (MTT, trypan blue, Sulforhodamine B, etc.) after 48 hours of exposure to the Illudofulvene Analog, and the IC50 determined. Tumor cells with an IC50 less than the median IC50 obtained for that Illudofulvene Analog in the NCI DTP 60 cell line panel can be considered sensitive whereas those with an IC50 greater than the median IC50 obtained for that Illudofulvene in the NCI DTP 60 cell line panel can be considered resistant.

Further Embodiments

Embodiments contemplated herein include Embodiments P1-P125 following.

Embodiment P1. An illudofulvene for use in the treatment of a cancer expressing an attenuated TCR biomarker, wherein said expression includes: (a) contacting a sample from a patient comprising one or more nucleic acid molecules with a device comprising single-stranded nucleic acid molecules capable of specifically hybridizing with the nucleotides of a TCR gene; (b) detecting a level of expression of a TCR biomarker by performing microarray analysis or quantitative reverse transcriptase polymerase chain reaction (qRT-PCR) of the sample; and (c) determining that the TCR biomarker is attenuated.

Embodiment P2. The illudofulvene of Embodiment P1, where the TCR gene is selected from the group consisting of an ERCC gene, a XPA gene, a GTF series gene, a UV gene, and a USP gene.

Embodiment P3. The illudofulvene of Embodiment P2, where the ERCC gene is selected from the group consisting of ERCC1 gene, ERCC2 gene, ERCC3 gene, ERCC4 gene, ERCC5 gene, ERCC6 gene, ERCC6L gene, ERCC6L2 gene, and ERCC8 gene.

Embodiment P4. The illudofulvene of Embodiment P1, where the illudofulvene is an acylfulvene.

Embodiment P5. The illudofulvene of Embodiment P1, where the illudofulvene is an illudin.

Embodiment P6. An illudofulvene for use in a method of treating a patient with cancer, wherein the method includes: (a) determining whether a test sample from a patient has an attenuated TCR biomarker; and (b) if the test sample from the patient includes the attenuated TCR biomarker, then administer an effective amount of the illudofulvene.

Embodiment P7. The illudofulvene of Embodiment P6, where the effective amount is administered in a dosage between: a lower limit of approximately 0.1 mg of the illudofulvene per kilogram of body weight of the patient; and an upper limit of approximately 5 mg of the illudofulvene per kilogram of body weight of the patient.

Embodiment P8. The illudofulvene of Embodiment P6, where the test sample includes one or more nucleic acid molecules.

Embodiment P9. The illudofulvene of Embodiment P6, where the test sample hybridized specifically with the nucleotides of a TCR gene.

Embodiment P10. The illudofulvene of Embodiment P9, where the TCR gene is selected from the group consisting of ERCC gene, XPA gene, GTF series gene, UV gene, and USP gene.

Embodiment P11. The illudofulvene of Embodiment P6, where the TCR biomarker is determined to be attenuated by performing microarray analysis or quantitative reverse transcriptase polymerase chain reaction (qRT-PCR) of the test sample.

Embodiment P12. The illudofulvene of Embodiment P6, where the illudofulvene is an acylfulvene.

Embodiment P13. The illudofulvene of Embodiment P6, where the illudofulvene is an illudin.

Embodiment P14. An illudofulvene for use in the treatment of a cancer expressing an enhanced MYC biomarker, wherein said expression includes: (a) contacting a sample from a patient comprising one or more nucleic acid molecules with a device comprising single-stranded nucleic acid molecules capable of specifically hybridizing with the nucleotides of a MYC gene; (b) detecting a level of expression of a MYC biomarker by performing microarray analysis or quantitative reverse transcriptase polymerase chain reaction (qRT-PCR) of the sample; and (c) determining that the MYC biomarker is enhanced.

Embodiment P15. The illudofulvene of Embodiment P14, further comprising where a PTGR biomarker is enhanced in the sample.

Embodiment P16. The illudofulvene of Embodiment P14, further comprising where a TCR biomarker is attenuated in the sample.

Embodiment P17. The illudofulvene of Embodiment P14, where the illudofulvene is an acylfulvene.

Embodiment P18. The illudofulvene of Embodiment P14, where the illudofulvene is an illudin.

Embodiment P19. An illudofulvene for use in a method of treating a patient with cancer, wherein the method includes: (a) determining whether a test sample from a patient has a MYC biomarker that is enhanced; and (b) if the test sample from the patient includes the enhanced MYC biomarker, then administer an effective amount of the illudofulvene.

Embodiment P20. The illudofulvene of Embodiment P18, where the effective amount is administered in a dosage between: a lower limit of approximately 0.1 mg of the illudofulvene per kilogram of body weight of the patient; and an upper limit of approximately 5 mg of the illudofulvene per kilogram of body weight of the patient.

Embodiment P21. The illudofulvene of Embodiment P19, where the test sample includes one or more nucleic acid molecules.

Embodiment P22. The illudofulvene of Embodiment P19, where the test sample hybridized specifically with the nucleotides of a MYC gene.

Embodiment P23. The illudofulvene of Embodiment P19, where the MYC biomarker is determined to be enhanced by performing microarray analysis or quantitative reverse transcriptase polymerase chain reaction (qRT-PCR) of the test sample.

Embodiment P24. The illudofulvene of Embodiment P19, where the illudofulvene is an acylfulvene.

Embodiment P25. The illudofulvene of Embodiment P19, where the illudofulvene is an illudin.

Embodiment P26. The illudofulvene of Embodiment P19, further comprising where a PTGR biomarker is enhanced in the test sample.

Embodiment P27. The illudofulvene of Embodiment P26, further comprising where a TCR biomarker is attenuated in the test sample.

Embodiment P28. An illudofulvene for use in the treatment of a cancer expressing an enhanced MYC biomarker and an attenuated TCR biomarker, wherein said expression includes: (a) contacting a sample from a patient comprising one or more nucleic acid molecules with a device comprising single-stranded nucleic acid molecules capable of specifically hybridizing with the nucleotides of a TCR gene and a MYC gene; (b) detecting a level of expression of a TCR biomarker and a MYC biomarker by performing microarray analysis or quantitative reverse transcriptase polymerase chain reaction (qRT-PCR) of the sample; and (c) determining that the MYC biomarker is enhanced and the TCR biomarker is attenuated.

Embodiment P29. The illudofulvene of Embodiment P28, further comprising where a PTGR biomarker is enhanced in the sample.

Embodiment P30. The illudofulvene of Embodiment P28, where the illudofulvene is an acylfulvene.

Embodiment P31. The illudofulvene of Embodiment P28, where the illudofulvene is an illudin.

Embodiment P32. The illudofulvene of Embodiment P28, where the TCR gene is selected from the group consisting of ERCC gene, XPA gene, GTF series gene, UV gene, and USP gene.

Embodiment P33. The illudofulvene of Embodiment P28, where the TCR biomarker is attenuated due to truncating mutations, mutations abolishing enzyme activity, deletions or other chromosomal, transcription, translational and post translation event that interfering with TCR gene expression and/or subsequent TCR gene activity.

Embodiment P34. The illudofulvene of Embodiment P28, where the MYC biomarker is enhanced when cells transform from a normal state to cancer cells, or when the cells are exposed to prior anticancer drug treatment and become upregulated as a response to the prior anticancer drug treatment.

Embodiment P35. An illudofulvene for use in a method of treating a patient with cancer, wherein the method includes: (a) determining whether a test sample from a patient has an enhanced MYC biomarker; (b) determining whether the test sample from a patient has an attenuated TCR biomarker; (c) if the test sample from the patient includes the enhanced MYC biomarker and the attenuated TCR biomarker, then administer an effective amount of the illudofulvene.

Embodiment P36. The illudofulvene of Embodiment P35, where the effective amount is administered in a dosage between: a lower limit of approximately 0.1 mg of the illudofulvene per kilogram of body weight of the patient; and an upper limit of approximately 5 mg of the illudofulvene per kilogram of body weight of the patient.

Embodiment P37. The illudofulvene of Embodiment P35, where the test sample includes one or more nucleic acid molecules.

Embodiment P38. The illudofulvene of Embodiment P35, where the test sample hybridized specifically with the nucleotides of a MYC gene.

Embodiment P39. The illudofulvene of Embodiment P35, where the test sample hybridized specifically with the nucleotides of a TCR gene.

Embodiment P40. The illudofulvene of Embodiment P35, where the MYC biomarker is determined to be enhanced by performing microarray analysis or quantitative reverse transcriptase polymerase chain reaction (qRT-PCR) of the test sample.

Embodiment P41. The illudofulvene of Embodiment P35, where the TCR biomarker is determined to be attenuated by performing microarray analysis or quantitative reverse transcriptase polymerase chain reaction (qRT-PCR) of the test sample.

Embodiment P42. The illudofulvene of Embodiment P35, where the illudofulvene is an acylfulvene.

Embodiment P43. The illudofulvene of Embodiment P35, where the illudofulvene is an illudin.

Embodiment P44. The illudofulvene of Embodiment P35, further comprising where a PTGR biomarker is enhanced in the test sample.

Embodiment P45. The illudofulvene of Embodiment P35, further comprising where the TCR gene is selected from the group consisting of ERCC gene, XPA gene, GTF series gene, UV gene, and USP gene.

Embodiment P46. The illudofulvene of Embodiment P35, where the MYC biomarker is enhanced when cells transform from a normal state to cancer cells, or when the cells are exposed to prior anticancer drug treatment and become upregulated as a response to the prior anticancer drug treatment.

Embodiment P47. An illudofulvene for use in the treatment of a cancer expressing an enhanced PTGR biomarker, wherein said expression includes: (a) contacting a sample from a patient comprising one or more nucleic acid molecules with a device comprising single-stranded nucleic acid molecules capable of specifically hybridizing with the nucleotides of a PTGR gene; (b) detecting a level of expression of a PTGR biomarker by performing microarray analysis or quantitative reverse transcriptase polymerase chain reaction (qRT-PCR) of the sample; and (c) determining that the PTGR biomarker is attenuated.

Embodiment P48. The illudofulvene of Embodiment P47, where the PTGR gene is selected from the group consisting of PTGR1 and PTGR2.

Embodiment P49. The illudofulvene of Embodiment P47, where the illudofulvene is an acylfulvene.

Embodiment P50. The illudofulvene of Embodiment P47, where the illudofulvene is an illudin.

Embodiment P51. The illudofulvene of Embodiment P47, where the PTGR biomarker is enhanced when cells transform from a normal state to cancer cells, or when the cells are exposed to prior anticancer drug treatment and become upregulated as a response to the prior anticancer drug treatment.

Embodiment P52. An illudofulvene for use in a method of treating a patient with cancer, wherein the method includes: (a) determining whether a test sample from a patient has an enhanced PTGR biomarker; and (b) if the test sample from the patient includes the enhanced PTGR biomarker, then administer an effective amount of the illudofulvene.

Embodiment P53. The illudofulvene of Embodiment P52, where the effective amount is administered in a dosage between: a lower limit of approximately 0.1 mg of the illudofulvene per kilogram of body weight of the patient; and an upper limit of approximately 5 mg of the illudofulvene per kilogram of body weight of the patient.

Embodiment P54. The illudofulvene of Embodiment P53, where the test sample includes one or more nucleic acid molecules.

Embodiment P55. The illudofulvene of Embodiment P53, where the test sample hybridized specifically with the nucleotides of a PTGR gene.

Embodiment P56. The illudofulvene of Embodiment P53, where the PTGR gene is selected from the group consisting of PTGR1 and PTGR2.

Embodiment P57. The illudofulvene of Embodiment P53, where the PTGR biomarker is determined to be attenuated by performing microarray analysis or quantitative reverse transcriptase polymerase chain reaction (qRT-PCR) of the test sample.

Embodiment P58. The illudofulvene of Embodiment P53, where the illudofulvene is an acylfulvene.

Embodiment P59. The illudofulvene of Embodiment P53, where the illudofulvene is an illudin.

Embodiment P60. The illudofulvene of Embodiment P53, where the PTGR gene includes PTGR1 and PTGR2.

Embodiment P61. The illudofulvene of Embodiment P53, where the PTGR biomarker is enhanced when cells transform from a normal state to cancer cells, or when the cells are exposed to prior anticancer drug treatment and become upregulated as a response to the prior anticancer drug treatment.

Embodiment P62. An illudofulvene for use in the treatment of a cancer expressing an enhanced MYC biomarker, an enhanced PTGR biomarker, and an attenuated TCR biomarker, wherein said expression includes: (a) contacting a sample from a patient comprising one or more nucleic acid molecules with a device comprising single-stranded nucleic acid molecules capable of specifically hybridizing with the nucleotides of a TCR gene, a PTGR gene, and a MYC gene; (b) detecting a level of expression of a TCR biomarker, a PTGR biomarker, and a MYC biomarker by performing microarray analysis or quantitative reverse transcriptase polymerase chain reaction (qRT-PCR) of the sample; and (c) determining that the MYC biomarker is enhanced, the PTGR biomarker is enhanced, and the TCR biomarker is attenuated.

Embodiment P63. The illudofulvene of Embodiment P62, where the PTGR gene is selected from the group consisting of PTGR1 and PTGR2.

Embodiment P64. The illudofulvene of Embodiment P62, where the TCR gene is selected from the group consisting of ERCC gene, XPA gene, GTF series gene, UV gene, and USP gene.

Embodiment P65. The illudofulvene of Embodiment P62, where the TCR biomarker is attenuated due to truncating mutations, mutations abolishing enzyme activity, deletions or other chromosomal, transcription, translational and post translation event that interfering with ERCC gene expression and subsequent gene activity.

Embodiment P66. The illudofulvene of Embodiment P62, where the PTGR biomarker is enhanced when cells transform from a normal state to cancer cells, or when the cells are exposed to prior anticancer drug treatment and become upregulated as a response to the prior anticancer drug treatment.

Embodiment P67. The illudofulvene of Embodiment P62, where the MYC biomarker is enhanced when cells transform from a normal state to cancer cells, or when the cells are exposed to prior anticancer drug treatment and become upregulated as a response to the prior anticancer drug treatment.

Embodiment P68. The illudofulvene of Embodiment P62, where the illudofulvene is an acylfulvene.

Embodiment P69. The illudofulvene of Embodiment P62, where the illudofulvene is an illudin.

Embodiment P70. An illudofulvene for use in a method of treating a patient with cancer, wherein the method includes: (a) determining whether a test sample from a patient has an enhanced MYC biomarker; (b) determining whether the test sample from a patient has an attenuated TCR biomarker; (c) determining whether the test sample from a patient has an enhanced PTGR biomarker; (d) if the test sample from the patient includes the enhanced MYC biomarker, the enhanced PTGR biomarker, and the attenuated TCR biomarker, then administer an effective amount of the illudofulvene.

Embodiment P71. The illudofulvene of Embodiment P70, where the effective amount is administered in a dosage between: a lower limit of approximately 0.1 mg of the illudofulvene per kilogram of body weight of the patient; and an upper limit of approximately 5 mg of the illudofulvene per kilogram of body weight of the patient.

Embodiment P72. The illudofulvene of Embodiment P70, where the test sample includes one or more nucleic acid molecules.

Embodiment P73. The illudofulvene of Embodiment P70, where the test sample hybridized specifically with the nucleotides of a MYC gene.

Embodiment P74. The illudofulvene of Embodiment P70, where the test sample hybridized specifically with the nucleotides of a TCR gene.

Embodiment P75. The illudofulvene of Embodiment P70, where the test sample hybridized specifically with the nucleotides of a PTGR gene.

Embodiment P76. The illudofulvene of Embodiment P70, where the MYC biomarker is determined to be enhanced by performing microarray analysis or quantitative reverse transcriptase polymerase chain reaction (qRT-PCR) of the test sample.

Embodiment P77. The illudofulvene of Embodiment P70, where the TCR biomarker is determined to be attenuated by performing microarray analysis or quantitative reverse transcriptase polymerase chain reaction (qRT-PCR) of the test sample.

Embodiment P78. The illudofulvene of Embodiment P70, where the illudofulvene is an acylfulvene.

Embodiment P79. The illudofulvene of Embodiment P70, where the illudofulvene is an illudin.

Embodiment P80. The illudofulvene of Embodiment P70, further comprising where the TCR gene is selected from the group consisting of ERCC gene, XPA gene, GTF series gene, UV gene, and USP gene.

Embodiment P81. The illudofulvene of Embodiment P70, where the PTGR gene is selected from the group consisting of PTGR1 and PTGR2.

Embodiment P82. The illudofulvene of Embodiment P70, where the MYC biomarker is enhanced when cells transform from a normal state to cancer cells, or when the cells are exposed to prior anticancer drug treatment and become upregulated as a response to the prior anticancer drug treatment.

Embodiment P83. The illudofulvene of Embodiment P70, where the TCR biomarker is attenuated due to truncating mutations, mutations abolishing enzyme activity, deletions or other chromosomal, transcription, translational and/or post translation event that interfering with TCR gene expression and/or subsequent TCR gene activity.

Embodiment P84. The illudofulvene of Embodiment P70, where the PTGR biomarker is enhanced when cells transform from a normal state to cancer cells, or when the cells are exposed to prior anticancer drug treatment and become upregulated as a response to the prior anticancer drug treatment.

Embodiment P85. An illudofulvene for use in the treatment of a cancer expressing an enhanced PTGR biomarker, and an attenuated TCR biomarker, wherein said expression includes: (a) contacting a sample from a patient comprising one or more nucleic acid molecules with a device comprising single-stranded nucleic acid molecules capable of specifically hybridizing with the nucleotides of a TCR gene, and a PTGR gene; (b) detecting a level of expression of a TCR biomarker and a PTGR biomarker by performing microarray analysis or quantitative reverse transcriptase polymerase chain reaction (qRT-PCR) of the sample; and (c) determining that the PTGR biomarker is enhanced, and the TCR biomarker is attenuated.

Embodiment P86. The illudofulvene of Embodiment P85, where the PTGR gene is selected from the group consisting of PTGR1 and PTGR2.

Embodiment P87. The illudofulvene of Embodiment P85, where the TCR gene is selected from the group consisting of ERCC gene, XPA gene, GTF series gene, UV gene, and USP gene.

Embodiment P88. The illudofulvene of Embodiment P85, where the TCR biomarker is attenuated due to truncating mutations, mutations abolishing enzyme activity, deletions or other chromosomal, transcription, translational and post translation event that interfering with ERCC gene expression and subsequent ERCC gene activity.

Embodiment P89. The illudofulvene of Embodiment P85, where the PTGR biomarker is enhanced when cells transform from a normal state to cancer cells, or when the cells are exposed to prior anticancer drug treatment and become upregulated as a response to the prior anticancer drug treatment.

Embodiment P90. The illudofulvene of Embodiment P85, where the illudofulvene is an acylfulvene.

Embodiment P91. The illudofulvene of Embodiment P85, where the illudofulvene is an illudin.

Embodiment P92. An illudofulvene for use in a method of treating a patient with cancer, wherein the method includes: (a) determining whether the test sample from a patient has an attenuated TCR biomarker; (b) determining whether the test sample from a patient has an enhanced PTGR biomarker; (c) if the test sample from the patient includes the enhanced PTGR biomarker, and the attenuated TCR biomarker, then administer an effective amount of the illudofulvene.

Embodiment P93. The illudofulvene of Embodiment P92, where the effective amount is administered in a dosage between: a lower limit of approximately 0.1 mg of the illudofulvene per kilogram of body weight of the patient; and an upper limit of approximately 5 mg of the illudofulvene per kilogram of body weight of the patient.

Embodiment P94. The illudofulvene of Embodiment P92, where the test sample includes one or more nucleic acid molecules.

Embodiment P95. The illudofulvene of Embodiment P92, where the test sample hybridized specifically with the nucleotides of a TCR gene.

Embodiment P96. The illudofulvene of Embodiment P92, where the test sample hybridized specifically with the nucleotides of a PTGR gene.

Embodiment P97. The illudofulvene of Embodiment P92, where the TCR biomarker is determined to be attenuated by performing microarray analysis or quantitative reverse transcriptase polymerase chain reaction (qRT-PCR) of the test sample.

Embodiment P98. The illudofulvene of Embodiment P92, where the illudofulvene is an acylfulvene.

Embodiment P99. The illudofulvene of Embodiment P92, where the illudofulvene is an illudin.

Embodiment P100. The illudofulvene of Embodiment P92, further comprising where the TCR gene is selected from the group consisting of ERCC gene, XPA gene, GTF series gene, UV gene, and USP gene.

Embodiment P101. The illudofulvene of Embodiment P92, where the PTGR gene is selected from the group consisting of PTGR1 and PTGR2.

Embodiment P102. The illudofulvene of Embodiment P92, where the TCR biomarker is attenuated due to truncating mutations, mutations abolishing enzyme activity, deletions or other chromosomal, transcription, translational and/or post translation event that interfering with TCR gene expression and/or subsequent TCR gene activity.

Embodiment P103. The illudofulvene of Embodiment P92, where the PTGR biomarker is enhanced when cells transform from a normal state to cancer cells, or when the cells are exposed to prior anticancer drug treatment and become upregulated as a response to the prior anticancer drug treatment.

Embodiment P104. An illudofulvene for use in the treatment of a cancer expressing an enhanced MYC biomarker, and an enhanced PTGR biomarker, wherein said expression includes: (a) contacting a sample from a patient comprising one or more nucleic acid molecules with a device comprising single-stranded nucleic acid molecules capable of specifically hybridizing with the nucleotides of a PTGR gene, and a MYC gene; (b) detecting a level of expression of a PTGR biomarker and a MYC biomarker by performing microarray analysis or quantitative reverse transcriptase polymerase chain reaction (qRT-PCR) of the sample; and (c) determining that the MYC biomarker is enhanced, and the PTGR biomarker is enhanced.

Embodiment P105. The illudofulvene of Embodiment P104, where the PTGR gene is selected from the group consisting of PTGR1 and PTGR2.

Embodiment P106. The illudofulvene of Embodiment P104, where the PTGR biomarker is enhanced when cells transform from a normal state to cancer cells, or when the cells are exposed to prior anticancer drug treatment and become upregulated as a response to the prior anticancer drug treatment.

Embodiment P107. The illudofulvene of Embodiment P104, where the MYC biomarker is enhanced when cells transform from a normal state to cancer cells, or when the cells are exposed to prior anticancer drug treatment and become upregulated as a response to the prior anticancer drug treatment.

Embodiment P108. The illudofulvene of Embodiment P104, where the illudofulvene is an acylfulvene.

Embodiment P109. The illudofulvene of Embodiment P104, where the illudofulvene is an illudin.

Embodiment P110. An illudofulvene for use in a method of treating a patient with cancer, wherein the method includes: (a) determining whether a test sample from a patient has an enhanced MYC biomarker; (b) determining whether the test sample from a patient has an enhanced PTGR biomarker; (c) if the test sample from the patient includes the enhanced MYC biomarker, and the enhanced PTGR biomarker, then administer an effective amount of the illudofulvene.

Embodiment P111. The illudofulvene of Embodiment P110, where the effective amount is administered in a dosage between: a lower limit of approximately 0.1 mg of the illudofulvene per kilogram of body weight of the patient; and an upper limit of approximately 5 mg of the illudofulvene per kilogram of body weight of the patient.

Embodiment P112. The illudofulvene of Embodiment P110, where the test sample includes one or more nucleic acid molecules.

Embodiment P113. The illudofulvene of Embodiment P110, where the test sample hybridized specifically with the nucleotides of a MYC gene.

Embodiment P114. The illudofulvene of Embodiment P110, where the test sample hybridized specifically with the nucleotides of a PTGR gene.

Embodiment P115. The illudofulvene of Embodiment P110, where the MYC biomarker is determined to be enhanced by performing microarray analysis or quantitative reverse transcriptase polymerase chain reaction (qRT-PCR) of the test sample.

Embodiment P116. The illudofulvene of Embodiment P110, where the illudofulvene is an acylfulvene.

Embodiment P117. The illudofulvene of Embodiment P110, where the illudofulvene is an illudin.

Embodiment P118. The illudofulvene of Embodiment P110, where the PTGR gene is selected from the group consisting of PTGR1 and PTGR2.

Embodiment P119. The illudofulvene of Embodiment P110, where the MYC biomarker is enhanced when cells transform from a normal state to cancer cells, or when the cells are exposed to prior anticancer drug treatment and become upregulated as a response to the prior anticancer drug treatment.

Embodiment P120. The illudofulvene of Embodiment P110, where the PTGR biomarker is enhanced when cells transform from a normal state to cancer cells, or when the cells are exposed to prior anticancer drug treatment and become upregulated as a response to the prior anticancer drug treatment.

Embodiment P121. An illudofulvene for use in the treatment of a cancer that is resistant to one or more Other Drugs, comprising: (a) contacting a sample from a patient comprising one or more nucleic acid molecules with a device comprising single-stranded nucleic acid molecules capable of specifically hybridizing with the nucleotides selected from the group consisting of ERCC8 (SEQ ID NOS:1, 2, 35-45), ERCC6 (SEQ ID NOS:3, 4, 46-56), GTF2H1 (SEQ ID NOS:5, 6, 57-67), GTF2H2 (SEQ ID NOS:7, 8, 68-78), GTF2H3 (SEQ ID NOS:9, 10, 79-89), GTF2H4 (SEQ ID NOS:11, 12, 90-100), GTF2H5 (SEQ ID NOS:13, 14, 101-111), USP7 (SEQ ID NOS:15, 16, 112-122), UVSSA (SEQ ID NOS:17, 18, 123-133), ERCC3 (SEQ ID NOS:19, 20, 134-144), ERCC2 (SEQ ID NOS:21, 22, 145-155), ERCC4 (SEQ ID NOS:23, 24, 156-166), ERCC5 (SEQ ID NOS:25, 26, 167-177), XPA (SEQ ID NOS:27, 28, 178-188), RAD18 (SEQ ID NOS:29, 30, 189-199), ERCC6L (SEQ ID NOS:31, 32, 200-210), ERCC6L2 (SEQ ID NOS:33, 34, 211-221), MYC (SEQ ID NOS:222, 223, 224-235), ERCC1 (SEQ ID NOS:236, 237, 238-248), PTGR1 (SEQ ID NOS:249, 250, 251-261), and/or PTGR2 (SEQ ID NOS:262, 263, 264-274); (b) detecting a level of expression of a plurality of biomarkers selected from ERCC8 (SEQ ID NOS:1, 2, 35-45), ERCC6 (SEQ ID NOS:3, 4, 46-56), GTF2H1 (SEQ ID NOS:5, 6, 57-67), GTF2H2 (SEQ ID NOS:7, 8, 68-78), GTF2H3 (SEQ ID NOS:9, 10, 79-89), GTF2H4 (SEQ ID NOS:11, 12, 90-100), GTF2H5 (SEQ ID NOS:13, 14, 101-111), USP7 (SEQ ID NOS:15, 16, 112-122), UVSSA (SEQ ID NOS:17, 18, 123-133), ERCC3 (SEQ ID NOS:19, 20, 134-144), ERCC2 (SEQ ID NOS:21, 22, 145-155), ERCC4 (SEQ ID NOS:23, 24, 156-166), ERCC5 (SEQ ID NOS:25, 26, 167-177), XPA (SEQ ID NOS:27, 28, 178-188), RAD18 (SEQ ID NOS:29, 30, 189-199), ERCC6L (SEQ ID NOS:31, 32, 200-210), ERCC6L2 (SEQ ID NOS:33, 34, 211-221), MYC (SEQ ID NOS:222, 223, 224-235), ERCC1 (SEQ ID NOS:236, 237, 238-248), PTGR1 (SEQ ID NOS:249, 250, 251-261), and/or PTGR2 (SEQ ID NOS:262, 263, 264-274) by performing microarray analysis or quantitative reverse transcriptase polymerase chain reaction (qRT-PCR) of the sample to generate a biomarker profile; and (c) determining to administer the illudofulvene based on the biomarker profile.

Embodiment P122. The illudofulvene of Embodiment P121, further comprising administering one or more additional therapies prior to, concurrently with, or after administration of the illudofulvene.

Embodiment P123. The illudofulvene of Embodiment P122, where one or more additional therapies includes surgery, radiation, or one or more Other Drugs.

Embodiment P124. The illudofulvene of Embodiment P121, where the cancer is selected from the group consisting of prostate cancer, ovarian cancer, hepatocellular carcinoma (HCC), cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, squamous cell carcinoma of the head and neck (SCCHN), acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), and Hodgkin's lymphoma.

Embodiment P125. The illudofulvene of Embodiment P121, where the biomarker profile includes (c) calculating a difference score by subtracting the mean expression levels of one or more of the plurality of biomarkers from the mean expression levels of the one or more of the plurality of biomarkers of sensitivity.

Embodiments contemplated herein further include Embodiments Q1-Q54 following.

Embodiment Q1. An illudofulvene for use in the treatment of a cancer expressing an attenuated TCR biomarker, wherein said expression includes: (a) contacting a sample from a human patient with a means for determining the regulation of a PTGR gene, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity; (b) determining the level of regulation of the PTGR gene; (b) determining the level of regulation of the PTGR gene; (c) analyzing the sample from the human patient with a means for determining the regulation of a MYC gene, where the means is selected from the group consisting of (i) quantification of gene mRNA expression by probe analysis, (ii) microarray analysis, (iii) RT-PCR, (iv) TCR Tumor Mutation Panel and (v) primary tumor cell sensitivity; (d) determining the level of regulation of the MYC gene; (e) analyzing the sample from the human patient with a means for determining the regulation of three (3) or more TCR genes, where the means is selected from the group consisting of (i) quantification of gene mRNA expression by probe analysis, (ii) microarray analysis, (iii) RT-PCR, (iv) TCR Tumor Mutation Panel and (v) primary tumor cell sensitivity; where one or more of the following conditions are fulfilled: (I) the PTGR gene is upregulated, the MYC gene is upregulated, and at least one (1) of the three (3) or more TCR genes is downregulated; (II)

the PTGR gene is upregulated, the MYC gene is not upregulated, and at least one (1) of the three (3) or more TCR genes is downregulated; (III) the PTGR gene is not upregulated, the MYC gene is upregulated, and at least two (2) of the three (3) or more TCR genes is downregulated; and (IV) the PTGR gene is not upregulated, the MYC gene is not upregulated, and at least three (3) of the three (3) or more TCR genes is downregulated.

Embodiment Q2. The illudofulvene of Embodiment Q1, where the TCR gene is selected from the group consisting of an ERCC gene, a XPA gene, a GTF series gene, a UV gene, and a USP gene.

Embodiment Q3. The illudofulvene of Embodiment Q1, where the PTGR gene upregulated is PTGR1, where the process of analysis is quantification of gene mRNA expression by probe analysis, where the primers selected to hybridize with the one or more nucleic acid molecules are selected from the group consisting of SEQ ID NO:307-308.

Embodiment Q4. An illudofulvene for use in a method of treating a patient with cancer, wherein the method includes: (a) determining whether a test sample from a patient has an upregulated PTGR gene; (b) analyzing the sample with a means for determining that at least one TCR gene is downregulated, where the test sample is analyzed with one or more methods selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity; and (c) if the test sample from the patient includes the upregulated PTGR gene and at least one downregulated TCR gene, then administer an effective amount of the illudofulvene.

Embodiment Q5. The illudofulvene of Embodiment Q4, where the TCR gene is selected from the group consisting of an ERCC gene, a XPA gene, a GTF series gene, a UV gene, and a USP gene.

Embodiment Q6. The illudofulvene of Embodiment Q4, where the PTGR gene upregulated is PTGR1, where the process of analysis is quantification of gene mRNA expression by probe analysis, where the primers selected to hybridize with the one or more nucleic acid molecules are selected from the group consisting of SEQ ID NO:307-308.

Embodiment Q7. The illudofulvene of Embodiment Q4, where the PTGR gene upregulated is PTGR1, where the process of analysis is microarray analysis, where the primers selected to hybridize with the one or more nucleic acid molecules are selected from the group consisting of SEQ ID NO:251-261.

Embodiment Q8. The illudofulvene of Embodiment Q4, where the PTGR gene upregulated is PTGR1, where the process of analysis is RT-PCR, where one or both the primers and probe are selected to hybridize with the one or more nucleic acid molecules are selected from the group consisting of SEQ ID NO:897-899.

Embodiment Q9. The illudofulvene of Embodiment Q4, where the PTGR gene upregulated is PTGR1, where the process of analysis is TCR Tumor Mutation panel, where the primers selected to hybridize with the one or more nucleic acid molecules are selected from the group consisting of SEQ ID NO:682-696.

Embodiment Q10. The illudofulvene of Embodiment Q4, where the PTGR gene upregulated is PTGR1, where the process of analysis is primary tumor cell sensitivity.

Embodiment Q11. The illudofulvene of Embodiment Q4, where the PTGR gene upregulated is PTGR2, where the process of analysis is quantification of gene mRNA expression by probe analysis, where the primers selected to hybridize with the one or more nucleic acid molecules are selected from the group consisting of SEQ ID NO:309-310.

Embodiment Q12. The illudofulvene of Embodiment Q4, where the PTGR gene upregulated is PTGR2, where the process of analysis is microarray analysis, where the primers selected to hybridize with the one or more nucleic acid molecules are selected from the group consisting of SEQ ID NO:264-274.

Embodiment Q13. The illudofulvene of Embodiment Q4, where the PTGR gene upregulated is PTGR2, where the process of analysis is RT-PCR, where one or both the primers and probe are selected to hybridize with the one or more nucleic acid molecules are selected from the group consisting of SEQ ID NO:900-902.

Embodiment Q14. The illudofulvene of Embodiment Q4, where the PTGR gene upregulated is PTGR2, where the process of analysis is TCR Tumor Mutation panel, where the primers selected to hybridize with the one or more nucleic acid molecules are selected from the group consisting of SEQ ID NO: 715-727.

Embodiment Q15. The illudofulvene of Embodiment Q4, where the PTGR gene upregulated is PTGR2, where the process of analysis is primary tumor cell sensitivity.

Embodiment Q16. The illudofulvene of Embodiment Q4, where the one or more TCR genes determined to be downregulated are analyzed using the TCR Tumor Mutation panel, where the primers selected to hybridize with the one or more nucleic acid molecules are selected from the group consisting of SEQ ID NO: 329-440, and 451-851.

Embodiment Q17. An illudofulvene for use in treating cancer in a human patient in need thereof including administering the illudofulvene to the human patient, where the human patient has been determined to be responsive to the illudofulvene according to a process including: (a) contacting a sample from the human patient including one or more nucleic acid molecules with a device including single-stranded nucleic acid molecules capable of specifically hybridizing with nucleotides of a PTGR gene; (b) detecting a level of expression of a PTGR mRNA by performing microarray analysis or quantitative reverse transcriptase polymerase chain reaction (qRT-PCR) of the sample; (c) determining that the PTGR mRNA is upregulated in the human patient; (d) contacting a sample from the human patient including one or more nucleic acid molecules with a device including single-stranded nucleic acid molecules capable of specifically hybridizing with nucleotides of a TCR gene; (e) detecting a level of expression of a plurality of TCR mRNAs by performing microarray analysis or quantitative reverse transcriptase polymerase chain reaction (qRT-PCR) of the sample; (I) determining that the level of expression of at least one of the plurality of TCR mRNAs is downregulated in the human patient; and (g) administering the illudofulvene to the human patient, thereby treating cancer in the human patient.

Embodiment Q18. An illudofulvene for use in treating cancer in a human patient in need thereof including administering the illudofulvene to the human patient, where the human patient has been determined to be responsive to the illudofulvene according to a process including: (a) contacting a sample from the human patient including one or more nucleic acid molecules with a device including a plurality of primers capable of specifically hybridizing with nucleotides of a PTGR gene selected from the group consisting of SEQ ID NO:307-310; (b) detecting a level of expression of a PTGR mRNA by performing microarray analysis or quantitative reverse transcriptase polymerase chain reaction (qRT-PCR) of the sample; (c) determining that the PTGR gene is upregulated in the human patient; (d) contacting a sample from the human patient including one or more nucleic acid molecules with a device including a plurality of primers capable of specifically hybridizing with nucleotides of a TCR gene selected from the group consisting of SEQ ID NO:275-304, and 311-322; (e) detecting a level of expression of a plurality of TCR mRNAs by performing microarray analysis or quantitative reverse transcriptase polymerase chain reaction (qRT-PCR) of the sample; (f) determining that at least one of the plurality of TCR mRNAs is not upregulated in the human patient; and (g) administering the illudofulvene to the human patient, thereby treating cancer in the human patient.

Embodiment Q19. An illudofulvene for use in treating cancer in a human patient in need thereof including administering the illudofulvene to the human patient, where the human patient has been determined to be responsive to the illudofulvene according to a process including: (a) analyzing a sample from the human patient with a means for determining the regulation of a PTGR gene, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity; (b) determining that the PTGR gene is not upregulated; (c) analyzing a sample from the human patient with a means for determining the regulation of a MYC gene, where the means is selected from the group consisting of (i) quantification of gene mRNA expression by probe analysis, (ii) microarray analysis, (iii) RT-PCR, (iv) TCR Tumor Mutation Panel and (v) primary tumor cell sensitivity; (d) determining that the MYC gene is upregulated; (e) analyzing a sample from the human patient with a means for determining the regulation of a plurality of TCR genes, where the means is selected from the group consisting of (i) quantification of gene mRNA expression by probe analysis, (ii) microarray analysis, (iii) RT-PCR, (iv) TCR Tumor Mutation Panel and (v) primary tumor cell sensitivity; (f) determining that at least two of the plurality of TCR genes are downregulated; and (g) administering the illudofulvene to the human patient, thereby treating cancer in the human patient.

Embodiment Q20. The illudofulvene of Embodiment Q19, where the MYC gene determined to be upregulated is analyzed using the TCR Tumor Mutation panel, where the primers selected to hybridize with one or more nucleic acid molecules are selected from the group consisting of SEQ ID NO:669-681.

Embodiment Q21. The illudofulvene of Embodiment Q19, where the process of analysis to determine that the PTGR gene is not upregulated is quantification of gene mRNA expression by probe analysis, where the primers selected to hybridize with one or more nucleic acid molecules are selected from the group consisting of SEQ ID NO:307-310.

Embodiment Q22. The illudofulvene of Embodiment Q19, where the process of analysis to determine that the PTGR gene is not upregulated is microarray analysis, where the primers selected to hybridize with one or more nucleic acid molecules are selected from the group consisting of SEQ ID NO:251-261, 264-274.

Embodiment Q23. The illudofulvene of Embodiment Q19, where the process of analysis to determine that the PTGR gene is not upregulated is RT-PCR, where one or both the primers and probe selected to hybridize with one or more nucleic acid molecules are selected from the group consisting of SEQ ID NO:897-902.

Embodiment Q24. The illudofulvene of Embodiment Q19, where the process of analysis to determine that the PTGR gene is not upregulated is TCR Tumor Mutation panel, where the primers selected to hybridize with one or more nucleic acid molecules are selected from the group consisting of SEQ ID NO:682-696, 715-727.

Embodiment Q25. The illudofulvene of Embodiment Q19, where the process of analysis to determine that the PTGR gene is not upregulated is primary tumor cell sensitivity.

Embodiment Q26. The illudofulvene of Embodiment Q19, where the process of analysis to determine that one or more TCR genes are downregulated is quantification of gene mRNA expression by probe analysis, where the primers selected to hybridize with one or more nucleic acid molecules are selected from the group consisting of SEQ ID NO:275-304 and 311-322.

Embodiment Q27. The illudofulvene of Embodiment Q19, where the process of analysis to determine that one or more TCR genes are downregulated is microarray analysis, where the primers selected to hybridize with one or more nucleic acid molecules are selected from the group consisting of SEQ ID NO:35-248.

Embodiment Q28. The illudofulvene of Embodiment Q19, where the process of analysis to determine that one or more TCR genes are downregulated is RT-PCR, where one or both the primers and probe selected to hybridize with one or more nucleic acid molecules are selected from the group consisting of SEQ ID NO:852-893 and 903-917.

Embodiment Q29. The illudofulvene of Embodiment Q19, where the process of analysis to determine that one or more TCR genes are downregulated is TCR Tumor Mutation panel, where the primers selected to hybridize with one or more nucleic acid molecules are selected from the group consisting of SEQ ID NO:329-440, and 451-851.

Embodiment Q30. The illudofulvene of Embodiment Q19, where the process of analysis to determine that one or more TCR genes are downregulated is primary tumor cell sensitivity.

Embodiment Q31. An illudofulvene for use in treating cancer in a human patient in need thereof including administering the illudofulvene to the human patient, where the human patient has been determined to be responsive to the illudofulvene according to a process including: (a) contacting a sample from the human patient including one or more nucleic acid molecules with one or more methods selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity to determine the level of expression of PTGR genes; (b) determining that the PTGR gene is not upregulated; (c) contacting a sample from the human patient including one or more nucleic acid molecules with one or more methods selected from the group consisting of (i) quantification of gene mRNA expression by probe analysis, (ii) microarray analysis, (iii) RT-PCR, (iv) TCR Tumor Mutation Panel and (v) primary tumor cell sensitivity to determine the level of expression of a MYC gene; (d) determining that the MYC gene is upregulated; (e) contacting a sample from the human patient including one or more nucleic acid molecules with one or more methods selected from the group consisting of (i) quantification of gene mRNA expression by probe analysis, (ii) microarray analysis, (iii) RT-PCR, (iv) TCR Tumor Mutation Panel and (v) primary tumor cell sensitivity to determine the level of expression of a plurality of TCR genes; (f) determining that the level of expression of at least two of the plurality of TCR genes are downregulated; and (g) administering the illudofulvene to the human patient, thereby treating cancer in the human patient.

Embodiment Q32. An illudofulvene for use in treating cancer in a human patient in need thereof including administering the illudofulvene to the human patient, where the human patient has been determined to be responsive to the illudofulvene according to a process including: (a) contacting a sample from the human patient including one or more nucleic acid molecules with a device including single-stranded nucleic acid molecules capable of specifically hybridizing with nucleotides of a PTGR gene; (b) detecting a level of expression of a PTGR mRNA by performing microarray analysis or quantitative reverse transcriptase polymerase chain reaction (qRT-PCR) of the sample; (c) determining that the level of expression of the PTGR mRNA is not upregulated in the human patient; (d) contacting a sample from the human patient including one or more nucleic acid molecules with a device including single-stranded nucleic acid molecules capable of specifically hybridizing with nucleotides of a MYC gene; (e) detecting a level of expression of a MYC mRNA by performing microarray analysis or quantitative reverse transcriptase polymerase chain reaction (qRT-PCR) of the sample; and (f) determining that the level of expression of the MYC mRNA is upregulated in the human patient; (g) contacting a sample from the human patient including one or more nucleic acid molecules with a device including single-stranded nucleic acid molecules capable of specifically hybridizing with nucleotides of a plurality of TCR genes; (h) detecting a level of expression of a plurality of TCR mRNAs by performing microarray analysis or quantitative reverse transcriptase polymerase chain reaction (qRT-PCR) of the sample; (i) determining that the level of expression of at least two of the plurality of TCR mRNAs is downregulated in the human patient; and (j) administering the illudofulvene to the human patient, thereby treating cancer in the human patient.

Embodiment Q33. An illudofulvene for use in treating cancer in a human patient in need thereof including administering the illudofulvene to the human patient, where the human patient has been determined to be responsive to the illudofulvene according to a process including: (a) contacting a sample from the human patient including one or more nucleic acid molecules with a device including single-stranded nucleic acid molecules capable of specifically hybridizing with nucleotides of a PTGR gene selected from the group consisting of SEQ ID NO:307-310; (b) detecting a level of expression of a PTGR mRNA by performing microarray analysis or quantitative reverse transcriptase polymerase chain reaction (qRT-PCR) of the sample; (c) determining that the level of expression of the PTGR mRNA is NOT upregulated in the human patient; (d) contacting a sample from the human patient including one or more nucleic acid molecules with a device including single-stranded nucleic acid molecules capable of specifically hybridizing with nucleotides of a MYC gene selected from the group consisting of SEQ ID NO:305-306; (e) detecting a level of expression of a MYC mRNA by performing microarray analysis or quantitative reverse transcriptase polymerase chain reaction (qRT-PCR) of the sample; and (f) determining that the level of expression of the MYC mRNA is upregulated in the human patient; (g) contacting a sample from the human patient including one or more nucleic acid molecules with a device including single-stranded nucleic acid molecules capable of specifically hybridizing with nucleotides of a plurality of TCR genes selected from the group consisting of SEQ ID NO:275-304, and 311-322; (h) detecting a level of expression of a TCR mRNA by performing microarray analysis or quantitative reverse transcriptase polymerase chain reaction (qRT-PCR) of the sample; (i) determining that the level of expression of at least two of the plurality of TCR mRNA is downregulated in the human patient; and (j) administering the illudofulvene to the human patient, thereby treating cancer in the human patient.

Embodiment Q34. An illudofulvene for use in treating cancer in a human patient in need thereof including administering the illudofulvene to the human patient, where the human patient has been determined to be responsive to the illudofulvene according to a process including: (a) analyzing a sample from the human patient with a means for determining the regulation of a PTGR gene, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity; (b) determining that the PTGR gene is not upregulated; (c) analyzing a sample from the human patient with a means for determining the regulation of a MYC gene, where the means is selected from the group consisting of (i) quantification of gene mRNA expression by probe analysis, (ii) microarray analysis, (iii) RT-PCR, (iv) TCR Tumor Mutation Panel and (v) primary tumor cell sensitivity; (d) determining that the MYC gene is not upregulated; (e) analyzing a sample from the human patient with a means for determining the regulation of three (3) or more TCR genes, where the means is selected from the group consisting of (i) quantification of gene mRNA expression by probe analysis, (ii) microarray analysis, (iii) RT-PCR, (iv) TCR Tumor Mutation Panel and (v) primary tumor cell sensitivity; (f) determining that at least three (3) of the three (3) or more TCR genes are downregulated; and (g) administering the illudofulvene to the human patient, thereby treating cancer in the human patient.

Embodiment Q35. The illudofulvene of Embodiment Q34, where the MYC gene determined to not be upregulated is analyzed using the TCR Tumor Mutation panel, where the primers selected to hybridize with one or more nucleic acid molecules are selected from the group consisting of SEQ ID NO:669-681.

Embodiment Q36. The illudofulvene of Embodiment Q34, where the process of analysis to determine that the PTGR gene is not upregulated is quantification of gene mRNA expression by probe analysis, where the primers selected to hybridize with one or more nucleic acid molecules are selected from the group consisting of SEQ ID NO:307-310.

Embodiment Q37. The illudofulvene of Embodiment Q34, where the process of analysis to determine that the PTGR gene is not upregulated is microarray analysis, where the primers selected to hybridize with one or more nucleic acid molecules are selected from the group consisting of SEQ ID NO:251-261, 264-274.

Embodiment Q38. The illudofulvene of Embodiment Q34, where the process of analysis to determine that the PTGR gene is not upregulated is RT-PCR, where one or both the primers and probe selected to hybridize with one or more nucleic acid molecules are selected from the group consisting of SEQ ID NO:897-902.

Embodiment Q39. The illudofulvene of Embodiment Q34, where the process of analysis to determine that the PTGR gene is not upregulated is TCR Tumor Mutation panel, where the primers selected to hybridize with one or more nucleic acid molecules are selected from the group consisting of SEQ ID NO:682-696, 715-727.

Embodiment Q40. The illudofulvene of Embodiment Q34, where the process of analysis to determine that the PTGR gene is not upregulated is primary tumor cell sensitivity.

Embodiment Q41. The illudofulvene of Embodiment Q34, where the process of analysis to determine that one or more TCR genes are downregulated is quantification of gene mRNA expression by probe analysis, where the primers selected to hybridize with one or more nucleic acid molecules are selected from the group consisting of SEQ ID NO:275-304 and 311-322.

Embodiment Q42. The illudofulvene of Embodiment Q34, where the process of analysis to determine that one or more TCR genes are downregulated is microarray analysis, where the primers selected to hybridize with one or more nucleic acid molecules are selected from the group consisting of SEQ ID NO:35-248.

Embodiment Q43. The illudofulvene of Embodiment Q34, where the process of analysis to determine that one or more TCR genes are downregulated is RT-PCR, where one or both the primers and probe selected to hybridize with one or more nucleic acid molecules are selected from the group consisting of SEQ ID NO:852-893 and 903-917.

Embodiment Q44. The illudofulvene of Embodiment Q34, where the process of analysis to determine that one or more TCR genes are downregulated is TCR Tumor Mutation panel, where the primers selected to hybridize with one or more nucleic acid molecules are selected from the group consisting of SEQ ID NO:329-440, and 451-851.

Embodiment Q45. The illudofulvene of Embodiment Q34, where the process of analysis to determine that one or more TCR genes are downregulated is primary tumor cell sensitivity.

Embodiment Q46. An illudofulvene for use in treating cancer in a human patient in need thereof including administering the illudofulvene to the human patient, where the human patient has been determined to be responsive to the illudofulvene according to a process including: (a) contacting a sample from the human patient including one or more nucleic acid molecules with one or more methods selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity to determine the level of expression of PTGR genes; (b) determining that the level of expression of the PTGR gene is not upregulated; (c) contacting a sample from the human patient including one or more nucleic acid molecules with one or more methods selected from the group consisting of (i) quantification of gene mRNA expression by probe analysis, (ii) microarray analysis, (iii) RT-PCR, (iv) TCR Tumor Mutation Panel and (v) primary tumor cell sensitivity to determine the level of expression of a MYC gene; (d) determining that the MYC gene is not upregulated; (e) contacting a sample from the human patient including one or more nucleic acid molecules with one or more methods selected from the group consisting of (i) quantification of gene mRNA expression by probe analysis, (ii) microarray analysis, (iii) RT-PCR, (iv) TCR Tumor Mutation Panel and (v) primary tumor cell sensitivity to determine the level of expression of three (3) or more TCR genes; (f) determining that the level of expression of at least three (3) of the three (3) or more TCR genes are downregulated; and (g) administering the illudofulvene to the human patient, thereby treating cancer in the human patient.

Embodiment Q47. An illudofulvene for use in treating cancer in a human patient in need thereof including administering the illudofulvene to the human patient, where the human patient has been determined to be responsive to the illudofulvene according to a process including: (a) contacting a sample from the human patient including one or more nucleic acid molecules with a device including single-stranded nucleic acid molecules capable of specifically hybridizing with nucleotides of a PTGR gene; (b) detecting a level of expression of a PTGR mRNA by performing microarray analysis or quantitative reverse transcriptase polymerase chain reaction (qRT-PCR) of the sample; (c) determining that the level of expression of the PTGR mRNA is not upregulated in the human patient; (d) contacting a sample from the human patient including one or more nucleic acid molecules with a device including single-stranded nucleic acid molecules capable of specifically hybridizing with nucleotides of a MYC gene; (e) detecting a level of expression of a MYC mRNA by performing microarray analysis or quantitative reverse transcriptase polymerase chain reaction (qRT-PCR) of the sample; and (f) determining that the level of expression of the MYC mRNA is not upregulated in the human patient; (g) contacting a sample from the human patient including one or more nucleic acid molecules with a device including single-stranded nucleic acid molecules capable of specifically hybridizing with nucleotides of a plurality of TCR genes; (h) detecting a level of expression of three (3) or more TCR mRNAs by performing microarray analysis or quantitative reverse transcriptase polymerase chain reaction (qRT-PCR) of the sample; (i) determining that the level of expression of at least three (3) of the three (3) or more TCR mRNAs is downregulated in the human patient; and (j) administering the illudofulvene to the human patient, thereby treating cancer in the human patient.

Embodiment Q48. An illudofulvene for use in treating cancer in a human patient in need thereof including administering the illudofulvene to the human patient, where the human patient has been determined to be responsive to the illudofulvene according to a process including: (a) contacting a sample from the human patient including one or more nucleic acid molecules with a device including single-stranded nucleic acid molecules capable of specifically hybridizing with nucleotides of a PTGR gene selected from the group consisting of SEQ ID NO:307-310; (b) detecting a level of expression of a PTGR mRNA by performing microarray analysis or quantitative reverse transcriptase polymerase chain reaction (qRT-PCR) of the sample; (c) determining that the level of expression of the PTGR mRNA is not upregulated in the human patient; (d) contacting a sample from the human patient including one or more nucleic acid molecules with a device including single-stranded nucleic acid molecules capable of specifically hybridizing with nucleotides of a MYC gene selected from the group consisting of SEQ ID NO:305-306; (e) detecting a level of expression of a MYC mRNA by performing microarray analysis or quantitative reverse transcriptase polymerase chain reaction (qRT-PCR) of the sample; and (f) determining that the level of expression of the MYC mRNA is not upregulated in the human patient; (g) contacting a sample from the human patient including one or more nucleic acid molecules with a device including single-stranded nucleic acid molecules capable of specifically hybridizing with nucleotides of a plurality of TCR genes selected from the group consisting of SEQ ID NO:275-304, and 311-322; (h) detecting a level of expression of three (3) or more TCR mRNAs by performing microarray analysis or quantitative reverse transcriptase polymerase chain reaction (qRT-PCR) of the sample; (i) determining that the level of expression of at least three (3) of the three (3) or more TCR mRNAs is downregulated in the human patient; and (j) administering the illudofulvene to the human patient, thereby treating cancer in the human patient.

Embodiment Q49. An illudofulvene for use in treating cancer in a human patient in need thereof including administering the illudofulvene to the human patient, where the human patient has been determined to be responsive to the illudofulvene according to a process including: (a) contacting a sample from the human patient including one or more nucleic acid molecules with a device including single-stranded nucleic acid molecules capable of specifically hybridizing with nucleotides of a PTGR gene; (b) detecting a level of expression of a PTGR mRNA by performing microarray analysis or quantitative reverse transcriptase polymerase chain reaction (qRT-PCR) of the sample; (c) determining that the level of expression of the PTGR mRNA is not upregulated in the human patient; (d) contacting a sample from the human patient including one or more nucleic acid molecules with a device including single-stranded nucleic acid molecules capable of specifically hybridizing with nucleotides of a MYC gene; (e) detecting a level of expression of a MYC mRNA by performing microarray analysis or quantitative reverse transcriptase polymerase chain reaction (qRT-PCR) of the sample; (f) determining that the level of expression of the MYC mRNA is not upregulated in the human patient; (g) contacting a sample from the human patient including one or more nucleic acid molecules with a device including single-stranded nucleic acid molecules capable of specifically hybridizing with nucleotides of three (3) or more TCR genes; (h) detecting a level of expression of at least three (3) of the three (3) or more TCR mRNAs by performing microarray analysis or quantitative reverse transcriptase polymerase chain reaction (qRT-PCR) of the sample; and (i) determining that at least three (3) of the three (3) or more TCR mRNAs are upregulated in the human patient.

Embodiment Q50. An illudofulvene for use in treating cancer in a human patient in need thereof including administering the illudofulvene to the human patient, where the human patient has been determined to be responsive to the illudofulvene according to a process including: (a) analyzing a sample from the human patient with a means for determining that a PTGR gene is upregulated; (b) analyzing a sample from the human patient with a means for determining that at least one of the TCR genes is downregulated; and (c) administering the illudofulvene to the human patient, thereby treating cancer in the human patient.

Embodiment Q51. The illudofulvene of Embodiment Q19, where the MYC gene determined to be upregulated is not upregulated is RT-PCR, where one or both the primers and probe selected to hybridize with one or more nucleic acid molecules are selected from the group consisting of SEQ ID NO:894-896.

Embodiment Q52. The illudofulvene of Embodiment Q19, where the MYC gene determined to be upregulated is microarray analysis, where the primers selected to hybridize with one or more nucleic acid molecules are selected from the group consisting of SEQ ID NO:224-235.

Embodiment Q53. The illudofulvene of Embodiment Q19, where the process of analysis to determine that the MYC gene is upregulated is primary tumor cell sensitivity.

Embodiment Q54. The illudofulvene of Embodiment Q19, where the MYC gene determined to be upregulated is quantification of gene mRNA expression by probe analysis, where the primers selected to hybridize with one or more nucleic acid molecules are selected from the group consisting of SEQ ID NO:305-306.

Embodiments contemplated herein further include Embodiments R1-R82 following.

Embodiment R1. An illudofulvene for use in the treatment of a cancer expressing an upregulated PTGR gene and an upregulated MYC gene, wherein said expression includes: (a) contacting a sample from a patient comprising one or more nucleic acid molecules with one or more means for determining the regulation of expression of one or more PTGR genes; (b) contacting the sample from the patient with one or more means for determining the regulation of expression of a MYC gene; (c) contacting the sample from the patient with one or more means for determining the regulation of expression of one or more TCR genes; (d) detecting a level of expression of the one or more PTGR genes that are upregulated; (e) detecting a level of expression of the MYC gene that is upregulated; and (f) detecting a deficiency in a level of expression of one or more TCR genes.

Embodiment R2. The illudofulvene of Embodiment R1, where the one or more TCR genes are selected from the group consisting of an ERCC gene, a XPA gene, a GTF series gene, a UV gene, and a USP gene.

Embodiment R3. The illudofulvene of Embodiments R1 or R2, where the one or more PTGR genes are selected from the group consisting of PTGR1 and PTGR2.

Embodiment R4. The illudofulvene of Embodiments R1-R3, where the one or more PTGR genes include PTGR1.

Embodiment R5. The illudofulvene of Embodiments R1-R4, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R6. The illudofulvene of Embodiments R1-R5, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R7. The illudofulvene of Embodiments R1-R3, where the one or more PTGR genes include PTGR2.

Embodiment R8. The illudofulvene of Embodiments R1-R3 or R7, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R9. The illudofulvene of Embodiments R1-R3 or R7-R8, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R10. An illudofulvene for use in a method of treating a patient with cancer, wherein the method includes: (a) determining whether a test sample from a patient has a level of expression of one or more PTGR genes that are upregulated, a level of expression of a MYC gene that is upregulated, and a deficiency in a level of expression of one or more TCR genes; and (b) if the test sample from the patient includes the one or more upregulated PTGR genes, the upregulated MYC gene, and the deficiency in the level of expression of one or more TCR genes, then administer an effective amount of the illudofulvene.

Embodiment R11. The illudofulvene of Embodiment R10, where the one or more TCR genes are selected from the group consisting of an ERCC gene, a XPA gene, a GTF series gene, a UV gene, and a USP gene.

Embodiment R12. The illudofulvene of Embodiments R10 or R11, where the one or more PTGR genes are selected from the group consisting of PTGR1 and PTGR2.

Embodiment R13. The illudofulvene of Embodiments R10-R12, where the means is where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R14. The illudofulvene of Embodiments R10-R13, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R15. The illudofulvene of Embodiments R10-R14, where the effective amount is administered in a dosage between: a lower limit of approximately 0.1 mg of the illudofulvene per kilogram of body weight of the patient; and an upper limit of approximately 5 mg of the illudofulvene per kilogram of body weight of the patient.

Embodiment R16. An illudofulvene for use in the treatment of a cancer expressing a PTGR gene and one or more TCR genes, wherein said expression includes: (a) contacting a sample from a patient comprising one or more nucleic acid molecules with one or more means for determining the regulation of expression of one or more PTGR genes; (b) contacting the sample from the patient with one or more means for determining the regulation of expression of one or more TCR genes; (c) detecting a level of expression of the one or more PTGR genes that are upregulated; and (d) detecting a deficiency in a level of expression of one or more TCR genes.

Embodiment R17. The illudofulvene of Embodiment R16, where the one or more TCR genes are selected from the group consisting of an ERCC gene, a XPA gene, a GTF series gene, a UV gene, and a USP gene.

Embodiment R18. The illudofulvene of Embodiments R16 or R17, where the one or more PTGR genes are selected from the group consisting of PTGR1 and PTGR2.

Embodiment R19. The illudofulvene of Embodiments R16-R8, where the one or more PTGR genes include PTGR1.

Embodiment R20. The illudofulvene of Embodiments R16-R19, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R21. The illudofulvene of Embodiments R16-R20, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R22. The illudofulvene of Embodiments R16-R18, where the one or more PTGR genes include PTGR2.

Embodiment R23. The illudofulvene of Embodiments R16-R18 or R22, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R24. The illudofulvene of Embodiments R16-R18 or R22-R23, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R25. An illudofulvene for use in the treatment of a cancer expressing a MYC gene and one or more TCR genes, wherein said expression includes: (a) contacting a sample from a patient comprising one or more nucleic acid molecules with one or more means for determining the regulation of expression of a MYC gene; (b) contacting the sample from the patient with one or more means for determining the regulation of expression of one or more TCR genes; (c) detecting a level of expression of the MYC gene that is upregulated; and (d) detecting a deficiency in a level of expression of one or more TCR genes.

Embodiment R26. The illudofulvene of Embodiment R25, where the one or more TCR genes are selected from the group consisting of an ERCC gene, a XPA gene, a GTF series gene, a UV gene, and a USP gene.

Embodiment R27. The illudofulvene of Embodiments R25 or R26, where the one or more PTGR genes are selected from the group consisting of PTGR1 and PTGR2.

Embodiment R28. The illudofulvene of Embodiments R25-R27, where the one or more PTGR genes include PTGR1.

Embodiment R29. The illudofulvene of Embodiments R25-R28, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R30. The illudofulvene of Embodiments R25-R29, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R31. The illudofulvene of Embodiments R25-R27, where the one or more PTGR genes include PTGR2.

Embodiment R32. The illudofulvene of Embodiments R25-R27 or R31, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R33. The illudofulvene of Embodiments R25-R27 or R31-R32, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R34. An illudofulvene for use in the treatment of a cancer expressing a PTGR gene, a MYC gene and one or more TCR genes, wherein said expression includes: (a) contacting a sample from a patient comprising one or more nucleic acid molecules with one or more means for determining the regulation of expression of one or more PTGR genes; (b) contacting the sample from the patient with one or more means for determining the regulation of expression of a MYC gene; (c) contacting the sample from the patient with one or more means for determining the regulation of expression of one or more TCR genes; (d) detecting either a level of expression of the one or more PTGR genes that are upregulated, or detecting a level of expression of the MYC gene that is upregulated; and (e) detecting a deficiency in a level of expression of one or more TCR genes.

Embodiment R35. The illudofulvene of Embodiment R34, where the one or more TCR genes are selected from the group consisting of one or more ERCC genes, a XPA gene, a GTF series gene, a UV gene, and a USP gene.

Embodiment R36. The illudofulvene of Embodiments R34 or R35, where the one or more PTGR genes are selected from the group consisting of PTGR1 and PTGR2.

Embodiment R37. The illudofulvene of Embodiments R34-R36, where the one or more PTGR genes include PTGR1.

Embodiment R38. The illudofulvene of Embodiments R34-R37, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R39. The illudofulvene of Embodiments R34-R38, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R40. The illudofulvene of Embodiments R34-R37, where the one or more PTGR genes include PTGR2.

Embodiment R41. The illudofulvene of Embodiments R34-R37 or R40, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R42. The illudofulvene of Embodiments R34-R37 or R40-R41, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R43. An illudofulvene for use in the treatment of a cancer expressing three or more TCR genes, wherein said expression includes: (a) contacting a sample from a patient comprising one or more nucleic acid molecules with one or more means for determining the regulation of expression of three or more TCR genes; and (b) detecting a deficiency in a level of expression of three or more TCR genes.

Embodiment R44. The illudofulvene of Embodiment R43, where the three or more TCR genes are selected from the group consisting of one or more ERCC genes, a XPA gene, a GTF series gene, a UV gene, and a USP gene.

Embodiment R45. The illudofulvene of Embodiments R43 or R44, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R46. An illudofulvene for use in the treatment of a cancer expressing a PTGR gene, a MYC gene and one or more TCR genes, wherein said expression includes: (a) contacting a sample from a patient comprising one or more nucleic acid molecules with one or more means for determining the regulation of expression of one or more PTGR genes; (b) contacting the sample from the patient with one or more means for determining the regulation of expression of a MYC gene; (c) contacting the sample from the patient with one or more means for determining the regulation of expression of one or more TCR genes; (d) detecting either a level of expression of the one or more PTGR genes that are upregulated, or detecting a level of expression of the MYC gene that is upregulated; (e) if one or more PTGR genes are upregulated then detecting a deficiency in a level of expression of one or more TCR genes; and (f) if the MYC gene is upregulated then detecting a deficiency in a level of expression of two or more TCR genes.

Embodiment R47. The illudofulvene of Embodiment R45, where the one or more TCR genes are selected from the group consisting of one or more ERCC genes, a XPA gene, a GTF series gene, a UV gene, and a USP gene.

Embodiment R48. The illudofulvene of Embodiment R46 or R47, where the one or more PTGR genes are selected from the group consisting of PTGR1 and PTGR2.

Embodiment R49. The illudofulvene of Embodiment R46 to R48, where the one or more PTGR genes include PTGR1.

Embodiment R50. The illudofulvene of Embodiment R46 to R49, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R51. The illudofulvene of Embodiment R46 to R50, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R52. The illudofulvene of Embodiment R46 to R48, where the one or more PTGR genes include PTGR2.

Embodiment R53. The illudofulvene of Embodiment R46 to R48 or R52, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R54. The illudofulvene of Embodiment R46 to R48 or R52 to 53, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R55. An illudofulvene for use in a method of treating a patient with cancer, wherein the method includes: (a) determining whether a test sample from a patient has a level of expression of one or more PTGR genes that are upregulated, a level of expression of a MYC gene that is upregulated, and a deficiency in a level of expression of one or more TCR genes; (b) if the test sample from the patient includes the one or more upregulated PTGR genes, and the deficiency in the level of expression of one or more TCR genes, then administer an effective amount of the illudofulvene; or (c) if the test sample from the patient includes the upregulated MYC gene, and the deficiency in the level of expression of two or more TCR genes, then administer an effective amount of the illudofulvene.

Embodiment R56. The illudofulvene of Embodiment R55, where the one or more TCR genes are selected from the group consisting of one or more ERCC genes, a XPA gene, a GTF series gene, a UV gene, and a USP gene.

Embodiment R57. The illudofulvene of Embodiment R55 or R56, where the one or more PTGR genes are selected from the group consisting of PTGR1 and PTGR2.

Embodiment R58. The illudofulvene of Embodiment R55 to R57, where the means is where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R59. The illudofulvene of Embodiment R55 to R58, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R60. The illudofulvene of Embodiment R55 to R59, where the effective amount is administered in a dosage between: a lower limit of approximately 0.1 mg of the illudofulvene per kilogram of body weight of the patient; and an upper limit of approximately 5 mg of the illudofulvene per kilogram of body weight of the patient.

Embodiment R61. An illudofulvene analog for use in the treatment of a cancerous tumor expressing a PTGR gene, a MYC gene or one or more TCR genes, wherein said expression includes: (a) contacting a sample from a patient comprising one or more nucleic acid molecules with one or more means for determining the regulation of expression of one or more PTGR genes, the regulation of expression of a MYC gene, and the regulation of expression of one or more TCR genes; and (b) determining if a cancerous tumor is sensitive to an illudofulvene analog based on a first relative ratio of expression of the one or more PTGR gene compared with a housekeeping gene and a second relative ratio of expression of the TCR genes compared with a housekeeping gene, or a third relative ratio of expression of the MYC gene compared with a housekeeping gene and the second relative ratio of expression.

Embodiment R62. The illudofulvene of Embodiment R61, where the one or more TCR genes are selected from the group consisting of one or more ERCC genes, a XPA gene, a GTF series gene, a UV gene, and a USP gene.

Embodiment R63. The illudofulvene of Embodiment R61 or 62, where the one or more PTGR genes are selected from the group consisting of PTGR1 and PTGR2.

Embodiment R64. The illudofulvene of Embodiment R61 to 63, where the one or more housekeeping genes are selecting from the group consisting of beta actin (ACTB), transferrin receptor (TFRC) and glyceraldehyde-3-phosphate dehydrogenase (GAPD).

Embodiment R65. The illudofulvene of Embodiment R61 to 64, where the one or more PTGR genes include PTGR1.

Embodiment R66. The illudofulvene of Embodiment R61 to 65, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R67. The illudofulvene of Embodiment R61 to 66, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R68. The illudofulvene of Embodiment R61 to 64, where the one or more PTGR genes include PTGR2.

Embodiment R69. The illudofulvene of Embodiment R61 to 44 or 68, where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R70. An illudofulvene for use in a method of treating a patient with cancer, wherein the method includes: (a) determining from a patient test sample a first relative ratio of expression of the one or more PTGR genes compared with at least one of the one or more housekeeping genes or determining a second relative ratio of expression of the MYC gene compared with at least one of the one or more housekeeping genes; (b) determining a third relative ratio of expression of the TCR genes compared with at least one of the one or more housekeeping genes; (c) if the first relative ratio of expression is high and the third relative ratio of expression is deficient or the second relative ratio of expression is high and the third relative ratio of expression is deficient, then administer an effective amount of the illudofulvene.

Embodiment R71. The illudofulvene of Embodiment R70, where the one or more TCR genes are selected from the group consisting of one or more ERCC genes, a XPA gene, a GTF series gene, a UV gene, and a USP gene.

Embodiment R72. The illudofulvene of Embodiment R70 or R71, where the one or more PTGR genes are selected from the group consisting of PTGR1 and PTGR2:

Embodiment R73. The illudofulvene of Embodiment R70 to R72, where the means is where the means is selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment R74. The illudofulvene of Embodiment R70 to R73, where one or more primers selected to hybridize with the one or more nucleic acid molecules used to quantify expression of one or more PTGR genes, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

Embodiment R75. The illudofulvene of Embodiment R70 to R74, where the effective amount is administered in a dosage between: a lower limit of approximately 0.1 mg of the illudofulvene per kilogram of body weight of the patient; and an upper limit of approximately 5 mg of the illudofulvene per kilogram of body weight of the patient.

Embodiment R76. An illudofulvene analog selected from the group consisting of illudin ring derivatives, illudin alkyl derivatives and acyl-fulvenes for use in the treatment of a cancerous tumor expressing a PTGR gene, a MYC gene or one or more TCR genes, wherein said expression includes: (a) contacting a sample from a patient comprising one or more nucleic acid molecules with one or more means for determining: (i) the regulation of expression of one or more PTGR genes; (ii) the regulation of expression of at least one TCR gene; (iii) the regulation of expression of at least one housekeeping gene; (b) determining if a cancerous tumor is sensitive to an illudofulvene analog based on a first relative ratio of expression of the one or more PTGR genes compared with the at least one housekeeping gene, when the first relative ratio of expression is high, and a second relative ratio of expression of the at least one TCR gene compared with the at least one housekeeping gene, when the second relative ratio of expression is deficient; or (c) contacting the sample comprising one or more nucleic acid molecules with one or more means for determining: (iv) the regulation of expression of a MYC gene; (v) the regulation of expression of two or more TCR genes; (vi) the regulation of expression of one or more housekeeping genes; (d) determining if the cancerous tumor is sensitive to the illudofulvene analog based on a third relative ratio of expression of the MYC gene compared with the one or more housekeeping genes, when the third relative ratio of expression is high, and a fourth relative ratio of expression of two or more TCR genes compared with the one or more housekeeping genes, when the fourth relative ratio of expression is deficient.

Embodiment R77. An illudofulvene analog selected from the group consisting of illudin ring derivatives and illudin alkyl derivatives for use in the treatment of a cancerous tumor expressing a PTGR gene, a MYC gene or one or more TCR genes, wherein said expression includes: (a) contacting a sample from a patient comprising one or more nucleic acid molecules with one or more means for determining: (i) the regulation of expression of one or more PTGR genes; (ii) the regulation of expression of at least one TCR gene; (iii) the regulation of expression of at least one housekeeping gene; (b) determining if a cancerous tumor is sensitive to an illudofulvene analog based on a first relative ratio of expression of the one or more PTGR genes compared with the at least one housekeeping gene, when the first relative ratio of expression is high, and a second relative ratio of expression of the at least one TCR gene compared with the at least one housekeeping gene, when the second relative ratio of expression is deficient; or (c) contacting the sample comprising one or more nucleic acid molecules with one or more means for determining: (iv) the regulation of expression of a MYC gene; (v) the regulation of expression of two or more TCR genes; (vi) the regulation of expression of one or more housekeeping genes; (d) determining if the cancerous tumor is sensitive to the illudofulvene analog based on a third relative ratio of expression of the MYC gene compared with the one or more housekeeping genes, when the third relative ratio of expression is high, and a fourth relative ratio of expression of two or more TCR genes compared with the one or more housekeeping genes, when the fourth relative ratio of expression is deficient.

Embodiment R78. An illudofulvene analog selected from the group consisting of illudins and acyl-fulvenes for use in the treatment of a cancerous tumor expressing a PTGR gene, a MYC gene or one or more TCR genes, wherein said expression includes: (a) contacting a sample from a patient comprising one or more nucleic acid molecules with one or more means for determining: (i) the regulation of expression of one or more PTGR genes; (ii) the regulation of expression of at least one TCR gene; (iii) the regulation of expression of at least one housekeeping gene; (b) determining if a cancerous tumor is sensitive to an illudofulvene analog based on a first relative ratio of expression of the one or more PTGR genes compared with the at least one housekeeping gene, when the first relative ratio of expression is high, and a second relative ratio of expression of the at least one TCR gene compared with the at least one housekeeping gene, when the second relative ratio of expression is deficient; or (c) contacting the sample comprising one or more nucleic acid molecules with one or more means for determining: (iv) the regulation of expression of a MYC gene; (v) the regulation of expression of two or more TCR genes; (vi) the regulation of expression of one or more housekeeping genes; (d) determining if the cancerous tumor is sensitive to the illudofulvene analog based on a third relative ratio of expression of the MYC gene compared with the one or more housekeeping genes, when the third relative ratio of expression is high, and a fourth relative ratio of expression of two or more TCR genes compared with the one or more housekeeping genes, when the fourth relative ratio of expression is deficient.

Embodiment R79. An illudofulvene analog selected from the group consisting of illudin ring derivatives, illudin alkyl derivatives and acyl-fulvenes for use in a method of treating a patient with cancer, wherein the method includes: (a) determining from a patient test sample a first relative ratio of expression based on expression of the one or more PTGR genes compared with expression of at least one housekeeping gene; (b) determining from the patient test sample a second relative ratio of expression based on expression of at least one TCR genes compared with expression of at least one housekeeping gene; (c) determining that the patient is sensitive, if the first relative ratio of expression is high and the second relative ratio of expression is deficient, then administer an effective amount of the illudofulvene; or (d) determining from a patient test sample a third relative ratio of expression based on expression of a MYC gene compared with at least one of the housekeeping genes; (e) determining from a patient test sample a fourth relative ratio of expression based on expression of two or more TCR genes compared with at least one of the housekeeping genes; (f) determining that the patient is sensitive, if the third relative ratio of expression is high and the fourth relative ratio of expression is deficient, then administer an effective amount of the illudofulvene.

Embodiment R80. An illudofulvene analog selected from the group consisting of illudin ring derivatives and illudin alkyl derivatives for use in a method of treating a patient with cancer, wherein the method includes: (a) determining from a patient test sample a first relative ratio of expression based on expression of the one or more PTGR genes compared with expression of at least one housekeeping gene; (b) determining from the patient test sample a second relative ratio of expression based on expression of at least one TCR genes compared with expression of at least one housekeeping gene; (c) determining that the patient is sensitive, if the first relative ratio of expression is high and the second relative ratio of expression is deficient, then administer an effective amount of the illudofulvene; or (d) determining from a patient test sample a third relative ratio of expression based on expression of a MYC gene compared with at least one of the housekeeping genes; (e) determining from a patient test sample a fourth relative ratio of expression based on expression of two or more TCR genes compared with at least one of the housekeeping genes; (f) determining that the patient is sensitive, if the third relative ratio of expression is high and the fourth relative ratio of expression is deficient, then administer an effective amount of the illudofulvene.

Embodiment R81. An illudofulvene analog selected from the group consisting of illudins and acyl-fulvenes for use in a method of treating a patient with cancer, wherein the method includes: (a) determining from a patient test sample a first relative ratio of expression based on expression of the one or more PTGR genes compared with expression of at least one housekeeping gene; (b) determining from the patient test sample a second relative ratio of expression based on expression of at least one TCR genes compared with expression of at least one housekeeping gene; (c) determining that the patient is sensitive, if the first relative ratio of expression is high and the second relative ratio of expression is deficient, then administer an effective amount of the illudofulvene; or (d) determining from a patient test sample a third relative ratio of expression based on expression of a MYC gene compared with at least one of the housekeeping genes; (e) determining from a patient test sample a fourth relative ratio of expression based on expression of two or more TCR genes compared with at least one of the housekeeping genes; (f) determining that the patient is sensitive, if the third relative ratio of expression is high and the fourth relative ratio of expression is deficient, then administer an effective amount of the illudofulvene.

Embodiment R82. An illudofulvene analog selected from the group consisting of illudin ring derivatives, illudin alkyl derivatives and acyl-fulvenes for in the treatment of a cancerous tumor expressing a PTGR gene, a MYC gene or one or more TCR genes, wherein said expression includes: (a) contacting a sample from a patient comprising one or more nucleic acid molecules with one or more means for determining: (i) the regulation of expression of one or more PTGR genes; (ii) the regulation of expression of at least one TCR gene; (iii) the regulation of expression of at least one housekeeping gene; (b) determining if a cancerous tumor is sensitive to an illudofulvene analog based on a first relative ratio of expression of the one or more PTGR genes compared with the at least one housekeeping gene, when the first relative ratio of expression is high, and a second relative ratio of expression of the at least one TCR gene compared with the at least one housekeeping gene, when the second relative ratio of expression is deficient; or (c) contacting the sample comprising one or more nucleic acid molecules with one or more means for determining: (iv) the regulation of expression of a MYC gene; (v) the regulation of expression of two or more TCR genes; (vi) the regulation of expression of one or more housekeeping genes; (d) determining if the cancerous tumor is sensitive to the illudofulvene analog based on a third relative ratio of expression of the MYC gene compared with the one or more housekeeping genes, when the third relative ratio of expression is high, and a fourth relative ratio of expression of two or more TCR genes compared with the one or more housekeeping genes, when the fourth relative ratio of expression is deficient; or (e) contacting the sample comprising one or more nucleic acid molecules with one or more means for determining: (vii) the regulation of expression of three or more TCR genes; (viii) the regulation of expression of one or more housekeeping genes; (f) determining if the cancerous tumor is sensitive to the illudofulvene analog based on a fifth relative ratio of expression of the three or more TCR genes compared with the one or more housekeeping genes.

Embodiments contemplated herein further include Embodiments S1-S21 following.

Embodiment S1. An illudofulvene analog for use in the treatment of a cancerous tumor expressing a PTGR gene, a MYC gene or one or more TCR genes in a patient, wherein said expression includes (a) increased expression of one or more PTGR genes compared to a housekeeping gene in the cancerous tumor; (b) increased expression of a MYC gene compared to a housekeeping gene in the cancerous tumor; and/or (c) decreased expression of one or more TCR genes compared with a housekeeping gene.

Embodiment S2. The illudofulvene analog of Embodiment S1, where the illudofulvene is selected from the group consisting of 002, 008, 012, 039, 040, 41, 42, 43, 44, 46, 75, 76, 77, 78, 79, 88, 90, 94, 103, 104, 108, 110, 112, 113, 114, 115, 116, 119, 120, 121, 122, 123, 124, 125, 126, 127, 128, 130, 141, 142, 146, 149, 150, 160, 164, 165, 177, 178, 184, 189, 190, 196, 198, 199, 201, 202, 203, 207, 208, 209, 210, 217, 221, 223, 233, 234, 235, 240, 244, 254, 255, 259, 262, 263, 266, 267, 268, 269, 275, 276, 284, 285, 286, 287, 288, 289, 290, 291, 292, 293, 294, 295, 296, 297, 298, 304, 305, 306, 310, 314, 315, 317, 321, 323, 324, 332, 333, 334, 335, 336, 337, 338, 339, 340, 345, 346, 347, 348, 351, 352, 354, 356, 357, 368, 359, 361, 362, 363, 364, 365, 366, 367, 369, 370, 371, 372, 373, 374, 375, 377, 378, 379, 380, 381, 382, 383, 384, 389, 392, 393, and 394.

Embodiment S3. The illudofulvene analog of Embodiment Si or S2, where the one or more housekeeping genes are selecting from the group consisting of beta actin (ACTB), transferrin receptor (TFRC) and glyceraldehyde-3-phosphate dehydrogenase (GAPD) and ubiquitin.

Embodiment S4. An illudofulvene analog for use in the treatment of a cancerous tumor expressing a PTGR gene, a MYC gene or one or more TCR genes in a patient, wherein said expression includes (a) messenger RNA and/or gene product (protein) of one or more PTGR genes is increased above a basal level of a housekeeping gene by at least approximately one point nine (1.9) standard deviations in the cancerous tumor; (b) messenger RNA and/or gene product (protein) of a MYC gene compared to a housekeeping gene in increased above a basal level of a housekeeping gene by at least approximately one point nine (1.9) standard deviations in the cancerous tumor; and/or (c) messenger RNA and/or gene product (protein) of one or more TCR genes is decreased below a basal level of a housekeeping gene by at least approximately one point nine (1.9) standard deviations.

Embodiment S5. The illudofulvene analog of Embodiment S4, where the one or more TCR genes are selected from the group consisting of one or more ERCC genes, a XPA gene, a GTF series gene, a UV gene, and a USP gene.

Embodiment S6. The illudofulvene analog of Embodiments S4 or S5, where the one or more PTGR genes are selected from the group consisting of PTGR1 and PTGR2.

Embodiment S7. The illudofulvene analog of Embodiments S4-S6, where the one or more housekeeping genes are selecting from the group consisting of beta actin (ACTB), transferrin receptor (TFRC) and glyceraldehyde-3-phosphate dehydrogenase (GAPD) and ubiquitin.

Embodiment S8. The illudofulvene analog of Embodiments S4-S7, where the gene expression was measured by means selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment S9. The illudofulvene analog of Embodiment S8, where the primers selected to hybridize with the one or more nucleic acid molecules are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, SEQ ID NO:900-902.

Embodiment S10. An illudofulvene analog for use in a method of treating a patient with cancer, wherein the method includes (a) determining from a patient test sample a first relative ratio of expression of messenger RNA and/or gene product (protein) of one or more PTGR genes compared with a basal level of a housekeeping gene or determining a second relative ratio of expression of messenger RNA and/or gene product (protein) of a MYC gene compared with a basal level of a housekeeping gene; and (b) determining a third relative ratio of expression of the TCR genes compared with a basal level of a housekeeping gene; wherein the patient is treated with the illudofulvene analog if the first relative ratio of expression is increased by at least approximately one point nine (1.9) standard deviations and the third relative ratio of expression is decreased by at least approximately one point nine (1.9) standard deviations or the second relative ratio of expression is increased by at least approximately one point nine (1.9) standard deviations and the third relative ratio of expression is decreased by at least approximately one point nine (1.9) standard deviations.

Embodiment S11. The illudofulvene analog for the use of Embodiment S10, where the one or more TCR genes are selected from the group consisting of one or more ERCC genes, a XPA gene, a GTF series gene, a UV gene, and a USP gene.

Embodiment S12. The illudofulvene analog for the use of Embodiment S10 or S11, where the one or more PTGR genes are selected from the group consisting of PTGR1 and PTGR2.

Embodiment S13. The illudofulvene analog for the use of Embodiment S10 to S12, where the ratio of gene expression is measured by means selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

Embodiment S14. The illudofulvene analog for the use of Embodiment S10 to S13, where the primers selected to hybridize with the one or more nucleic acid molecules are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, SEQ ID NO:900-902.

Embodiment S15. The illudofulvene analog for the use of Embodiment S10 to S14, where the effective amount is administered in a dosage between: a lower limit of approximately 0.1 mg of the illudofulvene per kilogram of body weight of the patient; and an upper limit of approximately 5 mg of the illudofulvene per kilogram of body weight of the patient.

Embodiment S16. The illudofulvene analog for the use of Embodiment S10 to S15, where the illudofulvene is selected from the group consisting of 002, 008, 012, 039, 040, 41, 42, 43, 44, 46, 75, 76, 77, 78, 79, 88, 90, 94, 103, 104, 108, 110, 112, 113, 114, 115, 116, 119, 120, 121, 122, 123, 124, 125, 126, 127, 128, 130, 141, 142, 146, 149, 150, 160, 164, 165, 177, 178, 184, 189, 190, 196, 198, 199, 201, 202, 203, 207, 208, 209, 210, 217, 221, 223, 233, 234, 235, 240, 244, 254, 255, 259, 262, 263, 266, 267, 268, 269, 275, 276, 284, 285, 286, 287, 288, 289, 290, 291, 292, 293, 294, 295, 296, 297, 298, 304, 305, 306, 310, 314, 315, 317, 321, 323, 324, 332, 333, 334, 335, 336, 337, 338, 339, 340, 345, 346, 347, 348, 351, 352, 354, 356, 357, 368, 359, 361, 362, 363, 364, 365, 366, 367, 369, 370, 371, 372, 373, 374, 375, 377, 378, 379, 380, 381, 382, 383, 384, 389, 392, 393, and 394.

Embodiment S17. An illudofulvene analog for use in the treatment of a cancerous tumor expressing a PTGR gene, a MYC gene or one or more TCR genes, wherein said expression includes (a) contacting a sample from a patient comprising one or more nucleic acid molecules with one or more means for determining (i) the regulation of expression of one or more PTGR genes; (ii) the regulation of expression of at least one TCR gene; (iii) the regulation of expression of at least one housekeeping gene; (b) determining if a cancerous tumor is sensitive to an illudofulvene analog based on a first relative ratio of expression of the one or more PTGR genes compared with the at least one housekeeping gene, when the first relative ratio of expression is high, and a second relative ratio of expression of the at least one TCR gene compared with the at least one housekeeping gene, when the second relative ratio of expression is deficient; or (c) contacting the sample comprising one or more nucleic acid molecules with one or more means for determining (iv) the regulation of expression of a MYC gene; (v) the regulation of expression of two or more TCR genes; (vi) the regulation of expression of one or more housekeeping genes; and (d) determining if the cancerous tumor is sensitive to the illudofulvene analog based on a third relative ratio of expression of the MYC gene compared with the one or more housekeeping genes, when the third relative ratio of expression is high, and a fourth relative ratio of expression of two or more TCR genes compared with the one or more housekeeping genes, when the fourth relative ratio of expression is deficient.

Embodiment S18. An illudofulvene analog for use in a method of treating a patient with cancer, wherein the method includes (a) determining from a patient test sample a first relative ratio of expression based on expression of the one or more PTGR genes compared with expression of at least one housekeeping gene; (b) determining from the patient test sample a second relative ratio of expression based on expression of at least one TCR genes compared with expression of at least one housekeeping gene; and (c) determining that the patient is sensitive, if the first relative ratio of expression is high and the second relative ratio of expression is deficient, then administer an effective amount of the illudofulvene; or (d) determining from a patient test sample a third relative ratio of expression based on expression of a MYC gene compared with at least one of the housekeeping genes; (e) determining from a patient test sample a fourth relative ratio of expression based on expression of two or more TCR genes compared with at least one of the housekeeping genes; and (f) determining that the patient is sensitive, if the third relative ratio of expression is high and the fourth relative ratio of expression is deficient, then administer an effective amount of the illudofulvene.

Embodiment S20. A method of treating a cancerous tumor in a patient including (a) determining gene expression of at least two genes compared with one or more housekeeping genes selected from the group consisting of PTGR1 gene, PTGR2 gene, MYC gene and one or more TCR genes and (b) treating with an effective amount of an illudofulvene analog if: (I) the expression of one of the one or more PTGR genes compared to a housekeeping gene in the cancerous tumor is upregulated and the expression of one of the one or more TCR genes compared with a housekeeping gene is downregulated, or (II) the expression of the MYC gene compared to a housekeeping gene in the cancerous tumor is upregulated and the expression of two of the one or more TCR genes compared with at least one housekeeping gene is downregulated.

Embodiment S21. The method of Embodiment 20, where the patient is treated with an effective amount of an illudofulvene analog when the gene expression of PTGR1 gene compared with at least one housekeeping gene is upregulated, the gene expression of PTGR2 gene compared with at least one housekeeping gene is upregulated and the gene expression of one TCR gene of the one or more TCR genes compared with at least one housekeeping gene is downregulated.

Embodiment S22. A method of treating a cancerous tumor in a patient including: (a) determining from a patient test sample a first relative ratio of expression of a MYC gene compared with a housekeeping gene, (b) determining a second relative ratio of expression of a first TCR gene of one or more TCR genes compared with at least one housekeeping gene; (c) determining a third relative ratio of expression of a second TCR gene of the one or more TCR genes compared with at least one housekeeping gene, and (d) treating with an effective amount of an illudofulvene analog if the first relative ratio of expression is upregulated, the second relative ratio of expression is downregulated, and the third relative ratio of expression is downregulated.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

What is claimed is:

1. A method of treating a cancerous tumor in a patient comprising:
   (a) receiving a tumor sample comprising a plurality of cancer cells from a patient;
   (b) determining a first relative gene expression of a MYC gene compared with one or more housekeeping genes selected from the group consisting of beta actin, transferrin receptor glyceraldehyde-3-phosphate dehydrogenase and ubiquitin in the tumor sample;
   (c) determining a second relative gene expression of one or more PTGR genes selected from the group consisting of a PTGR1 gene, and a PTGR2 gene compared with one or more housekeeping genes selected from the group consisting of beta actin, transferrin receptor glyceraldehyde-3-phosphate dehydrogenase and ubiquitin in the tumor sample;
   (d) determining a third relative gene expression of one or more TCR genes selected from the group consisting of one or more ERCC genes, a XPA gene, a GTF2H gene, a UVSSA gene, and a USP7 gene compared with one or more housekeeping genes selected from the group consisting of beta actin, transferrin receptor glyceraldehyde-3-phosphate dehydrogenase and ubiquitin in the tumor sample; and
   (e) treating the patient with an effective amount of an illudofulvene analog selected from the group consisting of an acylfulvene analog and an illudin analog, where the acylfulvene analog has a structural formula I:

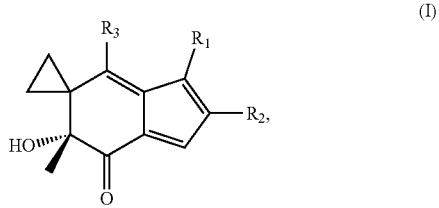

(I)

where $R_1$ represents —H, —$CR_9R_8OH$, —$CHR_9CHR_8OH$, —$CHR_{10}CHR_9CHR_8OH$, —$CH_2CHR_{10}CHR_9CHR_8OH$, —$CR_9R_8OH$, —$CHR_9CHR_8OH$, —$CHR_{10}CHR_9CHR_8OH$, —$CH_2CHR_{10}CHR_9CHR_8OH$, —C(=O)H, —$CH_2$(C=O)H, —$CH_2CH_2$(C=O)H, —$CH_2CH_2CH_2$(C=O)H, —$CH_2CH_2CH_2CH_2$(C=O)H, —$CR_9R_8$(C=O)H, —$CHR_9CHR_8$(C=O)H, —$CH_2CHR_9CHR_8$(C=O)H, —$CR_9R_8$(C=O)$R_{10}$, —$CHR_9CHR_8$(C=O)$R_{10}$, —$CH_2CHR_9CHR_8$(C=O)$R_{10}$, —$CH_2CH_2CHR_9CHR_8$(C=O)$R_{10}$, —$CO_2H$, —$CHR_9CO_2H$, —$CHR_8CHR_9CO_2H$, —$CHR_{10}CHR_8CHR_9CO_2H$, —$CO_2R_{10}$, —$CHR_9CO_2R_{10}$, —$CHR_8CHR_9CO_2R_{10}$, —$CH_2CHR_8CHR_9CO_2R_{10}$, —$CHR_9CH_2CH_2CHR_8CO_2H$, —$CHR_9CH_2CH_2CHR_8CO_2R_{10}$, —$CR_8$=$CH_2$, —$CHR_8CH$=$CH_2$, —$CH_2CHR_8CH$=$CH_2$, —$CH_2CH_2CHR_8CH$=$CH_2$, —$CR_8$=$CHR_9$, —$CHR_8CR_9$=$CH_2$, —$CH_2CHR_8CR_9$=$CH_2$, —$CH_2CH_2CHR_8CR_9$=$CH_2$, —$CR_8$=$CR_9R_{10}$, —$CHR_8CH$=$CR_9R_{10}$, —$CH_2CHR_8CH$=$CHR_9R_{10}$, —$CH_2CH_2CHR_8CH$=$CHR_9R_{10}$, —Cl, —Br, —I, —F, —$NO_2$, —$NR_8R_9$, —$CH_2Cl$, —$CH_2Br$, —$CH_2I$, —$CH_2F$, —$CR_8Cl_2$, —$CR_8Br_2$, —$CR_8I_2$, —$CR_8F_2$, —$CCl_3$, —$CBr_3$, —$CI_3$, —$CF_3$, —$CHR_8Cl$, —$CR_8R_9Cl$, —$CHR_8CHR_9Cl$, —$CHR_{10}CHR_8CHR_9Cl$, —$CH_2CHR_{10}CHR_8CHR_9Cl$, —$CHR_8Br$, —$CR_8R_9Br$, —$CHR_8CHR_9Br$, —$CHR_{10}CHR_8CHR_9Br$, —$CH_2CHR_{10}CHR_8CHR_9Br$, —$CHR_8I$, —$CR_8R_9I$, —$CHR_8CHR_9Br$, —$CHR_{10}CHR_8CHR_9I$, —$CH_2CHR_{10}CHR_8CHR_9I$, —$CR_8R_9NH_2$, —$CHR_8CHR_9NH_2$, —$CHR_{10}CHR_8CHR_9NH_2$, —$CH_2CHR_{10}CHR_8CHR_9NH_2$, —$CR_9R_{10}NHR_8$, —$CHR_9CHR_{10}NHR_8$, —$CH_2CHR_9CHR_{10}NHR_8$, —$CH_2CH_2CHR_9CHR_{10}NHR_8$, —$CHR_9NHR_8R_{10}$, —$CHR_9CH_2NHR_8R_{10}$, —$CH_2CH_2CHR_9NR_{10}R_8$, —$CH_2CH_2CH_2NHR_8$, —$CR_9R_8OR_{10}$, —$CH_2CR_9R_9OR_{10}$, —$CH_2CH_2CR_8R_9OR_{10}$, —$CH_2CH_2CH_2R_8R_9OR_{10}$, —$CH_2CH_2CH_2CH_2R_8R_9OR_{10}$, —$CHR_8OC$(=O)$CHR_9R_{10}$, —$CHR_8OC$(=O)$CHR_9R_{10}$, —$CH_2CH_2OC$(=O)$CHR_9R_{10}$, —$CH_2CH_2CHR_8OC$(=O)$CHR_9R_{10}$, —$CH_2CH_2CH_2CH_2OC$(=O)$CHR_9R_{10}$, —$CHR_8$(=O)$OCHR_9R_{10}$, —$CHR_8$(=O)$OCHR_9R_{10}$, —$CH_2CHR_8$(=O)$OCHR_9R_{10}$, —$CH_2CH_2CHR_8$(=O)$OCHR_9R_{10}$, —$CH_2CH_2CH_2CHR_8$(=O)$OCHR_9R_{10}$, —$R_{12}C$=$CR_9CH_2OH$, —$R_{12}C$=$CR_9C$(=O)H, —$R_{12}C$=$CR_9CH_2OR_{10}$, —$R_{12}C$=$CR_9C$(=O)$R_{10}$, —$CH_3$, —$CH_2CH_2$, —$CHR_8CH_2$, —$CHR_8CH_2CH_2$, —$CHR_8CHR_9CH_3$, —$OCH_3$, —$OCR_8R_9R_{10}$, —$OCH_2CR_8R_9R_{10}$, —$OCR_9R_8CHR_{10}$, —$OCHR_8CH_2CH_3$, —$OCHR_8CHR_9CH_3$—$NR_8CH_3$—$NR_8CH_2CH_3$, —$NR_9CHR_8CH_3$, —$NR_9CHR_8CH_2CH_3$, —$NR_{10}CHR_8CHR_9CH_3$, —$OCH_2OR_8$, —$OCHR_8OR_9$, —$OCHR_8CH_2OR_9$, —$OCHR_8CHR_9OR_{10}$, —OC(=O)$OR_8$, —$OCH_2C$(=O)$OR_8$, —$OCHR_9C$(=O)$OR_8$, —$CR_8$(=N)H, —$CH_2CR_8$(=N)H, —$CH_2CR_8$(=N)H, —$CH_2CH_2CR_8$(=N)H, —$CH_2CH_2CH_2CR_8$(=N)H, —$CH_2CH_2CH_2CH_2CR_8$(=N)H, —$CR_8$(=N)OH, —$CH_2CR_8$(=N)OH, —$CH_2CR_8$(=N)OH, —$CH_2CH_2CR_8$(=N)OH, —$CH_2CH_2CH_2CR_8$(=N)OH, —$CH_2CH_2CH_2CH_2CR_8$(=N)OH, —$CR_8$(=N)$R_9$, —$CH_2CR_8$(=N) $R_9$, —$CH_2CR_8$(=N) $R_9$, —$CH_2CH_2CR_8$(=N) $R_9$, —$CH_2CH_2CH_2CR_8$(=N)$R_9$, —$CH_2CH_2CH_2CH_2CR_8$(=N)$R_9$, —$CR_8$(=N)$OR_9$, —$CH_2CR_8$(=N)$OR_9$, —$CH_2CR_8$(=N)O $R_9$, —$CH_2CH_2CR_8$(=N)$OR_9$, —$CH_2CH_2CH_2CR_8$(=N)$OR_9$, —$CH_2CH_2CH_2CH_2CR_8$(=N)$OR_9$, —$CR_8$(=N)$NR_9$, —$CH_2CR_8$(=N)$NR_9$, —$CH_2CR_8$(=N)$NR_9$, —$CH_2CH_2CR_8$(=N)$NR_9$, —$CH_2CH_2CH_2$—$CR_8$(=N)$NR_9$, —$CH_2CH_2CH_2CH_2CR_8$(=N)$NR_9$, —$CR_8$(=N)$NR_9S$(=O)$_2R_{10}$, —$CH_2C(R_8)$(=N)$NR_9S$(=O)$_2R_{10}$, —$CH_2CH_2C(R_8)$(=N)$NR_9S$(=O)$_2R_{10}$, —$CH_2CH_2CH_2C$ ($R_8$)(=N)$NR_9S$(=O)$_2R_{10}$, —$CH_2CH_2CH_2C(R_8)$(=N) $NR_9S$(=O)$_2R_{10}$, —$R_{12}N(R_8)C$(=O)$NR_9R_{10}$, —$R_{12}N(R_8)$ C(=S)$NR_9R_{10}$, —$R_{12}N(OR_8)C$(=O)$NR_9R_{10}$, —$R_{12}N$ ($OR_8$)C(=S)$NR_9R_{10}$, —$R_{12}OS(O_2)NH_2$, —$R_{12}NHS(O_2)$ $NH_2$, —$R_{12}OS(O_2)NR_8R_9$, —$R_{12}NHS(O_2)NR_8R_9$, —$CH_2N(R_8)S(O_2)NR_9R_{10}$, —$CH_2CH_2N(R_8)S(O_2)$ $NR_9R_{10}$, —$CH_2CH_2CH_2N(R_8)S(O_2)NR_9R_{10}$, —$CH_2N(R_8)$ $S(O_2)CR_9R_{10}R_{11}$, —$CH_2CH_2N(R_8)S(O_2)CR_9R_{10}R_{11}$, —$CH_2CH_2CH_2N(R_8)S(O_2)CR_9R_{10}R_{11}$, —$N(R_8)C$(=O)$R_9$, —$CH_2N(R_8)C$(=O)$R_9$, —$CH_2CH_2N(R_8)C$(=O)$R_9$, —$CH_2CH_2CH_2N(R_8)C$(=O)$R_9$, —$CH_2N(R_8)(C$=O) $NR_9R_{10}$, —$CH_2CH_2N(R_8)(C$=O)$NR_9R_{10}$, —$CH_2CH_2N$ ($R_8$)(C=O)$NR_9R_{10}$, —$CH_2N(R_8)(C$=O)$CR_9R_{10}R_{11}$, —$CH_2CH_2N(R_8)(C$=O)$CR_9R_{10}R_{11}$, —$CH_2CH_2N(R_8)$ (C=O)$CR_9R_{10}R_{11}$, —$R_{12}N(OH)C$(=O)NHOH, —$R_{12}N$ (OH)C(=S)NHOH, —$R_{12}N(OR_8)C$(=O)$NHOR_9$, —$R_{12}N$ ($OR_8$)C(=S)$NHOR_9$, —$R_{12}OS(O_2)NHOH$, —$R_{12}NHS$ ($O_2$)NHOH, —$R_{12}OS(O_2)NHOR_9$, —$R_{12}OS(O_2)N(R_8)$ $OR_9$, —$R_{12}NR_8S(O_2)NHOR_9$, —$CR_9$(=N)$OR_8$, —NH ($OR_8$), —C(C=O)$NHR_8$, —C(C=O)$NR_9R_8$, —$NR_{10}$ ($OR_8$)C(=O)R9, —N($OR_8$)C(=O)$NR_9$, —$NR_8R_9$)S—, —N($R_8$)S(=O)$R_9$, —NR($R_8$)S(=O)$_2R_9$, —OC(=O)$NR_8$, —N($OR_8$)C(=O)$OR_9$, —N($R_8$)C(=S)$R_9$, —O(S(=O)$_2R_8$, —R$_{12}$O(S(=O)$_2$R$_8$, —O(S(=O)$_2$NR$_8$, —R$_{12}$O(S(=O)$_2$NR$_8$, —S(=O)R$_8$, —R$_{12}$S(=O)R$_8$, —S(=O)$_2$R$_8$, —R$_{12}$S(=O)$_2$R$_8$, —NR$_{10}$(R$_9$)S(=O)$_2$NHR$_8$, —NR$_9$(C=O)R$_8$, —NR$_9$(C=O)OR$_8$, —NR$_9$O(C=O)OR$_8$, —NR$_9$(C=O)NR$_8$R$_{10}$, —R$_{12}$N(R$_9$)S(=O)$_2$NHR$_8$, —R$_{12}$N(R$_9$)(C=O)R$_8$, —R$_{12}$N(R$_9$)(C=O)OR$_8$, —R$_{12}$N(R$_9$)(C=O)NR$_8$, —N(=NR$_{10}$)R$_8$, —R$_{12}$—N(=NR$_{10}$)R$_8$, —C(R$_{10}$)(=N—N=)CR$_8$R$_9$; —N$_3$, —CH$_2$N$_3$, —CH$_2$CH$_2$N$_3$, —CH$_2$CH$_2$CH$_2$N$_3$, —CH$_2$CH$_2$CH$_2$CH$_2$N$_3$, —CHR$_8$N$_3$, —CR$_9$R$_8$N$_3$, —CHR$_9$CHR$_8$N$_3$, —CH$_2$CHR$_9$CHR$_8$N$_3$, —CH$_2$CH$_2$CH$_2$CHR$_8$N$_3$, —C(R$_8$)=N—R$_9$, —CH$_2$C(R$_8$)=N—R$_9$, —CH$_2$CH$_2$C(R$_8$)=N—R$_9$, —CH$_2$CH$_2$CH$_2$C(R$_8$)=N—R$_9$, —N$_3$, —CH$_2$CH$_2$N$_3$, —CH$_2$CH$_2$CH$_2$N$_3$, —CH$_2$CH$_2$CH$_2$CH$_2$N$_3$; where R$_2$ and R$_3$ each independently represent —H, —OH, —CH$_3$, —OCH$_3$, —C(=O)CH$_3$, —OC(=O)CH$_3$, —C(=O)OCH$_3$, —C(=O)CH$_2$CH$_3$, —OC(=O)CH$_2$CH$_3$, —C(=O)OCH$_2$CH$_3$, —CH$_2$CH$_3$, —CH(CH$_3$)$_2$, —C(CH$_3$)$_3$, —CH$_2$CH$_2$CH$_3$, —CH$_2$CH(CH$_3$)$_2$, —CHC(CH$_3$)$_3$, —CH$_2$OH, —NH$_2$, —CH$_2$NH$_2$, —N$_3$, and (C1-C4)alkyl; where R$_8$, R$_9$, R$_{10}$, R$_{11}$ each independently represent —H, —OH, —CH$_3$, —CH$_2$CH$_3$, —CH$_2$=CH$_2$, —CH$_2$CH$_2$=CH$_2$, —CH$_2$CH$_2$CH$_2$=CH$_2$, —C(H)=O, —CH$_2$C(H)=O, —CH$_2$CH$_2$C(H)=O, —CH(CH$_3$)CH$_3$, —CH$_2$CH$_2$CH$_3$, —CH$_2$CH(CH$_3$)CH$_3$, —CHC(CH$_3$)$_2$CH$_3$, —C(=O)CH$_3$, —C(=O)CH$_2$CH$_3$, —C(=O)NH$_2$, —CH$_2$OH, —CH$_2$CH$_2$OH, —C(H)(OH)C(H$_2$)(OH), —OCH$_3$, —OC(CH$_3$)$_3$, —OCH$_2$CH$_3$, —OCH(CH$_3$)$_2$, —CO$_2$H, —C(=O)OCH$_3$, —C(=O)OCH$_2$CH$_3$, —OC(=O)CH$_3$, —OC(=O)CH$_2$CH$_3$, —OC(=O)OCH$_3$, —OC(=O)OCH$_2$CH$_3$, —C(CH$_3$)$_3$, —CH$_2$CH$_2$(CH$_3$)$_2$, —CHC(CH$_3$)$_3$, —CH$_2$CH$_2$OH, CH$_2$CH$_2$CH$_2$OH, —Cl, —Br, —I, —F, —CH$_2$Cl, —CH$_2$Br, —CH$_2$I, —CH$_2$F, —CHCl$_2$, —CHBr$_2$, —CHI$_2$, —CHF$_2$, —CCl$_3$, —CBr$_3$, —CI$_3$, —CF$_3$, —NH$_2$, —CH$_2$NH$_2$, —NH(OH), —CH$_2$N(OH), —NH(OCH$_3$), —N(OCH$_2$CH$_3$), —CH$_2$NH(OCH$_3$), —CH$_2$N(OCH$_2$CH$_3$), —N$_3$, —CH$_2$N$_3$, —CH$_2$CH$_2$N$_3$, —CH=NH, —CH=NOH, —CH=NOCH$_3$, —SH, —SCH$_3$, —SCH$_2$CH$_3$, —NO$_2$, —CN, cyclopropane ring, saturated or unsaturated cyclobutane ring, saturated or unsaturated cyclopentane ring, saturated or unsaturated cyclohexane ring, benzene ring, phenolic ring, xylene ring, an amino acid(s), (C$_1$-C$_4$)alkyl, and R$_{12}$ represents —CH$_2$—, —CH$_2$CH$_2$—, —CH(CH$_3$)CH$_2$—, —C(CH$_3$)CH$_2$—, —CH=CH—, —O—, —S—, —O(C=O)—, —(C=O)O—, —NH—, —N(R$_8$)—, —N(OH)—, —CH$_2$O—, —O—CH$_2$—, —CH$_2$CH$_2$O—, —O—CH$_2$CH$_2$—, —S(=O)—, —(S=O)$_2$, —NH(S=O)$_2$—, —N(OH)S(=O)$_2$—, —S(=O)$_2$NH—, —S(=O)$_2$N(OH)—, —NHS(=O)$_2$, —N(OH)S(=O)$_2$—, —CH$_2$NH—, —CH$_2$N(R$_8$)—, —CH$_2$N(OH)—, —NHCH$_2$—, —N(R$_8$)CH$_2$—, —N(OH)CH$_2$—, —OC(C=O)O—, —OC(=O)NR$_8$—, —NR$_8$C(=O)O— and where the illudin analog has a structural formula II:

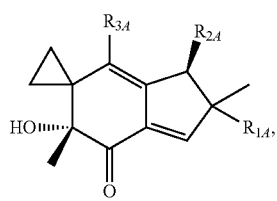

where R$_{1A}$, R$_{2A}$, and R$_{3A}$ each independently represent —H, —OH, —CH$_3$, —OCH$_3$, —C(=O)CH$_3$, —OC(=O)CH$_3$, —C(=O)OCH$_3$, —C(=O)CH$_2$CH$_3$, —OC(=O)CH$_2$CH$_3$, —C(=O)OCH$_2$CH$_3$, —CH$_2$CH$_3$, —CH(CH$_3$)$_2$, —C(CH$_3$)$_3$, —CH$_2$CH$_2$CH$_3$, —CH$_2$CH(CH$_3$)$_2$, —CHC(CH$_3$)$_3$, —CH$_2$OH, —NH$_2$, —NHOH, —CH$_2$NH$_2$, —CH$_2$NHOH, —N$_3$ and (C$_1$-C$_4$)alkyl, if:

(I) the first relative gene expression is upregulated;
(II) the second relative gene expression is upregulated; and
(III) the third relative gene expression is downregulated.

2. The method of claim 1, where the illudofulvene analog is selected from the group consisting of 002, 008, 012, 039, 040, 041, 042, 043, 044, 046, 075, 076, 077, 078, 079, 088, 090, 094, 103, 104, 108, 110, 112, 113, 114, 115, 116, 119, 120, 121, 122, 123, 124, 125, 126, 127, 128, 130, 141, 142, 146, 149, 150, 160, 164, 165, 177, 178, 184, 189, 190, 196, 198, 199, 201, 202, 203, 207, 208, 209, 210, 217, 221, 223, 233, 234, 235, 240, 244, 254, 255, 259, 262, 263, 266, 267, 268, 269, 275, 276, 284, 285, 286, 287, 288, 289, 290, 291, 292, 293, 294, 295, 296, 297, 298, 304, 305, 306, 310, 314, 315, 317, 321, 323, 324, 332, 333, 334, 335, 336, 337, 338, 339, 340, 345, 346, 347, 348, 351, 353, 354, 356, 357, 359, 361, 362, 363, 364, 365, 366, 367, 368, 369, 370, 371, 372, 373, 374, 375, 377, 378, 379, 380, 381, 382, 383, 384, 389, 392, 393, and 394.

3. The method of claim 1, where one or more primers selected to hybridize with one or more nucleic acid molecules used to quantify expression of the PTGR1 gene, the PTGR2 gene, the MYC gene and the one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:682-696, SEQ ID NO: 715-727, SEQ ID NO:897-899, and SEQ ID NO:900-902.

4. The method of claim 1, where the gene expression is measured by means selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

5. A method of treating a cancerous tumor in a patient comprising:
(a) receiving a test sample comprising a plurality of cancer cells from a patient;
(b) determining from the test sample a first relative ratio of expression of a MYC gene compared with a housekeeping gene selected from the group consisting of beta actin, transferrin receptor glyceraldehyde-3-phosphate dehydrogenase and ubiquitin in the test sample;
(c) determining from the test sample a second relative ratio of expression of a first TCR gene of one or more TCR genes selected from the group consisting of one or more ERCC genes, a XPA gene, a GTF2H gene, a UVSSA gene, and a USP7 gene compared with at least one housekeeping gene selected from the group consisting of beta actin, transferrin receptor glyceraldehyde-3-phosphate dehydrogenase and ubiquitin in the test sample;
(d) determining from the test sample a third relative ratio of expression of a second TCR gene of one or more TCR genes selected from the group consisting of one or more ERCC genes, a XPA gene, a GTF2H gene, a UVSSA gene, and a USP7 gene compared with at least one housekeeping gene selected from the group consisting of beta actin, transferrin receptor glyceraldehyde-3-phosphate dehydrogenase and ubiquitin in the test sample, where the first TCR gene is not the second TCR gene; and treating with an effective amount of an illudofulvene analog if the first relative ratio of expression is upregulated, the second relative ratio of expression is downregulated, and the third relative ratio of expression is downregulated, where the illudofulvene analog is selected from the group consisting of an acylfulvene analog and an illudin analog, where the acylfulvene analog has the structural formula I:

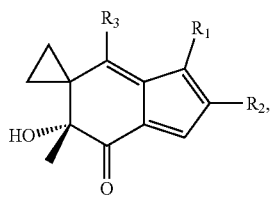

(I)

where $R_1$ represents —H, —$CR_9R_8OH$, —$CHR_9CHR_8OH$, —$CHR_{10}CHR_9CHR_8OH$, —$CH_2CHR_{10}CHR_9CHR_8OH$, —$CR_9R_8OH$, —$CHR_9CHR_8OH$, —$CHR_{10}CHR_9CHR_8OH$, —$CH_2CHR_{10}CHR_9CHR_8OH$, —C(=O)H, —$CH_2(C=O)$H, —$CH_2CH_2(C=O)$H, —$CH_2CH_2CH_2(C=O)$H, —$CH_2CH_2CH_2CH_2(C=O)$H, —$CR_9R_8(C=O)$H, —$CHR_9CHR_8(C=O)$H, —$CH_2CHR_9CHR_8(C=O)$H, —$CR_9R_8(C=O)R_{10}$, —$CHR_9CHR_8(C=O)R_{10}$, —$CH_2CHR_9CHR_8(C=O)R_{10}$, —$CH_2CH_2CHR_9CHR_8(C=O)R_{10}$, —$CO_2H$, —$CHR_9CO_2H$, —$CHR_8CHR_9CO_2H$, —$CHR_{10}CHR_8CHR_9CO_2H$, —$CO_2R_{10}$, —$CHR_9CO_2R_{10}$, —$CHR_8CHR_9CO_2R_{10}$, —$CH_2CHR_8CHR_9CO_2R_{10}$, —$CHR_9CH_2CH_2CHR_8CO_2H$, —$CHR_9CH_2CH_2CHR_8CO_2R_{10}$, —$CR_8$=$CH_2$, —$CHR_8CH$=$CH_2$, —$CH_2CHR_8CH$=$CH_2$, —$CH_2CH_2CHR_8CH$=$CH_2$, —$CR_8$=$CHR_9$, —$CHR_8CR_9$=$CH_2$, —$CH_2CHR_8CR_9$=$CH_2$, —$CH_2CH_2CHR_8CR_9$=$CH_2$, —$CR_8$=$CR_9R_{10}$, —$CHR_8CH$=$CR_9R_{10}$, —$CH_2CHR_8CH$=$CHR_9R_{10}$, —$CH_2CH_2CHR_8CH$=$CHR_9R_{10}$, —Cl, —Br, —I, —F, —$NO_2$, —$NR_8R_9$, —$CH_2Cl$, —$CH_2Br$, —$CH_2I$, —$CH_2F$, —$CR_8Cl_2$, —$CR_8Br_2$, —$CR_8I_2$, —$CR_8F_2$, —$CCl_3$, —$CBr_3$, —$CI_3$, —$CF_3$, —$CHR_8Cl$, —$CR_8R_9Cl$, —$CHR_8CHR_9Cl$, —$CHR_{10}CHR_8CHR_9Cl$, —$CH_2CHR_{10}CHR_8CHR_9Cl$, —$CHR_8Br$, —$CR_8R_9Br$, —$CHR_8CHR_9Br$, —$CHR_{10}CHR_8CHR_9Br$, —$CH_2CHR_{10}CHR_8CHR_9Br$, —$CHR_8I$, —$CR_8R_9I$, —$CHR_8CHR_9Br$, —$CHR_{10}CHR_8CHR_9I$, —$CH_2CHR_{10}CHR_8CHR_9I$, —$CR_8R_9NH_2$, —$CHR_8CHR_9NH_2$, —$CHR_{10}CHR_8CHR_9NH_2$, —$CH_2CHR_{10}CHR_8CHR_9NH_2$, —$CR_9R_{10}NHR_8$, —$CHR_9CHR_{10}NHR_8$, —$CH_2CHR_9CHR_{10}NHR_8$, —$CH_2CH_2CHR_9CHR_{10}NHR_8$, —$CHR_9NHR_8R_{10}$, —$CHR_9CH_2NHR_8R_{10}$, —$CH_2CH_2CHR_9NR_{10}R_8$, —$CH_2CH_2CH_2CH_2NHR_8$, —$CR_9R_8OR_{10}$, —$CH_2CR_8R_9OR_{10}$, —$CH_2CH_2CR_8R_9OR_{10}$, —$CH_2CH_2CH_2R_8R_9OR_{10}$, —$CH_2CH_2CH_2CH_2R_8R_9OR_{10}$, —$CHR_8OC(=O)CHR_9R_{10}$, —$CHR_8OC(=O)CHR_9R_{10}$, —$CH_2CH_2OC(=O)CHR_9R_{10}$, —$CH_2CH_2CHR_8OC(=O)CHR_9R_{10}$, —$CH_2CH_2CH_2CH_2OC(=O)CHR_9R_{10}$, —$CHR_8(=O)OCHR_9R_{10}$, —$CHR_8(=O)OCHR_9R_{10}$, —$CH_2CHR_8(=O)OCHR_9R_{10}$, —$CH_2CH_2CHR_8(=O)OCHR_9R_{10}$, —$CH_2CH_2CH_2CHR_8(=O)OCHR_9R_{10}$, —$R_{12}C$=$CR_9CH_2OH$, —$R_{12}C$=$CR_9C(=O)H$, —$R_{12}C$=$CR_9CH_2OR_{10}$, —$R_{12}C$=$CR_9C(=O)R_{10}$, —$CH_3$, —$CH_2CH_2$, —$CHR_8CH_2$, —$CHR_8CH_2CH_2$, —$CHR_8CHR_9CH_3$, —$OCH_3$, —$OCR_8R_9R_{10}$, —$OCH_2CR_8R_9R_{10}$, —$OCR_9R_8CHR_{10}$, —$OCHR_8CH_2CH_3$, —$OCHR_8CHR_9CH_3$, —$NR_8CH_3$, —$NR_8CH_2CH_3$, —$NR_9CHR_8CH_3$, —$NR_9CHR_8CH_2CH_3$, —$NR_{10}CHR_8CHR_9CH_3$, —$OCH_2OR_8$, —$OCHR_8OR_9$, —$OCHR_8CH_2OR_9$, —$OCHR_8CHR_9OR_{10}$, —$OC(=O)OR_8$, —$OCH_2C(=O)OR_8$, —$OCHR_9C(=O)OR_8$, —$CR_8(=N)H$, —$CH_2CR_8(=N)H$, —$CH_2CR_8(=N)H$, —$CH_2CH_2CR_8(=N)H$, —$CH_2CH_2CH_2CR_8(=N)H$, —$CH_2CH_2CH_2CH_2CR_8(=N)H$, —$CR_8(=N)OH$, —$CH_2CR_8(=N)OH$, —$CH_2CR_8(=N)OH$, —$CH_2CH_2CR_8(=N)OH$, —$CH_2CH_2CH_2CR_8(=N)OH$, —$CH_2CH_2CH_2CH_2CR_8(=N)OH$, —$CR_8(=N)R_9$, —$CH_2CR_8(=N)R_9$, —$CH_2CR_8(=N)R_9$, —$CH_2CH_2CR_8(=N)R_9$, —$CH_2CH_2CH_2CR_8(=N)R_9$, —$CH_2CH_2CH_2CH_2CR_8(=N)R_9$, —$CR_8(=N)OR_9$, —$CH_2CR_8(=N)OR_9$, —$CH_2CR_8(=N)OR_9$, —$CH_2CH_2CR_8(=N)OR_9$, —$CH_2CH_2CH_2CR_8(=N)OR_9$, —$CH_2CH_2CH_2CH_2CR_8(=N)OR_9$, —$CR_8(=N)NR_9$, —$CH_2CR_8(=N)NR_9$, —$CH_2CR_8(=N)NR_9$, —$CH_2CH_2CR_8(=N)NR_9$, —$CH_2CH_2CH_2CR_8(=N)NR_9$, —$CH_2CH_2CH_2CH_2CR_8(=N)NR_9$, —$CR_8(=N)NR_9S(=O)_2R_{10}$, —$CH_2C(R_8)(=N)NR_9S(=O)_2R_{10}$, —$CH_2CH_2C(R_8)(=N)NR_9S(=O)_2R_{10}$, —$CH_2CH_2CH_2C(R_8)(=N)NR_9S(=O)_2R_{10}$, —$CH_2CH_2CH_2CH_2C(R_8)(=N)NR_9S(=O)_2R_{10}$, —$R_{12}N(R_8)C(=O)NR_9R_{10}$, —$R_{12}N(R_8)C(=S)NR_9R_{10}$, —$R_{12}N(OR_8)C(=O)NR_9R_{10}$, —$R_{12}N(OR_8)C(=S)NR_9R_{10}$, —$R_{12}OS(O_2)NH_2$, —$R_{12}NHS(O_2)NH_2$, —$R_{12}OS(O_2)NR_8R_9$, —$R_{12}NHS(O_2)NR_8R_9$, —$CH_2N(R_8)S(O_2)NR_9R_{10}$, —$CH_2CH_2N(R_8)S(O_2)NR_9R_{10}$, —$CH_2CH_2CH_2N(R_8)S(O_2)NR_9R_{10}$, —$CH_2N(R_8)S(O_2)CR_9R_{10}R_{11}$, —$CH_2CH_2N(R_8)S(O_2)CR_9R_{10}R_{11}$, —$CH_2CH_2CH_2N(R_8)S(O_2)CR_9R_{10}R_{11}$, —$N(R_8)C(=O)R_9$, —$CH_2N(R_8)C(=O)R_9$, —$CH_2CH_2N(R_8)C(=O)R_9$, —$CH_2CH_2CH_2N(R_8)C(=O)R_9$, —$CH_2N(R_8)(C=O)NR_2R_{10}$, —$CH_2CH_2N(R_8)(C=O)NR_9R_{10}$, —$CH_2CH_2N(R_8)(C=O)NR_9R_{10}$, —$CH_2N(R_8)(C=O)CR_9R_{10}R_{11}$, —$CH_2CH_2N(R_8)(C=O)CR_9R_{10}R_{11}$, —$CH_2CH_2N(R_8)(C=O)CR_9R_{10}R_{11}$, —$R_{12}N(OH)C(=O)NHOH$, —$R_{12}N(OH)C(=S)NHOH$, —$R_{12}N(OR_8)C(=O)NHOR_9$, —$R_{12}N(OR_8)C(=S)NHOR_9$, —$R_{12}OS(O_2)NHOH$, —$R_{12}NHS(O_2)NHOH$, —$R_{12}OS(O_2)NHOR_9$, —$R_{12}OS(O_2)N(R_8)OR_9$, —$R_{12}NR_8S(O_2)NHOR_9$, —$CR_9(=N)OR_8$, —NH(OR_8), —C(C=O)NHR_8, —C(C=O)NR_9R_8, —$NR_{10}(OR_8)C(=O)R9$, —$N(OR_8)C(=O)NR_9$, —$NR_8(R_9)S$—, —$N(R_8)S(=O)R_9$, —$NR(R_8)S(=O)_2R_9$, —$OC(=O)NR_8$, —$N(OR_8)C(=O)OR_9$, —$N(R_8)C(=S)R_9$, —$O(S(=O)_2R_8$, —$R_{12}O(S(=O)_2R_8$, —$O(S(=O)_2NR_8$, —$R_{12}O(S(=O)_2NR_8$, —$S(=O)R_8$, —$R_{12}S(=O)R_8$, —$S(=O)_2R_8$, —$R_{12}S(=O)_2R_8$, —$NR_{10}(R_9)S(=O)_2NHR_8$, —$NR_9(C=O)R_8$, —$NR_9(C=O)OR_8$, —$NR_9(C=O)OR_8$, —$NR_9(C=O)NR_8R_{10}$, —$R_{12}N(R_9)S(=O)_2NHR_8$, —$R_{12}N(R_9)(C=O)R_8$, —$R_{12}N(R_9)(C=O)OR_8$, —$R_{12}N(R_9)(C=O)NR_8$, —$N(=NR_{10})R_8$, —$R_{12}$—$N(=NR_{10})R_8$, —$C(R_{10})(=N$—$N=)CR_8R_9$; —$N_3$, —$CH_2N_3$, —$CH_2CH_2N_3$, —$CH_2CH_2CH_2N_3$, —$CH_2CH_2CH_2CH_2N_3$, —$CHR_8N_3$, —$CR_9R_8N_3$, —$CHR_9CHR_8N_3$, —$CH_2CHR_9CHR_8N_3$, —$CH_2CH_2CH_2CHR_8N_3$, —$C(R_8)$=$N$—$R_9$, —$CH_2C(R_8)$=$N$—$R_9$, —$CH_2CH_2C(R_8)$=$N$—$R_9$, —$CH_2CH_2CH_2C(R_8)$=$N$—$R_9$, —$N_3$, —$CH_2CH_2N_3$, —$CH_2CH_2N_3$, —$CH_2CH_2CH_2CH_2N_3$; where $R_2$ and $R_3$ each independently represent —H, —OH, —$CH_3$, —$OCH_3$, —C(=O)$CH_3$, —OC(=O)$CH_3$, —C(=O)$OCH_3$, —C(=O)$CH_2CH_3$, —OC(=O)$CH_2CH_3$, —C(=O)$OCH_2CH_3$, —$CH_2CH_3$, —$CH(CH_3)_2$, —$C(CH_3)_3$, —$CH_2CH_2CH_3$, —CH$_2$CH(CH$_3$)$_2$, —CHC(CH$_3$)$_3$, —CH$_2$OH, —NH$_2$, —CH$_2$NH$_2$, —N$_3$, and (C1-C4)alkyl; where R$_8$, R$_9$, R$_{10}$, R$_{11}$ each independently represent —H, —OH, —CH$_3$, —CH$_2$CH$_3$, —CH$_2$=CH$_2$, —CH$_2$CH$_2$=CH$_2$, —CH$_2$CH$_2$CH$_2$=CH$_2$, —C(H)=O, —CH$_2$C(H)=O, —CH$_2$CH$_2$C(H)=O, —CH(CH$_3$)CH$_3$, —CH$_2$CH$_2$CH$_3$, —CH$_2$CH(CH$_3$)CH$_3$, —CHC(CH$_3$)$_2$CH$_3$, —C(=O)CH$_3$, —C(=O)CH$_2$CH$_3$, —C(=O)NH$_2$, —CH$_2$OH, —CH$_2$CH$_2$OH, —C(H)(OH)C(H$_2$)(OH), —OCH$_3$, —OC(CH$_3$)$_3$, —OCH$_2$CH$_3$, —OCH(CH$_3$)$_2$, —CO$_2$H, —C(=O)OCH$_3$, —C(=O)OCH$_2$CH$_3$, —OC(=O)CH$_3$, —OC(=O)CH$_2$CH$_3$, —OC(=O)OCH$_3$, —OC(=O)OCH$_2$CH$_3$, —C(CH$_3$)$_3$, —CH$_2$CH$_2$(CH$_3$)$_2$, —CHC(CH$_3$)$_3$, —CH$_2$CH$_2$OH, CH$_2$CH$_2$CH$_2$OH, —Cl, —Br, —I, —F, —CH$_2$Cl, —CH$_2$Br, —CH$_2$I, —CH$_2$F, —CHCl$_2$, —CHBr$_2$, —CHI$_2$, —CHF$_2$, —CCl$_3$, —CBr$_3$, —CI$_3$, —CF$_3$, —NH$_2$, —CH$_2$NH$_2$, —NH(OH), —CH$_2$N(OH), —NH(OCH$_3$), —N(OCH$_2$CH$_3$), —CH$_2$NH(OCH$_3$), —CH$_2$N(OCH$_2$CH$_3$), —N$_3$, —CH$_2$N$_3$, —CH$_2$CH$_2$N$_3$, —CH=NH, —CH=NOH, —CH=NOCH$_3$, —SH, —SCH$_3$, —SCH$_2$CH$_3$, —NO$_2$, —CN, cyclopropane ring, saturated or unsaturated cyclobutane ring, saturated or unsaturated cyclopentane ring, saturated or unsaturated cyclohexane ring, benzene ring, phenolic ring, xylene ring, an amino acid(s), (C$_1$-C$_4$)alkyl, and R$_{12}$ represents —CH$_2$, —CH$_2$CH$_2$, —CH(CH$_3$)CH$_2$, —C(CH$_3$)CH$_2$, —CH=CH—, —O—, —S—, —O(C=O)—, —(C=O)O—, —NH—, —N(R$_8$)—, —N(OH)—, —CH2-O—, —O—CH$_2$—, —CH$_2$CH$_2$—O—, —O—CH$_2$CH$_2$—, —S(=O)—, —(S=O)$_2$—, —NH(S=O)$_2$—, —N(OH)S(=O)$_2$—, —S(=O)$_2$NH—, —S(=O)$_2$N(OH)—, —NHS(=O)$_2$, —N(OH)S(=O)$_2$—, —CH$_2$NH—, —CH$_2$N(R$_8$)—, —CH$_2$N(OH)—, —NHCH$_2$—, —N(R$_8$)CH$_2$—, —N(OH)CH$_2$, —OC(C=O)O—, —OC(=O)NR$_8$—, —NR$_8$C(=O)O— and where the illudin analog means the following structural formula II:

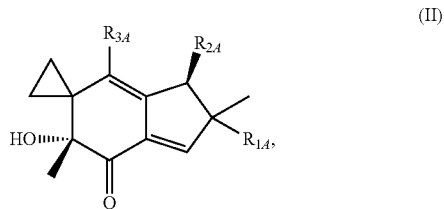

(II)

where R$_{1A}$, R$_{2A}$, and R$_{3A}$ each independently represent —H, —OH, —CH$_3$, —OCH$_3$, —C(=O)CH$_3$, —OC(=O)CH$_3$, —C(=O)OCH$_3$, —C(=O)CH$_2$CH$_3$, —OC(=O)CH$_2$CH$_3$, —C(=O)OCH$_2$CH$_3$, —CH$_2$CH$_3$, —CH(CH$_3$)$_2$, —C(CH$_3$)$_3$, —CH$_2$CH$_2$CH$_3$, —CH$_2$CH(CH$_3$)$_2$, —CHC(CH$_3$)$_2$, —CH$_2$OH, —NH$_2$, —NHOH, —CH$_2$NH$_2$, —CH$_2$NHOH, —N$_3$, and (C$_1$-C$_4$)alky.

6. The method of claim 5, where one or more primers used to quantify expression of the MYC gene and one or more TCR genes are selected from the group consisting of SEQ ID NO:251-261, SEQ ID NO:264-274, SEQ ID NO:307-308, SEQ ID NO:309-310, SEQ ID NO: 329-440, SEQ ID NO: 451-475, SEQ ID NO:669-681, SEQ ID NO:897-899, and SEQ ID NO:900-902.

7. The method of claim 5, where the effective amount is administered in a dosage between: a lower limit of approximately 0.1 mg of the illudofulvene analog per kilogram of body weight of the patient; and an upper limit of approximately 5 mg of the illudofulvene analog per kilogram of body weight of the patient.

8. The method of claim 5, where the gene expression is measured by means selected from the group consisting of (i) quantification of gene mRNA expression by probe analysis, (ii) microarray analysis, (iii) Real Time-Polymerase Chain Reaction (RT-PCR), (iv) Transcription Coupled Repair (TCR) Tumor Mutation Panel and (v) primary tumor cell sensitivity.

9. The method of claim 1, where the effective amount is administered in a dosage between: a lower limit of approximately 0.1 mg of the illudofulvene analog per kilogram of body weight of the patient; and an upper limit of approximately 5 mg of the illudofulvene analog per kilogram of body weight of the patient.

10. The method of claim 1, where a treatment regimen is at least once per week for at least three weeks.

11. The method of claim 10, where the treatment regimen is repeated between: a lower limit of two times; and an upper limit of twenty times.

12. The method of claim 1, where a treatment regimen is undertaken on day one and repeated on day eight.

13. The method of claim 12, where the treatment regimen is repeated between: a lower limit of two times; and an upper limit of twenty times.

14. The method of claim 1, where the effective amount is administered in a dosage between: a lower limit of approximately 0.1 mg of the illudofulvene analog per kilogram of body weight of the patient; and an upper limit of approximately 1 mg of the illudofulvene analog per kilogram of body weight of the patient.

15. The method of claim 5, where a treatment regimen is at least once per week for at least three weeks.

16. The method of claim 15, where the treatment regimen is repeated between: a lower limit of two times; and an upper limit of twenty times.

17. The method of claim 5, where a treatment regimen is undertaken on day one and repeated on day eight.

18. The method of claim 17, where the treatment regimen is repeated between: a lower limit of two times; and an upper limit of twenty times.

19. The method of claim 5, where the illudofulvene analog is selected from the group consisting of 002, 008, 012, 039, 040, 041, 042, 043, 044, 046, 075, 076, 077, 078, 079, 088, 090, 094, 103, 104, 108, 110, 112, 113, 114, 115, 116, 119, 120, 121, 122, 123, 124, 125, 126, 127, 128, 130, 141, 142, 146, 149, 150, 160, 164, 165, 177, 178, 184, 189, 190, 196, 198, 199, 201, 202, 203, 207, 208, 209, 210, 217, 221, 223, 233, 234, 235, 240, 244, 254, 255, 259, 262, 263, 266, 267, 268, 269, 275, 276, 284, 285, 286, 287, 288, 289, 290, 291, 292, 293, 294, 295, 296, 297, 298, 304, 305, 306, 310, 314, 315, 317, 321, 323, 324, 332, 333, 334, 335, 336, 337, 338, 339, 340, 345, 346, 347, 348, 351, 353, 354, 356, 357, 359, 361, 362, 363, 364, 365, 366, 367, 368, 369, 370, 371, 372, 373, 374, 375, 377, 378, 379, 380, 381, 382, 383, 384, 389, 392, 393, and 394.

* * * * *